United States Patent
Shoda et al.

(10) Patent No.: US 6,867,320 B2
(45) Date of Patent: Mar. 15, 2005

(54) SUBSTITUTED PHENYLALKANOIC ACID DERIVATIVES AND USE THEREOF

(75) Inventors: Motoshi Shoda, Shizuoka (JP); Hiroshi Kuriyama, Shizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 10/368,435

(22) Filed: Feb. 20, 2003

(65) Prior Publication Data

US 2004/0044258 A1 Mar. 4, 2004

Related U.S. Application Data

(60) Provisional application No. 60/358,337, filed on Feb. 22, 2002, and provisional application No. 60/419,098, filed on Oct. 18, 2002.

(30) Foreign Application Priority Data

Feb. 21, 2002 (JP) ........................................ 2002-045293
Oct. 16, 2002 (JP) ........................................ 2002-301543

(51) Int. Cl.$^7$ .......................... C07C 69/76; C07C 62/06; C07C 233/00
(52) U.S. Cl. ........................... 560/56; 562/466; 564/172
(58) Field of Search ........................... 560/56; 562/466; 564/172

(56) References Cited

U.S. PATENT DOCUMENTS

| | | | |
|---|---|---|---|
| 4,873,259 A | 10/1989 | Summers, Jr. et al. |
| 5,136,090 A | 8/1992 | Suzuki et al. |
| 5,155,259 A | 10/1992 | Suzuki et al. |
| 5,232,948 A | 8/1993 | Huang et al. |
| 5,237,091 A | 8/1993 | Yoshimura et al. |
| 5,262,565 A | 11/1993 | Yoshimura et al. |
| 5,319,139 A | 6/1994 | Yoshimura et al. |
| 5,391,817 A | 2/1995 | Springer et al. |
| 5,462,954 A | 10/1995 | Baker et al. |
| 5,478,857 A | 12/1995 | Clemens et al. |
| 5,482,941 A | 1/1996 | Terrett |
| 5,563,164 A | 10/1996 | Clemens et al. |
| 5,994,379 A | 11/1999 | Bayly et al. |
| 6,147,100 A | 11/2000 | Seno et al. |
| 6,200,980 B1 | 3/2001 | Piazza et al. |
| 6,376,546 B1 | 4/2002 | Shoda et al. |
| 2002/0161022 A1 | 10/2002 | Reich et al. |

FOREIGN PATENT DOCUMENTS

| | | |
|---|---|---|
| EP | 0 499 926 B1 | 9/1996 |
| WO | WO 93/07149 A1 | 4/1993 |
| WO | WO 00/35886 A2 | 6/2000 |

*Primary Examiner*—Paul J. Killos
(74) *Attorney, Agent, or Firm*—Birch, Stewart, Kolasch & Birch, LLP

(57) ABSTRACT

A compound represented by the formula (I) or a salt thereof:

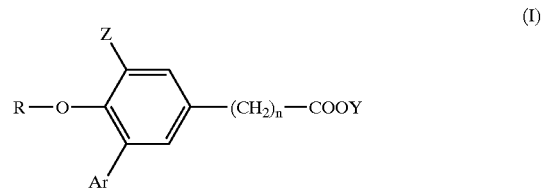

(I)

wherein n represents an integer of 1 to 3, R represents an alkyl group having 3 to 8 carbon atoms, a group represented by the following formula: $R^1(CH_2)_k$— (wherein k represents 0 or an integer of 1 to 3; $R^1$ represents a saturated cyclic alkyl group having 3 to 7 carbon atoms or a saturated condensed cyclic alkyl group having 6 to 8 carbon atoms, and the group $R^1$ may be substituted with a lower alkyl group having 1 to 4 carbon atoms) and the like, and Ar represents a condensed bicyclic group such as naphthalen-1-yl group, which has suppressing action on prostaglandin and leukotriene production and is useful for prophylactic and/or therapeutic treatment of various inflammatory diseases and the like caused by these lipid mediators.

28 Claims, No Drawings

SUBSTITUTED PHENYLALKANOIC ACID DERIVATIVES AND USE THEREOF

This application claims priority on provisional Application No. 60/358,337 filed on Feb. 22, 2002, and 60/419,098 filed on Oct. 18, 2002, and claims priority on Japanese Patent Application No. 045293/2002 filed on Feb. 21, 2002, and Japanese Patent Application No. 301543/2002 filed on Oct. 16, 2003, the entire contents of which are hereby incorporated by reference.

TECHNICAL FIELD

The present invention relates to a novel substituted phenylalkanoic acid derivative. More precisely, the present invention relates to a substituted phenylalkanoic acid derivative having an activity as a pharmaceutical.

BACKGROUND ART

In living bodies of mammals, various prostaglandins and various leukotrienes are produced by various stimulations such as inflammatory and physical stimulations. Both of prostaglandins and leukotrienes are metabolites of arachidonic acid, and they are physiologically active substances called lipid mediators. They trigger various kinds of physiological reactions of mammals by binding to their respective receptors expressed on cell surfaces or expressed intracellularly.

Arachidonic acid is produced from phospholipids such as phosphatidylcholine as substrates, which are components of cell membranes, with the aid of the enzymatic activity of phospholipase $A_2$ ($PLA_2$). Arachidonic acid produced by $PLA_2$ is converted into prostaglandin (PG) $H_2$ by an enzymatic activity of constitutive-type cyclooxygenase (COX) 1 or inducible-type COX-2 and further converted into $PGE_2$, $PGD_2$, $PGF_2$, $PGI_2$, thromboxane (TX) $A_2$ and the like by each synthetic enzyme. Further, arachidonic acid is also metabolized by 5-lipoxygenase (5-LO) to give leukotriene (LT) $A_4$, and further converted into $LTB_4$, $LTC_4$, $LTD_4$, $LTE_4$ and the like by enzymatic activities of $LTA_4$ hydrolase, $LTC_4$ synthase, and glutathione-S-transferase [Goodman and Gilman's the Pharmacological Basis of Therapeutics, 9th edition (Hirokawa Shoten), 1999, p.801; C. D. Funk, SCIENCE, 2001, vol. 294, p.1871].

Each of the prostaglandins binds with a specific receptor to cause, for example, inflammatory reactions such as fervescence, increase of blood vessel permeability, vasodilation, swelling, and pain, bronchial smooth muscle contraction, platelet aggregation, tumor cell proliferation, bone resorption promotion, nerve cell degeneration and the like, and plays an important role in expression of symptoms or formation of pathological states in various diseases. Each of the leukotrienes binds with a specific receptor to cause, for example, inflammatory reactions such as excessive accumulation of leucocytes and increase of blood vessel permeability, smooth muscle contraction, mucus secretion, tumor cell proliferation and the like, and also plays an important role in expression of symptoms or formation of pathological states in various diseases.

Although inflammatory reactions, per se, are essential reactions in order that living bodies can survive when they face a pathogenic substance or affection, inflammatory reactions sometimes occur in excess levels in certain conditions or diseases, or they may sometimes continue without any reason for bringing evident benefits [Goodman and Gilman's the Pharmacological Basis of Therapeutics, 9th edition (Hirokawa Shoten), 1999, p.827]. Conditions of living bodies exhibiting acute or chronic inflammatory reactions referred to in the present specification mean conditions where excess or non-profitable inflammatory reactions are generated acutely and transiently or chronically and continuously. Further, inflammatory reactions are a series of events caused by stimulations including physical hazards such as those caused by heat, infectious substance, ischemia, antigen-antibody reaction and the like, and they are accompanied by flare, swelling, algesia, and pain generation as well-known macroscopic clinical symptoms. As histological mechanisms of these symptoms, it is known that vasodilation, increase of blood vessel permeability, invasion of leucocytes and phagocytes, decomposition or fibrosis of tissues and the like are caused [Goodman and Gilman's the Pharmacological Basis of Therapeutics, 9th edition (Hirokawa Shoten), 1999, p.827]. It is known that many of these histological reactions are triggered by prostaglandins and/or leukotrienes, and prostaglandins and/or leukotrienes have important roles in the inflammatory reactions.

For example, in a pathological tissue of rheumatoid arthritis, which is an autoimmune disease and is one of chronic inflammatory diseases, expression of COX-2 and production of $PGE_2$ or $TXA_2$ as well as expression of 5-LO and production of $LTB_4$ are observed [Bonnet et al., Prostaglandins, 1995, vol. 50, p.127]. In a mouse deficient in FLAP which is a protein required for activation of 5-LO, symptoms of collagen-induced arthritis, as a disease model of chronic rheumatoid arthritis, are reported to be milder compared with those in a wild-type mouse [Griffiths et al., J. Exp. Med, 1997, vol. 185, p.1123]. Thus, prostaglandins and leukotrienes are demonstrated to be responsible for important roles in the formation of pathologies of chronic rheumatoid arthritis. In a pathological tissue of bronchial asthma, which is one of chronic allergic diseases, overproduction of $PGD_2$ and $TXA_2$ as well as overproduction of $LTC_4$ and $LTD_4$ are observed [Wenzel et al., Am. Rev. Respir. Dis, 1990, vol. 142, p.112], and airway hypersensitivity, which is a disease model of bronchial asthma, is reported to unlikely occur in a $PGD_2$ receptor deficient mouse [Matsuoka et al., SCIENCE, 2000, vol. 287, p.20131. Accordingly, roles of prostaglandins and leukotrienes are demonstrated to be important in bronchial asthma.

In a cerebral tissue after ischemia and reperfusion, expression of COX-2 is increased to increase $PGE_2$ and $TXA_2$ concentrations, whereas activity of 5-LO is increased to increase production of $LTC_4$ [Ohtsuki et al., Am. J. Physiol., 1995, vol. 268, p.1249]. Thus, it is known that prostaglandins and leukotrienes are responsible for important roles in the formation of infarct, which is recognized as a disorder from ischemia and reperfusion.

In a pathological tissue of Alzheimer's disease, which is one of diseases accompanied by neurodegeneration, it is demonstrated that COX activity and 5-LO activity are increased, and prostaglandins and leukotrienes cause formation of β amyloid proteins which constitute one class of pathogenic substances of Alzheimer's disease to induce degeneration of nerve cells [Sugaya et al., Jpn. J. Pharmacol., 2000, vol. 82, p.85]. Thus, it is considered that prostaglandins and leukotrienes are responsible for important roles in formation of neurodegenerative diseases such as Alzheimer's disease.

In a pathological tissue of colon cancer, for example, COX and 5-LO are expressed, and the production of prostaglandins and leukotrienes are increased [Dreyling et al., Biochim. Biophys. Acta, 1986, vol. 878, p.184]. Further, leukotrienes are reported to cause proliferation of colon cancer cells [Qiao et al., Biochim. Biophys. Acta, 1995, vol.

1258, p.215; Hong et al., Cancer Res., 1999, vol. 59, p.2223]. Thus, it is considered that prostaglandins and leukotrienes also play important roles in tissues of colon cancer.

Involvements of prostaglandins and/or leukotrienes in diseases and pathological conditions are not limited to the diseases exemplified above. It has been demonstrated that prostaglandin and/or leukotrienes are involved in various conditions, diseases, and pathological states accompanied by acute or chronic inflammatory reactions, and that their roles are important.

From the above facts, various kinds of inhibitors against prostaglandin production or against leukotriene production have been used as agents for prophylactic or therapeutic treatment of conditions, diseases, and pathological conditions with acute or chronic inflammatory reactions. Drugs having suppressing actions on prostaglandin production include various kinds of non-steroidal anti-inflammatory drugs (NSAIDS), and they have been used as agents for therapeutic treatment of chronic rheumatoid arthritis and osteoarthritis, anti-inflammatory analgesics for external injury and the like, agents for prophylactic treatment of cerebral infarction or myocardial infarction, agents for prophylactic treatment of colorectal polyposis and the like. However, various kinds of NSAIDS inhibit only the production of prostaglandins, and as a result, they increase production of leukotrienes to cause side effects such as asthmatic attack and gastrointestinal injury, and in addition, exhibit side effects of nephropathy and the like. Further, differences in an effective dose and a dose inducing the side effects are small in these NSAIDS, and no satisfactory drug is available also from a viewpoint of a therapeutic effect. 5-LO inhibitors described in EP279263 are available as drugs having suppressing action on leukotriene production and are known as prophylactic agents for asthma. However, their doses are limited because of induction of side effects such as hepatotoxicity, which results in unsatisfactoriness from a viewpoint of a therapeutic effect. Steroids inhibit productions of both of prostaglandins and leukotrienes, and accordingly, they are used as prophylactic or therapeutic agents for treatment of conditions of living bodies, various diseases, or pathological states with various acute or chronic inflammatory reactions. However, their actions are not limited to the suppressing action on lipid mediator production, but they have severe side effects such as induction and exacerbation of infection due to immune suppressing effects, growth delay and dermatrophy due to suppressing action on normal cell proliferation, digestive ulcer and the like. Therefore, their use has been limited.

DISCLOSURE OF THE INVENTION

Compounds inhibiting production of both of prostaglandins and leukotrienes and having reduced side effects are considered to be effective as prophylactic or therapeutic agents for treatment of such conditions of living bodies, diseases, and pathological states as mentioned above in mammals. In addition, a combination therapy using the aforementioned compound and a drug available at present is expected to be a more effective therapeutic or prophylactic method. Therefore, development of compounds inhibiting production of both of prostaglandins and leukotrienes and their clinical applications are considered necessary.

An object of the present invention is to provide compounds that inhibit production of prostaglandins and leukotrienes to prevent and/or cure various kinds of inflammatory diseases, autoimmune diseases, allergic diseases, and pain in mammals resulting from the lipid mediators.

In order to achieve the aforementioned object, the inventors of the present invention conducted various researches, and as a result, they found that the substituted phenylalkanoic acid derivatives represented by the general formula mentioned below, which are novel compounds, had superior suppressing action on prostaglandin production and on leukotriene production. The present invention was achieved on the basis of these findings.

The present invention thus provides a compound represented by the formula (I) or a salt thereof:

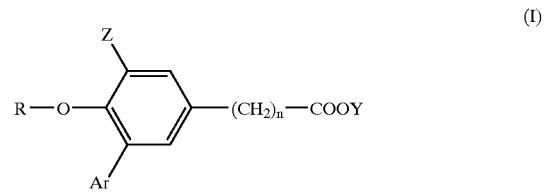

(I)

wherein n represents an integer of 1 to 3, R represents a linear or branched alkyl group having 3 to 8 carbon atoms, a group Ra represented by the following formula:

(Ra)

or a group Rb represented by the following formula:

[Formula 5]

(Rb)

wherein k in the substituent Ra represents 0 or an integer of 1 to 3; $R^1$ represents a saturated cyclic alkyl group having 3 to 7 carbon atoms or a saturated condensed cyclic alkyl group having 6 to 8 carbon atoms, and the group $R^1$ may be substituted with a lower alkyl group having 1 to 4 carbon atoms; Q in the group Rb represents a monocyclic or bicyclic aryl group, and Q may contain 1 or 2 heteroatoms; $A^1$ represents a single bond or an alkylene (a) having 1 to 3 carbon atoms, and the alkylene (a) may be substituted with a lower alkyl group having 1 to 4 carbon atoms or phenyl group; $A^2$ represents a single bond, oxygen atom, sulfur atom, —S(O)—, —S(O)$_2$—, or —N(R$^4$)— (wherein, when $A^2$ represents oxygen atom, sulfur atom, —S(O)—, —S(O)$_2$—, or —N(R$^4$)—, $A^1$ represents ethylene or trimethylene); $R^2$ and $R^3$ both or each independently represent hydrogen atom, a linear or branched saturated alkyl group having 1 to 4 carbon atoms, phenyl group, fluorine atom, chlorine atom, bromine atom, trifluoromethyl group, an —OR$^5$ group, an —N(R$^6$)$_2$ group, an —NHCOR$^7$ group, or an NHSO$_2$R$^8$ group, wherein R$^4$, R$^6$ and R$^7$ each independently represent hydrogen atom or a lower alkyl group having 1 to 4 carbon atoms, and R$^5$ and R$^8$ represent a lower alkyl group having 1 to 4 carbon atoms; Z represents hydrogen atom, fluorine atom, chlorine atom, nitro group, amino group, methyl group, or an OR$^9$ group wherein R$^9$ represents hydrogen atom or a lower alkyl group having 1 to 4 carbon atoms; the substituent Ar represents a substituent selected from the group consisting of condensed bicyclic substituents of ArI, ArII, ArIII, ArIV, ArV, ArVI, ArVII, ArVIII, ArIX, ArX, ArXI and ArXII represented by the following formulas:

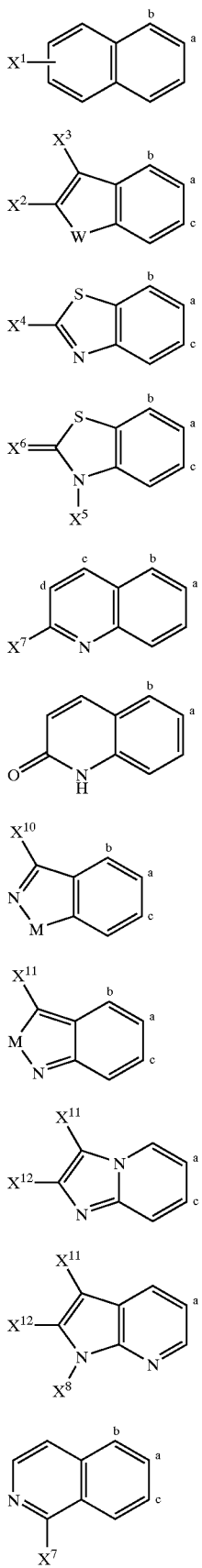

(ArI)
(ArII)
(ArIII)
(ArIV)
(ArV)
(ArVI)
(ArVII)
(ArVIII)
(ArIX)
(ArX)
(ArXI)

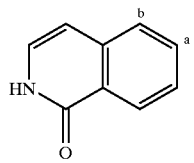

(ArXII)

which bind at any of the positions of a, b, c and d on the rings, and wherein the substituent $X^1$ in the group ArI represents hydrogen atom, a —$OR^{10}$ group, a —$N(R^{11})(R^{12})$ group, a —$SO_2R^{13}$ group, or carboxyl group, wherein $R^{10}$ represents hydrogen atom, a lower alkyl group having 1 to 4 carbon atoms, or a $(CH_2)_iR^{14}$ group wherein i represents an integer of 1 to 3, and $R^{14}$ represents hydroxyl group, carboxyl group, or N,N-dimethylcarbamoyl group, $R^{11}$ represents hydrogen atom or a lower alkyl group having 1 to 4 carbon atoms, $R^{12}$ represents hydrogen atom, a lower alkyl group having 1 to 4 carbon atoms, 2-hydroxyethyl group, a —$COR^{15}$ group, or a $SO_2R^{16}$ group, wherein $R^{15}$ represents amino group, a lower alkyl group having 1 to 4 carbon atoms, hydroxymethyl group, aminomethyl group, dimethylaminomethyl group, phenyl group, or furyl group, and $R^{13}$ and $R^{16}$ each independently represent a lower alkyl group having 1 to 4 carbon atoms, amino group, methylamino group, or dimethylamino group; in the group ArII, W represents oxygen atom, sulfur atom, or $NX^8$, the substituent $X^2$ represents hydrogen atom, a linear or branched saturated alkyl group having 1 to 4 carbon atoms, or carboxyl group, the substituent $X^3$ represents hydrogen atom, a linear or branched saturated alkyl group having 1 to 4 carbon atoms, acetyl group, formyl group, carboxymethyl group, or hydroxymethyl group, the substituent $X^8$ represents hydrogen atom, a linear or branched saturated alkyl group having 1 to 4 carbon atoms, a saturated cyclic alkyl group having 3 to 7 carbon atoms, or a $(CH_2)_jR^{17}$ group wherein j represents an integer of 1 to 3, and $R^{17}$ represents hydroxyl group or carboxyl group; the substituent $X^4$ in the group ArIII represents hydrogen atom, methyl group, methoxy group, amino group, methylamino group, or dimethylamino group; in the group ArIV, $X^6$ represents oxygen atom, sulfur atom, or $NX^9$, and the substituents $X^5$ and $X^9$ both represent hydrogen atom or methyl group; the substituent $X^7$ in the groups ArV and ArXI represents hydrogen atom or methyl group; M in the groups ArVII and ArVIII represents sulfur atom or $NX^8$; the substituent $X^{10}$ in the group ArVII represents hydrogen atom, a linear or branched saturated alkyl group having 1 to 4 carbon atoms, carboxyl group, acetyl group, formyl group, or an $OR^{22}$ group (wherein, when M in the group ArVII represents sulfur atom, the substituent $X^{10}$ represents hydrogen atom or a linear or branched saturated alkyl group having 1 to 4 carbon atoms), wherein $R^{22}$ represents hydrogen atom or a lower alkyl group having 1 to 4 carbon atoms; the substituent $X^{11}$ in the groups ArVIII, ArIX and ArX represents hydrogen atom or a linear or branched saturated alkyl group having 1 to 4 carbon atoms; and the substituent $X^{12}$ in the groups ArIX and ArX represents hydrogen atom, a linear or branched saturated alkyl group having 1 to 4 carbon atoms, or carboxyl group; and the group Y represents hydrogen atom, a lower alkyl group having 1 to 4 carbon atoms, a —$(CH_2)_m N(R^{18})(R^{19})$ group, or a —$C(R^{20})_2OC(O)A^3R^{21}$ group, wherein m represents an integer of 2 or 3, $R^{18}$ is the same as $R^{19}$, or represents a saturated alkyl group binding to $R^{19}$ to form a 3- to 6-membered ring together with the nitrogen atom or forms morpholino group together with the nitrogen atom, $R^{19}$ represents methyl group, ethyl group, or propyl group, $R^{20}$ represents hydrogen atom, methyl group, ethyl group, or propyl group, $R^{21}$ represents a lower alkyl group having 1 to 4 carbon atoms, a saturated cyclic alkyl group having 3 to 6 carbon atoms, or phenyl group, and $A^3$ represents a single bond or oxygen atom (the compound will hereinafter also referred to simply as "compound (I) of the present invention").

The present invention also provides a medicament comprising a compound represented by the aforementioned formula (I) or a pharmacologically acceptable salt thereof; and use of a compound represented by the aforementioned formula (I) or a pharmacologically acceptable salt thereof for manufacture of the medicament mentioned above.

BEST MODE FOR CARRYING OUT THE INVENTION

Symbol "n" in the aforementioned formula (I) is an integer of 1 to 3. When n is 0 or 4, the desired effect can hardly be expected, whilst the desired effect is obtained most characteristically when n is 1, 2, or 3. Methylene where n is 1, ethylene where n is 2, or trimethylene where n is 3 is preferred, and ethylene where n is 2 is particularly preferred.

The group R in the aforementioned formula (I) represents a linear or branched saturated alkyl group having 3 to 8 carbon atoms or the aforementioned group Ra or group Rb.

Examples of the linear or branched saturated alkyl group having 3 to 8 carbon atoms among the group R include propyl group, isopropyl group, butyl group, isobutyl group, 1-methylpropyl group, t-butyl group, pentyl group, isopentyl group, 2-methylbutyl group, 2,2-dimethylpropyl group, hexyl group, 4-methylpentyl group, 2,3-dimethylbutyl group, 2-ethylbutyl group, heptyl group, octyl group and the like, and butyl group, isobutyl group, and 2-ethylbutyl group are particularly preferred.

The group $R^1$ of the substituent Ra among the group R is defined as a saturated cyclic alkyl group having 3 to 7 carbon atoms or a saturated condensed cyclic alkyl group having 6 to 8 carbon atoms, which is substituted with a lower alkyl group having 1 to 4 carbon atoms or unsubstituted. Examples of the saturated cyclic alkyl group having 3 to 7 carbon atoms among the group $R^1$ include cyclopropyl group, cyclobutyl group, cyclopentyl group, cyclohexyl group, cycloheptyl group and the like, and cyclopentyl group and cyclohexyl group are particularly preferred. Cycloheptyl group is also a particularly preferred example. Examples of the saturated condensed cyclic alkyl group having 6 to 8 carbon atoms as $R^1$ include bicyclo[2,2,1] heptyl group, bicyclo[2,2,2]octyl group and the like.

Examples of the lower alkyl group having 1 to 4 carbon atoms that substitutes on $R^1$ include methyl group, ethyl group, propyl group, isopropyl group, butyl group, isobutyl group, t-butyl group and the like. Examples of $R^1$ substituted with a lower alkyl group having 1 to 4 carbon atoms include methylcyclopentyl group, methylcyclohexyl group, methylbicyclo[2,2,1]heptyl group and the like.

Symbol "k" is defined as 0 or an integer of 1 to 3. A single bond where n is 0, methylene where n is 1, and ethylene where n is 2 are preferred, and a single bond where n is 0 and methylene where n is 1 are particularly preferred.

Examples of the substituent Ra thus include cyclopropyl group, cyclobutyl group, cyclopentyl group, cyclohexyl group, cycloheptyl group, cyclopropylmethyl group, cyclobutylmethyl group, cyclopentylmethyl group, cyclohexylmethyl group, cycloheptylmethyl group, 2-cyclopentylethyl group, 2-cyclohexylethyl group, 3-cyclohexylpropyl group, 2-methylcyclopentyl group, 3-methylcyclopentyl group, 3,4-dimethylcyclopentyl group, 4-methylcyclohexyl group, 4,4-dimethylcyclohexyl group, 4-ethylcyclohexyl group, 4-methylcyclohexylmethyl group, bicyclo[2,2,1]heptane-2-methyl group, bicyclo[2,2,2] octane-2-methyl group, 3-methylbicyclo[2,2,1]heptane-2-methyl group, bicyclo[2,2,1]hept-1-ylmethyl group, bicyclo [2,2,2]oct-1-ylmethyl group and the like, cyclopentyl group, cyclohexyl group, cyclopentylmethyl group, cyclohexylmethyl group, 2-cyclopentylethyl group and 2-cyclohexylethyl group are preferred. Cyclopentyl group, cyclohexyl group, cyclopentylmethyl group, and cyclohexylmethyl group are particularly preferred. Cycloheptyl group is also a particularly preferred example.

$A^2$ in the substituent Rb among the group R is defined as a single bond, oxygen atom, sulfur atom, —S(O)—, $S(O)_2$—, or —N($R^4$)—. $R^4$ is defined as a lower alkyl group having 1 to 4 carbon atoms. Examples include methyl group, ethyl group, propyl group, isopropyl group, butyl group, isobutyl group, t-butyl group and the like, and methyl group and ethyl group are particularly preferred examples. Therefore, particularly preferred examples of $A^2$ include a single bond, oxygen atom, sulfur atom, —N(methyl)-, and —N(ethyl)-.

$A^1$ is defined as a single bond or an alkylene (a) having 1 to 3 carbon atoms, i.e., methylene, ethylene, or trimethylene. When $A^2$ represents oxygen atom, sulfur atom, —S(O)—, —S(O)$_2$—, or —N($R^4$)—, $A^1$ is ethylene or trimethylene. Alkylenes substituted with a lower alkyl group having 1 to 4 carbon atoms or phenyl group fall within the alkylene (a). Examples of the lower alkyl group having 1 to 4 carbon atoms for the above group include methyl group, ethyl group, propyl group, isopropyl group, butyl group, isobutyl group, t-butyl group and the like, and methyl group and ethyl group are preferred examples. Specific examples of $A^1$ include methylene, methylmethylene, ethylmethylene, phenylmethylene, ethylene, methylethylene, dimethylethylene, ethylethylene, phenylethylene, trimethylene, methyltrimethylene and the like. Among them, when $A^2$ represents a single bond, $A^1$ is most preferably a single bond, or methylene, methylmethylene, or ethylene. Further, when $A^2$ represents oxygen atom, sulfur atom, —S(O)—, —S(O)$_2$—, or —N($R^4$)—, $A^1$ is most preferably ethylene.

Q is defined as a monocyclic or bicyclic aryl group. The monocyclic aryl group means a substituent consisting of a carbon ring or a heteroring comprising 1 or 2 heteroatoms selected from nitrogen, oxygen, or sulfur atom, which is partially or completely unsaturated. Examples include phenyl group, thienyl group, furyl group, pyridyl group, oxazolyl group, isoxazolyl group, thiazolyl group and the like, and phenyl group, thienyl group, furyl group, pyridyl group, and oxazolyl group are preferred examples. Phenyl group is particularly preferred. Further, the bicyclic aryl group means a cyclic substituent formed by fusion of two rings selected from a carbon ring or a heterocyclic ring comprising 1 or 2 heteroatoms chosen from nitrogen, oxygen or sulfur atom, which is partially or completely unsaturated. Examples include naphthyl group, quinolyl group, isoquinolyl group, indolyl group, benzo[b]furyl group, benzo[b]thienyl group, benzimidazolyl group, benzoxazolyl group, benzothiazolyl group and the like, and naphthyl group and indolyl group are preferred examples. Examples also include indanyl group, indenyl group and the like, and an indanyl group is one of the particularly preferred examples.

In the group Rb, $R^2$ and $R^3$ are defined to both or each independently represent hydrogen atom, a linear or branched saturated alkyl group having 1 to 4 carbon atoms, phenyl group, fluorine atom, chlorine atom, bromine atom, trifluoromethyl group, —OR$^5$, —N(R$^6$)$_2$, —NHCOR$^7$, or —NHSO$_2$R$^8$. Examples of the linear or branched saturated alkyl group having 1 to 4 carbon atoms include methyl group, ethyl group, propyl group, isopropyl group, butyl group, isobutyl group, t-butyl group and the like, and methyl group is a particularly preferred example. R$^5$ and R$^8$ are each defined to be a lower alkyl group having 1 to 4 carbon atoms, and R$^6$ and R$^7$ each represent hydrogen atom or a lower alkyl group having 1 to 4 carbon atoms. Examples of the lower alkyl group having 1 to 4 carbon atoms include methyl group, ethyl group, propyl group, isopropyl group, butyl group, isobutyl group, t-butyl group and the like, and each of R$^5$ and R$^6$ most preferably represents methyl group. Preferred examples of R$^2$ and R$^3$ include hydrogen atom, methyl group, fluorine atom, chlorine atom, trifluoromethyl group, methoxy group, dimethylamino group, acetylamino group, and methanesulfonylamino group, and hydrogen atom, methyl group, fluorine atom, chlorine atom, trifluoromethyl group, methoxy group, and dimethylamino group are particularly preferred. When Q represents phenyl group, A$^1$ represents a single bond or an unsubstituted methylene, and A$^2$ represents a single bond, at least one of R$^2$ and R$^3$ preferably represents a substituent other than hydrogen atom.

Particularly preferred examples of the group Rb thus include 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group and the like. Further, indan-2-yl group is also mentioned as one of the particularly preferred examples.

The group Z in the aforementioned formula (I) is defined as hydrogen atom, fluorine atom, chlorine atom, nitro group, amino group, methyl group, or an OR$^9$ group, and R$^9$ is defined as hydrogen atom or a lower alkyl group having 1 to 4 carbon atoms such as methyl group, ethyl group, propyl group, isopropyl group, butyl group, isobutyl group, and t-butyl group. As the group Z, hydrogen atom, fluorine atom, chlorine atom, amino group, and methoxy group are preferred examples, and hydrogen atom, fluorine atom and amino group are particularly preferred examples.

Ar in the aforementioned formula (I) is defined as a substituent selected from the group consisting of condensed bicyclic substituents of ArI, ArII, ArIII, ArIV, ArV, and ArVI, which is bound at any of positions of a, b, c and d on the ring, or as a substituent selected from the group consisting of condensed bicyclic substituents of ArVII, ArVIII, ArIX, ArX, ArXI and ArXII, which is bound at any of positions of a, b and c on the ring.

The "condensed bicyclic ring" means a cyclic substituent formed by fusion of two rings selected from a carbon ring and a heterocyclic ring comprising 1 or 2 heteroatoms chosen from nitrogen, oxygen or sulfur atom, which are partially or completely unsaturated. The wording "bound at any of positions of a, b, c, and d on the ring" means that the benzene ring in the aforementioned formula (I) is bound at any one of positions of a, b, c, and d on the ring of ArI, ArII, ArIII, ArIV, ArV, or ArVI by means of a single bond. Similarly, the wording means that the benzene ring in the aforementioned formula (I) is bound at any one of positions of a, b, and c on the ring of ArVII, ArVIII, ArIX, ArX, ArXI, or ArXII by means of a single bond.

The substituent ArI among Ar is defined as a substituent in which the benzene ring in the aforementioned formula (I) is bound at position a or b on the substituent ArI by means of a single bond. Both of the binding positions are preferred, and binding at the position a is particularly preferred.

The substituent X$^1$ is defined as a group substituting at any one of 5-, 6-, 7- or 8-position on Ar. The 5-, 6-, and 7-position are preferred examples of the substituting position, and the 6-position is particularly preferred.

The substituent X$^1$ is defined as hydrogen atom, a —OR$^{10}$ group, a —NR$^{11}$R$^{12}$ group, a —SO$_2$R$^{13}$ group, or carboxyl group. Hydrogen atom and carboxyl group are preferred examples, and hydrogen atom is a particularly preferred example.

R$^{10}$ is defined as hydrogen atom, a lower alkyl group having 1 to 4 carbon atoms, or a (CH$_2$)$_i$R$^{14}$ group. Examples of the lower alkyl group having 1 to 4 carbon atoms include methyl group, ethyl group, propyl group, isopropyl group, butyl group, isobutyl group, t-butyl group and the like. Among them, methyl group is a particularly preferred example. Symbol "i" is defined as an integer of 1 to 3, methylene where i is 1 and ethylene where i is 2 are preferred, and ethylene is particularly preferred. R$^{14}$ is defined as hydroxyl group, carboxyl group, or N,N-dimethylcarbamoyl group. Each of them is a preferred example, and hydroxyl group is particularly preferred.

R$^{11}$ is defined to as hydrogen atom or a lower alkyl group having 1 to 4 carbon atoms, and hydrogen atom is a particularly preferred example. Examples of the lower alkyl group having 1 to 4 carbon atoms include methyl group, ethyl group, propyl group, isopropyl group, butyl group, isobutyl group, t-butyl group and the like, and methyl group is a particularly preferred example.

R$^{12}$ is defined as hydrogen atom, a lower alkyl group having 1 to 4 carbon atoms, 2-hydroxyethyl group, a —COR$^{15}$ group, or an SO$_2$R$^{16}$ group, and hydrogen atom and 2-hydroxyethyl group are particularly preferred examples. Examples of the lower alkyl group having 1 to 4 carbon atoms include methyl group, ethyl group, propyl group, isopropyl group, butyl group, isobutyl group, t-butyl group and the like, and methyl group is a particularly preferred example. $R^{15}$ is defined as amino group, a lower alkyl group having 1 to 4 carbon atoms, hydroxymethyl group, aminomethyl group, dimethylaminomethyl group, phenyl group, or furyl group. Among them, amino group, hydroxymethyl group, aminomethyl group, and furyl group are preferred examples. $R^{16}$ is defined as a lower alkyl group having 1 to 4 carbon atoms, amino group, methylamino group, or dimethylamino group, and dimethylamino group is a preferred example. Examples of the lower alkyl group having 1 to 4 carbon atoms include methyl group, ethyl group, propyl group, isopropyl group, butyl group, isobutyl group, t-butyl group and the like, and methyl group is a preferred example.

Examples of the —$COR^{15}$ group include carbamoyl group, acetyl group, propionyl group, 2-hydroxyacetyl group, 2-aminoacetyl group, 2-(N,N-dimethylamino)acetyl group, benzoyl group, furan-2-carboxy group and the like, and carbamoyl group, acetyl group, 2-hydroxyacetyl group, 2-aminoacetyl group, and furan-2-carboxy group are preferred examples.

Examples of the —$SO_2R^{16}$ group include methanesulfonyl group, ethanesulfonyl group, sulfamoyl group, N,N-dimethylsulfamoyl group and the like, and methanesulfonyl group, N,N-dimethylsulfamoyl group and the like are preferred examples.

$R^{13}$ is defined as a lower alkyl group having 1 to 4 carbon atoms, amino group, methylamino group, or dimethylamino group, and examples of the lower alkyl group having 1 to 4 carbon atoms include methyl group, ethyl group, propyl group, isopropyl group, butyl group, isobutyl group, t-butyl group and the like. As $R^{13}$, methyl group, amino group, methylamino group and dimethylamino group are preferred.

Preferred examples of the substituent $X^1$ include hydrogen atom, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, 2-hydroxyacetylamino group, 2-aminoacetylamino group, furan-2-carboxyamino group, methanesulfonylamino group, (N,N-dimethylsulfamoyl)amino group, methanesulfonyl group, sulfamoyl group, N-methylsulfamoyl group, N,N-dimethylsulfamoyl group, carboxyl group and the like, and hydrogen atom, hydroxyl group, methoxy group, 2-hydroxyethyloxy group, amino group, methylamino group, dimethylamino group, and 2-hydroxyethylamino group are particularly preferred examples.

Preferred examples of ArI include naphthalen-1-yl group, naphthalen-2-yl group, 5-hydroxynaphthalen-1-yl group, 5-hydroxynaphthalen-2-yl group, 6-hydroxynaphthalen-1-yl group, 6-hydroxynaphthalen-2-yl group, 7-hydroxynaphthalen-1-yl group, 7-hydroxynaphthalen-2-yl group, 5-methoxynaphthalen-1-yl group, 5-methoxynaphthalen-2-yl group, 6-methoxynaphthalen-1-yl group, 6-methoxynaphthalen-2-yl group, 7-methoxynaphthalen-1-yl group, 7-methoxynaphthalen-2-yl group, 5-(2-hydroxyethyloxy)naphthalen-2-yl group, 6-(2-hydroxyethyloxy)naphthalen-2-yl group, 7-(2-hydroxyethyloxy)naphthalen-2-yl group, 5-(carboxymethyloxy)naphthalen-2-yl group, 6-(carboxymethyloxy)naphthalen-2-yl group, 7-(carboxymethyloxy)naphthalen-2-yl group, 5-(N,N-dimethylcarbamoylmethyloxy)naphthalen-2-yl group, 6-(N,N-dimethylcarbamoylmethyloxy)naphthalen-2-yl group, 7-(N,N-dimethylcarbamoylmethyloxy)naphthalen-2-yl group, 5-aminonaphthalen-1-yl group, 5-aminonaphthalen-2-yl group, 6-aminonaphthalen-1-yl group, 6-aminonaphthalen-2-yl group, 7-aminonaphthalen-1-yl group, 7-aminonaphthalen-2-yl group, 5-(N-methylamino)naphthalen-1-yl group, 5-(N-methylamino)naphthalen-2-yl group, 6-(N-methylamino)naphthalen-1-yl group, 6-(N-methylamino)naphthalen-2-yl group, 7-(N-methylamino)naphthalen-1-yl group, 7-(N-methylamino)naphthalen-2-yl group, 5-(N,N-dimethylamino)naphthalen-1-yl group, 5-(N,N-dimethylamino)naphthalen-2-yl group, 6-(N,N-dimethylamino)naphthalen-1-yl group, 6-(N,N-dimethylamino)naphthalen-2-yl group, 7-(N,N-dimethylamino)naphthalen-1-yl group, 7-(N,N-dimethylamino)naphthalen-2-yl group, 5-(2-hydroxyethylamino)naphthalen-2-yl group, 6-(2-hydroxyethylamino)naphthalen-2-yl group, 7-(2-hydroxyethylamino)naphthalen-2-yl group, 5-acetylaminonaphthalen-2-yl group, 6-acetylaminonaphthalen-2-yl group, 6-(2-aminoacetylamino)naphthalen-2-yl group, 6-(2-hydroxyacetylamino)naphthalen-2-yl group, 7-(2-hydroxyacetylamino)naphthalen-2-yl group, 6-[(furan-2-carbonyl)amino]naphthalen-2-yl group, 7-[(furan-2-carbonyl)amino]naphthalen-2-yl group, 6-[(benzene-2-carbonyl)amino]naphthalen-2-yl group, 7-[(benzene-2-carbonyl)amino]naphthalen-2-yl group, 6-carbamoylaminonaphthalen-2-yl group, 6-methanesulfonylaminonaphthalen-2-yl group, 6-sulfamoylaminonaphthalen-2-yl group, 6-(N,N-dimethylsulfamoylamino)naphthalen-2-yl group, 6-methanesulfonylnaphthalen-2-yl group, 6-sulfamoylnaphthalen-2-yl group, 6-(N-methylsulfamoyl)naphthalen-2-yl group, 6-(N,N-dimethylsulfamoyl)naphthalen-2-yl group, 6-carboxynaphthalen-2-yl group and the like, and particularly preferred examples are naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group and the like.

The substituent ArII as Ar is defined as a substituent in which the benzene ring in the aforementioned formula (I) is bound at the position of a, b or c on the substituent ArII by means of a single bond. The substituent is preferably bound at the position of a or b, and is most preferably bound at the position of a. In the substituent ArII, W is defined as oxygen atom, sulfur atom, or $NX^8$. Particularly preferred examples are oxygen atom and sulfur atom. The substituent $X^8$ is defined as hydrogen atom, a linear or branched saturated alkyl group having 1 to 4 carbon atoms, a saturated cyclic alkyl group having 3 to 7 carbon atoms, or a $(CH_2)_jR^{17}$ group, and hydrogen atom is particularly preferred. Examples of the linear or branched saturated alkyl group having the 1 to 4 carbon atoms include methyl group, ethyl group, propyl group, isopropyl group, butyl group, isobutyl group, t-butyl group and the like, and methyl group, ethyl group and propyl group are particularly preferred. Examples of the saturated cyclic alkyl group having 3 to 7 carbon atoms include cyclopropyl group, cyclobutyl group, cyclopentyl group, cyclohexyl group, cycloheptyl group and the like. Symbol "j" in the —$(CH_2)_jR^{17}$ group is defined as an integer of 1 to 3. Methylene where j is 1 and ethylene where j is 2 are preferred, and ethylene where j is 2 is particularly preferred. $R^{17}$ is defined as hydroxyl group or carboxyl group, and the both are preferred examples. Hydroxyl group is particularly preferred.

Preferred example of W include oxygen atom, sulfur atom, NH, N-methyl, N-ethyl, N-propyl, N-(2-hydroxyethyl), N-carboxymethyl and N-(2-carboxyethyl), and among them, oxygen atom, sulfur atom, NH, N-methyl, N-ethyl, N-propyl and N-(2-hydroxyethyl) are particularly preferred examples.

The substituent $X^2$ is defined as hydrogen atom, a linear or branched saturated alkyl group having 1 to 4 carbon atoms such as methyl group, ethyl group, propyl group, isopropyl group, butyl group, isobutyl group, and t-butyl group, or as carboxyl group. Among them, hydrogen atom, methyl group, and carboxyl group are preferred examples, and hydrogen atom and methyl group are particularly preferred.

The substituent $X^3$ is defined as hydrogen atom, a linear or branched saturated alkyl group having 1 to 4 carbon atoms such as methyl group, ethyl group, propyl group, isopropyl group, butyl group, isobutyl group, and t-butyl group, acetyl group, formyl group, carboxymethyl group, or hydroxymethyl group. Among them, hydrogen atom, methyl group, acetyl group, and hydroxymethyl group are preferred examples, and hydrogen atom and methyl group are particularly preferred.

Preferred examples of the substituent ArII include benzo[b]furan-4-yl group, benzo[b]furan-5-yl group, 2-methylbenzo[b]furan-4-yl group, 2-methylbenzo[b]furan-5-yl group, 3-methylbenzo[b]furan-4-yl group, 3-methylbenzo[b]furan-5-yl group, 2,3-dimethylbenzo[b]furan-4-yl group, 2,3-dimethylbenzo[b]furan-5-yl group, 2-carboxybenzo[b]furan-4-yl group, 2-carboxybenzo[b]furan-5-yl group, 2-carboxy-3-methylbenzo[b]furan-4-yl group, 2-carboxy-3-methylbenzo[b]furan-5-yl group, 3-acetylbenzo[b]furan-4-yl group, 3-acetylbenzo[b]furan-5-yl group, 3-acetyl-2-methylbenzo[b]furan-4-yl group, 3-acetyl-2-methylbenzo[b]furan-5-yl group, 3-hydroxymethylbenzo[b]furan-4-yl group, 3-hydroxymethylbenzo[b]furan-5-yl group, 3-hydroxymethyl-2-methylbenzo[b]furan-4-yl group, 3-hydroxymethyl-2-methylbenzo[b]furan-5-yl group, benzo[b]thiophen-4-yl group, benzo[b]thiophen-5-yl group, 2-methylbenzo[b]thiophen-4-yl group, 2-methylbenzo[b]thiophen-5-yl group, 3-methylbenzo[b]thiophen-4-yl group, 3-methylbenzo[b]thiophen-5-yl group, 2,3-dimethylbenzo[b]thiophen-4-yl group, 2,3-dimethylbenzo[b]thiophen-5-yl group, 2-carboxybenzo[b]thiophen-4-yl group, 2-carboxybenzo[b]thiophen-5-yl group, 2-carboxy-3-methylbenzo[b]thiophen-4-yl group, 2-carboxy-3-methylbenzo[b]thiophen-5-yl group, 3-acetylbenzo[b]thiophen-4-yl group, 3-acetylbenzo[b]thiophen-5-yl group, 3-acetyl-2-methylbenzo[b]thiophen-4-yl group, 3-acetyl-2-methylbenzo[b]thiophen-5-yl group, 3-hydroxymethylbenzo[b]thiophen-4-yl group, 3-hydroxymethylbenzo[b]thiophen-5-yl group, 3-hydroxymethyl-2-methylbenzo[b]thiophen-4-yl group, 3-hydroxymethyl-2-methylbenzo[b]thiophen-5-yl group, 1H-indol-4-yl group, 1H-indol-5-yl group, 2-methyl-1H-indol-4-yl group, 2-methyl-1H-indol-5-yl group, 3-methyl-1H-indol-4-yl group, 3-methyl-1H-indol-5-yl group, 2,3-dimethyl-1H-indol-4-yl group, 2,3-dimethyl-1H-indol-5-yl group, 2-carboxy-1H-indol-4-yl group, 2-carboxy-1H-indol-5-yl group, 2-carboxy-3-methyl-1H-indol-4-yl group, 2-carboxy-3-methyl-1H-indol-5-yl group, 3-acetyl-1H-indol-4-yl group, 3-acetyl-1H-indol-5-yl group, 3-acetyl-2-methyl-1H-indol-4-yl group, 3-acetyl-2-methyl-1H-indol-5-yl group, 3-hydroxymethyl-1H-indol-4-yl group, 3-hydroxymethyl-1H-indol-5-yl group, 3-hydroxymethyl-2-methyl-1H-indol-4-yl group, 3-hydroxymethyl-2-methyl-1H-indol-5-yl group, 1-methyl-1H-indol-4-yl group, 1-methyl-1H-indol-5-yl group, 1,2-dimethyl-1H-indol-4-yl group, 1,2-dimethyl-1H-indol-5-yl group, 1,3-dimethyl-1H-indol-4-yl group, 1,3-dimethyl-1H-indol-5-yl group, 1,2,3-trimethyl-1H-indol-4-yl group, 1,2,3-trimethyl-1H-indol-5-yl group, 2-carboxy-1-methyl-1H-indol-4-yl group, 2-carboxy-1-methyl-1H-indol-5-yl group, 2-carboxy-1,3-dimethyl-1H-indol-4-yl group, 2-carboxy-1,3-dimethyl-1H-indol-5-yl group, 3-acetyl-1-methyl-1H-indol-4-yl group, 3-acetyl-1-methyl-1H-indol-5-yl group, 3-acetyl-1,2-dimethyl-1H-indol-4-yl group, 3-acetyl-1,2-dimethyl-1H-indol-5-yl group, 3-hydroxymethyl-1-methyl-1H-indol-4-yl group, 3-hydroxymethyl-1-methyl-1H-indol-5-yl group, 3-hydroxymethyl-1,2-dimethyl-1H-indol-4-yl group, 3-hydroxymethyl-1,2-dimethyl-1H-indol-5-yl group, 1-ethyl-1H-indol-4-yl group, 1-ethyl-1H-indol-5-yl group, 1-ethyl-2-methyl-1H-indol-4-yl group, 1-ethyl-2-methyl-1H-indol-5-yl group, 1-ethyl-3-methyl-1H-indol-4-yl group, 1-ethyl-3-methyl-1H-indol-5-yl group, 1-ethyl-2,3-dimethyl-1H-indol-4-yl group, 1-ethyl-2,3-dimethyl-1H-indol-5-yl group, 2-carboxy-1-ethyl-1H-indol-4-yl group, 2-carboxy-1-ethyl-1H-indol-5-yl group, 2-carboxy-1-ethyl-3-methyl-1H-indol-4-yl group, 2-carboxy-1-ethyl-3-methyl-1H-indol-5-yl group, 3-acetyl-1-ethyl-1H-indol-4-yl group, 3-acetyl-1-ethyl-1H-indol-5-yl group, 3-acetyl-1-ethyl-2-methyl-1H-indol-4-yl group, 3-acetyl-1-ethyl-2-methyl-1H-indol-5-yl group, 1-ethyl-3-hydroxymethyl-1H-indol-4-yl group, 1-ethyl-3-hydroxymethyl-1H-indol-5-yl group, 1-ethyl-3-hydroxymethyl-2-methyl-1H-indol-4-yl group, 1-ethyl-3-hydroxymethyl-2-methyl-1H-indol-5-yl group, 1-propyl-1H-indol-4-yl group, 1-propyl-1H-indol-5-yl group, 2-methyl-1-propyl-1H-indol-4-yl group, 2-methyl-1-propyl-1H-indol-5-yl group, 3-methyl-1-propyl-1H-indol-4-yl group, 3-methyl-1-propyl-1H-indol-5-yl group, 2,3-dimethyl-1-propyl-1H-indol-4-yl group, 2,3-dimethyl-1-propyl-1H-indol-5-yl group, 2-carboxy-1-propyl-1H-indol-4-yl group, 2-carboxy-1-propyl-1H-indol-5-yl group, 2-carboxy-3-methyl-1-propyl-1H-indol-4-yl group, 2-carboxy-3-methyl-1-propyl-1H-indol-5-yl group, 3-acetyl-1-propyl-1H-indol-4-yl group, 3-acetyl-1-propyl-1H-indol-5-yl group, 3-acetyl-2-methyl-1-propyl-1H-indol-4-yl group, 3-acetyl-2-methyl-1-propyl-1H-indol-5-yl group, 3-hydroxymethyl-1-propyl-1H-indol-4-yl group, 3-hydroxymethyl-1-propyl-1H-indol-5-yl group, 3-hydroxymethyl-2-methyl-1-propyl-1H-indol-4-yl group, 3-hydroxymethyl-2-methyl-1-propyl-1H-indol-5-yl group, 1-(2-hydroxyethyl)-1H-indol-4-yl group, 1-(2-hydroxyethyl)-1H-indol-5-yl group, 1-(2-hydroxyethyl)-2-methyl-1H-indol-4-yl group, 1-(2-hydroxyethyl)-2-methyl-1H-indol-5-yl group, 1-(2-hydroxyethyl)-3-methyl-1H-indol-4-yl group, 1-(2-hydroxyethyl)-3-methyl-1H-indol-5-yl group, 2,3-dimethyl-1-(2-hydroxyethyl)-1H-indol-4-yl group, 2,3-dimethyl-1-(2-hydroxyethyl)-1H-indol-5-yl group, 2-carboxy-1-(2-hydroxyethyl)-1H-indol-4-yl group, 2-carboxy-1-(2-hydroxyethyl)-1H-indol-5-yl group, 2-carboxy-1-(2-hydroxyethyl)-3-methyl-1H-indol-4-yl group, 2-carboxy-1-(2-hydroxyethyl)-3-methyl-1H-indol-5-yl group, 3-acetyl-1-(2-hydroxyethyl)-1H-indol-4-yl group, 3-acetyl-1-(2-hydroxyethyl)-1H-indol-5-yl group, 3-acetyl-1-(2-hydroxyethyl)-2-methyl-1H-indol-4-yl group, 3-acetyl-1-(2-hydroxyethyl)-2-methyl-1H-indol-5-yl group, 1-(2-hydroxyethyl)-3-hydroxymethyl-1H-indol-4-yl group, 1-(2-hydroxyethyl)-3-hydroxymethyl-1H-indol-5-yl group, 1-(2-hydroxyethyl)-3-hydroxymethyl-2-methyl-1H-indol-4-yl group, 1-(2-hydroxyethyl)-3-hydroxymethyl-2-methyl-1H-indol-5-yl group, 1-carboxymethyl-1H-indol-4-yl group, 1-carboxymethyl-1H-indol-5-yl group, 1-carboxymethyl-2-methyl-1H-indol-4-yl group, 1-carboxymethyl-2-methyl-1H-indol-5-yl group, 1-carboxymethyl-3-methyl-1H-indol-4-yl group, 1-carboxymethyl-3-methyl-1H-indol-5-yl group, 1-carboxymethyl-2,3-dimethyl-1H-indol-4-yl group, 1-carboxymethyl-2,3-dimethyl-1H-indol-5-yl group, 2-carboxy-1-carboxymethyl-1H-indol-4-yl group, 2-carboxy-1-carboxymethyl-1H-indol-5-yl group, 2-carboxy-1-carboxymethyl-3-methyl-1H-indol-4-yl group, 2-carboxy-1-carboxymethyl-3-methyl-1H-indol-5-yl group, 3-acetyl-1-carboxymethyl-1H-indol-4-yl group, 3-acetyl-1-carboxymethyl-1H-indol-5-yl group, 3-acetyl-1-carboxymethyl-2-methyl-1H-indol-4-yl group, 3-acetyl-1-carboxymethyl-2-methyl-1H-indol-5-yl group, 1-carboxymethyl-3-hydroxymethyl-1H-indol-4-yl group, 1-carboxymethyl-3-hydroxymethyl-1H-indol-5-yl group, 1-carboxymethyl-3-hydroxymethyl-2-methyl-1H-indol-4-yl group, 1-carboxymethyl-3-hydroxymethyl-2-methyl-1H-indol-5-yl group and the like. Particularly preferred examples are benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group and the like.

The substituent ArIII among Ar is defined as s substituent in which the benzene ring in the aforementioned formula (I) is bound at the position of a, b, or c on the substituent ArIII by means of a single bond, and the substituent is most preferably bound at the position of a.

In the substituent ArIII, the substituent $X^4$ is defined as hydrogen atom, methyl group, methoxy group, amino group, methylamino group, or dimethylamino group. All of them are preferred, and hydrogen atom, methyl group, methoxy group, and amino group are particularly preferred. Preferred examples of ArIII thus include benzothiazol-6-yl group, 2-methylbenzothiazol-6-yl group, 2-methoxybenzothiazol-6-yl group, 2-aminobenzothiazol-6-yl group, 2-(N-methylamino)benzothiazol-6-yl group, and 2-(N,N-dimethylamino)benzothiazol-6-yl group. Particularly preferred examples are benzothiazol-6-yl group, 2-methylbenzothiazol-6-yl group, 2-methoxybenzothiazol-6-yl group, and 2-aminobenzothiazol-6-yl group.

The substituent ArIV among Ar is defined as a substituent in which the benzene ring in the aforementioned formula (I) is bound at the positions of a, b, or c on the substituent ArIV by means of a single bound, and the substituent is most preferably bound at the position of a.

The substituent $X^5$ in the substituent ArIV is defined as hydrogen atom or methyl group, and the both are particularly preferred. The group $X^6$ is defined as oxygen atom, sulfur atom, NH, or N-methyl group. All of them are preferred, and oxygen atom and sulfur atom are particularly preferred. Preferred examples of ArIV include 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, 2-imino-3-methyl-2,3-dihydrobenzothiazol-6-yl group, and 3-methyl-2-(methylimino)-2,3-dihydrobenzothiazol-6-yl group. Particularly preferred examples are 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, and 2-thioxo-3-methyl-2,3-dihydrobenzothiazol-6-yl group.

The substituent ArV among Ar is defined as a substituent in which the benzene ring in the aforementioned formula (I) is bound at the position of a, b, c, or d on the substituent ArV by means of a single bond, and the substituent is most preferably bound at the position of a or d.

The substituent $X^7$ in the substituent ArV is defined as hydrogen atom or methyl group, and the both are preferred. Hydrogen atom is particularly preferred. Preferred examples of ArV thus include quinolin-3-yl group, 2-methylquinolin-3-yl group, quinolin-6-yl group, and 2-methylquinolin-6-yl group, and quinolin-3-yl group and quinolin-6-yl group are particularly preferred examples.

The substituent ArVI among Ar is defined as a substituent in which the benzene ring in the aforementioned formula (I) is bound at the position of a or b on the substituent ArVI by means of a single bond, and the substituent is particularly preferably bound at the position of a.

Particularly preferred example of ArVI is 2-oxo-1,2-dihydroquinolin-6-yl group.

The substituent ArVII among Ar is defined as a substituent in which the benzene ring in the aforementioned formula (I) is bound at the position of a, b, or c on the substituent ArVII by means of a single bond, and the substituent is most preferably bound at the position of a.

M in the substituent ArVII is defined as sulfur atom or $NX^8$. The substituent $X^8$ has the same meaning as that explained above.

Preferred examples of M include sulfur atom, NH, N-methyl, N-ethyl, N-propyl, N-(2-hydroxyethyl), N-carboxymethyl and the like, and among them, sulfur atom, NH, N-methyl, N-ethyl, N-propyl, N-(2-hydroxyethyl) and the like are particularly preferred examples.

The substituent $X^{10}$ is defined as hydrogen atom, a linear or branched saturated alkyl group having 1 to 4 carbon atoms such as methyl group, ethyl group, propyl group, isopropyl group, butyl group, isobutyl group, and t-butyl group, acetyl group, formyl group, or a group $—OR^{22}$. The substituent $X^{22}$ is defined as hydrogen atom or a linear or branched saturated alkyl group having 1 to 4 carbon atoms such as methyl group, ethyl group, propyl group, isopropyl group, butyl group, isobutyl group, and t-butyl group. However, when M in the substituent ArVII represents sulfur atom, the substituent $X^{10}$ is defined as hydrogen atom or a linear or branched saturated alkyl group having 1 to 4 carbon atoms such as methyl group, ethyl group, propyl group, isopropyl group, butyl group, isobutyl group, and t-butyl group. Hydrogen atom and methyl group are preferred examples of the substituent $X^{10}$, and hydrogen atom is a particularly preferred example.

Preferred example of the substituents ArVII include benzo[d]isothiazol-5-yl group, 3-methylbenzo[d]isothiazol-5-yl group, 1H-indazol-5-yl group, 3-methyl-1H-indazol-5-yl group, 1-methyl-1H-indazol-5-yl group, 1,3-dimethyl-1H-indazol-5-yl group, 1-ethyl-1H-indazol-5-yl group, 1-ethyl-3-methyl-1H-indazol-5-yl group, 1-propyl-1H-indazol-5-yl group, 3-methyl-1-propyl-1H-indazol-5-yl group, 1-(2-hydroxyethyl)-1H-indazol-5-yl group, 1-(2-hydroxyethyl)-3-methyl-1H-indazol-5-yl group, 1-(carboxymethyl)-1H-indazol-5-yl group, 1-(carboxymethyl)-3-methyl-1H-indazol-5-yl group and the like. Particularly preferred examples are benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group and the like.

The substituent ArVIII among Ar is defined as a substituent in which the benzene ring in the aforementioned formula (I) is bound at the position of a, b, or c on the substituent ArVIII by means of a single bond, and the substituent is preferably bound at the position of a. M and the substituent $X^8$ have the same meanings as those explained above. The substituent $X^{11}$ is defined as hydrogen atom or a linear or branched saturated alkyl group having 1 to 4 carbon atoms such as methyl group, ethyl group, propyl group, isopropyl group, butyl group, isobutyl group, and t-butyl group. Preferred examples of the substituent $X^{11}$ are hydrogen atom and methyl group, and hydrogen atom is a particularly preferred example.

Preferred examples of the substituent ArVIII include benzo[c]isothiazol-5-yl group, 3-methylbenzo[c]isothiazol-5-yl group, 2-methyl-2H-indazol-5-yl group, 2,3-dimethyl-2H-indazol-5-yl group, 2-ethyl-2H-indazol-5-yl group, 2-ethyl-3-methyl-2H-indazol-5-yl group, 2-propyl-2H-indazol-5-yl group, 3-methyl-2-propyl-2H-indazol-5-yl group, 2-(2-hydroxyethyl)-2H-indazol-5-yl group, 2-(2-hydroxyethyl)-3-methyl-2H-indazol-5-yl group, 2-(carboxymethyl)-2H-indazol-5-yl group, 2-(carboxymethyl)-3-methyl-2H-indazol-5-yl group and the like.

The substituent ArIX among Ar is defined as a substituent in which the benzene ring in the aforementioned formula (I) is bound at the position of a on the substituent ArIX by means of a single bond, and the substituent is most preferably bound at this position. The substituent $X^{11}$ has the same meaning as that explained above. The substituent $X^{12}$ is defined as hydrogen atom or a linear or branched saturated alkyl group having 1 to 4 carbon atoms such as or methyl group, ethyl group, propyl group, isopropyl group, butyl group, isobutyl group, and t-butyl group, or as carboxyl group. Hydrogen atom and methyl group are preferred examples of the substituent $X^{12}$, and hydrogen atom is a particularly preferred example.

Preferred examples of the substituents ArIX thus include imidazo[1,2-a]pyridin-6-yl group, 2-methyl-imidazo[1,2-a]pyridin-6-yl group, 3-methyl-imidazo[1,2-a]pyridin-6-yl group, 2,3-dimethyl-imidazo[1,2-a]pyridin-6-yl group and the like, and imidazo[1,2-a]pyridin-6-yl group is a particularly preferred example.

The substituent ArX among Ar is defined as a substituent in which the benzene ring in the aforementioned formula (I) is bound at the position of a on the substituent ArX by means of a single bond, and the substituent is most preferably bound at this position. The substituents $X^8$, $X^{11}$ and $X^{12}$ have the same meanings as those explained above.

Preferred examples of the substituents ArX include 1H-pyrrolo[2,3-b]pyridin-5-yl group, 2-methyl-1H-pyrrolo[2,3-b]pyridin-5-yl group, 3-methyl-1H-pyrrolo[2,3-b]pyridin-5-yl group, 1-methyl-1H-pyrrolo[2,3-b]pyridin-5-yl group, 1,2-dimethyl-1H-pyrrolo[2,3-b]pyridin-5-yl group, 1,3-dimethyl-1H-pyrrolo[2,3-b]pyridin-5-yl group, 2,3-dimethyl-1H-pyrrolo[2,3-b]pyridin-5-yl group, 1,2,3-trimethyl-1H-pyrrolo[2,3-b]pyridin-5-yl group, 1-ethyl-1H-pyrrolo[2,3-b]pyridin-5-yl group, 1-ethyl-2-methyl-1H-pyrrolo[2,3-b]pyridin-5-yl group, 1-ethyl-3-methyl-1H-pyrrolo[2,3-b]pyridin-5-yl group, 1-ethyl-2,3-dimethyl-1H-pyrrolo[2,3-b]pyridin-5-yl group, 1-propyl-1H-pyrrolo[2,3-b]pyridin-5-yl group, 2-methyl-1-propyl-1H-pyrrolo[2,3-b]pyridin-5-yl group, 3-methyl-1-propyl-1H-pyrrolo[2,3-b]pyridin-5-yl group, 2,3-dimethyl-1-propyl-1H-pyrrolo[2,3-b]pyridin-5-yl group, 1-(2-hydroxyethyl)-1H-pyrrolo[2,3-b]pyridin-5-yl group, 1-(2-hydroxyethyl)-2-methyl-1H-pyrrolo[2,3-b]pyridin-5-yl group, 1-(2-hydroxyethyl)-3-methyl-1H-pyrrolo[2,3-b]pyridin-5-yl group, 2,3-dimethyl-1-(2-hydroxyethyl)-1H-pyrrolo[2,3-b]pyridin-5-yl group, 1-(carboxymethyl)-1H-pyrrolo[2,3-b]pyridin-5-yl group, 1-(carboxymethyl)-2-methyl-1H-pyrrolo[2,3-b]pyridin-5-yl group, 1-(carboxymethyl)-3-methyl-1H-pyrrolo[2,3-b]pyridin-5-yl group, 1-(carboxymethyl)-2,3-dimethyl-1H-pyrrolo[2,3-b]pyridin-5-yl group and the like. Particularly preferred examples are 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group and the like.

The substituent ArXI among Ar is defined as a substituent in which the benzene ring in the aforementioned formula (I) is bound at the position of a, b, or c on the substituent ArXI by means of a single bond, and the substituent is most preferably bound at the position of a.

The substituent $X^7$ in the substituent ArXI has the same meaning as that explained above. Preferred example of ArXI include isoquinolin-6-yl group and 1-methylisoquinolin-6-yl group, and isoquinolin-6-yl group is a particularly preferred example.

The substituent ArXII among Ar is defined as a substituent in which the benzene ring in the aforementioned formula (I) is bound at the position of a or b on the substituent ArXII by means of a single bond, and the substituent is most preferably bound at the position of a.

A particularly preferred example of ArXII is 1-oxo-1,2-dihydroisoquinolin-6-yl group.

The group Y in the aforementioned formula (I) is defined as hydrogen atom, a lower alkyl group having 1 to 4 carbon atoms, a —$(CH_2)_m NR^{18}R^{19}$ group, or a $C(R^{20})_2 OC(O) A^3 R^{21}$ group, and hydrogen atom is a particularly preferred example among them.

Examples of the lower alkyl group having 1 to 4 carbon atoms include methyl group, ethyl group, propyl group, isopropyl group, butyl group, isobutyl group, t-butyl group and the like. Among them, methyl group and ethyl group are preferred examples.

Symbol "m" in the substituent —$(CH_2)_m NR^{18}R^{19}$ is defined as an integer of 2 or 3. $R^{18}$ is the same as $R^{19}$, or $R^{18}$ represents a saturated alkyl group that binds to $R^{19}$ to form a 3- to 6-membered ring together with the nitrogen atom, or forms morpholino group together with the nitrogen atom. $R^{19}$ is defined as methyl group, ethyl group, or propyl group. Examples of the substituent —$(CH_2)_m NR^{18}R^{19}$ include 2-(N,N-dimethylamino)ethyl group, 2-(N,N-diethylamino)ethyl group, 2-(N,N-dipropylamino)ethyl group, 3-(N,N-dimethylamino)propyl group, 3-(N,N-diethylamino)propyl group, 2-(N,N-dipropylamino)propyl group, 2-pyrrolidin-1-ylethyl group, 2-piperidin-1-ylethyl group, 2-morpholin-4-ylethyl group, 3-pyrrolidin-1-ylpropyl group, 3-piperidin-1-ylpropyl group, 3-morpholin-4-ylpropyl group and the like.

$R^{20}$ in the —C($R^{20}$)$_2$OC(O)$A^3R^{21}$ group is defined as hydrogen atom, methyl group, ethyl group, or propyl group. $R^{21}$ is defined as a lower alkyl group having 1 to 4 carbon atoms, a saturated cyclic alkyl group having 3 to 6 carbon atoms, or phenyl group. Examples of the lower alkyl group having 1 to 4 carbon atoms include methyl group, ethyl group, propyl group, isopropyl group, butyl group, isobutyl group, t-butyl group and the like, and examples of the saturated cyclic alkyl group having 3 to 6 carbon atoms include cyclopropyl group, cyclobutyl group, cyclopentyl group, and cyclohexyl group. $A^3$ is defined as a single bond or oxygen atom. Examples of the —C($R^{20}$)$_2$OC(O)$A^3R^{21}$ group include acetoxymethyl group, propionyloxymethyl group, butyryloxymethyl group, (2-methylpropionyl) oxymethyl group, (2,2-dimethylpropionyl) oxymethyl group, cyclopropionyloxymethyl group, cyclopentanoyloxymethyl group, cyclohexanoyloxymethyl group, phenylcarboxymethyl group, 1-acetoxy-1-methylethyl group, 1-methyl-1-(2-methylpropionyloxy)ethyl group, 1-cyclopentanoyloxy-1-methylethyl group, 1-cyclohexanoyloxy-1-methylethyl group, methoxycarbonyloxymethyl group, ethoxycarbonyloxymethyl group, isopropyloxycarbonyloxymethyl group, t-butyloxycarbonyloxymethyl group, cyclopropyloxycarbonyloxymethyl group, cyclopentyloxycarbonyloxymethyl group, cyclohexyloxycarbonyloxymethyl group, phenyloxycarbonyloxymethyl group, 1-methoxycarbonyloxy-1-methylethyl group, 1-ethoxycarbonyloxy-1-methylethyl group, 1-isopropyloxycarbonyloxy-1-methylethyl group, 1-t-butyloxycarbonyloxy-1-methylethyl group, 1-cyclopropyloxycarbonyloxy-1-methylethyl group, 1-cyclopentyloxycarbonyloxy-1-methylethyl group, 1-cyclohexyloxycarbonyloxy-1-methylethyl group, 1-methyl-1-phenyloxycarbonyloxyethyl group and the like.

According to preferred embodiments of the present invention, the compounds represented by the formula (I) or salts thereof satisfy all of the following conditions: n represents an integer of 1 to 3; R represents butyl group, isobutyl group, 2-ethylbutyl group, cyclopentyl group, cyclohexyl group, cyclopentylmethyl group, cyclohexylmethyl group, 2-cyclopentylethyl group, 2-cyclohexylethyl group, or the group Rb; Q in the group Rb represents phenyl group, thienyl group, furyl group, pyridyl group, oxazolyl group, naphthyl group, or indolyl group; $A^1$ represents a single bond or represents methylene, methyl methylene, or ethylene; $A^2$ represents a single bond, oxygen atom, sulfur atom, —N(methyl)- or —N(ethyl)- (wherein, when $A^2$ represents oxygen atom, sulfur atom, —N(methyl)-, or —N(ethyl)-, $A^1$ represents ethylene); either or both of $R^2$ and $R^3$ independently represent hydrogen atom, methyl group, fluorine atom, chlorine atom, trifluoromethyl group, methoxy group, dimethylamino group, acetylamino group, or methanesulfonylamino group (wherein, when Q represents phenyl group, $A^1$ represents a single bond or unsubstituted methylene, and $A^2$ represents a single bond, one of $R^2$ and $R^3$ represents the substituent other than hydrogen atom); Z represents hydrogen atom, fluorine atom, chlorine atom, amino group, or methoxy group; the substituent Ar represents a substituent selected from the group consisting of condensed bicyclic substituents of ArI, ArII, ArIII, ArIV, ArV, and ArVI, which bind at any one of the positions of a, b, and d; the substituent $X^1$ in the group ArI is a group substituted at the 5-, 6- or 7-position on the group ArI, and represents hydrogen atom, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, 2-hydroxyacetylamino group, 2-aminoacetylamino group, furan-2-carboxyamino group, methanesulfonyl amino group, N,N-dimethylsulfamoylamino group, methanesulfonyl group, sulfamoyl group, N-methylsulfamoyl group, N,N-dimethylsulfamoyl group or carboxyl group; W in the group ArII represents oxygen atom, sulfur atom, NH, N-methyl, N-ethyl, N-propyl, N-(2-hydroxyethyl), N-carboxymethyl or N-(2-carboxyethyl); the substituent $X^2$ represents hydrogen atom, methyl group, or carboxyl group; the substituent $X^3$ represents hydrogen atom, methyl group, acetyl group, or hydroxymethyl group; the substituent $X^4$ in the group ArIII represents hydrogen atom, methyl group, methoxy group, amino group, methylamino group, or dimethylamino group; in the group ArIV, the substituent $X^5$ represents hydrogen atom or methyl group, and $X^6$ represents oxygen atom, sulfur atom, NH, or N-methyl group; the substituent $X^7$ in the group ArV represents hydrogen atom or methyl group; and the group Y represents hydrogen atom, methyl group or ethyl group.

According to further preferred embodiments of the present invention, the compounds represented by the formula (I) or salts thereof satisfy all of the following conditions: n represents an integer of 1 to 3; R represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, 2-cyclohexylethyl group, or the group Rb; Q in the group Rb represents phenyl group, thienyl group, furyl group, pyridyl group, oxazolyl group, naphthyl group, indolyl group, or indanyl group; $A^1$ represents a single bond or methylene, methyl methylene, or ethylene; $A^2$ represents a single bond, oxygen atom, sulfur atom, —N(methyl)- or —N(ethyl)- (wherein, when $A^2$ represents oxygen atom, sulfur atom, —N(methyl)-, or —N(ethyl)-, $A^1$ represents ethylene); either or both of $R^2$ and $R^3$ independently represent hydrogen atom, methyl group, fluorine atom, chlorine atom, trifluoromethyl group, methoxy group, dimethylamino group, acetylamino group, or methanesulfonylamino group (wherein, when Q represents phenyl group, $A^1$ represents a single bond or unsubstituted methylene, and $A^2$ represents a single bond, one of $R^2$ and $R^3$ represents the substituent other than hydrogen atom); Z represents hydrogen atom, fluorine atom, chlorine atom, amino group, or methoxy group; the substituent Ar represents a substituent selected from the group consisting of condensed bicyclic substituents of ArVII, ArVIII, ArIX, ArX, ArXI, and ArXII, which binds at the position of a on the rings; M in the groups ArVII and ArVIII represents sulfur atom or $NX^8$; the substituent $X^8$ represents hydrogen atom, methyl group, ethyl group, propyl group, 2-hydroxyethyl group, or carboxymethyl group; each or all of the substituents $X^{10}$, $X^{11}$, and $X^{12}$ independently represent hydrogen atom or methyl group; the substituent $X^7$ in the group ArXIa represents hydrogen atom; and the group Y represents hydrogen atom, methyl group or ethyl group.

According to most preferred embodiments of the present invention, the compounds represented by the formula (I) or salts thereof satisfy all of the following conditions: n represents an integer of 2; R represents butyl group, isobutyl group, 2-ethylbutyl group, cyclopentyl group, cyclohexyl group, cyclopentylmethyl group, cyclohexylmethyl group, or the group Rb; Q in the group Rb represents phenyl group; $A^1$ represents a single bond, or methylene, methylmethylene, or ethylene; $A^2$ represents a single bond, oxygen atom, sulfur atom, —N(methyl)-, or —N(ethyl)-

(wherein, when $A^2$ represents oxygen atom, sulfur atom, —N(methyl)-, or —N(ethyl)-, $A^1$ represents ethylene); each or both of $R^2$ and $R^3$ independently represent hydrogen atom, methyl group, fluorine atom, chlorine atom, trifluoromethyl group, methoxy group, or dimethylamino group (wherein, when $A^1$ represents a single bond or unsubstituted methylene, and $A^2$ represents a single bond, one of $R^2$ and $R^3$ represents the substituent other than hydrogen atom); Z represents hydrogen atom, fluorine atom or amino group; the substituent Ar represents a substituent selected from the group consisting of condensed bicyclic substituents ArI, ArII, ArIII, ArIV, ArV, and ArVI, which binds at the position of a or d on the rings; the substituent $X^1$ in the group ArI is a group substituting at the 6-position on the group ArI and represents hydrogen atom, hydroxyl group, methoxy group, 2-hydroxyethyloxy group, amino group, methylamino group, dimethylamino group, or 2-hydroxyethylamino group; W in the group ArII represents oxygen atom, sulfur atom, NH, N-methyl, N-ethyl, N-propyl, or N-(2-hydroxyethyl); each or both of the substituent $X^2$ and substituent $X^3$ independently represent hydrogen atom or methyl group; the substituent $X^4$ in the group ArIII represents hydrogen atom, methyl group, methoxy group, or amino group; in the group ArIV, the substituent $X^5$ represents hydrogen atom or methyl group, and $X^6$ represents oxygen atom or sulfur atom; the substituent $X^7$ in the group ArV represents hydrogen atom; and the group Y represents hydrogen atom.

Further, according to another class of particularly preferred embodiments of the present invention, the compounds represented by the formula (I) or salts thereof satisfy all of the following conditions: n represents an integer of 2; R represents butyl group, isobutyl group, 2-ethylbutyl group, cyclopentyl group, cyclohexyl group, cycloheptyl group, cyclopentylmethyl group, cyclohexylmethyl group, indan-2-yl group or the group Rb; Q in the group Rb represents phenyl group; $A^1$ represents a single bond or methylene, methylmethylene, or ethylene; $A^2$ represents a single bond, oxygen atom, sulfur atom, —N(methyl)-, or —N(ethyl)- (wherein, when $A^2$ represents oxygen atom, sulfur atom, —N(methyl)-, or —N(ethyl)-, $A^1$ represents ethylene); each or both of $R^2$ and $R^3$ independently represent hydrogen atom, methyl group, fluorine atom, chlorine atom, trifluoromethyl group, methoxy group, or dimethylamino group (wherein, when $A^1$ represents a single bond or unsubstituted methylene, and $A^2$ represents a single bond, one of $R^2$ and $R^3$ represents a substituent other than hydrogen atom); Z represents hydrogen atom, fluorine atom, or amino group; the substituent Ar represents a substituent selected from the group consisting of condensed bicyclic substituents of ArVII, ArIX, ArX, ArXI, and ArXII, which binds at the position of a on the ring; M in the group ArVII represents sulfur atom, NH, N-methyl, N-ethyl, N-propyl, or N-(2-hydroxyethyl); the substituent $X^8$ represents hydrogen atom, methyl group, ethyl group, propyl group, or 2-hydroxyethyl group; the substituents $X^7$, $X^{10}$, $X^{11}$, and $X^{12}$ represent hydrogen atom; and the group Y represents hydrogen atom.

According to particularly preferred embodiments of the present invention, all of the following conditions are satisfied in the formula (I): n represents an integer of 2; R represents butyl group, isobutyl group, 2-ethylbutyl group, cyclopentyl group, cyclohexyl group, cyclopentylmethyl group, cyclohexylmethyl group, indan-2-yl group, or the group Rb; Q in the group Rb represents phenyl group; $A^1$ represents a single bond, or represents methylene, methylmethylene, or ethylene; $A^2$ represents a single bond, oxygen atom, sulfur atom, —N(methyl)-, or —N(ethyl)- (wherein, when $A^2$ represents oxygen atom, sulfur atom, —N(methyl)-, or —N(ethyl)-, $A^1$ represents ethylene); each or both of $R^2$ and $R^3$ independently represent hydrogen atom, methyl group, fluorine atom, chlorine atom, trifluoromethyl group, methoxy group, or dimethylamino group (wherein, when $A^1$ represents a single bond or unsubstituted methylene, and $A^2$ represents a single bond, one of $R^2$ and $R^3$ represents a substituent other than hydrogen atom); Z represents hydrogen atom, fluorine atom or amino group; the substituent Ar represents a substituent selected from the group consisting of condensed bicyclic substituents of ArI, ArII, ArIII, ArIV, ArV, ArVI, ArVII, ArIX, ArX, ArXI, and ArXII, which binds at the position of a or d on the ring; the substituent $X^1$ in the group ArI is a group substituting at the 6-position on the group ArI, and represents hydrogen atom, hydroxyl group, methoxy group, 2-hydroxyethyloxy group, amino group, methylamino group, dimethylamino group, or 2-hydroxyethylamino group; W in the group ArII represents oxygen atom, sulfur atom, NH, N-methyl, N-ethyl, N-propyl, or N-(2-hydroxyethyl); each or both of the substituent $X^2$ and substituent $X^3$ independently represent hydrogen atom or methyl group; the substituent $X^4$ in the group ArIII represents hydrogen atom, methyl group, methoxy group, or amino group; in the group ArIVa, the substituent $X^5$ represents hydrogen atom or methyl group, and $X^6$ represents oxygen atom or sulfur atom; the substituent $X^7$ in the groups ArV and ArXI represents hydrogen atom; M in the group ArVII represents sulfur atom, NH, N-methyl, N-ethyl, N-propyl, or N-(2-hydroxyethyl); the substituent $X^8$ represents hydrogen atom, methyl group, ethyl group, propyl group, or 2-hydroxyethyl group; the substituents $X^{10}$, $X^{11}$, and $X^{12}$ represent hydrogen atom; and the group Y represents hydrogen atom.

Further, particularly preferred specific compounds of the present invention or salts thereof satisfy all of the following conditions in the formula (I): n represents an integer of 2; R represents butyl group, isobutyl group, 2-ethylbutyl group, cyclopentyl group, cyclohexyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group or 2-(N-ethyl-N-phenylamino)ethyl group; Z represents hydrogen atom, fluorine atom or amino group; the substituent Ar represents naphthalen-2-yl group, 6-hydroxynaphthalen-2-yl group, 6-methoxynaphthalen-2-yl group, 6-(2-hydroxyethyloxy) naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, or 2-oxo-1,2-dihydroquinolin-6-yl group; and the group Y represents hydrogen atom.

Further, other particularly preferred specific compounds of the present invention or salts thereof satisfy all of the following conditions in the formula (I): n represents an integer of 2; R represents butyl group, isobutyl group, 2-ethylbutyl group, cyclopentyl group, cyclohexyl group, cycloheptyl group, cyclopentylmethyl group, cyclohexylmethyl group, indan-2-yl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl) phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl) ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group or 2-(N-ethyl-N-phenylamino)ethyl group; Z represents hydrogen atom, fluorine atom or amino group; the substituent Ar represents benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, or 1-oxo-1,2-dihydroisoquinolin-6-yl group; and the group Y represents hydrogen atom.

Further, the most preferred specific compounds of the present invention represented or salts thereof satisfy all of the following conditions in the formula (I): n represents an integer of 2; R represents butyl group, isobutyl group, 2-ethylbutyl group, cyclopentyl group, cyclohexyl group, cycloheptyl group, cyclopentylmethyl group, cyclohexylmethyl group, indan-2-yl group, 1-phenylethyl group, 1-(4-fluorophenyl)ethyl group, 1-(4-chlorophenyl)ethyl group, 4-methylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 4-(trifluoromethyl) phenylmethyl group, 2-(2-methylphenyl)ethyl group, 2-(4-methylphenyl)ethyl group, 2-(2-methoxyphenyl)ethyl group, 2-(2-fluorophenyl)ethyl group, 2-(3-fluorophenyl) ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(4-chlorophenyloxy)ethyl group or 2-(N-phenyl-N-methylamino)ethyl group; Z represents hydrogen atom, fluorine atom or amino group; the substituent Ar represents naphthalen-2-yl group, 6-hydroxynaphthalen-2-yl group, 6-methoxynaphthalen-2-yl group, 6-aminonaphthalen-2-yl group, 6-(N-methylamino)naphthalen-2-yl group, 6-(N,N-dimethylamino)naphthalen-2-yl group, benzo[b]furan-5-yl group, benzo[b]thiophen-5-yl group, 1H-indol-5-yl group, 1-methyl-1H-indol-5-yl group, 1-ethyl-1H-indol-5-yl group, benzothiazol-6-yl group, 2-aminobenzothiazol-6-yl group, quinolin-3-yl group, quinolin-6-yl group, 2-oxo-1,2-dihydro quinolin-6-yl group, benzo[d]isothiazol-5-yl group, 1H-indazol-5-yl group, 1-methyl-1H-indazol-5-yl group, 1-ethyl-1H-indazol-5-yl group, imidazo[1,2-a]pyridin-6-yl group, 1H-pyrrolo[2,3-b]pyridin-5-yl group, 1-methyl-1H- pyrrolo[2,3-b]pyridin-5-yl group, 1-ethyl-1H-pyrrolo[2,3-b]pyridin-5-yl group, isoquinolin-6-yl group, or 1-oxo-1,2-dihydroisoquinolin-6-yl group; and the group Y represents hydrogen atom.

The compounds (I) of the present invention may have one or more asymmetric carbons depending on types of substituents. For example, where the group R contains one or more asymmetric carbons, two kinds of optical isomers exist when the number of asymmetric carbon is 1, and when the number of asymmetric carbons is 2, four kinds of optical isomers and two kinds of diastereomers exist. Pure stereoisomers including optical isomers and diastereoisomers, any mixtures, racemates and the like of stereoisomers all fall within the scope of the present invention. Further, the compounds (I) of the present invention may exist as geometrical isomers based on a cycloalkyl ring structure, and any geometrical isomers in pure forms and any mixtures of geometrical isomers also fall within the scope of the present invention. Mixtures such as racemates may sometimes be preferred from a viewpoint of easiness for manufacture.

Specific examples of the compounds (I) of the present invention include the following compounds:

methyl 3-[4-cyclohexylmethyloxy-3-(6-hydroxynaphthalen-2-yl)phenyl]propionate;

3-[4-cyclohexylmethyloxy-3-(6-hydroxynaphthalen-2-yl)phenyl]propionic acid;

methyl 3-[4-cyclopentylmethyloxy-3-(6-hydroxynaphthalen-2-yl)phenyl]propionate;

3-[4-cyclopentylmethyloxy-3-(6-hydroxynaphthalen-2-yl)phenyl]propionic acid;

methyl 3-{4-[2-(2-fluorophenyl)ethyloxy]-3-(6-hydroxynaphthalen-2-yl)phenyl}propionate;

3-{4-[2-(2-fluorophenyl)ethyloxy]-3-(6-hydroxynaphthalen-2-yl)phenyl}propionic acid;

methyl 3-[4-cyclopentylmethyloxy-3-(7-hydroxynaphthalen-2-yl)phenyl]propionate;

3-[4-cyclopentylmethyloxy-3-(7-hydroxynaphthalen-2-yl)phenyl]propionic acid;

methyl 3-[4-cyclopentylmethyloxy-3-(5-hydroxynaphthalen-2-yl)phenyl]propionate;

3-[4-cyclopentylmethyloxy-3-(5-hydroxynaphthalen-2-yl)phenyl]propionic acid;

methyl 3-[3-(6-aminonaphthalen-2-yl)-4-cyclopentylmethyloxyphenyl]propionate;

3-[3-(6-aminonaphthalen-2-yl)-4-cyclopentylmethyloxyphenyl]propionic acid;

methyl 3-[3-(7-aminonaphthalen-2-yl)-4-cyclopentylmethyloxyphenyl]propionate;

3-[3-(7-aminonaphthalen-2-yl)-4-cyclopentylmethyloxyphenyl]propionic acid;

methyl 3-{4-cyclopentylmethyloxy-3-[6-(N-methylamino)naphthalen-2-yl]phenyl}-propionate;

3-{4-cyclopentylmethyloxy-3-[6-(N-methylamino)naphthalen-2-yl]phenyl}propionic acid;

methyl 3-{4-cyclopentylmethyloxy-3-[6-(N,N-dimethylamino)naphthalen-2-yl]phenyl}-propionate;

3-{4-cyclopentylmethyloxy-3-[6-(N,N-dimethylamino)naphthalen-2-yl]phenyl}-propionic acid;

methyl 3-[4-cyclopentylmethyloxy-3-(6-sulfamoylaminonaphthalen-2-yl)phenyl]-propionate;

3-[4-cyclopentylmethyloxy-3-(6-sulfamoylaminonaphthalen-2-yl)phenyl]propionic acid;

methyl 3-[4-cyclopentylmethyloxy-3-(6-methanesulfonylnaphthalen-2-yl)phenyl]-propionate;

3-[4-cyclopentylmethyloxy-3-(6-methanesulfonylnaphthalen-2-yl)phenyl]propionic acid;

methyl 3-[4-cyclopentylmethyloxy-3-(6-sulfamoylnaphthalen-2-yl)phenyl]propionate;

3-[4-cyclopentylmethyloxy-3-(6-sulfamoylnaphthalen-2-yl)phenyl]propionic acid;

methyl 3-{4-cyclopentylmethyloxy-3-[6-(N-methylsulfamoyl)naphthalen-2-yl]phenyl}-propionate;

3-{4-cyclopentylmethyloxy-3-[6-(N-methylsulfamoyl)naphthalen-2-yl]phenyl}propionic acid;

methyl 3-{4-cyclopentylmethyloxy-3-[6-(N,N-dimethylsulfamoyl)naphthalen-2-yl]-phenyl}propionate;

3-{4-cyclopentylmethyloxy-3-[6-(N,N-dimethylsulfamoyl)naphthalen-2-yl]phenyl}-propionic acid;

3-[3-(6-carboxynaphthalen-2-yl)-4-cyclohexylmethyloxyphenyl]propionic acid;

methyl 3-[4-(2-fluorophenylmethyloxy)-3-(naphthalen-2-yl)phenyl]propionate;

3-[4-(2-fluorophenylmethyloxy)-3-(naphthalen-2-yl)phenyl]propionic acid;

methyl 3-[4-(3-fluorophenylmethyloxy)-3-(naphthalen-2-yl)phenyl]propionate;

3-[4-(3-fluorophenylmethyloxy)-3-(naphthalen-2-yl)phenyl]propionic acid;

methyl 3-[4-(4-fluorophenylmethyloxy)-3-(naphthalen-2-yl)phenyl]propionate;

3-[4-(4-fluorophenylmethyloxy)-3-(naphthalen-2-yl)phenyl]propionic acid;

methyl 3-[4-butyloxy-3-(naphthalen-2-yl)phenyl]propionate;

3-[4-butyloxy-3-(naphthalen-2-yl)phenyl]propionic acid;

methyl 3-[4-cyclopentylmethyloxy-3-(naphthalen-2-yl)phenyl]propionate;

3-[4-cyclopentylmethyloxy-3-(naphthalen-2-yl)phenyl]propionic acid;

methyl 3-[4-isopropyloxy-3-(naphthalen-2-yl)phenyl]propionate;

3-[4-isopropyloxy-3-(naphthalen-2-yl)phenyl]propionic acid;

methyl 3-[4-cyclopentyloxy-3-(naphthalen-2-yl)phenyl]propionate;

3-[4-cyclopentyloxy-3-(naphthalen-2-yl)phenyl]propionic acid;

methyl 3-[4-cyclohexyloxy-3-(naphthalen-2-yl)phenyl]propionate;

3-[4-cyclohexyloxy-3-(naphthalen-2-yl)phenyl]propionic acid;

methyl 3-[4-(2-cyclopentylethyloxy)-3-(naphthalen-2-yl)phenyl]propionate;

3-[4-(2-cyclopentylethyloxy)-3-(naphthalen-2-yl)phenyl]propionic acid;

methyl 3-[4-(2-cyclohexylethyloxy)-3-(naphthalen-2-yl)phenyl]propionate;

3-[4-(2-cyclohexylethyloxy)-3-(naphthalen-2-yl)phenyl]propionic acid;

methyl 3-[3-(naphthalen-2-yl)-4-(2-phenylethyloxy)phenyl]propionate;

3-[3-(naphthalen-2-yl)-4-(2-phenylethyloxy)phenyl] propionic acid;

methyl 3-{4-[2-(2-fluorophenyl)ethyloxy]-3-(naphthalen-2-yl)phenyl}propionate;

3-{4-[2-(2-fluorophenyl)ethyloxy]-3-(naphthalen-2-yl) phenyl}propionic acid;

methyl 3-{4-[2-(3-fluorophenyl)ethyloxy]-3-(naphthalen-2-yl)phenyl}propionate;

3-{4-[2-(3-fluorophenyl)ethyloxy]-3-(naphthalen-2-yl) phenyl}propionic acid;

methyl 3-{4-[2-(4-fluorophenyl)ethyloxy]-3-(naphthalen-2-yl)phenyl}propionate;

3-{4-[2-(4-fluorophenyl)ethyloxy]-3-(naphthalen-2-yl) phenyl}propionic acid;

3-{4-[(furan-2-yl)methyloxy]-3-(naphthalen-2-yl) phenyl}propionic acid;

methyl 3-{3-(naphthalen-2-yl)-4-[(pyridin-3-yl) methyloxy]phenyl}propionate;

3-{3-(naphthalen-2-yl)-4-[(pyridin-3-yl) methyloxy] phenyl}propionic acid;

methyl 3-{4-[2-(5-ethylpyridin-2-yl)ethyloxy]-3-(naphthalen-2-yl)phenyl}propionate;

3-{4-[2-(5-ethylpyridin-2-yl)ethyloxy]-3-(naphthalen-2-yl)phenyl}propionic acid;

methyl 3-{4-[2-(5-methyl-2-phenyloxazol-4-yl) ethyloxy]-3-(naphthalen-2-yl)phenyl}-propionate;

3-{4-[2-(5-methyl-2-phenyloxazol-4-yl)ethyloxy]-3-(naphthalen-2-yl)phenyl}propionic acid;

ethyl 3-[4-cyclohexylmethyloxy-3-(naphthalen-2-yl) phenyl]propionate;

3-[4-cyclohexylmethyloxy-3-(naphthalen-2-yl)phenyl] propionic acid;

ethyl 3-[4-cyclohexylmethyloxy-3-(6-methoxynaphthalen-2-yl)phenyl]propionate;

3-[4-cyclohexylmethyloxy-3-(6-methoxynaphthalen-2-yl)phenyl]propionic acid;

ethyl 3-[4-cyclohexylmethyloxy-3-(naphthalen-1-yl) phenyl]propionate;

3-[4-cyclohexylmethyloxy-3-(naphthalen-1-yl)phenyl] propionic acid;

3-{4-cyclohexylmethyloxy-3-[6-(2-hydroxyethyloxy) naphthalen-2-yl]phenyl}propionic acid;

3-[3-(6-carboxymethyloxynaphthalen-2-yl)-4-cyclohexylmethyloxyphenyl]propionic acid;

methyl 3-{4-cyclohexylmethyloxy-3-[6-(N,N-dimethylcarbamoylmethyloxy)naphthalen-2-yl] phenyl}propionate;

3-{4-cyclohexylmethyloxy-3-[6-(N,N-dimethylcarbamoylmethyloxy)naphthalen-2-yl]phenyl}-propionic acid;

3-{4-cyclopentylmethyloxy-3-[6-(2-hydroxyethylamino) naphthalen-2-yl]phenyl}-propionic acid;

methyl 3-[3-(6-acetylaminonaphthalen-2-yl)-4-cyclopentylmethyloxyphenyl]-propionate;

3-[3-(6-acetylaminonaphthalen-2-yl)-4-cyclopentylmethyloxyphenyl]propionic acid;

3-{3-[6-(2-aminoacetylamino)naphthalen-2-yl]-4-cyclopentylmethyloxyphenyl}-propionic acid;

3-{4-cyclopentylmethyloxy-3-[6-(2-hydroxyacetylamino)naphthalen-2-yl]phenyl}-propionic acid;

methyl 3-(4-cyclopentylmethyloxy-3-{6-[(furan-2-carbonyl)amino]naphthalen-2-yl}-phenyl)propionate;

3-(4-cyclopentylmethyloxy-3-{6-[(furan-2-carbonyl) amino]naphthalen-2-yl}phenyl)propionic acid;

methyl 3-[3-(6-carbamoylaminonaphthalen-2-yl)-4-cyclopentylmethyloxyphenyl]-propionate;

3-[3-(6-carbamoylaminonaphthalen-2-yl)-4-cyclopentylmethyloxyphenyl]propionic acid;

methyl 3-[4-cyclopentylmethyloxy-3-(6-methanesulfonylaminonaphthalen-2-yl)-phenyl] propionate;

3-[4-cyclopentylmethyloxy-3-(6-methanesulfonylaminonaphthalen-2-yl)phenyl]-propionic acid;

methyl 3-{4-cyclopentylmethyloxy-3-[6-(N,N-dimethylsulfamoylamino) naphthalen-2-yl] phenyl}propionate;

3-{4-cyclopentylmethyloxy-3-[6-(N,N-dimethylsulfamoylamino)naphthalen-2-yl]phenyl}-propionic acid;

3-{4-cyclopentylmethyloxy-3-[7-(2-hydroxyacetylamino)naphthalen-2-yl]phenyl}-propionic acid;

methyl 3-(4-cyclopentylmethyloxy-3-{7-[(furan-2-carbonyl)amino]naphthalen-2-yl}-phenyl)propionate;

3-(4-cyclopentylmethyloxy-3-{7-[(furan-2-carbonyl) amino]naphthalen-2-yl}phenyl)-propionic acid;

methyl 3-[3-chloro-4-cyclopentylmethyloxy-5-(naphthalen-2-yl)phenyl]propionate;

3-[3-chloro-4-cyclopentylmethyloxy-5-(naphthalen-2-yl) phenyl]propionic acid;

methyl 3-[4-cyclopentylmethyloxy-3-(naphthalen-2-yl)-5-nitrophenyl]propionate;

methyl 3-[3-amino-4-cyclopentylmethyloxy-5-(naphthalen-2-yl)phenyl]propionate;

3-[3-amino-4-cyclopentylmethyloxy-5-(naphthalen-2-yl) phenyl]propionic acid;

4-cyclohexylmethyloxy-3-(naphthalen-2-yl)phenylacetic acid;

methyl 4-[4-cyclopentylmethyloxy-3-(naphthalen-2-yl) phenyl]butyrate;

4-[4-cyclopentylmethyloxy-3-(naphthalen-2-yl)phenyl] butyric acid;

methyl 3-[4-cyclopentylmethyloxy-3-(1H-indol-5-yl) phenyl]propionate;

3-[4-cyclopentylmethyloxy-3-(1H-indol-5-yl)phenyl] propionic acid;

methyl 3-[4-cyclopentyloxy-3-(1H-indol-5-yl)phenyl] propionate;

3-[4-cyclopentyloxy-3-(1H-indol-5-yl)phenyl]propionic acid;

methyl 3-[4-cyclohexyloxy-3-(1H-indol-5-yl)phenyl] propionate;

3-[4-cyclohexyloxy-3-(1H-indol-5-yl)phenyl]propionic acid;

methyl 3-{4-[2-(2-fluorophenyl)ethyloxy]-3-(1H-indol-5-yl)phenyl}propionate;

3-{4-[2-(2-fluorophenyl)ethyloxy]-3-(1H-indol-5-yl) phenyl}propionic acid;

methyl 3-[4-cyclopentyloxy-3-(1-methyl-1H-indol-5-yl) phenyl]propionate;

3-[4-cyclopentyloxy-3-(1-methyl-1H-indol-5-yl)phenyl] propionic acid;

methyl 3-[4-cyclohexyloxy-3-(1-methyl-1H-indol-5-yl) phenyl]propionate;

3-[4-cyclohexyloxy-3-(1-methyl-1H-indol-5-yl)phenyl] propionic acid;

methyl 3-[4-cyclopentylmethyloxy-3-(3-methyl-1H-indol-5-yl)phenyl]propionate;

3-[4-cyclopentylmethyloxy-3-(3-methyl-1H-indol-5-yl) phenyl]propionic acid;

methyl 3-[4-cyclopentylmethyloxy-3-(1H-indol-4-yl) phenyl]propionate;

3-[4-cyclopentylmethyloxy-3-(1H-indol-4-yl)phenyl] propionic acid;

methyl 3-[4-cyclohexylmethyloxy-3-(1H-indol-4-yl) phenyl]propionate;

3-[4-cyclohexylmethyloxy-3-(1H-indol-4-yl)phenyl] propionic acid;

methyl 3-[4-cyclopentyloxy-3-(1H-indol-4-yl)phenyl] propionate;

3-[4-cyclopentyloxy-3-(1H-indol-4-yl)phenyl]propionic acid;

methyl 3-[4-cyclohexyloxy-3-(1H-indol-4-yl)phenyl] propionate;

3-[4-cyclohexyloxy-3-(1H-indol-4-yl)phenyl]propionic acid;

methyl 3-[4-cyclopentylmethyloxy-3-(1-methyl-1H-indol-4-yl)phenyl]propionate;

3-[4-cyclopentylmethyloxy-3-(1-methyl-1H-indol-4-yl) phenyl]propionic acid;

methyl 3-[4-cyclopentyloxy-3-(1-methyl-1H-indol-4-yl) phenyl]propionate;

3-[4-cyclopentyloxy-3-(1-methyl-1H-indol-4-yl)phenyl] propionic acid;

methyl 3-[4-cyclohexyloxy-3-(1-methyl-1H-indol-4-yl) phenyl]propionate;

3-[4-cyclohexyloxy-3-(1-methyl-1H-indol-4-yl)phenyl] propionic acid;

methyl 3-[4-cyclohexylmethyloxy-3-(1H-indol-6-yl) phenyl]propionate;

3-[4-cyclohexylmethyloxy-3-(1H-indol-6-yl)phenyl] propionic acid;

methyl 3-[4-butyloxy-3-(1H-indol-5-yl)phenyl] propionate;

3-[4-butyloxy-3-(1H-indol-5-yl)phenyl]propionic acid;

methyl 3-[3-(1H-indol-5-yl)-4-(1-phenylethyloxy) phenyl]propionate;

3-[3-(1H-indol-5-yl)-4-(1-phenylethyloxy)phenyl] propionic acid;

methyl 3-[3-(1H-indol-5-yl)-4-(2-methylphenylmethyloxy)phenyl]propionate;

3-[3-(1H-indol-5-yl)-4-(2-methylphenylmethyloxy) phenyl]propionic acid;

methyl 3-[3-(1H-indol-5-yl)-4-(3-methylphenylmethyloxy)phenyl]propionate;

3-[3-(1H-indol-5-yl)-4-(3-methylphenylmethyloxy) phenyl]propionic acid;

methyl 3-[3-(1H-indol-5-yl)-4-(4-methylphenylmethyloxy)phenyl]propionate;

3-[3-(1H-indol-5-yl)-4-(4-methylphenylmethyloxy) phenyl]propionic acid;

methyl 3-{4-[(biphenyl-2-yl)methyloxy]-3-(1H-indol-5-yl)phenyl}propionate;

3-{4-[(biphenyl-2-yl)methyloxy]-3-(1H-indol-5-yl) phenyl}propionic acid;

methyl 3-[4-(2-fluorophenylmethyloxy)-3-(1H-indol-5-yl)phenyl]propionate;

3-[4-(2-fluorophenylmethyloxy)-3-(1H-indol-5-yl) phenyl]propionic acid;

methyl 3-[4-(3-fluorophenylmethyloxy)-3-(1H-indol-5-yl)phenyl]propionate;

3-[4-(3-fluorophenylmethyloxy)-3-(1H-indol-5-yl) phenyl]propionic acid;

methyl 3-[4-(4-fluorophenylmethyloxy)-3-(1H-indol-5-yl)phenyl]propionate;

3-[4-(4-fluorophenylmethyloxy)-3-(1H-indol-5-yl) phenyl]propionic acid;

methyl 3-[4-(2-chlorophenylmethyloxy)-3-(1H-indol-5-yl)phenyl]propionate;

3-[4-(2-chlorophenylmethyloxy)-3-(1H-indol-5-yl) phenyl]propionic acid;

methyl 3-[4-(3-chlorophenylmethyloxy)-3-(1H-indol-5-yl)phenyl]propionate;

3-[4-(3-chlorophenylmethyloxy)-3-(1H-indol-5-yl) phenyl]propionic acid;

methyl 3-[4-(4-chlorophenylmethyloxy)-3-(1H-indol-5-yl)phenyl]propionate;

3-[4-(4-chlorophenylmethyloxy)-3-(1H-indol-5-yl) phenyl]propionic acid;

methyl 3-[4-(2-bromophenylmethyloxy)-3-(1H-indol-5-yl)phenyl]propionate;

3-[4-(2-bromophenylmethyloxy)-3-(1H-indol-5-yl) phenyl]propionic acid;

methyl 3-[4-(2,4-difluorophenylmethyloxy)-3-(1H-indol-5-yl)phenyl]propionate;

3-[4-(2,4-difluorophenylmethyloxy)-3-(1H-indol-5-yl) phenyl]propionic acid;

methyl 3-[4-(3,4-difluorophenylmethyloxy)-3-(1H-indol-5-yl)phenyl]propionate;

3-[4-(3,4-difluorophenylmethyloxy)-3-(1H-indol-5-yl) phenyl]propionic acid;

methyl 3-[4-(2,3-dichlorophenylmethyloxy)-3-(1H-indol-5-yl)phenyl]propionate;

3-[4-(2,3-dichlorophenylmethyloxy)-3-(1H-indol-5-yl) phenyl]propionic acid;

methyl 3-[4-(2,4-dichlorophenylmethyloxy)-3-(1H-indol-5-yl)phenyl]propionate;

3-[4-(2,4-dichlorophenylmethyloxy)-3-(1H-indol-5-yl) phenyl]propionic acid;

methyl 3-[4-(2,6-dichlorophenylmethyloxy)-3-(1H-indol-5-yl)phenyl]propionate;

3-[4-(2,6-dichlorophenylmethyloxy)-3-(1H-indol-5-yl) phenyl]propionic acid;

methyl 3-[4-(3,4-dichlorophenylmethyloxy)-3-(1H-indol-5-yl)phenyl]propionate;

3-[4-(3,4-dichlorophenylmethyloxy)-3-(1H-indol-5-yl) phenyl]propionic acid;

methyl 3-[4-(4-bromo-2-fluorophenylmethyloxy)-3-(1H-indol-5-yl)phenyl]propionate;

3-[4-(4-bromo-2-fluorophenylmethyloxy)-3-(1H-indol-5-yl)phenyl]propionic acid;

methyl 3-{3-(1H-indol-5-yl)-4-[2-(trifluoromethyl) phenylmethyloxy]phenyl}propionate;

3-{3-(1H-indol-5-yl)-4-[2-(trifluoromethyl) phenylmethyloxy]phenyl}propionic acid;

methyl 3-{3-(1H-indol-5-yl)-4-[4-(trifluoromethyl) phenylmethyloxy]phenyl}propionate;

3-{3-(1H-indol-5-yl)-4-[4-(trifluoromethyl)phenylmethyloxy]phenyl}propionic acid;
3-[4-isopropyloxy-3-(1H-indol-5-yl)phenyl]propionic acid;
methyl 3-[4-(3,5-dimethylphenylmethyloxy)-3-(1H-indol-5-yl)phenyl]propionate;
3-[4-(3,5-dimethylphenylmethyloxy)-3-(1H-indol-5-yl)phenyl]propionic acid;
methyl 3-[4-(bicyclo[2,2,1]hept-2-ylmethyloxy)-3-(1H-indol-5-yl)phenyl]propionate;
3-[4-(bicyclo[2,2,1]hept-2-ylmethyloxy)-3-(1H-indol-5-yl)phenyl]propionic acid;
methyl 3-{4-[(biphenyl-4-yl)methyloxy]-3-(1H-indol-5-yl)phenyl}propionate;
3-{4-[(biphenyl-4-yl)methyloxy]-3-(1H-indol-5-yl)phenyl}propionic acid;
methyl 3-[4-(2,3-dimethylbutyloxy)-3-(1H-indol-5-yl)phenyl]propionate;
3-[4-(2,3-dimethylbutyloxy)-3-(1H-indol-5-yl)phenyl]propionic acid;
methyl 3-[4-(2-ethylbutyloxy)-3-(1H-indol-5-yl)phenyl]propionate;
3-[4-(2-ethylbutyloxy)-3-(1H-indol-5-yl)phenyl]propionic acid;
3-[4-cycloheptyloxy-3-(1H-indol-5-yl)phenyl]propionic acid;
methyl 3-{4-[4-(butyloxy)phenylmethyloxy]-3-(1H-indol-5-yl)phenyl}propionate;
3-{4-[4-(butyloxy)phenylmethyloxy]-3-(1H-indol-5-yl)phenyl}propionic acid;
methyl 3-[4-(3,5-dichlorophenylmethyloxy)-3-(1H-indol-5-yl)phenyl]propionate;
3-[4-(3,5-dichlorophenylmethyloxy)-3-(1H-indol-5-yl)phenyl]propionic acid;
methyl 3-{3-(1H-indol-5-yl)-4-[(naphthalen-1-yl)methyloxy]phenyl}propionate;
3-{3-(1H-indol-5-yl)-4-[(naphthalen-1-yl)methyloxy]phenyl}propionic acid;
methyl 3-{3-(1H-indol-5-yl)-4-[(naphthalen-2-yl)methyloxy]phenyl}propionate;
3-{3-(1H-indol-5-yl)-4-[(naphthalen-2-yl)methyloxy]phenyl}propionic acid;
methyl 3-{4-[(furan-2-yl)methyloxy]-3-(1H-indol-5-yl)phenyl]propionate;
3-{4-[(furan-2-yl)methyloxy]-3-(1H-indol-5-yl)phenyl}propionic acid;
methyl 3-{4-[(furan-3-yl)methyloxy]-3-(1H-indol-5-yl)phenyl}propionate;
3-{4-[(furan-3-yl)methyloxy]-3-(1H-indol-5-yl)phenyl}propionic acid;
methyl 3-{3-(1H-indol-5-yl)-4-[(thiophen-2-yl)methyloxy]phenyl}propionate;
3-{3-(1H-indol-5-yl)-4-[(thiophen-2-yl)methyloxy]phenyl}propionic acid;
methyl 3-{3-(1H-indol-5-yl)-4-[2-(2-methylphenyl)ethyloxy]phenyl}propionate;
3-3-{1H-indol-5-yl)-4-[2-(2-methylphenyl)ethyloxy]phenyl}propionic acid;
methyl 3-{3-(1H-indol-5-yl)-4-[2-(3-methylphenyl)ethyloxy]phenyl}propionate;
3-{3-(1H-indol-5-yl)-4-[2-(3-methylphenyl)ethyloxy]phenyl}propionic acid;
methyl 3-{3-(1H-indol-5-yl)-4-[2-(4-methylphenyl)ethyloxy]phenyl}propionate;
3-{3-(1H-indol-5-yl)-4-[2-(4-methylphenyl)ethyloxy]phenyl}propionic acid;
3-{3-(1H-indol-5-yl)-4-[2-(2-methoxyphenyl)ethyloxy]phenyl}propionic acid;
methyl 3-{3-(1H-indol-5-yl)-4-[2-(4-methoxyphenyl)ethyloxy]phenyl}propionate;
3-{3-(1H-indol-5-yl)-4-[2-(4-methoxyphenyl)ethyloxy]phenyl}propionic acid;
methyl 3-{4-[2-(2-chlorophenyl)ethyloxy]-3-(1H-indol-5-yl)phenyl}propionate;
3-{4-[2-(2-chlorophenyl)ethyloxy]-3-(1H-indol-5-yl)phenyl}propionic acid;
methyl 3-{4-[2-(3-chlorophenyl)ethyloxy]-3-(1H-indol-5-yl)phenyl}propionate;
3-{4-[2-(3-chlorophenyl)ethyloxy]-3-(1H-indol-5-yl)phenyl}propionic acid;
methyl 3-{4-[2-(4-chlorophenyl)ethyloxy]-3-(1H-indol-5-yl)phenyl}propionate;
3-{4-[2-(4-chlorophenyl)ethyloxy]-3-(1H-indol-5-yl)phenyl}propionic acid;
3-[3-(1H-indol-5-yl)-4-{2-[2-(trifluoromethyl)phenyl]ethyloxy}phenyl]propionic acid;
3-(4-{2-[4-(N,N-dimethylamino)phenyl]ethyloxy}-3-[1H-indol-5-yl]phenyl)propionic acid;
methyl 3-{4-[2-(naphthalen-2-yl)ethyloxy]-3-(1H-indol-5-yl)phenyl}propionate;
3-{4-[2-(naphthalen-2-yl)ethyloxy]-3-(1H-indol-5-yl)phenyl}propionic acid;
methyl 3-{3-(1H-indol-5-yl)-4-[2-(1H-indol-3-yl)ethyloxy]phenyl}propionate;
3-{3-(1H-indol-5-yl)-4-[2-(1H-indol-3-yl)ethyloxy]phenyl}propionic acid;
3-[3-(1H-indol-5-yl)-4-(3-phenylpropyloxy)phenyl]propionic acid;
methyl 3-{3-(1H-indol-5-yl)-4-[2-(phenyloxy)ethyloxy]phenyl}propionate;
3-{3-(1H-indol-5-yl)-4-[2-(phenyloxy)ethyloxy]phenyl}propionic acid;
methyl 3-{4-[2-(2-chlorophenyloxy)ethyloxy]-3-(1H-indol-5-yl)phenyl}propionate;
3-{4-[2-(2-chlorophenyloxy)ethyloxy]-3-(1H-indol-5-yl)phenyl}propionic acid;
methyl 3-{4-[2-(4-chlorophenyloxy)ethyloxy]-3-(1H-indol-5-yl)phenyl}propionate;
3-{4-[2-(4-chlorophenyloxy)ethyloxy]-3-(1H-indol-5-yl)phenyl}propionic acid;
methyl 3-{3-(1H-indol-5-yl)-4-[2-(phenylthio)ethyloxy]phenyl}propionate;
3-{3-(1H-indol-5-yl)-4-[2-(phenylthio)ethyloxy]phenyl}propionic acid;
3-{3-(1H-indol-5-yl)-4-[2-(N-phenyl-N-methylamino)ethyloxy]phenyl}propionic acid;
ethyl 3-[4-cyclohexylmethyloxy-3-(1H-indol-5-yl)phenyl]propionate;
3-[4-cyclohexylmethyloxy-3-(1H-indol-5-yl)phenyl]propionic acid;
methyl 3-[4-cyclohexylmethyloxy-3-(1-methyl-1H-indol-5-yl)phenyl]propionate;
3-[4-cyclohexylmethyloxy-3-(1-methyl-1H-indol-5-yl)phenyl]propionic acid;

methyl 3-[4-cyclopentylmethyloxy-3-(1-methyl-1H-indol-5-yl)phenyl]propionate;
3-[4-cyclopentylmethyloxy-3-(1-methyl-1H-indol-5-yl)phenyl]propionic acid;
3-[4-cyclopentylmethyloxy-3-(1-ethyl-1H-indol-5-yl)phenyl]propionic acid;
methyl 3-[4-cyclopentylmethyloxy-3-(1-isopropyl-1H-indol-5-yl)phenyl]propionate;
3-[4-cyclopentylmethyloxy-3-(1-isopropyl-1H-indol-5-yl)phenyl]propionic acid;
methyl 3-[3-(1-butyl-1H-indol-5-yl)-4-cyclopentylmethyloxyphenyl]propionate;
3-[3-(1-butyl-1H-indol-5-yl)-4-cyclopentylmethyloxyphenyl]propionic acid;
methyl 3-[3-(1H-cyclopentyl-1H-indol-5-yl)-4-cyclopentylmethyloxyphenyl]propionate;
3-[3-(1-cyclopentyl-1H-indol-5-yl)-4-cyclopentylmethyloxyphenyl]propionic acid;
3-{4-cyclopentylmethyloxy-3-[1H-(2-hydroxyethyl)-1H-indol-5-yl]phenyl}propionic acid;
methyl 3-[4-(2-chlorophenylmethyloxy)-3-(1-methyl-1H-indol-5-yl)phenyl]propionate;
3-[4-(2-chlorophenylmethyloxy)-3-(1-methyl-1H-indol-5-yl)phenyl]propionic acid;
3-[4-cyclopentyloxy-3-(1-ethyl-1H-indol-5-yl)phenyl]propionic acid;
methyl 3-[4-cyclohexyloxy-3-(1-ethyl-1H-indol-5-yl)phenyl]propionate;
3-[4-cyclohexyloxy-3-(1-ethyl-1H-indol-5-yl)phenyl]propionic acid;
methyl 3-[4-(2-chlorophenylmethyloxy)-3-(1-ethyl-1H-indol-5-yl)phenyl]propionate;
3-[4-(2-chlorophenylmethyloxy)-3-(1-ethyl-1H-indol-5-yl)phenyl]propionic acid;
methyl 3-[4-cyclopentylmethyloxy-3-(1,3-dimethyl-1H-indol-5-yl)phenyl]propionate;
3-[4-cyclopentylmethyloxy-3-(1,3-dimethyl-1H-indol-5-yl)phenyl]propionic acid;
methyl 3-[4-cyclopentylmethyloxy-3-(3-formyl-1H-indol-5-yl)phenyl]propionate;
3-[4-cyclopentylmethyloxy-3-(3-formyl-1H-indol-5-yl)phenyl]propionic acid;
3-[4-cyclopentylmethyloxy-3-(3-formyl-1-methyl-1H-indol-5-yl)phenyl]propionic acid;
methyl 3-[3-(3-acetyl-1H-indol-5-yl)-4-cyclopentylmethyloxyphenyl]propionate;
3-[3-(3-acetyl-1H-indol-5-yl)-4-cyclopentylmethyloxyphenyl]propionic acid;
methyl 3-[3-(3-acetyl-1-methyl-1H-indol-5-yl)-4-cyclopentylmethyloxyphenyl]-propionate;
3-[3-(3-acetyl-1-methyl-1H-indol-5-yl)-4-cyclopentylmethyloxyphenyl]propionic acid;
methyl 3-[4-cyclopentylmethyloxy-3-fluoro-5-(1H-indol-5-yl)phenyl]propionate;
3-[4-cyclopentylmethyloxy-3-fluoro-5-(1H-indol-5-yl)phenyl]propionic acid;
methyl 3-[3-chloro-4-cyclopentylmethyloxy-5-(1H-indol-5-yl)phenyl]propionate;
3-[3-chloro-4-cyclopentylmethyloxy-5-(1H-indol-5-yl)phenyl]propionic acid;
methyl 3-[4-cyclopentylmethyloxy-3-(1H-indol-5-yl)-5-nitrophenyl]propionate;
methyl 3-[3-amino-4-cyclopentylmethyloxy-5-(1H-indol-5-yl)phenyl]propionate;
3-[3-amino-4-cyclopentylmethyloxy-5-(1H-indol-5-yl)phenyl]propionic acid;
methyl 3-[4-cyclopentylmethyloxy-3-(1-methyl-1H-indol-5-yl)-5-nitrophenyl]-propionate;
methyl 3-[3-amino-4-cyclopentylmethyloxy-5-(1-methyl-1H-indol-5-yl)phenyl]-propionate;
3-[3-amino-4-cyclopentylmethyloxy-5-(1-methyl-1H-indol-5-yl)phenyl]propionic acid;
methyl 4-[4-cyclopentylmethyloxy-3-(1H-indol-5-yl)phenyl]butyrate;
4-[4-cyclopentylmethyloxy-3-(1H-indol-5-yl)phenyl]butyric acid;
methyl 3-[4-cyclohexylmethyloxy-3-(2,3-dimethyl-1H-indol-5-yl)phenyl]propionate;
3-[4-cyclohexylmethyloxy-3-(2,3-dimethyl-1H-indol-5-yl)phenyl]propionic acid;
methyl 3-[4-cyclopentylmethyloxy-3-(1,2,3-trimethyl-1H-indol-5-yl)phenyl]propionate;
3-[4-cyclopentylmethyloxy-3-(1,2,3-trimethyl-1H-indol-5-yl)phenyl]propionic acid;
methyl 3-[3-(benzo[b]furan-5-yl)-4-cyclopentylmethyloxyphenyl]propionate;
3-[3-(benzo[b]furan-5-yl)-4-cyclopentylmethyloxyphenyl]propionic acid;
methyl 3-[4-cyclohexylmethyloxy-3-(2,3-dimethylbenzo[b]furan-5-yl)phenyl]-propionate;
3-[4-cyclohexylmethyloxy-3-(2,3-dimethylbenzo[b]furan-5-yl)phenyl]propionic acid;
methyl 3-[3-(benzo[b]thiophen-5-yl)-4-cyclopentylmethyloxyphenyl]propionate;
3-[3-(benzo[b]thiophen-5-yl)-4-cyclopentylmethyloxyphenyl]propionic acid;
methyl 3-[4-cyclopentylmethyloxy-3-(2-methylbenzothiazol-5-yl)phenyl]propionate;
3-[4-cyclopentylmethyloxy-3-(2-methylbenzothiazol-5-yl)phenyl]propionic acid;
methyl-[3-(2-aminobenzothiazol-5-yl)-4-cyclopentylmethyloxyphenyl]propionate;
3-[3-(2-aminobenzothiazol-5-yl)-4-cyclopentylmethyloxyphenyl]propionic acid;
ethyl 3-[3-(2-aminobenzothiazol-6-yl)-4-cyclopentylmethyloxyphenyl]propionate;
3-[3-(2-aminobenzothiazol-6-yl)-4-cyclopentylmethyloxyphenyl]propionic acid;
methyl 3-[3-(2-aminobenzothiazol-6-yl)-4-cyclohexylmethyloxyphenyl]propionate;
3-[3-(2-aminobenzothiazol-6-yl)-4-cyclohexylmethyloxyphenyl]propionic acid;
ethyl 3-[3-(2-aminobenzothiazol-6-yl)-4-butyloxyphenyl]propionate;
3-[3-(2-aminobenzothiazol-6-yl)-4-butyloxyphenyl]propionic acid;
ethyl 3-[3-(2-aminobenzothiazol-6-yl)-4-cyclopentyloxyphenyl]propionate;
3-[3-(2-aminobenzothiazol-6-yl)-4-cyclopentyloxyphenyl]propionic acid;
ethyl 3-[3-(2-aminobenzothiazol-6-yl)-4-cyclohexyloxyphenyl]propionate;
3-[3-(2-aminobenzothiazol-6-yl)-4-cyclohexyloxyphenyl]propionic acid;

ethyl 3-[4-cyclopentylmethyloxy-3-(2-methylaminobenzothiazol-6-yl)phenyl]-propionate;

3-[4-cyclopentylmethyloxy-3-(2-methylaminobenzothiazol-6-yl)phenyl]propionic acid;

ethyl 3-[3-(benzothiazol-6-yl)-4-cyclopentylmethyloxyphenyl]propionate;

3-[3-(benzothiazol-6-yl)-4-cyclopentylmethyloxyphenyl]propionic acid;

ethyl 3-{4-cyclopentylmethyloxy-3-[2-(N,N-dimethylamino)benzothiazol-6-yl]-phenyl}propionate;

3-{4-cyclopentylmethyloxy-3-[2-(N,N-dimethylamino)benzothiazol-6-yl]phenyl}-propionic acid;

ethyl 3-[4-cyclopentylmethyloxy-3-(2-imino-3-methyl-2,3-dihydrobenzothiazol-6-yl)-phenyl]propionate;

3-[4-cyclopentylmethyloxy-3-(2-imino-3-methyl-2,3-dihydrobenzothiazol-6-yl)-phenyl]propionic acid;

ethyl 3-{4-cyclopentylmethyloxy-3-[3-methyl-2-(methylimino)-2,3-dihydrobenzothiazol-6-yl]phenyl}propionate;

3-{4-cyclopentylmethyloxy-3-[3-methyl-2-(methylimino)-2,3-dihydrobenzothiazol-6-yl]phenyl}propionic acid;

3-[4-cyclopentylmethyloxy-3-(2-methoxybenzothiazol-6-yl)phenyl]propionic acid;

ethyl 3-[4-cyclopentylmethyloxy-3-(2-methylbenzothiazol-6-yl)phenyl]propionate;

3-[4-cyclopentylmethyloxy-3-(2-methylbenzothiazol-6-yl)phenyl]propionic acid;

3-[4-cyclopentylmethyloxy-3-(2-thioxo-2,3-dihydrobenzothiazol-6-yl)phenyl]propionic acid;

3-[4-cyclopentylmethyloxy-3-(2-oxo-2,3-dihydrobenzothiazol-6-yl)phenyl]propionic acid;

methyl 3-[4-cyclopentylmethyloxy-3-(2-oxo-2,3-dihydrobenzothiazol-6-yl)phenyl]-propionate;

methyl 3-[4-cyclopentylmethyloxy-3-(2-oxo-3-methyl-2,3-dihydrobenzothiazol-6-yl)-phenyl]propionate;

3-[4-cyclopentylmethyloxy-3-(2-oxo-3-methyl-2,3-dihydrobenzothiazol-6-yl)phenyl]-propionic acid;

methyl 3-[4-cyclopentylmethyloxy-3-(quinolin-3-yl)phenyl]propionate;

3-[4-cyclopentylmethyloxy-3-(quinolin-3-yl)phenyl]propionic acid;

methyl 3-[4-cyclohexylmethyloxy-3-(quinolin-3-yl)phenyl]propionate;

3-[4-cyclohexylmethyloxy-3-(quinolin-3-yl)phenyl]propionic acid;

methyl 3-[4-cyclohexylmethyloxy-3-(quinolin-6-yl)phenyl]propionate;

3-[4-cyclohexylmethyloxy-3-(quinolin-6-yl)phenyl]propionic acid;

methyl 3-[4-cyclohexylmethyloxy-3-(2-oxo-1,2-dihydroquinolin-6-yl)phenyl]propionate;

3-[4-cyclohexylmethyloxy-3-(2-oxo-1,2-dihydroquinolin-6-yl)phenyl]propionic acid;

methyl 3-[4-benzyloxy-3-(naphthalen-2-yl)phenyl]propionate;

3-[4-benzyloxy-3-(naphthalen-2-yl)phenyl]propionic acid;

methyl 3-[4-benzyloxy-3-(1H-indol-5-yl)phenyl]propionate;

3-[4-benzyloxy-3-(1H-indol-5-yl)phenyl]propionic acid;

methyl 3-[4-(4-t-butylphenylmethyloxy)-3-(1H-indol-5-yl)phenyl]propionate;

3-[4-(4-t-butylphenylmethyloxy)-3-(1H-indol-5-yl)phenyl]propionic acid;

methyl 3-[3-(naphthalen-2-yl)-4-phenyloxyphenyl]propionate;

3-[3-(naphthalen-2-yl)-4-phenyloxyphenyl]propionic acid;

3-[3-(benzothiazol-6-yl)-4-cyclohexyloxyphenyl]propionic acid;

3-[3-(1H-indol-5-yl)-4-(3-methylcyclopentyloxy)phenyl]propionic acid;

3-[4-(2-fluorophenyloxy)-3-(1H-indol-5-yl)phenyl]propionic acid;

3-{4-[2-(acetylamino)phenylmethyloxy]-3-(1H-indol-5-yl)phenyl}propionic acid;

3-[3-(1H-indol-5-yl)-4-(2-methanesulfonylaminophenylmethyloxy)phenyl]propionic acid;

3-{4-[(2-chlorothiophen-5-yl)methyloxy]-3-(1H-indol-5-yl)phenyl}propionic acid;

3-{4-[2-(benzenesulfonyl)ethyloxy]-3-(1H-indol-5-yl)phenyl}propionic acid;

3-[4-cyclopentylmethyloxy-3-(2-methyl-1H-indol-5-yl)phenyl]propionic acid;

3-[4-cyclopentylmethyloxy-3-(3-hydroxymethyl-1H-indol-5-yl)phenyl]propionic acid;

3-[3-(2-carboxy-1H-indol-5-yl)-4-cyclopentylmethyloxyphenyl]propionic acid;

3-[3-(3-carboxymethyl-1H-indol-5-yl)-4-cyclopentylmethyloxyphenyl]propionic acid;

3-[4-(4-fluorophenylmethyloxy)-3-(1-methyl-1H-indol-5-yl)phenyl]propionic acid;

3-{3-(1-methyl-1H-indol-5-yl)-4-[4-(trifluoromethyl)phenylmethyloxy]phenyl}propionic acid;

3-(4-{2-[4-(N,N-dimethylamino)phenyl]ethyloxy}-3-[1-methyl-1H-indol-5-yl]phenyl)-propionic acid;

3-[3-(1-ethyl-1H-indol-5-yl)-4-(4-fluorophenylmethyloxy)phenyl]propionic acid;

3-{3-(1-ethyl-1H-indol-5-yl)-4-[4-(trifluoromethyl)phenylmethyloxy]phenyl}propionic acid;

3-(3-[1-ethyl-1H-indol-5-yl]-4-{2-[4-(N,N-dimethylamino)phenyl]ethyloxy}phenyl)-propionic acid;

3-[5-(1-carboxymethyl-1H-indol-5-yl)-4-cyclopentylmethyloxyphenyl]propionic acid;

3-[4-cyclopentylmethyloxy-3-(1H-indol-5-yl)-5-methoxyphenyl]propionic acid;

3-[4-cyclopentyloxy-3-fluoro-5-(1H-indol-5-yl)phenyl]propionic acid;

3-[4-cyclohexyloxy-3-fluoro-5-(1H-indol-5-yl)phenyl]propionic acid;

3-[4-cyclopentyloxy-3-fluoro-5-(1-methyl-1H-indol-5-yl)phenyl]propionic acid;

3-[4-cyclohexyloxy-3-fluoro-5-(1-methyl-1H-indol-5-yl)phenyl]propionic acid;

3-[4-cyclopentyloxy-3-(1-ethyl-1H-indol-5-yl)-5-fluorophenyl]propionic acid;

3-[4-cyclohexyloxy-3-(1-ethyl-1H-indol-5-yl)-5-fluorophenyl]propionic acid;

3-[3-amino-4-cyclopentyloxy-5-(1H-indol-5-yl)phenyl]propionic acid;

3-[3-amino-4-cyclohexyloxy-5-(1H-indol-5-yl)phenyl]propionic acid;

3-[3-amino-4-cyclopentyloxy-5-(1-methyl-1H-indol-5-yl)phenyl]propionic acid;
3-[3-amino-4-cyclohexyloxy-5-(1-methyl-1H-indol-5-yl)phenyl]propionic acid;
3-[4-cyclopentylmethyloxy-3-(1-propyl-1H-indol-5-yl)phenyl]propionic acid;
3-[4-cyclopentyloxy-3-(1-propyl-1H-indol-5-yl)phenyl]propionic acid;
3-[4-cyclohexyloxy-3-(1-propyl-1H-indol-5-yl)phenyl]propionic acid;
3-[3-(benzo[b]thiophen-5-yl)-4-cyclopentyloxyphenyl]propionic acid;
3-[3-(benzo[b]thiophen-5-yl)-4-cyclohexyloxyphenyl]propionic acid;
3-[3-(benzothiazol-6-yl)-4-cyclopentyloxyphenyl]propionic acid;
3-[3-(benzothiazol-6-yl)-4-(2-chlorophenylmethyloxyphenyl]propionic acid;
3-[3-(benzothiazol-6-yl)-4-(4-fluorophenylmethyloxy)phenyl]propionic acid;
3-{3-(benzothiazol-6-yl)-4-[4-(trifluoromethyl)phenylmethyloxy]phenyl}propionic acid;
3-(3-[benzothiazol-6-yl]-4-{2-[4-(N,N-dimethylamino)phenyl]ethyl}phenyl)propionic acid;
3-[3-(2-aminobenzothiazol-6-yl)-4-(4-fluorophenylmethyloxy)phenyl]propionic acid;
3-[3-(2-aminobenzothiazol-6-yl)-4-(2-chlorophenylmethyloxy)phenyl]propionic acid;
3-{3-(2-aminobenzothiazol-6-yl)-4-[4-(trifluoromethyl)phenylmethyloxy]phenyl}-propionic acid;
3-(3-[2-aminobenzothiazol-6-yl]-4-{2-[4-(N,N-dimethylamino)phenyl]ethyl}phenyl)-propionic acid;
3-[3-(2-aminobenzothiazol-6-yl)-4-(cyclopentyloxy)-5-fluorophenyl]propionic acid;
3-[3-(2-aminobenzothiazol-6-yl)-4-(cyclohexyloxy)-5-fluorophenyl]propionic acid;
3-[4-cyclopentyloxy-3-(quinolin-3-yl)phenyl]propionic acid;
3-[4-cyclohexyloxy-3-(quinolin-3-yl)phenyl]propionic acid;
3-[4-(2-chlorophenylmethyloxy)-3-(quinolin-3-yl)phenyl]propionic acid;
3-[4-cyclopentyloxy-3-(quinolin-6-yl)phenyl]propionic acid;
3-[4-cyclohexyloxy-3-(quinolin-6-yl)phenyl]propionic acid;
3-[4-(2-chlorophenylmethyloxy)-3-(quinolin-6-yl)phenyl]propionic acid;
3-[4-cyclohexylmethyloxy-3-(2-methylquinolin-6-yl)phenyl]propionic acid.

Specific examples of the compounds (I) of the present invention include the following compounds:

methyl 3-[4-cyclopentyloxy-3-(naphthalen-2-yl)-5-nitrophenyl]propionate;
methyl 3-[3-amino-4-cyclopentyloxy-5-(naphthalen-2-yl)phenyl]propionate;
3-[3-amino-4-cyclopentyloxy-5-(naphthalen-2-yl)phenyl]propionic acid;
methyl 3-[4-cyclohexyloxy-3-(naphthalen-2-yl)-5-nitrophenyl]propionate;
methyl 3-[3-amino-4-cyclohexyloxy-5-(naphthalen-2-yl)phenyl]propionate;
3-[3-amino-4-cyclohexyloxy-5-(naphthalen-2-yl)phenyl]propionic acid;
methyl 3-[3-(naphthalen-2-yl)-5-nitro-4-(1-phenylethyloxy)phenyl]propionate;
methyl 3-[3-amino-5-(naphthalen-2-yl)-4-(1-phenylethyloxy)phenyl]propionate;
3-[3-amino-5-(naphthalen-2-yl)-4-(1-phenylethyloxy)phenyl]propionic acid;
methyl 3-[4-(4-methylbenzyloxy)-3-(naphthalen-2-yl)-5-nitrophenyl]propionate;
methyl 3-[3-amino-4-(4-methylbenzyloxy)-5-(naphthalen-2-yl)phenyl]propionate;
3-[3-amino-4-(4-methylbenzyloxy)-5-(naphthalen-2-yl)phenyl]propionic acid;
methyl 3-{4-[2-(4-methylphenyl)ethyloxy]-3-(naphthalen-2-yl)-5-nitrophenyl}-propionate;
methyl 3-{3-amino-4-[2-(4-methylphenyl)ethyloxy]-5-(naphthalen-2-yl)phenyl}-propionate;
3-{3-amino-4-[2-(4-methylphenyl)ethyloxy]-5-(naphthalen-2-yl)phenyl}propionic acid;
methyl 3-[3-(naphthalen-2-yl)-5-nitro-4-(3-phenylpropyloxy)phenyl]propionate;
methyl 3-[3-amino-5-(naphthalen-2-yl)-4-(3-phenylpropyloxy)phenyl]propionate;
3-[3-amino-5-(naphthalen-2-yl)-4-(3-phenylpropyloxy)phenyl]propionic acid;
methyl 3-(3-[naphthalen-2-yl]-5-nitro-4-{1-[4-(trifluoromethyl)phenyl]ethyloxy}-phenyl)propionate;
methyl 3-(3-amino-5-[naphthalen-2-yl]-4-{1-[4-(trifluoromethyl)phenyl]ethyloxy}-phenyl)propionate;
3-(3-amino-5-[naphthalen-2-yl]-4-{1-[4-(trifluoromethyl)phenyl]ethyloxy}phenyl)propionic acid;
methyl 3-[4-(indan-2-yloxy)-3-(naphthalen-2-yl)-5-nitrophenyl]propionate;
methyl 3-[3-amino-4-(indan-2-yloxy)-5-(naphthalen-2-yl)phenyl]propionate;
3-[3-amino-4-(indan-2-yloxy)-5-(naphthalen-2-yl)phenyl]propionic acid;
methyl 3-{4-[2-(2-fluorophenyl)ethyloxy]-3-(naphthalen-2-yl)-5-nitrophenyl}-propionate;
methyl 3-{3-amino-4-[2-(2-fluorophenyl)ethyloxy]-5-(naphthalen-2-yl)phenyl}-propionate;
3-{3-amino-4-[2-(2-fluorophenyl)ethyloxy]-5-(naphthalen-2-yl)phenyl}propionic acid;
methyl 3-[4-(3-methylbutyloxy)-3-(naphthalen-2-yl)-5-nitrophenyl]propionate;
methyl 3-[3-amino-4-(3-methylbutyloxy)-5-(naphthalen-2-yl)phenyl]propionate;
3-[3-amino-4-(3-methylbutyloxy)-5-(naphthalen-2-yl)phenyl]propionic acid;
methyl 3-[4-(2,3-dimethylbutyloxy)-3-(naphthalen-2-yl)-5-nitrophenyl]propionate;
methyl 3-[3-amino-4-(2,3-dimethylbutyloxy)-5-(naphthalen-2-yl)phenyl]propionate;
3-[3-amino-4-(2,3-dimethylbutyloxy)-5-(naphthalen-2-yl)phenyl]propionic acid;
methyl 3-(4-{2-[4-(N,N-dimethylamino)phenyl]ethyloxy}-3-[naphthalen-2-yl]-5-nitrophenyl)propionate;
methyl 3-(3-amino-4-{2-[4-(N,N-dimethylamino)phenyl]ethyloxy}-5-[naphthalen-2-yl]-phenyl)propionate;

3-(3-amino-4-{2-[4-(N,N-dimethylamino)phenyl]ethyloxy}-5-[naphthalen-2-yl]-phenyl)propionic acid;

methyl 3-{3-(naphthalen-2-yl)-5-nitro-4-[2-(N-phenyl-N-methylamino)ethyloxy]-phenyl}propionate;

methyl 3-{3-amino-5-(naphthalen-2-yl)-4-[2-(N-phenyl-N-methylamino)ethyloxy]-phenyl}propionate;

3-(3-amino-5-(naphthalen-2-yl)-4-[2-(N-phenyl-N-methylamino)ethyloxy]phenyl}-propionic acid;

methyl 3-{3-(naphthalen-2-yl)-5-nitro-4-[4-(trifluoromethyl)phenylmethyloxy]phenyl}-propionate;

methyl 3-{3-amino-5-(naphthalen-2-yl)-4-[4-(trifluoromethyl)phenylmethyloxy]-phenyl}propionate;

3-{3-amino-5-(naphthalen-2-yl)-4-[4-(trifluoromethyl)phenylmethyloxy]phenyl}-propionic acid;

methyl 3-[4-(cis-2-methylcyclopentyloxy)-3-(naphthalen-2-yl)-5-nitrophenyl]-propionate;

methyl 3-[3-amino-4-(cis-2-methylcyclopentyloxy)-5-(naphthalen-2-yl)phenyl]-propionate;

3-[3-amino-4-(cis-2-methylcyclopentyloxy)-5-(naphthalen-2-yl)phenyl]propionic acid;

methyl 3-[4-(2-methylpropyloxy)-3-(naphthalen-2-yl)-5-nitrophenyl]-propionate;

methyl 3-[3-amino-4-(2-methylpropyloxy)-3-(naphthalen-2-yl)phenyl]-propionate;

3-[3-amino-4-(2-methylpropyloxy)-3-(naphthalen-2-yl)phenyl]propionic acid;

methyl 3-[4-(trans-4-methylcyclohexyloxy)-5-(naphthalen-2-yl)-5-nitrophenyl]propionate;

methyl 3-[3-amino-4-(trans-4-methylcyclohexyloxy)-5-(naphthalen-2-yl)phenyl]propionate;

3-[3-amino-4-(trans-4-methylcyclohexyloxy)-5-(naphthalen-2-yl)phenyl]propionic acid;

methyl 3-[4-cyclopentyloxy-3-(1H-indol-5-yl)-5-nitrophenyl]propionate;

methyl 3-[3-amino-4-cyclopentyloxy-5-(1H-indol-5-yl)phenyl]propionate;

methyl 3-[4-cyclopentyloxy-3-(1-methyl-1H-indol-5-yl)-5-nitrophenyl]propionate;

methyl 3-[3-amino-4-cyclopentyloxy-5-(1-methyl-1H-indol-5-yl)phenyl]propionate;

methyl 3-[4-cyclopentyloxy-3-(1-ethyl-1H-indol-5-yl)-5-nitrophenyl]propionate;

methyl 3-[3-amino-4-cyclopentyloxy-5-(1-ethyl-1H-indol-5-yl)phenyl]propionate;

3-[3-amino-4-cyclopentyloxy-5-(1-ethyl-1H-indol-5-yl)phenyl]propionic acid;

methyl 3-[4-cyclohexyloxy-3-(1H-indol-5-yl)-5-nitrophenyl]propionate;

methyl 3-[3-amino-4-cyclohexyloxy-5-(1H-indol-5-yl)phenyl]propionate;

methyl 3-[4-cyclohexyloxy-3-(1-methyl-1H-indol-5-yl)-5-nitrophenyl]propionate;

methyl 3-[3-amino-4-cyclohexyloxy-5-(1-methyl-1H-indol-5-yl)phenyl]propionate;

methyl 3-[4-cyclohexyloxy-3-(1-ethyl-1H-indol-5-yl)-5-nitrophenyl]propionate;

methyl 3-[3-amino-4-cyclohexyloxy-5-(1-ethyl-1H-indol-5-yl)phenyl]propionate;

3-[3-amino-4-cyclohexyloxy-5-(1-ethyl-1H-indol-5-yl)phenyl]propionic acid;

methyl 3-[3-(1H-indol-5-yl)-5-nitro-4-(1-phenylethyloxy)phenyl]propionate;

methyl 3-[3-amino-5-(1H-indol-5-yl)-4-(1-phenylethyloxy)phenyl]propionate;

3-[3-amino-5-(1H-indol-5-yl)-4-(1-phenylethyloxy)phenyl]propionic acid;

methyl 3-[3-(1-methyl-1H-indol-5-yl)-5-nitro-4-(1-phenylethyloxy)phenyl]propionate;

methyl 3-[3-amino-5-(1-methyl-1H-indol-5-yl)-4-(1-phenylethyloxy)phenyl]propionate;

3-[3-amino-5-(1-methyl-1H-indol-5-yl)-4-(1-phenylethyloxy)phenyl]propionic acid;

methyl 3-[4-(indan-2-yloxy)-3-(1H-indol-5-yl)-5-nitrophenyl]propionate;

methyl 3-[3-amino-4-(indan-2-yloxy)-5-(1H-indol-5-yl)phenyl]propionate;

3-[3-amino-4-(indan-2-yloxy)-5-(1H-indol-5-yl)phenyl]propionic acid;

methyl 3-[4-(indan-2-yloxy)-3-(1-methyl-1H-indol-5-yl)-5-nitrophenyl]propionate;

methyl 3-[3-amino-4-(indan-2-yloxy)-5-(1-methyl-1H-indol-5-yl)phenyl]propionate;

3-[3-amino-4-(indan-2-yloxy)-5-(1-methyl-1H-indol-5-yl)phenyl]propionic acid;

methyl 3-{3-(1H-indol-5-yl)-5-nitro-4-[4-(trifluoromethyl)benzyloxy]phenyl}propionate;

methyl 3-{3-amino-5-(1H-indol-5-yl)-4-[4-(trifluoromethyl)benzyloxy]phenyl}-propionate;

3-{3-amino-5-(1H-indol-5-yl)-4-[4-(trifluoromethyl)benzyloxy]phenyl}propionic acid;

3-[4-(2-ethylbutyloxy)-3-(1H-indol-5-yl)-5-nitrophenyl]propionate;

methyl 3-[3-amino-4-(2-ethylbutyloxy)-5-(1H-indol-5-yl)phenyl]propionate;

3-[3-amino-4-(2-ethylbutyloxy)-5-(1H-indol-5-yl)phenyl]propionic acid;

methyl 3-[4-cyclopentyloxy-3-(1H-indazol-4-yl)phenyl]propionate;

3-[4-cyclopentyloxy-3-(1H-indazol-4-yl)phenyl]propionic acid;

methyl 3-[4-cyclopentyloxy-3-(1-methyl-1H-indazol-4-yl)phenyl]propionate;

3-[4-cyclopentyloxy-3-(1-methyl-1H-indazol-4-yl)phenyl]propionic acid;

methyl 3-[4-cyclopentyloxy-3-(2-methyl-2H-indazol-4-yl)phenyl]propionate;

3-[4-cyclopentyloxy-3-(2-methyl-2H-indazol-4-yl)phenyl]propionic acid;

methyl 3-[4-cyclopentyloxy-3-(1H-indazol-6-yl)phenyl]propionate;

3-[4-cyclopentyloxy-3-(1H-indazol-6-yl)phenyl]propionic acid;

methyl 3-[4-cyclopentyloxy-3-(1-methyl-1H-indazol-6-yl)phenyl]propionate;

3-[4-cyclopentyloxy-3-(1-methyl-1H-indazol-6-yl)phenyl]propionic acid;

methyl 3-[4-cyclopentyloxy-3-(2-methyl-2H-indazol-6-yl)phenyl]propionate;

3-[4-cyclopentyloxy-3-(2-methyl-2H-indazol-6-yl)phenyl]propionic acid;

methyl 3-[4-cyclopentyloxy-3-(1H-indazol-5-yl)phenyl]propionate;

3-[4-cyclopentyloxy-3-(1H-indazol-5-yl)phenyl] propionic acid;

methyl 3-[4-cyclopentyloxy-3-(1-methyl-1H-indazol-5-yl)phenyl]propionate;

3-[4-cyclopentyloxy-3-(1-methyl-1H-indazol-5-yl)phenyl]propionic acid;

methyl 3-[4-cyclopentyloxy-3-(2-methyl-2H-indazol-5-yl)phenyl]propionate;

3-[4-cyclopentyloxy-3-(2-methyl-2H-indazol-5-yl)phenyl]propionic acid;

methyl 3-[4-cyclopentyloxy-3-(1-ethyl-1H-indazol-5-yl)phenyl]propionate;

3-[4-cyclopentyloxy-3-(1-ethyl-1H-indazol-5-yl)phenyl] propionic acid;

methyl 3-[4-cyclopentyloxy-3-(2-ethyl-2H-indazol-5-yl)phenyl]propionate;

3-[4-cyclopentyloxy-3-(2-ethyl-2H-indazol-5-yl)phenyl] propionic acid;

methyl 3-[4-cyclopentylmethyloxy-3-(1H-indazol-5-yl)phenyl]propionate;

3-[4-cyclopentylmethyloxy-3-(1H-indazol-5-yl)phenyl] propionic acid;

methyl 3-[4-cyclohexyloxy-3-(1H-indazol-5-yl)phenyl] propionate;

3-[4-cyclohexyloxy-3-(1H-indazol-5-yl)phenyl] propionic acid;

methyl 3-[4-cyclohexyloxy-3-(1-methyl-1H-indazol-5-yl)phenyl]propionate;

3-[4-cyclohexyloxy-3-(1-methyl-1H-indazol-5-yl)phenyl]propionic acid;

methyl 3-[4-cyclohexyloxy-3-(2-methyl-2H-indazol-5-yl)phenyl]propionate;

3-[4-cyclohexyloxy-3-(2-methyl-2H-indazol-5-yl)phenyl]propionic acid;

methyl 3-[4-cycloheptyloxy-3-(1H-indazol-5-yl)phenyl] propionate;

3-[4-cycloheptyloxy-3-(1H-indazol-5-yl)phenyl] propionic acid;

methyl 3-[4-(2-ethylbutyloxy)-3-(1H-indazol-5-yl)phenyl]propionate;

3-[4-(2-ethylbutyloxy)-3-(1H-indazol-5-yl)phenyl] propionic acid;

methyl 3-[4-(indan-2-yloxy)-3-(1H-indazol-5-yl)phenyl] propionate;

3-[4-(indan-2-yloxy)-3-(1H-indazol-5-yl)phenyl] propionic acid;

methyl 3-[4-(indan-2-yloxy)-3-(1-methyl-1H-indazol-5-yl)phenyl]propionate;

3-[4-(indan-2-yloxy)-3-(1-methyl-1H-indazol-5-yl)phenyl]propionic acid;

methyl 3-[3-(1-ethyl-1H-indazol-5-yl)-4-(indan-2-yloxy)phenyl]propionate;

3-[3-(1-ethyl-1H-indazol-5-yl)-4-(indan-2-yloxy)phenyl]propionic acid;

methyl 3-[4-(4-fluorobenzyloxy)-3-(1H-indazol-5-yl)phenyl]propionate;

3-[4-(4-fluorobenzyloxy)-3-(1H-indazol-5-yl)phenyl] propionic acid;

methyl 3-[4-(4-fluorobenzyloxy)-3-(1-methyl-1H-indazol-5-yl)phenyl]propionate;

3-[4-(4-fluorobenzyloxy)-3-(1-methyl-1H-indazol-5-yl)phenyl]propionic acid;

methyl 3-{3-(1H-indazol-5-yl)-4-[4-(trifluoromethyl)benzyloxy]phenyl}propionate;

3-{3-(1H-indazol-5-yl)-4-[4-(trifluoromethyl)benzyloxy]phenyl}propionic acid;

methyl 3-{4-[2-(2-fluorophenyl)ethyloxy]-3-(1H-indazol-5-yl)phenyl}propionate;

3-{4-[2-(2-fluorophenyl)ethyloxy]-3-(1H-indazol-5-yl)phenyl}propionic acid;

methyl 3-{4-[2-(2-fluorophenyl)ethyloxy]-3-(1-methyl-1H-indazol-5-yl)phenyl}-propionate;

3-{4-[2-(2-fluorophenyl)ethyloxy]-3-(1-methyl-1H-indazol-5-yl)phenyl}propionic acid;

methyl 3-[4-cyclopentyloxy-3-fluoro-5-(1H-indazol-5-yl)phenyl]propionate;

3-[4-cyclopentyloxy-3-fluoro-5-(1H-indazol-5-yl)phenyl]propionic acid;

methyl 3-[4-cyclopentyloxy-3-fluoro-5-(1-methyl-1H-indazol-5-yl)phenyl]propionate;

3-[4-cyclopentyloxy-3-fluoro-5-(1-methyl-1H-indazol-5-yl)phenyl]propionic acid;

methyl 3-[4-(indan-2-yloxy)-3-(1H-indazol-5-yl)-5-nitrophenyl]propionate;

methyl 3-[3-amino-4-(indan-2-yloxy)-5-(1H-indazol-5-yl)phenyl]propionate;

3-[3-amino-4-(indan-2-yloxy)-5-(1H-indazol-5-yl)phenyl]propionic acid;

methyl 3-[3-(1-ethyl-1H-indazol-5-yl)-4-(indan-2-yloxy)-5-nitrophenyl]propionate;

methyl 3-[3-amino-5-(1-ethyl-1H-indazol-5-yl)-4-(indan-2-yloxy)phenyl]propionate;

3-[3-amino-5-(1-ethyl-1H-indazol-5-yl)-4-(indan-2-yloxy)phenyl]propionic acid;

methyl 3-[3-(benzo[d]isothiazol-5-yl)-4-cyclopentyloxyphenyl]propionate;

3-[3-(benzo[d]isothiazol-5-yl)-4-cyclopentyloxyphenyl] propionic acid;

methyl 3-[3-(benzo[c]isothiazol-5-yl)-4-cyclopentyloxyphenyl]propionate;

3-[3-(benzo[c]isothiazol-5-yl)-4-cyclopentyloxyphenyl] propionic acid;

methyl 3-[4-cyclopentyloxy-3-(imidazo[1,2-a]pyridin-6-yl)phenyl]propionate;

3-[4-cyclopentyloxy-3-(imidazo[1,2-a]pyridin-6-yl)phenyl]propionic acid;

methyl 3-[4-cyclopentyloxy-3-(1H-pyrrolo[2,3-b]pyridin-6-yl)phenyl]propionate;

3-[4-cyclopentyloxy-3-(1H-pyrrolo[2,3-b]pyridin-6-yl)phenyl]propionic acid;

methyl 3-[4-cyclopentyloxy-3-(1-methyl-1H-pyrrolo[2,3-b]pyridin-6-yl)phenyl]-propionate;

3-[4-cyclopentyloxy-3-(1-methyl-1H-pyrrolo[2,3-b]pyridin-6-yl)phenyl]propionic acid;

methyl 3-[4-cyclohexyloxy-3-(isoquinolin-6-yl)phenyl]-propionate;

3-[4-cyclohexyloxy-3-(isoquinolin-6-yl)phenyl] propionic acid;

methyl 3-[4-cyclopentyloxy-3-(isoquinolin-6-yl)phenyl] propionate;

3-[4-cyclopentyloxy-3-(isoquinolin-6-yl)phenyl] propionic acid;

methyl 3-{4-[4-(trifluoromethyl)phenylmethyloxy]-3-(isoquinolin-6-yl)phenyl}-propionate;

3-{4-[4-(trifluoromethyl)phenylmethyloxy]-3-(isoquinolin-6-yl)phenyl}propionic acid;

methyl 3-[4-(indan-2-yloxy)-3-(isoquinolin-6-yl)phenyl]propionate;

3-[4-(indan-2-yloxy)-3-(isoquinolin-6-yl)phenyl]propionic acid;

methyl 3-[4-cyclopentyloxy-3-(1-oxo-1,2-dihydroisoquinolin-6-yl)phenyl]propionate;

3-[4-cyclopentyloxy-3-(1-oxo-1,2-dihydroisoquinolin-6-yl)phenyl]propionic acid;

3-[4-n-butyloxy-3-(1H-indazol-5-yl)phenyl]propionic acid;

3-[3-(1H-indazol-5-yl)-4-(2-methylpropyloxy)phenyl]propionic acid;

3-[4-cyclohexylmethyloxy-3-(1H-indazol-5-yl)phenyl]propionic acid;

3-[3-(1H-indazol-5-yl)-4-(1-phenylethyloxy)phenyl]propionic acid;

3-[3-(1H-indazol-5-yl)-4-(4-methylphenylmethyloxy)phenyl]propionic acid;

3-[4-(2-fluorophenylmethyloxy)-3-(1H-indazol-5-yl)phenyl]propionic acid;

3-[4-(3-fluorophenylmethyloxy)-3-(1H-indazol-5-yl)phenyl]propionic acid;

3-[4-(4-chlorophenylmethyloxy)-3-(1H-indazol-5-yl)phenyl]propionic acid;

3-{3-(1H-indazol-5-yl)-4-[2-(2-methylphenyl)ethyloxy]phenyl}propionic acid;

3-{3-(1H-indazol-5-yl)-4-[2-(4-methylphenyl)ethyloxy]phenyl}propionic acid;

3-{4-[2-(3-fluorophenyl)ethyloxy]-3-(1H-indazol-5-yl)phenyl}propionic acid;

3-{4-[2-(4-fluorophenyl)ethyloxy]-3-(1H-indazol-5-yl)phenyl}propionic acid;

3-{4-[2-(2-chlorophenyl)ethyloxy]-3-(1H-indazol-5-yl)phenyl}propionic acid;

3-{3-[1H-indazol-5-yl]-4-(2-[2-(trifluoromethyl)phenyl]ethyloxy}phenyl)propionic acid;

3-(4-{2-[4-(N,N-dimethylamino)phenyl]ethyl}-3-[1H-indazol-5-yl]phenyl)propionic acid;

3-{3-(1H-indazol-5-yl)-4-[2-(N-phenyl-N-methylamino)ethyloxy]phenyl}propionic acid;

3-[4-n-butyloxy-3-(1-methyl-1H-indazol-5-yl)phenyl]propionic acid;

3-[3-(1-methyl-1H-indazol-5-yl)-4-(2-methylpropyloxy)phenyl]propionic acid;

3-[4-(2-ethylbutyloxy)-3-(1-methyl-1H-indazol-5-yl)phenyl]propionic acid;

3-[4-cycloheptyloxy-3-(1-methyl-1H-indazol-5-yl)phenyl]propionic acid;

3-[4-cyclopentylmethyloxy-3-(1-methyl-1H-indazol-5-yl)phenyl]propionic acid;

3-[4-cyclohexylmethyloxy-3-(1-methyl-1H-indazol-5-yl)phenyl]propionic acid;

3-[3-(1-methyl-1H-indazol-5-yl)-4-(1-phenylethyloxy)phenyl]propionic acid;

3-[3-(1-methyl-1H-indazol-5-yl)-4-(4-methylphenyl-methyloxy)phenyl]propionic acid;

3-[4-(2-fluorophenylmethyloxy)-3-(1-methyl-1H-indazol-5-yl)phenyl]propionic acid;

3-[4-(3-fluorophenylmethyloxy)-3-(1-methyl-1H-indazol-5-yl)phenyl]propionic acid;

3-[4-(4-chlorophenylmethyloxy)-3-(1-methyl-1H-indazol-5-yl)phenyl]propionic acid;

3-{3-(1-methyl-1H-indazol-5-yl)-4-[4-(trifluoromethyl)phenylmethyloxy]phenyl}-propionic acid;

3-{3-(1-methyl-1H-indazol-5-yl)-4-[2-(2-methylphenyl)ethyloxy]phenyl}propionic acid;

3-{3-(1-methyl-1H-indazol-5-yl)-4-[2-(4-methylphenyl)ethyloxy]phenyl}propionic acid;

3-{4-[2-(3-fluorophenyl)ethyloxy]-3-(1-methyl-1H-indazol-5-yl)phenyl}propionic acid;

3-{4-[2-(4-fluorophenyl)ethyloxy]-3-(1-methyl-1H-indazol-5-yl)phenyl}propionic acid;

3-{4-[2-(2-chlorophenyl)ethyloxy]-3-(1-methyl-1H-indazol-5-yl)phenyl}propionic acid;

3-(3-[1-methyl-1H-indazol-5-yl]-4-{2-[2-(trifluoromethyl)phenyl]ethyloxy}phenyl)-propionic acid;

3-(4-{2-[4-(N,N-dimethylamino)phenyl]ethyl}-3-[1-methyl-1H-indazol-5-yl]phenyl)-propionic acid;

3-{3-(1-methyl-1H-indazol-5-yl)-4-[2-(N-phenyl-N-methylamino)ethyloxy]phenyl}-propionic acid;

3-[4-n-butyloxy-3-(1-ethyl-1H-indazol-5-yl)phenyl]propionic acid;

3-[3-(1-ethyl-1H-indazol-5-yl)-4-(2-methylpropyloxy)phenyl]propionic acid;

3-[4-(2-ethylbutyloxy)-3-(1-ethyl-1H-indazol-5-yl)phenyl]propionic acid;

3-[4-cyclohexyloxy-3-(1-ethyl-1H-indazol-5-yl)phenyl]propionic acid;

3-[4-cycloheptyloxy-3-(1-ethyl-1H-indazol-5-yl)phenyl]propionic acid;

3-[4-cyclopentylmethyloxy-3-(1-ethyl-1H-indazol-5-yl)phenyl]propionic acid;

3-[4-cyclohexylmethyloxy-3-(1-ethyl-1H-indazol-5-yl)phenyl]propionic acid;

3-[3-(1-ethyl-1H-indazol-5-yl)-4-(1-phenylethyloxy)phenyl]propionic acid;

3-[3-(1-ethyl-1H-indazol-5-yl)-4-(4-methylphenyl-methyloxy)phenyl]propionic acid;

3-[3-(1-ethyl-1H-indazol-5-yl)-4-(2-fluorophenyl-methyloxy)phenyl]propionic acid;

3-[3-(1-ethyl-1H-indazol-5-yl)-4-(3-fluorophenyl-methyloxy)phenyl]propionic acid;

3-[3-(1-ethyl-1H-indazol-5-yl)-4-(4-fluorophenyl-methyloxy)phenyl]propionic acid;

3-[4-(4-chlorophenylmethyloxy)-3-(1-ethyl-1H-indazol-5-yl)phenyl]propionic acid;

3-{3-(1-ethyl-1H-indazol-5-yl)-4-[4-(trifluoromethyl)phenylmethyloxy]phenyl}propionic acid;

3-{3-(1-ethyl-1H-indazol-5-yl)-4-[2-(2-methylphenyl)ethyloxy]phenyl}propionic acid;

3-{3-(1-ethyl-1H-indazol-5-yl)-4-[2-(4-methylphenyl)ethyloxy]phenyl}propionic acid;

3-{3-(1-ethyl-1H-indazol-5-yl)-4-[2-(2-fluorophenyl)ethyloxy]phenyl}propionic acid;

3-{3-(1-ethyl-1H-indazol-5-yl)-4-[2-(3-fluorophenyl)ethyloxy]phenyl}propionic acid;

3-{3-(1-ethyl-1H-indazol-5-yl)-4-[2-(4-fluorophenyl)ethyloxy]phenyl}propionic acid;

3-{4-[2-(2-chlorophenyl)ethyloxy]-3-(1-ethyl-1H-indazol-5-yl)phenyl}propionic acid;

3-(3-[1-ethyl-1H-indazol-5-yl]-4-{2-[2-(trifluoromethyl)phenyl]ethyloxy}phenyl)-propionic acid;

3-(4-{2-[4-(N,N-dimethylamino)phenyl]ethyl}-3-[1-ethyl-1H-indazol-5-yl]phenyl)-propionic acid;

3-{3-(1-ethyl-1H-indazol-5-yl)-4-[2-(N-phenyl-N-methylamino)ethyloxy]phenyl}-propionic acid;

3-[4-cyclohexyloxy-3-fluoro-5-(1H-indazol-5-yl)phenyl] propionic acid;

3-[3-fluoro-4-(indan-2-yloxy)-5-(1H-indazol-5-yl) phenyl]propionic acid;

3-[3-fluoro-4-(4-fluorophenylmethyloxy)-5-(1H-indazol-5-yl)phenyl]propionic acid;

3-{3-fluoro-4-[2-(2-fluorophenyl)ethyloxy]-5-(1H-indazol-5-yl)phenyl}propionic acid;

3-[4-cyclohexyloxy-3-fluoro-5-(1-methyl-1H-indazol-5-yl)phenyl]propionic acid;

3-[3-fluoro-4-(indan-2-yloxy)-5-(1-methyl-1H-indazol-5-yl)phenyl]propionic acid;

3-[4-cyclopentyloxy-3-(1-ethyl-1H-indazol-5-yl)-5-fluorophenyl]propionic acid;

3-[4-cyclohexyloxy-3-(1-ethyl-1H-indazol-5-yl)-5-fluorophenyl]propionic acid;

3-[3-(1-ethyl-1H-indazol-5-yl)-5-fluoro-4-(indan-2-yloxy)phenyl]propionic acid;

3-[3-(1-ethyl-1H-indazol-5-yl)-5-fluoro-4-(1-phenylethyloxy)phenyl]propionic acid;

3-[3-amino-4-cyclopentyloxy-5-(1H-indazol-5-yl) phenyl]propionic acid;

3-[3-amino-4-cyclohexyloxy-5-(1H-indazol-5-yl)phenyl] propionic acid;

3-[3-amino-4-(4-fluorophenylmethyloxy)-5-(1H-indazol-5-yl)phenyl]propionic acid;

3-{3-amino-4-[2-(2-fluorophenyl)ethyloxy]-5-(1H-indazol-5-yl)phenyl}propionic acid;

3-[3-amino-5-(1H-indazol-5-yl)-4-(1-phenylethyloxy) phenyl]propionic acid;

3-[3-amino-4-cyclopentyloxy-5-(1-methyl-1H-indazol-5-yl)phenyl]propionic acid;

3-[3-amino-4-cyclohexyloxy-5-(1-methyl-1H-indazol-5-yl)phenyl]propionic acid;

3-[3-amino-4-(indan-2-yloxy)-5-(1-methyl-1H-indazol-5-yl)phenyl]propionic acid;

3-[3-amino-5-(1-methyl-1H-indazol-5-yl)-4-(1-phenylethyloxy)phenyl]propionic acid;

3-[3-amino-4-cyclopentyloxy-5-(1-ethyl-1H-indazol-5-yl)phenyl]propionic acid;

3-[3-amino-4-cyclohexyloxy-5-(1-ethyl-1H-indazol-5-yl) phenyl]propionic acid;

3-[3-amino-5-(1-ethyl-1H-indazol-5-yl)-4-(1-phenylethyloxy)phenyl]propionic acid;

3-[4-cyclopentyloxy-3-(3-methyl-1H-indazol-5-yl) phenyl]propionic acid;

3-[4-cyclopentyloxy-3-(1,3-dimethyl-1H-indazol-5-yl) phenyl]propionic acid;

3-[4-cyclopentyloxy-3-(1-ethyl-3-methyl-1H-indazol-5-yl)phenyl]propionic acid;

3-[3-(3-carboxyl-1H-indazol-5-yl)-4-cyclopentyloxyphenyl]propionic acid;

3-[3-(3-carboxyl-1-methyl-1H-indazol-5-yl)-4-cyclopentyloxyphenyl]propionic acid;

3-[3-(3-acetyl-1H-indazol-5-yl)-4-cyclopentyloxyphenyl]propionic acid;

3-[3-(3-acetyl-1-methyl-1H-indazol-5-yl)-4-cyclopentyloxyphenyl]propionic acid;

3-[4-cyclopentyloxy-3-(3-formyl-1H-indazol-5-yl) phenyl]propionic acid;

3-[4-cyclopentyloxy-3-(3-hydroxy-1H-indazol-5-yl) phenyl]propionic acid;

3-[4-cyclopentyloxy-3-(3-hydroxy-1-methyl-1H-indazol-5-yl)phenyl]propionic acid;

3-[4-cyclopentyloxy-3-(3-methoxy-1H-indazol-5-yl) phenyl]propionic acid;

3-[4-cyclopentyloxy-3-(3-methoxy 1-methyl-1H-indazol-5-yl)phenyl]propionic acid.

Among them, examples of compounds wherein enantiomers exist include:

methyl 3-[3-(1H-indol-5-yl)-4-(1-phenylethyloxy) phenyl]propionate;

3-[3-(1H-indol-5-yl)-4-(1-phenylethyloxy)phenyl] propionic acid;

3-[4-(bicyclo[2,2,1]hept-2-ylmethyloxy)-3-(1H-indol-5-yl)phenyl]propionic acid;

methyl 3-[4-(2,3-dimethylbutyloxy)-3-(1H-indol-5-yl) phenyl]propionate;

3-[4-(2,3-dimethylbutyloxy)-3-(1H-indol-5-yl)phenyl] propionic acid;

3-[3-(1H-indol-5-yl)-4-(3-methylcyclopentyloxy)phenyl] propionic acid.

Specific examples of the compound (I) of the present invention also include enantiomers of these compounds and mixtures thereof.

Other examples of compounds where enantiomers exist include the followings:

3-[3-amino-5-(naphthalen-2-yl)-4-(1-phenylethyloxy) phenyl]propionic acid;

3-[3-amino-5-(1H-indol-5-yl)-4-(1-phenylethyloxy) phenyl]propionic acid;

3-[3-amino-5-(1-methyl-1H-indol-5-yl)-4-(1-phenylethyloxy)phenyl]propionic acid;

3-[3-(1H-indazol-5-yl)-4-(1-phenylethyloxy)phenyl] propionic acid;

3-[3-(1-methyl-1H-indazol-5-yl)-4-(1-phenylethyloxy) phenyl]propionic acid;

3-[3-(1-ethyl-1H-indazol-5-yl)-4-(1-phenylethyloxy) phenyl]propionic acid;

3-[3-amino-5-(1H-indazol-5-yl)-4-(1-phenylethyloxy) phenyl]propionic acid;

3-[3-amino-5-(1-methyl-1H-indazol-5-yl)-4-(1-phenylethyloxy)phenyl]propionic acid;

3-[3-amino-5-(1-ethyl-1H-indazol-5-yl)-4-(1-phenylethyloxy)phenyl]propionic acid;

Specific examples of the compound (I) of the present invention include enantiomers of these compounds and mixtures thereof.

Particularly preferred examples of the compound (I) of the present invention include the following compounds:

3-[4-cyclohexylmethyloxy-3-(6-hydroxynaphthalen-2-yl) phenyl]propionic acid;

3-[4-cyclopentylmethyloxy-3-(6-hydroxynaphthalen-2-yl)phenyl]propionic acid;

3-{4-[2-(2-fluorophenyl)ethyloxy]-3-(6-hydroxy-naphthalen-2-yl)phenyl}propionic acid;

3-[3-(6-aminonaphthalen-2-yl)-4-cyclopentylmethyl-oxyphenyl]propionic acid;

3-{4-cyclopentylmethyloxy-3-[6-(N-methylamino) naphthalen-2-yl]phenyl}propionic acid;

3-{4-cyclopentylmethyloxy-3-[6-(N,N-dimethylamino)naphthalen-2-yl]phenyl}-propionic acid;
3-[4-(2-fluorophenylmethyloxy)-3-(naphthalen-2-yl)phenyl]propionic acid;
3-[4-(3-fluorophenylmethyloxy)-3-(naphthalen-2-yl)phenyl]propionic acid;
3-[4-(4-fluorophenylmethyloxy)-3-(naphthalen-2-yl)phenyl]propionic acid;
3-[4-butyloxy-3-(naphthalen-2-yl)phenyl]propionic acid;
3-[4-cyclopentylmethyloxy-3-(naphthalen-2-yl)phenyl]propionic acid;
3-[4-cyclopentyloxy-3-(naphthalen-2-yl)phenyl]propionic acid;
3-[4-cyclohexyloxy-3-(naphthalen-2-yl)phenyl]propionic acid;
3-[3-(naphthalen-2-yl)-4-(2-phenylethyloxy)phenyl]propionic acid;
3-{4-[2-(2-fluorophenyl)ethyloxy]-3-(naphthalen-2-yl)phenyl}propionic acid;
3-{4-[2-(3-fluorophenyl)ethyloxy]-3-(naphthalen-2-yl)phenyl}propionic acid;
3-{4-[2-(4-fluorophenyl)ethyloxy]-3-(naphthalen-2-yl)phenyl}propionic acid;
3-[4-cyclohexylmethyloxy-3-(naphthalen-2-yl)phenyl]propionic acid;
3-[4-cyclohexylmethyloxy-3-(6-methoxynaphthalen-2-yl)phenyl]propionic acid;
3-{4-cyclohexylmethyloxy-3-[6-(2-hydroxyethyloxy)naphthalen-2-yl]phenyl}propionic acid;
3-{4-cyclopentylmethyloxy-3-[6-(2-hydroxyethylamino)naphthalen-2-yl]phenyl}propionic acid;
3-[3-amino-4-cyclopentylmethyloxy-5-(naphthalen-2-yl)phenyl]propionic acid;
3-[4-cyclopentylmethyloxy-3-(1H-indol-5-yl)phenyl]propionic acid;
3-[4-cyclopentyloxy-3-(1H-indol-5-yl)phenyl]propionic acid;
3-[4-cyclohexyloxy-3-(1H-indol-5-yl)phenyl]propionic acid;
3-{4-[2-(2-fluorophenyl)ethyloxy]-3-(1H-indol-5-yl)phenyl}propionic acid;
3-[4-cyclopentyloxy-3-(1-methyl-1H-indol-5-yl)phenyl]propionic acid;
3-[4-cyclohexyloxy-3-(1-methyl-1H-indol-5-yl)phenyl]propionic acid;
3-[4-cyclopentylmethyloxy-3-(3-methyl-1H-indol-5-yl)phenyl]propionic acid;
3-[4-butyloxy-3-(1H-indol-5-yl)phenyl]propionic acid;
3-[3-(1H-indol-5-yl)-4-(1-phenylethyloxy)phenyl]propionic acid;
3-[3-(1H-indol-5-yl)-4-(2-methylphenylmethyloxy)phenyl]propionic acid;
3-[3-(1H-indol-5-yl)-4-(3-methylphenylmethyloxy)phenyl]propionic acid;
3-[3-(1H-indol-5-yl)-4-(4-methylphenylmethyloxy)phenyl]propionic acid;
3-[4-(2-fluorophenylmethyloxy)-3-(1H-indol-5-yl)phenyl]propionic acid;
3-[4-(3-fluorophenylmethyloxy)-3-(1H-indol-5-yl)phenyl]propionic acid;
3-[4-(4-fluorophenylmethyloxy)-3-(1H-indol-5-yl)phenyl]propionic acid;
3-[4-(2-chlorophenylmethyloxy)-3-(1H-indol-5-yl)phenyl]propionic acid;
3-[4-(3-chlorophenylmethyloxy)-3-(1H-indol-5-yl)phenyl]propionic acid;
3-[4-(4-chlorophenylmethyloxy)-3-(1H-indol-5-yl)phenyl]propionic acid;
3-[4-(2,4-difluorophenylmethyloxy)-3-(1H-indol-5-yl)phenyl]propionic acid;
3-[4-(3,4-difluorophenylmethyloxy)-3-(1H-indol-5-yl)phenyl]propionic acid;
3-[4-(2,3-dichlorophenylmethyloxy)-3-(1H-indol-5-yl)phenyl]propionic acid;
3-[4-(2,4-dichlorophenylmethyloxy)-3-(1H-indol-5-yl)phenyl]propionic acid;
3-[4-(2,6-dichlorophenylmethyloxy)-3-(1H-indol-5-yl)phenyl]propionic acid;
3-[4-(3,4-dichlorophenylmethyloxy)-3-(1H-indol-5-yl)phenyl]propionic acid;
3-{3-(1H-indol-5-yl)-4-[2-(trifluoromethyl)phenylmethyloxy]phenyl}propionic acid;
3-{3-(1H-indol-5-yl)-4-[4-(trifluoromethyl)phenylmethyloxy]phenyl}propionic acid;
3-[4-(3,5-dimethylphenylmethyloxy)-3-(1H-indol-5-yl)phenyl]propionic acid;
3-[4-(2-ethylbutyloxy)-3-(1H-indol-5-yl)phenyl]propionic acid;
3-[4-(3,5-dichlorophenylmethyloxy)-3-(1H-indol-5-yl)phenyl]propionic acid;
3-{3-(1H-indol-5-yl)-4-[2-(2-methylphenyl)ethyloxy]phenyl}propionic acid;
3-{3-(1H-indol-5-yl)-4-[2-(3-methylphenyl)ethyloxy]phenyl}propionic acid;
3-{3-(1H-indol-5-yl)-4-[2-(4-methylphenyl)ethyloxy]phenyl}propionic acid;
3-{3-(1H-indol-5-yl)-4-[2-(2-methoxyphenyl)ethyloxy]phenyl}propionic acid;
3-{3-(1H-indol-5-yl)-4-[2-(4-methoxyphenyl)ethyloxy]phenyl}propionic acid;
3-{4-[2-(2-chlorophenyl)ethyloxy]-3-(1H-indol-5-yl)phenyl}propionic acid;
3-{4-[2-(3-chlorophenyl)ethyloxy]-3-(1H-indol-5-yl)phenyl}propionic acid;
3-{4-[2-(4-chlorophenyl)ethyloxy]-3-(1H-indol-5-yl)phenyl}propionic acid;
3-[3-(1H-indol-5-yl)-4-{2-[2-(trifluoromethyl)phenyl]ethyloxy}phenyl]propionic acid;
3-{4-{2-[4-(N,N-dimethylamino)phenyl]ethyloxy}-3-[1H-indol-5-yl]phenyl)propionic acid;
3-{3-(1H-indol-5-yl)-4-[2-(phenyloxy)ethyloxy]phenyl}propionic acid;
3-{4-[2-(2-chlorophenyloxy)ethyloxy]-3-(1H-indol-5-yl)phenyl}propionic acid;
3-(4-[2-(4-chlorophenyloxy)ethyloxy]-3-(1H-indol-5-yl)phenyl}propionic acid;
3-{3-(1H-indol-5-yl)-4-[2-phenylthio)ethyloxy]phenyl}propionic acid;
3-{3-(1H-indol-5-yl)-4-[2-(N-phenyl-N-methylamino)ethyloxy]phenyl}propionic acid;
3-[4-cyclohexylmethyloxy-3-(1H-indol-5-yl)phenyl]propionic acid;
3-[4-cyclohexylmethyloxy-3-(1-methyl-1H-indol-5-yl)phenyl]propionic acid;

3-[4-cyclopentylmethyloxy-3-(1-methyl-1H-indol-5-yl)phenyl]propionic acid;
3-[4-cyclopentylmethyloxy-3-(1-ethyl-1H-indol-5-yl)phenyl]propionic acid;
3-[4-(2-chlorophenylmethyloxy)-3-(1-methyl-1H-indol-5-yl)phenyl]propionic acid;
3-[4-cyclopentyloxy-3-(1-ethyl-1H-indol-5-yl)phenyl]propionic acid;
3-[4-cyclohexyloxy-3-(1-ethyl-1H-indol-5-yl)phenyl]propionic acid;
3-[4-(2-chlorophenylmethyloxy)-3-(1-ethyl-1H-indol-5-yl)phenyl]propionic acid;
3-[4-cyclopentylmethyloxy-3-(1,3-dimethyl-1H-indol-5-yl)phenyl]propionic acid;
3-[4-cyclopentylmethyloxy-3-fluoro-5-(1H-indol-5-yl)phenyl]propionic acid;
3-[3-amino-4-cyclopentylmethyloxy-5-(1H-indol-5-yl)phenyl]propionic acid;
3-[3-amino-4-cyclopentylmethyloxy-5-(1-methyl-1H-indol-5-yl)phenyl]propionic acid;
3-[4-cyclohexylmethyloxy-3-(2,3-dimethyl-1H-indol-5-yl)phenyl]propionic acid;
3-[4-cyclopentylmethyloxy-3-(1,2,3-trimethyl-1H-indol-5-yl)phenyl]propionic acid;
3-[3-(benzo[b]furan-5-yl)-4-cyclopentylmethyloxyphenyl]propionic acid;
3-[4-cyclohexylmethyloxy-3-(2,3-dimethylbenzo[b]furan-5-yl)phenyl]propionic acid;
3-[3-(benzo[b]thiophen-5-yl)-4-cyclopentylmethyloxyphenyl]propionic acid;
3-[3-(2-aminobenzothiazol-6-yl)-4-cyclopentylmethyloxyphenyl]propionic acid;
3-[3-(2-aminobenzothiazol-6-yl)-4-cyclohexylmethyloxyphenyl]propionic acid;
3-[3-(2-aminobenzothiazol-6-yl)-4-butyloxyphenyl]propionic acid;
3-[3-(2-aminobenzothiazol-6-yl)-4-cyclopentyloxyphenyl]propionic acid;
3-[3-(2-aminobenzothiazol-6-yl)-4-cyclohexyloxyphenyl]propionic acid;
3-[3-(benzothiazol-6-yl)-4-cyclopentylmethyloxyphenyl]propionic acid;
3-[4-cyclopentylmethyloxy-3-(2-methoxybenzothiazol-6-yl)phenyl]propionic acid;
3-[4-cyclopentylmethyloxy-3-(2-methylbenzothiazol-6-yl)phenyl]propionic acid;
3-[4-cyclopentylmethyloxy-3-(2-thioxo-2,3-dihydrobenzothiazol-6-yl)phenyl]propionic acid;
3-[4-cyclopentylmethyloxy-3-(2-oxo-2,3-dihydrobenzothiazol-6-yl)phenyl]propionic acid;
3-[4-cyclopentylmethyloxy-3-(2-oxo-3-methyl-2,3-dihydrobenzothiazol-6-yl)phenyl]propionic acid;
3-[4-cyclopentylmethyloxy-3-(quinolin-3-yl)phenyl]propionic acid;
3-[4-cyclohexylmethyloxy-3-(quinolin-3-yl)phenyl]propionic acid;
3-[4-cyclohexylmethyloxy-3-(quinolin-6-yl)phenyl]propionic acid;
3-[4-cyclohexylmethyloxy-3-(2-oxo-1,2-dihydroquinolin-6-yl)phenyl]propionic acid;
3-[3-(benzothiazol-6-yl)-4-cyclohexyloxyphenyl]propionic acid;
3-[4-(2-fluorophenyloxy)-3-(1H-indol-5-yl)phenyl]propionic acid;
3-[4-cyclopentylmethyloxy-3-(2-methyl-1H-indol-5-yl)phenyl]propionic acid;
3-[4-(4-fluorophenylmethyloxy)-3-(1-methyl-1H-indol-5-yl)phenyl]propionic acid;
3-{3-(1-methyl-1H-indol-5-yl)-4-[4-(trifluoromethyl)phenylmethyloxy]phenyl}propionic acid;
3-(4-{2-[4-(N,N-dimethylamino)phenyl]ethyloxy}-3-[1-methyl-1H-indol-5-yl]phenyl)-propionic acid;
3-[3-(1-ethyl-1H-indol-5-yl)-4-(4-fluorophenylmethyloxy)phenyl]propionic acid;
3-{3-(1-ethyl-1H-indol-5-yl)-4-[4-(trifluoromethyl)phenylmethyloxy]phenyl}propionic acid;
3-(3-[1-ethyl-1H-indol-5-yl]-4-{2-[4-(N,N-dimethylamino)phenyl]ethyloxy}phenyl)-propionic acid;
3-[4-cyclopentyloxy-3-fluoro-5-(1H-indol-5-yl)phenyl]propionic acid;
3-[4-cyclohexyloxy-3-fluoro-5-(1H-indol-5-yl)phenyl]propionic acid;
3-[4-cyclopentyloxy-3-fluoro-5-(1-methyl-1H-indol-5-yl)phenyl]propionic acid;
3-[4-cyclohexyloxy-3-fluoro-5-(1-methyl-1H-indol-5-yl)phenyl]propionic acid;
3-[4-cyclopentyloxy-3-(1-ethyl-1H-indol-5-yl)-5-fluorophenyl]propionic acid;
3-[4-cyclohexyloxy-3-(1-ethyl-1H-indol-5-yl)-5-fluorophenyl]propionic acid;
3-[3-amino-4-cyclopentyloxy-5-(1H-indol-5-yl)phenyl]propionic acid;
3-[3-amino-4-cyclohexyloxy-5-(1H-indol-5-yl)phenyl]propionic acid;
3-[3-amino-4-cyclopentyloxy-5-(1-methyl-1H-indol-5-yl)phenyl]propionic acid;
3-[3-amino-4-cyclohexyloxy-5-(1-methyl-1H-indol-5-yl)phenyl]propionic acid;
3-[4-cyclopentylmethyloxy-3-(1-propyl-1H-indol-5-yl)phenyl]propionic acid;
3-[4-cyclopentyloxy-3-(1-propyl-1H-indol-5-yl)phenyl]propionic acid;
3-[4-cyclohexyloxy-3-(1-propyl-1H-indol-5-yl)phenyl]propionic acid;
3-[3-(benzo[b]thiophen-5-yl)-4-cyclopentyloxyphenyl]propionic acid;
3-[3-(benzo[b]thiophen-5-yl)-4-cyclohexyloxyphenyl]propionic acid;
3-[3-(benzothiazol-6-yl)-4-cyclopentyloxyphenyl]propionic acid;
3-[3-(benzothiazol-6-yl)-4-(2-chlorophenylmethyloxy)phenyl]propionic acid;
3-[3-(benzothiazol-6-yl)-4-(4-fluorophenylmethyloxy)phenyl]propionic acid;
3-{3-(benzothiazol-6-yl)-4-[4-(trifluoromethyl)phenylmethyloxy]phenyl}propionic acid;
3-(3-[benzothiazol-6-yl]-4-{2-[4-(N,N-dimethylamino)phenyl]ethyl}phenyl)propionic acid;
3-[3-(2-aminobenzothiazol-6-yl)-4-(4-fluorophenylmethyloxy)phenyl]propionic acid;
3-[3-(2-aminobenzothiazol-6-yl)-4-(2-chlorophenylmethyloxy)phenyl]propionic acid;
3-{3-(2-aminobenzothiazol-6-yl)-4-[4-(trifluoromethyl)phenylmethyloxy]phenyl}-propionic acid;

3-(3-[2-aminobenzothiazol-6-yl]-4-{2-[4-(N,N-dimethylamino)phenyl]ethyl}phenyl)-propionic acid;

3-[3-(2-aminobenzothiazol-6-yl)-4-(cyclopentyloxy)-5-fluorophenyl]propionic acid;

3-[3-(2-aminobenzothiazol-6-yl)-4-(cyclohexyloxy)-5-fluorophenyl]propionic acid;

3-[4-cyclopentyloxy-3-(quinolin-3-yl)phenyl]propionic acid;

3-[4-cyclohexyloxy-3-(quinolin-3-yl)phenyl]propionic acid;

3-[4-(2-chlorophenylmethyloxy)-3-(quinolin-3-yl)phenyl]propionic acid;

3-[4-cyclopentyloxy-3-(quinolin-6-yl)phenyl]propionic acid;

3-[4-cyclohexyloxy-3-(quinolin-6-yl)phenyl]propionic acid;

3-[4-(2-chlorophenylmethyloxy)-3-(quinolin-6-yl)phenyl]propionic acid.

Particularly preferred specific examples of the compound (I) of the present inventions include the following compounds:

3-[3-amino-4-cyclopentyloxy-5-(naphthalen-2-yl)phenyl]propionic acid;

3-[3-amino-4-cyclohexyloxy-5-(naphthalen-2-yl)phenyl]propionic acid;

3-[3-amino-5-(naphthalen-2-yl)-4-(1-phenylethyloxy)phenyl]propionic acid;

3-[3-amino-4-(4-methyl benzyloxy)-5-(naphthalen-2-yl)phenyl]propionic acid;

3-{3-amino-4-[2-(4-methylphenyl)ethyloxy]-5-(naphthalen-2-yl)phenyl}propionic acid;

3-(3-amino-5-[naphthalen-2-yl]-4-{1'-[4-(trifluoromethyl)phenyl]ethyloxy}phenyl)-propionic acid;

3-[3-amino-4-(indan-2-yloxy)-5-(naphthalen-2-yl)phenyl]propionic acid;

3-{3-amino-4-[2-(2-fluorophenyl)ethyloxy]-5-(naphthalen-2-yl)phenyl}propionic acid;

3-(3-amino-4-{2-[4-(N,N-dimethylamino)phenyl]ethyloxy}-5-[naphthalen-2-yl]phenyl)-propionic acid;

3-{3-amino-5-(naphthalen-2-yl)-4-[2-(N-phenyl-N-methylamino)ethyloxy]phenyl}-propionic acid;

3-{3-amino-5-(naphthalen-2-yl)-4-[4-(trifluoromethyl)phenylmethyloxy]phenyl}-propionic acid;

3-[3-amino-4-(2-methylpropyloxy)-3-(naphthalen-2-yl)phenyl]propionic acid;

3-[3-amino-4-cyclopentyloxy-5-(1-ethyl-1H-indol-5-yl)phenyl]propionic acid;

3-[3-amino-4-cyclohexyloxy-5-(1-ethyl-1H-indol-5-yl)phenyl]propionic acid;

3-[3-amino-5-(1H-indol-5-yl)-4-(1-phenylethyloxy)phenyl]propionic acid;

3-[3-amino-5-(1-methyl-1H-indol-5-yl)-4-(1-phenylethyloxy)phenyl]propionic acid;

3-[3-amino-4-(indan-2-yloxy)-5-(1H-indol-5-yl)phenyl]propionic acid;

3-[3-amino-4-(indan-2-yloxy)-5-(1-methyl-1H-indol-5-yl)phenyl]propionic acid;

3-{3-amino-5-(1H-indol-5-yl)-4-[4-(trifluoromethyl)benzyloxy]phenyl}propionic acid;

3-[3-amino-4-(2-ethylbutyloxy)-5-(1H-indol-5-yl)phenyl]propionic acid;

3-[4-cyclopentyloxy-3-(1H-indazol-5-yl)phenyl]propionic acid;

3-[4-cyclopentyloxy-3-(1-methyl-1H-indazol-5-yl)phenyl]propionic acid;

3-[4-cyclopentyloxy-3-(1-ethyl-1H-indazol-5-yl)phenyl]propionic acid;

3-[4-cyclopentylmethyloxy-3-(1H-indazol-5-yl)phenyl]propionic acid;

3-[4-cyclohexyloxy-3-(1H-indazol-5-yl)phenyl]propionic acid;

3-[4-cyclohexyloxy-3-(1-methyl-1H-indazol-5-yl)phenyl]propionic acid;

3-[4-cycloheptyloxy-3-(1H-indazol-5-yl)phenyl]propionic acid;

3-[4-(2-ethylbutyloxy)-3-(1H-indazol-5-yl)phenyl]propionic acid;

3-[4-(indan-2-yloxy)-3-(1H-indazol-5-yl)phenyl]propionic acid;

3-[4-(indan-2-yloxy)-3-(1-methyl-1H-indazol-5-yl)phenyl]propionic acid;

3-[3-(1-ethyl-1H-indazol-5-yl)-4-(indan-2-yloxy)phenyl]propionic acid;

3-[4-(4-fluorobenzyloxy)-3-(1H-indazol-5-yl)phenyl]propionic acid;

3-[4-(4-fluorobenzyloxy)-3-(1-methyl-1H-indazol-5-yl)phenyl]propionic acid;

3-{3-(1H-indazol-5-yl)-4-[4-(trifluoromethyl)benzyloxy]phenyl}propionic acid;

3-{4-[2-(2-fluorophenyl)ethyloxy]-3-(1H-indazol-5-yl)phenyl}propionic acid;

3-{4-[2-(2-fluorophenyl)ethyloxy]-3-(1-methyl-1H-indazol-5-yl)phenyl}propionic acid;

3-[4-cyclopentyloxy-3-fluoro-5-(1H-indazol-5-yl)phenyl]propionic acid;

3-[4-cyclopentyloxy-3-fluoro-5-(1-methyl-1H-indazol-5-yl)phenyl]propionic acid;

3-[3-amino-4-(indan-2-yloxy)-5-(1H-indazol-5-yl)phenyl]propionic acid;

3-[3-amino-5-(1-ethyl-1H-indazol-5-yl)-4-(indan-2-yloxy)phenyl]propionic acid;

3-[3-(benzo[d]isothiazol-5-yl)-4-cyclopentyloxyphenyl]propionic acid;

3-[4-cyclopentyloxy-3-(imidazo[1,2-a]pyridin-6-yl)phenyl]propionic acid;

3-[4-cyclopentyloxy-3-(1H-pyrrolo[2,3-b]pyridin-6-yl)phenyl]propionic acid;

3-[4-cyclopentyloxy-3-(1-methyl-1H-pyrrolo[2,3-b]pyridin-6-yl)phenyl]propionic acid;

3-[4-cyclohexyloxy-3-(isoquinolin-6-yl)phenyl]propionic acid;

3-[4-cyclopentyloxy-3-(isoquinolin-6-yl)phenyl]propionic acid;

3-{4-[4-(trifluoromethyl)phenylmethyloxy]-3-(isoquinolin-6-yl)phenyl}propionic acid;

3-[4-(indan-2-yloxy)-3-(isoquinolin-6-yl)phenyl]propionic acid;

3-[4-cyclopentyloxy-3-(1-oxo-1,2-dihydroisoquinolin-6-yl)phenyl]propionic acid;

3-[4-n-butyloxy-3-(1H-indazol-5-yl)phenyl]propionic acid;

3-[3-(1H-indazol-5-yl)-4-(2-methylpropyloxy)phenyl]propionic acid;

3-[4-cyclohexylmethyloxy-3-(1H-indazol-5-yl)phenyl]
propionic acid;
3-[3-(1H-indazol-5-yl)-4-(1-phenylethyloxy)phenyl]
propionic acid;
3-[3-(1H-indazol-5-yl)-4-(4-methylphenylmethyloxy)
phenyl]propionic acid;
3-[4-(2-fluorophenylmethyloxy)-3-(1H-indazol-5-yl)
phenyl]propionic acid;
3-[4-(3-fluorophenylmethyloxy)-3-(1H-indazol-5-yl)
phenyl]propionic acid;
3-[4-(4-chlorophenylmethyloxy)-3-(1H-indazol-5-yl)
phenyl]propionic acid;
3-{3-(1H-indazol-5-yl)-4-[2-(2-methylphenyl)ethyloxy]
phenyl}propionic acid;
3-{3-(1H-indazol-5-yl)-4-[2-(4-methylphenyl)ethyloxy]
phenyl}propionic acid;
3-{4-[2-(3-fluorophenyl)ethyloxy]-3-(1H-indazol-5-yl)
phenyl}propionic acid;
3-{4-[2-(4-fluorophenyl)ethyloxy]-3-(1H-indazol-5-yl)
phenyl}propionic acid;
3-{4-[2-(2-chlorophenyl)ethyloxy]-3-(1H-indazol-5-yl)
phenyl}propionic acid;
3-(3-[1H-indazol-5-yl]-4-{2-[2-(trifluoromethyl)phenyl]
ethyloxy}phenyl)propionic acid;
3-(4-{2-[4-(N,N-dimethylamino)phenyl]ethyl}-3-[1H-
indazol-5-yl]phenyl)propionic acid;
3-{3-(1H-indazol-5-yl)-4-[2-(N-phenyl-N-methylamino)
ethyloxy]phenyl}-propionic acid;
3-[4-n-butyloxy-3-(1-methyl-1H-indazol-5-yl)phenyl]
propionic acid;
3-[3-(1-methyl-1H-indazol-5-yl)-4-(2-methylpropyloxy)
phenyl]propionic acid;
3-[4-(2-ethylbutyloxy)-3-(1-methyl-1H-indazol-5-yl)
phenyl]propionic acid;
3-[4-cycloheptyloxy-3-(1-methyl-1H-indazol-5-yl)
phenyl]propionic acid;
3-[4-cyclopentylmethyloxy-3-(1-methyl-1H-indazol-5-
yl)phenyl]propionic acid;
3-[4-cyclohexylmethyloxy-3-(1-methyl-1H-indazol-5-yl)
phenyl]propionic acid;
3-[3-(1-methyl-1H-indazol-5-yl)-4-(1-phenylethyloxy)
phenyl]propionic acid;
3-[3-(1-methyl-1H-indazol-5-yl)-4-(4-methylphenyl-
methyloxy)phenyl]propionic acid;
3-[4-(2-fluorophenylmethyloxy)-3-(1-methyl-1H-
indazol-5-yl)phenyl]propionic acid;
3-[4-(3-fluorophenylmethyloxy)-3-(1-methyl-1H-
indazol-5-yl)phenyl]propionic acid;
3-[4-(4-chlorophenylmethyloxy)-3-(1-methyl-1H-
indazol-5-yl)phenyl]propionic acid;
3-{3-(1-methyl-1H-indazol-5-yl)-4-[4-(trifluoromethyl)
phenylmethyloxy]phenyl}-propionic acid;
3-{3-(1-methyl-1H-indazol-5-yl)-4-[2-(2-methylphenyl)
ethyloxy]phenyl}propionic acid;
3-{3-(1-methyl-1H-indazol-5-yl)-4-[2-(4-methylphenyl)
ethyloxy]phenyl}propionic acid;
3-{4-[2-(3-fluorophenyl)ethyloxy]-3-(1-methyl-1H-
indazol-5-yl)phenyl}propionic acid;
3-{4-[2-(4-fluorophenyl)ethyloxy]-3-(1-methyl-1H-
indazol-5-yl)phenyl}propionic acid;
3-{4-[2-(2-chlorophenyl)ethyloxy]-3-(1-methyl-1H-
indazol-5-yl)phenyl}propionic acid;

3-(3-[1-methyl-1H-indazol-5-yl]-4-{2-[2-(trifluoromethyl)phenyl]ethyloxy}phenyl)-propionic
acid;
3-(4-{2-[4-(N,N-dimethylamino)phenyl]ethyl}-3-[1-
methyl-1H-indazol-5-yl]phenyl)-propionic acid;
3-{3-(1-methyl-1H-indazol-5-yl)-4-[2-(N-phenyl-N-
methylamino)ethyloxy]phenyl}-propionic acid;
3-[4-n-butyloxy-3-(1-ethyl-1H-indazol-5-yl)phenyl]
propionic acid;
3-[3-(1-ethyl-1H-indazol-5-yl)-4-(2-methylpropyloxy)
phenyl]propionic acid;
3-[4-(2-ethylbutyloxy)-3-(1-ethyl-1H-indazol-5-yl)
phenyl]propionic acid;
3-[4-cyclohexyloxy-3-(1-ethyl-1H-indazol-5-yl)phenyl]
propionic acid;
3-[4-cycloheptyloxy-3-(1-ethyl-1H-indazol-5-yl)phenyl]
propionic acid;
3-[4-cyclopentylmethyloxy-3-(1-ethyl-1H-indazol-5-yl)
phenyl]propionic acid;
3-[4-cyclohexylmethyloxy-3-(1-ethyl-1H-indazol-5-yl)
phenyl]propionic acid;
3-[3-(1-ethyl-1H-indazol-5-yl)-4-(1-phenylethyloxy)
phenyl]propionic acid;
3-[3-(1-ethyl-1H-indazol-5-yl)-4-(4-methylphenyl-
methyloxy)phenyl]propionic acid;
3-[3-(1-ethyl-1H-indazol-5-yl)-4-(2-fluorophenyl-
methyloxy)phenyl]propionic acid;
3-[3-(1-ethyl-1H-indazol-5-yl)-4-(3-fluorophenyl-
methyloxy)phenyl]propionic acid;
3-[3-(1-ethyl-1H-indazol-5-yl)-4-(4-fluorophenyl-
methyloxy)phenyl]propionic acid;
3-[4-(4-chlorophenylmethyloxy)-3-(1-ethyl-1H-indazol-
5-yl)phenyl]propionic acid;
3-{3-(1-ethyl-1H-indazol-5-yl)-4-[4-(trifluoromethyl)
phenylmethyloxy]phenyl}propionic acid;
3-{3-(1-ethyl-1H-indazol-5-yl)-4-[2-(2-methylphenyl)
ethyloxy]phenyl}propionic acid;
3-{3-(1-ethyl-1H-indazol-5-yl)-4-[2-(4-methylphenyl)
ethyloxy]phenyl}propionic acid;
3-{3-(1-ethyl-1H-indazol-5-yl)-4-[2-(2-fluorophenyl)
ethyloxy]phenyl}propionic acid;
3-{3-(1-ethyl-1H-indazol-5-yl)-4-[2-(3-fluorophenyl)
ethyloxy]phenyl}propionic acid;
3-{3-(1-ethyl-1H-indazol-5-yl)-4-[2-(4-fluorophenyl)
ethyloxy]phenyl}propionic acid;
3-{4-[2-(2-chlorophenyl)ethyloxy]-3-(1-ethyl-1H-
indazol-5-yl)phenyl}propionic acid;
3-(3-[1-ethyl-1H-indazol-5-yl]-4-{2-[2-(trifluoromethyl)
phenyl]ethyloxy}phenyl)-propionic acid;
3-(4-{2-[4-(N,N-dimethylamino)phenyl]ethyl}-3-[1-
ethyl-1H-indazol-5-yl]phenyl)-propionic acid;
3-{3-(1-ethyl-1H-indazol-5-yl)-4-[2-(N-phenyl-N-
methylamino)ethyloxy]phenyl}-propionic acid;
3-[4-cyclohexyloxy-3-fluoro-5-(1H-indazol-5-yl)phenyl]
propionic acid;
3-[3-fluoro-4-(indan-2-yloxy)-5-(1H-indazol-5-yl)
phenyl]propionic acid;
3-[3-fluoro-4-(4-fluorophenylmethyloxy)-5-(1H-indazol-
5-yl)phenyl]propionic acid;
3-{3-fluoro-4-[2-(2-fluorophenyl)ethyloxy]-5-(1H-
indazol-5-yl)phenyl}propionic acid;
3-[4-cyclohexyloxy-3-fluoro-5-(1-methyl-1H-indazol-5-
yl)phenyl]propionic acid;

3-[3-fluoro-4-(indan-2-yloxy)-5-(1-methyl-1H-indazol-5-yl)phenyl]propionic acid;

3-[4-cyclopentyloxy-3-(1-ethyl-1H-indazol-5-yl)-5-fluorophenyl]propionic acid;

3-[4-cyclohexyloxy-3-(1-ethyl-1H-indazol-5-yl)-5-fluorophenyl]propionic acid;

3-[3-(1-ethyl-1H-indazol-5-yl)-5-fluoro-4-(indan-2-yloxy)phenyl]propionic acid;

3-[3-(1-ethyl-1H-indazol-5-yl)-5-fluoro-4-(1-phenylethyloxy)phenyl]propionic acid;

3-[3-amino-4-cyclopentyloxy-5-(1H-indazol-5-yl)phenyl]propionic acid;

3-{3-amino-4-cyclohexyloxy-5-(1H-indazol-5-yl)phenyl}propionic acid;

3-[3-amino-4-(4-fluorophenylmethyloxy)-5-(1H-indazol-5-yl)phenyl]propionic acid;

3-{3-amino-4-[2-(2-fluorophenyl)ethyloxy]-5-(1H-indazol-5-yl)phenyl}propionic acid;

3-[3-amino-5-(1H-indazol-5-yl)-4-(1-phenylethyloxy)phenyl]propionic acid;

3-[3-amino-4-cyclopentyloxy-5-(1-methyl-1H-indazol-5-yl)phenyl]propionic acid;

3-[3-amino-4-cyclohexyloxy-5-(1-methyl-1H-indazol-5-yl)phenyl]propionic acid;

3-[3-amino-4-(indan-2-yloxy)-5-(1-methyl-1H-indazol-5-yl)phenyl]propionic acid;

3-[3-amino-5-(1-methyl-1H-indazol-5-yl)-4-(1-phenylethyloxy)phenyl]propionic acid;

3-[3-amino-4-cyclopentyloxy-5-(1-ethyl-1H-indazol-5-yl)phenyl]propionic acid;

3-[3-amino-4-cyclohexyloxy-5-(1-ethyl-1H-indazol-5-yl)phenyl]propionic acid;

3-[3-amino-5-(1-ethyl-1H-indazol-5-yl)-4-(1-phenylethyloxy)phenyl]propionic acid.

As a salt of Compound (I) of the present invention, a pharmaceutically acceptable salt is preferred. It is meant that, when at least one of the conditions is satisfied that Y is hydrogen atom, the group Ar contains carboxyl group or phenolic hydroxyl group, and the group Z is phenolic hydroxyl group, then the compound forms 1 to 3 alkali salts depending on the number of acidic groups. Examples include, for example, salts with inorganic bases such as sodium and ammonia and salts with organic bases such as triethylamine. Alternatively, it is meant that, when at least one of the conditions is satisfied that the group R contains a substituted or unsubstituted amino group, the group Ar contains a substituted or unsubstituted amino group, and the group Z is amino group, then the compound forms 1 to 3 acidic salts depending on the number of basic groups. Examples include, for example, salts with inorganic acids such as hydrochloric acid and sulfuric acid and salts with organic acids such as acetic acid and citric acid.

As compounds structurally similar to those of the compounds of the present invention, biphenyl-5-alkanoic acid derivatives and use thereof are described in WO99/19291. However, they have a different structural feature in that a moiety corresponding to the group "Ar" in the aforementioned formula (I) of the compounds of the present invention is a phenyl group. Further, U.S. Pat. No. 5,391,817 (corresponding to Japanese Patent Unexamined Publication (KOKAI) No. 7-22399) discloses biaryl phospholipase $A_2$ inhibitors. However, they have a different structural feature in that a moiety corresponding to the group "Ar" in the aforementioned formula (I) of the compounds of the present invention is only a phenyl group.

The compounds (I) of the present invention can be produced by, for example, using the reactions according to the following various methods.

[Preparation Method 1] (Step a)

As shown in the following scheme 1:

(Scheme 1)

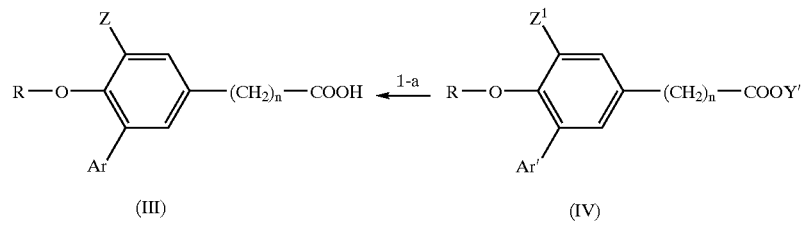

(III)        (IV)

the compounds of the present invention represented by the formula (III) [wherein n, R, Z, and Ar have the same meanings as those defined above (this compound is hereinafter simply referred to as "Compound (III)"), which constitute a part of the scope of Compound (I) of the present invention and correspond to those wherein the group Y represents hydrogen atom, can be prepared by hydrolyzing a compound represented by the formula (IV) [wherein $Z^1$ is the same as Z mentioned above, or when Z of Compound (I) of the present invention is hydroxyl group or amino group, the group may be a protected hydroxyl group or a protected amino group; Ar' is the same as Ar mentioned above or when Ar of Compound (I) of the present invention is hydroxyl group, carboxyl group, or amino group, the group may be a protected hydroxyl group, a protected carboxyl group, or a protected amino group; Y' represents a lower alkyl group having 1 to 4 carbon atoms; and n and R have the same meanings as those defined above: hereinafter this compound is simply referred to as "Compound (IV)"] to convert the group OY' into hydroxyl group, and simultaneously or successively eliminating a protective group of the hydroxyl group, amino group or carboxyl group, if it exists.

In Compound (IV), although the protective group where $Z^1$ is a protected hydroxyl group is not particularly limited so long as the group is not changed in other reactions and can be eliminated when required. Examples of $Z^1$ of Compound (IV) includes an acyloxy group including substitution with acetyl group or the like, and hydroxyl group substituted with a protective group that can be eliminated by a conventional method such as a trialkylsilyl group such as t-butyldimethylsilyl group. Further, examples of the protected amino group as $Z^1$ of Compound (IV) include an amino group substituted with a protective group that can be eliminated by hydrolysis or a conventional manner such as carbamate-type protective groups including Boc group and the like.

Further, examples of the protected hydroxyl group as Ar' of Compound (IV) include an acyloxy group including substitution with acetyl group or the like, and a hydroxyl group substituted with a protective group that can be eliminated by a conventional method such as a trialkylsilyl group including t-butyldimethylsilyl group. Further, examples of the protected carboxyl group as Ar' include an alkyloxycarbonyl group including substitution with methyl group, ethyl group or the like which can be converted into carboxyl group by hydrolysis, or that including substitution with t-butyl group which can be eliminated by a conventional method. Further, examples of the protected amino group as Ar' include an amino group substituted with a protective group that can be eliminated by hydrolysis or a conventional manner such as carbamate-type protective groups including Boc group and the like. As for selection, introduction, and elimination of the protective group of these hydroxyl group and amino group, ordinary chemical literatures such as Protective Group In Organic Synthesis, THIRD EDITION, published by John Wiley & Sons and references cited therein and the like can be referred to.

Y' of Compound (IV) is preferably a lower alkyl group having 1 to 4 carbon atoms. An ordinary protective group for carboxyl group can also be used, because the group is removed as a result of the reaction of the scheme (1). Those skilled in the art can easily understand that, for that purpose, a preparation in a step preceding to the preparation of Compound (IV) or that in a further preceding step can be performed by appropriate substitution by a protective group to be used.

For the reaction of converting Compound (IV) into Compound (III), in general, the compound is preferably reacted in a base. Further, for the reaction of converting Compound (IV) to Compound (III), in general, the compound is preferably reacted in an inert medium that does not inhibit the reaction, preferably a polar solvent.

Examples of the base used in the above reaction include, for example, alkali metal bases such as sodium hydroxide, potassium hydroxide, sodium carbonate, potassium carbonate, sodium methoxide and potassium t-butoxide and organic bases such as triethylamine. As for amounts of the bases, generally 1 to 20 moles, preferably 1 to 10 moles for alkali metal bases, or 1 to a large excess moles for organic bases based on Compound (IV).

Examples of the polar solvent include water, methanol, ethanol, tetrahydrofuran, dioxane and the like, and these solvents may be used as a mixture as required. As the reaction temperature, an appropriate temperature of, for example, from room temperature to the reflux temperature of a solvent is chosen. The reaction time is, for example, generally 0.5 to 72 hours, preferably 1 to 48 hours, when an alkali metal base is used, or generally 5 hours to 14 days when an organic base is used. Since progress of the reaction can be monitored by thin layer chromatography (TLC), high performance liquid chromatography (HPLC) or the like, the reaction can generally be terminated appropriately so as to maximize a yield of Compound (III). Further, when a protective group of hydroxyl group, carboxyl group, or amino group that cannot be removed by the aforementioned reaction is present on $Z^1$ or Ar', such a protective group can be removed by a method ordinarily used, for example, a reaction with a mineral acid such as hydrochloric acid or sulfuric acid in an inert solvent at room temperature or under heating.

For collection of Compound (III) obtained as described above from the reaction solution as a free carboxylic acid, operations may preferably be carried out by, when the polar solvent is a water-soluble solvent, evaporating the solvent, neutralizing the residue with an inorganic acid such as aqueous hydrochloric acid, dissolving the residue in a water-insoluble solvent, then washing the solution with a weakly acidic aqueous solution, water or the like, and evaporating the solvent. When the polar solvent is a water-insoluble solvent, operations may preferably carried out by neutralizing the reaction solution with an inorganic acid, washing the solution with a weakly acidic aqueous solution, water or the like, and then evaporating the solvent.

Further, when Compound (III) forms a salt with the base used after the reaction to give a solid, the salt of Compound (III) can be obtained by isolation and purification of the solid by a conventional method.

[Preparation Method 2] (Step b)

As shown by the following scheme 2:

(Scheme 2)

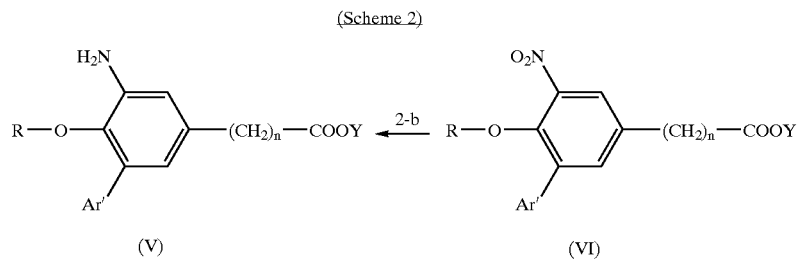

a compound represented by the formula (V) [hereinafter simply referred to as "Compound (V)"], as the compounds (I) of the present invention or the compounds (IV) wherein Z represents amino group, can be prepared from a compound represented by the formula (VI) wherein Z represents nitro group [hereinafter simply referred to as "Compound (VI)"]. In the formulas of the compounds (V) and (VI), n, R and Ar' have the same meanings as those defined above. Examples of specific method include, for preparation of Compound (V), a method of hydrogenating the nitro group in Compound (VI) by an ordinarily used method such as hydrogenation in a solvent such as methanol or the like in the presence of a catalyst such as palladium/carbon powder or platinum oxide at room temperature or under heating, and a method of reducing the nitro group into amino group by using hydrochloric acid at a temperature of from room temperature to the reflux temperature in the presence of iron powder or divalent tin.

[Preparation Method 3] (Step c)
As shown by the following scheme 3:

(Scheme 3)

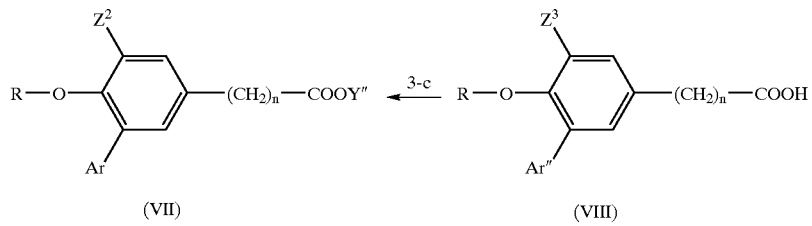

a compound represented by the formula (VII) [hereinafter simply referred to as "Compound (VII)"], as Compound (I) of the present invention wherein the group Y represents Y" and Z represents $Z^2$, can be produced by esterifying the carboxyl group (COOH) of the compound of the present invention represented by the formula (VIII) [hereinafter simply referred to as "Compound (VIII)"] by a conventional method. In the formula of Compound (VII), Y" represents a lower alkyl group having 1 to 4 carbon atoms, a —$(CH_2)_m$NR$^{18}$R$^{19}$ group, or a C(R$^{20}$)$_2$OC(O)A$_3$R$^{21}$ group, $Z^2$ represents hydrogen atom, fluorine atom, chlorine atom, nitro group, methyl group, or an OR$^9$ group, and n, R, and Ar have the same meanings as those defined above. $Z^3$ of Compound (VIII) represents hydrogen atom, fluorine atom, chlorine atom, nitro group, methyl group, or an OR$^{9'}$ group, and R$^{9'}$ represents a trialkylsilyl group that can be removed by a conventional method such as t-butyldimethylsilyl group or a lower alkyl group having 1 to 4 carbon atoms. Ar" is the same as Ar mentioned above, or when hydroxyl group is contained in Ar of Compound (I) of the present invention, Ar" represents the hydroxyl group substituted with a trialkylsilyl group that can be removed by a conventional method such as t-butyldimethylsilyl group, or when carboxyl group is contained in Ar of Compound (I) of the present invention, Ar" represents an alkyloxycarbonyl group including substitution with t-butyl group or the like that can be removed by a conventional method and hence convertible into carboxyl group, or when amino group is contained in Ar of Compound (I) of the present invention, Ar" represents an amino group substituted with a carbamate-type protective group that can be removed by a conventional method such as Boc group. Symbol "n" and R have the same meanings as those defined above.

Examples of the method for producing Compound (VII) include a method of allowing Compound (VIII) to react with an inorganic halide without solvent or in an inert solvent to convert the compound into an acid halide and then allowing the acid halide per se or the same dissolved in an inert solvent to react with an excess amount of hydroxide of the targeted Y". Examples of the inorganic halide used in this method include thionyl chloride, phosphoryl chloride, phosphorus pentachloride, phosphorus trichloride and the like, and thionyl chloride is a preferred example. Examples of an amount used include generally an equimolar to a large excess amount, preferably 1.5 to 5 moles based on Compound (VIII). Examples of the inert solvent used in this reaction include, for example, halogenated hydrocarbons such as dichloromethane, chloroform and 1,2-dichloroethane, ethers such as tetrahydrofuran and dioxane, and benzene compounds such as benzene, toluene, xylene and chlorobenzene. These solvents can be used, for example, each alone or as a mixed solvent. In order to promote the reaction, a catalytic amount of N,N-dimethylformamide may be added. As a reaction temperature, an appropriate temperature of from room temperature to the reflux temperature of a solvent is generally chosen. Examples of the reaction time include generally 0.5 to 24 hours, preferably 1 to 6 hours.

Examples of the inert solvent used for the reaction with hydroxide of the targeted Y" include, for example, halogenated hydrocarbons such as dichloromethane, chloroform and 1,2-dichloroethane, ethers such as tetrahydrofuran and dioxane, and benzene compounds such as benzene, toluene, and xylene. The reaction can also be performed with an excess amount of the hydroxide of the targeted Y" without using a solvent. As the reaction temperature, an appropriate temperature of from −10° C. to room temperature is chosen. Examples of the reaction time include generally 0.5 to 24 hours, preferably 0.5 to 6 hours.

Further, when a protective group of hydroxyl group, carboxyl group or amino group is present on $Z^3$ or Ar", Compound (VII) can be obtained by removing the protective group by a method generally used.

Other methods for producing the desired compound (VII) include, for example, the "esterification using an alcohol" described in Shin Jikken Kagaku Koza (edited by the Chemical Society of Japan, published by Maruzen Co., Ltd.), vol. 14, p.1002, "esterification using an O-alkylating agent", ibid, the same volume, p.1002, "esterification using an alkyl halide", ibid, the same volume, p.1008, "esterification reaction using a dehydrating agent", ibid, vol. 22, p.45 and the like.

In order to produce the compounds (I) of the present invention, the aforementioned Compound (IV), Compound (V), and Compound (VI) [including parts of Compound (III), Compound (VII), and Compound (VIII)] used in the preparation methods 1 to 3 can be produced by, for example, any of the preparation methods 4 to 16 shown below.

[Preparation Method 4] (Step d-1)
As shown in the following scheme 4:

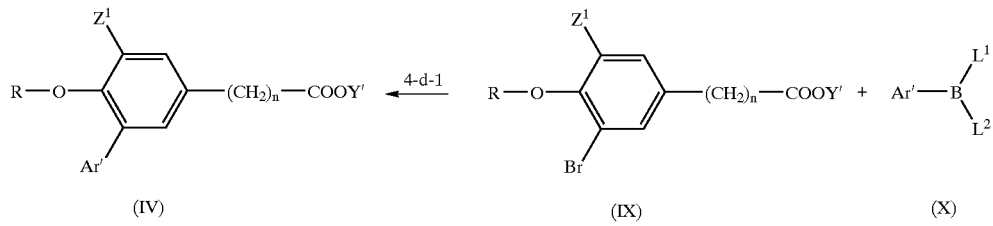

an example of the method for producing the aforementioned Compound (IV) includes a method of allowing a compound represented by the formula (IX) [hereinafter simply referred to as "Compound (IX)"] to react with a boronic acid derivative represented by the formula (X) [hereinafter simply referred to as "Compound (X)"]. In the formula of Compound (IX), n, R, $Z^1$, and Y' have the same meanings as those defined above. In the formula of Compound (X), $L^1$ and $L^2$ each or both represent hydroxyl group or an alkoxyl group having 1 to 8 carbon atoms (e.g., methoxy group, ethoxy group, propoxy group, isopropoxy group, cyclohexyloxy group), a substituted or unsubstituted phenyloxy group, or $L^1$ and $L^2$ may bind to each other to form a ring including the boron atom [this ring may be saturated of unsaturated, and may contain a heteroatom other than boron (e.g., oxygen atom), and the ring may be further substituted] to represent a 5- or 6-membered cyclic ester of arylboronic acid (e.g., 9-borabicyclo[3,3,1]nonane, 1,3,2-dioxaborolane, 4,4,5,5-tetramethyl-1,3,2-dioxaborolane), and Ar' has the same meaning as that defined above.

Further, as shown in the following scheme 5:

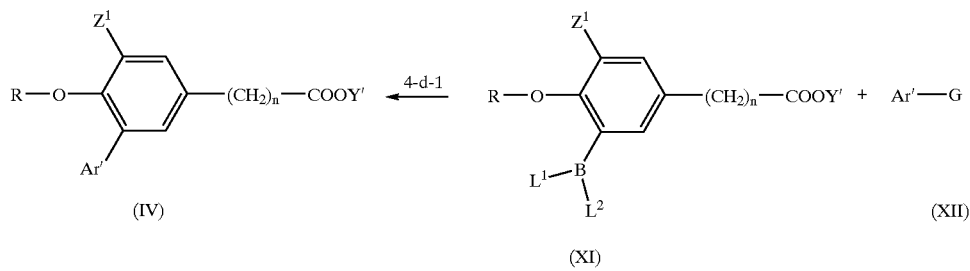

an example of the method for producing the aforementioned compound (IV) includes a method of reaction of a combination of a compound represented by the formula (XI) [hereinafter simply referred to as "Compound (XI)"] and a compound represented by the formula (XII) [hereinafter simply referred to as "Compound (XII)"]. In the formula of Compound (XI), n, R, $Z^1$, Y', $L^1$, and $L^2$ have the same meanings as those defined above. G of Compound (XII) represents chlorine, bromine, iodine, mesylate group, triflate group, or an arenesulfonate group, and Ar' has the same meaning as that defined above.

Specifically, an examples include a method for preparation of Compound (IV) by performing the Suzuki reaction described in, for example, Jikken Kagaku Koza, 4th Edition (edited by Chemical Society of Japan, published by Maruzen Co., Ltd.), vol. 25, p.403 with a combination mentioned either in the scheme 4 or scheme 5 or the both.

A specific example includes a reaction of Compound (IX) [or Compound (XI)] with Compound (X) [or Compound (XII)] in a solvent in the presence of a commercially available palladium catalyst or a catalyst prepared from a palladium complex and a ligand and a base.

As the palladium catalyst, a commercially available catalyst such as tetrakis(triphenylphosphine)palladium, tetrakis(methyldiphenylphosphine)palladium, dichlorobis(triphenylphosphine)palladium, dichlorobis(tri-o-tolylphosphine)palladium, dichlorobis(tricyclohexylphosphine)palladium, dichlorobis(triethylphosphine) palladium, palladium acetate, palladium chloride, bis(acetonitrile)palladium chloride, tris(dibenzylideneacetone) dipalladium and bis(diphenylphosphinoferrocene)palladium chloride may be purchased and added to the reaction system, per se, or a catalyst may be added which is separately prepared from palladium acetate, tris(dibenzylideneacetone) dipalladium or the like and arbitrary ligands and isolated. Further, a catalyst considered to actually participate in the reaction may also be prepared by mixing palladium acetate, tris(dibenzylideneacetone)dipalladium or the like and arbitrary ligands in the reaction system. The valence of palladium may be 0 or may be +2. Examples of the ligand include phosphine ligands such as trifurylphosphine, tri(o-tolyl) phosphine, tri(cyclohexyl)phosphine, tri(t-butyl)phosphine, dicyclohexylphenylphosphine, 1,1'-bis(di-t-butylphosphino) ferrocene, 2-dicyclohexylphosphino-2'-dimethylamino-1,1'-biphenyl and 2-(di-t-butylphosphino)biphenyl and phosphine mimic ligands such as imidazol-2-ylidenecarbenes. Chemical equivalents of the palladium catalyst may be one equivalent or a catalytic amount, and the amount may preferably be 0.01 to 20.0 mol %, and most preferably be 0.10 to 10.0 mol %.

Examples of the base include sodium carbonate, potassium carbonate, cesium carbonate, cesium fluoride, potassium fluoride, potassium phosphate, potassium acetate, triethylamine, potassium hydroxide, sodium hydroxide, sodium methoxide, lithium methoxide and the like. The reaction temperature is, for example, preferably 20° C. to 150° C., and particularly preferable examples include 20° C. to 120° C.

The reaction system may be either a two-phase system of water and an organic solvent, or a homogeneous system of a water-containing organic solvent or an organic solvent. As for the organic solvent, examples include uses of hydrocarbon-type solvents such as toluene, xylene and hexane, halogen-type solvents such as methylene chloride, sulfoxide-type solvents such as dimethyl sulfoxide, amide-type solvents such as dimethylformamide, ether-type solvents such as tetrahydrofuran, dioxane and diglyme, alcohol-type solvents such as methanol and ethanol, nitrile-type solvents such as acetonitrile, ketone-type solvents such as acetone and cyclohexanone, ester-type solvents such as ethyl acetate, heterocyclic-type solvents such as pyridine and the like. Two or more kinds of organic solvents may be mixed and used.

For the reaction conditions, Miyaura, N., Suzuki, A., Chemical Review, 1995, vol. 95, p.2457; Snieckus, V., Chemical Review, 1990, vol. 90, p.879 and the like and references cited therein can be referred to.

[Preparation Method 4] (Step d-2)

As Compound (X), the compound commercially available as a reagent may be used, or as shown in the following scheme 6:

(Scheme 6)

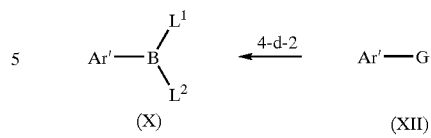

the compound can be produced from Compound (XII), which is commercially available or can be synthesized by a known method or a similar method thereto, according to the method described in the aforementioned reference [Chemical Review, 1995, vol. 95, p.2457] or the method described in Satoh, Y., SYNTHESIS, 1994, p.1146 or according to references cited therein.

For example, examples include a method of preparing Compound (X) by converting Compound (XII) into a lithio-compound using an alkyl lithium such as n-butyl lithium and t-butyl lithium, then reacting the product with a trialkyl borate and treating the product with a mineral acid such as hydrochloric acid, sulfuric acid, and phosphoric acid; and a method of to preparing Compound (X) by performing a cross-coupling reaction of Compound (XII) and an (alkoxyl) diboron in the presence of a palladium catalyst and a base.

An example of the preparation method of Compound (XI) includes a method of subjecting Compound (IX) to a reaction similar to that of the aforementioned Step d-2, as shown in the following scheme 7:

(Scheme 7)

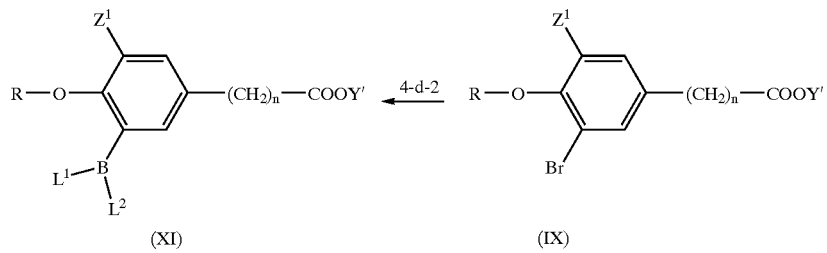

[Preparation Method 4]
As shown in the following scheme 8:

(Scheme 8)

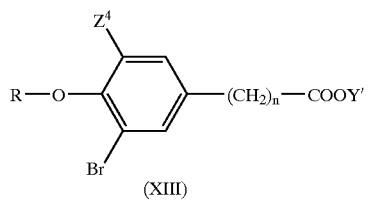

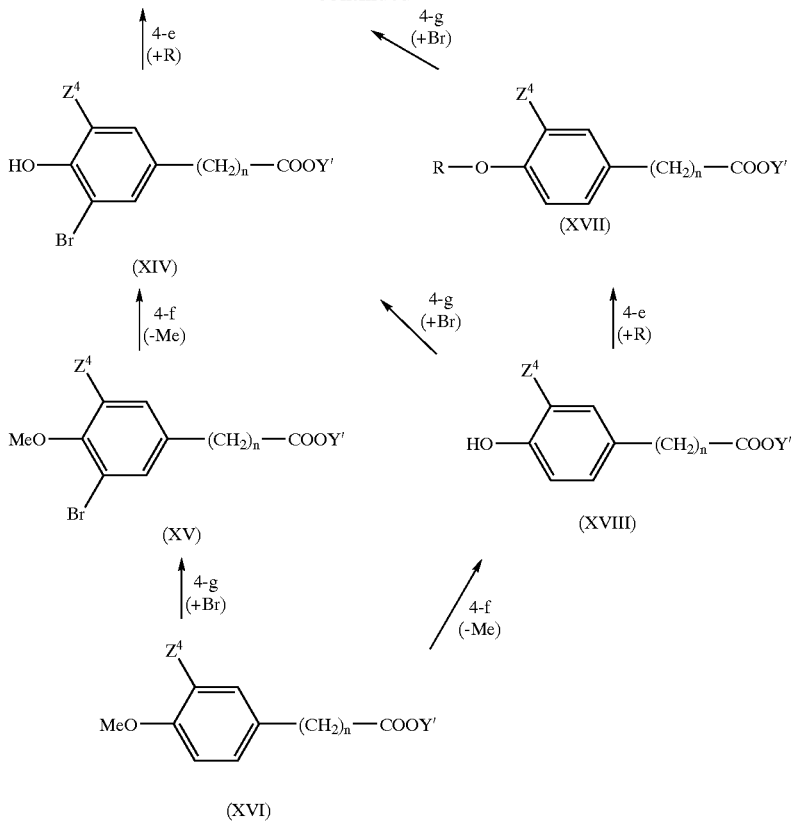

a compound represented by the formula (XIII) [hereinafter simply referred to as "Compound (XIII)"], as Compound (IX) wherein the group $Z^1$ represents $Z^4$, can be prepared by treating intermediates or starting materials represented by the formulas (XIV) to (XVIII) [hereinafter simply referred to as "Compound (XIV)" to "Compound (XVIII)"] by any one of the following methods or a combination of plural methods.

In the formulas of Compound (XIII) to Compound (XVIII), $Z^4$ represents hydrogen atom, fluorine atom, chlorine atom, nitro group, methyl group, an amino group protected with a carbamate type protective group such as Boc group, or an $OR^{9'}$ group, and $R^{9'}$ represents a trialkylsilyl groups such as t-butyldimethylsilyl group, an acyl group such as acetyl group, or a lower alkyl group having 1 to 4 carbon atoms. Symbol "n", R, and Y' have the same meanings as those defined above. Depending on n, Y', R, and $Z^4$ of Compound (XIII) used as an intermediate of Compound (I) of the present invention, Compound (XIV) to Compound (XVIII), which are commercially available or can be synthesized by a known method or a similar method thereto, can be chosen, and Compound (XIII) can be prepared by any one of the steps or a combination of some of the steps.

[Preparation Method 4] (Step e-1)

An example of the method for preparing Compound (XIII) from Compound (XIV) or Compound (XVII) from Compound (XVIII) includes a method of reacting Compound (XIV) or Compound (XVIII) with an alkylating agent, i.e., a compound represented by R-G (XIX) (in the formula, R and G have the same meanings as those defined above: hereinafter this compound is simply referred to as the "alkylating agent"). For example, an example includes a reaction in an inert solvent in the presence of an appropriate base.

Examples of the alkylating agent used in this reaction include iodides, bromides, and chlorides of alkyl or aryl compounds, which are commercially available or can be prepared according to a known method or a similar method thereto, and sulfuric acid esters of alkyl or aryl compounds which can be obtained by mesylation, arenesulfonylation, or trifluoromethanesulfonylation of alkyl alcohols or aryl alcohols. Examples of the amount of these agents include generally 1 to 40 moles, preferably 1 to 10 moles based on Compound (XIV) [or Compound (XVIII)]. Examples of the inert solvent used for this reaction include, for example, alcohols such as methanol and ethanol, ethers such as tetrahydrofuran and dioxane, benzene compounds such as benzene, toluene, and xylene, N,N-dimethylformamide, acetonitrile, acetone and the like, and these solvents may be used as a mixture as required. Examples of the base used for this reaction include, for example, alkali metal compounds such as sodium hydroxide, potassium hydroxide, sodium carbonate, potassium carbonate, sodium hydride, sodium methoxide and potassium t-butoxide and organic tertiary amines such as pyridine, 4-dimethylaminopyridine, 1,8-diazabicyclo[5,4,0]undecene, trimethylamine, and triethylamine. Examples of the amount of the bases include generally 1 to 10 moles, preferably 1 to 5 moles based on Compound (XIV) [or Compound (XVIII)]. As a reaction temperature, an appropriate temperature of from room temperature to the reflux temperature of a solvent can be generally chosen, and preferable examples include a temperature of from room temperature to 80° C. Reaction time may generally be 1 hour to 6 days, preferably 2 to 48 hours. Since progress of the reaction can be monitored by thin layer chromatography (TLC), high performance liquid chromatography (HPLC) or the like, the reaction can generally be terminated appropriately so as to maximize an yield of Compound (XIII) [or Compound (XVII)]. When the reaction progresses slowly, a catalyst such as potassium iodide and copper powder may be added as required in an amount of 0.1 to 1.5 moles based on the starting material.

[Preparation Method 4] (Step e-2)

Further, synthesis of Compound (XIII) from Compound (XIV) or that of Compound (XVII) from Compound (XVIII) can be performed by the Mitsunobu reaction described in the literature [Mitsunobu, O., SYNTHESIS, 1981, p.1]. Specifically, a method is available in which Compound (XIV) or Compound (XIII) is reacted with an alkyl alcohol (ROH), which provides the substituent R and is commercially available or can be synthesized by a known method or a similar method thereto, in an organic solvent in the presence of a phosphine such as triphenylphosphine and tributylphosphine and an azo compound such as diethyl azodicarboxylate, diisopropyl asodicarboxylate, N,N,N',N'-tetramethylazodicarboxamide, 1,1'-(azodicarbonyl)dipiperidine, and N,N,N',N'-tetraisopropylcarboxamide. Examples of the solvent include ethers such as diethyl ether, tetrahydrofuran and dimethoxyethane, halogen-type solvents such as methylene chloride, benzene compounds such as benzene, toluene, and xylene, and these solvents may be used as a mixture as required. Examples of the amount of the phosphine used include generally 1 to 10 moles, preferably 1.5 to 5 moles based on Compound (XIV) [or Compound (XVIII)]. Examples of the amount of the azo compound used include generally 1 to 10 moles, preferably 1.5- to 5 moles, based on Compound (XIV) [or Compound (XVIII)]. Examples of the amount of the alcohol used include generally 1 to 10 moles, preferably 1.5 to 5 moles, based on Compound (XIV) [or Compound (XVIII)]. As the reaction temperature, an appropriate temperature of from −20° C. to 60° C. is generally chosen. Preferred examples include a temperature of from 0° C. to room temperature. The reaction time may generally be 1 hour to 3 days, preferably 3 to 24 hours. Since progress of the reaction can be monitored by thin layer chromatography (TLC), high performance liquid chromatography (HPLC) or the like, the reaction can generally be terminated appropriately so as to maximize an yield of Compound (XIII) [or Compound (XVII)].

[Preparation Method 4] (Step e-3)

An example of preparation of Compound (XIII) or Compound (XVII) also include a process of adding an alkene, which is commercially available or can be prepared by a known method or a method similar thereto, to the phenolic hydroxyl group of Compound (XIV) or Compound (XVIII) in the presence of an acid catalyst for conversion into the substituent R, as described in Jikken Kagaku Koza, 4th Edition (edited by Chemical Society of Japan, published by Maruzen Co., Ltd.), vol. 20, p.200. Examples of the alkene used in this reaction include, for example, isobutylene, cyclopentene, cyclohexene, cycloheptene, alkenes having an aromatic ring such as substituted or unsubstituted styrene and α-methylstyrene and the like. Examples of the amount of the alkene used include generally 1 mole to a large excess amount, preferably 1.5 to 10 moles, based on Compound (XIV) [or Compound (XVIII)]. Examples of the acid catalyst used include mineral acids such as hydrochloric acid and sulfuric acid, boron trifluoride (including solvent complex thereof), tetrafluoroboric acid, trifluorosulfonic acid and the like. Examples of the amount of the acid catalyst used include generally 0.05 to 5 moles, preferably 0.1 to 2 moles, based on Compound (XIV) [or Compound (XVIII)]. Examples of the solvent include ethers such as diethyl ether, tetrahydrofuran and dimethoxyethane, halogen-type solvents such as methylene chloride and benzene compounds such as benzene, toluene and xylene, and these solvents can be used as a mixture as required. Further, the alkene to be reacted may be used as a solvent. As the reaction temperature, an appropriate temperature of from −20° C. to 60° C. is generally chosen, and preferred examples include a temperature of from 0° C. to 50° C. The reaction time is generally 1 hour to 3 days, preferably 3 to 24 hours. Since progress of the reaction can be monitored by thin layer chromatography (TLC), high performance liquid chromatography (HPLC) or the like, the reaction can generally be terminated appropriately so as to maximize an yield of Compound (XIII) [or Compound (XVII)].

[Preparation Method 4] (Step e-4)

Among Compound (XIII) and Compound (XVII), those wherein the substituent R represents the aforementioned group Rb, and each of $A^1$ and $A^2$ represents a single bond can be prepared by reacting Compound (XIV) or Compound (XVIII) with an aryl halide under a basic condition, as described in Jikken Kagaku Koza, 4th Edition (edited by Chemical Society of Japan, published by Maruzen Co., Ltd.), vol. 20, p.191. Examples of the aryl halide used in this reaction include chlorides, bromides, or iodides of a substituted or unsubstituted aryl, which are commercially available or can be synthesized by a known method or a method similar thereto, and bromides and iodides are preferred. Alternatively, an aryl triflate may also be used instead of the aryl halide. Examples of the amount of the aryl halide used include generally 1 mole to a large excess amount, preferably 2 to 10 moles, based on Compound (XIV) [or Compound (XVIII)]. Examples of the base used for this reaction include, for example, alkali metal compounds such as sodium hydroxide, potassium hydroxide, sodium carbonate, potassium carbonate, sodium hydride, sodium methoxide and potassium t-butoxide and organic tertiary amines such as pyridine, 4-dimethylaminopyridine, 1,8-diazabicyclo[5,4,0]undecene, trimethylamine, and triethylamine. Examples of the amount of these bases include generally 1 to 10 moles, preferably 1 to 5 moles, based on Compound (XIV) [or Compound (XVIII)]. To the reaction system, copper powder, cuprous halide, or copper alkoxide may be added as a catalyst. Further, for example, a phase transfer catalyst or crown ether may also be added. Examples of the amount of these additives include generally 0.05 to 3 moles, preferably 0.1 to 1 mole, based on Compound (XIV) [or Compound (XVIII)]. As the reaction solvent, hydrocarbon-type solvents such as toluene, xylene, chlorobenzene, dichlorobenzene and nitrobenzene, sulfoxide-type solvents such as dimethyl sulfoxide, amide-type solvents such as dimethylformamide, ether-type solvents such as dioxane and diglyme, heterocyclic-type solvents such as pyridine and the like may be used. Further, two or more kinds of organic solvents may be used as a mixture. As the reaction temperature, an appropriate temperature of from room temperature to the 300° C. is generally chosen, and preferred examples include a temperature of from room temperature to 200° C. The reaction time is generally 1 hour to 7 days, preferably 16 hours to 3 days. Since progress of the reaction can be monitored by thin layer chromatography (TLC), high performance liquid chromatography (HPLC) or the like, the reaction can generally be terminated appropriately so as to maximize an yield of Compound (XIII) [or Compound (XVII)].

An example of method for preparation of Compound (XIII) or Compound (XVII) wherein the substituent R represents the group Rb, and each of $A^1$ and $A^2$ represents a single bond include the method described in J. Tsuji, Journal of Organic Synthesis Association, 2001, vol. 59, No. 6, p.609] or references cited therein. Specifically, the target compound can be prepared by reacting Compound (XIV) or Compound (XVIII) with an aryl halide or aryl triflate, which is commercially available or can be prepared by a known method or a method similar thereto, in a solvent in the presence of a commercially available palladium catalyst or catalyst prepared from a palladium complex and a ligand and a base.

As the palladium catalyst, a commercially available catalyst such as tetrakis(triphenylphosphine)palladium, tetrakis (methyldiphenylphosphine)palladium, dichlorobis (triphenylphosphine) palladium, dichlorobis(tri-o-tolylphosphine)palladium, dichlorobis (tricyclohexyl-phosphine)palladium, dichlorobis(triethylphosphine) palladium, palladium acetate, palladium chloride, bis (acetonitrile)palladium chloride, tris(dibenzylideneacetone) dipalladium and bis(diphenylphosphinoferrocene)palladium chloride may be purchased and added to the reaction system, per se, or a catalyst may be added which is separately prepared from palladium acetate, tris(dibenzylideneacetone) dipalladium or the like and arbitrary ligands and isolated. Further, a catalyst considered to actually participate in the reaction may also be prepared by mixing palladium acetate, tris(dibenzylideneacetone)dipalladium or the like and arbitrary ligands in the reaction system. The valence of palladium may be 0 or may be +2. Examples of the ligand include phosphine ligands such as trifurylphosphine, tri(o-tolyl) phosphine, tri(cyclohexyl)phosphine, tri(t-butyl)phosphine, dicyclohexylphenylphosphine, 1,1'-bis(di-t-butylphosphino) ferrocene, 2-dicyclohexylphosphino-2'-dimethylamino-1,1'-biphenyl and 2-(di-t-butylphosphino)biphenyl, and phosphine mimic ligands such as imidazol-2-ylidenecarbenes. Chemical equivalents of the palladium catalyst may one equivalent or a catalytic amount, and preferably be 0.01 to 20.0 mol %, and most preferably be 0.10 to 10.0 mol %.

Examples of the base include sodium carbonate, potassium carbonate, cesium carbonate, cesium fluoride, potassium fluoride, potassium phosphate, potassium acetate, triethylamine, potassium hydroxide, sodium hydroxide, sodium methoxide, lithium methoxide and the like. The reaction temperature is preferably from 20° C. to 150° C., and most preferred examples include a temperature of from 20° C. to 120° C.

Examples of the organic solvent include hydrocarbon-type solvents such as toluene, xylene and hexane, halogen-type solvents such as methylene chloride, sulfoxide-type solvents such as dimethyl sulfoxide, amide-type solvents such as dimethylformamide, ether-type solvents such as tetrahydrofuran, dioxane, and diglyme, heterocyclic-type solvents such as pyridine and the like. Two or more kinds of organic solvents may be mixed and used.

[Preparation Method 4] (Step f)

Conversion from Compound (XV) to Compound (XIV) or that from Compound (XVI) to Compound (XVIII) can be carried out by conversion of the methoxy group of Compound (XV) or Compound (XVI) into hydroxyl group by means of a conventional demethylation reaction, and when the group COOY' is simultaneously converted into carboxyl group, performing a conventional esterification reaction of the carboxyl group for preparation of target compounds. Examples of the demethylation include a method of reaction in pyridine/hydrochloric acid complex at about 180° C., a method of using boron tribromide and the like. An example of the esterification reaction includes the method mentioned in the step c of the preparation method 3.

[Preparation Method 4] (Step g)

Examples of conversion from Compound (XVI) to Compound (XV), that from Compound (XVII) to Compound (XIII), or that from Compound (XVIII) to Compound (XIV) include bromination of Compound (XVI), Compound (XVII), or Compound (XVIII) according to a method described in ordinary literature in the filed of chemistry, for example, Shin Jikken Kagaku Koza (edited by Chemical Society of Japan, published by Maruzen Co., Ltd.), vol. 14, p.354 for preparation of the target compounds. Examples include a method of using bromine ($Br_2$), method of using N-bromosuccinimide and the like.

[Preparation Method 4] (Step b)

As shown in the following scheme 9:

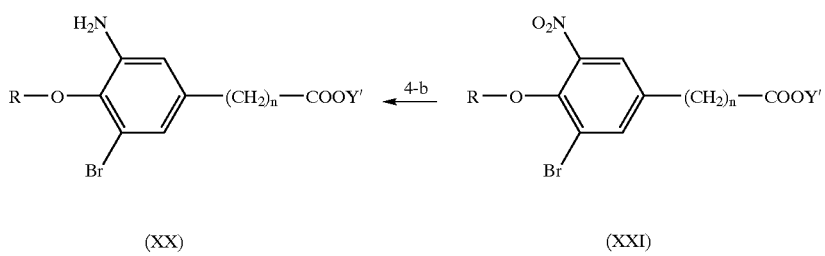

(Scheme 9)

(XX)    (XXI)

an example of synthesis of a compound represented by the formula (XX) (in the formula, n, R, and Y' the same meanings as those defined above: hereinafter this compound is simply referred to as "Compound (XX)"), as Compound (IX) wherein the group $Z^1$ represents is amino group, include a method of reducing the nitro group of the compound represented by the formula (XXI) (in the formula, n, R, and Y' have the same meanings as those defined above: hereinafter this compound is simply referred to as "Compound (XXI)"), which is Compound (IX) wherein the group $Z^1$ represents amino group, according to an ordinarily used method, for example, a method of reducing nitro group into amino group at a temperature of from room temperature to reflux temperature using hydrochloric acid in the presence of iron powder or divalent tin and the like.

[Preparation Method 5]
As shown in the following scheme 10:

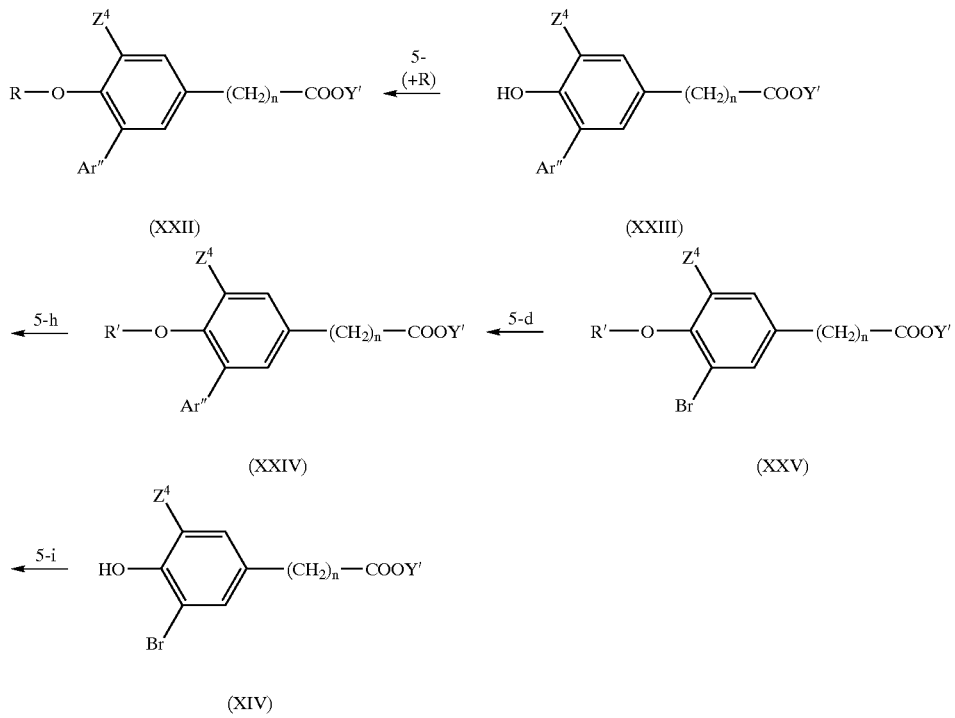

a compound represented by the formula (XXII) [n, R, $Z^4$, Ar", and Y' have the same meanings as those defined above: hereinafter this compound is simply referred to as "Compound (XXII)"], as Compound (I) of the present invention [or Compound (IV) mentioned above] wherein the substituent Z represents $Z^4$, and Ar represents Ar", can also be prepared by the method described below.

[Preparation Method 5] (Step e)

Compound (XXII) can be prepared by introducing the substituent R to the hydroxyl group of the compound represented by the formula (XXIII) [n, $Z^4$, Ar", and Y' have the same meanings as those defined above: hereinafter this compound is simply referred to as "Compound (XXIII)"] according to any of the methods described in the step e of the preparation method 4 mentioned above.

[Preparation Method 5] (Step h)

When R' in a compound represented by the formula (XXIV) [in the formula, R' represents hydrogen atom or a protective group of hydroxyl group that can be removed by a conventional method (the group represents, for example, an alkyl group such as methyl group, an arylmethyl group such as benzyl group, an alkyloxymethyl group such as methoxymethyl group and tetrahydropyranyl group, an acyl group such as acetyl group or a trialkylsilyl group such as t-butyldimethylsilyl group), and n, $Z^4$, Ar", and Y' have the same meanings as those defined above: hereinafter this compound is simply referred to as "Compound (XXIV)"] is a protective group of the hydroxyl group, Compound (XXIII) can be prepared by removing the protective group according to a method described in the ordinary literature in the filed of chemistry, for example, the aforementioned Protective Group in Organic Chemistry, 3rd Edition, p.246 or references cited therein (note that Compound (XXI) and Compound (XX) are the same compounds when R' is hydrogen atom). Examples include, when R' is methyl group, a method of reaction at about 180° C. in pyridine/hydrochloric acid complex and demethylation reaction using boron tribromide. When R' is benzyl group, examples include debenzylation reaction through hydrogenation using a hydrogen source such as hydrogen gas in the presence of a catalyst such as palladium/carbon powder. When R' is an alkyloxymethyl group such as methoxymethyl group and tetrahydropyranyl group or an acyl group such as acetyl group, examples include a deprotection reaction in which a reaction is performed in a mineral acid such as hydrochloric acid. Further, when R' is a trialkylsilyl group such as t-butyldimethylsilyl group, examples include a method of performing a reaction with a fluoride such as tetra-n-butylammonium fluoride in a solvent and desilylation reaction in which the reaction is performed in a mineral acid such as hydrochloric acid.

[Preparation Method 5] (Step d)

Compound (XXIV) can be prepared by introducing the substituent Ar" into a compound represented by the formula (XXV) [in the formula, R', $Z^4$, n, and Y' have the same meanings as those defined above; hereinafter this compound is simply referred to as "Compound (XXV)"] according to any of the methods described in the step d of the preparation method 4 mentioned above.

[Preparation Method 5] (Step i)

Compound (XXV) can be prepared by introducing a protective group (for example, an alkyl group such as methyl group, an arylmethyl group such as benzyl group, an alkyloxymethyl group such as methoxymethyl group and tetrahydropyranyl group, an acyl group such as acetyl group or a trialkylsilyl group such as t-butyldimethylsilyl group) into the hydroxyl group of Compound (XIV) mentioned above according to a method described in the ordinary literature in the filed of chemistry, for example, the aforementioned Protective Group in Organic Chemistry, 3rd Edition or references cited therein (when R' is hydrogen atom, Compound (XXV) and Compound (XIV) are the same compounds).
[Preparation Method 6]
As shown in the following scheme 11:

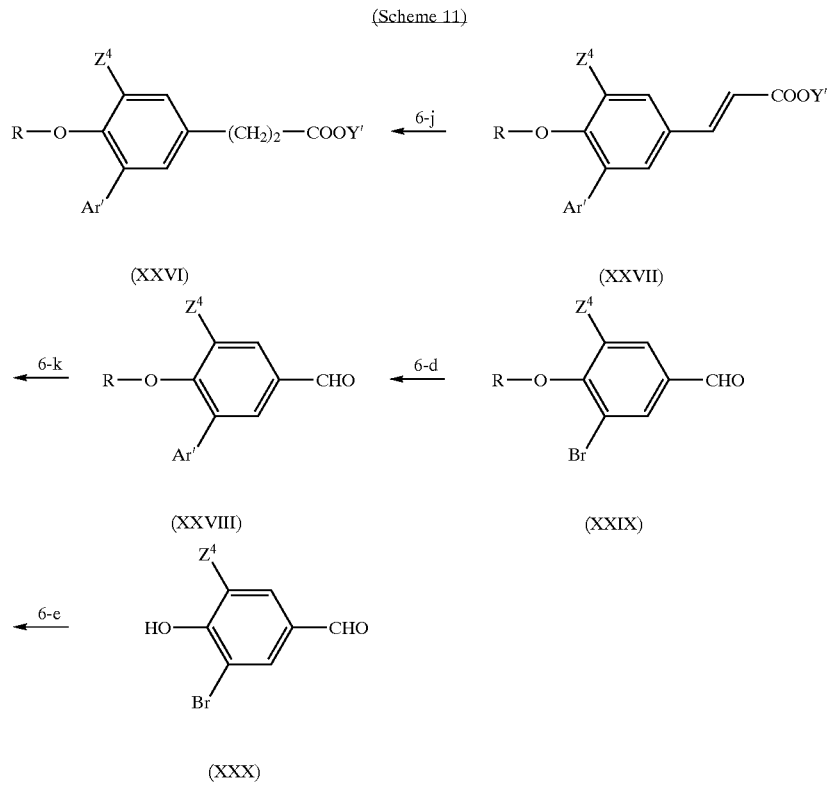

a compound represented by the formula (XXVI) (in the formula, R, $Z^4$, Ar', and Y' have the same meanings as those defined above: hereinafter this compound is simply referred to as "Compound (XXVI)"), as Compound (I) of the present invention [or Compound (IV) mentioned above] wherein n is an integer of 2 (ethylene), can also be prepared by the method shown below.
[Preparation Method 6] (Step j)
Compound (XXVI) can be prepared by reducing the double bond of a compound represented by the formula (XXVII) (in the formula, R, $Z^4$, Ar', and Y' have the same meanings as those defined above: hereinafter this compound is simply referred to as "Compound (XXVII)") using a reduction reaction described in the ordinary literature in the filed of chemistry. Examples of the reaction include a method of converting the double bond of Compound (XIV) into a single bond by hydrogenation using a hydrogen source such as hydrogen gas, ammonium formate, and hydrazine hydrate in a single solvent or a mixed solvent of alcoholic-type solvents such as methanol, ester-type solvents such as ethyl acetate in the presence of a catalyst such as palladium/carbon powder.
[Preparation Method 6] (Step k)
Compound (XXVII) can be prepared from a compound represented by the formula (XXVIII) [in the formula, R, $Z^4$, and Ar' have the same meanings as those defined above: hereinafter this compound is simply referred to as "Compound (XXVIII)"]. An example of the preparation method includes a method utilizing the Horner-Emonds reaction described in Shin Jikken Kagaku Koza (edited by Chemical Society of Japan, published by Maruzen Co., Ltd.), vol. 14, p.238. Specifically, the compound can be obtained by reacting Compound (XXVIII) with a commercially available dialkylphosphonoacetic acid ester in an inert solvent, for example, an alcohol-type solvent such as methanol and ethanol or ether-type solvent such as tetrahydrofuran and dimethoxyethane in the presence of a base such as sodium hydride and sodium alkoxide. As the reaction temperature, an appropriate temperature of from –10° C. to the reflux temperature of a solvent is generally chosen, and preferred examples include a temperature of from 0° C. to room temperature. The reaction time is generally 1 to 16 hours, preferably 2 to 8 hours. Since progress of the reaction can be monitored by thin layer chromatography (TLC), high performance liquid chromatography (HPLC) or the like, the reaction can generally be terminated appropriately so as to maximize an yield of Compound (XXVII).
[Preparation Method 6] (Step d)
Compound (XXVIII) can be prepared by introducing the substituent Ar' into a compound represented by the formula (XXIX) [in the formula, R and $Z^4$ have the same meanings as those defined above: hereinafter this compound is simply referred to as "Compound (XXIX)"] according to any of the methods described in the step d of the preparation method 4 mentioned above.
[Preparation Method 6] (Step e)
Compound (XXIX) can be prepared by introducing the substituent R into a compound represented by the formula (XXX) [in the formula, $Z^4$ has the same meaning as that defined above: hereinafter this compound is simply referred to as "Compound (XXX)"], which is commercially available or can be prepared by a known method or a method similar thereto, according to any of the methods described in the step e of the preparation method 4 mentioned above.

[Preparation Method 7]

As shown in the following scheme 12:

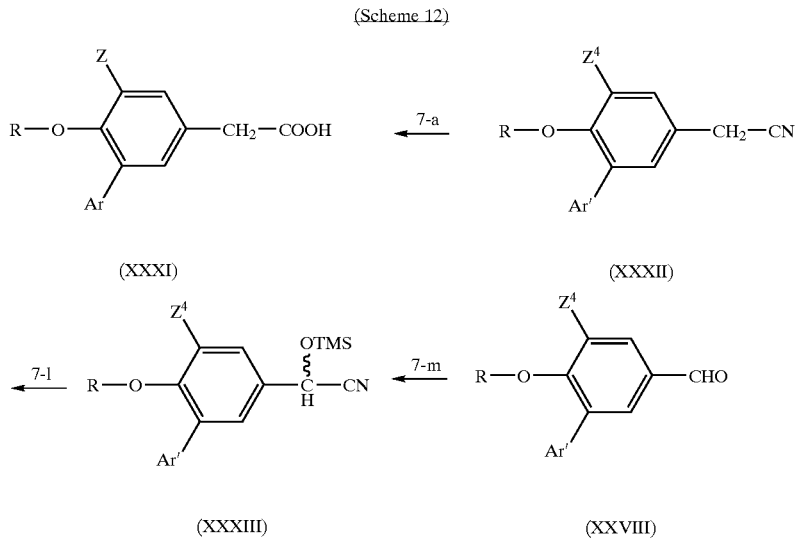

(Scheme 12)

a compound represented by the formula (XXXI) [in the formula, R, Z, and Ar have the same meanings as those defined above: hereinafter this compound is simply referred to as "Compound (XXXI)"], as Compound (I) of the present invention [or the compound III] wherein n is an integer of 1 (methylene), can also be prepared by the method described below.

[Preparation Method 7] (Step a)

Specifically, Compound (XXXI) can be prepared by hydrolyzing nitrile group of a compound represented by the formula (XXXII) [in the formula, R, $Z^4$, and Ar' have the same meanings as those defined above: hereinafter this compound is simply referred to as "Compound (XXXII)"] into carboxyl group according to a method similar to the method shown in the step a of the preparation method 1 mentioned above.

[Preparation Method 7] (Step l)

Compound (XXXII) can be prepared by subjecting a compound represented by the formula (XXXIII) [in the formula, R, $Z^4$, and Ar' have the same meanings as those defined above: hereinafter this compound is simply referred to as "Compound (XXXIII)"] to, for example, the reduction reaction using a hydrosilane described in Jikken Kagaku Koza, 4th Edition (edited by Chemical Society of Japan, published by Maruzen Co., Ltd.), vol. 26, p.197. For example, the oxygen atom on the methylene of Compound (XXXIII) can be reduced with a hydrosilane such as triethylsilane and a protonic acid such as trifluoroacetic acid or a Lewis acid such as boron trifluoride in a halogenated solvent such as dichloromethane to obtain Compound (XXXII).

[Preparation Method 7] (Step m)

Compound (XXXIII) can be obtained by reacting the aforementioned compound (XXVIII) with a trimethylsilyl cyanide using a Lewis acid, particularly zinc iodide, as a catalyst in an inert solvent such as tetrahydrofuran as described in Jikken Kagaku Koza, 4th Edition (edited by Chemical Society of Japan, published by Maruzen Co., Ltd.), vol. 20, p.445.

[Preparation Method 8]

As shown in the following scheme 13:

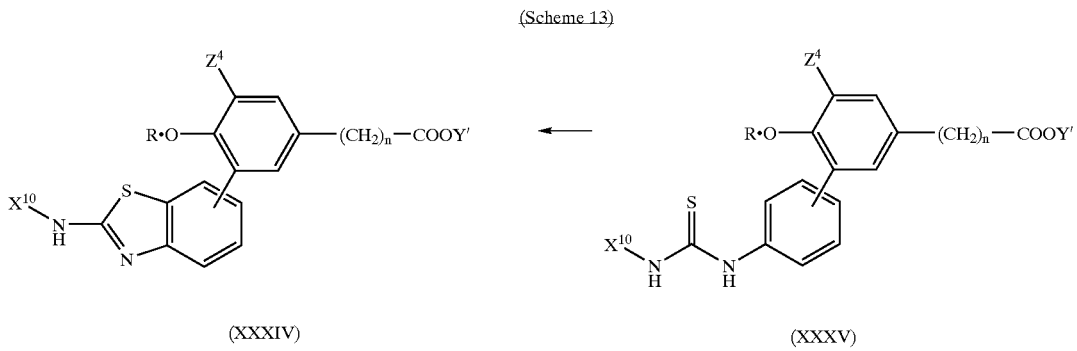

(Scheme 13)

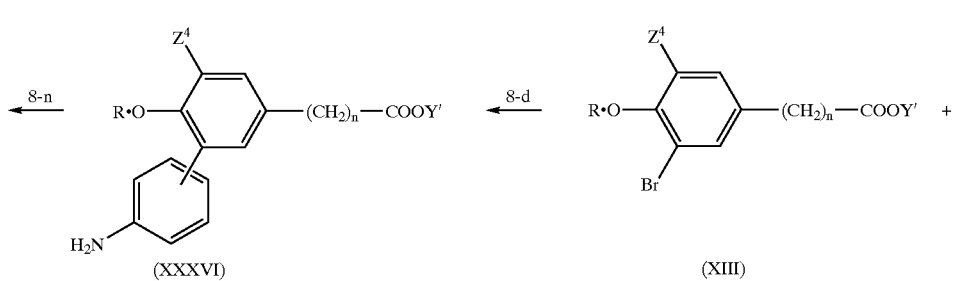

(XXXVI)　　　(XIII)　　　(XXXVII)

a compound represented by the formula (XXXIV) [in the formula, $X^9$ represents hydrogen atom or methyl group, and n, R, $Z^4$, and Y' have the same meanings as those defined above: hereinafter this compound is simply referred to as "Compound (XXXIV)"], as Compound (I) of the present invention [or Compound (IV)] wherein the substituent Z represents $Z^4$, and Ar represents 2-aminobenzothiazole structure can also be prepared by the method described below.

[Preparation Method 8] (Step n)

Specifically, Compound (XXXIV) can be synthesized by reacting a thiourea derivative represented by the formula (XXXV) (in the formula, n, R, Y', and $X^9$ have the same meanings as those defined above: hereinafter this compound is simply referred to as "Compound (XXXV)"), which is obtained by reacting an aniline derivative represented by the formula (XXXVI) [in the formula, n, R, and $Z^4$ have the same meanings as those defined above: hereinafter this compound is simply referred to as "Compound (XXXVI)"] with an alkali thiocyanate such as potassium thiocyanate or methyl isothiocyanate described in Shin Jikken Kagaku Koza (edited by Chemical Society of Japan, published by Maruzen Co., Ltd.), vol. 14, p.1628, with bromine or sulfuryl chloride in an inert solvent such as chloroform, and thereby cyclized into a benzothiazole ring by the method described in Shin Jikken Kagaku Koza (edited by Chemical Society of Japan, published by Maruzen Co., Ltd.), vol. 14, p.2212. Further, Compound (XXXIV) wherein $X^9$ represents hydrogen atom can be directly obtained from Compound (XXXVI) by a method known such as those described in the literature [F. H. Jackson et al., Journal of the Chemical Society Chemical Communications (J. Chem. Soc. Chem. Commun.), 1969, p.268 and the like], specifically, by reacting Compound (XXXVI) with an alkali salt of thiocyanic acid such as potassium thiocyanate in acetic acid using bromine.

[Preparation Method 8] (Step d)

Compound (XXXVI) can be prepared from Compound (XIII) mentioned above and an aminophenylboronic acid derivative represented by the formula (XXXVII) (in the formula, $L^1$ and $L^2$ have the same meanings as those defined above), which is commercially available or can be prepared by a known method or a method similar thereto, according to the method described in the step d of the preparation method 4 mentioned above.

Compound (I) of the present invention or a precursor thereof can also be prepared by modifying or converting the group Ar (including Ar' and Ar") of the compounds obtained by any of the aforementioned preparation methods according to the method described below.

[Preparation Method 9] (Step e)

As shown in the following scheme 14:

(Scheme 14)

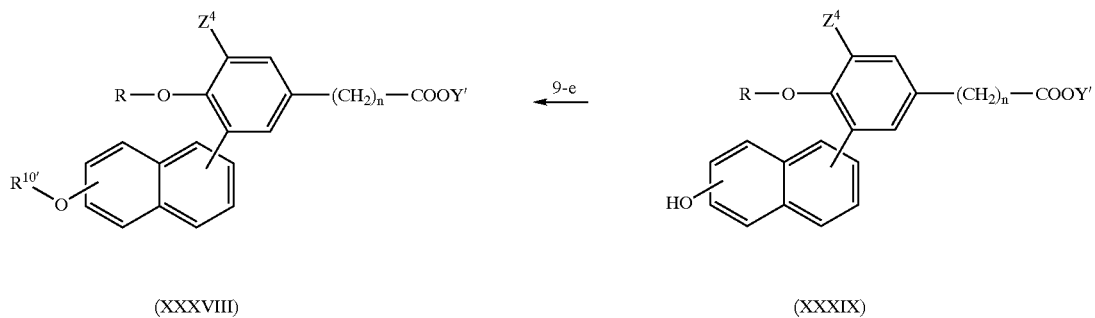

(XXXVIII)　　　(XXXIX)

a compound represented by the formula (XXXVIII) [hereinafter simply referred to as "Compound (XXXVIII)"], as Compound (I) of the present invention [or Compound (IV) mentioned above] wherein Ar has an alkoxynaphthyl structure, can be obtained by alkylating hydroxyl group on naphthalene ring of a compound represented by the formula (XXXIX) [in the formula, n, R, $Z^4$, and Y' have the same meanings as those defined above: hereinafter this compound is simply referred to as "Compound (XXXIX)"] by the method described in the step e of the preparation method 4 mentioned above. In the formula of Compound (XXXVIII), $R^{10}$ is the same as $R^{10}$ mentioned above, or when $R^{10}$ of Compound (I) of the present invention contains hydroxyl group, the group may represent an acyloxy group consisting of the hydroxyl group substituted with a protective group such as acetyl group, which can be converted into hydroxyl group by hydrolysis, or the hydroxyl group substituted with a protective group, for example, a trialkylsilyl group such as t-butyldimethylsilyl group, which can be removed by a conventional method. Further, when $R^{10}$ of Compound (I) of the present invention contains carboxyl group, the group may represent an alkyloxycarbonyl group consisting of the carboxyl group substituted with methyl group, ethyl group or the like, which can be converted into carboxyl group by hydrolysis, or an alkyloxycarbonyl group consisting of the carboxyl group substituted with t-butyl group or the like, which can be removed by a conventional method. Symbol "n", R, $Z^4$ and Y' have the same meanings as those defined above.

[Preparation Method 10] (Step o)

As shown in the following scheme 15:

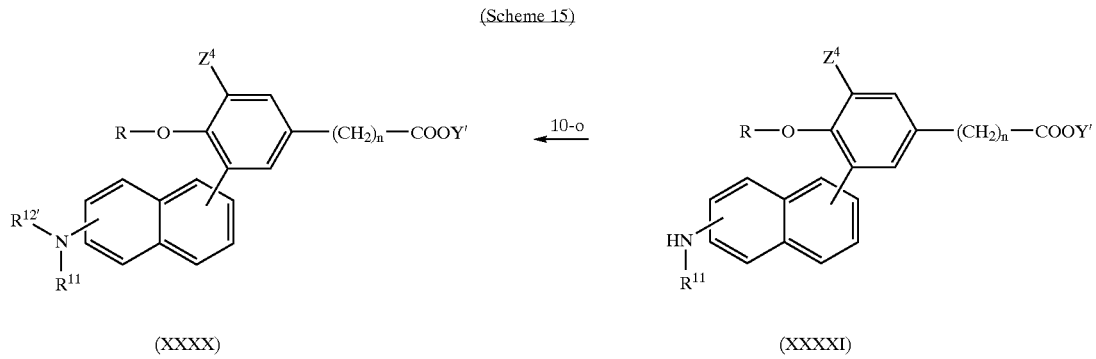

a compound represented by the formula (XXXX) [hereinafter simply referred to as "Compound (XXXX)"], as Compound (I) of the present invention [or Compound (IV) mentioned above] wherein Ar has an aminonaphthyl structure, can also be prepared from a compound represented by the formula (XXXXI) [in the formula, n, R, $Z^4$, Y', and $R^{11}$ have the same meanings as those defined above: hereinafter this compound is simply referred to as "Compound (XXXXI)"]. In the formula of Compound (XXXX), $R^{12'}$ is the same as $R^{12}$ mentioned above, or when $R^{12}$ of Compound (I) of the present invention contains hydroxyl group, the group may represent an acyloxy group consisting of the hydroxyl group substituted with a protective group such as acetyl group, which can be converted into hydroxyl group by hydrolysis, or the hydroxyl group substituted with a protective group, for example, a trialkylsilyl group such as t-butyldimethylsilyl group, which can be removed by a conventional method. Further, when $R^{12}$ of Compound (I) of the present invention contains amino group, the group may represent an amino group substituted with a carbamate-type protective group such as Boc group, which can be removed by hydrolysis or by a conventional method. Symbol "n", R, $Z^4$, Y' and $R^{11}$ have the same meanings as those defined above.

[Preparation Method 10] (Step o-1)

Specifically, Compound (XXXX) can be prepared by condensing Compound (XXXXI) with any of acylating agents including an acid anhydride, acid halide, N,N-dialkylcarbamoyl chloride, alkylsulfonyl chloride, N,N-dialkylsulfamoyl chloride and the like in an inert solvent, and if necessary, in the presence of a base. Examples of the inert solvent used in this reaction include, for example, halogenated hydrocarbons such as dichloromethane and chloroform, ethers such as tetrahydrofuran, dioxane and diethyl ether, dimethyl sulfoxide, N,N-dimethylformamide, acetonitrile and the like. These solvents can be used each alone or as a mixed solvent.

Among the aforementioned acylating agents, examples of the acid anhydride include acetic anhydride, propionic anhydride, butyric anhydride, valeric anhydride, isobutyric anhydride, pivalic anhydride and the like. Examples of the acid halide include acetyl chloride, propionyl chloride, butyryl chloride, isobutyryl chloride, isovaleryl chloride, pivaloyl chloride, acetoxyacetyl chloride and the like. Examples of the N,N-dialkylcarbamoyl chloride include N,N-dimethylcarbamoyl chloride. Examples of the alkylsulfonyl chloride include methylsulfonyl chloride, ethylsulfonyl chloride and the like. Examples of the N,N-dialkylsulfamoyl chloride include N,N-dimethylsulfamoyl chloride and the like. Examples of the amount of these agents include 1 to 20 moles, preferably 1 to 10 moles, based on Compound (XXXXI).

Examples of the base used in the aforementioned reaction include, for example, alkali metal compounds such as sodium hydrogencarbonate, sodium hydroxide, potassium carbonate, sodium carbonate, potassium hydroxide, and sodium methylate, and organic tertiary amines such as pyridine, trimethylamine, triethylamine, and N-methylmorpholine. Examples of the amount of these based include generally 1 to 20 moles, preferably 1 to 10 moles, based on Compound (XXVII).

Examples of the reaction temperature include generally −30 to 120° C., preferably −20 to 50° C. The reaction time is generally 0.5 to 72 hours, preferably 0.5 to 48 hours. Since progress of the reaction can be monitored by thin layer chromatography (TLC), high performance liquid chromatography (HPLC) or the like, the reaction can generally be terminated appropriately so as to maximize an yield of Compound (XXXX).

[Preparation Method 10] (Step o-2)

When Compound (XXXX) is an acid amide, the target compound can be prepared from Compound (XXXXI) and a carboxylic acid containing $R^{12'}$ by a method using a condensing agent described in the ordinary literature in the filed of chemistry, for example, Jikken Kagaku Koza, 4th Edition (edited by Chemical Society of Japan, published by Maruzen Co., Ltd.), vol. 22, p.139. An example includes a method of carrying out a reaction by using dicyclohexylcarbodiimide (DCC), N-ethyl-N'-3-dimethylaminopropylcarbodiimide hydrochloride (WSC.HCl), O-(7-azabenzotriazol-1-yl)-N,N,N',N'-tetramethyluronium hexafluorophosphate (HATU) or the like as the condensing agent in an inert solvent such as tetrahydrofuran and dichloromethane, and if necessary, with addition of an additive such as N-hydroxysuccinimide (HONSu) and 1-hydroxybenzotriazole (HOBT) or a tertiary amine such as triethylamine, diisopropylethylamine and 4-(N,N-dimethylamino)pyridine.

[Preparation Method 10] (Step o-3)

Further, among Compound (XXXX), the compound wherein $R^{12'}$ is particularly —$CONH_2$ group, the target compound can be prepared, for example, by reacting Compound (XXXXI) with a 1 to 5 moles of a cyanic acid alkali metal salt (NaOCN, KOCN and the like) in a mixed solvent of water/acetic acid. For this purpose, examples of the reaction temperature include generally a temperature of from room temperature to 100° C., and examples of the reaction time include generally 1 to 24 hours.

[Preparation Method 11] (Step e)

As shown in the following scheme 16:

group such as t-butyldimethylsilyl group, which can be removed by a conventional method. Further, when $X^2$, $X^3$ and $X^8$ of Compound (I) of the present invention contains carboxyl group, they may represent an alkyloxycarbonyl group consisting of the carboxyl group substituted with methyl group, ethyl group or the like, which can be converted into carboxyl group by hydrolysis, or an alkyloxycarbonyl group consisting of the carboxyl group substituted with t-butyl group or the like, which can be removed by a

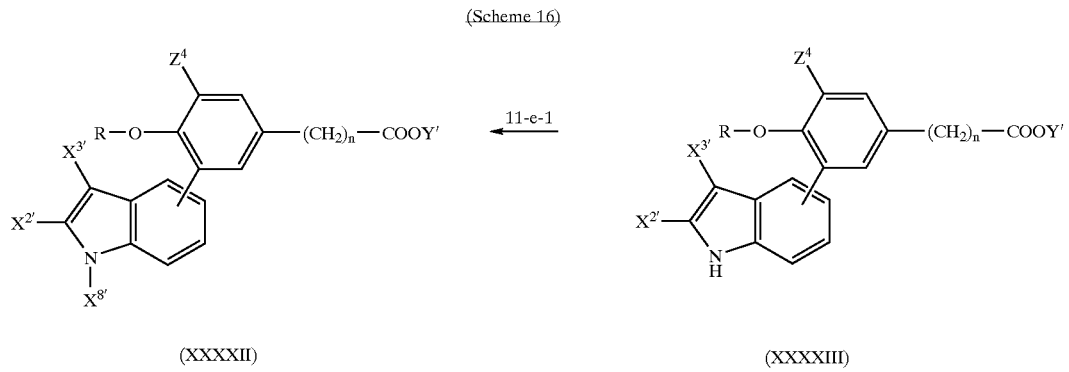

a compound represented by the formula (XXXXII) [hereinafter simply referred to as "Compound (XXXXII)"] as Compound (I) of the present invention [or Compound (IV) mentioned above] wherein Ar represents an indole structure can be prepared from a compound represented by the formula (XXXXIII) [hereinafter simply referred to as "Compound (XXXXIII)"]. In the formulas of the compounds (XXXXII) and (XXXXIII), n, R, $Z^4$ and Y' have the same meanings as those defined above. $X^{2'}$, $X^{3'}$, and $X^8$ are the same as $X^2$, $X^3$ and $X^8$ mentioned above, or when $X^2$, $X^3$, and $X^8$ of Compound (I) of the present invention contain hydroxyl group, they may represent an acyloxy group consisting of the hydroxyl group substituted with a protective group such as acetyl group, which can be converted into hydroxyl group by hydrolysis, or the hydroxyl group substituted with a protective group, for example, a trialkylsilyl conventional method. Examples of the preparation method include performing an alkylation reaction of the NH portion of the indole of Compound (XXXXIII) by a method similar to that of the preparation method 4, step e-1 mentioned above. An specific example includes a method of preparing Compound (XXXXII) by reacting Compound (XXXXIII) with an alkylating agent such as commercially available alkyl halides in an inert solvent such as N,N-dimethylformamide in the presence of a base such as sodium hydride.

[Preparation Method 12] (Step p-1)

As shown in the following scheme 17:

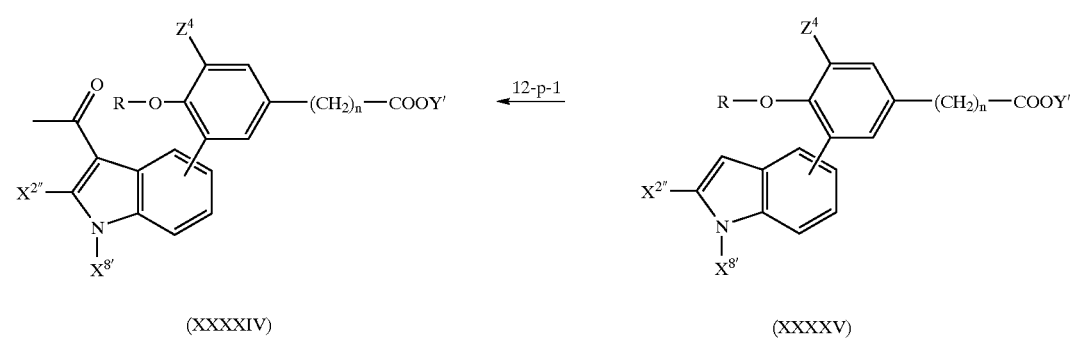

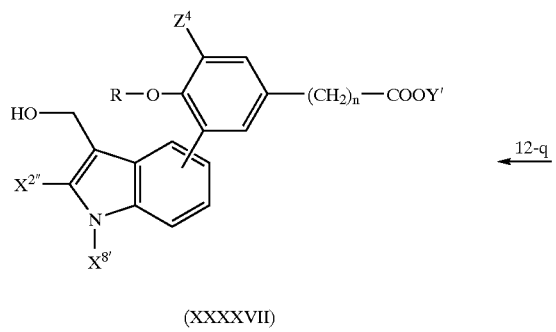

(XXXXVII)

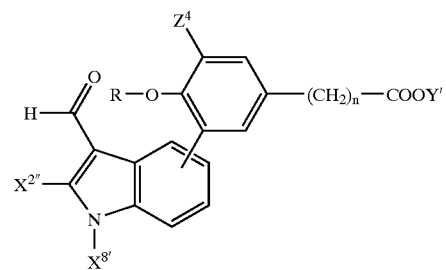

(XXXXVI)

a compound represented by the formula (XXXXIV) [in the formula, $X^{2''}$ represents hydrogen atom or a linear or branched saturated alkyl group having 1 to 4 carbon atoms, and n, R, $Z^4$, Y' and $X^8$ have the same meanings as those defined above: hereinafter this compound is simply referred to as "Compound (XXXXIV)"], as Compound (I) of the present invention [or Compound (IV) mentioned above] wherein Ar has an indole structure having acetyl group, can be prepared from a compound represented by the formula (XXXXV) [in the formula, n, R, $Z^4$, Y', $X^{2''}$, and $X^8$ have the same meanings as those defined above: hereinafter this compound is simply referred to as "Compound (XXXXV)"]. An example includes a preparation by the Friedel-Crafts reaction described in the ordinary literature in the filed of chemistry, e.g., Jikken Kagaku Koza, 4th Edition, (edited by Chemical Society of Japan, published by Maruzen Co., Ltd.), vol. 21, p.278 by using Compound (XXXXV) in the presence of acetyl chloride and a Lewis acid catalyst. Examples of the amount of acetyl chloride include generally 1 to 10 moles, preferably 1.5- to 4 moles, based on Compound (XXXXV). Examples of the Lewis acid used for the reaction include aluminum chloride, tin chloride, titanium chloride and the like. Examples of the amount of these acids include generally 1 to 10 moles, preferably 1- to 4 moles, based on the starting material. Examples of the solvent used for this reaction include halogenated hydrocarbons such as dichloromethane and 1,2-dichloroethane, nitrobenzene, carbon disulfide and the like. An appropriate temperature of from −10 to 100° C. is generally chosen as the reaction temperature, and preferred examples include a temperature of from 0° C. to room temperature. The reaction time is generally 1 to 16 hours, preferably 2 to 8 hours. Since progress of the reaction can be monitored by thin layer chromatography (TLC), high performance liquid chromatography (HPLC) or the like, the reaction can generally be terminated appropriately so as to maximize an yield of Compound (XXXXIV).

[Preparation Method 12] (Step p-2)

A compound represented by the formula (XXXXVI) [in the formula, n, R, $Z^4$, Y', $X^{2''}$ and $X^{8'}$ have the same meanings as those defined above: hereinafter this compound is simply referred to as "Compound (XXXXVI)"], as Compound (I) of the present invention [or Compound (IV) mentioned above] wherein Ar has an indole structure having formyl group, can also be prepared from Compound (XXXXV) mentioned above. Specifically, the target compound can be prepared by subjecting Compound (XXXXV) to the Vilsmeier reaction described in ordinary literatures of chemistry [Jikken Kagaku Koza, 4th Edition (edited by Chemical Society of Japan, published by Maruzen Co., Ltd.), vol. 21, p.110; M. L. Borgne et al., Bioorganic & Medicinal Chemistry Letters (Bioorg. Med. Chem. Lett.), 1999, vol. 9, p.333 and the like]. Examples of the method include a method of reacting Compound (XXXXV) with N,N-dimethylformamide, which serves as both of a regent and a solvent, together with a halogenating reagent such as oxalyl chloride. As the reaction temperature is, an appropriate temperature of from −10 to 100° C. is generally chosen. Preferred examples include a temperature of from 0 to 60° C. The reaction time is generally 1 to 16 hours, preferably 2 to 8 hours. Since progress of the reaction can be monitored by thin layer chromatography (TLC), high performance liquid chromatography (HPLC) or the like, the reaction can generally be terminated appropriately so as to maximize an yield of Compound (XXXXVI).

[Preparation Method 12] (Step q)

The compound represented by the formula (XXXXVII) [in the formula, n, R, $Z^4$, Y', $X^{2''}$ and $X^{8'}$ have the same meanings as those defined above: hereinafter this compound is simply referred to as "Compound (XXXXVII)"], as Compound (I) of the present invention [or Compound (IV) mentioned above] wherein Ar has an indole structure having hydroxymethyl group, can also be prepared from Compound (XXXXVI) mentioned above. Specifically, the target compound can be prepared by reducing the formyl group of Compound (XXXXVI) according to a method described in the ordinary literature in the filed of chemistry, e.g., Shin Jikken Kagaku Koza (edited by Chemical Society of Japan, published by Maruzen Co., Ltd.), vol. 15, p.179. An example includes, for example, a method of subjecting Compound (XXXXVI) to a reaction by using a reducing agent such as sodium borohydride in an alcohol such as methanol or a mixed solution of an alcohol and an ether-type solvent such as tetrahydrofuran so as to convert the formyl group into hydroxymethyl group.

[Preparation Method 13] (Step r)
As shown in the following scheme 18:
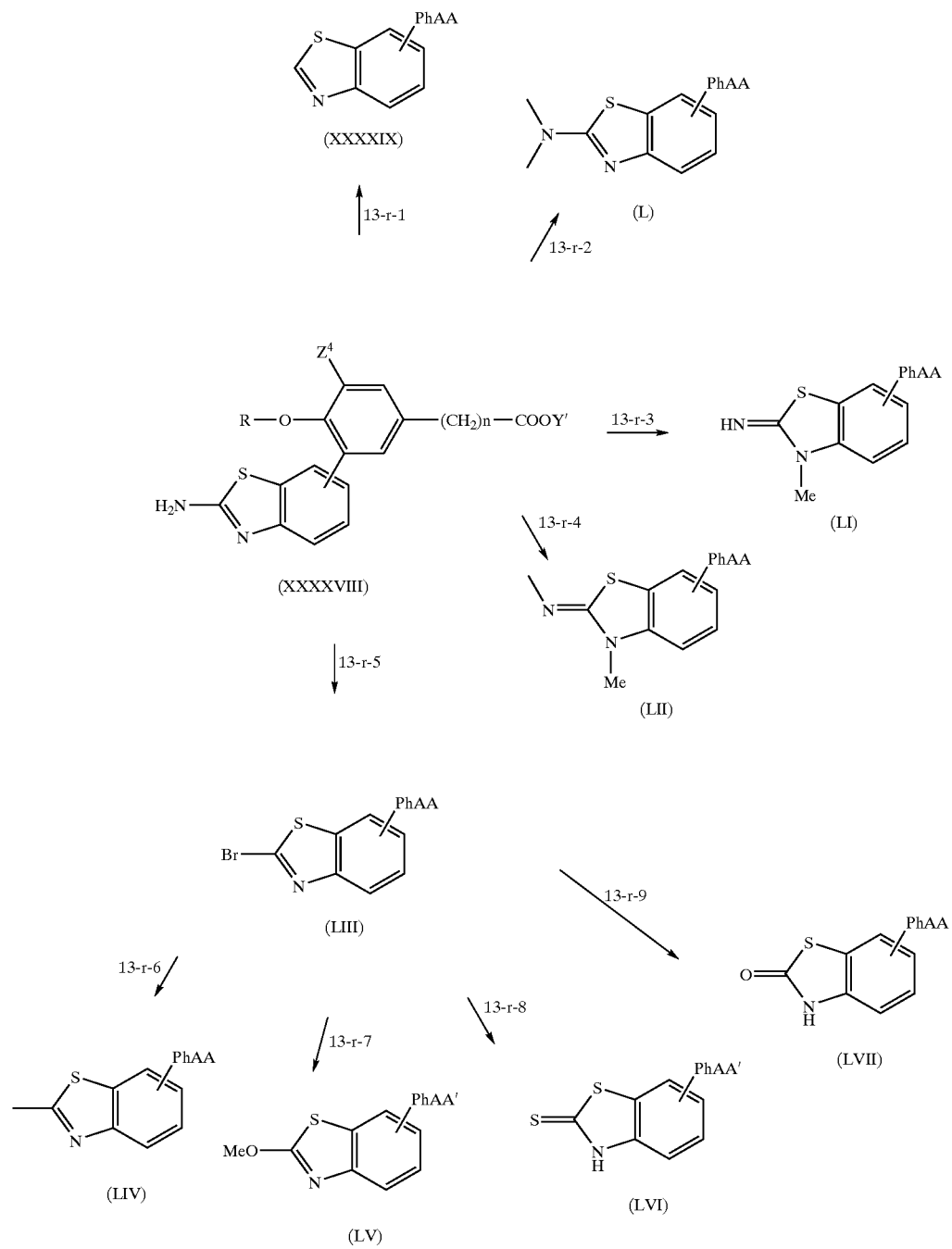

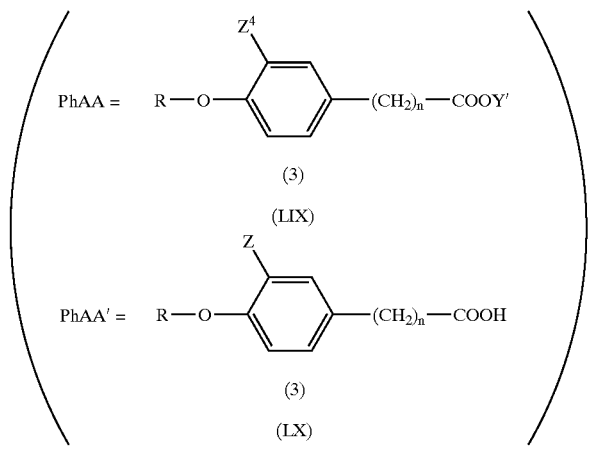

(LIX)

(LX)

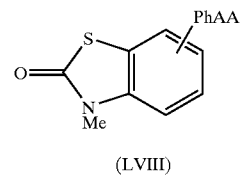

(LVIII)

Compound (I) of the present invention [or Compound (IV) mentioned above] having a benzothiazole or 2,3-dihydrobenzothiazole structure in Ar can also be prepared from a 2-aminobenzothiazole derivative represented by the formula (XXXXVIII) [in the formula, n, R, $Z^4$ and Y' have the same meanings as those defined above: hereinafter this compound is simply referred to as "Compound (XXXXVIII)"].

[Preparation Method 13] (Step r-1)

A compound represented by the formula (XXXXIX) {in the formula, PhAA represents a residue represented by the formula (LIX) [in the formula, n, R, $Z^4$ and Y' have the same meanings as those defined above, and the residue binds to a benzothiazole structure at the 3-position on the benzene ring]: hereinafter this compound is simply referred to as "Compound (XXXXIX)"}, as Compound (I) of the present invention [or Compound (IV) mentioned above] having a benzothiazole structure in Ar, can be prepared from Compound (XXXXVIII) according to a method similar to a known method described in the literature [L. Grehn, Journal of Heterocyclic Chemistry (J. Heterocycl. Chem.), 1978, vol. 15 p.81]. Specifically, a method is available in which Compound (XXXXVIII) is reacted with aqueous hypophosphorous acid ($H_3PO_2$) and sodium nitrite in a water-miscible organic solvent such as acetonitrile to diazotize the amino group of the 2-aminothiazole structure and to simultaneously perform a reduction reaction. Examples of the amount of sodium nitrite include generally 1 to 10 moles, preferably 1 to 3 moles, based on Compound (XXXXVIII). As the reaction temperature, an appropriate temperature of from −20° C. to 100° C. is generally chosen. Preferred examples include a temperature of from room temperature to 60° C. The reaction time is generally 30 minutes to 7 days, preferably 2 to 48 hours. Since progress of the reaction can be monitored by thin layer chromatography (TLC), high performance liquid chromatography (HPLC) or the like, the reaction can generally be terminated appropriately so as to maximize an yield of Compound (XXXXIX).

[Preparation Method 13] (Step r-2)

A compound represented by the formula (L) {in the formula, PhAA has the same meaning as defined above: hereinafter this compound is simply referred to as "Compound (L)"}, as Compound (I) of the present invention [or Compound (IV) mentioned above] having a 2-(N,N-dimethylamino)benzothiazole structure in Ar, can be prepared from Compound (XXXXVIII). An example includes, for example, a method of reacting Compound (XXXXVIII) with methyl iodide in N,N-dimethylformamide in the presence of sodium hydride. Examples of the amount of methyl iodide include generally 2 moles to a large excess amount, preferably 3 to 10 moles, based on Compound (XXXXVIII). Examples of the amount of sodium hydride used include generally 1 to 10 moles, preferably 1 to 3 moles, based on the starting material. As the reaction temperature, an appropriate temperature of from −10° C. to 50° C. is generally chosen. Preferred examples include a temperature of from 0° C. to room temperature. The reaction time is generally 1 to 16 hours, preferably 2 to 8 hours. Since progress of the reaction can be monitored by thin layer chromatography (TLC), high performance liquid chromatography (HPLC) or the like, the reaction can generally be terminated appropriately so as to maximize an yield of Compound (L).

[Preparation Method 13] (Step r-3)

A compound represented by the formula (LI) [in the formula, PhAA has the same meaning as that defined above: hereinafter this compound is simply referred to as "Compound (LI)"], as Compound (I) of the present invention [or Compound (IV) mentioned above] having a 2-imino-3-methyl-2,3-dihydrobenzothiazole structure in Ar, can be prepared from Compound (XXXXVIII). An example includes, for example, a method of reacting Compound (XXXXVIII) with methyl iodide in an ether-type solvent such as dimethoxyethane. Examples of the amount of methyl iodide includes generally 1 mole to a large excess amount, preferably 3 to 10 moles, based on Compound (XXXXVIII). As the reaction temperature, an appropriate temperature of from room temperature to 100° C. is generally chosen. Preferred examples include a temperature of from room temperature to 60° C. The reaction time is generally 1 hour to 2 days, preferably 8 to 24 hours. Since progress of the reaction can be monitored by thin layer chromatography (TLC), high performance liquid chromatography (HPLC) or the like, the reaction can generally be terminated appropriately so as to maximize an yield of Compound (LI).

[Preparation Method 13] (Step r-4)

A compound represented by the formula (LII) [in the formula, PhAA has the same meaning as that defined above: hereinafter this compound is simply referred to as "Compound (LII)"], as Compound (I) of the present invention [or Compound (IV) mentioned above] having a 2-(N-methylimino)-3-methyl-2,3-dihydrobenzothiazole structure in Ar, can be prepared from Compound (XXXXVIII). An example includes, for example, a method of reacting Compound (XXXXVIII) with methyl iodide in acetone in the presence of potassium carbonate. Examples of the amount of methyl iodide include generally 2 moles to a large excess amount, preferably 3 to 10 moles, based on Compound (XXXXVIII). Examples of the amount of potassium carbonate used include generally 1 to 10 moles, preferably 2 to 5 moles, based on the starting material. As the reaction temperature, an appropriate temperature of from room temperature to the boiling temperature of a solvent is generally chosen. The reaction time is generally 3 hours to 1 week. Since progress of the reaction can be monitored by thin layer chromatography (TLC), high performance liquid chromatography (HPLC) or the like, the reaction can generally be terminated appropriately so as to maximize an yield of Compound (LII).

[Preparation Method 13] (Step r-5)

A compound represented by the formula (LIII) [in the formula, PhAA has the same meaning as that defined above: hereinafter this compound is simply referred to as "Compound (LIII)"], as a preparation intermediate of Compound (I) of the present invention [or Compound (IV) mentioned above] having a 2-bromobenzothiazole structure in Ar, can be prepared from Compound (XXXXVIII). An example includes, for example, a method similar to a known method described in the literature [A. Roessler et al., Journal of the Chemical Society Perkin Trans 1 (J. Chem. Soc. Perkin Trans 1), 1998, vol. 4, p.685]. Specifically, a method is available in which Compound (XXXXVIII) is reacted with a nitrous acid ester such as t-butyl nitrite and copper(I) bromide in acetonitrile to convert the amino group of the 2-aminobenzothiazole structure into bromo group. Examples of the amount of the nitrous acid ester include generally 1 to 10 moles, preferably 1.5 to 3 moles, based on Compound (XXXXVIII). Examples of the amount of copper (I) bromide used include generally 1 to 10 moles, preferably 1.2- to 2 moles, based on the starting material. As the reaction temperature, an appropriate temperature of from room temperature to the boiling temperature of the solvent is generally chosen. The reaction time is generally 10 minutes to 8 hours. Since progress of the reaction can be monitored by thin layer chromatography (TLC), high performance liquid chromatography (HPLC) or the like, the reaction can generally be terminated appropriately so as to maximize an yield of Compound (LIII).

[Preparation Method 13] (Step r-6)

A compound represented by the formula (LIV) [in the formula, PhAA has the same meaning as that defined above: hereinafter this compound is simply referred to as "Compound (LIV)"], as Compound (I) of the present invention [or Compound (IV) mentioned above] having a 2-methylbenzothiazole structure in Ar, can be prepared from Compound (LIII) mentioned above. An example includes, for example, a preparation method similar to a known method described in the literature [M. Gray et al., Tetrahedron Letters (Tetrahedron Lett.), 2000, vol. 41, No. 32, p.6237]. Specifically, the compound can be prepared by subjecting Compound (LIII) and trimethylboroxine to the Suzuki reaction described in the step 4 of the preparation method 4.

[Preparation Method 13] (Step r-7)

A compound represented by the formula (LV) {in the formula, PhAA' represents a residue represented by the formula (LX) [in the formula, n, R, and Z have the same meanings as those defined above, and the residue binds to the benzothiazole structure at the 3-position on the benzene ring]: hereinafter this compound is simply referred to as "Compound (LV)"}, as Compound (I) of the present invention [or Compound (III) mentioned above] having a 2-methoxybenzothiazole structure in Ar, can be prepared from Compound (LIII) mentioned above. Specifically, the target compound can be prepared by hydrolyzing Compound (LIII) using methanol as a polar solvent and an alkali metal base such as sodium hydroxide, potassium hydroxide, and sodium methoxide, or an aqueous solution thereof as a base according the method described in the step a of the preparation method 1, and converting the bromo group of the 2-bromobenzothiazole structure into methoxy group. For example, a method is available in which a reaction is carried out in methanol by using 2 to 10 moles of an aqueous solution of sodium hydroxide based on Compound (LIII) at a temperature of from room temperature to 60° C. The reaction time is generally 1 hour to 2 days. Since progress of the reaction can be monitored by thin layer chromatography (TLC), high performance liquid chromatography (HPLC) or the like, the reaction can generally be terminated appropriately so as to maximize an yield of Compound (LV).

[Preparation Method 13] (Step r-8)

A compound represented by the formula (LVI) [in the formula, PhAA' has the same meaning as that defined above: hereinafter this compound is simply referred to as "Compound (LVI)"], as Compound (I) of the present invention [or Compound (III) mentioned above] having a 2-thioxo-2,3-dihydrobenzothiazole structure in Ar, can be prepared from Compound (LIII) mentioned above. An example includes, for example, a preparation method similar to a known method described in the literature [M. Mackie, Journal of the Chemical Society (J. Chem. Soc.), 1955, p.1030]. Specifically, the compound can be prepared by converting the 2-bromobenzothiazole structure of Compound (LIII)

into 2-thioxo-2,3-dihydrobenzothiazole structure by using thiourea in a water-miscible solvent such as ethanol and acetonitrile in the presence of a mineral acid such as sulfuric acid and simultaneously performing a hydrolysis reaction. For example, a method is available in which a reaction is carried out using 2 to 10 moles of thiourea based on Compound (LIII) at a temperature of from room temperature to 90° C. The reaction time is generally 3 hours to 7 days. Since progress of the reaction can be monitored by thin layer chromatography (TLC), high performance liquid chromatography (HPLC) or the like, the reaction can generally be terminated appropriately so as to maximize an yield of Compound (LVI).

[Preparation Method 13] (Step r-9)

A compound represented by the formula (LVII) [in the formula, PhAA has the same meaning as that defined above: hereinafter this compound is simply referred to as "Compound (LVII)"], as Compound (I) of the present invention [or Compound (IV) mentioned above] having a 2-oxo-2,3-dihydrobenzothiazole structure, can be prepared from Compound (LIII) mentioned above. Specifically, a method is available in which Compound (LIII) is reacted with a methyl-2,3-dihydrobenzothiazole structure, can be prepared from Compound (LVII) mentioned above. Specifically, the compound can be prepared by reacting Compound (LII) with methyl iodide in an ether-type solvent such as 1,2-dimethoxyethane in the presence of potassium t-butoxide. Examples of the amount of methyl iodide include generally 2 moles to a large excess amount, preferably 3 to 10 moles, based on Compound (LVII). Examples of the amount of potassium t-butoxide used include generally 1 to 10 moles, preferably 1.2- to 5 moles, based on the starting material. As the reaction temperature, an appropriate temperature of from 0° C. to the boiling temperature of the solvent is generally chosen. The reaction time is generally 1 hour to 3 days. Since progress of the reaction can be monitored by thin layer chromatography (TLC), high performance liquid chromatography (HPLC) or the like, the reaction can generally be terminated appropriately so as to maximize an yield of Compound (LVIII).

[Preparation Method 14] (Step s)

As shown in the following scheme 19:

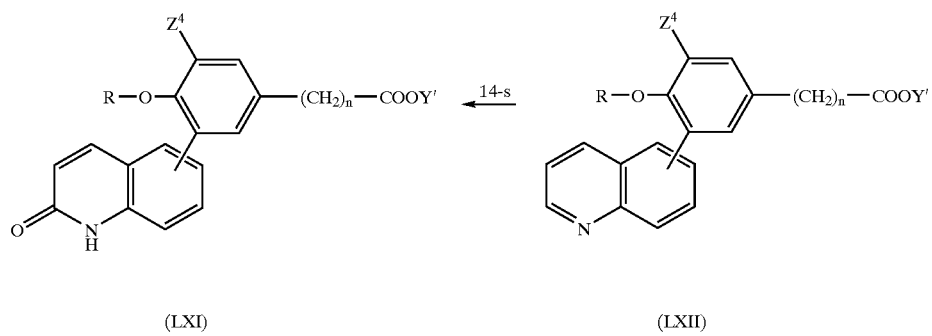

(Scheme 19)

(LXI)   (LXII)

mineral acid such as a hydrochloric acid and sulfuric acid in an alcohol such as methanol and ethanol to convert the 2-bromobenzothiazole structure into the 2-oxo-2,3-dihydrobenzothiazole structure. Examples of the amount of the mineral acid used include generally 2 moles to a large excess amount based on Compound (VIII). As the reaction temperature, an appropriate temperature of from room temperature to the boiling temperature of the solvent is generally chosen. The reaction time is generally 1 hour to 3 days. Since progress of the reaction can be monitored by thin layer chromatography (TLC), high performance liquid chromatography (HPLC) or the like, the reaction can generally be terminated appropriately so as to maximize an yield of Compound (LVII).

[Preparation Method 13] (Step r-10)

A compound represented by the formula (LVIII) [in the formula, PhAA has the same meaning as defined above: hereinafter this compound is simply referred to as "Compound (LVIII)"], as Compound (I) of the present invention [or Compound (IV) mentioned above] having a 2-oxo-3- a compound represented by the formula (LXI) [in the formula, n, R, $Z^4$, and Y' have the same meanings as those defined above: hereinafter this compound is simply referred to as "Compound (LXI)"], as Compound (I) of the present invention [or Compound (IV) mentioned above] wherein Ar has a 2-oxo-1,2-dihydroquinoline structure, can also be prepared from a compound represented by the formula (LXII) [in the formula, n, R, $Z^4$, and Y' have the same meanings as those defined above: hereinafter this compound is simply referred to as "Compound (LXII)"]. An example includes, for example, a preparation method similar to the method described in the known literature [M. R. Sabol et al., Synthetic Communications (Synth. Commun.), 2000, vol. 30, p.427]. Specifically, a method is available in which Compound (LXII) is reacted with 3-chloroperbenzoic acid in chloroform to form an N-oxide of quinoline structure and then the product is heated in acetic anhydride for conversion into the 2-oxo-1,2-dihydroquinoline structure.

[Preparation Method 15]

As shown in the following scheme 20:

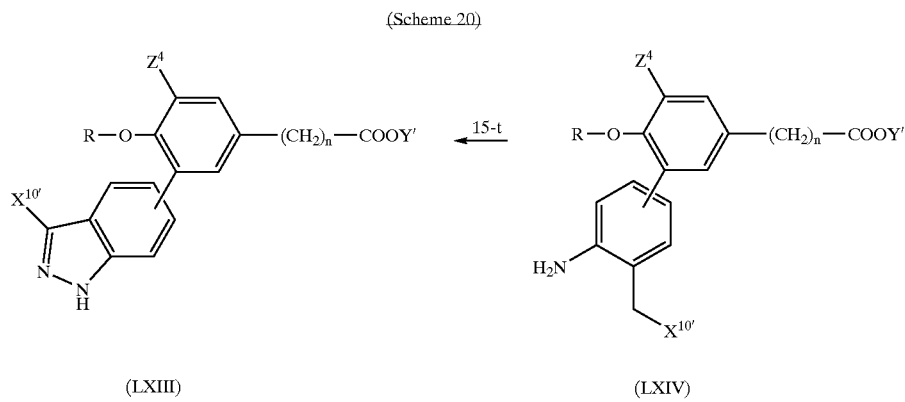

a compound represented by the formula (LXIII) [in the formula, $X^{10'}$ represents hydrogen atom or a linear or branched saturated alkyl group having 1 to 4 carbon atoms, and n, R, $Z^4$, and Y' have the same meanings as those defined above: hereinafter this compound is simply referred to as "Compound (LXIII)"], as Compound (I) of the present invention [or Compound (IV) mentioned above] wherein the substituent Z represents $Z^4$, and Ar represents an indazole structure, can also be prepared by the method described below.

[Preparation Method 15] (Step t)

Specifically, Compound (LXIII) can be prepared from an ortho-alkylaniline derivative represented by the formula (LXIV) [in the formula, n, R, $Z^4$, and $X^{10'}$ have the same meanings as those defined above: hereinafter this compound is simply referred to as "Compound (LXIV)"]. An example includes, for example, a method of reacting Compound (LXIV) with nitrous acid, nitrous acid salt, dinitrogen trioxide gas, nitrous acid ester or the like to diazotize the amino group in Compound (LXIV) and preparing Compound (LXIII) form the produced diazo compound or diazonium salt by an intramolecular cyclization reaction. Examples of the reagent used for the diazotization reaction include nitrous acid, nitrous acid salts such as sodium nitrite, dinitrogen trioxide gas which can be purified from nitrous acid salt and nitric acid, nitrous acid esters such as isoamyl nitrite and t-butyl nitrite. Examples of the amount of the regent include generally 0.8 to 10 moles, preferably 1 to 3 moles, based on Compound (LXIV).

The reaction system may be any one of a system consisting of acidic water, a system consisting of an organic acid, a two-phase system of water and an organic solvent, and a homogenous system of water-containing organic solvent or that of organic solvents. Examples of the acidic water include aqueous solutions of mineral acids such as hydrochloric acid, hydrobromic acid, sulfuric acid, and tetrafluoroboric acid. Examples of the organic acid include acetic acid, acetic anhydride and methanesulfonic acid and the like, and acetic acid is a preferred example among them. Examples of the organic solvent include hydrocarbon-type solvents such as toluene, xylene and hexane, halogen-type solvents such as methylene chloride, sulfoxide-type solvents such as dimethyl sulfoxide, amide-type solvents such as dimethylformamide, ether-type solvents such as tetrahydrofuran, dioxane and diglyme, alcohol-type solvents such as methanol and ethanol, nitrile-type solvents such as acetonitrile and the like. Two or more kinds of these solvents may also be used as a mixture. An additive may further be added to the system depending on the reagent and solvent. Examples of the additive include bases such as sodium carbonate, potassium carbonate, cesium carbonate, cesium fluoride, potassium fluoride, potassium phosphate, potassium acetate, triethylamine, potassium hydroxide, sodium hydroxide, sodium methoxide and lithium methoxide, quaternary ammonium salts such as tetrabutylammonium bromide, crown ethers such as 18-crown 6-ether and the like. Examples of the reaction temperature include generally an appropriate temperature of from −20 to 100° C., and preferred examples include a temperature of from −10 to 60° C. The reaction time is generally 5 minutes to 24 hours, and preferred examples include 15 minutes to 16 hours. An example includes a method of subjecting the resulting diazo compound or diazonium salt, without any treatment, to the cyclization reaction. For that purpose, water, solvents, or additives mentioned above may further be added to the system. In order to decompose excess nitrous acid, urea or the like may be added. Further, it is also possible to perform the cyclization reaction after purification of the resulting diazo compound or diazonium salt by known methods such as concentration, extraction and crystallization. Examples of the reaction temperature used for the cyclization reaction include generally an appropriate temperature of from −20 to 200° C., and preferred examples include a temperature of from 0 to 60° C. The reaction time is generally 1 hour to 7 days, and preferred examples include 1 hour to 3 days. Since progress of the reaction can be monitored by thin layer chromatography (TLC), high performance liquid chromatography (HPLC) or the like, the reaction can generally be terminated appropriately so as to maximize an yield of Compound (LXIII).

[Preparation Method 15] (Step d)
As shown in the following scheme 21:

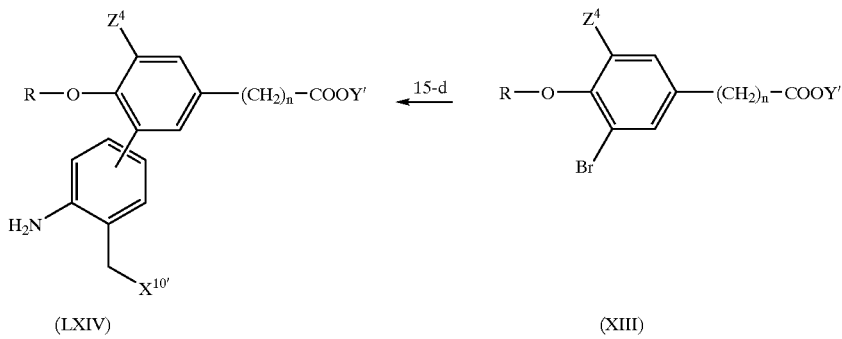

Compound (LXIV) can be prepared from Compound (XIII) mentioned above. An example includes a preparation by reacting Compound (XIII) with a boronic acid derivative of ortho-alkylaniline represented by the following formula (LXV):

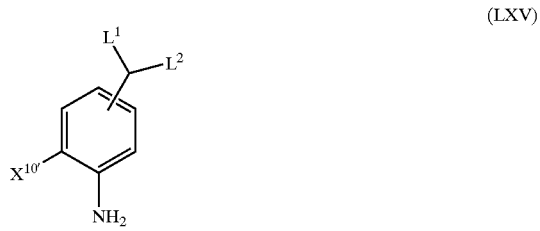

(in the formula, $L^1$, $L^2$, and $X^{10'}$ have the same meanings as those defined above) which can be prepared by a known method or a method similar thereto, according to the method described in the step d of the preparation method 4 mentioned above.

[Preparation Method 16] (Step e)

As shown in the following scheme 22:

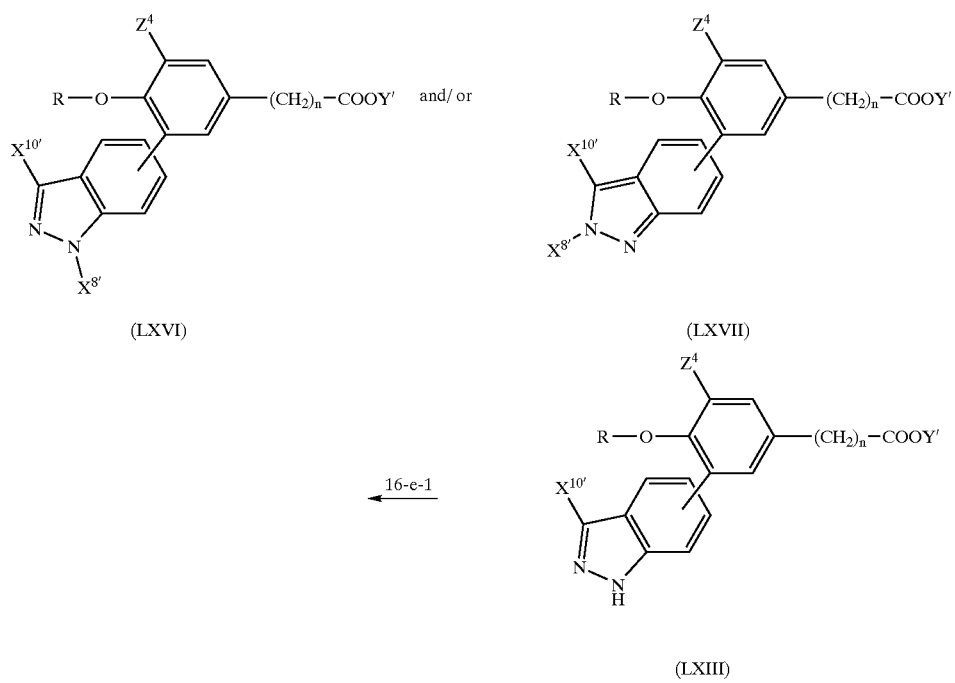

a compound represented by the formula (LXVI) [hereinafter simply referred to as "Compound (LXVI)"] and/or a compound represented by the formula (LXVII) [hereinafter simply referred to as "Compound (LXVII)"], as Compound (I) of the present invention [or Compound (IV) mentioned above] wherein Ar represents an indazole structure, can be prepared from a compound represented by the formula (LXVIII) [hereinafter simply referred to as "Compound (LXVIII)"]. In the formulas of the compounds (LXVI), (LXVII) and (LXVIII), n, R, $Z^4$, Y', and $X^{10'}$ have the same meanings as those defined above. $X^{8'}$ may be the same as $X^8$ mentioned above, or when $X^8$ of Compound (I) of the present invention contains hydroxyl group, the group may represent an acyloxy group consisting of the hydroxyl group substituted with a protective group such as acetyl group, which can be converted into hydroxyl group by hydrolysis, or the hydroxyl group substituted with a protective group, for example, a trialkylsilyl group such as t-butyldimethylsilyl group, which can be removed by a conventional method. Further, when $X^8$ of Compound (I) of the present invention contains carboxyl group, the group may represent an alkyloxycarbonyl group consisting of the carboxyl group substituted with methyl group, ethyl group or the like, which can be converted into carboxyl group by hydrolysis, or an alkyloxycarbonyl group consisting of the carboxyl group substituted with t-butyl group or the like, which can be removed by a conventional method. An example of the preparation method includes an alkylation reaction of Compound (LXVIII) by a method similar to that of the step e-1 of the preparation method 4 mentioned above. Specifically, an example includes a method of reacting Compound (LXVIII) with an alkylating agent such as commercially available alkyl halides in an inert solvent such as N,N-dimethylformamide in the presence of a base such as sodium hydride. In this reaction, when the alkylation advances on the nitrogen atom at the 1-position of the indazole portion of Compound (LXVIII), Compound (LXVI) is produced, and when the alkylation advances on the nitrogen atom at the 2-position, Compound (LXVII) is produced. A production ratio of each compound may change depending reaction conditions. If it is desired to obtain a single product, these compounds can be separated by a known method such as column chromatography.

Examples of the preparation method for Compound (I) of the present invention which contains an asymmetric carbon in the substituent R include a method of using, as a reagent for alkylation in the step e of the preparation method 4, the step e of the preparation method 5, or the step e of the preparation method 6 mentioned above, an alkylating agent in which a moiety corresponding to the asymmetric carbon in the substituent R is already optically active, which is commercially available (or can be prepared by a known method or a method similar thereto). A method is also available in which the compound of the present invention or a precursor thereof is separated as an optically active isomer by a conventional method. Examples of such method include, for example, a method utilizing high performance liquid chromatography (HPLC) using a chiral column, a method comprising condensation with an optically active regent to form a diastereomer, successive separation and purification, followed by decomposition. When a precursor is separated to obtain an optical isomer, an optically active compound (I) of the present invention can then be prepared by performing the aforementioned preparation methods.

When Compound (I) of the present invention contains an acidic functional group such as carboxyl group or phenolic hydroxyl group, the compound can be converted into pharmaceutically acceptable salt (e.g., inorganic salts with sodium, ammonia and the like, or organic salts with triethylamine and the like) by a known means. For example, when an inorganic salt is to be obtained, it is preferable to dissolve Compound (I) of the present invention in water containing at least 1 equivalence of hydroxide, carbonate, bicarbonate or the like corresponding to a desired inorganic salt. For the reaction, an inactive water-miscible organic solvent such as methanol, ethanol, acetone, and dioxane may be mixed. For example, by using sodium hydroxide, sodium carbonate, or sodium bicarbonate, a solution of sodium salt can be obtained.

When Compound (I) of the present invention contains a basic functional group such as amino group, the compound can be converted into a pharmaceutically acceptable salt (e.g., salt with inorganic acids such as hydrochloric acid and sulfuric acid, or salts with organic acids such as acetic acid and citric acid) by a known means. For example, when an inorganic salt is to be obtained, it is preferable to dissolve Compound (I) of the present invention in water containing at least 1 equivalence of a desired inorganic acid. For the reaction, an inactive water-miscible organic solvent such as methanol, ethanol, acetone, and dioxane may be mixed. For example, by using hydrochloric acid, a solution of hydrochloride can be obtained.

If a solid salt is desired, a solution may be evaporated, or a water-miscible organic solvent having polarity to some extent, such as butanol or ethyl methyl ketone, can be added to obtain a solid salt thereof.

The various compounds disclosed by the present invention can be purified by known methods such as recrystallization, and variety of chromatography techniques (column chromatography, flash column chromatography, thin layer chromatography, high performance liquid chromatography).

The compounds (I) of the present invention and pharmaceutically acceptable salts thereof have an action of suppressing the production of both of prostaglandins and leukotrienes. The action of suppressing the production of prostaglandins and/or leukotrienes herein referred to includes, for example, an action of suppressing $PGE_2$ production, observed when cultured cells of MG-63 which is a human osteosarcoma cell line are stimulated with IL-1β and/or $PGD_2$ and $LTB_4$ production observed when cultured cells of RBL-2H3 which is a rat mastocytoma cell line are stimulated with IgE, by 10% or more, preferably 30% or more, particularly preferably 50% or more, compared with a positive control at a concentration not showing cytotoxicity. As for a mode of action at a molecular level, it is considered that the compounds of the present invention inhibit both of COX-1 and/or COX-2, which produce prostaglandins, and 5-LO, which produces leukotrienes. It is also considered that the compounds of the present invention inhibit enzymatic activity of type 2A, 4, or 5 $PLA_2$ involved in prostaglandin and leukotriene production and thereby suppress the production of arachidonic acid.

For example, as for the enzymatic inhibitory action against COX-1, methods for measuring the enzymatic activity are described in the published literature [Yokoyama and Tanabe, Biochemical and Biophysical Research Communications (Biochem. Biophys. Res. Commun.), 1989, vol. 165, p.888; Funk et al., FASEB Journal (FASEB. J), 1992, vol. 5, p.2304; Kraemer et al., Archive of Biochemistry and Biophysics (Arch. Biochem. Biophys), 1992, vol. 293, p.391 and the like], and the COX-1 inhibitory action of the compounds of the present invention will be elucidated by employing these methods. As for the enzyme inhibitory action against COX-2, methods for measuring the enzymatic activity are described in the published literature [Xie et al., Proceeding of National Academy of Science USA (Proc. Natl. Acad. Sci. USA), 1991, vol. 88, p.2692; Kujubu et al., Journal of Biological Chemistry (J. Biol. Chem), 1991, vol. 266, p.12866; O'Banion et al., Journal of Biological Chemistry (J. Biol. Chem), 1991, vol. 266, p.23261; Hla et al., a Proceeding of National Academy of Science USA (Proc. Natl. Acad. Sci. USA), 1992, vol. 89, p.7384; Jones et al., Journal of Biological Chemistry (J. Biol. Chem), vol. 268, p.9049 and the like], and the COX-2 inhibitory action of the compounds of the present invention will be elucidated by employing these methods.

As for the enzyme inhibitory action against 5-LO, methods for measuring the enzymatic activity are described in the published literature [Dixon et al., Proceeding of National Academy of Science USA (Proc. Natl. Acad. Sci. USA), 1988, vol. 85, p.416; Rouzer et al., Journal of Biological Chemistry (J. Biol. Chem.), 1989, vol. 263, p.10135; Chen et al., Journal of Biological Chemistry (J. Biol. Chem.), 1995, vol. 270, p.17993 and the like], and the 5-LO inhibitory action of the compounds of the present invention will be elucidated by employing these methods. As for the enzyme inhibitory action against type 2A $PLA_2$, methods for measuring the enzymatic activity are described in the published literature [Seilhamer et al., Journal of Biological Chemistry (J. Biol. Chem.), 1989, vol. 264, p.5335; Kramer et al., Journal of Biological Chemistry (J. Biol. Chem.), 1989, vol. 264, p.5768; Johansen et al., Biochemical and Biophysical Research Communications (Biochem. Biophys. Res. Commun.), 1992, vol. 187, p.544 and the like], and the type 2A $PLA_2$ inhibitory action of the compounds of the present invention will be elucidated by employing these methods.

As for the enzyme inhibitory action against type 4 $PLA_2$, methods for measuring the enzymatic activity are described in the published literature [Clark et al., Proceeding of National Academy of Science USA (Proc. Natl. Acad. Sci. USA), 1990, vol. 87, p.7708; Gronich et al., Biochemical Journal (Biochem. J.), 1990, vol. 271, p.37; Clark et al., Cell, 1991, vol. 65, p.1043; Kramer et al., Journal of Biological Chemistry (J. Biol. Chem), 1991, vol. 266, p.5268 and the like], and the type 4 $PLA_2$ inhibitory action of the compounds of the present invention will be elucidated by employing these methods. As for the enzyme inhibitory action against type 5 $PLA_2$, methods for measuring the enzymatic activity are described in the published literature [Chen et al., Journal of Biological Chemistry (J. Biol. Chem.), 1994, vol. 269, p.2365; Chen et al., Biochimica Biophysica Acta (Biochim. Biophys. Acta), 1994, vol. 1215, p.115 and the like], and the type 5 $PLA_2$ inhibitory action of the compounds of the present invention will be elucidated by employing these methods.

The compounds (I) of the present invention and pharmaceutically acceptable salts thereof inhibited mouse inflammatory edema, allergic edema, acetic acid writhing reaction, and rat adjuvant arthritis by oral administration at a dose of 0.1 to 500 mg/kg, and caused no death among mice by oral administration at a dose of 500 mg/kg/day for 3 days. Therefore, they are safe compounds as drugs for mammals, preferably humans, pets or companion animals such as dogs and cats, and farm animals, and they are useful substances as active ingredients of medicaments. Preferred examples of the medicaments for mammals, preferably humans, pets or companion animals such as dogs and cats, and farm animals include agents for prophylactic and/or therapeutic treatment of various conditions, various diseases, and pathological conditions in which an acute or chronic inflammatory reaction resulted from production of prostaglandin and/or leukotriene is observed, specifically inflammatory diseases, allergic diseases, autoimmune diseases, and pain.

More specifically, the conditions or diseases include arthritis, chronic rheumatoid arthritis, malignant rheumatoid arthritis, juvenile rheumatoid arthritis, Felty's syndrome, adult Still's disease, osteoarthritis, synovitis, gout, slack of artificial joint implant, fervescence, common cold, algesia, burn, thermal injury, keloplasty, menstrual pain, dysmenorrhea, menstrual cramp, allergic reaction, allergic contact hypersensitivity, allergic rhinitis, pollinosis, allergic conjunctivitis, hypersensitivity pneumonitis, allergic bronchopulmonary mycosis, emphysema, acute respiratory distress syndrome, asthma, bronchitis, chronic obstructive pulmonary disease, chronic bronchitis, pulmonary emphysema, diffuse panbronchiolitis, respiratory obstruction, graft versus host syndrome, urticaria, ultraviolet radiation dermatitis, atopic dermatitis, cancer, myelogenous leukemia, sarcomata, brain tumor, cachexia, tissue ulcer, digestive ulcer, gastritis, acute and chronic pancreatitis, regional enteritis, ulcerative colitis, diverticulitis, recurrent gastroenteric disorder, gastroenteric bleeding, inflammatory bowel disease, Crohn's disease, intestinal tract type Behcet's disease, infectious enteritis, ischemic enteritis, radiation enteritis, drug-induced enteritis, irritable bowel syndrome, hepatic diseases (hepatopathies, liver failures) such as acute hepatitis, fulminant hepatitis, chronic hepatitis, hepatic cirrhosis, fatty liver, alcoholic liver injury, drug liver injury (drug-induced hepatitis), congestive hepatitis, autoimmune hepatitis, primary biliary cirrhosis and hepatic porphyria, coagulation, anemia, ankylosing spondilitis, restenosis, periodontosis, epidermolysis bullosa, atherosclerosis, aortic aneurysm, periarteritis nodosa, congestive cardiac failure, arrhythmia, myocardial infarction, cerebral infarction, attack, cerebral ischemia, head injury, spinal cord injury, myelopathic muscular atrophy, neuralgia, neurodegenerative disease, Alzheimer's disease, Lewy body disease, Shy-Drager syndrome, Reye's syndrome, progressive supranuclear palsy, progressive multifocal leukoencephalopathy, normal pressure hydrocephalus, subacute sclerosing panencephalitis, frontal lobe type dementia, acute anterior poliomyelitis (poliomyelitis), poliomyelitis neurosis, viral encephalitis, Creutzfeldt-Jakob disease, Kuru disease, bovine spongiform encephalopathy (mad cow disease), scrapie, epilepsy, cerebral amyloid angiopathy, autoimmune disease, Huntington's disease, Parkinson's disease, migraine, depression, mania, manic-depressive psychosis, hereditary cerebellar ataxia, peripheral neuropathy, glaucoma, pain, gingivitis, postoperative pain, amyotrophic lateral sclerosis, osteoporosis, multiple sclerosis, ocular angiogenesis, cornea damage, macular degeneration, conjunctivitis, abnormal wound healing, sprain or strain of muscle or joint, tendinitis, skin disease, psoriasis vulgaris, pustular psoriasis, erythroderma psoriaticum, arthritic psoriasis, myasthenia gravis, multiple myositis, myositis, bursitis, diabetes mellitus, tumor invasion, tumor growth, tumor metastasis, cornea scar, scleritis, immunodeficiency disease, pachydermia, eosinophilic fasciitis, sepsis, endotoxin shock, premature delivery, hypoprothrombinemia, hemophilia, thyroiditis, sarcoidosis, Behcet's syndrome, hypersensitivity, renal disease, rickettsial infectious disease, protozoal disease, reproduction disease, sepsis shock and the like. Other specific conditions and diseases include toothache, pain after tooth extraction, back or low back pain, periarthritis humeroscapularis, cervico-omo-brachial syndrome, tenosynovitis, acute upper respiratory inflammation, herpes zoster, fibrosis, pulmonary fibrosis, pneumoconiosis, chronic interstitial pneumonia, granulomatous interstitial pneumonia, fibrosing interstitial pneumonia, renal fibrosis, nephropyelitis, various types of secondary contracted kidney, glomerular nephritis, chronic nephritis, glomerulosclerosis, hepatic fibrosis, cardiac fibrosis after myocardial infarction, idiopathic cardiomyopathy, pancreatic sclerosis, pancreatic fibrosis, pancreatolithiasis, Takayasu's arteritis, chronic thyroiditis, dermatomyositis, multiple myositis, myelofibrosis, Banti disease, retroperitoneal fibrosis, various radiation injuries and the like. Further, the medicament comprising the compounds (I) of the present invention as active ingredients can be used for the aforementioned conditions or diseases of mammals, preferably humans, pets or companion animals such as dogs and cats or farm animals together with or in combination with one or more kinds of other prophylactic or therapeutic drugs.

Examples of the drugs that can be used together or in combination include, for example, the following drugs: immunomodulation-type antirheumatic drugs and antimetabolite used as therapeutic drugs for rheumatoid arthritis, specifically, gold preparations, bucillamine, lobenzarit, hydroxychlorokin, D-penicillamine, salazosulfapyridine, methotrexate, azathiopurin, mizoribine, leflunomide, tacrolimus, cyclosporin and the like and preparations containing the same; anti-cytokine antibody preparations directed to cytokines such as interleukin (IL) 1, IL-6, and tumor necrosis factor (TNF)-α or preparations of soluble receptors for those cytokines, which are biological preparations, specifically, infliximab, etanercept and the like and preparations containing the same; steroid preparations, specifically, dexamethasone, betamethasone, prednisolone, fluticasone, beclometasone and the like and preparations containing the same; bronchodilators used as therapeutic agents for chronic bronchial asthma, specifically, salmeterol and salbutamol, which are adrenalin β2 stimulants, ipratropium, which is an anticholinergic drug, and the like and preparations containing the same; therapeutic drugs for allergic diseases, for example, theophyline, which is a xanthine analogue drug, and the like, fexoquinadine, epinastatine, cetirizine, ketotifen, disodium cromoglycate, pemirolast and the like, which are antiallergic agents, and preparations containing the same; irinotecan, 5-fluorouracil and the like, which are antitumor agents, and preparations containing the same. Further, the medicament comprising the compounds (I) of the present invention as active ingredients are used, for example, together with or in combination with radiotherapy.

In order to use the compounds (I) of the present invention or pharmaceutically acceptable salts thereof for the medicaments described above, an effective amount of the compounds (I) of the present invention or pharmaceutically acceptable salts thereof per se may be used, or they may be mixed with a pharmaceutically acceptable carrier to form a pharmaceutical composition. The carrier may be, for example, a suspending agent such as carboxymethylcellulose, or purified water, physiological saline or the like, if desired. Other known carriers can also be used. An example include a method of dissolving Compound (I) of the present invention or a pharmaceutically acceptable salt thereof in purified water containing 0.5% carboxymethylcellulose and using the solution.

Examples of formulations for preparing the aforementioned pharmaceutical composition include tablet, powder, granule, syrup, suspension, capsule, and injection. For the manufacture of these formulations, various carriers suitable for these preparations are used. For example, examples of the carrier for oral preparations include excipients, binders, lubricants, fluid accelerators, and colorants.

When the compounds of the present invention are formulated as a parenteral preparation such as an injection, water for injection, physiological saline, glucose aqueous solution, vegetable oil for injection, propylene glycol, polyethylene glycol and the like can generally be used as a diluent. Disinfectants, antiseptics, stabilizers, isotonic agents, soothing agents and the like may be further added, as required.

When the compounds of the present invention are administered to mammals, e.g., humans, they can be administered in the form of a tablet, a powder, a granule, a suspension, a capsule or the like. They can also be parenterally administered in the form of a suppository, a gel, a lotion, an ointment, a cream, or a spray. A dose thereof varies depending on a disease to be applied, an administration route, the age, weight, degree of symptom of a patient and the like. Examples of the dose include generally an administration at a dose of 1 to 1,000 mg per day for an adult once to three times a day. In general, an administration period may be for every several days to two months. Both of the daily dose and the administration period may be increased or decreased depending on symptoms of a patient.

EXAMPLES

The present invention will be further specifically explained with reference to examples. However, the scope of the present invention is not limited to the following examples. In the examples, for thin layer chromatography (TLC), Precoated Silica Gel 60 F254 (produced by Merck, product number: 5715-1M)) was used. After development with chloroform:methanol (1:0 to 1:1), acetonitrile:acetic acid:water (200:1:1 to 100:4:4) or ethyl acetate:hexane (1:0 to 0:1), spots were observed by UV irradiation (254 nm) or coloration with ninhydrine or dinitrophenylhydrazine solution in hydrochloric acid. For drying organic solvent, anhydrous magnesium sulfate or anhydrous sodium sulfate was used. As for column chromatography, the indication of "Quad" means use of Quad 1 preparative chromatography system (produced by Biotage), and one or several columns selected from cartridge columns KP-Sil-12M, 40S and 40M produced by the same manufacturer were used depending on the amount of sample. For flash column chromatography, Silica gel 60N (spherical shape, neutral, 40 to 100 µm, produced by Kanto Chemicals) was used. Preparative thin layer chromatography (hereinafter abbreviated as "PTLC") was performed by using one or several plates of PLC Plate Silica Gel 60 F254 (20×20 cm, thickness: 2 mm, concentration zone: 4 cm, produced by Merck, product number: 13793-1M) were used depending on the amount of sample.

For the measurement of nuclear magnetic resonance (NMR) spectra, the measurement was performed by using Gemini-300 (FT-NMR, produced by Varian). As a solvent, deuterated chloroform (CDCl$_3$) or deuterated dimethyl sulfoxide (DMSO-d$_6$) was used, and the measurement was performed by using CDCl$_3$ unless otherwise indicated. Chemical shifts were measured by using tetramethylsilane (TMS) as an internal standard, and indicated with δ (ppm). Binding constant was indicated with J (Hz). The abbreviations for splitting patterns have the following meanings: s: singlet, d: doublet, t: triplet, q: quartet, qu: quintet, dd: doublet doublet, td: triplet doublet, m: multiplet and br: broad. Mass spectrum (Mass) was measured by fast atomic bombardment mass spectrometry (FAB-MS) using JEOL-JMS-SX102 (produced by JEOL Co., Ltd.). Further, the indication of "LCMS" means that mass spectrum was measured by liquid chromatography-mass spectrometry (LC-MS). Platform-LC type mass spectrometry apparatus (produced by Micromass) was used as the mass spectrometer, and the measurement was performed by the electrospray ionization (ESI) method. The indication "N.D" means that no molecular ion peak was detected.

As the liquid chromatography apparatus used in LC-MS, an apparatus produced by GILSON was used. As the separation column, Mightysil RP-18 GP 50-4.6 (produced by Kanto Chemicals) was used. Elution was generally performed at a flow rate of 2 ml/minute using a linear gradient of 5 to 100% (v/v) Solution B [acetonitrile [containing 0.1% (v/v) acetic acid] in Solution A [water containing 0.1% (v/v) acetic acid] from 0 minute to 5 minutes as the solvent. In particular, for the indication of retention time in the liquid chromatography, the indication A for elution condition means that measurement was performed by eluting with a linear gradient of 5 to 100% (v/v) Solution B from 0 minute to 5 minutes and then with 100% Solution B until 6 minutes. Similarly, the indication B for elution condition means that measurement was performed by eluting with 30% (v/v) Solution B from 0 minute to 0.5 minute, then with a linear gradient of 30 to 95% (v/v) Solution B from 0.5 minute to 4 minutes and then with 95% (v/v) Solution B until 6 minutes.

The manufacturers of regents used will be occasionally indicated with the following abbreviations: "TCI" for Tokyo Kasei Kogyo Co., Ltd., "Ald" for Aldrich Co., "KANTO" for Kanto Chemical Co., Inc., "WAKO" for Wako Pure Chemical Industries, Ltd., "LANC" for Lancaster Synthesis, and "MAYB" for Maybridge, plc.

The data of the compounds and intermediates up to the example number 330 obtained by using the apparatuses are shown in Table 1. In the table, the numbers indicated with Exp. mean example numbers of compounds, and the indications of Int. mean intermediate numbers.

Reference Example 1
Synthesis of methyl 3-(4-hydroxyphenyl)propionate (Intermediate 1) (Step c)

A solution obtained beforehand by adding thionyl chloride (18.3 ml, WAKO) dropwise to methanol (250 ml) under ice cooling was added dropwise with a solution of 3-(4-hydroxyphenyl)propionic acid (16.6 g, TCI) in methanol (50 ml) under ice cooling, stirred for 30 minutes, then warmed to room temperature and further stirred for 1.5 hours. The reaction mixture was concentrated under reduced pressure and then extracted with diethyl ether (200 ml). The organic layer was washed successively with saturated aqueous sodium hydrogencarbonate, saturated aqueous ammonium chloride and saturated brine. The organic layer was dried, and then the solvent was evaporated under reduced pressure to obtain the title compound (Intermediate 1, 17.95 g).
Synthesis of methyl 3-(4-cyclopentylmethyloxyphenyl)propionate (Intermediate 2) (Step e-1)

A solution of cyclopentane-methanol (4.05 ml, Ald) in anhydrous tetrahydrofuran (henceforth abbreviated as "THF", 40 ml) was added with triethylamine (6.49 ml, WAKO), added dropwise with methanesulfonyl chloride (3.48 ml, WAKO) under ice cooling and stirred for 30 minutes. The reaction mixture was added with water (50 ml) and extracted with diethyl ether (80 ml×2). The organic layer was washed with saturated brine and dried, and then the solvent was evaporated under reduced pressure. A solution obtained beforehand by adding 60% sodium hydride (1.15 g, KANTO) to a solution of Intermediate 1 (4.50 g) in N,N-dimethylformamide (henceforth abbreviated as "DMF", 35 ml) and stirring the mixture for 15 minutes under ice cooling was added with a solution of the aforementioned residue in DMF (10 ml) under ice cooling. The reaction mixture was stirred for 15 minutes, warmed to room temperature, then stirred for 45 minutes and further stirred at 60° C. for 15 hours. The reaction mixture was added with water (100 ml) and diethyl ether (200 ml) for extraction. The organic layer was washed successively with saturated aqueous sodium hydrogencarbonate, saturated aqueous ammonium chloride and saturated brine and dried, and the solvent was evaporated under reduced pressure. The residue was purified by flash column chromatography (hexane:isopropyl ether=9:1) to obtain the title compound (Intermediate 2, 5.58 g).
Synthesis of methyl 3-(3-bromo-4-cyclopentylmethyloxyphenyl)propionate (Intermediate 3) (Step g)

A solution of Intermediate 2 (1.31 g, TCI) in acetonitrile (50 ml) was added with N-bromosuccinimide (henceforth abbreviated as "NBS", 979 mg, KANTO), stirred at room temperature for 2 hours, then heated to 40° C. and stirred for 3 hours. The reaction mixture was concentrated under reduced pressure, then added with ethyl acetate (200 ml) and washed successively with saturated aqueous ammonia chloride, 5% aqueous sodium sulfite, saturated aqueous sodium hydrogencarbonate and saturated brine. The organic layer was dried, and the solvent was evaporated under reduced pressure to obtain the title compound (Intermediate 3, 1.69 g).

Reference Example 2
Synthesis of 3-(3-bromo-4-methoxyphenyl)propionate (Intermediate 4) (Step g)

According to the procedure described in the synthesis method of Intermediate 3 in Reference Example 1 (Step g) with the modification that the reaction was carried out under ice cooling for 30 minutes and at room temperature for 3 hours, 3-(4-methoxyphenyl)propionic acid (27.0 g, TCI) and NBS (29.4 g) were reacted and treated to obtain the title compound (Intermediate 4, 38.1 g).
Synthesis of 3-(3-bromo-4-hydroxyphenyl)propionic acid (Intermediate 5) (Step f)

According to the procedure described in a reference [M. C. Carreno et al., Journal of Organic Chemistry (J. Org. Chem.), 60, p.5328, 1995], 1 M boron tribromide solution in methylene chloride (200 ml, Fluka) was added dropwise with a solution of Intermediate 4 (23.5 g) in methylene chloride (200 ml) at −78° C., warmed to room temperature after 30 minutes and further stirred for 1.5 hours. The reaction mixture was poured into ice water (750 ml) and stirred at room temperature for 1 hour. The reaction mixture was added with diethyl ether (750 ml) for extraction. The organic layer was added with 2 N aqueous sodium hydroxide (250 ml×2) for extraction, and the aqueous layer was acidified with 5 N aqueous hydrochloric acid under ice cooling and extracted with diethyl ether (375 ml×2) again. The organic layer was washed with saturated brine and dried, and the solvent was evaporated under reduced pressure to obtain the title compound (Intermediate 5, 23.5 g).
Synthesis of methyl 3-(3-bromo-4-hydroxyphenyl)propionate (Intermediate 6) (Step c)

According to the procedure described in the synthesis method of Intermediate 1 in Reference Example 1 (Step c) with the modification that purification was performed by flash column chromatography (hexane:ethyl acetate=4:1), Intermediate 5 (21.15 g) and thionyl chloride (15.0 ml) were reacted in methanol and treated to obtain the title compound (Intermediate 6, 20.36 g).
Synthesis of methyl (3-bromo-4-cyclohexylmethyloxyphenyl)propionate (Intermediate 7) (Step e-1)

A solution of Intermediate 6 (1.29 g) in DMF (25 ml) was added with potassium carbonate (0.86 g) and bromomethylcyclohexane (1.05 ml, TCI), stirred at room temperature under argon atmosphere for 2 hours, then heated to 60° C. and stirred for 17 hours. The reaction mixture was poured into ice water and extracted with isopropyl ether (200 ml). The organic layer was washed successively with saturated aqueous sodium hydrogencarbonate, saturated aqueous ammonium chloride and saturated brine and dried, and then the solvent was evaporated under reduced pressure. The residue was purified by flash column chromatography (hexane:isopropyl ether=9:1) to obtain the title compound (Intermediate 7, 1.45 g).

Synthesis of methyl 3-(3-bromo-4-cyclopentyloxyphenyl)propionate (Intermediate 8) (Step e-1)

A solution of Intermediate 6 (4.50 g) in DMF (20 ml) was added with 60% sodium hydride (440 mg, KANTO) under ice cooling. The reaction mixture was stirred for 10 minutes, then added with cyclopentane bromide (1.61 ml, TCI), warmed to room temperature, stirred for 1.5 hours, then heated to 60° C. and further stirred for 16 hours. The reaction mixture was added with water (50 ml) and isopropyl ether (300 ml) for extraction. The organic layer was washed successively with saturated aqueous sodium hydrogencarbonate, saturated aqueous ammonium chloride and saturated brine and dried, and then the solvent was evaporated under reduced pressure. The residue was purified by flash column chromatography (hexane:isopropyl ether=7:1) to obtain the title compound (Intermediate 8, 2.50 g).

Synthesis of methyl 3-(3-bromo-4-cyclohexyloxyphenyl)propionate (Intermediate 9) (Step e-2)

A solution of Intermediate 6 (2.06 g), triphenylphosphine (henceforth abbreviated as "$Ph_3P$", 6.28 g, WAKO) and cyclohexanol (2.53 ml, WAKO) in anhydrous THF (60 ml) was added dropwise with 40% solution of diisopropyl azodicarboxylic acid ester (henceforth abbreviated as "40% DIAD", 11.35 ml, WAKO) in toluene under ice cooling over 10 minutes. The reaction mixture was stirred for 10 minutes, then warmed to room temperature and stirred for 18.5 hours. The reaction mixture was added with water (50 ml) and ethyl acetate (200 ml) for extraction. The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:isopropyl ether=8:1) to obtain the title compound (Intermediate 9, 2.35 g).

Synthesis of methyl 3-{3-bromo-4-[2-(2-fluorophenyl)ethyloxy]phenyl}propionate (Intermediate 10) (Step e-2)

According to the procedure described in the synthesis method of Intermediate 9 in Reference Example 2 (Step e-2), Intermediate 6 (2.58 g), $Ph_3P$ (5.24 g), 2-fluorophenethyl alcohol (2.68 ml, Ald) and 40% DIAD (9.46 ml) were reacted and treated to obtain the title compound (Intermediate 10, 2.74 g).

Reference Example 3

Synthesis of 4-(3-bromo-4-methoxyphenyl)butyric acid (Intermediate 11) (Step g)

According to the procedure described in the synthesis method of Intermediate 3 in Reference Example 1 (Step g) with the modifications that the reaction was carried out under ice cooling for 30 minutes and at room temperature for 20 hours, 4-(4-methoxyphenyl)butyric acid (11.64 g, Ald) and NBS (11.21 g) were reacted and treated to obtain the title compound (Intermediate 11, 16.30 g).

Synthesis of methyl 4-(3-bromo-4-hydroxyphenyl)butyrate (Intermediate 12) (Steps f and c)

The residue obtained by allowing Intermediate 11 (12.51 g) and 1 M boron tribromide solution in methylene chloride (100 ml) to react and treating the mixture according to the procedure described in the synthesis method of Intermediate 1 in Reference Example 1 (Step f) was reacted and treated with thionyl chloride (8.4 ml) in methanol according to the procedure described in the synthesis method of Intermediate 5 in Reference Example 2 (Step f) to obtain the title compound (Intermediate 12, 10.48 g).

Synthesis of methyl 4-(3-bromo-4-cyclopentylmethyloxyphenyl)butyrate (Intermediate 13)

According to the procedure described in the synthesis method of Intermediate 9 in Reference Example 2 (Step e-2) with the modification that purification was performed by column chromatography (Quad, hexane:isopropyl alcohol=10:1), Intermediate 12 (2.72 g), $Ph_3P$ (7.86 g), cyclopentanemethanol (3.24 ml) and 40% DIAD (14.2 ml) were reacted and treated to obtain the title compound (Intermediate 13, 3.33 g).

Reference Example 4

Synthesis of methyl 3-(3-bromo-4-cyclopentylmethyloxy-5-nitrophenyl)propionate (Intermediate 14)

A solution obtained beforehand by adding 70% nitric acid (3.9 ml) to acetic anhydride (30 ml) and stirring the mixture for 10 minutes under ice cooling was added dropwise with a solution of Intermediate 3 (5.12 g) in acetonitrile (25 ml) at −15° C. over 15 minutes and stirred for 15 minutes. The reaction mixture was poured into 1 N aqueous sodium hydroxide (500 ml) containing ice and extracted with diethyl ether (300 ml×2). The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=10:1) to obtain the title compound (Intermediate 14, 3.68 g).

Reference Example 5

Synthesis of methyl 3-(3-bromo-5-chloro-4-hydroxyphenyl)propionate (Intermediate 15)

A solution of Intermediate 6 (516 mg) in chloroform (5 ml) was added with sulfuryl chloride (177 μl) and stirred at room temperature for 21 hours. The reaction mixture was poured into saturated aqueous sodium hydrogencarbonate (20 ml) and extracted with ethyl acetate. The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=10:1) to obtain the title compound (Intermediate 15, 290 mg).

Synthesis of methyl 3-(3-bromo-5-chloro-4-cyclopentylmethyloxyphenyl)propionate (Intermediate 16) (Step e-2)

According to the procedure described in the synthesis method of Intermediate 9 in Reference Example 2 (Step e-2) with the modification that purification was performed by column chromatography (Quad, hexane:ethyl acetate=30:1), Intermediate 15 (278 mg), $Ph_3P$ (747 mg), cyclopentanemethanol (308 u 1) and 40% DIAD (1.34 ml) were reacted and treated to obtain the title compound (Intermediate 16, 337 mg).

Reference Example 6

Synthesis of ethyl 3-(3-fluoro-4-methyloxyphenyl)acrylate (Intermediate 17) (Step k)

A solution of 3-fluoro-4-methoxybenzaldehyde (2.20 g, Ald) in 1,2-diethoxyethane (5 ml) was added with ethyl diethylphosphonoacetate (3.12 ml, TCI) and then added with 60% sodium hydride (624 mg) under ice cooling. The reaction mixture was stirred for 10 minutes, then warmed to room temperature and stirred for 5 hours. The reaction mixture was added with ethyl acetate (90 ml) and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (Quad, hexane:ethyl acetate=10:1) to obtain the title compound (Intermediate 17, 3.16 g).

Synthesis of ethyl 3-(3-fluoro-4-methoxyphenyl)propionate (Intermediate 18) (Step j)

A mixed solution of Intermediate 17 (3.01 g) and ethyl acetate (50 ml) in methanol (25 ml) was added with 10% palladium carbon (300 mg, Merck) and stirred at room temperature under hydrogen atmosphere for 2 hours. The reaction mixture was filtered, and the solvent of the filtrate was evaporated under reduced pressure to obtain the title compound (Intermediate 18, 3.02 g).

Synthesis of 3-(3-fluoro-4-methoxyphenyl)propionic acid (Intermediate 19) (Step a)

A solution of Intermediate 18 (2.97 g) in methanol (40.0 ml) was added with 2 N aqueous sodium hydroxide (15.0 ml) and stirred at 60° C. for 16 hours. The reaction mixture was concentrated under reduced pressure, then acidified with 5% aqueous hydrochloric acid under ice cooling and extracted with ethyl acetate (200 ml). The organic layer was washed with saturated brine and dried, and then the solvent was evaporated under reduced pressure to obtain the title compound (Intermediate 19, 2.40 g).

Synthesis of 3-(3-fluoro-4-hydroxyphenyl)propionic acid (Intermediate 20) (Step f)

A pyridine/hydrochloric acid complex prepared by mixing pyridine and concentrated hydrochloric acid (30 ml each) and then heating the mixture at 190° C. for 1 hour was added with Intermediate 19 (2.40 g) and stirred at 190° C. for 1.5 hours. The reaction mixture was poured into ice cooled 1 N hydrochloric acid (100 ml) and extracted with ethyl acetate (200 ml). The organic layer was washed with saturated brine and dried, and then the solvent was evaporated under reduced pressure to obtain the title compound (Intermediate 20, 1.98 g).

Synthesis of methyl 3-(3-fluoro-4-hydroxyphenyl)propionate (Intermediate 21) (Step c)

According to the procedure described in the synthesis method of Intermediate 1 in Reference Example 1 (Step c), Intermediate 20 (1.77 g) and thionyl chloride (1.65 ml) were reacted and treated in methanol to obtain the title compound (Intermediate 21, 1.85 g).

Synthesis of methyl 3-(3-bromo-5-fluoro-4-hydroxyphenyl)propionate (Intermediate 22) (Step g)

According to the procedure described in the synthesis method of Intermediate 3 in Reference Example 1 (Step g) with the modifications that the reaction was carried out under ice cooling for 2 hours, and the purification was performed by column chromatography (Quad, hexane:ethyl acetate=10:1), Intermediate 21 (1.84 g) and NBS (1.74 g) were reacted and treated to obtain the title compound (Intermediate 22, 1.74 g).

Synthesis of methyl 3-(3-bromo-4-cyclopentylmethyloxy-5-fluorophenyl)propionate (Intermediate 23) (Step e-2)

According to the procedure described in the synthesis method of Intermediate 9 in Reference Example 2 (Step e-2) with the modifications that the reaction was carried out for 22 hours, and the purification was performed by column chromatography (Quad, hexane:ethyl acetate=50:1), Intermediate 22 (310 mg), tributylphosphine (henceforth abbreviated as "Bu$_3$P, 405 µl, WAKO) instead of Ph$_3$P, cyclopentane-methanol (176 µl) and N,N,N',N'-tetramethylazodicarboxyamide (henceforth abbreviated as "TMAD", 279 mg, TCI) instead of 40% DIAD were reacted and treated to obtain the title compound (Intermediate 23, 386 mg).

Reference Example 7
Synthesis of 3-bromo-4-hydroxybenzaldehyde (Intermediate 24)

According to the procedure described in the synthesis method of Intermediate 20 in Reference Example 6 (Step f) with the modification that t-butyl methyl ether was used as an extraction solvent, 3-bromo-4-methoxybenzaldehyde (43.0 g, TCI), pyridine (260 ml) and concentrated hydrochloric acid (260 ml) were reacted and treated to obtain the title compound (Intermediate 24, 31.5 g).

Synthesis of 3-bromo-4-cyclohexylmethyloxybenzaldehyde (Intermediate 25)

According to the procedure described in the synthesis method of Intermediate 7 in Reference Example 2 (Step e-1) with the modification that purification was performed by flash column chromatography (hexane:isopropyl ether=5:1), Intermediate 24 (17.4 g), potassium carbonate (23.9 g) and bromomethylcyclohexane (36.2 ml) were reacted and treated to obtain the title compound (Intermediate 25, 18.7 g).

Example 1
Synthesis of methyl 3-[4-cyclohexylmethyloxy-3-(6-hydroxynaphthalen-2-yl)-phenyl]propionate (Compound No. 001) (Preparation Method 4, Step d-1)

A solution of 2-bromo-6-hydroxynaphthalene (1.15 g, TCI) in anhydrous THF (50 ml) was cooled to −78° C. under argon atmosphere, added dropwise with 1.6 M solution of n-butyllithium in hexane (6.88 ml, Ald) over 20 minutes and stirred for 30 minutes. The reaction mixture was added dropwise with triisopropyloxyborane (henceforth abbreviated as "($^i$PrO)$_3$B, 1.73 ml, Ald) over 10 minutes, stirred for 30 minutes, then warmed to room temperature and further stirred for 2 hours. The reaction mixture was added with 0.5 M aqueous sulfuric acid (10 ml) and extracted with diethyl ether (100 ml×3). The organic layer was washed with saturated brine and dried, and then the solvent was evaporated under reduced pressure to obtain crude 6-hydroxy-2-naphthaleneboronic acid (1.85 g). A solution of this product in ethanol (5.0 ml), Intermediate 7 (1.16 g) and 2 M aqueous sodium carbonate (12.0 ml) were added with toluene (10.0 ml) and tetrakistriphenylphosphine palladium (0) (henceforth abbreviated as "(Ph$_3$P)$_4$Pd", 570 mg, Nacalai Tesque) and stirred at 100° C. for 25 hours. The reaction mixture was added with ethyl acetate (300 ml) and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=6:1) to obtain the title compound (Compound No. 001, 1.04 g).

Example 2
Synthesis of 3-[4-cyclohexylmethyloxy-3-(6-hydroxynaphthalen-2-yl)phenyl]propionic acid (Compound No. 002) (Preparation Method 1, Step a)

A solution of Compound of Example 001 (269 mg) in methanol (5.0 ml) was added with 2 N aqueous sodium hydroxide (1.0 ml) and stirred at 60° C. for 16 hours. The reaction mixture was concentrated under reduced pressure, acidified with 5% aqueous hydrochloric acid under ice cooling and extracted with ethyl acetate (100 ml). The organic layer washed with saturated brine and dried, and then the solvent was evaporated under reduced pressure to obtain the title compound (Compound No. 002, 172 mg). Rf=0.43 (chloroform:methanol=10:1).

Example 3

Synthesis of methyl 3-[4-cyclopentylmethyloxy-3-(6-hydroxynaphthalen-2-yl)phenyl]-propionate (Compound No. 003) (Preparation Method 4, Step d-1)

According to the procedure described in the synthesis method of Compound of Example 001 (Preparation Method 4, Step d-1) with the modifications that the reaction was carried out for 13 hours, and the purification was performed by flash column chromatography (hexane:ethyl acetate= 6:1), crude 6-hydroxy-2-naphthaleneboronic acid (376 mg), Intermediate 3 (230 mg), 2 M aqueous sodium carbonate (2.4 ml) and $(Ph_3P)_4Pd$ (115.8 mg) were reacted and treated to obtain the title compound (Compound No. 003, 270 mg).

Example 4

Synthesis of 3-[4-cyclopentylmethyloxy-3-(6-hydroxynaphthalen-2-yl)phenyl]propionic acid (Compound No. 004) (Preparation Method 1, Step a)

According to the procedure described in the synthesis method of Compound of Example 002 (Preparation Method 1, Step a) with the modification that the reaction was carried out for 14 hours, Compound of Example 003 (149 mg) and 2 N aqueous sodium hydroxide (370 μl) were reacted and treated to obtain the title compound (Compound No. 004, 117 mg). Rf=0.37 (chloroform:methanol=10:1).

Example 5

Synthesis of methyl 3-{4-[2-(2-fluorophenyl)ethyloxy]-3-(6-hydroxynaphthalen-2-yl)-phenyl}(Compound No. 005) (Preparation Method 4, Step d-1)

According to the procedure described in the synthesis method of Compound of Example 001 (Preparation Method 4, Step d-1) with the modifications that the reaction was carried out for 12 hours, and the purification was performed by flash column chromatography (hexane:ethyl acetate= 6:1), crude 6-hydroxy-2-naphthaleneboronic acid (174 mg), Intermediate 10 (126 mg), 2 M aqueous sodium carbonate (1.2 ml) and $(Ph_3P)_4Pd$ (57 mg) were reacted and treated to obtain the title compound (Compound No. 005, 145 mg).

Example 6

Synthesis of 3-{4-[2-(2-fluorophenyl)ethyloxy]-3-(6-hydroxynaphthalen-2-yl)phenyl}propionic acid (Compound No. 006) (Preparation Method 1, Step a)

According to the procedure described in the synthesis method of Compound of Example 002 (Preparation Method 1, Step a) with the modification that the reaction was carried out for 14 hours, Compound of Example 005 (70 mg) and 2 N aqueous sodium hydroxide (160 u 1) were reacted and treated to obtain the title compound (Compound No. 006, 39 mg). Rf=0.37 (chloroform:methanol=10:1).

Example 7

Synthesis of methyl 3-[4-cyclopentylmethyloxy-3-(7-hydroxynaphthalen-2-yl)-phenyl]-propionate (Compound No. 007) (Preparation Method 4, Step d-1)

According to the procedure described in the synthesis method of Compound of Example 001 (Preparation Method 4, Step d-1) with the modifications that the reaction was carried out for 4 hours, and the purification was performed by flash column chromatography (hexane:ethyl acetate= 6:1), crude 7-hydroxy-2-naphthaleneboronic acid prepared from 2-bromo-7-hydroxynaphthalene (559 mg, MAYB), 1.6 M solution of n-butyllithium in hexane (3.91 ml) and $(iPrO)_3B$ (1.16 ml), Intermediate 3 (386 mg), 2 M aqueous sodium carbonate (4.0 ml) and $(Ph_3P)_4Pd$ (195 mg) were reacted and treated to obtain the title compound (Compound No. 007, 460 mg).

Example 8

Synthesis of 3-[4-cyclopentylmethyloxy-3-(7-hydroxynaphthalen-2-yl)-phenyl]propionic acid (Compound No. 008) (Preparation Method 1, Step a)

According to the procedure described in the synthesis method of Compound of Example 002 (Preparation Method 1, Step a) with the modification that the reaction was carried out for 27 hours, Compound of Example 007 (176 mg) and 2 N aqueous sodium hydroxide (436 μl) were reacted and treated to obtain the title compound (Compound No. 008, 109 mg). Rf=0.41 (chloroform:methanol=10:1).

Example 9

Synthesis of methyl 3-[4-cyclopentylmethyloxy-3-(5-hydroxynaphthalen-2-yl)phenyl]-propionate (Compound No. 009) (Preparation Method 4, Step d-1)

2-Amino-5-hydroxynaphthalene (4.80 g, TCI) was dissolved in 6 N hydrochloric acid (300 ml), added dropwise with an aqueous solution (22.5 ml) of sodium nitrite (2.25 g, WAKO) under ice cooling over 30 minutes and stirred for 30 minutes. The reaction mixture was added dropwise with an aqueous solution (75 ml) of potassium iodide (9.90 g, WAKO), stirred for 30 minutes, then warmed to room temperature and further stirred for 3.5 hours. The reaction mixture was neutralized with aqueous ammonia and then filtered by using Celite. The filtrate was added with ethyl acetate (90 ml×2) for extraction. The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate= 10:1) to obtain 1-hydroxy-6-iodonaphthalene (1.48 g). A solution of this compound (539 mg) in anhydrous THF (10 ml) was added with 60% sodium hydride (171 mg) under ice cooling and stirred for 1 hour. The reaction mixture was cooled to −78° C. under argon atmosphere, added dropwise with 1.6 M solution of n-butyllithium in hexane (3.75 ml, Ald) over 10 minutes and stirred for 30 minutes. This reaction mixture was added dropwise with $(^iPrO)_3B$ (1.16 ml) over 10 minutes, stirred for 30 minutes, then warmed to room temperature and further stirred for 3 hours. The reaction mixture was added with water (3 ml) and 0.5 M aqueous sulfuric acid (7 ml) and extracted with diethyl ether (100 ml×3). The organic layer was washed with saturated brine and dried, and then the solvent was evaporated under reduced pressure to obtain crude 7-hydroxy-2-naphthaleneboronic acid. According to the procedure described in the synthesis method of Compound of Example 001 (Preparation Method 4, Step d-1) with the modifications that the reaction was carried out for 14 hours, and the purification was performed by column chromatography (Quad, hexane:ethyl acetate=6:1), a solution of the above compound in ethanol (1 ml), Intermediate 3 (350 mg), 2 M aqueous sodium carbonate (2.4 ml) and $(Ph_3P)_4Pd$ (116 mg) were reacted and treated to obtain the title compound (Compound No. 009, 388 mg).

Example 10
Synthesis of 3-[4-cyclopentylmethyloxy-3-(5-hydroxynaphthalen-2-yl)phenyl]propionic acid (Compound No. 010) (Preparation Method 1, Step a)

According to the procedure described in the synthesis method of Compound of Example 002 (Preparation Method 1, Step a) with the modification that the reaction was carried out for 12 hours, Compound of Example 009 (355 mg) and 2 N aqueous sodium hydroxide (1.75 ml) were reacted and treated to obtain the title compound (Compound No. 010, 158 mg). Rf=0.61 (chloroform:methanol=10:1).

Example 11
Synthesis of methyl 3-[3-(6-aminonaphthalen-2-yl)-4-cyclopentylmethyloxyphenyl]-propionate (Compound No. 011) (Preparation Method 4, Step d-1)

According to a known method described in a reference [L. C. Anderson et al., Journal of the American Chemical Society (J. Am. Chem. Soc.), vol. 65, p.241, 1943], a solution of 2-amino-6-bromonaphthalene (223 mg) obtained from commercially available 2-bromo-6-hydroxynaphthalene (TCI) in anhydrous THF (10 ml) was added with 30% potassium hydride (191 mg, Ald) under ice cooling and stirred for 1 hour. The reaction mixture was cooled to −78° C. under argon atmosphere, added dropwise with 1.7 M solution of t-butyllithium in pentane (1.88 ml) over 10 minutes and stirred for 30 minutes. The reaction mixture was added dropwise with ($^i$PrO)$_3$B (0.92 ml) over 10 minutes, stirred for 30 minutes, then warmed to room temperature and further stirred for 3 hours. The reaction mixture was added with water (3 ml) and 0.5 M aqueous sulfuric acid (4 ml) and extracted with diethyl ether (100 ml×3). The organic layer was washed with saturated brine and dried, and then the solvent was evaporated under reduced pressure to obtain crude 6-amino-2-naphthaleneboronic acid (402 mg). According to the procedure described in the synthesis method of Compound of Example 001 (Preparation Method 4, Step d-1) with the modifications that the reaction was carried out for 13 hours, and the purification was performed by flash column chromatography (hexane:ethyl acetate=4:1), a solution of the above compound in ethanol (0.5 ml), Intermediate 3 (119 mg), 2 M aqueous sodium carbonate (1.5 ml) and (Ph$_3$P)$_4$Pd (61 mg) were reacted and treated to obtain the title compound (Compound No. 011, 129 mg).

Example 12
Synthesis of 3-[3-(6-aminonaphthalen-2-yl)-4-cyclopentylmethyloxyphenyl]propionic acid (Compound No. 012) (Preparation Method 1, Step a)

According to the procedure described in the synthesis method of Compound of Example 002 (Preparation Method 1, Step a) with the modification that the reaction was carried out for 14 hours, Compound of Example 011 (120 mg) and 2 N aqueous sodium hydroxide (1.75 ml) were reacted and treated to obtain the title compound (Compound No. 012, 89 mg). Rf=0.51 (chloroform:methanol=10:1).

Example 13
Synthesis of 2-amino-7-bromonaphthalene (Intermediate 26)

According to the procedure described in the aforementioned reference [L. C. Anderson et al., Journal of the American Chemical Society (J. Am. Chem. Soc.), vol. 65, p.241, 1943], 2-bromo-7-hydroxynaphthalene (2.23 g, MAYB) was added with 30% aqueous ammonia (30 ml) and ammonium sulfite monohydrate (2.69 g, WAKO) and stirred in a shield tube at 150° C. for 27 hours. The reaction mixture was added with ethyl acetate (90 ml) for extraction and then added with 1 N aqueous hydrochloric acid (1.5 l). The aqueous layer was separated, washed with ethyl acetate, then neutralized by adding 5 N aqueous sodium hydroxide (300 ml) under ice cooling and extracted with ethyl acetate again. The organic layer was washed with saturated brine and dried, and then the solvent was evaporated under reduced pressure to obtain the title compound (Intermediate 26, 1.00 g).

Synthesis of methyl 3-[3-(7-aminonaphthalen-2-yl)-4-cyclopentylmethyloxyphenyl]-propionate (Compound No. 013) (Preparation Method 4, Step d-1)

According to the procedure described in the synthesis method of Compound of Example 011 (Preparation Method 4, Step d-1) with the modifications that the reaction was carried out for 18 hours, and the purification was performed by flash column chromatography (hexane:ethyl acetate= 5:1), crude 7-amino-2-naphthaleneboronic acid prepared from Intermediate 26 (666.5 mg), 1.7 M solution of n-butyllithium in pentane (5.65 ml) and ($^i$PrO)$_3$B (2.77 ml), Intermediate 3 (523 mg), 2 M aqueous sodium carbonate (6.5 ml) and (Ph$_3$P)$_4$Pd (260 mg) were reacted and treated to obtain the title compound (Compound No. 013, 597 mg).

Example 14
Synthesis of 3-[3-(7-aminonaphthalen-2-yl)-4-cyclopentylmethyloxyphenyl]propionic acid (Compound No. 014) (Preparation Method 1, Step a)

According to the procedure described in the synthesis method of Compound of Example 002 (Preparation Method 1, Step a) with the modification that the reaction was carried out for 3 hours, Compound of Example 013 (219 mg) and 2 N aqueous sodium hydroxide (1.0 ml) were reacted and treated to obtain the title compound (Compound No. 014, 180 mg). Rf=0.42 (chloroform:methanol=10:1).

Example 15
Synthesis of 2-bromo-6-(N-methylamino)naphthalene (Intermediate 27)

A solution of 2-amino-6-bromonaphthalene (2.0 g) in 1,4-dioxane (30 ml) was added dropwise with dimethyl sulfate (1300 µl) and stirred at room temperature for 46 hours. The reaction mixture was added with ethyl acetate (90 ml) and then added with 1 N aqueous sodium hydroxide (5 ml). This mixture was extracted with ethyl acetate (150 ml×3). The organic layer was washed with saturated brine and dried, and then the solvent was evaporated under reduced pressure. The residue was purified by flash column chromatography (hexane:ethyl acetate=15:1) to obtain the title compound (Intermediate 27, 152 mg).

Synthesis of methyl 3-{4-cyclopentylmethyloxy-3-[6-(N-methylamino)naphthalen-2-yl]phenyl}propionate (Compound No. 015) (Preparation Method 4, Step d-1)

According to the procedure described in the synthesis method of Compound of Example 011 (Preparation Method 4, Step d-1) with the modifications that the reaction was carried out for 14 hours, and the purification was performed by PTLC (hexane:ethyl acetate=3:1), crude 6-(N-methylamino)-2-naphthaleneboronic acid prepared from Intermediate 27 (84 mg), 1.7 M solution of n-butyllithium in pentane (0.67 ml) and ($^i$PrO)$_3$B (0.33 ml), Intermediate 3 (100 mg), 2 M aqueous sodium carbonate (1.1 ml) and (Ph$_3$P)$_4$Pd (48 mg) were reacted and treated to obtain the title compound (Compound No. 015, 76 mg).

Example 16
Synthesis of 3-{4-cyclopentylmethyloxy-3-[6-(N-methylamino)naphthalen-2-yl]phenyl}propionic acid (Compound No. 016) (Preparation Method 1, Step a)

According to the procedure described in the synthesis method of Compound of Example 002 (Preparation Method 1, Step a) with the modification that the reaction was carried out 8 hours, Compound of Example 015 (65 mg) and 2 N aqueous sodium hydroxide (310 μl) were reacted and treated to obtain the title compound (Compound No. 016, 41 mg). Rf=0.56 (chloroform:methanol=10:1).

Example 17
Synthesis of methyl 3-{4-cyclopentylmethyloxy-3-[6-(N,N-dimethylamino)-naphthalen-2-yl]phenyl}propionate (Compound No. 017) (Preparation Method 4, Step d-1)

According to the procedure described in the synthesis method of Compound of Example 011 (Preparation Method 4, Step d-1) with the modifications that the reaction was carried out for 14 hours, and the purification was performed by flash column chromatography (hexane:ethyl acetate=10:1), crude 6-(N,N-dimethylamino)-2-naphthaleneboronic acid prepared from 2-bromo-6-(N,N-dimethylamino)naphthalene (180 mg) obtained from 2-amino-6-bromonaphthalene by a method known from a reference [W. Adcock et al., Australian Journal of Chemistry (Aust. J. Chem.), vol. 18, p.1351, 1965], 1.7 M solution of n-butyllithium in pentane (1.35 ml) and ($^i$PrO)$_3$B (0.66 ml), Intermediate 3 (191 mg), 2 M aqueous sodium carbonate (1.1 ml) and (Ph$_3$P)$_4$Pd (96 mg) were reacted and treated to obtain the title compound (Compound No. 017, 137 mg).

Example 18
Synthesis of 3-{4-cyclopentylmethyloxy-3-[6-(N,N-dimethylamino)naphthalen-2-yl]phenyl}propionic acid (Compound No. 018) (Preparation Method 1, Step a)

According to the procedure described in the synthesis method of Compound of Example 002 (Preparation Method 1, Step a) with the modification that the reaction was carried out for 11 hours, Compound of Example 017 (134 mg) and 2 N aqueous sodium hydroxide (625 μl) were reacted and treated to obtain the title compound (Compound No. 018, 115 mg). Rf=0.65 (chloroform:methanol=10:1).

Example 19
Synthesis of 2-bromo-6-sulfamoylaminonaphthalene (Intermediate 28)

A solution of chlorosulfonyl isocyanate (870 μl, WAKO) in benzene (10 ml) was added dropwise with formic acid (377 μl, WAKO) under ice cooling, warmed to room temperature, stirred for 19.5 hours, then heated to 40° C. and further stirred for 4 hours. The reaction mixture was added dropwise with a solution (5 ml) of 2-amino-6-bromonaphthalene (443 mg) in benzene under ice cooling, warmed to room temperature and stirred for 21.5 hours. The reaction mixture was filtered, and the obtained solid was added with ethyl acetate and mixed. The mixture was filtered again, and then the solvent was evaporated under reduced pressure. The residue was purified by column chromatography (Quad, hexane:ethyl acetate=2:1) to obtain the title compound (Intermediate 28, 158 mg).

Synthesis of methyl 3-[4-cyclopentylmethyloxy-3-(6-sulfamoylaminonaphthalen-2-yl)phenyl]propionate (Compound No. 019) (Preparation Method 4, Step d-1)

According to the procedure described in a reference [N. Miyaura et al., Tetrahedron Letters (Tetrahedron. Lett.), 1997, p.3447], Intermediate 3 (209 mg), bispinacolate diboron (177 mg, Ald), [1,1'-bis(diphenylphosphono)ferrocene]palladium(II) dichloride (henceforth abbreviated as PdCl$_2$(dppf), 28 mg, TCI) and potassium acetate (182.3 mg, Ald) were added to DMF (6 ml) and stirred with heating at 80° C. under argon atmosphere for 5 hours. The reaction mixture was cooled to room temperature, then added with Intermediate 28 (130 mg), PdCl$_2$(dppf) (30 mg) and 2 M aqueous sodium carbonate (0.9 ml) and stirred with heating at 80° C. under argon atmosphere for 21 hours. The reaction mixture was added with ethyl acetate (100 ml), washed with saturated brine and dried, and then the solvent was evaporated under reduced pressure. The residue was purified by column chromatography (Quad, hexane:ethyl acetate=3:1) to obtain the title compound (Compound No. 019, 46 mg).

Example 20
Synthesis of 3-[4-cyclopentylmethyloxy-3-(6-sulfamoylaminonaphthalen-2-yl)phenyl]propionic acid (Compound No. 020) (Preparation Method 1, Step a)

According to the procedure described in the synthesis method of Compound of Example 002 (Preparation Method 1, Step a) with the modification that the reaction was carried out for 24 hours, Compound of Example 019 (41 mg) and 2 N aqueous sodium hydroxide (340 μl) were reacted and treated to obtain the title compound (Compound No. 020, 22 mg). Rf=0.16 (chloroform:methanol=10:1).

Example 21
Synthesis of methyl 3-[4-cyclopentylmethyloxy-3-(6-methanesulfonylnaphthalen-2-yl)phenyl]propionate (Compound No. 021) (Preparation Method 4, Step d-1)

According to the procedure described in the synthesis method of Compound of Example 019 (Preparation Method 4, Step d-1) with the modifications that purification was performed by flash column chromatography (hexane:ethyl acetate=5:1), and then the residue was further purified by PTLC (hexane:ethyl acetate=2:1), Intermediate 3 (266 mg), bispinacolate diboron (224 mg), PdCl$_2$(dppf) (33 mg) and potassium acetate (249 mg) were reacted at 80° C. for 4.5 hours, and then this reaction mixture was added with 2-bromo-6-methane sulfonylnaphthalene (158 mg) obtained by a method known from a reference (M. Janczewski et al., Roczniki Chemii, vol. 49, p.715, 1975), PdCl$_2$(dppf) (29.3 mg) and 2 M aqueous sodium carbonate (0.9 ml), reacted at 80° C. for 11 hours and treated to obtain the title compound (Compound No. 021, 118 mg).

Example 22
Synthesis of 3-[4-cyclopentylmethyloxy-3-(6-methanesulfonylnaphthalen-2-yl)phenyl]propionic acid (Compound No. 022) (Preparation Method 1, Step a)

According to the procedure described in the synthesis method of Compound of Example 002 (Preparation Method 1, Step a) with the modification that the reaction was carried out for 3 hours, Compound of Example 021 (118 mg) and 2 N aqueous sodium hydroxide (570 μl) were reacted and treated to obtain the title compound (Compound No. 022, 88 mg). Rf=0.51 (chloroform:methanol=10:1).

Example 23
Synthesis of 6-bromo-naphthalene-2-sulfonic acid amide (Intermediate 29)

6-Bromonaphthalene-2-sulfonyl chloride (447 mg) obtained by the aforementioned method known from the reference [M. Janczewski et al., Roczniki Chemii, vol. 49, p.715, 1975] was suspended in diethyl ether (40 ml), added with 25% aqueous ammonia (12 ml) and stirred at room temperature for 16 hours. The deposited solid was collected by filtration to obtain the title compound (Intermediate 29, 295 mg).

Synthesis of methyl 3-[4-cyclopentylmethyloxy-3-(6-sulfamoylnaphthalen-2-yl)phenyl]propionate (Compound No. 023) (Preparation Method 4, Step d-1)

According to the procedure described in the synthesis method of Compound of Example 019 (Preparation Method 4, Step d-1) with the modification that purification was performed by flash column chromatography (hexane:ethyl acetate=3:1), Intermediate 3 (274 mg), bispinacolate diboron (225 mg), $PdCl_2$(dppf) (37 mg) and potassium acetate (243 mg) were reacted at 80° C. for 4 hours, and then this reaction mixture was added with Intermediate 29 (161 mg), $PdCl_2$(dppf) (37 mg) and 2 M aqueous sodium carbonate (0.9 ml), reacted at 80° C. for 17 hours and treated to obtain the title compound (Compound No. 023, 163 mg).

Example 24

Synthesis of 3-[4-cyclopentylmethyloxy-3-(6-sulfamoylnaphthalen-2-yl)phenyl]propionic acid (Compound No. 024) (Preparation Method 1, Step a)

According to the procedure described in the synthesis method of Compound of Example 002 (Preparation Method 1, Step a) with the modification that the reaction was carried out for 2 hours, Compound of Example 023 (151 mg) and 2 N aqueous sodium hydroxide (650 μl) were reacted and treated to obtain the title compound (Compound No. 024, 55 mg). Rf=0.28 (chloroform:methanol=10:1).

Example 25

Synthesis of 6-bromonaphthalene-2-sulfonic acid methylamide (Intermediate 30)

6-Bromonaphthalene-2-sulfonyl chloride (576 mg) was added portionwise to 40% methylamine solution (5 ml, WAKO), added with 3.6 N aqueous potassium hydroxide (5 ml), stirred at room temperature, then heated to 60° C. and further stirred for 3 hours. The reaction mixture was cooled to room temperature, then added with 2 N hydrochloric acid (15 ml) and extracted with ethyl acetate. The organic layer was washed successively with saturated aqueous sodium hydrogencarbonate and saturated brine and dried, and then the solvent was evaporated under reduced pressure. The residue was purified by flash column chromatography (hexane:ethyl acetate=5:1) to obtain the title compound (Intermediate 30, 484 mg).

Synthesis of methyl 3-{4-cyclopentylmethyloxy-3-[6-(N-methylsulfamoyl)naphthalen-2-yl]phenyl}propionate (Compound No. 025) (Preparation Method 4, Step d-1)

According to the procedure described in the synthesis method of Compound of Example 019 (Preparation Method 4, Step d-1) with the modifications that the purification was performed by flash column chromatography (hexane:ethyl acetate=5:2), and then the residue was further purified by PTLC (hexane:ethyl acetate=5:2), Intermediate 3 (282 mg), bispinacolate diboron (229 mg), $PdCl_2$(dppf) (39 mg) and potassium acetate (238 mg) were reacted at 80° C. for 8 hours, and then this reaction mixture was added with Intermediate 30 (169 mg), $PdCl_2$(dppf) (38 mg) and 2 M aqueous sodium carbonate (0.9 ml), reacted at 80° C. for 21 hours and treated to obtain the title compound (Compound No. 025, 144 mg).

Example 26

Synthesis of 3-{4-cyclopentylmethyloxy-3-[6-(N-methylsulfamoyl)naphthalen-2-yl]phenyl}propionic acid (Compound No. 026) (Preparation Method 1, Step a)

According to the procedure described in the synthesis method of Compound of Example 002 (Preparation Method 1, Step a) with the modification that the reaction was carried out for 2 hours, Compound of Example 025 (136 mg) and 2 N aqueous sodium hydroxide (565 μl) were reacted and treated to obtain the title compound (Compound No. 026, 102 mg). Rf=0.41 (chloroform:methanol=10:1).

Example 27

Synthesis of 6-bromonaphthalene-2-sulfonic acid dimethylamide (Intermediate 31)

According to the procedure described in the synthesis method of Intermediate 30 in Example 25 (Preparation Method 4, Step d-1) with the modifications that the reaction was carried out for 3 hours, and the purification was performed by flash column chromatography (hexane:ethyl acetate=7:1), 6-bromo-naphthalene-2-sulfonyl chloride (639 g) was reacted with 50% dimethylamine solution (2.5 ml, WAKO) and 3.6 N aqueous potassium hydroxide (2.5 ml) and treated to obtain the title compound (Intermediate 31, 492 mg).

Synthesis of methyl 3-{4-cyclopentylmethyloxy-3-[6-(N,N-dimethylsulfamoyl)-naphthalen-2-yl]phenyl}propionate (Compound No. 027) (Preparation Method 4, Step d-1)

According to the procedure described in the synthesis method of Compound of Example 019 (Preparation Method 4, Step d-1) with the modification that the purification was performed by flash column chromatography (hexane:ethyl acetate=6:1), Intermediate 3 (282 mg), bispinacolate diboron (225 mg), $PdCl_2$(dppf) (36 mg) and potassium acetate (234 mg) were reacted at 80° C. for 4 hours, and then this reaction mixture was added with Intermediate 31 (177 mg), $PdCl_2$(dppf) (36 mg) and 2 M aqueous sodium carbonate (0.9 ml), reacted at 80° C. for 12 hours and treated to obtain the title compound (Compound No. 027, 177 mg).

Example 28

Synthesis of 3-{4-cyclopentylmethyloxy-3-[6-(N,N-dimethylsulfamoyl)naphthalen-2-yl]phenyl}propionic acid (Compound No. 028) (Preparation Method 1, Step a)

According to the procedure described in the synthesis method of Compound of Example 002 (Preparation Method 1, Step a) with the modification that the reaction was carried out for 3 hours, Compound of Example 027 (175 mg) and 2 N aqueous sodium hydroxide (710 μl) were reacted and treated to obtain the title compound (Compound No. 028, 122 mg). Rf=0.54 (chloroform:methanol=10:1).

Example 29

Synthesis of methyl 3-[4-cyclohexylmethyloxy-3-(6-methoxycarbonylnaphthalen-2-yl)phenyl]propionate (Intermediate 32)

According to the procedure described in the synthesis method of Compound of Example 019 (Preparation Method 4, Step d-1) with the modification that the purification was performed by flash column chromatography (hexane:ethyl acetate=10:1), Intermediate 7 (758 mg), bispinacolate diboron (571 mg), $PdCl_2$(dppf) (59 mg) and potassium acetate (334 mg) were reacted at 80° C. for 4 hours, and then this reaction mixture was added with methyl 6-bromo-2-naphthalenecarboxylate (801 mg, LANC), $PdCl_2$(dppf) (48 mg) and 2 M aqueous sodium carbonate (2.0 ml), reacted at 80° C. for 15 hours and treated to obtain the title compound (Intermediate 32, 418 mg).

Synthesis of 3-[3-(6-carboxynaphthalen-2-yl)-4-cyclohexylmethyloxyphenyl]propionic acid (Compound No. 029) (Preparation Method 1, Step a)

According to the procedure described in the synthesis method of Compound of Example 002 (Preparation Method 1, Step a) with the modification that the reaction was carried out for 3 hours, Intermediate 32 (399 mg) and 2 N aqueous sodium hydroxide (1.5 ml) were reacted and treated to obtain the title compound (Compound No. 029, 374 mg). Rf=0.33 (chloroform:methanol=10:1).

Example 30

Synthesis of methyl 3-(3-bromo-4-methoxyphenyl) propionate (Intermediate 33) (Step c)

According to the procedure described in the synthesis method of Intermediate 1 in Reference Example 1 (Step c) with the modification that the purification was performed by flash column chromatography (hexane:ethyl acetate=6:1), Intermediate 4 (1.60 g) and thionyl chloride (1.44 ml) were reacted in methanol and treated to obtain the title compound (Intermediate 33, 1.63 g).

Synthesis of methyl 3-[4-methoxy-3-(naphthalen-2-yl) phenyl]propionate (Intermediate 34) (Step d-1)

According to the procedure described in the synthesis method of Compound of Example 001 (Preparation Method 4, Step d-1) with the modifications that the reaction was carried out for 2 hours, and the purification was performed by flash column chromatography (hexane:isopropyl ether=8:1), Intermediate 33 (460 mg), 2-naphthaleneboronic acid (886 mg, Ald), 2 M aqueous sodium carbonate (1.6 ml) and $(Ph_3P)_4Pd$ (298 mg) were reacted and treated to obtain the title compound (Intermediate 34, 1010 mg).

Synthesis of 3-[4-methoxy-3-(naphthalen-2-yl)phenyl] propionic acid (Intermediate 35) (Step a)

According to the procedure described in the synthesis method of Compound of Example 002 (Preparation Method 1, Step a) with the modification that the reaction was carried out for 2 hours, Intermediate 34 (773 mg) and 2 N aqueous sodium hydroxide (2.3 ml) were reacted and treated to obtain the title compound (Intermediate 35, 674 mg).

Synthesis of methyl 3-[4-hydroxy-3-(naphthalen-2-yl) phenyl]propionate (Intermediate 36) (Steps f and c)

According to the procedure described in the synthesis method of Intermediate 20 in Reference Example 6 (Step f), Intermediate 35 (551 mg), pyridine and concentrated hydrochloric acid (5 ml each) were reacted and treated. According to the procedure described in the synthesis method of Intermediate 1 in Reference Example 1 (Step c), the obtained residue was reacted with thionyl chloride (0.33 ml) in methanol to obtain the title compound (Intermediate 36, 531 mg).

Synthesis of methyl 3-[4-(2-fluorophenylmethyloxy)-3-(naphthalen-2-yl)phenyl]propionate (Compound No. 030) (Preparation Method 5, Step e-1)

A solution of Intermediate 36 (100 mg) in DMF (5 ml) was added with potassium carbonate (68 mg, WAKO) and 2-fluorobenzyl bromide (43 µl, TCI) and stirred at room temperature for 15.5 hours. The reaction mixture was added with ethyl acetate (100 ml) and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=8:1) to obtain the title compound (Compound No. 030, 132 mg).

Example 31

Synthesis of 3-[4-(2-fluorophenylmethyloxy)-3-(naphthalen-2-yl)phenyl]propionic acid (Compound No. 031) (Preparation Method 1, Step a)

According to the procedure described in the synthesis method of Compound of Example 002 (Preparation Method 1, Step a) with the modification that the reaction was carried out for 4 hours, Compound of Example 030 (120 mg) and 2 N aqueous sodium hydroxide (1.0 ml) were reacted and treated to obtain the title compound (Compound No. 031, 110 mg). Rf=0.65 (chloroform:methanol=10:1).

Example 32

Synthesis of methyl 3-[4-(3-fluorophenylmethyloxy)-3-(naphthalen-2-yl)phenyl]propionate (Compound No. 032) (Preparation Method 5, Step e-1)

According to the procedure described in the synthesis method of Compound of Example 030 (Preparation Method 5, Step e-1) with the modifications that the reaction was carried out for 16 hours, and the purification was performed by flash column chromatography (hexane:ethyl acetate=8:1), Intermediate 36 (100 mg), potassium carbonate (68 mg) and 3-fluorobenzyl bromide (44 µl, TCI) were reacted and treated to obtain the title compound (Compound No. 032, 132 mg).

Example 33

Synthesis of 3-[4-(3-fluorophenylmethyloxy)-3-(naphthalen-2-yl)phenyl]propionic acid (Compound No. 033) (Preparation Method 1, Step a)

According to the procedure described in the synthesis method of Compound of Example 002 (Preparation Method 1, Step a) with the modification that the reaction was carried out for 4 hours, Compound of Example 032 (120 mg) and 2 N aqueous sodium hydroxide (1.0 ml) were reacted and treated to obtain the title compound (Compound No. 033, 105 mg). Rf=0.66 (chloroform:methanol=10:1).

Example 34

Synthesis of methyl 3-[4-(4-fluorophenylmethyloxy)-3-(naphthalen-2-yl)phenyl]propionate (Compound No. 034) (Preparation Method 5, Step e-1)

According to the procedure described in the synthesis method of Compound of Example 030 (Preparation Method 5, Step e-1) with the modifications that the reaction was carried out for 16 hours, and the purification was performed by flash column chromatography (hexane:ethyl acetate=8:1), Intermediate 36 (100 mg), potassium carbonate (68 mg) and 4-fluorobenzyl bromide (45 µl, TCI) were reacted and treated to obtain the title compound (Compound No. 034, 134 mg).

Example 35

Synthesis of 3-[4-(3-fluorophenylmethyloxy)-3-(naphthalen-2-yl)phenyl]propionic acid (Compound No. 035) (Preparation Method 1, Step a)

According to the procedure described in the synthesis method of Compound of Example 002 (Preparation Method 1, Step a) with the modifications that the reaction was carried out for 4 hours, Compound of Example 034 (120 mg) and 2 N aqueous sodium hydroxide (1.0 ml) were reacted and treated to obtain the title compound (Compound No. 035, 107 mg). Rf=0.70 (chloroform:methanol=10:1).

Example 36

Synthesis of methyl 3-[4-butyloxy-3-(naphthalen-2-yl) phenyl]propionate (Compound No. 036) (Preparation Method 5, Step e-1)

According to the procedure described in the synthesis method of Compound of Example 030 (Preparation Method 5, Step e-1) with the modifications that the reaction was carried out for 19 hours, and the purification was performed by flash column chromatography (hexane:ethyl acetate=9:1), Intermediate 36 (100 mg), potassium carbonate (68 mg) and 1-iodobutane (115 µl, TCI) were reacted and treated to obtain the title compound (Compound No. 036, 110 mg).

Example 37
Synthesis of 3-[4-butyloxy-3-(naphthalen-2-yl)phenyl] propionic acid (Compound No. 037) (Preparation Method 1, Step a)

According to the procedure described in the synthesis method of Compound of Example 002 (Preparation Method 1, Step a) with the modification that the reaction was carried out for 17 hours, Compound of Example 036 (105 mg) and 2 N aqueous sodium hydroxide (0.75 ml) were reacted and treated to obtain the title compound (Compound No. 037, 91 mg). Rf=0.54 (chloroform:methanol=10:1).

Example 38
Synthesis of methyl 3-[4-cyclopentylmethyloxy-3-(naphthalen-2-yl)phenyl]propionate (Compound No. 038) (Preparation Method 5, Step e-2)

A solution of Intermediate 36 (153 mg) in anhydrous THF (5 ml) was added with $Ph_3P$ (393 mg) and cyclopentane-methanol (162 µl). The mixture was added dropwise with 40% DIAD (710 µl) under ice cooling, gradually warmed to room temperature and stirred for 21 hours. The reaction mixture was added with ethyl acetate (100 ml) and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=7:1) to obtain the title compound (Compound No. 038, 176 mg).

Example 39
Synthesis of 3-[4-cyclopentylmethyloxy-3-(naphthalen-2-yl)phenyl]propionic acid (Compound No. 039) (Preparation Method 1, Step a)

According to the procedure described in the synthesis method of Compound of Example 002 (Preparation Method 1, Step a) with the modification that the reaction was carried out at 45° C. for 15 hours, Compound of Example 038 (170 mg) and 2 N aqueous sodium hydroxide (0.50 ml) were reacted and treated to obtain the title compound (Compound No. 039, 147 mg). Rf=0.63 (chloroform:methanol=10:1).

Example 40
Synthesis of methyl 3-[4-isopropyloxy-3-(naphthalen-2-yl)phenyl]propionate (Compound No. 040) (Preparation Method 5, Step e-2)

According to the procedure described in the synthesis method of Compound of Example 038 (Preparation Method 5, Step e-2) with the modifications that the reaction was carried out for 20 hours, and the purification was performed by flash column chromatography (hexane:isopropyl ether=7:1), Intermediate 36 (122 mg), $Ph_3P$ (262 mg), isopropyl alcohol (76 µl, TCI) and 40% DIAD (470 µl) were reacted and treated to obtain the title compound (Compound No. 040, 137 mg).

Example 41
Synthesis of 3-[4-isopropyloxy-3-(naphthalen-2-yl)phenyl] propionic acid (Compound No. 041) (Preparation Method 1, Step a)

According to the procedure described in the synthesis method of Compound of Example 002 (Preparation Method 1, Step a) with the modification that the reaction was carried out for 15 hours, Compound of Example 040 (125 mg) and 2 N aqueous sodium hydroxide (0.50 ml) were reacted and treated to obtain the title compound (Compound No. 041, 118 mg). Rf=0.55 (chloroform:methanol=10:1).

Example 42
Synthesis of methyl 3-[4-cyclopentyloxy-3-(naphthalen-2-yl)phenyl]propionate (Compound No. 042) (Preparation Method 5, Step e-2)

According to the procedure described in the synthesis method of Compound of Example 038 (Preparation Method 5, Step e-2) with the modifications that the reaction was carried out for 15 hours, and the purification was performed by flash column chromatography (hexane:isopropyl ether=6:1), Intermediate 36 (100 mg), $Ph_3P$ (262 mg), cyclopentanol (91 µl, TCI) and 40% DIAD (473 µl) were reacted and treated to obtain the title compound (Compound No. 042, 120 mg).

Example 43
Synthesis of 3-[4-cyclopentyloxy-3-(naphthalen-2-yl) phenyl]propionic acid (Compound No. 043) (Preparation Method 1, Step a)

According to the procedure described in the synthesis method of Compound of Example 002 (Preparation Method 1, Step a) with the modification that the reaction was carried out for 4 hours, Compound of Example 042 (115 mg) and 2 N aqueous sodium hydroxide (0.75 ml) were reacted and treated to obtain the title compound (Compound No. 043, 108 mg). Rf=0.57 (chloroform:methanol=10:1).

Example 44
Synthesis of methyl 3-[4-cyclohexyloxy-3-(naphthalen-2-yl)phenyl]propionate (Compound No. 044) (Preparation Method 5, Step e-2)

According to the procedure described in the synthesis method of Compound of Example 038 (Preparation Method 5, Step e-2) with the modifications that the reaction was carried out for 22 hours, and the purification was performed by flash column chromatography (hexane:isopropyl ether=7:1), Intermediate 36 (122 mg), $Ph_3P$ (262 mg), cyclohexyl alcohol (95 µl, Ald) and 40% DIAD (473 µl) were reacted and treated to obtain the title compound (Compound No. 044, 84 mg).

Example 45
Synthesis of 3-[4-cyclohexyloxy-3-(naphthalen-2-yl) phenyl]propionic acid (Compound No. 045) (Preparation Method 1, Step a)

According to the procedure described in the synthesis method of Compound of Example 002 (Preparation Method 1, Step a) with the modification that the reaction was carried out for 4 hours, Compound of Example 043 (75 mg) and 2 N aqueous sodium hydroxide (300 µl) were reacted and treated to obtain the title compound (Compound No. 045, 70 mg). Rf=0.45 (chloroform:methanol=10:1).

Example 46
Synthesis of methyl 3-[4-(2-cyclopentylethyloxy)-3-(naphthalen-2-yl)phenyl]propionate (Compound No. 046) (Preparation Method 5, Step e-2)

According to the procedure described in the synthesis method of Compound of Example 038 (Preparation Method 5, Step e-2) with the modifications that the reaction was carried out for 18 hours, and the purification was performed by flash column chromatography (hexane:isopropyl ether=6:1), Intermediate 36 (122 mg), $Ph_3P$ (262 mg), 2-cyclopentane-ethanol (124 µl, TCI) and 40% DIAD (473 µl) were reacted and treated to obtain the title compound (Compound No. 046, 123 mg).

Example 47

Synthesis of 3-[4-(2-cyclopentylethyloxy)-3-(naphthalen-2-yl)phenyl]propionic acid (Compound No. 047) (Preparation Method 1, Step a)

According to the procedure described in the synthesis method of Compound of Example 002 (Preparation Method 1, Step a) with the modification that the reaction was carried out for 14 hours, Compound of Example 046 (115 mg) and 2 N aqueous sodium hydroxide (0.75 ml) were reacted and treated to obtain the title compound (Compound No. 047, 108 mg). Rf=0.61 (chloroform:methanol=10:1).

Example 48

Synthesis of methyl 3-[4-(2-cyclohexylethyloxy)-3-(naphthalen-2-yl)phenyl]propionate (Compound No. 048) (Preparation Method 5, Step e-2)

According to the procedure described in the synthesis method of Compound of Example 038 (Preparation Method 5, Step e-2) with the modifications that the reaction was carried out for 15 hours, and the purification was performed by flash column chromatography (hexane:ethyl acetate=10:1), Intermediate 36 (153 mg), $Ph_3P$ (393 mg), cyclohexane-ethanol (209 μl,1 TCI) and 40% DIAD (710 μl) were reacted and treated to obtain the title compound (Compound No. 048, 200 mg).

Example 49

Synthesis of 3-[4-(2-cyclohexylethyloxy)-3-(naphthalen-2-yl)phenyl]propionic acid (Compound No. 049) (Preparation Method 1, Step a)

According to the procedure described in the synthesis method of Compound of Example 002 (Preparation Method 1, Step a) with the modification that the reaction was carried out at 65° C. for 4 hours, Compound of Example 048 (195 mg) and 2 N aqueous sodium hydroxide (0.60 ml) were reacted and treated to obtain the title compound (Compound No. 049, 146 mg). Rf=0.64 (chloroform:methanol=10:1).

Example 50

Synthesis of methyl 3-[3-(naphthalen-2-yl)-4-(2-phenylethyloxy)phenyl]propionate (Compound No. 050) (Preparation Method 5, Step e-2)

According to the procedure described in the synthesis method of Compound of Example 038 (Preparation Method 5, Step e-2) with the modifications that the reaction was carried out for 14 hours, and the purification was performed by flash column chromatography (hexane:isopropyl ether=8:1), Intermediate 36 (100 mg), $Ph_3P$ (262 mg), 2-phenylethyl alcohol (120 μl, TCI) and 40% DIAD (473 μl) were reacted and treated to obtain the title compound (Compound No. 050, 108 mg).

Example 51

Synthesis of 3-[3-(naphthalen-2-yl)-4-(2-phenylethyloxy)phenyl]propionic acid (Compound No. 051) (Preparation Method 1, Step a)

According to the procedure described in the synthesis method of Compound of Example 002 (Preparation Method 1, Step a) with the modification that the reaction was carried out for 13 hours, Compound of Example 050 (100 mg) and 2 N aqueous sodium hydroxide (0.75 ml) were reacted and treated to obtain the title compound (Compound No. 051, 86 mg). Rf=0.62 (chloroform:methanol=10:1).

Example 52

Synthesis of methyl 3-{4-[2-(2-fluorophenyl)ethyloxy]-3-(naphthalen-2-yl)phenyl}propionate (Compound No. 052) (Preparation Method 5, Step e-2)

According to the procedure described in the synthesis method of Compound of Example 038 (Preparation Method 5, Step e-2) with the modifications that the reaction was carried out for 17 hours, and the purification was performed by flash column chromatography (hexane:ethyl acetate=6:1), Intermediate 36 (153 mg), $Ph_3P$ (393 mg), 2-(2-fluorophenyl)ethyl alcohol (209 μl, TCI) and 40% DIAD (710 μl) were reacted and treated to obtain the title compound (Compound No. 052, 186 mg).

Example 53

Synthesis of 3-{4-[2-(2-fluorophenyl)ethyloxy]-3-(naphthalen-2-yl)phenyl}propionic acid (Compound No. 053) (Preparation Method 1, Step a)

According to the procedure described in the synthesis method of Compound of Example 002 (Preparation Method 1, Step a) with the modification that the reaction was carried out at 65° C. for 2 hours, Compound of Example 052 (180 mg) and 2 N aqueous sodium hydroxide (0.50 ml) were reacted and treated to obtain the title compound (Compound No. 053, 164 mg). Rf=0.64 (chloroform:methanol=10:1).

Example 54

Synthesis of methyl 3-{4-[2-(3-fluorophenyl)ethyloxy]-3-(naphthalen-2-yl)phenyl}propionate (Compound No. 054) (Preparation Method 5, Step e-2)

According to the procedure described in the synthesis method of Compound of Example 038 (Preparation Method 5, Step e-2) with the modifications that the reaction was carried out for 14 hours, and the purification was performed by flash column chromatography (hexane:isopropyl ether=8:1), Intermediate 36 (100 mg), $Ph_3P$ (262 mg), 2-(3-fluorophenyl)ethyl alcohol (125 μl, TCI) and 40% DIAD (473 μl) were reacted and treated to obtain the title compound (Compound No. 054, 130 mg).

Example 55

Synthesis of 3-{4-[2-(3-fluorophenyl)ethyloxy]-3-(naphthalen-2-yl)phenyl}propionic acid (Compound No. 055) (Preparation Method 1, Step a)

According to the procedure described in the synthesis method of Compound of Example 002 (Preparation Method 1, Step a) with the modification that the reaction was carried out for 13 hours, Compound of Example 054 (120 mg) and 2 N aqueous sodium hydroxide (0.75 ml) were reacted and treated to obtain the title compound (Compound No. 055, 107 mg). Rf=0.60 (chloroform:methanol=10:1).

Example 56

Synthesis of methyl 3-{4-[2-(4-fluorophenyl)ethyloxy]-3-(naphthalen-2-yl)phenyl}propionate (Compound No. 056) (Preparation Method 5, Step e-2)

According to the procedure described in the synthesis method of Compound of Example 038 (Preparation Method 5, Step e-2) with the modifications that the reaction was carried out for 14 hours, and the purification was performed by flash column chromatography (hexane:isopropyl ether=8:1), Intermediate 36 (100 mg), $Ph_3P$ (262 mg), 2-(4-fluorophenyl)ethyl alcohol (125 μl, TCI) and 40% DIAD (473 μl) were reacted and treated to obtain the title compound (Compound No. 056, 125 mg).

Example 57
Synthesis of 3-{4-[2-(4-fluorophenyl)ethyloxy]-3-(naphthalen-2-yl)phenyl}propionic acid (Compound No. 057) (Preparation Method 1, Step a)

According to the procedure described in the synthesis method of Compound of Example 002 (Preparation Method 1, Step a) with the modification that the reaction was carried out for 13 hours, Compound of Example 056 (115 mg) and 2 N aqueous sodium hydroxide (0.75 ml) were reacted and treated to obtain the title compound (Compound No. 057, 108 mg). Rf=0.60 (chloroform:methanol=10:1).

Example 58
Synthesis of 3-{4-[(furan-2-yl)methyloxy]-3-(naphthalen-2-yl)phenyl}propionic acid (Compound No. 058) (Preparation Method 5, Step e-2 and Preparation Method 1, Step a)

According to the procedure described in the synthesis method of Compound of Example 038 (Preparation Method 5, Step e-2) with the modifications that the reaction was carried out for 16 hours, and the purification was performed by column chromatography (Quad, hexane:isopropyl ether=5:1), Intermediate 36 (122 mg), Ph$_3$P (315 mg), furfuryl alcohol (104 µl, TCI) and 40% DIAD (473 µl) were reacted and treated to obtain oily substance. According to the procedure described in the synthesis method of Compound of Example 002 (Preparation Method 1, Step a) with the modification that the reaction was carried out for 13 hours, the oily substance was reacted with 2 N aqueous sodium hydroxide (0.50 ml) and treated to obtain the title compound (Compound No. 058, 65 mg). Rf=0.56 (chloroform:methanol=10:1).

Example 59
Synthesis of methyl 3-{3-(naphthalen-2-yl)-4-[(pyridin-3-yl)methyloxy]-phenyl}propionate (Compound No. 059) (Preparation Method 5, Step e-2)

According to the procedure described in the synthesis method of Compound of Example 038 (Preparation Method 5, Step e-2) with the modifications that the reaction was carried out for 16 hours, and the purification was performed by flash column chromatography (hexane:ethyl acetate=4:3), Intermediate 36 (100 mg), Ph$_3$P (262 mg), 3-pyridine-methanol (96 µl, TCI) and 40% DIAD (473 µl) were reacted and treated to obtain the title compound (Compound No. 059, 104 mg).

Example 60
Synthesis of 3-{3-(naphthalen-2-yl)-4-[(pyridin-3-yl)methyloxy]phenyl}propionic acid (Compound No. 060) (Preparation Method 1, Step a)

According to the procedure described in the synthesis method of Compound of Example 002 (Preparation Method 1, Step a) with the modification that the reaction was carried out for 16 hours, Compound of Example 059 (100 mg) and 2 N aqueous sodium hydroxide (0.75 ml) were reacted and treated to obtain the title compound (Compound No. 060, 86 mg). Rf=0.48 (chloroform:methanol=10:1).

Example 61
Synthesis of methyl 3-{4-[2-(5-ethylpyridin-2-yl)ethyloxy]-3-(naphthalen-2-yl)phenyl}propionate (Compound No. 061) (Preparation Method 5, Step e-2)

According to the procedure described in the synthesis method of Compound of Example 038 (Preparation Method 5, Step e-2) with the modifications that the reaction was carried out for 20 hours, and the purification was performed by column chromatography (Quad, hexane:ethyl acetate=5:2), Intermediate 36 (100 mg), Ph$_3$P (262 mg), 2-(5-ethylpyridin-2-yl)ethanol (151 mg, MAYB) and 40% DIAD (473 µl) were reacted and treated to obtain the title compound (Compound No. 061, 126 mg).

Example 62
Synthesis of 3-{4-[2-(5-ethylpyridin-2-yl)ethyloxy]-3-(naphthalen-2-yl)phenyl}propionic acid (Compound No. 062) (Preparation Method 1, Step a)

According to the procedure described in the synthesis method of Compound of Example 002 (Preparation Method 1, Step a) with the modification that the reaction was carried out for 20 hours, Compound of Example 061 (120 mg) and 2 N aqueous sodium hydroxide (350 µl) were reacted and treated to obtain the title compound (Compound No. 062, 108 mg). Rf=0.53 (chloroform:methanol=10:1).

Example 63
Synthesis of methyl 3-{4-[2-(5-methyl-2-phenyloxazol-4-yl)ethyloxy]-3-(naphthalen-2-yl)phenyl}propionate (Compound No. 063) (Preparation Method 5, Step e-1)

A solution of 2-(5-methyl-2-phenyloxazol-4-yl)ethanol (122 mg, MAYB) in anhydrous THF (3 ml) was added with triethylamine (104 µl), then added with methanesulfonyl chloride (56 µl) under ice cooling and stirred for 30 minutes. The reaction mixture was added with water (5 ml) and extracted with diethyl ether (80 ml). The organic layer was washed with saturated brine and dried, and then the solvent was evaporated under reduced pressure. A solution obtained beforehand by adding 60% sodium hydride (18 mg) to a solution of Intermediate 36 (122 mg) in DMF (3 ml) under ice cooling and stirring the mixture for 15 minutes was added with a solution of the aforementioned residue in DMF (3 ml) under ice cooling. The reaction mixture was stirred for 15 minutes, then warmed to room temperature, stirred for 45 minutes and further stirred at 60° C. for 48 hours. The reaction mixture was added with water (10 ml) and diethyl ether (100 ml) for extraction. The organic layer was washed successively with saturated aqueous sodium hydrogencarbonate, saturated aqueous ammonium chloride and saturated brine and dried, and then the solvent was evaporated under reduced pressure. The residue was purified by flash column chromatography (Quad, hexane:isopropyl ether=7:1) to obtain the title compound (Compound No. 063, 94 mg).

Example 64
Synthesis of 3-{4-[2-(5-methyl-2-phenyloxazol-4-yl)ethyloxy]-3-(naphthalen-2-yl)phenyl}propionic acid (Compound No. 064) (Preparation Method 1, Step a)

According to the procedure described in the synthesis method of Compound of Example 002 (Preparation Method 1, Step a) with the modification that the reaction was carried out for 2 hours, Compound of Example 063 (90 mg) and 2 N aqueous sodium hydroxide (400 µl) were reacted and treated to obtain the title compound (Compound No. 064, 80 mg). Rf=0.52 (chloroform:methanol=10:1).

Example 65
Synthesis of 4-cyclohexylmethyloxy-3-(naphthalen-2-yl)benzaldehyde (Intermediate 37) (Preparation Method 6, Step d)

According to the procedure described in the synthesis method of Compound of Example 001 (Preparation Method 4, Step d-1) with the modifications that the reaction was carried out at 80° C. for 17 hours, and the purification was performed by flash column chromatography (hexane:isopropyl ether=10:1), Intermediate 25 (298 mg), 2-naphthaleneboronic acid (535 mg), 2 M aqueous sodium carbonate (0.9 ml) and (Ph$_3$P)$_4$Pd (116 mg) were reacted and treated to obtain the title compound (Intermediate 37, 345 mg).

Synthesis of ethyl 3-[4-cyclohexylmethyloxy-3-(naphthalen-2-yl)phenyl]acrylate (Intermediate 38) (Preparation Method 6, Step k)

A solution of Intermediate 37 (344 mg) in 1,2-diethoxyethane (5 ml) was added with ethyl diethylphosphonoacetate (240 μl) and then added with 60% sodium hydride (66 mg) under ice cooling. The mixture was stirred for 10 minutes as it was, then warmed to room temperature and further stirred for 2 hours. The reaction mixture was added with ethyl acetate (90 ml) and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=10:1) to obtain the title compound (Intermediate 38, 398 mg).

Synthesis of ethyl 3-[4-cyclohexylmethyloxy-3-(naphthalen-2-yl)phenyl]propionate (Compound No. 065) (Preparation Method 6, Step j)

A mixed solution of Intermediate 17 (293 mg) in ethyl acetate (5 ml)/methanol (2 ml) was added with 10% palladium carbon (33 mg) and stirred under hydrogen atmosphere at room temperature for 1 hour. The reaction mixture was filtered, and the solvent of the filtrate was evaporated under reduced pressure to obtain the title compound (Compound No. 065, 209 mg).

Example 66

Synthesis of 3-[4-cyclohexylmethyloxy-3-(naphthalen-2-yl)phenyl]propionic acid (Compound No. 066) (Preparation Method 1, Step a)

According to the procedure described in the synthesis method of Compound of Example 002 (Preparation Method 1, Step a) with the modification that the reaction was carried out for 2 hours, Compound of Example 065 (209 mg) and 2 N aqueous sodium hydroxide (0.50 ml) were reacted and treated to obtain the title compound (Compound No. 066, 194 mg). Rf=0.66 (chloroform:methanol=10:1).

Example 67

Synthesis of 4-cyclohexylmethyloxy-3-(6-methyloxynaphthalen-2-yl)benzaldehyde (Intermediate 39) (Preparation Method 6, Step d)

According to the procedure described in the synthesis method of Compound of Example 001 (Preparation Method 4, Step d-1) with the modifications that the reaction was carried out for 14 hours, and the purification was performed by flash column chromatography (hexane:isopropyl ether=5:1), crude 6-methoxy-2-naphthaleneboronic acid (218 mg) prepared from 2-bromo-6-methoxynaphthalene (240 mg), 1.6 M solution of n-butyllithium in hexane (1.25 ml) and ($^i$PrO)$_3$B (350 μl), Intermediate 25 (115 mg), 2 M aqueous sodium carbonate (0.9 ml) and (Ph$_3$P)$_4$Pd (58.2 mg) were reacted and treated to obtain the title compound (Intermediate 39, 153 mg).

Synthesis of ethyl 3-[4-cyclohexylmethyloxy-3-(6-methoxynaphthalen-2-yl)phenyl]acrylate (Intermediate 40) (Preparation Method 6, Step k)

According to the procedure described in the synthesis method of Intermediate 38 in Example 65 (Preparation Method 6, Step k) with the modification that the reaction was carried out for 1 hour, Intermediate 39 (150 mg), ethyl diethylphosphonoacetate (80 μl) and 60% sodium hydride (21 mg) were reacted and treated to obtain the title compound (Intermediate 40, 136 mg).

Synthesis of ethyl 3-[4-cyclohexylmethyloxy-3-(6-methoxynaphthalen-2-yl)phenyl]propionate (Compound No. 067) (Preparation Method 6, Step j)

According to the procedure described in the synthesis method of Compound of Example 065 (Preparation Method 6, Step j) with the modification that the purification was performed by flash column chromatography (hexane:ethyl acetate=10:1), Intermediate 40 (143 mg) and 10% palladium carbon (21 mg) were reacted and treated to obtain the title compound (Compound No. 067, 131 mg).

Example 68

Synthesis of 3-[4-cyclohexylmethyloxy-3-(6-methoxynaphthalen-2-yl)phenyl]propionic acid (Compound No. 068) (Preparation Method 1, Step a)

According to the procedure described in the synthesis method of Compound of Example 002 (Preparation Method 1, Step a) with the modification that the reaction was carried out for 2 hours, Compound of Example 067 (124 mg) and 2 N aqueous sodium hydroxide (280 μl) were reacted and treated to obtain the title compound (Compound No. 068, 115 mg). Rf=0.53 (chloroform:methanol=10:1).

Example 69

Synthesis of 4-cyclohexylmethyloxy-3-(naphthalen-1-yl)benzaldehyde (Intermediate 41) (Preparation Method 6, Step d)

According to the procedure described in the synthesis method of Compound of Example 001 (Preparation Method 4, Step d-1) with the modifications that the reaction was carried out for 15 hours, and the purification was performed by flash column chromatography (hexane:ethyl acetate=10:1), Intermediate 25 (302 mg), naphthalene-1-boronic acid (538 mg, LANC), 2 M aqueous sodium carbonate (0.9 ml) and (Ph$_3$P)$_4$Pd (117 mg) were reacted and treated to obtain the title compound (Intermediate 41, 362 mg).

Synthesis of ethyl 3-[4-cyclohexylmethyloxy-3-(naphthalen-1-yl)phenyl]acrylate (Intermediate 42)

According to the procedure describe in the synthesis method of Intermediate 38 in Example 65 (Preparation Method 6, Step k) with the modification that the reaction was carried out for 1 hour, Intermediate 41 (361 mg), ethyl diethylphosphonoacetate (240 μl) and 60% sodium hydride (69 mg) were reacted and treated to obtain the title compound (Intermediate 42, 377 mg).

Synthesis of ethyl 3-[4-cyclohexylmethyloxy-3-(naphthalen-1-yl)phenyl]propionate (Compound No. 069) (Preparation Method 6, Step j)

According to the procedure described in the synthesis method of Compound of Example 065 (Preparation Method 6, Step j) with the modifications that the reaction was carried out for 1.5 hours, and the purification was performed by flash column chromatography (hexane:ethyl acetate=10:1), Intermediate 42 (361 mg) and 10% palladium carbon (49 mg) were reacted and treated to obtain the title compound (Compound No. 069, 344 mg).

Example 70

Synthesis of 3-[4-cyclohexylmethyloxy-3-(naphthalen-1-yl)phenyl]propionic acid (Compound No. 070) (Preparation Method 1, Step a)

According to the procedure described in the synthesis method of Compound of Example 002 (Preparation Method 1, Step a) with the modification that the reaction was carried out for 1.5 hours, Compound of Example 069 (332 mg) and 2 N aqueous sodium hydroxide (900 μl) were reacted and treated to obtain the title compound (Compound No. 070, 295 mg). Rf=0.66 (chloroform:methanol=10:1).

Example 71

Synthesis of methyl 3-{4-cyclohexylmethyloxy-3-[6-(2-hydroxyethyloxy)naphthalen-2-yl]phenyl}propionate (Intermediate 43) (Preparation Method 9, Step e)

A solution of Compound of Example 001 (221 mg) in DMF (5 ml) was added with potassium carbonate (151 mg) and ethylene carbonate (188 mg, WAKO) and stirred at 80° C. for 14 hours. The reaction mixture was added with ethyl acetate (90 ml) and washed with saturated brine. The organic layer was dried, and then the solvent was evaporated under reduced pressure. The residue was purified by flash column chromatography (hexane:ethyl acetate=3:1) to obtain the title compound (Intermediate 43, 100 mg).

Synthesis of 3-{4-cyclohexylmethyloxy-3-[6-(2-hydroxyethyloxy)naphthalen-2-yl]phenyl}propionic acid (Compound No. 071) (Preparation Method 1, Step a)

According to the procedure described in the synthesis method of Compound of Example 002 (Preparation Method 1, Step a) with the modification that the reaction was carried out for 11 hours, Intermediate 43 (96 mg) and 2 N aqueous sodium hydroxide (280 µl) were reacted and treated to obtain the title compound (Compound No. 071, 68 mg). Rf=0.44 (chloroform:methanol=10:1).

Example 72

Synthesis of methyl 3-[4-cyclohexylmethyloxy-3-(6-methoxycarbonyl-methyloxynaphthalen-2-yl)phenyl]propionate (Intermediate 44) (Preparation Method 9, Step e)

According to the procedure described in the synthesis method of Intermediate 43 in Example 71 (Preparation Method 9, Step e) with the modifications that the reaction was carried out at room temperature for 18 hours, and the purification was performed by PTLC (hexane:ethyl acetate=2:1), Compound of Example 001 (62 mg), potassium carbonate (34 mg) and methyl bromoacetate (43 µl, TCI) were reacted and treated to obtain the title compound (Intermediate 44, 60 mg).

Synthesis of 3-[3-(6-carboxymethyloxynaphthalen-2-yl)-4-cyclohexylmethyloxyphenyl]propionic acid (Compound No. 072) (Preparation Method 1, Step a)

According to the procedure described in the synthesis method of Compound of Example 002 (Preparation Method 1, Step a) with the modification that the reaction was carried out for 20 hours, Intermediate 44 (60 mg) and 2 N aqueous sodium hydroxide (500 µl) were reacted and treated to obtain the title compound (Compound No. 072, 41 mg). Rf=0.18 (chloroform:methanol=2:1).

Example 73

Synthesis of methyl 3-{4-cyclohexylmethyloxy-3-[6-(N,N-dimethylcarbamoylmethyloxy)naphthalen-2-yl]phenyl}propionate (Compound No. 073) (Preparation Method 9, Step e)

According to the procedure described in the synthesis method of Intermediate 43 in Example 71 (Preparation Method 9, Step e) with the modifications that the reaction was carried out at 50° C. for 18 hours, and the purification was performed by PTLC (chloroform:methanol=10:1), Compound of Example 001 (185 mg), potassium carbonate (274 mg), 2-chloro-N,N-dimethylacetamide (411 µl, KANTO) were reacted and treated to obtain the title compound (Compound No. 073, 213 mg).

Example 74

Synthesis of 3-{4-cyclohexylmethyloxy-3-[6-(N,N-dimethylcarbamoylmethyloxy)-naphthalen-2-yl]phenyl}propionic acid (Compound No. 074) (Preparation Method 1, Step a)

According to the procedure described in the synthesis method of Compound of Example 002 (Preparation Method 1, Step a) with the modifications that the reaction was carried out at room temperature for 18 hours and at 60° C. for 8 hours, and the purification was performed by PTLC (chloroform:methanol=10:1), Compound of Example 073 (213 mg) and 2 N aqueous sodium hydroxide (420 µl) were reacted and treated to obtain the title compound (Compound No. 074, 115 mg). Rf=0.51 (chloroform:methanol=10:1).

Example 75

Synthesis of methyl 3-{3-[6-(2-chloroethyloxycarbonylamino)-naphthalen-2-yl]-4-cyclopentylmethyloxyphenyl}propionate (Intermediate 45) (Preparation Method 10, Step o-1)

A solution of Compound of Example 011 (314 mg) in 1,2-dichloroethane (10 ml) was successively added with N-methylmorpholine (103 µl, WAKO) and 2-chloroethyl chloroformate (96 µl, TCI) and stirred for 13 hours. The reaction mixture was added with water (30 ml) and extracted with ethyl acetate (90 ml). The organic layer was washed successively with saturated aqueous sodium hydrogencarbonate, saturated aqueous ammonium chloride and saturated brine and dried, and then the solvent was evaporated under reduced pressure. The residue was purified by flash column chromatography (hexane:ethyl acetate=3:1) to obtain the title compound (Intermediate 45, 391 mg).

Synthesis of 3-{4-cyclopentylmethyloxy-3-[6-(2-hydroxyethylamino)naphthalen-2-yl]phenyl}propionic acid (Compound No. 075) (Preparation Method 1, Step a)

According to the procedure described in the synthesis method of Compound of Example 002 (Preparation Method 1, Step a) with the modifications that the reaction was carried out in ethanol at 80° C. for 4 hours, and the purification was performed by PTLC (chloroform:methanol=10:1), Intermediate 45 (147 mg) and 5 N aqueous sodium hydroxide (5.0 ml) were reacted and treated to obtain the title compound (Compound No. 075, 44 mg). Rf=0.32 (chloroform:methanol=10:1).

Example 76

Synthesis of methyl 3-[3-(6-acetylaminonaphthalen-2-yl)-4-cyclopentylmethyloxy-phenyl]propionate (Compound No. 076) (Preparation Method 10, Step o-1)

According to the procedure described in the synthesis method of Intermediate 45 in Example 75 (Preparation Method 10, Step o-1) with the modifications that the reaction was carried out at room temperature for 4 hours, and the purification was performed by PTLC (hexane:ethyl acetate=1:1), Compound of Example 011 (139 mg), N-methylmorpholine (45 µl) and acetyl chloride (29 µl, TCI) were reacted and treated to obtain the title compound (Compound No. 076, 119 mg).

Example 77

Synthesis of 3-[3-(6-acetylaminonaphthalen-2-yl)-4-cyclopentylmethyloxy-phenyl]propionic acid (Compound No. 077) (Preparation Method 1, Step a)

According to the procedure described in the synthesis method of Compound of Example 002 (Preparation Method 1, Step a) with the modification that the reaction was carried out at room temperature for 5 hours and at 60° C. for 1 hour, Compound of Example 076 (119 mg) and 2 N aqueous sodium hydroxide (530 µl) were reacted and treated to obtain the title compound (Compound No. 077, 105 mg). Rf=0.35 (chloroform:methanol=10:1).

Example 78

Synthesis of methyl 3-(3-{[6-(2-t-butyloxycarbonylamino) acetylamino]Naphthalen-2-yl}-4-cyclopentylmethyloxyphenyl)propionate (Intermediate 46) (Preparation Method 10, Step o-2)

A solution of Compound of Example 011 (150.2 mg) in DMF (4 ml) was successively added with diisopropylethylamine (259 µl, WAKO), N-Boc-glycine (133 mg, Ald) and O-(7-azabenzotriazol-1-yl)-N,N,N',N'-tetramethyluronium hexafluorophosphate (HATU, 285 mg, Ald) and stirred for 1.5 hours. The reaction mixture was added with water (30 ml), extracted with ethyl acetate (90 ml) and washed successively with saturated aqueous sodium hydrogencarbonate, saturated aqueous ammonium chloride and saturated brine. The organic layer was dried, and then the solvent was evaporated under reduced pressure. The residue was purified by PTLC (hexane:ethyl acetate=1:1) to obtain the title compound (Intermediate 46, 206 mg).

Synthesis of 3-(3-{6-[(2-aminoacetyl)amino]Naphthalen-2-yl}-4-cyclopentyl-methyloxyphenyl)propionic acid (Compound No. 078)

The Intermediate 46 (206.5 mg) was added with 10% hydrochloric acid solution in methanol (2 ml) and stirred at 60° C. for 1.5 hours. The reaction mixture was neutralized with 2 N aqueous sodium hydroxide under ice cooling and the extracted with ethyl acetate (90 ml). The organic layer was washed with saturated brine and dried, and then the solvent was evaporated under reduced pressure. The residue was purified by PTLC (chloroform:methanol=5:1) to obtain oily substance. According to the procedure described in the synthesis method of Compound of Example 002 (Preparation Method 1, Step a) with the modification that the reaction was carried out for 3 hours, the oily substance was reacted with 2 N aqueous sodium hydroxide (470 µl) and treated to obtain the title compound (Compound No. 078, 25 mg). Rf=0.11 (chloroform:methanol=2:1).

Example 79

Synthesis of methyl 3-(3-{6-[(acetyloxyacetyl)amino] Naphthalen-2-yl}-4-cyclopentyl-methyloxyphenyl) propionic (Intermediate 47) (Preparation Method 10, Step o-1)

According to the procedure described in the synthesis method of Intermediate 45 in Example 75 (Preparation Method 10, Step o-1) with the modifications that the reaction was carried out at room temperature for 4 hours, and the purification was performed by PTLC (hexane:ethyl acetate=1:1), Compound of Example 011 (151 mg), N-methylmorpholine (50 µl) and acetyloxyacetyl chloride (48.3 µl, TCI) were reacted and treated to obtain the title compound (Intermediate 47, 136 mg).

Synthesis of 3-(4-cyclopentylmethyloxy-3-{6-[2-(hydroxyacetyl)amino]naphthalen-2-yl}phenyl)propionic acid (Compound No. 079) (Preparation Method 1, Step a)

According to the procedure described in the synthesis method of Compound of Example 002 (Preparation Method 1, Step a) with the modification that the reaction was carried out at room temperature for 5 hours and at 60° C. for 1 hour, Intermediate 47 (135 mg) and 2 N aqueous sodium hydroxide (1120 µl) were reacted and treated to obtain the title compound (Compound No. 079, 102 mg). Rf=0.29 (chloroform:methanol=10:1).

Example 80

Synthesis of methyl 3-(4-cyclopentylmethyloxy-3-{6-[(furan-2-carbonyl)amino]naphthalen-2-yl}phenyl) propionate (Compound No. 080) (Preparation Method 10, Step o-1)

According to the procedure described in the synthesis method of Intermediate 45 in Example 75 (Preparation Method 10, Step o-1) with the modifications that the reaction was carried out at room temperature for 17 hours, and the purification was performed by PTLC (hexane:ethyl acetate=2:1), Compound of Example 011 (149 mg), N-methylmorpholine (50 µl) and 2-furoyl chloride (43.7 µl, TCI) were reacted and treated to obtain the title compound (Compound No. 080, 139 mg).

Example 81

Synthesis of 3-(4-cyclopentylmethyloxy-3-{6-[(furan-2-carbonyl)amino]naphthalen-2-yl}phenyl)propionic acid (Compound No. 081) (Preparation Method 1, Step a)

According to the procedure described in the synthesis method of Compound of Example 002 (Preparation Method 1, Step a) with the modification that the reaction was carried out for 2 hours, Compound of Example 080 (130 mg) and 2 N aqueous sodium hydroxide (520 µl) were reacted and treated to obtain the title compound (Compound No. 081, 106 mg). Rf=0.48 (chloroform:methanol=10:1).

Example 82

Synthesis of methyl 3-[3-(6-carbamoylaminonaphthalen-2-yl)-4-cyclopentyl-methyloxyphenyl]propionate (Compound No. 082) (Preparation Method 10, Step o-3)

A solution of Compound of Example 011 (119 mg) in a mixture of acetic acid (5 ml)/water (1 ml) was added with potassium cyanate (48 mg, WAKO) and stirred for 4 hours. The solvent was evaporated from the reaction mixture under reduced pressure, and the residue was added with water (30 ml) and isopropyl ether (90 ml) for extraction. The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=1:2) to obtain the title compound (Compound No. 082, 71 mg).

Example 83

Synthesis of 3-[3-(6-carbamoylaminonaphthalen-2-yl)-4-cyclopentyl-methyloxyphenyl]propionic acid (Compound No. 083) (Preparation Method 1, Step a)

According to the procedure described in the synthesis method of Compound of Example 002 (Preparation Method 1, Step a) with the modification that the reaction was carried out for 1.5 hours, Compound of Example 082 (69 mg) and 2 N aqueous sodium hydroxide (310 µl) were reacted and treated to obtain the title compound (Compound No. 083, 54 mg). Rf=0.16 (chloroform:methanol=10:1).

Example 84

Synthesis of methyl 3-[4-cyclopentylmethyloxy-3-(6-methanesulfonyl-aminonaphthalen-2-yl)phenyl]propionate (Compound No. 084) (Preparation Method 10, Step o-1)

A solution of Compound of Example 011 (149.1 mg) in 1,2-dichloroethane (5 ml) was successively added with pyridine (500 µl, WAKO) and methanesulfonyl chloride (62 µl, KANTO) under ice cooling, stirred for 1.5 hours, then warmed to room temperature and stirred for 12 hours. The reaction mixture was added with water (30 ml) and ethyl acetate (90 ml) for extraction. The organic layer was washed successively with saturated aqueous sodium hydrogencarbonate, saturated aqueous ammonium chloride and saturated brine and dried, and then the solvent was evaporated under reduced pressure. The residue was purified by PTLC (hexane:ethyl acetate=2:1) to obtain the title compound (Compound No. 084, 126 mg).

Example 85

Synthesis of 3-[4-cyclopentylmethyloxy-3-(6-methanesulfonylaminonaphthalen-2-yl)phenyl]propionic acid (Compound No. 085) (Preparation Method 1, Step a)

According to the procedure described in the synthesis method of Compound of Example 002 (Preparation Method 1, Step a) with the modification that the reaction was carried out at room temperature for 3 hours and at 60° C. for 1 hour, Compound of Example 84 (129 mg) and 2 N aqueous sodium hydroxide (535 μl) were reacted and treated to obtain the title compound (Compound No. 085, 98 mg). Rf=0.38 (chloroform:methanol=10:1).

Example 86

Synthesis of methyl 3-{4-cyclopentylmethyloxy-3-[6-(N,N-dimethylsulfamoylamino)-naphthalen-2-yl]phenyl}propionate (Compound No. 086) (Preparation Method 10, Step o-1)

A solution of Compound of Example 011 (163 mg) in pyridine (5 ml) was successively added with 4-dimethylaminopyridine (104 mg, TCI) and dimethylsulfamoyl chloride (520 μl, TCI), stirred for 5 days and then further stirred at 50° C. for 4 hours. The reaction mixture was added with water (30 ml) and ethyl acetate (90 ml) for extraction. The organic layer was washed with saturated brine and dried, and then the solvent was evaporated under reduced pressure. The residue was purified by column chromatography (Quad, hexane:ethyl acetate=6:1) to obtain the title compound (Compound No. 086, 125 mg).

Example 87

Synthesis of 3-{4-cyclopentylmethyloxy-3-[6-(N,N-dimethylsulfamoylamino)naphthalen-2-yl]phenyl}propionic acid (Compound No. 087) (Preparation Method 1, Step a)

According to the procedure described in the synthesis method of Compound of Example 002 (Preparation Method 1, Step a) with the modification that the reaction was carried out for 1.5 hours, Compound of Example 086 (118 mg) and 2 N aqueous sodium hydroxide (460 μl) were reacted and treated to obtain the title compound (Compound No. 087, 87 mg). Rf=0.42 (chloroform:methanol=10:1).

Example 88

Synthesis of methyl 3-(3-{7-[2-(acetyloxyacetyl)amino]naphthalen-2-yl}-4-cyclopentylmethyloxyphenyl)propionate (Intermediate 48) (Preparation Method 10, Step o-1)

According to the procedure described in the synthesis method of Intermediate 45 in Example 75 (Preparation Method 10, Step o-1) with the modifications that the reaction was carried out at room temperature for 17 hours, and the purification was performed by PTLC (hexane:ethyl acetate= 1:1), Compound of Example 014 (181 mg), N-methylmorpholine (59 u 1) and acetyloxyacetyl chloride (58 μl) were reacted and treated to obtain the title compound (Intermediate 48, 194 mg).
Synthesis of 3-{4-cyclopentylmethyloxy-3-(7-[2-(hydroxyacetyl)amino]naphthalen-2-yl}phenyl)propionic acid (Compound No. 088) (Preparation Method 1, Step a)

According to the procedure described in the synthesis method of Compound of Example 002 (Preparation Method 1, Step a) with the modification that the reaction was carried out for 20 hours, Intermediate 48 (194 mg) and 2 N aqueous sodium hydroxide (1.54 ml) were reacted and treated to obtain the title compound (Compound No. 088, 147 mg). Rf=0.27 (chloroform:methanol=10:1).

Example 89

Synthesis of methyl 3-{4-cyclopentylmethyloxy-3-(7-[(furan-2-carbonyl)amino]naphthalen-2-yl}phenyl)propionate (Compound No. 089) (Preparation Method 10, Step o-1)

According to the procedure described in the synthesis method of Intermediate 45 in Example 75 (Preparation Method 10, Step o-1) with the modifications that the reaction was carried out at room temperature for 19 hours, and the purification was performed by PTLC (hexane:ethyl acetate= 3:1), Compound of Example 014 (188 mg), N-methylmorpholine (62 μl) and 2-furoyl chloride (55 μl) were reacted and treated to obtain the title compound (Compound No. 089, 211 mg).

Example 90

Synthesis of 3-(4-cyclopentylmethyloxy-3-{7-[(furan-2-carbonyl)amino]naphthalen-2-yl}phenyl)propionic acid (Compound No. 090) (Preparation Method 1, Step a)

According to the procedure described in the synthesis method of Compound of Example 002 (Preparation Method 1, Step a) with the modification that the reaction was carried out for 2 hours, Compound of Example 089 (207 mg) and 2 N aqueous sodium hydroxide (830 u 1) were reacted and treated to obtain the title compound (Compound No. 090, 190 mg). Rf=0.51 (chloroform:methanol=10:1).

Example 91

Synthesis of methyl 3-[3-chloro-4-hydroxy-5-(Naphthalen-2-yl)phenyl]propionate (Intermediate 49)

A solution of Intermediate 36 (100 mg) in chloroform (3 ml) was added with sulfuryl chloride (29 μl) under ice cooling, warmed to room temperature and stirred for 20 hours. The reaction mixture was concentrated under reduced pressure, and the residue was purified by column chromatography (Quad, hexane:ethyl acetate=10:1) to obtain the title compound (Intermediate 49, 100 mg).
Synthesis of methyl 3-[3-chloro-4-cyclopentylmethyloxy-5-(naphthalen-2-yl)phenyl]propionate (Compound No. 091) (Preparation Method 5, Step e-2)

According to the procedure described in the synthesis method of Compound of Example 038 (Preparation Method 5, Step e-2) with the modifications that the reaction was carried out for 22 hours, and the purification was performed by flash column chromatography (hexane:isopropyl ether= 10:1), Intermediate 49 (90 mg), Ph$_3$P (210 mg), cyclopentane-methanol (86 μl) and 40% DIAD (375 μl) were reacted and treated to obtain the title compound (Compound No. 091, 110 mg).

Example 92

Synthesis of 3-[3-chloro-4-cyclopentylmethyloxy-5-(naphthalen-2-yl)phenyl]propionic acid (Compound No. 092) (Preparation Method 1, Step a)

According to the procedure described in the synthesis method of Compound of Example 002 (Preparation Method 1, Step a) with the modification that the reaction was carried out for 2 hours, Compound of Example 091 (100 mg) and 2 N aqueous sodium hydroxide (300 μl) were reacted and treated to obtain the title compound (Compound No. 092, 84 mg). Rf=0.32 (chloroform:methanol=50:1).

Example 93
Synthesis of methyl 3-[4-cyclopentylmethyloxy-3-(naphthalen-2-yl)-5-nitrophenyl]propionate (Compound No. 093) (Preparation Method 4, Step d-1)

According to the procedure described in the synthesis method of Compound of Example 001 (Preparation Method 4, Step d-1) with the modifications that the reaction was carried out at 80° C. for 16.5 hours, and the purification was performed by column chromatography (Quad, hexane:ethyl acetate=10:1), Intermediate 14 (530 mg), 2-naphthaleneboronic acid (473 mg), 2 M aqueous sodium carbonate (1.25 ml) and $(Ph_3P)_4Pd$ (158 mg) were reacted and treated to obtain the title compound (Compound No. 093, 560 mg).

Example 94
Synthesis of methyl 3-[3-amino-4-cyclopentylmethyloxy-5-(naphthalen-2-yl)phenyl]propionate (Compound No. 094) (Preparation Method 2, Step b)

A solution of Compound of Example 093 (78 mg) in methanol (3 ml) was added with diisopropylethylamine (61 µl) and tin(II) chloride dihydrate (162 mg, Ald) and stirred at room temperature for 17 hours. The reaction mixture was concentrated under reduced pressure and then added with water (50 ml) and ethyl acetate (150 ml) for extraction. The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane-:ethyl acetate=7:1) to obtain the title compound (Compound No. 094, 40 mg). Rf=0.26 (chloroform).

Example 95
Synthesis of 3-[3-amino-4-cyclopentylmethyloxy-5-(naphthalen-2-yl)phenyl]propionic acid (Compound No. 095) (Preparation Method 1, Step a)

According to the procedure described in the synthesis method of Compound of Example 002 (Preparation Method 1, Step a) with the modification that the reaction was carried out for 15.5 hours, Compound of Example 094 (38 mg) and 2 N aqueous sodium hydroxide (200 µl) were reacted and treated to obtain the title compound (Compound No. 095, 35 mg). Rf=0.42 (chloroform:methanol=10:1).

Example 96
Synthesis of 4-cyclohexylmethyloxy-3-(naphthalen-2-yl) phenylacetonitrile (Intermediate 50) (Preparation Method 7, Steps m and l)

A solution of Intermediate 37 (172 mg) in dry THF (5 ml) was successively added with trimethylsilylnitrile (133 µl, TCI) and zinc iodide (16 mg, WAKO) with ice cooling under argon atmosphere, stirred for 15 minutes, then warmed to room temperature and further stirred for 27 hours. The reaction mixture was added with ethyl acetate (90 ml) and washed successively with saturated aqueous sodium hydrogencarbonate, saturated aqueous ammonium chloride and saturated brine. The organic layer was dried, and then the solvent was evaporated under reduced pressure. A solution of the residue in anhydrous methylene chloride (5 ml) was added with triethylsilane (240 µl, TCI) and boron trifluoride/diethyl ether complex (366 µl, TCI) with ice cooling under argon atmosphere, warmed to room temperature and stirred for 3.5 hours. The reaction mixture was poured into ice water (50 ml) and extracted with ethyl acetate (90 ml). The organic layer was washed successively with saturated aqueous sodium hydrogencarbonate, saturated aqueous ammonium chloride, saturated brine and dried, and then the solvent was evaporated under reduced pressure. The residue was purified by column chromatography (Quad, hexane:ethyl acetate=10:1) to obtain the title compound (Intermediate 50, 116 mg).

Synthesis of 4-cyclohexylmethyloxy-3-(naphthalen-2-yl) phenylacetic acid (Compound No. 096) (Preparation Method 7, Step a)

According to the procedure described in the synthesis method of Compound of Example 002 (Preparation Method 1, Step a) with the modifications that the reaction was carried out for 24 hours with reflux by heating, and the purification was performed by column chromatography (Quad, hexane:ethyl acetate 2:1), Intermediate 50 (110 mg) and 5 N aqueous sodium hydroxide (900 µl) were reacted and treated to obtain the title compound (Compound No. 096, 62 mg). Rf=0.54 (chloroform:methanol=10:1).

Example 97
Synthesis of methyl 4-[4-cyclopentylmethyloxy-3-(naphthalen-2-yl)phenyl]butyrate (Compound No. 097) (Preparation Method 4, Step d-1)

According to the procedure described in the synthesis method of Compound of Example 001 (Preparation Method 4, Step d-1) with the modifications that the reaction was carried out for 18 hours, and the purification was performed by column chromatography (Quad, hexane:isopropyl ether= 8:1), Intermediate 13 (355 mg), 2-naphthaleneboronic acid (344 mg), 2 M aqueous sodium carbonate (2.1 ml) and $(Ph_3P)_4Pd$ (115 mg) were reacted and treated to obtain the title compound (Compound No. 097, 392 mg).

Example 98
Synthesis of 4-[4-cyclopentylmethyloxy-3-(naphthalen-2-yl)phenyl]butyric acid (Compound No. 098, Preparation Method 1, Step a)

According to the procedure described in the synthesis method of Compound of Example 002 (Preparation Method 1, Step a) with the modification that the reaction was carried out for 3.5 hours, Compound of Example 097 (380 mg) and 2 N aqueous sodium hydroxide (1.0 ml) were reacted and treated to obtain the title compound (Compound No. 098, 342 mg). Rf=0.33 (chloroform:methanol=50:1).

Example 99
Synthesis of methyl 3-[4-cyclopentylmethyloxy-3-(1H-indol-5-yl)phenyl]propionate (Compound No. 099) (Preparation Method 4, Step d-1)

According to the procedure described in the synthesis method of Compound of Example 001 (Preparation Method 4, Step d-1) with the modifications that the reaction was carried out at 80° C. for 5 hours, and the purification was performed by flash column chromatography (hexane:ethyl acetate=5:1), Intermediate 3 (367 mg), 5-indoleboronic acid (310 mg, Frontier), 2 M aqueous sodium carbonate (0.9 ml) and $(Ph_3P)_4Pd$ (132 mg) were reacted and treated to obtain the title compound (Compound No. 099, 340 mg). Rf=0.42 (chloroform).

Example 100
Synthesis of 3-[4-cyclopentylmethyloxy-3-(1H-indol-5-yl) phenyl]propionic acid (Compound No. 100) (Preparation Method 1, Step a)

According to the procedure described in the synthesis method of Compound of Example 002 (Preparation Method 1, Step a) with the modification that the reaction was carried out for 2 hours, Compound of Example 099 (330 mg) and 2 N aqueous sodium hydroxide (1.40 ml) were reacted and treated to obtain the title compound (Compound No. 100, 310 mg). Rf=0.48 (chloroform:methanol=10:1).

Example 101

Synthesis of methyl 3-[4-cyclopentyloxy-3-(1H-indol-5-yl)phenyl]propionate (Compound No. 101) (Preparation Method 4, Step d-1)

According to the procedure described in the synthesis method of Compound of Example 001 (Preparation Method 4, Step d-1) with the modifications that the reaction was carried out for 3 hours, and the purification was performed by flash column chromatography (hexane:ethyl acetate= 4:1), Intermediate 8 (833 mg), 5-indoleboronic acid (657 mg), 2 M aqueous sodium carbonate (2.4 ml) and $(Ph_3P)_4Pd$ (233 mg) were reacted and treated to obtain the title compound (Compound No. 101, 900 mg).

Example 102

Synthesis of 3-[4-cyclopentyloxy-3-(1H-indol-5-yl)phenyl]propionic acid (Compound No. 102) (Preparation Method 1, Step a)

According to the procedure described in the synthesis method of Compound of Example 002 (Preparation Method 1, Step a) with the modification that the reaction was carried out for 2 hours, Compound of Example 101 (144 mg) and 2 N aqueous sodium hydroxide (420 u 1) were reacted and treated to obtain the title compound (Compound No. 102, 127 mg). Rf=0.46 (chloroform:methanol=10:1).

Example 103

Synthesis of methyl 3-[4-cyclohexyloxy-3-(1H-indol-5-yl)phenyl]propionate (Compound No. 103) (Preparation Method 4, Step d-1)

According to the procedure described in the synthesis method of Compound of Example 001 (Preparation Method 4, Step d-1) with the modifications that the reaction was carried out for 24 hours, and the purification was performed by column chromatography (Quad, hexane:ethyl acetate= 6:1), Intermediate 9 (340 mg), 5-indoleboronic acid (322 mg), 2 M aqueous sodium carbonate (1.0 ml) and $(Ph_3P)_4Pd$ (116 mg) were reacted and treated to obtain the title compound (Compound No. 103, 366 mg).

Example 104

Synthesis of 3-[4-cyclohexyloxy-3-(1H-indol-5-yl)phenyl]propionic acid (Compound No. 104) (Preparation Method 1, Step a)

According to the procedure described in the synthesis method of Compound of Example 002 (Preparation Method 1, Step a) with the modification that the reaction was carried out for 2 hours, Compound of Example 103 (325 mg) and 2 N aqueous sodium hydroxide (1.0 ml) were reacted and treated to obtain the title compound (Compound No. 104, 300 mg). Rf=0.48 (chloroform:methanol=10:1).

Example 105

Synthesis of methyl 3-{4-[2-(2-fluorophenyl)ethyloxy]-3-(1H-indol-5-yl)phenyl}propionate (Compound No. 105) (Preparation Method 4, Step d-1)

According to the procedure described in the synthesis method of Compound of Example 001 (Preparation Method 4, Step d-1) with the modifications that the reaction was carried out for 22 hours, and the purification was performed by flash column chromatography (hexane:ethyl acetate= 5:1), Intermediate 10 (373 mg), 5-indoleboronic acid (483 mg), 2 M aqueous sodium carbonate (0.9 ml) and $(Ph_3P)_4Pd$ (141 mg) were reacted and treated to obtain the title compound (Compound No. 105, 380 mg).

Example 106

Synthesis of 3-{4-[2-(2-fluorophenyl)ethyloxy]-3-(1H-indol-5-yl)phenyl}propionic acid (Compound No. 106) (Preparation Method 1, Step a)

According to the procedure described in the synthesis method of Compound of Example 002 (Preparation Method 1, Step a) with the modification that the reaction was carried out for 3.5 hours, Compound of Example 105 (371 mg) and 2 N aqueous sodium hydroxide (1.80 ml) were reacted and treated to obtain the title compound (Compound No. 106, 312 mg). Rf=0.47 (chloroform:methanol=10:1).

Example 107

Synthesis of methyl 3-[4-cyclopentyloxy-3-(1-methyl-1H-indol-5-yl)phenyl]propionate (Compound No. 107) (Preparation Method 4, Step d-1)

According to the procedure described in the synthesis method of Compound of Example 001 (Preparation Method 4, Step d-1) with the modifications that the reaction was carried out for 21 hours, and the purification was performed by column chromatography (Quad, hexane:ethyl acetate= 9:1), Intermediate 8 (200 mg), N-methyl-5-indoleboronic acid (188 mg, Frontier), 2 M aqueous sodium carbonate (555 µl) and $(Ph_3P)_4Pd$ (60 mg) were reacted and treated to obtain the title compound (Compound No. 107, 157 mg).

Example 108

Synthesis of 3-[4-cyclopentyloxy-3-(1-methyl-1H-indol-5-yl)phenyl]propionic acid (Compound No. 108) (Preparation Method 1, Step a)

According to the procedure described in the synthesis method of Compound of Example 002 (Preparation Method 1, Step a) with the modification that the reaction was carried out for 20 hours, Compound of Example 107 (150 mg) and 2 N aqueous sodium hydroxide (0.50 ml) were reacted and treated to obtain the title compound (Compound No. 108, 130 mg). Rf=0.54 (chloroform:methanol=10:1).

Example 109

Synthesis of methyl 3-[4-cyclohexyloxy-3-(1-methyl-1H-indol-5-yl)phenyl]propionate (Compound No. 109) (Preparation Method 4, Step d-1)

According to the procedure described in the synthesis method of Compound of Example 001 (Preparation Method 4, Step d-1) with the modifications that the reaction was carried out for 21 hours, and the purification was performed by column chromatography (Quad, hexane:ethyl acetate= 9:1), Intermediate 9 (209 mg), N-methyl-5-indoleboronic acid (188 mg), 2 M aqueous sodium carbonate (555 µl) and $(Ph_3P)_4Pd$ (60 mg) were reacted and treated to obtain the title compound (Compound No. 109, 164 mg).

Example 110

Synthesis of 3-[4-cyclohexyloxy-3-(1-methyl-1H-indol-5-yl)phenyl]propionic acid (Compound No. 110) (Preparation Method 1, Step a)

According to the procedure described in the synthesis method of Compound of Example 002 (Preparation Method 1, Step a) with the modification that the reaction was carried out for 21 hours, Compound of Example 109 (160 mg) and 2 N aqueous sodium hydroxide (0.70 ml) were reacted and treated to obtain the title compound (Compound No. 110, 141 mg). Rf=0.56 (chloroform:methanol=10:1).

Example 111
Synthesis of methyl 3-[4-cyclopentylmethyloxy-3-(3-methyl-1H-indol-5-yl)phenyl]propionate (Compound No. 111) (Preparation Method 4, Step d-1)

According to the procedure described in the synthesis method of Compound of Example 011 (Preparation Method 4, Step d-1) with the modifications that the reaction was carried out for 13 hours, and the purification was performed by flash column chromatography (hexane:ethyl acetate=4:1), crude 3-methyl-5-indoleboronic acid was prepared from 5-bromo-3-methylindole (1.63 g) obtained from 5-bromoindole (TCI) by a method known from a reference [E. N. Wayland et al., Journal of Organic Chemistry (J. Org. Chem.), vol. 32, p.828, 1967], 30% potassium hydride (1.08 g), 1.7 M solution of n-butyllithium in pentane (9.7 ml) and ($^{i}$PrO)$_3$B (3.75 ml), and then this compound was reacted with Intermediate 3 (803 mg), 2 M aqueous sodium carbonate (2 ml) and (Ph$_3$P)$_4$Pd (241 mg) to obtain the title compound (Compound No. 111, 552 mg).

Example 112
Synthesis of 3-[4-cyclopentylmethyloxy-3-(3-methyl-1H-indol-5-yl)phenyl]propionic acid (Compound No. 112) (Preparation Method 1, Step a)

According to the procedure described in the synthesis method of Compound of Example 002 (Preparation Method 1, Step a) with the modification that the reaction was carried out for 2 hours, Compound of Example 111 (130 mg) and 2 N aqueous sodium hydroxide (370 μl) were reacted and treated to obtain the title compound (Compound No. 112, 127 mg). Rf=0.50 (chloroform:methanol=10:1).

Example 113
Synthesis of methyl 3-[4-cyclopentylmethyloxy-3-(1H-indol-4-yl)phenyl]propionate (Compound No. 113) (Preparation Method 4, Step d-1)

According to the procedure described in the synthesis method of Compound of Example 001 (Preparation Method 4, Step d-1) with the modifications that the reaction was carried out for 21 hours, and the purification was performed by column chromatography (Quad, hexane:ethyl acetate=6:1), Intermediate 3 (200 mg), 4-indoleboronic acid (170 mg) obtained from 4-bromoindole (TCI) by a method known from a reference [M. Doll et al., Journal of Organic Chemistry (J. Org. Chem.), vol. 64, p.1372, 1999], 2 M aqueous sodium carbonate (550 μl) and (Ph$_3$P)$_4$Pd (60 mg) were reacted and treated to obtain the title compound (Compound No. 113, 214 mg).

Example 114
Synthesis of 3-[4-cyclopentylmethyloxy-3-(1H-indol-4-yl)phenyl]propionic acid (Compound No. 114) (Preparation Method 1, Step a)

According to the procedure described in the synthesis method of Compound of Example 002 (Preparation Method 1, Step a) with the modification that the reaction was carried out for 1 hour, Compound of Example 113 (210 mg) and 2 N aqueous sodium hydroxide (0.60 ml) were reacted and treated to obtain the title compound (Compound No. 114, 173 mg). Rf=0.44 (chloroform:methanol=10:1).

Example 115
Synthesis of methyl 3-[4-cyclohexylmethyloxy-3-(1H-indol-4-yl)phenyl]propionate (Compound No. 115) (Preparation Method 4, Step d-1)

According to the procedure described in the synthesis method of Compound of Example 001 (Preparation Method 4, Step d-1) with the modifications that the reaction was carried out for 17 hours, and the purification was performed by flash column chromatography (hexane:ethyl acetate=4:1), Intermediate 7 (385 mg), 4-indoleboronic acid (315 mg), 2 M aqueous sodium carbonate (0.90 ml) and (Ph$_3$P)$_4$Pd (119 mg) were reacted and treated to obtain the title compound (Compound No. 115, 191 mg).

Example 116
Synthesis of 3-[4-cyclohexylmethyloxy-3-(1H-indol-4-yl)phenyl]propionic acid (Compound No. 116) (Preparation Method 1, Step a)

According to the procedure described in the synthesis method of Compound of Example 002 (Preparation Method 1, Step a) with the modification that the reaction was carried out for 3 hours, Compound of Example 115 (189 mg) and 2 N aqueous sodium hydroxide (0.50 ml) were reacted and treated to obtain the title compound (Compound No. 116, 155 mg). Rf=0.41 (chloroform:methanol=10:1).

Example 117
Synthesis of methyl 3-[4-cyclopentyloxy-3-(1H-indol-4-yl)phenyl]propionate (Compound No. 117) (Preparation Method 4, Step d-1)

According to the procedure described in the synthesis method of Compound of Example 001 (Preparation Method 4, Step d-1) with the modifications that the reaction was carried out for 17 hours, and the purification was performed by column chromatography (Quad, hexane:ethyl acetate=6:1), Intermediate 8 (200 mg), 4-indoleboronic acid (177 mg), 2 M aqueous sodium carbonate (555 μl) and (Ph$_3$P)$_4$Pd (60 mg) were reacted and treated to obtain the title compound (Compound No. 117, 189 mg).

Example 118
Synthesis of 3-[4-cyclopentyloxy-3-(1H-indol-4-yl)phenyl]propionic acid (Compound No. 118) (Preparation Method 1, Step a)

According to the procedure described in the synthesis method of Compound of Example 002 (Preparation Method 1, Step a) with the modification that the reaction was carried out for 1.5 hours, Compound of Example 117 (180 mg) and 2 N aqueous sodium hydroxide (0.55 ml) were reacted and treated to obtain the title compound (Compound No. 118, 172 mg). Rf=0.73 (ethyl acetate:hexane=3:2).

Example 119
Synthesis of methyl 3-[4-cyclohexyloxy-3-(1H-indol-4-yl)phenyl]propionate (Compound No. 119) (Preparation Method 4, Step d-1)

According to the procedure described in the synthesis method of Compound of Example 001 (Preparation Method 4, Step d-1) with the modifications that the reaction was carried out for 18 hours, and the purification was performed by column chromatography (Quad, hexane:ethyl acetate=6:1), Intermediate 9 (209 mg), 4-indoleboronic acid (177 mg), 2 M aqueous sodium carbonate (555 μl) and (Ph$_3$P)$_4$Pd (60 mg) were reacted and treated to obtain the title compound (Compound No. 119, 205 mg).

Example 120
Synthesis of 3-[4-cyclohexyloxy-3-(1H-indol-4-yl)phenyl]propionic acid (Compound No. 120) (Preparation Method 1, Step a)

According to the procedure described in the synthesis method of Compound of Example 002 (Preparation Method 1, Step a) with the modification that the reaction was carried out for 1.5 hours, Compound of Example 119 (195 mg) and 2 N aqueous sodium hydroxide (0.60 ml) were reacted and

Example 121
Synthesis of 4-bromo-1-methyl-1H-indole (Intermediate 51)

A solution of 4-bromoindole (5 g, TCI) in DMF (30 ml) was added with 60% sodium hydride (1.14 g) under ice cooling and stirred for 10 minutes. The mixture was added dropwise with methyl iodide (3.18 ml, TCI), stirred for 10 minutes, then warmed to room temperature and further stirred for 30 minutes. The reaction mixture was poured into ice water and added with ethyl acetate (300 ml) for extraction. The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=10:1) to obtain the title compound (Intermediate 51, 4.95 g).

Synthesis of 1-methyl-1H-indole-4-boronic acid (Intermediate 52)

A solution of Intermediate 51 (4.90 g) in anhydrous THF (30 ml) was cooled to −78° C. under argon atmosphere, then added dropwise with 1.62 M solution of n-butyllithium in pentane (28.8 ml) over 30 minutes and stirred for 30 minutes. The mixture was added dropwise with ($^i$PrO)$_3$B (10.77 ml) over 10 minutes, stirred for 1 hour, then warmed to room temperature and further stirred for 2.5 hours. The reaction mixture was poured into 1.2 N aqueous phosphoric acid (250 ml) added with ice, and extracted with diethyl ether (200 ml×3). The organic layer was extracted with 0.4 N aqueous sodium hydroxide (150 ml×3), and the aqueous layer was acidified with 5 N aqueous hydrochloric acid under ice cooling and extracted with diethyl ether (200 ml×3) again. The organic layer was washed with saturated brine and dried, and then the solvent was evaporated under reduced pressure. The residue was washed with hexane to obtain the title compound (Intermediate 52, 3.17 g).

Synthesis of methyl 3-[4-cyclopentylmethyloxy-3-(1-methyl-1H-indol-4-yl)phenyl]propionate (Compound No. 121) (Preparation Method 4, Step d-1)

According to the procedure described in the synthesis method of Compound of Example 001 (Preparation Method 4, Step d-1) with the modifications that the reaction was carried out for 18 hours, and the purification was performed by column chromatography (Quad, hexane:ethyl acetate= 9:1), Intermediate 3 (200 mg), Intermediate 52 (185 mg), 2 M aqueous sodium carbonate (550 µl) and (Ph$_3$P)$_4$Pd (60 mg) were reacted and treated to obtain the title compound (Compound No. 121, 208 mg).

Example 122
Synthesis of 3-[4-cyclopentylmethyloxy-3-(1-methyl-1H-indol-4-yl)phenyl]propionic acid (Compound No. 122) (Preparation Method 1, Step a)

According to the procedure described in the synthesis method of Compound of Example 002 (Preparation Method 1, Step a) with the modification that the reaction was carried out for 3 hours, Compound of Example 121 (200 mg) and 2 N aqueous sodium hydroxide (0.60 ml) were reacted and treated to obtain the title compound (Compound No. 122, 182 mg). Rf=0.66 (ethyl acetate:hexane=1:1).

Example 123
Synthesis of methyl 3-[4-cyclopentyloxy-3-(1-methyl-1H-indol-4-yl)phenyl]propionate (Compound No. 123) (Preparation Method 4, Step d-1)

According to the procedure described in the synthesis method of Compound of Example 001 (Preparation Method 4, Step d-1) with the modifications that the reaction was carried out for 18 hours, and the purification was performed by column chromatography (Quad, hexane:ethyl acetate= 9:1), Intermediate 8 (200 mg), Intermediate 52 (188 mg), 2 M aqueous sodium carbonate (550 µl) and (Ph$_3$P)$_4$Pd (60 mg) were reacted and treated to obtain the title compound (Compound No. 123, 207 mg).

Example 124
Synthesis of 3-[4-cyclopentyloxy-3-(1-methyl-1H-indol-4-yl)phenyl]propionic acid (Compound No. 124) (Preparation Method 1, Step a)

According to the procedure described in the synthesis method of Compound of Example 002 (Preparation Method 1, Step a) with the modification that the reaction was carried out for 1 hour, Compound of Example 123 (200 mg) and 2 N aqueous sodium hydroxide (0.60 ml) were reacted and treated to obtain the title compound (Compound No. 124, 181 mg). Rf=0.72 (ethyl acetate:hexane=1:1).

Example 125
Synthesis of methyl 3-[4-cyclohexyloxy-3-(1-methyl-1H-indol-4-yl)phenyl]propionate (Compound No. 125) (Preparation Method 4, Step d-1)

According to the procedure described in the synthesis method of Compound of Example 001 (Preparation Method 4, Step d-1) with the modifications that the reaction was carried out for 18 hours, and the purification was performed by column chromatography (Quad, hexane:ethyl acetate= 9:1), Intermediate 9 (209 mg), Intermediate 52 (188 mg), 2 M aqueous sodium carbonate (550 µl) and (Ph$_3$P)$_4$Pd (60 mg) were reacted and treated to obtain the title compound (Compound No. 125, 216 mg).

Example 126
Synthesis of 3-[4-cyclohexyloxy-3-(1-methyl-1H-indol-4-yl)phenyl]propionic acid (Compound No. 126) (Preparation Method 1, Step a)

According to the procedure described in the synthesis method of Compound of Example 002 (Preparation Method 1, Step a) with the modification that the reaction was carried out for 1 hour, Compound of Example 125 (210 mg) and 2 N aqueous sodium hydroxide (0.60 ml) were reacted and treated to obtain the title compound (Compound No. 126, 182 mg). Rf=0.73 (ethyl acetate:hexane=1:1).

Example 127
Synthesis of methyl 3-[4-cyclohexylmethyloxy-3-(1H-indol-6-yl)phenyl]propionate (Compound No. 127) (Preparation Method 4, Step d-1)

According to the procedure described in the synthesis method of Compound of Example 011 (Preparation Method 4, Step d-1) with the modifications that the reaction was carried out for 17 hours, and the purification was performed by flash column chromatography (hexane:ethyl acetate= 4:1), crude 6-indoleboronic acid prepared from 6-bromoindole (981 mg, TCI), 30% potassium hydride (703 mg), 1.7 M solution of n-butyllithium in pentane (6.25 ml) and ($^i$PrO)$_3$B (2.50 ml), Intermediate 7 (391 mg), 2 M aqueous sodium carbonate (0.90 ml) and (Ph$_3$P)$_4$Pd (113 mg) were reacted and treated to obtain the title compound (Compound No. 127, 340 mg).

Example 128
Synthesis of 3-[4-cyclohexylmethyloxy-3-(1H-indol-6-yl)phenyl]propionic acid (Compound No. 128) (Preparation Method 1, Step a)

According to the procedure described in the synthesis method of Compound of Example 002 (Preparation Method (treated to obtain the title compound (Compound No. 120, 185 mg). Rf=0.76 (ethyl acetate:hexane=3:2).)

1, Step a) with the modification that the reaction was carried out for 0.5 hour, Compound of Example 127 (170 mg) and 2 N aqueous sodium hydroxide (0.45 ml) were reacted and treated to obtain the title compound (Compound No. 128, 139 mg). Rf=0.48 (chloroform:methanol=10:1).

Example 129
Synthesis of methyl 3-(3-bromo-4-t-butyldimethylsilyloxyphenyl)propionate (Intermediate 53) (Preparation Method 5, Step i)

A solution of Intermediate 6 (5.18 g) in anhydrous DMF (50 ml) was added with imidazole (2.04 g, TCI), added dropwise with a solution of t-butyldimethylsilyl chloride (4.52 g, TCI) in DMF (50 ml) under ice cooling, stirred for 30 minutes, then warmed to room temperature and further stirred for 16.5 hours. The reaction mixture was added with water (100 ml) and extracted with ethyl acetate (100 ml). The organic layer was washed successively with water and saturated brine and dried, and then the solvent was evaporated under reduced pressure. The residue was purified by flash column chromatography (hexane:ethyl acetate=9:1) to obtain the title compound (Intermediate 53, 8.42 g).

Synthesis of methyl 3-[4-(t-butyldimethylsilyloxy-3-(1H-indol-5-yl)phenyl)propionate (Intermediate 54) (Preparation Method 5, Step d)

According to the procedure described in the synthesis method of Compound of Example 001 (Preparation Method 4, Step d-1) with the modifications that the reaction was carried out for 12.5 hours, and the purification was performed by flash column chromatography (hexane:ethyl acetate=9:1), 5-indoleboronic acid (4.83 g), Intermediate 53 (7.46 g), 2 M aqueous sodium carbonate (18 ml) and $(Ph_3P)_4Pd$ (1.62 g) were reacted and treated to obtain the title compound (Intermediate 54, 5.04 g).

Synthesis of methyl 3-[4-hydroxy-3-(1H-indol-5-yl)phenyl] propionic acid (Intermediate 55) (Preparation Method 5, Step h)

A solution of Intermediate 54 (5.04 g) in THF (100 ml) was added with acetic acid (2.8 ml, WAKO), 1 M solution of tetrabutylammonium fluoride in THF (49 ml, TCI) and stirred for 2 hours. The reaction mixture was added with saturated aqueous sodium hydrogencarbonate (150 ml) and extracted with ethyl acetate (150 ml). The organic layer was washed with saturated brine and dried, and the solvent was evaporated under reduced pressure. The residue was purified by flash column chromatography (hexane:ethyl acetate=3:1) to obtain the title compound (Intermediate 55, 3.13 g).

Synthesis of methyl 3-[4-butyloxy-3-(1H-indol-5-yl) phenyl]propionate (Compound No. 129) (Preparation Method 5, Step e-1)

According to the procedure described in the synthesis method of Compound of Example 030 (Preparation Method 5, Step e-1) with the modifications that the reaction was carried out for 23 hours, and the purification was performed by flash column chromatography (hexane:isopropyl ether= 5:1), Intermediate 55 (100 mg), potassium carbonate (70 mg) and 1-iodobutane (192 μl) were reacted and treated to obtain the title compound (Compound No. 129, 110 mg).

Example 130
Synthesis of 3-[4-butyloxy-3-(1H-indol-5-yl)phenyl] propionic acid (Compound No. 130) (Preparation Method 1, Step a)

According to the procedure described in the synthesis method of Compound of Example 002 (Preparation Method 1, Step a) with the modification that the reaction was carried out for 2 hours, Compound of Example 129 (100 mg) and 2 N aqueous sodium hydroxide (500 μl) were reacted and treated to obtain the title compound (Compound No. 130, 94 mg). Rf=0.48 (chloroform:methanol=10:1).

Example 131
Synthesis of methyl 3-[3-(1H-indol-5-yl)-4-(1-phenylethyloxy)phenyl]propionate (Compound No. 131) (Preparation Method 5, Step e-1)

According to the procedure described in the synthesis method of Compound of Example 030 (Preparation Method 5, Step e-1) with the modifications that the reaction was carried out for 13 hours, and the purification was performed by column chromatography (Quad, hexane:ethyl acetate= 8:1), Intermediate 55 (113 mg), potassium carbonate (82 mg) and (1-bromoethyl)benzene (60 μl, TCI) were reacted and treated to obtain the title compound (Compound No. 131, 108 mg).

Example 132
Synthesis of 3-[3-(1H-indol-5-yl)-4-(1-phenylethyloxy) phenyl]propionic acid (Compound No. 132) (Preparation Method 1, Step a)

According to the procedure described in the synthesis method of Compound of Example 002 (Preparation Method 1, Step a) with the modification that the reaction was carried out for 1.5 hours, Compound of Example 131 (106 mg) and 2 N aqueous sodium hydroxide (400 μl) were reacted and treated to obtain the title compound (Compound No. 132, 101 mg). Rf=0.43 (chloroform:methanol=10:1).

Example 133
Synthesis of methyl 3-[3-(1H-indol-5-yl)-4-(2-methylphenylmethyloxy)-phenyl]propionate (Compound No. 133) (Preparation Method 5, Step e-1)

According to the procedure described in the synthesis method of Compound of Example 030 (Preparation Method 5, Step e-1) with the modifications that the reaction was carried out for 15 hours, and the purification was performed by column chromatography (Quad, hexane:ethyl acetate= 5:1), Intermediate 55 (82 mg), potassium carbonate (116 mg) and 2-methylbenzyl bromide (55 μl, TCI) were reacted and treated to obtain the title compound (Compound No. 133, 97 mg).

Example 134
Synthesis of 3-[3-(1H-indol-5-yl)-4-(2-methylphenylmethyloxy)phenyl]propionic acid (Compound No. 134) (Preparation Method 1, Step a)

According to the procedure described in the synthesis method of Compound of Example 002 (Preparation Method 1, Step a) with the modification that the reaction was carried out for 2 hours, Compound of Example 133 (88 mg) and 2 N aqueous sodium hydroxide (450 μl) were reacted and treated to obtain the title compound (Compound No. 134, 65 mg). Rf=0.46 (chloroform:methanol=10:1).

Example 135
Synthesis of methyl 3-[3-(1H-indol-5-yl)-4-(3-methylphenylmethyloxy)-phenyl]propionate (Compound No. 135) (Preparation Method 5, Step e-1)

According to the procedure described in the synthesis method of Compound of Example 030 (Preparation Method 5, Step e-1) with the modifications that the reaction was carried out for 15 hours, and the purification was performed by column chromatography (Quad, hexane:ethyl acetate= 5:1), Intermediate 55 (81 mg), potassium carbonate (115 mg) and 3-methylbenzyl bromide (56 μl, TCI) were reacted and treated to obtain the title compound (Compound No. 135, 100 mg).

Example 136

Synthesis of 3-[3-(1H-indol-5-yl)-4-(3-methylphenylmethyloxy)phenyl]propionic acid (Compound No. 136) (Preparation Method 1, Step a)

According to the procedure described in the synthesis method of Compound of Example 002 (Preparation Method 1, Step a) with the modification that the reaction was carried out for 2 hours, Compound of Example 135 (99 mg) and 2 N aqueous sodium hydroxide (500 µl) were reacted and treated to obtain the title compound (Compound No. 136, 71 mg). Rf=0.47 (chloroform:methanol=10:1).

Example 137

Synthesis of methyl 3-[3-(1H-indol-5-yl)-4-(4-methylphenylmethyloxy)phenyl]propionate (Compound No. 137) (Preparation Method 5, Step e-1)

According to the procedure described in the synthesis method of Compound of Example 030 (Preparation Method 5, Step e-1) with the modifications that the reaction was carried out for 15 hours, and the purification was performed by column chromatography (Quad, hexane:ethyl acetate=5:1), Intermediate 55 (80 mg), potassium carbonate (114 mg) and 4-methylbenzyl bromide (54 µl, TCI) were reacted and treated to obtain the title compound (Compound No. 137, 104 mg).

Example 138

Synthesis of 3-[3-(1H-indol-5-yl)-4-(4-methylphenylmethyloxy)phenyl]propionic acid (Compound No. 138) (Preparation Method 1, Step a)

According to the procedure described in the synthesis method of Compound of Example 002 (Preparation Method 1, Step a) with the modification that the reaction was carried out for 3 hours, Compound of Example 137 (99 mg) and 2 N aqueous sodium hydroxide (500 µl) were reacted and treated to obtain the title compound (Compound No. 138, 84 mg). Rf=0.49 (chloroform:methanol=10:1).

Example 139

Synthesis of methyl 3-{4-[(biphenyl-2-yl)methyloxy]-3-(1H-indol-5-yl)phenyl}-propionate (Compound No. 139) (Preparation Method 5, Step e-1)

According to the procedure described in the synthesis method of Compound of Example 030 (Preparation Method 5, Step e-1) with the modifications that the reaction was carried out for 4.5 hours, and the purification was performed by column chromatography (Quad, hexane:ethyl acetate=6:1), Intermediate 55 (80 mg), potassium carbonate (113 mg) and 2-phenylbenzyl bromide (74 µl, Ald) were reacted and treated to obtain the title compound (Compound No. 139, 112 mg).

Example 140

Synthesis of 3-{4-[(biphenyl-2-yl)methyloxy]-3-(1H-indol-5-yl)phenyl}propionic acid (Compound No. 140) (Preparation Method 1, Step a)

According to the procedure described in the synthesis method of Compound of Example 002 (Preparation Method 1, Step a) with the modification that the reaction was carried out for 2.5 hours, Compound of Example 139 (110 mg) and 2 N aqueous sodium hydroxide (480 µl) were reacted and treated to obtain the title compound (Compound No. 140, 42 mg). Rf=0.42 (chloroform:methanol=10:1).

Example 141

Synthesis of methyl 3-[4-(2-fluorophenylmethyloxy)-3-(1H-indol-5-yl)phenyl]-propionate (Compound No. 141) (Preparation Method 5, Step e-1)

According to the procedure described in the synthesis method of Compound of Example 030 (Preparation Method 5, Step e-1) with the modifications that the reaction was carried out for 17 hours, and the purification was performed by column chromatography (Quad, hexane:ethyl acetate=9:1), Intermediate 55 (100 mg), potassium carbonate (75 mg) and 2-fluorobenzyl chloride (70 µl, TCI) were reacted and treated to obtain the title compound (Compound No. 141, 97 mg).

Example 142

Synthesis of 3-[4-(2-fluorophenylmethyloxy)-3-(1H-indol-5-yl)phenyl]propionic acid (Compound No. 142) (Preparation Method 1, Step a)

According to the procedure described in the synthesis method of Compound of Example 002 (Preparation Method 1, Step a) with the modification that the reaction was carried out for 2 hours, Compound of Example 141 (88 mg) and 2 N aqueous sodium hydroxide (230 µl) were reacted and treated to obtain the title compound (Compound No. 142, 80 mg). Rf=0.47 (chloroform:methanol=10:1).

Example 143

Synthesis of methyl 3-[4-(3-fluorophenylmethyloxy)-3-(1H-indol-5-yl)-phenyl]propionate (Compound No. 143) (Preparation Method 5, Step e-1)

According to the procedure described in the synthesis method of Compound of Example 030 (Preparation Method 5, Step e-1) with the modifications that the reaction was carried out for 14.5 hours, and the purification was performed by column chromatography (Quad, hexane:ethyl acetate=10:1), Intermediate 55 (104 mg), potassium carbonate (105 mg) and 3-fluorobenzyl chloride (80 µl, TCI) were reacted and treated to obtain the title compound (Compound No. 143, 119 mg).

Example 144

Synthesis of 3-[4-(3-fluorophenylmethyloxy)-3-(1H-indol-5-yl)phenyl]propionic acid (Compound No. 144) (Preparation Method 1, Step a)

According to the procedure described in the synthesis method of Compound of Example 002 (Preparation Method 1, Step a) with the modification that the reaction was carried out for 3 hours, Compound of Example 143 (117 mg) and 2 N aqueous sodium hydroxide (380 µl) were reacted and treated to obtain the title compound (Compound No. 144, 112 mg). Rf=0.47 (chloroform:methanol=10:1).

Example 145

Synthesis of methyl 3 [4-(4-fluorophenylmethyloxy)-3-(1H-indol-5-yl)phenyl]-propionate (Compound No. 145) (Preparation Method 5, Step e-1)

According to the procedure described in the synthesis method of Compound of Example 030 (Preparation Method 5, Step e-1) with the modifications that the reaction was carried out for 14.5 hours, and the purification was performed by column chromatography (Quad, hexane:ethyl acetate=10:1), Intermediate 55 (105 mg), potassium carbonate (90 mg) and 4-fluorobenzyl bromide (76 µl, TCI) were reacted and treated to obtain the title compound (Compound No. 145, 90 mg).

Example 146

Synthesis of 3-[4-(4-fluorophenylmethyloxy)-3-(1H-indol-5-yl)phenyl]propionic acid (Compound No. 146) (Preparation Method 1, Step a)

According to the procedure described in the synthesis method of Compound of Example 002 (Preparation Method 1, Step a) with the modification that the reaction was carried out for 2 hours, Compound of Example 145 (89 mg) and 2 N aqueous sodium hydroxide (380 μl) were reacted and treated to obtain the title compound (Compound No. 146, 87 mg). Rf=0.47 (chloroform:methanol=10:1).

Example 147

Synthesis of methyl 3-[4-(2-chlorophenylmethyloxy)-3-(1H-indol-5-yl)phenyl]-propionate (Compound No. 147) (Preparation Method 5, Step e-1)

According to the procedure described in the synthesis method of Compound of Example 030 (Preparation Method 5, Step e-1) with the modifications that the reaction was carried out for 9 hours, and the purification was performed by column chromatography (Quad, hexane:ethyl acetate= 6:1), Intermediate 55 (99 mg), potassium carbonate (74 mg) and 2-chlorobenzyl chloride (60 μl, TCI) were reacted and treated to obtain the title compound (Compound No. 147, 113 mg).

Example 148

Synthesis of 3-[4-(2-chlorophenylmethyloxy)-3-(1H-indol-5-yl)phenyl]propionic acid (Compound No. 148) (Preparation Method 1, Step a)

According to the procedure described in the synthesis method of Compound of Example 002 (Preparation Method 1, Step a) with the modification that the reaction was carried out for 2 hours, Compound of Example 147 (111 mg) and 2 N aqueous sodium hydroxide (280 μl) were reacted and treated to obtain the title compound (Compound No. 148, 102 mg). Rf=0.48 (chloroform:methanol=10:1).

Example 149

Synthesis of methyl 3-[4-(3-chlorophenylmethyloxy)-3-(1H-indol-5-yl)phenyl]-propionate (Compound No. 149) (Preparation Method 5, Step e-1)

According to the procedure described in the synthesis method of Compound of Example 030 (Preparation Method 5, Step e-1) with the modifications that the reaction was carried out for 13 hours, and the purification was performed by column chromatography (Quad, hexane:ethyl acetate= 10:1), Intermediate 55 (88 mg), potassium carbonate (59 mg) and 3-chlorobenzyl bromide (46 μl, TCI) were reacted and treated to obtain the title compound (Compound No. 149, 100 mg).

Example 150

Synthesis of 3-[4-(3-chlorophenylmethyloxy)-3-(1H-indol-5-yl)phenyl]propionic acid (Compound No. 150) (Preparation Method 1, Step a)

According to the procedure described in the synthesis method of Compound of Example 002 (Preparation Method 1, Step a) with the modification that the reaction was carried out for 1.5 hours, Compound of Example 149 (100 mg) and 2 N aqueous sodium hydroxide (300 μl) were reacted and treated to obtain the title compound (Compound No. 150, 92 mg). Rf=0.47 (chloroform:methanol=10:1).

Example 151

Synthesis of methyl 3-[4-(4-chlorophenylmethyloxy)-3-(1H-indol-5-yl)phenyl]-propionate (Compound No. 151) (Preparation Method 5, Step e-1)

According to the procedure described in the synthesis method of Compound of Example 030 (Preparation Method 5, Step e-1) with the modifications that the reaction was carried out for 14 hours, and the purification was performed by column chromatography (Quad, hexane:ethyl acetate= 6:1), Intermediate 55 (81 mg), potassium carbonate (117 mg) and 4-chlorobenzyl chloride (70 mg, TCI) were reacted and treated to obtain the title compound (Compound No. 151, 104 mg).

Example 152

Synthesis of 3-[4-(4-chlorophenylmethyloxy)-3-(1H-indol-5-yl)phenyl]propionic acid (Compound No. 152) (Preparation Method 1, Step a)

According to the procedure described in the synthesis method of Compound of Example 002 (Preparation Method 1, Step a) with the modification that the reaction was carried out for 2 hours, Compound of Example 151 (99 mg) and 2 N aqueous sodium hydroxide (475 μl) were reacted and treated to obtain the title compound (Compound No. 152, 88 mg). Rf=0.45 (chloroform:methanol=10:1).

Example 153

Synthesis of methyl 3-[4-(2-bromophenylmethyloxy)-3-(1H-indol-5-yl)-phenyl]propionate (Compound No. 153) (Preparation Method 5, Step e-1)

According to the procedure described in the synthesis method of Compound of Example 030 (Preparation Method 5, Step e-1) with the modifications that the reaction was carried out for 5.5 hours, and the purification was performed by column chromatography (Quad, hexane:ethyl acetate= 10:1), Intermediate 55 (84 mg), potassium carbonate (69 mg) and 2-bromobenzyl bromide (53 μl, TCI) were reacted and treated to obtain the title compound (Compound No. 153, 106 mg).

Example 154

Synthesis of 3-[4-(2-bromophenylmethyloxy)-3-(1H-indol-5-yl)phenyl]propionic acid (Compound No. 154) (Preparation Method 1, Step a)

According to the procedure described in the synthesis method of Compound of Example 002 (Preparation Method 1, Step a) with the modification that the reaction was carried out for 3 hours, Compound of Example 153 (104 mg) and 2 N aqueous sodium hydroxide (300 μl) were reacted and treated to obtain the title compound (Compound No. 154, 94 mg). Rf=0.48 (chloroform:methanol=10:1).

Example 155

Synthesis of methyl 3-[4-(2,4-difluorophenylmethyloxy)-3-(1H-indol-5-yl)-phenyl]propionate (Compound No. 155) (Preparation Method 5, Step e-1)

According to the procedure described in the synthesis method of Compound of Example 030 (Preparation Method 5, Step e-1) with the modifications that the reaction was carried out for 14 hours, and the purification was performed by column chromatography (Quad, hexane:ethyl acetate= 4:1), Intermediate 55 (80 mg), potassium carbonate (80 mg) and 2,4-difluorobenzyl bromide (38 μl, Ald) were reacted and treated to obtain the title compound (Compound No. 155, 97 mg).

Example 156

Synthesis of 3-[4-(2,4-difluorophenylmethyloxy)-3-(1H-indol-5-yl)phenyl]propionic acid (Compound No. 156) (Preparation Method 1, Step a)

According to the procedure described in the synthesis method of Compound of Example 002 (Preparation Method 1, Step a) with the modification that the reaction was carried out for 1 hour, Compound of Example 155 (97 mg) and 2 N aqueous sodium hydroxide (500 µl) were reacted and treated to obtain the title compound (Compound No. 156, 64 mg). Rf=0.49 (chloroform:methanol=10:1).

Example 157

Synthesis of methyl 3-[4-(3,4-difluorophenylmethyloxy)-3-(1H-indol-5-yl)-phenyl]propionate (Compound No. 157) (Preparation Method 5, Step e-1)

According to the procedure described in the synthesis method of Compound of Example 030 (Preparation Method 5, Step e-1) with the modifications that the reaction was carried out for 14 hours, and the purification was performed by column chromatography (Quad, hexane:ethyl acetate=4:1), Intermediate 55 (80 mg), potassium carbonate (80 mg) and 3,4-difluorobenzyl bromide (38 µl, Ald) were reacted and treated to obtain the title compound (Compound No. 157, 104 mg).

Example 158

Synthesis of 3-[4-(3,4-difluorophenylmethyloxy)-3-(1H-indol-5-yl)phenyl]propionic acid (Compound No. 158) (Preparation Method 1, Step a)

According to the procedure described in the synthesis method of Compound of Example 002 (Preparation Method 1, Step a) with the modification that the reaction was carried out for 1 hour, Compound of Example 157 (104 mg) and 2 N aqueous sodium hydroxide (500 µl) were reacted and treated to obtain the title compound (Compound No. 158, 84 mg). Rf=0.47 (chloroform:methanol=10:1).

Example 159

Synthesis of methyl 3-[4-(2,3-dichlorophenylmethyloxy)-3-(1H-indol-5-yl)-phenyl]propionate (Compound No. 159) (Preparation Method 5, Step e-1)

According to the procedure described in the synthesis method of Compound of Example 030 (Preparation Method 5, Step e-1) with the modifications that the reaction was carried out for 17.5 hours, and the purification was performed by column chromatography (Quad, hexane:ethyl acetate=6:1), Intermediate 55 (80 mg), potassium carbonate (113 mg) and 2,3-dichlorobenzyl bromide (56 µl, TCI) were reacted and treated to obtain the title compound (Compound No. 159, 106 mg).

Example 160

Synthesis of 3-[4-(2,3-dichlorophenylmethyloxy)-3-(1H-indol-5-yl)phenyl]propionic acid (Compound No. 160) (Preparation Method 1, Step a)

According to the procedure described in the synthesis method of Compound of Example 002 (Preparation Method 1, Step a) with the modification that the reaction was carried out for 2.5 hours, Compound of Example 159 (106 mg) and 2 N aqueous sodium hydroxide (490 µl) were reacted and treated to obtain the title compound (Compound No. 160, 94 mg). Rf=0.47 (chloroform:methanol=10:1).

Example 161

Synthesis of methyl 3-[4-(2,4-dichlorophenylmethyloxy)-3-(1H-indol-5-yl)-phenyl]propionate (Compound No. 161) (Preparation Method 5, Step e-1)

According to the procedure described in the synthesis method of Compound of Example 030 (Preparation Method 5, Step e-1) with the modifications that the reaction was carried out for 14 hours, and the purification was performed by column chromatography (Quad, hexane:ethyl acetate=6:1), Intermediate 55 (83 mg), potassium carbonate (120 mg) and 2,4-dichlorobenzyl chloride (59 µl, TCI) were reacted and treated to obtain the title compound (Compound No. 161, 113 mg).

Example 162

Synthesis of 3-[4-(2,4-dichlorophenylmethyloxy)-3-(1H-indol-5-yl)phenyl]propionic acid (Compound No. 162) (Preparation Method 1, Step a)

According to the procedure described in the synthesis method of Compound of Example 002 (Preparation Method 1, Step a) with the modification that the reaction was carried out for 2 hours, Compound of Example 161 (107 mg) and 2 N aqueous sodium hydroxide (475 µl) were reacted and treated to obtain the title compound (Compound No. 162, 95 mg). Rf=0.45 (chloroform:methanol=10:1).

Example 163

Synthesis of methyl 3-[4-(2,6-dichlorophenylmethyloxy)-3-(1H-indol-5-yl)-phenyl]propionate (Compound No. 163) (Preparation Method 5, Step e-1)

According to the procedure described in the synthesis method of Compound of Example 030 (Preparation Method 5, Step e-1) with the modifications that the reaction was carried out for 4.5 hours, and the purification was performed by column chromatography (Quad, hexane:ethyl acetate=6:1), Intermediate 55 (80 mg), potassium carbonate (111 mg) and 2,6-dichlorobenzyl bromide (74 µl, TCI) were reacted and treated to obtain the title compound (Compound No. 163, 105 mg).

Example 164

Synthesis of 3-[4-(2,6-dichlorophenylmethyloxy)-3-(1H-indol-5-yl)phenyl]propionic acid (Compound No. 164) (Preparation Method 1, Step a)

According to the procedure described in the synthesis method of Compound of Example 002 (Preparation Method 1, Step a) with the modification that the reaction was carried out for 2.5 hours, Compound of Example 163 (104 mg) and 2 N aqueous sodium hydroxide (460 µl) were reacted and treated to obtain the title compound (Compound No. 164, 83 mg). Rf=0.42 (chloroform:methanol=10:1).

Example 165

Synthesis of methyl 3-[4-(3,4-dichlorophenylmethyloxy)-3-(1H-indol-5-yl)-phenyl]propionate (Compound No. 165) (Preparation Method 5, Step e-1)

According to the procedure described in the synthesis method of Compound of Example 030 (Preparation Method 5, Step e-1) with the modifications that the reaction was carried out for 14 hours, and the purification was performed by column chromatography (Quad, hexane:ethyl acetate=6:1), Intermediate 55 (81 mg), potassium carbonate (116 mg) and 3,4-dichlorobenzyl chloride (57 µl, TCI) were reacted and treated to obtain the title compound (Compound No. 165, 113 mg).

Example 166
Synthesis of 3-[4-(3,4-dichlorophenylmethyloxy)-3-(1H-indol-5-yl)phenyl]propionic acid (Compound No. 166) (Preparation Method 1, Step a)

According to the procedure described in the synthesis method of Compound of Example 002 (Preparation Method 1, Step a) with the modification that the reaction was carried out for 2 hours, Compound of Example 165 (107 mg) and 2 N aqueous sodium hydroxide (470 µl) were reacted and treated to obtain the title compound (Compound No. 166, 97 mg). Rf=0.45 (chloroform:methanol=10:1).

Example 167
Synthesis of methyl 3-[4-(4-bromo-2-fluorophenylmethyloxy)-3-(1H-indol-5-yl)phenyl]propionate (Compound No. 167) (Preparation Method 5, Step e-1)

According to the procedure described in the synthesis method of Compound of Example 030 (Preparation Method 5, Step e-1) with the modifications that the reaction was carried out for 16 hours, and the purification was performed by column chromatography (Quad, hexane:ethyl acetate=6:1), Intermediate 55 (80 mg), potassium carbonate (80 mg) and 4-bromo-2-fluorobenzyl bromide (80 mg, FluoroChem) were reacted and treated to obtain the title compound (Compound No. 167, 154 mg).

Example 168
Synthesis of 3-[4-(4-bromo-2-fluorophenylmethyloxy-3-(1H-indol-5-yl)phenyl)propionic acid (Compound No. 168) (Preparation Method 1, Step a)

According to the procedure described in the synthesis method of Compound of Example 002 (Preparation Method 1, Step a) with the modification that the reaction was carried out for 2.5 hours, Compound of Example 167 (154 mg) and 2 N aqueous sodium hydroxide (540 µl) were reacted and treated to obtain the title compound (Compound No. 168, 102 mg). Rf=0.45 (chloroform:methanol=10:1).

Example 169
Synthesis of methyl 3-{3-(1H-indol-5-yl)-4-[2-(trifluoromethyl)phenylmethyloxy]-phenyl}propionate (Compound No. 169) (Preparation Method 5, Step e-1)

According to the procedure described in the synthesis method of Compound of Example 030 (Preparation Method 5, Step e-1) with the modifications that the reaction was carried out for 13 hours, and the purification was performed by column chromatography (Quad, hexane:ethyl acetate=6:1), Intermediate 55 (81 mg), potassium carbonate (115 mg) and 2-(trifluoromethyl)benzyl bromide (100 mg, Ald) were reacted and treated to obtain the title compound (Compound No. 169, 105 mg).

Example 170
Synthesis of 3-{3-(1H-indol-5-yl)-4-[2-(trifluoromethyl)phenylmethyloxy]-phenyl}propionic acid (Compound No. 170) (Preparation Method 1, Step a)

According to the procedure described in the synthesis method of Compound of Example 002 (Preparation Method 1, Step a) with the modification that the reaction was carried out for 1.5 hours, Compound of Example 169 (98 mg) and 2 N aqueous sodium hydroxide (450 µl) were reacted and treated to obtain the title compound (Compound No. 170, 84 mg). Rf=0.44 (chloroform:methanol=10:1).

Example 171
Synthesis of methyl 3-{3-(1H-indol-5-yl)-4-[4-(trifluoromethyl)phenylmethyloxy]-phenyl}propionate (Compound No. 171) (Preparation Method 5, Step e-1)

According to the procedure described in the synthesis method of Compound of Example 030 (Preparation Method 5, Step e-1) with the modifications that the reaction was carried out for 16 hours, and the purification was performed by column chromatography (Quad, hexane:ethyl acetate=6:1), Intermediate 55 (80 mg), potassium carbonate (80 mg) and 4-(trifluoromethyl)benzyl bromide (71 mg, TCI) were reacted and treated to obtain the title compound (Compound No. 171, 38 mg).

Example 172
Synthesis of 3-{3-(1H-indol-5-yl)-4-[4-(trifluoromethyl)phenylmethyloxy]-phenyl}propionic acid (Compound No. 172) (Preparation Method 1, Step a)

According to the procedure described in the synthesis method of Compound of Example 002 (Preparation Method 1, Step a) with the modification that the reaction was carried out for 2.5 hours, Compound of Example 171 (38 mg) and 2 N aqueous sodium hydroxide (200 µl) were reacted and treated to obtain the title compound (Compound No. 172, 32 mg). Rf=0.45 (chloroform:methanol=10:1).

Example 173
Synthesis of 3-[4-isopropyloxy-3-(1H-indol-5-yl)phenyl]propionate (Compound No. 173) (Preparation Method 5, Step e-2 and Preparation Method 1, Step a)

According to the procedure described in the synthesis method of Compound of Example 038 (Preparation Method 5, Step e-2) with the modifications that the reaction was carried out for 22 hours, and the purification was performed by flash column chromatography (hexane:ethyl acetate=5:1), Intermediate 55 (100 mg), Ph$_3$P (355 mg), isopropyl alcohol (104 µl) and 40% DIAD (640 µl) were reacted and treated to obtain oily substance. According to the procedure described in the synthesis method of Compound of Example 002 (Preparation Method 1, Step a) with the modification that the reaction was carried out for 2 hours, the oily substance was reacted with 2 N aqueous sodium hydroxide (500 µl) and treated to obtain the title compound (Compound No. 173, 59 mg). Rf=0.46 (chloroform:methanol=10:1).

Example 174
Synthesis of methyl 3-[4-(3,5-dimethylphenylmethyloxy)-3-(1H-indol-5-yl)-phenyl]propionate (Compound No. 174) (Preparation Method 5, Step e-2)

A solution of Intermediate 55 (80 mg) and TMAD (69 mg, TCI) in anhydrous THF (1.5 ml) was added with 3,5-dimethylbenzyl alcohol (59 µl, Ald), added dropwise with $^n$Bu$_3$P (110 µl, KANTO) under ice cooling, gradually warmed to room temperature and stirred for 13 hours. The reaction mixture was filtered, and the solvent of the filtrate was evaporated under reduced pressure. The residue was purified by column chromatography (Quad, hexane:ethyl acetate=7:1) to obtain the title compound (Compound No. 174, 123 mg).

Example 175
Synthesis of 3-[4-(3,5-dimethylphenylmethyloxy)-3-(1H-indol-5-yl)phenyl]propionic acid (Compound No. 175) (Preparation Method 1, Step a)

According to the procedure described in the synthesis method of Compound of Example 002 (Preparation Method 1, Step a) with the modification that the reaction was carried out for 1 hour, Compound of Example 174 (120 mg) and 2

N aqueous sodium hydroxide (500 µl) were reacted and treated to obtain the title compound (Compound No. 175, 76 mg). Rf=0.54 (chloroform:methanol=10:1).

Example 176

Synthesis of methyl 3-[4-(bicyclo[2,2,1]hept-2-ylmethyloxy)-3-(1H-indol-5-yl)phenyl]-propionate (Compound No. 176) (Preparation Method 5, Step e-2)

A solution of Intermediate 55 (100 mg), TMAD (119 mg) and Ph$_3$P (180 mg) in anhydrous THF (5 ml) was added dropwise with norbornane-2-methanol (91 µl, TCI) and stirred for 16.5 hours. The reaction mixture was filtered, and the solvent of the filtrate was evaporated under reduced pressure. The residue was purified by column chromatography (Quad, hexane:ethyl acetate=15:1) to obtain the title compound (Compound No. 176, 93 mg).

Example 177

Synthesis of 3-[4-(bicyclo[2,2,1]hept-2-ylmethyloxy)-3-(1H-indol-5-yl)phenyl]propionic acid (Compound No. 177) (Preparation Method 1, Step a)

According to the procedure described in the synthesis method of Compound of Example 002 (Preparation Method 1, Step a) with the modification that the reaction was carried out for 4 hours, Compound of Example 176 (93 mg) and 2 N aqueous sodium hydroxide (400 µl) were reacted and treated to obtain the title compound (Compound No. 177, 79 mg). Rf=0.38 (chloroform:methanol=10:1).

Example 178

Synthesis of methyl 3-{4-[(biphenyl-4-yl)methyloxy]-3-(1H-indol-5-yl)-phenyl}propionate (Compound No. 178) (Preparation Method 5, Step e-2)

According to the procedure described in the synthesis method of Compound of Example 174 (Preparation Method 5, Step e-2) with the modifications that the reaction was carried out for 26 hours, and the purification was performed by column chromatography (Quad, hexane:ethyl acetate=5:1), Intermediate 55 (81 mg), TMAD (71 mg), 4-hydroxymethylbiphenyl (75 mg, TCI) and "Bu$_3$P (101 µl) were reacted and treated to obtain the title compound (Compound No. 178, 127 mg).

Example 179

Synthesis of 3-{4-[(biphenyl-4-yl)methyloxy]-3-(1H-indol-5-yl)phenyl}propionic acid (Compound No. 179) (Preparation Method 1, Step a)

According to the procedure described in the synthesis method of Compound of Example 002 (Preparation Method 1, Step a) with the modification that the reaction was carried out for 3 hours, Compound of Example 178 (119 mg) and 2 N aqueous sodium hydroxide (515 µl) were reacted and treated to obtain the title compound (Compound No. 179, 102 mg). Rf=0.46 (chloroform:methanol=10:1).

Example 180

Synthesis of methyl 3-[4-(2,3-dimethylbutyloxy)-3-(1H-indol-5-yl)phenyl]propionate (Compound No. 180) (Preparation Method 5, Step e-2)

According to the procedure described in the synthesis method of Compound of Example 174 (Preparation Method 5, Step e-2) with the modifications that the reaction was carried out for 13.5 hours, and the purification was performed by column chromatography (Quad, hexane:ethyl acetate=8:1), Intermediate 55 (81 mg), TMAD (94.6 mg), 2,3-dimethyl-1-butanol (67 µl, SIGMA) and "Bu$_3$P (135 µl) were reacted and treated to obtain the title compound (Compound No. 180, 67 mg).

Example 181

Synthesis of 3-[4-(2,3-dimethylbutyloxy)-3-(1H-indol-5-yl)phenyl]propionic acid (Compound No. 181) (Preparation Method 1, Step a)

According to the procedure described in the synthesis method of Compound of Example 002 (Preparation Method 1, Step a) with the modification that the reaction was carried out for 2 hours, Compound of Example 180 (59 mg) and 2 N aqueous sodium hydroxide (310 µl) were reacted and treated to obtain the title compound (Compound No. 181, 44 mg). Rf=0.46 (chloroform:methanol=10:1).

Example 182

Synthesis of methyl 3-[4-(2-ethylbutyloxy)-3-(1H-indol-5-yl)phenyl]propionate (Compound No. 182) (Preparation Method 5, Step e-2)

According to the procedure described in the synthesis method of Compound of Example 174 (Preparation Method 5, Step e-2) with the modifications that the reaction was carried out for 13.5 hours, and the purification was performed by column chromatography (Quad, hexane:ethyl acetate=8:1), Intermediate 55 (80 mg), TMAD (94 mg), 2-ethyl-1-butanol (67 µl, TCI) and "Bu$_3$P (135 µl) were reacted and treated to obtain the title compound (Compound No. 182, 95 mg).

Example 183

Synthesis of 3-[4-(2-ethylbutyloxy)-3-(1H-indol-5-yl)phenyl]propionic acid (Compound No. 183) (Preparation Method 1, Step a)

According to the procedure described in the synthesis method of Compound of Example 002 (Preparation Method 1, Step a) with the modification that the reaction was carried out for 4.5 hours, Compound of Example 182 (75 mg) and 2 N aqueous sodium hydroxide (390 µl) were reacted and treated to obtain the title compound (Compound No. 183, 54 mg). Rf=0.48 (chloroform:methanol=10:1).

Example 184

Synthesis of 3-[4-cycloheptyloxy-3-(1H-indol-5-yl)phenyl]propionic acid (Compound No. 184) (Preparation Method 5, Step e-2 and Preparation Method 1, Step a)

According to the procedure described in the synthesis method of Compound of Example 174 (Preparation Method 5, Step e-2) with the modifications that the reaction was carried out for 13.5 hours, and the purification was performed by column chromatography (Quad, hexane:ethyl acetate=8:1), Intermediate 55 (81 mg), TMAD (141 mg), cycloheptanol (98 µl, TCI) and "Bu$_3$P (202 µl) were reacted and treated to obtain oily substance. According to the procedure described in the synthesis method of Compound of Example 002 (Preparation Method 1, Step a) with the modification that the reaction was carried out for 4.5 hours, the oily substance was reacted with 2 N aqueous sodium hydroxide (400 µl) and treated to obtain the title compound (Compound No. 184, 59 mg). Rf=0.51 (chloroform:methanol=10:1).

Example 185

Synthesis of methyl 3-{4-[4-(butyloxy)phenylmethyloxy]-3-(1H-indol-5-yl)-phenyl}propionate (Compound No. 185) (Preparation Method 5, Step e-2)

According to the procedure described in the synthesis method of Compound of Example 174 (Preparation Method 5, Step e-2) with the modifications that the reaction was carried out for 26 hours, and the purification was performed by column chromatography (Quad, hexane:ethyl acetate=5:1), Intermediate 55 (80 mg), TMAD (70 mg), 4-butoxybenzyl alcohol (79 mg, Ald) and $^n$Bu$_3$P (101 μl) were reacted and treated to obtain the title compound (Compound No. 185, 124 mg).

Example 186

Synthesis of 3-{4-[4-(butyloxy)phenylmethyloxy]-3-(1H-indol-5-yl)phenyl}propionic acid (Compound No. 186) (Preparation Method 1, Step a)

According to the procedure described in the synthesis method of Compound of Example 002 (Preparation Method 1, Step a) with the modification that the reaction was carried out for 3 hours, Compound of Example 185 (106 mg) and 2 N aqueous sodium hydroxide (470 μl) were reacted and treated to obtain the title compound (Compound No. 186, 65 mg). Rf=0.48 (chloroform:methanol=10:1).

Example 187

Synthesis of methyl 3-[4-(3,5-dichlorophenylmethyloxy)-3-(1H-indol-5-yl)phenyl]propionate (Compound No. 187) (Preparation Method 5, Step e-2)

According to the procedure described in the synthesis method of Compound of Example 174 (Preparation Method 5, Step e-2) with the modifications that the reaction was carried out for 17.5 hours, and the purification was performed by column chromatography (Quad, hexane:ethyl acetate=15:1), Intermediate 55 (81 mg), TMAD (69 mg), 3,5-dichlorobenzyl alcohol (71 mg, Avocado) and $^n$Bu$_3$P (101 μl) were reacted and treated to obtain the title compound (Compound No. 187, 105 mg).

Example 188

Synthesis of 3-[4-(3,5-dichlorophenylmethyloxy)-3-(1H-indol-5-yl)phenyl]propionic acid (Compound No. 188) (Preparation Method 1, Step a)

According to the procedure described in the synthesis method of Compound of Example 002 (Preparation Method 1, Step a) with the modification that the reaction was carried out for 3.5 hours, Compound of Example 187 (105 mg) and 2 N aqueous sodium hydroxide (590 μl) were reacted and treated to obtain the title compound (Compound No. 188, 91 mg). Rf=0.39 (chloroform:methanol=10:1).

Example 189

Synthesis of methyl 3-{3-(1H-indol-5-yl)-4-[(naphthalen-1-yl)methyloxy]-phenyl}propionate (Compound No. 189) (Preparation Method 5, Step e-2)

According to the procedure described in the synthesis method of Compound of Example 174 (Preparation Method 5, Step e-2) with the modifications that the reaction was carried out for 20 hours, and the purification was performed by column chromatography (Quad, hexane:ethyl acetate=10:1), Intermediate 55 (80 mg), TMAD (71 mg), 1-naphthalenemethanol (65 mg, Ald) and $^n$Bu$_3$P (101 μl) were reacted and treated to obtain the title compound (Compound No. 189, 111 mg).

Example 190

Synthesis of 3-{3-(1H-indol-5-yl)-4-[(naphthalen-1-yl)methyloxy]phenyl}propionic acid (Compound No. 190) (Preparation Method 1, Step a)

According to the procedure described in the synthesis method of Compound of Example 002 (Preparation Method 1, Step a) with the modification that the reaction was carried out for 1.5 hours, Compound of Example 189 (110 mg) and 2 N aqueous sodium hydroxide (560 μl) were reacted and treated o obtain the title compound (Compound No. 190, 71 mg). Rf=0.42 (chloroform:methanol=10:1).

Example 191

Synthesis of methyl 3-{3-(1H-indol-5-yl)-4-[(naphthalen-2-yl)methyloxy]-phenyl}propionate (Compound No. 191) (Preparation Method 5, Step e-2)

According to the procedure described in the synthesis method of Compound of Example 174 (Preparation Method 5, Step e-2) with the modifications that the reaction was carried out for 20 hours, and the purification was performed by column chromatography (Quad, hexane:ethyl acetate=10:1), Intermediate 55 (80 mg), TMAD (73 mg), 2-naphthalene-methanol (65 mg, Ald) and $^n$Bu$_3$P (101 μl) were reacted and treated to obtain the title compound (Compound No. 191, 99 mg).

Example 192

Synthesis of 3-{3-(1H-indol-5-yl)-4-[(Naphthalen-2-yl)methyloxy]phenyl}propionic acid (Compound No. 192) (Preparation Method 1, Step a)

According to the procedure described in the synthesis method of Compound of Example 002 (Preparation Method 1, Step a) with the modification that the reaction was carried out for 1 hour, Compound of Example 191 (99 mg) and 2 N aqueous sodium hydroxide (460 μl) were reacted and treated to obtain the title compound (Compound No. 192, 75 mg). Rf=0.46 (chloroform:methanol=10:1).

Example 193

Synthesis of methyl 3-{4-[(furan-2-yl)methyloxy]-3-(1H-indol-5-yl)phenyl}propionate (Compound No. 193) (Preparation Method 5, Step e-2)

According to the procedure described in the synthesis method of Compound of Example 174 (Preparation Method 5, Step e-2) with the modifications that the reaction was carried out for 15.5 hours, and the purification was performed by column chromatography (Quad, hexane:ethyl acetate=8:1), Intermediate 55 (105 mg), TMAD (87 mg), furfuryl alcohol (44 μl, TCI) and $^n$Bu$_3$P (127 μl) were reacted and treated to obtain the title compound (Compound No. 193, 125 mg).

Example 194

Synthesis of 3-{4-[(furan-2-yl)methyloxy]-3-(1H-indol-5-yl)phenyl}propionic acid (Compound No. 194) (Preparation Method 1, Step a)

According to the procedure described in the synthesis method of Compound of Example 002 (Preparation Method 1, Step a) with the modification that the reaction was carried out for 2.5 hours, Compound of Example 193 (118 mg) and 2 N aqueous sodium hydroxide (630 μl) were reacted and treated to obtain the title compound (Compound No. 194, 87 mg). Rf=0.44 (chloroform:methanol=10:1).

Example 195

Synthesis of methyl 3-{4-[(furan-3-yl)methyloxy]-3-(1H-indol-5-yl)phenyl}propionate (Compound No. 195) (Preparation Method 5, Step e-2)

According to the procedure described in the synthesis method of Compound of Example 174 (Preparation Method 5, Step e-2) with the modifications that the reaction was carried out for 15.5 hours, and the purification was performed by column chromatography (Quad, hexane:ethyl acetate=8:1), Intermediate 55 (101 mg), TMAD (89 mg), 3-furanmethanol (44 μl, TCI) and $^n$Bu$_3$P (127 μl) were reacted and treated to obtain the title compound (Compound No. 195, 115 mg).

Example 196
Synthesis of 3-{4-[(furan-3-yl)methyloxy]-3-(1H-indol-5-yl)phenyl}propionic acid (Compound No. 196) (Preparation Method 1, Step a)

According to the procedure described in the synthesis method of Compound of Example 002 (Preparation Method 1, Step a) with the modification that the reaction was carried out for 2.5 hours, Compound of Example 195 (115 mg) and 2 N aqueous sodium hydroxide (360 µl) were reacted and treated to obtain the title compound (Compound No. 196, 93 mg). Rf=0.46 (chloroform:methanol=10:1).

Example 197
Synthesis of methyl 3-{3-(1H-indol-5-yl)-4-[(Thiophen-2-yl)methyloxy]-phenyl}propionate (Compound No. 197) (Preparation Method 5, Step e-2 and Preparation Method 4, Step d-1)

According to the procedure described in the synthesis method of Compound of Example 174 (Preparation Method 5, Step e-2) with the modifications that the reaction was carried out for 3 hours, and the purification was performed by column chromatography (Quad, hexane:ethyl acetate=9:1), Intermediate 6 (130 mg), TMAD (172 mg), 2-thiophene-methanol (95 µl, TCI) and $^n$Bu$_3$P (250 µl) were reacted and treated to obtain oily substance. According to the procedure described in the synthesis method of Compound of Example 001 (Preparation Method 4, Step d-1) with the modifications that the reaction was carried out for 16 hours, and the purification was performed by flash column chromatography (hexane:ethyl acetate=4:1), the oily substance was reacted with 5-indoleboronic acid (120 mg), 2 M aqueous sodium carbonate (0.5 ml) and (Ph$_3$P)$_4$Pd (58 mg) and treated to obtain the title compound (Compound No. 197, 176 mg).

Example 198
Synthesis of 3-{3-(1H-indol-5-yl)-4-[(thiophen-2-yl)methyloxy]phenyl}propionic acid (Compound No. 198) (Preparation Method 1, Step a)

According to the procedure described in the synthesis method of Compound of Example 002 (Preparation Method 1, Step a) with the modification that the reaction was carried out for 1 hour, Compound of Example 197 (176 mg) and 2 N aqueous sodium hydroxide (1 ml) were reacted and treated to obtain the title compound (Compound No. 198, 130 mg). Rf=0.38 (chloroform:methanol=10:1).

Example 199
Synthesis of methyl 3-{3-(1H-indol-5-yl)-4-[2-(2-methylphenyl)ethyloxy]phenyl}-propionate (Compound No. 199) (Preparation Method 5, Step e-2)

According to the procedure described in the synthesis method of Compound of Example 174 (Preparation Method 5, Step e-2) with the modifications that the reaction was carried out for 12 hours, and the purification was performed by column chromatography (Quad, hexane:ethyl acetate=8:1), Intermediate 55 (85 mg), TMAD (91 mg), 2-methylphenethyl alcohol (75 µl, Ald) and $^n$Bu$_3$P (120 µl) were reacted and treated to obtain the title compound (Compound No. 199, 114 mg).

Example 200
Synthesis of 3-{3-(1H-indol-5-yl)-4-[2-(2-methylphenyl)ethyloxy]phenyl}propionic acid (Compound No. 200) (Preparation Method 1, Step a)

According to the procedure described in the synthesis method of Compound of Example 002 (Preparation Method 1, Step a) with the modification that the reaction was carried out for 4.5 hours, Compound of Example 199 (112 mg) and 2 N aqueous sodium hydroxide (280 µl) were reacted and treated to obtain the title compound (Compound No. 200, 106 mg). Rf=0.44 (chloroform:methanol=10:1).

Example 201
Synthesis of methyl 3-{3-(1H-indol-5-yl)-4-[2-(3-methylphenyl)ethyloxy]-phenyl}propionate (Compound No. 201) (Preparation Method 5, Step e-2)

According to the procedure described in the synthesis method of Compound of Example 174 (Preparation Method 5, Step e-2) with the modifications that the reaction was carried out for 12 hours, and the purification was performed by column chromatography (Quad, hexane:ethyl acetate=8:1), Intermediate 55 (69 mg), TMAD (91 mg), 3-methylphenethyl alcohol (78 µl, Ald) and $^n$Bu$_3$P (120 µl) were reacted and treated to obtain the title compound (Compound No. 201, 91 mg).

Example 202
Synthesis of 3-{3-(1H-indol-5-yl)-4-[2-(3-methylphenyl)ethyloxy]phenyl}propionic acid (Compound No. 202) (Preparation Method 1, Step a)

According to the procedure described in the synthesis method of Compound of Example 002 (Preparation Method 1, Step a) with the modification that the reaction was carried out for 4.5 hours, Compound of Example 201 (90 mg) and 2 N aqueous sodium hydroxide (280 µl) were reacted and treated to obtain the title compound (Compound No. 202, 86 mg). Rf=0.49 (chloroform:methanol=10:1).

Example 203
Synthesis of methyl 3-{3-(1H-indol-5-yl)-4-[2-(4-methylphenyl)ethyloxy]-phenyl}propionate (Compound No. 203) (Preparation Method 5, Step e-2)

According to the procedure described in the synthesis method of Compound of Example 174 (Preparation Method 5, Step e-2) with the modifications that the reaction was carried out for 18 hours, and the purification was performed by column chromatography (Quad, hexane:ethyl acetate=8:1), Intermediate 55 (79 mg), TMAD (141 mg), 4-methylphenethyl alcohol (83 µl, Ald) and $^n$Bu$_3$P (120 µl) were reacted and treated to obtain the title compound (Compound No. 203, 81 mg).

Example 204
Synthesis of 3-{3-(1H-indol-5-yl)-4-[2-(4-methylphenyl)ethyloxy]phenyl}propionic acid (Compound No. 204) (Preparation Method 1, Step a)

According to the procedure described in the synthesis method of Compound of Example 002 (Preparation Method 1, Step a) with the modification that the reaction was carried out for 7 hours, Compound of Example 203 (80 mg) and 2 N aqueous sodium hydroxide (210 µl) were reacted and treated to obtain the title compound (Compound No. 204, 70 mg). Rf=0.56 (chloroform:methanol=10:1).

Example 205
Synthesis of 3-{3-(1H-indol-5-yl)-4-[2-(2-methoxyphenyl)ethyloxy]phenyl}propionic acid (Compound No. 205) (Preparation Method 5, Step e-2 and Preparation Method 1, Step a)

According to the procedure described in the synthesis method of Compound of Example 174 (Preparation Method 5, Step e-2) with the modifications that the reaction was carried out for 16 hours, and the purification was performed by column chromatography (Quad, hexane:ethyl acetate=7:1), Intermediate 55 (118 mg), TMAD (207 mg), 2-methoxyphenethyl alcohol (170 µl, Ald) and ⁿBu₃P (400 µl) were reacted and treated to obtain oily substance. According to the procedure described in the synthesis method of Compound of Example 002 (Preparation Method 1, Step a) with the modification that the reaction was carried out for 2 hours, the oily substance was reacted with 2 N aqueous sodium hydroxide (600 µl) and treated to obtain the title compound (Compound No. 205, 98 mg). Rf=0.41 (chloroform:methanol=10:1).

Example 206
Synthesis of methyl 3-{3-(1H-indol-5-yl)-4-[2-(4-methoxyphenyl)ethyloxy]-phenyl}propionate (Compound No. 206) (Preparation Method 5, Step e-2)
According to the procedure described in the synthesis method of Compound of Example 174 (Preparation Method 5, Step e-2) with the modifications that the reaction was carried out for 18 hours, and the purification was performed by column chromatography (Quad, hexane:ethyl acetate=7:1), Intermediate 55 (80 mg), TMAD (69 mg), 4-methoxyphenethyl alcohol (41 mg, TCI) and ⁿBu₃P (100 µl) were reacted and treated to obtain the title compound (Compound No. 206, 83 mg).

Example 207
Synthesis of 3-{3-(1H-indol-5-yl)-4-[2-(4-methoxyphenyl)ethyloxy]phenyl}propionic acid (Compound No. 207) (Preparation Method 1, Step a)
According to the procedure described in the synthesis method of Compound of Example 002 (Preparation Method 1, Step a) with the modification that the reaction was carried out for 1 hour, Compound of Example 206 (83 mg) and 2 N aqueous sodium hydroxide (400 µl) were reacted and treated to obtain the title compound (Compound No. 207, 54 mg). Rf=0.43 (chloroform:methanol=10:1).

Example 208
Synthesis of methyl 3-{4-[2-(2-chlorophenyl)ethyloxy]-3-(1H-indol-5-yl)phenyl}propionate (Compound No. 208) (Preparation Method 5, Step e-2)
According to the procedure described in the synthesis method of Compound of Example 174 (Preparation Method 5, Step e-2) with the modifications that the reaction was carried out for 10 hours, and the purification was performed by column chromatography (Quad, hexane:ethyl acetate=8:1), Intermediate 55 (87 mg), TMAD (109 mg), 2-chlorophenethyl alcohol (80 µl, Ald) and ⁿBu₃P (120 µl) were reacted and treated to obtain the title compound (Compound No. 208, 128 mg).

Example 209
Synthesis of 3-{4-[2-(2-chlorophenyl)ethyloxy]-3-(1H-indol-5-yl)phenyl}propionic acid (Compound No. 209) (Preparation Method 1, Step a)
According to the procedure described in the synthesis method of Compound of Example 002 (Preparation Method 1, Step a) with the modification that the reaction was carried out for 4 hours, Compound of Example 208 (124 mg) and 2 N aqueous sodium hydroxide (500 µl) were reacted and treated to obtain the title compound (Compound No. 209, 113 mg). Rf=0.42 (chloroform:methanol=10:1).

Example 210
Synthesis of methyl 3-{4-[2-(3-chlorophenyl)ethyloxy]-3-(1H-indol-5-yl)phenyl}propionate (Compound No. 210) (Preparation Method 5, Step e-2)
According to the procedure described in the synthesis method of Compound of Example 174 (Preparation Method 5, Step e-2) with the modifications that the reaction was carried out for 12 hours, and the purification was performed by column chromatography (Quad, hexane:ethyl acetate=10:1), Intermediate 55 (86 mg), TMAD (165 mg), 3-chlorophenethyl alcohol (80 µl, Ald) and ⁿBu₃P (120 µl) were reacted and treated to obtain the title compound (Compound No. 210, 115 mg).

Example 211
Synthesis of 3-{4-[2-(3-chlorophenyl)ethyloxy]-3-(1H-indol-5-yl)phenyl}propionic acid (Compound No. 211) (Preparation Method 1, Step a)
According to the procedure described in the synthesis method of Compound of Example 002 (Preparation Method 1, Step a) with the modification that the reaction was carried out for 4 hours, Compound of Example 210 (112 mg) and 2 N aqueous sodium hydroxide (300 µl) were reacted and treated to obtain the title compound (Compound No. 211, 99 mg). Rf=0.40 (chloroform:methanol=10:1).

Example 212
Synthesis of methyl 3-{4-[2-(4-chlorophenyl)ethyloxy]-3-(1H-indol-5-yl)-phenyl}propionate (Compound No. 212) (Preparation Method 5, Step e-2)
According to the procedure described in the synthesis method of Compound of Example 174 (Preparation Method 5, Step e-2) with the modifications that the reaction was carried out for 7 hours, and the purification was performed by column chromatography (Quad, hexane:ethyl acetate=8:1), Intermediate 55 (86 mg), TMAD (113 mg), 4-chlorophenethyl alcohol (140 µl, Ald) and ⁿBu₃P (120 µl) were reacted and treated to obtain the title compound (Compound No. 212, 87 mg).

Example 213
Synthesis of 3-{4-[2-(4-chlorophenyl)ethyloxy]-3-(1H-indol-5-yl)phenyl}propionic acid (Compound No. 213) (Preparation Method 1, Step a)
According to the procedure described in the synthesis method of Compound of Example 002 (Preparation Method 1, Step a) with the modification that the reaction was carried out for 2.5 hours, Compound of Example 212 (87 mg) and 2 N aqueous sodium hydroxide (300 µl) were reacted and treated to obtain the title compound (Compound No. 213, 80 mg). Rf=0.54 (chloroform:methanol=10:1).

Example 214
Synthesis of 3-[3-(1H-indol-5-yl)-4-{2-[2-(trifluoromethyl)phenyl]-ethyloxy}phenyl]propionic acid (Compound No. 214) (Preparation Method 5, Step e-2 and Preparation Method 1, Step a)
According to the procedure described in the synthesis method of Compound of Example 174 (Preparation Method 5, Step e-2) with the modifications that the reaction was carried out for 38 hours, and the purification was performed by column chromatography (Quad, hexane:ethyl acetate=5:1), Intermediate 55 (75 mg), TMAD (69 mg), 2-(trifluoromethyl)phenethyl alcohol (64 µl, Ald) and ⁿBu₃P (100 µl) were reacted and treated to obtain oily substance. According to the procedure described in the synthesis method of Compound of Example 002 (Preparation Method 1, Step a) with the modification that the reaction was carried out for 1 hour, the oily substance was reacted with 2 N aqueous sodium hydroxide (500 µl) and treated to obtain the title compound (Compound No. 214, 76 mg). Rf=0.37 (chloroform:methanol=10:1).

Example 215
Synthesis of 3-(4-{2-[4-(N,N-dimethylamino)phenyl]Ethyloxy}-3-[1H-indol-5-yl]phenyl)propionic acid (Compound No. 215) (Preparation Method 5, Step e-2 and Preparation Method 1, Step a)

According to the procedure described in the synthesis method of Compound of Example 174 (Preparation Method 5, Step e-2) with the modifications that the reaction was carried out for 12 hours, and the purification was performed by column chromatography (Quad, hexane:ethyl acetate= 5:1), Intermediate 55 (82 mg), TMAD (110 mg), 4-(N,N-dimethylamino)phenethyl alcohol (203 mg, Ald) and $^n$Bu$_3$P (120 μl) were reacted and treated to obtain oily substance. According to the procedure described in the synthesis method of Compound of Example 002 (Preparation Method 1, Step a) with the modification that the reaction was carried out for 2 hours, the oily substance was reacted with 2 N aqueous sodium hydroxide (100 μl) and treated to obtain the title compound (Compound No. 215, 50 mg). Rf=0.51 (chloroform:methanol=10:1).

Example 216

Synthesis of methyl 3-{4-[2-(naphthalen-2-yl)ethyloxy]-3-(1H-indol-5-yl)-phenyl}propionate (Compound No. 216) (Preparation Method 5, Step e-2)

According to the procedure described in the synthesis method of Compound of Example 174 (Preparation Method 5, Step e-2) with the modifications that the reaction was carried out for 18 hours, and the purification was performed by column chromatography (Quad, hexane:ethyl acetate= 8:1), Intermediate 55 (82 mg), TMAD (132 mg), 2-naphthalene-ethanol (96 mg, Ald) and $^n$Bu$_3$P (130 μl) were reacted and treated to obtain the title compound (Compound No. 216, 109 mg).

Example 217

Synthesis of 3-{4-[2-(naphthalen-2-yl)ethyloxy]-3-(1H-indol-5-yl)phenyl}propionic acid (Compound No. 217) (Preparation Method 1, Step a)

According to the procedure described in the synthesis method of Compound of Example 002 (Preparation Method 1, Step a) with the modification that the reaction was carried out for 7 hours, Compound of Example 216 (98 mg) and 2 N aqueous sodium hydroxide (230 μl) were reacted and treated to obtain the title compound (Compound No. 217, 85 mg). Rf=0.52 (chloroform:methanol=10:1).

Example 218

Synthesis of methyl 3-{3-(1H-indol-5-yl)-4-[2-(1H-indol-3-yl)ethyloxy]-phenyl}propionate (Compound No. 218) (Preparation Method 5, Step e-2)

According to the procedure described in the synthesis method of Compound of Example 174 (Preparation Method 5, Step e-2) with the modifications that the reaction was carried out for 7 hours, the purification was performed by PTLC (hexane:ethyl acetate=5:1, developed 3 times), Intermediate 55 (79 mg), TMAD (168 mg), 2-(3-indole)-ethanol (Tryptophol, 86 mg, Ald) and $^n$Bu$_3$P (120 u 1) were reacted and treated to obtain the title compound (Compound No. 218, 49 mg).

Example 219

Synthesis of 3-{3-(1H-indol-5-yl)-4-[2-(1H-indol-3-yl)ethyloxy]phenyl}propionic A (Compound No. 219) (Preparation Method 1, Step a)

According to the procedure described in the synthesis method of Compound of Example 002 (Preparation Method 1, Step a) with the modification that the reaction was carried out for 1 hour, Compound of Example 218 (48 mg) and 2 N aqueous sodium hydroxide (250 μl) were reacted and treated to obtain the title compound (Compound No. 219, 42 mg). Rf=0.41 (chloroform:methanol=10:1).

Example 220

Synthesis of 3-[3-(1H-indol-5-yl)-4-(3-phenylpropyloxy)phenyl]propionic acid (Compound No. 220) (Preparation Method 5, Step e-2 and Preparation Method 1, Step a)

According to the procedure described in the synthesis method of Compound of Example 174 (Preparation Method 5, Step e-2) with the modifications that the reaction was carried out for 12.5 hours, and the purification was performed by column chromatography (Quad, hexane:ethyl acetate=7:1), Intermediate 55 (75 mg), TMAD (69 mg), 3-phenylpropanol (54 μl, TCI) and $^n$Bu$_3$P (100 μl) were reacted and treated to obtain oily substance. According to the procedure described in the synthesis method of Compound of Example 002 (Preparation Method 1, Step a) with the modification that the reaction was carried out for 1 hour, the oily substance was reacted with 2 N aqueous sodium hydroxide (500 μl) and treated to obtain the title compound (Compound No. 220, 36 mg). Rf=0.37 (chloroform:methanol=10:1).

Example 221

Synthesis of methyl 3-{3-(1H-indol-5-yl)-4-[2-(phenyloxy)ethyloxy]phenyl}propionate (Compound No. 221) (Preparation Method 5, Step e-2)

According to the procedure described in the synthesis method of Compound of Example 174 (Preparation Method 5, Step e-2) with the modifications that the reaction was carried out for 12.5 hours, and the purification was performed by column chromatography (Quad, hexane:ethyl acetate=7:1), Intermediate 55 (80 mg), TMAD (69 mg), 2-phenoxyethanol (50 μl, TCI) and $^n$Bu$_3$P (100 μl) were reacted and treated to obtain the title compound (Compound No. 221, 99 mg).

Example 222

Synthesis of 3-{3-(1H-indol-5-yl)-4-[2-(phenyloxy)ethyloxy]phenyl}propionic acid (Compound No. 222) (Preparation Method 1, Step a)

According to the procedure described in the synthesis method of Compound of Example 002 (Preparation Method 1, Step a) with the modification that the reaction was carried out for 1.5 hours, Compound of Example 221 (99 mg) and 2 N aqueous sodium hydroxide (500 μl) were reacted and treated to obtain the title compound (Compound No. 222, 82 mg). Rf=0.43 (chloroform:methanol=10:1).

Example 223

Synthesis of methyl 3-{4-[2-(2-chlorophenyloxy)ethyloxy]-3-(1H-indol-5-yl)phenyl}propionate (Compound No. 223) (Preparation Method 5, Step e-2)

According to the procedure described in the synthesis method of Compound of Example 174 (Preparation Method 5, Step e-2) with the modifications that the reaction was carried out for 13 hours, and the purification was performed by column chromatography (Quad, hexane:ethyl acetate= 7:1), Intermediate 55 (80 mg), TMAD (69 mg), 2-(2-chlorophenoxy)ethanol (55 μl, Ald) and $^n$Bu$_3$P (100 μl) were reacted and treated to obtain the title compound (Compound No. 223, 67 mg).

Example 224

Synthesis of 3-{4-[2-(2-chlorophenyloxy)ethyloxy]-3-(1H-indol-5-yl)phenyl}propionic acid (Compound No. 224) (Preparation Method 1, Step a)

According to the procedure described in the synthesis method of Compound of Example 002 (Preparation Method 1, Step a) with the modification that the reaction was carried out for 2 hours, Compound of Example 223 (67 mg) and 2

N aqueous sodium hydroxide (300 µl) were reacted and treated to obtain the title compound (Compound No. 224, 23 mg). Rf=0.42 (chloroform:methanol=10:1).

Example 225
Synthesis of methyl 3-{4-[2-(4-chlorophenyloxy)ethyloxy]-3-(1H-indol-5-yl)phenyl}propionate (Compound No. 225) (Preparation Method 5, Step e-2)

According to the procedure described in the synthesis method of Compound of Example 174 (Preparation Method 5, Step e-2) with the modifications that the reaction was carried out for 13 hours, and the purification was performed by column chromatography (Quad, hexane:ethyl acetate= 7:1), Intermediate 55 (80 mg), TMAD (69 mg), 2-(4-chlorophenoxy)ethanol (55 µl, LANC) and "Bu$_3$P (100 µl) were reacted and treated to obtain the title compound (Compound No. 225, 78 mg).

Example 226
Synthesis of 3-{4-[2-(4-chlorophenyloxy)ethyloxy]-3-(1H-indol-5-yl)phenyl}propionic acid (Compound No. 226) (Preparation Method 1, Step a)

According to the procedure described in the synthesis method of Compound of Example 002 (Preparation Method 1, Step a) with the modification that the reaction was carried out for 2 hours, Compound of Example 225 (78 mg) and 2 N aqueous sodium hydroxide (350 µl) were reacted and treated to obtain the title compound (Compound No. 226, 56 mg). Rf=0.40 (chloroform:methanol=10:1).

Example 227
Synthesis of methyl 3-{3-(1H-indol-5-yl)-4-[2-(phenylthio)ethyloxy]phenyl}propionate (Compound No. 227) (Preparation Method 5, Step e-2)

According to the procedure described in the synthesis method of Compound of Example 174 (Preparation Method 5, Step e-2) with the modifications that the reaction was carried out for 13.5 hours, and the purification was performed by column chromatography (Quad, hexane:ethyl acetate=7:1), Intermediate 55 (80 mg), TMAD (69 mg), 2-(phenylthio)ethyl alcohol (43 µl, TCI) and "Bu$_3$P (100 µl) were reacted and treated to obtain the title compound (Compound No. 227, 60 mg).

Example 228
Synthesis of 3-{3-(1H-indol-5-yl)-4-[2-(phenylthio)ethyloxy]phenyl}propionic acid (Compound No. 228) (Preparation Method 1, Step a)

According to the procedure described in the synthesis method of Compound of Example 002 (Preparation Method 1, Step a) with the modification that the reaction was carried out for 1.5 hours, Compound of Example 227 (60 mg) and 2 N aqueous sodium hydroxide (300 µl) were reacted and treated to obtain the title compound (Compound No. 228, 46 mg). Rf=0.40 (chloroform:methanol=10:1).

Example 229
Synthesis of 3-{3-(1H-indol-5-yl)-4-[2-(N-phenyl-N-methylamino)-ethyloxy]phenyl}propionic acid (Compound No. 229) (Preparation Method 5, Step e-2 and Preparation Method 1, Step a)

According to the procedure described in the synthesis method of Compound of Example 174 (Preparation Method 5, Step e-2) with the modifications that the reaction was carried out for 13.5 hours, and the purification was performed by column chromatography (Quad, hexane:ethyl acetate=7:1), Intermediate 55 (80 mg), TMAD (69 mg), 2-(N-methylanilino)ethanol (45 µl, TCI) and "Bu$_3$P (100 µl) were reacted and treated to obtain oily substance. According to the procedure described in the synthesis method of Compound of Example 002 (Preparation Method 1, Step a) with the modification that the reaction was carried out for 1.5 hours, the oily substance was reacted with 2 N aqueous sodium hydroxide (300 µl) to obtain the title compound (Compound No. 229, 45 mg). Rf=0.38 (chloroform:methanol=10:1).

Example 230
Synthesis of 4-cyclohexylmethyloxy-3-(1H-indol-5-yl)benzaldehyde (Intermediate 56) (Preparation Method 6, Step d)

According to the procedure described in the synthesis method of Compound of Example 001 (Preparation Method 4, Step d-1) with the modifications that the reaction was carried out for 15.5 hours, and the purification was performed by flash column chromatography (hexane:ethyl acetate=4:1), Intermediate 25 (460 mg), 5-indoleboronic acid (445 mg), 2 M aqueous sodium carbonate (1.35 ml) and (Ph$_3$P)$_4$Pd (263 mg) were reacted and treated to obtain the title compound (Intermediate 56, 478 mg).

Synthesis of ethyl 3-[4-cyclohexylmethyloxy-3-(1H-indol-5-yl)phenyl]acrylate (Intermediate 57) (Preparation Method 6, Step k)

According to the procedure described in the synthesis method of Intermediate 38 in Example 65 (Preparation Method 6, Step k) with the modifications that the reaction was carried out for 1 hour, and the purification was performed by flash column chromatography (hexane:ethyl acetate=10:1), Intermediate 56 (468 mg), ethyl diethylphosphonoacetate (370 µl) and 60% sodium hydride (74 mg) were reacted and treated to obtain the title compound (Intermediate 57, 407 mg).

Synthesis of ethyl 3-[4-cyclohexylmethyloxy-3-(1H-indol-5-yl)phenyl]propionate (Compound No. 230) (Preparation Method 6, Step j)

According to the procedure described in the synthesis method of Compound of Example 065 (Preparation Method 6, Step j) with the modifications that the reaction was carried out for 1 hour, and the purification was performed by flash column chromatography (hexane:ethyl acetate=10:1), Intermediate 57 (301 mg) and 10% palladium carbon (40 mg) were reacted and treated to obtain the title compound (Compound No. 230, 287 mg).

Example 231
Synthesis of 3-[4-cyclohexylmethyloxy-3-(1H-indol-5-yl)phenyl]propionic acid (Compound No. 231) (Preparation Method 1, Step a)

According to the procedure described in the synthesis method of Compound of Example 002 (Preparation Method 1, Step a) with the modification that the reaction was carried out for 1 hour, Compound of Example 230 (268 mg) and 2 N aqueous sodium hydroxide (700 µl) were reacted and treated to obtain the title compound (Compound No. 231, 250 mg). Rf=0.50 (chloroform:methanol=10:1).

Example 232
Synthesis of methyl 3-[4-cyclohexylmethyloxy-3-(1-methyl-1H-indol-5-yl)phenyl]propionate (Compound No. 232) (Preparation Method 11, Step e)

A solution of Compound of Example 230 (238 mg) in DMF (5 ml) was added with 60% sodium hydride (84 mg) under ice cooling and stirred for 10 minutes. This mixture was added dropwise with methyl iodide (150 so 1), stirred for 10 minutes, then warmed to room temperature and further stirred for 2 hours. The reaction mixture was poured into ice water and added with ethyl acetate (100 ml) for extraction. The organic layer was washed successively with saturated aqueous sodium hydrogencarbonate, saturated aqueous ammonium chloride and saturated brine and dried, and then the solvent was evaporated under reduced pressure. The residue was purified by flash column chromatography (hexane:ethyl acetate=10:1) to obtain the title compound (Compound No. 232, 168 mg).

Example 233

Synthesis of 3-[4-cyclohexylmethyloxy-3-(1-methyl-1H-indol-5-yl)phenyl]propionic acid (Compound No. 233) (Preparation Method 1, Step a)

According to the procedure described in the synthesis method of Compound of Example 002 (Preparation Method 1, Step a) with the modification that the reaction was carried out for 2 hours, Compound of Example 232 (141 mg) and 2 N aqueous sodium hydroxide (360 µl) were reacted and treated to obtain the title compound (Compound No. 233, 126 mg). Rf=0.55 (chloroform:methanol=10:1).

Example 234

Synthesis of methyl 3-[4-cyclopentylmethyloxy-3-(1-methyl-1H-indol-5-yl)phenyl]propionate (Compound No. 234) (Preparation Method 11, Step e)

According to the procedure described in the synthesis method of Compound of Example 232 (Preparation Method 11, Step e) with the modifications that the reaction was carried out for 1 hour, and the purification was performed by flash column chromatography (hexane:ethyl acetate=8:1), Compound of Example 099 (123 mg), 60% sodium hydride (19 mg) and methyl iodide (100 µl) were reacted and treated to obtain the title compound (Compound No. 234, 126 mg).

Example 235

Synthesis of 3-[4-cyclopentylmethyloxy-3-(1-methyl-1H-indol-5-yl)phenyl]propionic acid (Compound No. 235) (Preparation Method 1, Step a)

According to the procedure described in the synthesis method of Compound of Example 002 (Preparation Method 1, Step a) with the modification that the reaction was carried out for 1 hour, Compound of Example 234 (123 mg) and 2 N aqueous sodium hydroxide (330 µl) were reacted and treated to obtain the title compound (Compound No. 233, 110 mg). Rf=0.54 (chloroform:methanol=10:1).

Example 236

Synthesis of 3-[4-cyclopentylmethyloxy-3-(1-ethyl-1H-indol-5-yl)phenyl]propionic acid (Compound No. 236) (Preparation Method 11, Step e and Preparation Method 1, Step a)

According to the procedure described in the synthesis method of Compound of Example 232 (Preparation Method 11, Step e) with the modifications that the reaction was carried out for 1 hour, and the purification was performed by column chromatography (Quad, hexane:ethyl acetate=7:1), Compound of Example 099 (110 mg), 60% sodium hydride (51 mg) and ethyl iodide (30 µl, TCI) were reacted and treated to obtain oily substance. According to the procedure described in the synthesis method of Compound of Example 002 (Preparation Method 1, Step a) with the modification that the reaction was carried out for 1.5 hours, the oily substance was reacted with 2 N aqueous sodium hydroxide (330 µl) and treated to obtain the title compound (Compound No. 236, 97 mg). Rf=0.56 (chloroform:methanol=10:1).

Example 237

Synthesis of Methyl 3-[4-cyclopentylmethyloxy-3-(1-isopropyl-1H-indol-5-yl)phenyl]propionate (Compound No. 237) (Preparation Method 11, Step e)

According to the procedure described in the synthesis method of Compound of Example 232 (Preparation Method 11, Step e) with the modifications that the reaction was carried out for 1.5 hours, and the purification was performed by flash column chromatography (hexane:ethyl acetate=4:1), Compound of Example 099 (152 mg), 60% sodium hydride (51 mg) and isopropyl iodide (120 µl, TCI) were reacted and treated to obtain the title compound (Compound No. 237, 115 mg).

Example 238

Synthesis of 3-[4-cyclopentylmethyloxy-3-(1-isopropyl-1H-indol-5-yl)phenyl]propionic acid (Compound No. 238) (Preparation Method 1, Step a)

According to the procedure described in the synthesis method of Compound of Example 002 (Preparation Method 1, Step a) with the modification that the reaction was carried out for 2 hours, Compound of Example 237 (111 mg) and 2 N aqueous sodium hydroxide (270 µl) were reacted and treated to obtain the title compound (Compound No. 238, 108 mg). Rf=0.61 (chloroform:methanol=10:1).

Example 239

Synthesis of Methyl 3-[3-(1-butyl-1H-indol-5-yl)-4-cyclopentylmethyloxyphenyl]propionate (Compound No. 239) (Preparation Method 11, Step e)

According to the procedure described in the synthesis method of Compound of Example 232 (Preparation Method 11, Step e) with the modifications that the reaction was carried out for 1.5 hours, and the purification was performed by flash column chromatography (hexane:ethyl acetate=4:1), Compound of Example 099 (143 mg), 60% sodium hydride (42 mg) and butyl iodide (140 µl, TCI) were reacted and treated to obtain the title compound (Compound No. 239, 134 mg).

Example 240

Synthesis of 3-[3-(1-butyl-1H-indol-5-yl)-4-cyclopentylmethyloxyphenyl]propionic acid (Compound No. 240) (Preparation Method 1, Step a)

According to the procedure described in the synthesis method of Compound of Example 002 (Preparation Method 1, Step a) with the modification that the reaction was carried out for 3 hours, Compound of Example 239 (128 mg) and 2 N aqueous sodium hydroxide (300 µl) were reacted and treated to obtain the title compound (Compound No. 240, 125 mg). Rf=0.68 (chloroform:methanol=10:1).

Example 241

Synthesis of Methyl 3-[3-(1-cyclopentyl-1H-indol-5-yl)-4-cyclopentylmethyloxyphenyl]propionate (Compound No. 241) (Preparation Method 11, Step e)

According to the procedure described in the synthesis method of Compound of Example 232 (Preparation Method 11, Step e) with the modifications that the reaction was carried out 7.5 hours, and the purification was performed by flash column chromatography (hexane:ethyl acetate=4:1), Compound of Example 099 (128 mg), 60% sodium hydride (45 mg) and bromocyclopentane (150 µl, TCI) were reacted and treated to obtain the title compound (Compound No. 241, 79 mg).

Example 242
Synthesis of 3-[3-(1-cyclopentyl-1H-indol-5-yl)-4-cyclopentylmethyloxyphenyl]propionic acid (Compound No. 242) (Preparation Method 1, Step a)

According to the procedure described in the synthesis method of Compound of Example 002 (Preparation Method 1, Step a) with the modification that the reaction was carried out for 2 hours, Compound of Example 241 (77 mg) and 2 N aqueous sodium hydroxide (200 µl) were reacted and treated to obtain the title compound (Compound No. 242, 74 mg). Rf=0.62 (chloroform:methanol=10:1).

Example 243
Synthesis of 3-{4-cyclopentylmethyloxy-3-[1-(2-hydroxyethyl)-1H-indol-5-yl]phenyl}propionic acid (Compound No. 243) (Preparation Method 11, Step e and Preparation Method 1, Step a)

According to the procedure described in the synthesis method of Compound of Example 232 (Preparation Method 11, Step e) with the modifications that the reaction was carried out for 1.5 hours, and the purification was performed by column chromatography (Quad, hexane:ethyl acetate=8:1), Compound of Example 099 (144 mg), 60% sodium hydride (38 mg) and ethyl bromoacetate (160 µl, TCI) were reacted and treated to obtain oily substance. According to the procedure described in the synthesis method of Compound of Example 002 (Preparation Method 1, Step a) with the modification that the reaction was carried out for 1 hour, the oily substance was reacted with 2 N aqueous sodium hydroxide (300 u 1) and treated to obtain the title compound (Compound No. 243, 36 mg). Rf=0.42 (chloroform:methanol=10:1).

Example 244
Synthesis of Methyl 3-[4-(t-butyldimethylsilyloxy)-3-(1-methyl-1H-indol-5-yl)-phenyl]propionate (Intermediate 58) (Preparation Method 11, Step e)

According to the procedure described in the synthesis method of Compound of Example 232 (Preparation Method 11, Step e) with the modifications that the reaction was carried out for 5.5 hours, and the purification was performed by column chromatography (Quad, hexane:ethyl acetate=8:1), Intermediate 54 (668 mg), 60% sodium hydride (113 mg) and methyl iodide (210 µl) were reacted and treated to obtain the title compound (Intermediate 58, 304 mg).

Synthesis of methyl 3-[4-hydroxy-3-(1-methyl-1H-indol-5-yl)phenyl]propionate (Intermediate 59) (Preparation Method 5, Step h)

According to the procedure described in the synthesis method of Intermediate 55 in Example 129 (Preparation Method 5, Step h) with the modifications that the reaction was carried out for 1 hour, and the purification was performed by column chromatography (Quad, hexane:ethyl acetate=6:1), Intermediate 58 (301 mg) and 1 M solution of tetrabutylammonium fluoride in THF (2.8 ml) were reacted and treated to obtain the title compound (Intermediate 59, 164 mg).

Synthesis of methyl 3-[4-(2-chlorophenylmethyloxy)-3-(1-methyl-1H-indol-5-yl)-phenyl]propionate (Compound No. 244) (Preparation Method 5, Step e-1)

According to the procedure described in the synthesis method of Compound of Example 030 (Preparation Method 5, Step e-1) with the modifications that the reaction was carried out for 12.5 hours, and the purification was performed by column chromatography (Quad, hexane:ethyl acetate=8:1), Intermediate 59 (87 mg), potassium carbonate (65 mg) and 2-chlorobenzyl chloride (60 µl, TCI) were reacted and treated to obtain the title compound (Compound No. 244, 85 mg).

Example 245
Synthesis of 3-[4-(2-chlorophenylmethyloxy)-3-(1-methyl-1H-indol-5-yl)phenyl]propionic acid (Compound No. 245) (Preparation Method 1, Step a)

According to the procedure described in the synthesis method of Compound of Example 002 (Preparation Method 1, Step a) with the modification that the reaction was carried out for 4 hours, Compound of Example 244 (84 mg) and 2 N aqueous sodium hydroxide (210 µl) were reacted and treated to obtain the title compound (Compound No. 245, 77 mg). Rf=0.54 (chloroform:methanol=10:1).

Example 246
Synthesis of 3-[4-cyclopentyloxy-3-(1-ethyl-1H-indol-5-yl)phenyl]propionic acid (Compound No. 246) (Preparation Method 11, Step e and Preparation Method 1, Step a)

According to the procedure described in the synthesis method of Compound of Example 232 (Preparation Method 11, Step e) with the modifications that the reaction was carried out for 1 hour, and the purification was performed by column chromatography (Quad, hexane:ethyl acetate=8:1), Compound of Example 101 (103 mg), 60% sodium hydride (36 mg) and ethyl iodide (60 µl) were reacted and treated to obtain oily substance. According to the procedure described in the synthesis method of Compound of Example 002 (Preparation Method 1, Step a) with the modification that the reaction was carried out for 1.5 hours, the oily substance was reacted with 2 N aqueous sodium hydroxide (300 µl) and treated to obtain the title compound (Compound No. 246, 70 mg). Rf=0.53 (chloroform:methanol=10:1).

Example 247
Synthesis of methyl 3-[4-(t-butyldimethylsilyloxy)-3-(1-ethyl-1H-indol-5-yl)phenyl]-propionate (Intermediate 60) (Preparation Method 11, Step e)

According to the procedure described in the synthesis method of Compound of Example 232 (Preparation Method 11, Step e) with the modifications that the reaction was carried out for 5.5 hours, and the purification was performed by column chromatography (Quad, hexane:ethyl acetate=8:1), Intermediate 54 (709 mg), 60% sodium hydride (122 mg) and ethyl iodide (220 µl) were reacted and treated to obtain the title compound (Intermediate 60, 374 mg).

Synthesis of methyl 3-[3-(1-ethyl-1H-indol-5-yl)-4-hydroxyphenyl]propionate (Intermediate 61) (Preparation Method 5, Step h)

According to the procedure described in the synthesis method of Intermediate 55 in Example 129 (Preparation Method 5, Step h) with the modifications that the reaction was carried out for 1 hour, and the purification was performed by column chromatography (Quad, hexane:ethyl acetate=6:1), Intermediate 60 (372 mg) and 1 M solution of tetrabutylammonium fluoride in THF (3.4 ml) were reacted and treated to obtain the title compound (Intermediate 61, 272 mg).

Synthesis of methyl 3-[4-cyclohexyloxy-3-(1-ethyl-1H-indol-5-yl)phenyl]propionate (Compound No. 247) (Preparation Method 5, Step e-2)

According to the procedure described in the synthesis method of Compound of Example 038 (Preparation Method 5, Step e-2) with the modifications that the reaction was carried out for 12 hours, and the purification was performed by flash column chromatography (hexane:isopropyl ether=8:1), Intermediate 61 (87 mg), Ph$_3$P (184 mg), cyclohexyl alcohol (60 µl) and 40% DIAD (320 µl) were reacted and treated to obtain the title compound (Compound No. 247, 45 mg).

Example 248

Synthesis of 3-[4-cyclohexyloxy-3-(1-ethyl-1H-indol-5-yl) phenyl]propionic acid (Compound No. 248) (Preparation Method 1, Step a)

According to the procedure described in the synthesis method of Compound of Example 002 (Preparation Method 1, Step a) with the modification that the reaction was carried out for 4 hours, Compound of Example 247 (42 mg) and 2 N aqueous sodium hydroxide (130 µl) were reacted and treated to obtain the title compound (Compound No. 248, 40 mg). Rf=0.53 (chloroform:methanol=10:1).

Example 249

Synthesis of methyl 3-[4-(2-chlorophenylmethyloxy)-3-(1-ethyl-1H-indol-5-yl)phenyl]propionate (Compound No. 249) (Preparation Method 5, Step e-1)

According to the procedure described in the synthesis method of Compound of Example 030 (Preparation Method 5, Step e-1) with the modifications that the reaction was carried out for 12.5 hours, and the purification was performed by column chromatography (Quad, hexane:ethyl acetate=8:1), Intermediate 61 (87 mg), potassium carbonate (65 mg) and 2-chlorobenzyl chloride (60 µl, TCI) were reacted and treated to obtain the title compound (Compound No. 249, 85 mg).

Example 250

Synthesis of 3-[4-(2-chlorophenylmethyloxy)-3-(1-ethyl-1H-indol-5-yl)phenyl]propionic acid (Compound No. 250) (Preparation Method 1, Step a)

According to the procedure described in the synthesis method of Compound of Example 002 (Preparation Method 1, Step a) with the modification that the reaction was carried out for 4 hours, Compound of Example 249 (84 mg) and 2 N aqueous sodium hydroxide (210 µl) were reacted and treated to obtain the title compound (Compound No. 250, 76 mg). Rf=0.58 (chloroform:methanol=10:1).

Example 251

Synthesis of methyl 3-[4-cyclopentylmethyloxy-3-(1,3-dimethyl-1H-indol-5-yl)phenyl]propionate (Compound No. 251) (Preparation Method 11, Step e)

According to the procedure described in the synthesis method of Compound of Example 232 (Preparation Method 11, Step e) with the modifications that the reaction was carried out for 2.5 hours, and the purification was performed by flash column chromatography (hexane:ethyl acetate=4:1), Compound of Example 111 (157 mg), 60% sodium hydride (43 mg) and methyl iodide (80 µl, TCI) were reacted and treated to obtain the title compound (Compound No. 251, 118 mg).

Example 252

Synthesis of 3-[4-cyclopentylmethyloxy-3-(1,3-dimethyl-1H-indol-5-yl)phenyl]propionic acid (Compound No. 252) (Preparation Method 1, Step a)

According to the procedure described in the synthesis method of Compound of Example 002 (Preparation Method 1, Step a) with the modification that the reaction was carried out for 2 hours, Compound of Example 251 (30 mg) and 2 N aqueous sodium hydroxide (80 µl) were reacted and treated to obtain the title compound (Compound No. 252, 28 mg). Rf=0.61 (chloroform:methanol=10:1).

Example 253

Synthesis of methyl 3-[4-cyclopentylmethyloxy-3-(3-formyl-1H-indol-5-yl)phenyl]propionate (Compound No. 253) (Preparation Method 12, Step p-2)

A solution of Compound of Example 099 (75 mg) in DMF (6 ml) was added dropwise with phosphoryl chloride (30 µl, TCI) under ice cooling, stirred for 1 hour, then heated to 35° C. and further stirred for 1 hour. The reaction mixture was added with 1 N aqueous sodium hydroxide (3 ml) containing ice and extracted with ethyl acetate (90 ml). The organic layer was washed with saturated brine and dried, and then the solvent was evaporated under reduced pressure. The residue was purified by flash column chromatography (hexane:ethyl acetate=5:1) to obtain the title compound (Compound No. 253, 86 mg).

Example 254

Synthesis of 3-[4-cyclopentylmethyloxy-3-(3-formyl-1H-indol-5-yl)phenyl]propionic acid (Compound No. 254) (Preparation Method 1, Step a)

According to the procedure described in the synthesis method of Compound of Example 002 (Preparation Method 1, Step a) with the modification that the reaction was carried out for 3 hours, Compound of Example 253 (86 mg) and 2 N aqueous sodium hydroxide (110 µl) were reacted and treated to obtain the title compound (Compound No. 254, 60 mg). Rf=0.32 (chloroform:methanol=10:1).

Example 255

Synthesis of 3-[4-cyclopentylmethyloxy-3-(3-formyl-1-methyl-1H-indol-5-yl)phenyl]propionic acid (Compound No. 255) (Preparation Method 11, Step e and Preparation Method 1, Step a)

According to the procedure described in the synthesis method of Compound of Example 232 (Preparation Method 11, Step e) with the modifications that the reaction was carried out for 1 hour, and the purification was performed by column chromatography (Quad, hexane:ethyl acetate=6:1), Compound of Example 253 (63 mg), 60% sodium hydride (15 mg) and methyl iodide (40 µl) were reacted and treated to obtain oily substance. According to the procedure described in the synthesis method of Compound of Example 002 (Preparation Method 1, Step a) with the modification that the reaction was carried out for 2 hours, the oily substance was reacted with 2 N aqueous sodium hydroxide (100 µl) and treated to obtain the title compound (Compound No. 255, 18 mg). Rf=0.47 (chloroform:methanol=10:1).

Example 256

Synthesis of methyl 3-[3-(3-acetyl-1H-indol-5-yl)-4-cyclopentylmethyloxyphenyl]-propionate (Compound No. 256) (Preparation Method 12, Step p-1)

A solution of Compound of Example 099 (98 mg) in methylene chloride (2 ml) was added with aluminum chloride (81 mg, Ald) and acetyl chloride (60 µl, WAKO) and stirred for 4 hours. The reaction mixture was added with 1 N hydrochloric acid (2 ml) and extracted with methylene chloride (60 ml). The organic layer was washed with saturated brine and dried, and then the solvent was evaporated under reduced pressure. The residue was purified by flash column chromatography (hexane:ethyl acetate=4:1) to obtain the title compound (Compound No. 256, 47 mg).

Example 257

Synthesis of 3-[3-(3-acetyl-1H-indol-5-yl)-4-cyclopentylmethyloxyphenyl]propionic acid (Compound No. 257) (Preparation Method 1, Step a)

According to the procedure described in the synthesis method of Compound of Example 002 (Preparation Method 1, Step a) with the modification that the reaction was carried out for 4 hours, Compound of Example 256 (45 mg) and 2 N aqueous sodium hydroxide (110 μl) were reacted and treated to obtain the title compound (Compound No. 257, 44 mg). Rf=0.32 (chloroform:methanol=10:1).

Example 258

Synthesis of methyl 3-[3-(3-acetyl-1-methyl-1H-indol-5-yl)-4-cyclopentylmethyloxyphenyl]propionate (Compound No. 258) (Preparation Method 12, Step p-1)

According to the procedure described in the synthesis method of Compound of Example 256 (Preparation Method 12, Step p-1) with the modifications that the reaction was carried out for 3 hours, and the purification was performed by flash column chromatography (hexane:ethyl acetate= 4:1), Compound of Example 234 (96 mg), aluminum chloride (92 mg) and acetyl chloride (52 μl) were reacted and treated to obtain the title compound (Compound No. 258, 85 mg).

Example 259

Synthesis of 3-[3-(3-acetyl-1-methyl-1H-indol-5-yl)-4-cyclopentylmethyloxyphenyl]propionic acid (Compound No. 259) (Preparation Method 1, Step a)

According to the procedure described in the synthesis method of Compound of Example 002 (Preparation Method 1, Step a) with the modification that the reaction was carried out for 3 hours, Compound of Example 258 (84 mg) and 2 N aqueous sodium hydroxide (200 μl) were reacted and treated to obtain the title compound (Compound No. 259, 71 mg). Rf=0.51 (chloroform:methanol=10:1).

Example 260

Synthesis of methyl 3-[4-cyclopentylmethyloxy-3-fluoro-5-(1H-indol-5-yl)phenyl]propionate (Compound No. 260) (Preparation Method 4, Step d-1)

According to the procedure described in the synthesis method of Compound of Example 001 (Preparation Method 4, Step d-1) with the modifications that the reaction was carried out for 13 hours, and the purification was performed by column chromatography (Quad, hexane:ethyl acetate= 10:1), Intermediate 23 (154 mg), 5-indoleboronic acid (100 mg), 2 M aqueous sodium carbonate (1.5 ml) and $(Ph_3P)_4Pd$ (50 mg) were reacted and treated to obtain the title compound (Compound No. 260, 125 mg).

Example 261

Synthesis of 3-[4-cyclopentylmethyloxy-3-fluoro-5-(1H-indol-5-yl)phenyl]propionic acid (Compound No. 261) (Preparation Method 1, Step a)

According to the procedure described in the synthesis method of Compound of Example 002 (Preparation Method 1, Step a) with the modification that the reaction was carried out for 2 hours, Compound of Example 260 (124 mg) and 2 N aqueous sodium hydroxide (630 μl) were reacted and treated to obtain the title compound (Compound No. 261, 97 mg). Rf=0.31 (chloroform:methanol=10:1).

Example 262

Synthesis of methyl 3-[3-chloro-4-cyclopentylmethyloxy-5-(1H-indol-5-yl)phenyl]propionate (Compound No. 262) (Preparation Method 4, Step d-1)

According to the procedure described in the synthesis method of Compound of Example 001 (Preparation Method 4, Step d-1) with the modifications that the reaction was carried out for 13 hours, and the purification was performed by column chromatography (Quad, hexane:ethyl acetate= 10:1), Intermediate 16 (151 mg), 5-indoleboronic acid (97 mg), 2 M aqueous sodium carbonate (1.5 ml) and $(Ph_3P)_4Pd$ (46 mg) were reacted and treated to obtain the title compound (Compound No. 262, 160 mg).

Example 263

Synthesis of 3-[3-chloro-4-cyclopentylmethyloxy-5-(1H-indol-5-yl)phenyl]propionic acid (Compound No. 263) (Preparation Method 1, Step a)

According to the procedure described in the synthesis method of Compound of Example 002 (Preparation Method 1, Step a) with the modification that the reaction was carried out for 2 hours, Compound of Example 262 (135 mg) and 2 N aqueous sodium hydroxide (660 μl) were reacted and treated to obtain the title compound (Compound No. 263, 97 mg). Rf=0.33 (chloroform:methanol=10:1).

Example 264

Synthesis of methyl 3-[4-cyclopentylmethyloxy-3-(1H-indol-5-yl)-5-nitrophenyl]-propionate (Compound No. 264) (Preparation Method 4, Step d-1)

According to the procedure described in the synthesis method of Compound of Example 001 (Preparation Method 4, Step d-1) with the modifications that the reaction was carried out for 16 hours, and the purification was performed by column chromatography (Quad, hexane:ethyl acetate= 5:1), Intermediate 14 (535 mg), 5-indoleboronic acid (446 mg), 2 M aqueous sodium carbonate (1.00 ml) and $(Ph_3P)_4Pd$ (160 mg) were reacted and treated to obtain the title compound (Compound No. 264, 568 mg).

Example 265

Synthesis of methyl 3-[3-amino-4-cyclopentylmethyloxy-5-(1H-indol-5-yl)phenyl]propionate (Compound No. 265) (Preparation Method 2, Step b)

According to the procedure described in the synthesis method of Compound of Example 094 (Preparation Method 2, Step b) with the modifications that the reaction was carried out for 20 hours, and the purification was performed by column chromatography (Quad, hexane:ethyl acetate= 5:1), Compound of Example 264 (557 mg), diisopropylethylamine (1120 μl) and tin(II) chloride dihydrate (1.49 g) were reacted and treated to obtain the title compound (Compound No. 265, 246 mg).

Example 266

Synthesis of 3-[3-amino-4-cyclopentylmethyloxy-5-(1H-indol-5-yl)phenyl]propionic acid (Compound No. 266) (Preparation Method 1, Step a)

According to the procedure described in the synthesis method of Compound of Example 002 (Preparation Method 1, Step a) with the modification that the reaction was carried out for 1.5 hours, Compound of Example 265 (210 mg) and 2 N aqueous sodium hydroxide (600 μl) were reacted and treated to obtain the title compound (Compound No. 266, 188 mg). Rf=0.40 (chloroform:methanol=10:1).

Example 267

Synthesis of methyl 3-[4-cyclopentylmethyloxy-3-(1-methyl-1H-indol-5-yl)-5-nitrophenyl]propionate (Compound No. 267) (Preparation Method 11, Step e)

According to the procedure described in the synthesis method of Compound of Example 232 (Preparation Method 11, Step e) with the modifications that the reaction was carried out for 1 hour, and the purification was performed by column chromatography (Quad, hexane:ethyl acetate=5:1), Compound of Example 264 (434 mg), 60% sodium hydride (45 mg) and methyl iodide (192 μl, TCI) were reacted and treated to obtain the title compound (Compound No. 267, 418 mg).

Example 268
Synthesis of methyl 3-[3-amino-4-cyclopentylmethyloxy-5-(1-methyl-1H-indol-5-yl)phenyl]propionate (Compound No. 268) (Preparation Method 2, Step b)

According to the procedure described in the synthesis method of the compound 094 in Example 94 (Preparation Method 2, Step b) with the modifications that the reaction was carried out for 20 hours, and the purification was performed by column chromatography (Quad, hexane:ethyl acetate=5:1), Compound of Example 267 (400 mg), diisopropylethylamine (780 µl) and tin(II) chloride dihydrate (1.03 g) were reacted and treated to obtain the title compound (Compound No. 268, 239 mg).

Example 269
Synthesis of 3-[3-amino-4-cyclopentylmethyloxy-5-(1-methyl-1H-indol-5-yl)phenyl]propionic acid (Compound No. 269) (Preparation Method 1, Step a)

According to the procedure described in the synthesis method of Compound of Example 002 (Preparation Method 1, Step a) with the modification that the reaction was carried out for 2 hours, Compound of Example 268 (210 mg) and 2 N aqueous sodium hydroxide (600 µl) were reacted and treated to obtain the title compound (Compound No. 269, 197 mg). Rf=0.45 (chloroform:methanol=10:1).

Example 270
Synthesis of methyl 4-[4-cyclopentylmethyloxy-3-(1H-indol-5-yl)phenyl]butyrate (Compound No. 270) (Preparation Method 4, Step d-1)

According to the procedure described in the synthesis method of Compound of Example 001 (Preparation Method 4, Step d-1) with the modifications that the reaction was carried out for 18 hours, and the purification was performed by column chromatography (Quad, hexane:ethyl acetate=6:1), Intermediate 13 (355 mg), 5-indoleboronic acid (322 mg), 2 M aqueous sodium carbonate (1.10 ml) and $(Ph_3P)_4Pd$ (115 mg) were reacted and treated to obtain the title compound (Compound No. 270, 344 mg).

Example 271
Synthesis of 4-[4-cyclopentylmethyloxy-3-(1H-indol-5-yl)phenyl]butyrate (Compound No. 271) (Preparation Method 1, Step a)

According to the procedure described in the synthesis method of Compound of Example 002 (Preparation Method 1, Step a) with the modification that the reaction was carried out for 3.5 hours, Compound of Example 270 (334 mg) and 2 N aqueous sodium hydroxide (1.0 ml) were reacted and treated to obtain the title compound (Compound No. 271, 304 mg). Rf=0.24 (chloroform:methanol=50:1).

Example 272
Synthesis of methyl 3-[4-cyclohexylmethyloxy-3-(2,3-dimethyl-1H-indol-5-yl)phenyl]-propionate (Compound No. 272) (Preparation Method 4, Step d-1)

According to the procedure described in the synthesis method of Compound of Example 011 (Preparation Method 4, Step d-1) with the modifications that the reaction was carried out for 18 hours, and the purification was performed by flash column chromatography (hexane:ethyl acetate=5:1), 5-bromo-2,3-dimethylindole (295 mg) obtained by a method known from a reference [T. Wagner-Jauregg et al., Justus Liebigs Ann. Chem., p.30, 1963] was reacted with 30% potassium hydride (240 mg), 1.7 M solution of t-butyllithium in pentane (1.75 ml) and $(^iPrO)_3B$ (690 µl) and treated to prepare crude 2,3-dimethyl-5-indoleboronic acid, and the above product was reacted with Intermediate 7 (150 mg), 2 M aqueous sodium carbonate (0.50 ml) and $(Ph_3P)_4Pd$ (55 mg) and treated to obtain the title compound (Compound No. 272, 67 mg).

Example 273
Synthesis of 3-[4-cyclohexylmethyloxy-3-(2,3-dimethyl-1H-indol-5-yl)phenyl]propionic acid (Compound No. 273) (Preparation Method 1, Step a)

According to the procedure described in the synthesis method of Compound of Example 002 (Preparation Method 1, Step a) with the modification that the reaction was carried out for 2.5 hours, Compound of Example 272 (62 mg) and 2 N aqueous sodium hydroxide (300 µl) were reacted and treated to obtain the title compound (Compound No. 273, 55 mg). Rf=0.54 (chloroform:methanol=10:1).

Example 274
Synthesis of methyl 3-[4-cyclopentylmethyloxy-3-(1,2,3-trimethyl-1H-indol-5-yl)phenyl]propionate (Compound No. 274)

According to a method described in a reference [J-Y. Merour et al., Synthetic Communications, vol. 26, p.3267, 1996], a solution of Compound of Example 251 (89 mg) in anhydrous THF (6 ml) was cooled to −78° C., added with 2 M solution of lithium diisopropylamide (LDA) in heptane/THF/ethyl benzene (145 µl, Ald) and methyl iodide (50 µl), stirred for 20 minutes, then warmed to room temperature and further stirred for 2 hours. The reaction mixture was added with water (2 ml) and extracted with ethyl acetate (90 ml). The organic layer was washed with saturated brine and dried, and then the solvent was evaporated under reduced pressure. The residue was purified by flash column chromatography (hexane:ethyl acetate=8:1) to obtain the title compound (Compound No. 274, 71 mg).

Example 275
Synthesis of 3-[4-cyclopentylmethyloxy-3-(1,2,3-trimethyl-1H-indol-5-yl)phenyl]propionic acid (Compound No. 275) (Preparation Method 1, Step a)

According to the procedure described in the synthesis method of Compound of Example 002 (Preparation Method 1, Step a) with the modification that the reaction was carried out for 3.5 hours, Compound of Example 274 (70 mg) and 2 N aqueous sodium hydroxide (240 µl) were reacted and treated to obtain the title compound (Compound No. 275, 66 mg). Rf=0.70 (chloroform:methanol=10:1).

Example 276
Synthesis of methyl 3-[3-(benzo[b]furan-5-yl)-4-cyclopentylmethyloxyphenyl]-propionate (Compound No. 276) (Preparation Method 4, Step d-1)

According to the procedure described in the synthesis method of Compound of Example 019 (Preparation Method 4, Step d-1) with the modification that the purification was performed by column chromatography (Quad, hexane:ethyl acetate=10:1), Intermediate 7 (171 mg), bispinacolate diboron (138 mg), $PdCl_2(dppf)$ (31 mg) and potassium acetate (144 mg) were reacted at 80° C. for 10 hours, and then the reaction mixture was added with 5-bromobenzo[b]furan (176 mg) obtained from 4-bromophenol (TCI) by a method known from a reference [A. S. Tasker et al., Journal of Medicinal Chemistry (J. Med. Chem.), vol. 40, p.322, 1997], $PdCl_2(dppf)$ (31 mg) and 2 M aqueous sodium carbonate (0.5 ml) and reacted at 80° C. for 14 hours and treated to obtain the title compound (Compound No. 276, 31 mg).

Example 277
Synthesis of 3-[3-(benzo[b]furan-5-yl)-4-cyclopentylmethyloxyphenyl]propionic acid (Compound No. 277) (Preparation Method 1, Step a)

According to the procedure described in the synthesis method of Compound of Example 002 (Preparation Method 1, Step a) with the modification that the reaction was carried out for 3 hours, Compound of Example 276 (27 mg) and 2 N aqueous sodium hydroxide (100 µl) were reacted and treated to obtain the title compound (Compound No. 277, 25 mg). Rf=0.51 (chloroform:methanol=10:1).

Example 278
Synthesis of methyl 3-[4-cyclohexylmethyloxy-3-(2,3-dimethylbenzo[b]furan-5-yl)phenyl]propionate (Compound No. 278) (Preparation Method 4, Step d-1)

According to the procedure described in the synthesis method of Compound of Example 019 (Preparation Method 4, Step d-1) with the modification that the purification was performed by column chromatography (Quad, hexane:ethyl acetate 10:1), Intermediate 7 (395 mg), bispinacolate diboron (300 mg), PdCl$_2$(dppf) (69 mg) and potassium acetate (310 mg) were reacted at 80° C. for 10 hours, and then the reaction mixture was added with 5-bromo-2,3-dimethylbenzo[b]furan (300 mg) obtained from 4-bromophenol (TCI) by a method known from a reference [E. Bisagni et al., Bulletin de la Societe Chimique France, p.1466, 1965], PdCl$_2$(dppf) (67 mg) and 2 M aqueous sodium carbonate (0.9 ml), reacted at 80° C. for 16 hours and treated to obtain the title compound (Compound No. 278, 111 mg).

Example 279
Synthesis of 3-[4-cyclohexylmethyloxy-3-(2,3-dimethylbenzo[b]furan-5-yl)phenyl]propionic acid (Compound No. 279) (Preparation Method 1, Step a)

According to the procedure described in the synthesis method of Compound of Example 002 (Preparation Method 1, Step a) with the modification that the reaction was carried out for 2 hours, Compound of Example 278 (106 mg) and 2 N aqueous sodium hydroxide (100 µl) were reacted and treated to obtain the title compound (Compound No. 279, 96 mg). Rf=0.61 (chloroform:methanol=10:1).

Example 280
Synthesis of methyl 3-[3-(benzo[b]thiophen-5-yl)-4-cyclopentylmethyloxyphenyl]-propionate (Compound No. 280) (Preparation Method 4, Step d-1)

According to the procedure described in the synthesis method of Compound of Example 019 (Preparation Method 4, Step d-1) with the modification that the purification was performed by column chromatography (Quad, hexane:ethyl acetate=10:1), Intermediate 3 (371 mg), bispinacolate diboron (294 mg), PdCl$_2$(dppf) (67 mg) and potassium acetate (308 mg) were reacted at 80° C. for 10 hours, and then the reaction mixture was added with 5-bromobenzo[b]thiophene (301.4 mg) obtained from 4-bromothiophenol (TCI) by a method known from a reference [A. J. Seed et al., Journal of Materials Chemistry (J. Mater. Chem.), vol. 10, p.2069, 2000], PdCl$_2$(dppf) (65 mg) and 2 M aqueous sodium carbonate (0.9 ml), reacted at 80° C. for 16 hours and treated to obtain the title compound (Compound No. 280, 97 mg).

Example 281
Synthesis of 3-[3-(benzo[b]thiophen-5-yl)-4-cyclopentylmethyloxyphenyl]propionic acid (Compound No. 281) (Preparation Method 1, Step a)

According to the procedure described in the synthesis method of Compound of Example 002 (Preparation Method 1, Step a) with the modification that the reaction was carried out for 3 hours, Compound of Example 280 (95 mg) and 2 N aqueous sodium hydroxide (250 u 1) were reacted and treated to obtain the title compound (Compound No. 281, 93 mg). Rf=0.51 (chloroform:methanol=10:1).

Example 282
Synthesis of methyl 3-[4-cyclopentylmethyloxy-3-(2-methylbenzothiazol-5-yl)phenyl]propionate (Compound No. 282) (Preparation Method 4, Step d-1)

According to the procedure described in the synthesis method of the compound 011 in Example 11 (Preparation Method 4, Step d-1) with the modifications that the reaction was carried out for 13 hours, and the purification was performed by flash column chromatography (hexane:ethyl acetate=5:1), crude 2-methyl-5-benzothiazoleboronic acid prepared from 5-bromo-2-methylbenzothiazole (684 mg, TCI), 1.7 M solution of t-butyllithium in pentane (7.06 ml) and ($^i$PrO)$_3$B (3.46 ml) was reacted with Intermediate 3 (515 mg), 2 M aqueous sodium carbonate (6.5 ml) and (Ph$_3$P)$_4$Pd (258 mg) and treated to obtain the title compound (Compound No. 282, 240 mg).

Example 283
Synthesis of 3-[4-cyclopentylmethyloxy-3-(2-methylbenzothiazol-5-yl)phenyl]propionic acid (Compound No. 283) (Preparation Method 1, Step a)

According to the procedure described in the synthesis method of Compound of Example 002 (Preparation Method 1, Step a) with the modification that the reaction was carried out for 4 hours, Compound of Example 282 (227 mg) and 2 N aqueous sodium hydroxide (1.11 ml) were reacted and treated to obtain the title compound (Compound No. 283, 132 mg). Rf=0.51 (chloroform:methanol=10:1).

Example 284
Synthesis of (3-bromophenyl)thiourea (Intermediate 62)

A solution of 3-bromoaniline (10.89 ml, TCI) in 20% aqueous hydrochloric acid (18.2 ml) was added with ammonium thiocyanate (8.02 g, WAKO) and sodium hydrogensulfite (701 mg, WAKO) and stirred at 100° C. for 22 hours. The reaction mixture was added with chloroform (20 ml) for extraction. The organic layer was dried, and then the solvent was evaporated under reduced pressure. The residue was purified by column chromatography (Quad, hexane:ethyl acetate=2:1) to obtain the title compound (Intermediate 62, 4.45 g).

Synthesis of 2-amino-5-bromobenzothiazole (Intermediate 63)

A solution of Intermediate 62 (1.29 g) in chloroform (12 ml) was added dropwise with a solution of bromine (272 µl, WAKO) in chloroform (1.5 ml), refluxed with heating for 2.5 hours and then stirred at room temperature for 16 hours. The reaction mixture was concentrated under reduced pressure, neutralized with 5% aqueous ammonia and then added with water (50 ml) and methylene chloride (150 ml) for extraction. The organic layer was dried, and then the solvent was evaporated under reduced pressure. The residue was purified by column chromatography (Quad, hexane:ethyl acetate=2:1) to obtain the title compound (Intermediate 63, 609 mg).

Synthesis of methyl 3-[3-(2-aminobenzothiazol-5-yl)-4-cyclopentylmethyloxyphenyl]-propionate (Compound No. 284) (Preparation Method 4, Step d-1)

A solution of Intermediate 63 (459.1 mg) in anhydrous THF (30 ml) was added with N,N,N',N'-tetramethylethylenediamine (1.51 ml, WAKO), cooled to −78° C. under argon atmosphere, then added dropwise with 1.62 M solution of t-butyllithium in pentane (7.06 ml) and stirred for 30 minutes. The reaction mixture was added dropwise with ($^i$PrO)$_3$B (2.77 ml), stirred for 30 minutes, then warmed to room temperature and further stirred for 1.5 hours. The reaction mixture was added with 0.5 M aqueous sulfuric acid (7.5 mL) and extracted with diethyl ether (50 ml×3). The organic layer was washed with saturated brine and dried, and then the solvent was evaporated under reduced pressure to obtain crude 2-amino-5-benzothiazoleboronic acid. According to the procedure described in the synthesis method of Compound of Example 001 (Preparation Method 4, Step d-1) with the modifications that the reaction was carried out for 12 hours, and the purification was performed by flash column chromatography (hexane:ethyl acetate=2:1), the above compound was reacted with Intermediate 3 (344 mg), 2 M aqueous sodium carbonate (4.5 ml) and (Ph$_3$P)$_4$Pd (179 mg) and treated to obtain the title compound (Compound No. 284, 76 mg).

Example 285

Synthesis of 3-[3-(2-aminobenzothiazol-5-yl)-4-cyclopentylmethyloxyphenyl]propionic acid (Compound No. 285) (Preparation Method 1, Step a)

According to the procedure described in the synthesis method of Compound of Example 002 (Preparation Method 1, Step a) with the modification that the reaction was carried out for 2.5 hours, Compound of Example 284 (77 mg) and 2 N aqueous sodium hydroxide (380 µl) were reacted and treated to obtain the title compound (Compound No. 285, 69 mg). Rf=0.23 (chloroform:methanol=10:1).

Example 286

Synthesis of ethyl 3-(4'-amino-2-cyclopentylmethyloxybiphenyl-5-yl)propionate (Intermediate 64) (Preparation Method 8, Step d-1)

According to the procedure described in the synthesis method of Intermediate 6 in Reference Example 2 (Step c), Intermediate 5 was reacted with thionyl chloride in ethanol and treated to obtain ethyl 3-(3-bromo-4-hydroxyphenyl)propionate. According to the procedure described in the synthesis method of Compound of Example 001 (Preparation Method 4, Step d-1) with the modifications that the reaction was carried out for 18 hours, and the purification was performed by flash column chromatography (hexane:ethyl acetate=7:1), ethyl 3-(3-bromo-4-cyclopentylmethyloxyphenyl)propionate (2.40 g) obtained by reacting and treating the above product according to the procedure described in the synthesis method of Intermediate 2 in Reference Example 1 (Step e-1) was reacted with 4-(4,4,5,5-tetramethyl-1,3,2-dioxaborolan-2-yl)aniline (2.31 g, Ald), 2 M aqueous sodium carbonate (5.4 ml) and (Ph$_3$P)$_4$Pd (600 mg) to obtain the title compound (Intermediate 64, 1.65 g).

Synthesis of ethyl 3-[3-(2-aminobenzothiazol-6-yl)-4-cyclopentylmethyloxyphenyl]-propionate (Compound No. 286) (Preparation Method 8, Step n)

A solution of Intermediate 64 (1.41 g) and potassium thiocyanate (1.50 g) in acetic acid (15 ml) was added dropwise with a solution of bromine (236 µl) in acetic acid (5 ml) and stirred for 22 hours. The reaction mixture was poured into ice water (100 ml), neutralized with 25% aqueous ammonia (25 ml) and added with ethyl acetate (250 ml) for extraction. The organic layer was washed with saturated brine and dried, and then the solvent was evaporated under reduced pressure. The residue was purified by column chromatography (Quad, hexane:ethyl acetate=2:1) to obtain the title compound (Compound No. 286, 1.47 g).

Example 287

Synthesis of 3-[3-(2-aminobenzothiazol-6-yl)-4-cyclopentylmethyloxyphenyl]propionic acid (Compound No. 287) (Preparation Method 1, Step a)

According to the procedure described in the synthesis method of Compound of Example 002 (Preparation Method 1, Step a) with the modification that the reaction was carried out for 18.5 hours, Compound of Example 286 (96 mg) and 2 N aqueous sodium hydroxide (470 µl) were reacted and treated to obtain the title compound (Compound No. 287, 52 mg). Rf=0.26 (chloroform:methanol=10:1).

Example 288

Synthesis of methyl 3-(4'-amino-2-cyclopentylmethyloxybiphenyl-5-yl)propionate (Intermediate 65) (Preparation Method 8, Step d-1)

According to the procedure described in the synthesis method of Compound of Example 001 (Preparation Method 4, Step d-1) with the modifications that the reaction was carried out for 16.5 hours, and the purification was performed by column chromatography (Quad, hexane:ethyl acetate=6:1), Intermediate 7 (397 mg), 4-(4,4,5,5-tetramethyl-1,3,2-dioxaborolan-2-yl)aniline (370 mg), 2 M aqueous sodium carbonate (0.9 ml) and (Ph$_3$P)$_4$Pd (106 mg) were reacted and treated to obtain the title compound (Intermediate 65, 290 mg).

Synthesis of methyl 3-[3-(2-aminobenzothiazol-6-yl)-4-cyclohexylmethyloxyphenyl]-propionate (Compound No. 288) (Preparation Method 8, Step n)

According to the procedure described in the synthesis method of Compound of Example 286 (Preparation Method 8, Step n) with the modifications that the reaction was carried out for 24 hours, and the purification was performed by column chromatography (Quad, hexane:ethyl acetate=2:1), Intermediate 65 (266 mg), potassium thiocyanate (293 mg) and bromine (38 µl) were reacted and treated to obtain the title compound (Compound No. 288, 258 mg).

Example 289

Synthesis of 3-[3-(2-aminobenzothiazol-6-yl)-4-cyclohexylmethyloxyphenyl]propionic acid (Compound No. 289) (Preparation Method 1, Step a)

According to the procedure described in the synthesis method of Compound of Example 002 (Preparation Method 1, Step a) with the modification that the reaction was carried out for 1 hour, Compound of Example 288 (102 mg) and 2 N aqueous sodium hydroxide (480 µl) were reacted and treated to obtain the title compound (Compound No. 289, 91 mg). Rf=0.27 (chloroform:methanol=10:1).

Example 290

Synthesis of ethyl 3-(4'-amino-2-butyloxybiphenyl-5-yl)propionate (Intermediate 65) (Preparation Method 8, Step d-1)

According to the procedure described in the synthesis method of the compound 036 in Example 36 (Preparation Method 5, Step e-1), ethyl 3-(3-bromo-4-hydroxyphenyl)propionate and 1-iodobutane were reacted and treated to obtain ethyl 3-(3-bromo-4-butyloxyphenyl)propionate (400 mg). According to the procedure described in the synthesis method of Compound of Example 001 (Preparation Method 4, Step d-1) with the modifications that the reaction was carried out for 16 hours, and the purification was performed by flash column chromatography (hexane:ethyl acetate=8:1), the above product was reacted with 4-(4,4,5,5-tetramethyl-1,3,2-dioxaborolan-2-yl)aniline (360 mg), 2 M aqueous sodium carbonate (0.9 ml) and (Ph$_3$P)$_4$Pd (110 mg) and treated to obtain the title compound (Intermediate 66, 270 mg).

Synthesis of ethyl 3-[3-(2-aminobenzothiazol-6-yl)-4-butyloxyphenyl]propionate (Compound No. 290) (Preparation Method 8, Step n)

According to the procedure described in the synthesis method of Compound of Example 286 (Preparation Method 8, Step n) with the modifications that the reaction was carried out for 12 hours, and the purification was performed by column chromatography (Quad, hexane:ethyl acetate= 9:5), Intermediate 66 (250 mg), potassium thiocyanate (285 mg) and bromine (38 µl) were reacted and treated to obtain the title compound (Compound No. 290, 204 mg).

Example 291

Synthesis of 3-[3-(2-aminobenzothiazol-6-yl)-4-butyloxyphenyl]propionic acid (Compound No. 290) (Preparation Method 1, Step a)

According to the procedure described in the synthesis method of Compound of Example 002 (Preparation Method 1, Step a) with the modification that the reaction was carried out for 1 hour, Compound of Example 290 (193 mg) and 2 N aqueous sodium hydroxide (1.00 ml) were reacted and treated to obtain the title compound (Compound No. 291, 159 mg). Rf=0.24 (chloroform:methanol=10:1).

Example 292

Synthesis of ethyl 3-(4'-amino-2-cyclopentyloxybiphenyl-5-yl)propionate (Intermediate 67) (Preparation Method 8, Step d-1)

According to the procedure described in the synthesis method of Intermediate 8 in Reference Example 2 (Step e-1), ethyl 3-(3-bromo-4-hydroxyphenyl)propionate and cyclopentane bromide were reacted and treated to obtain ethyl 3-(3-bromo-4-cyclopentyloxyphenyl)propionate (410 mg). According to the procedure described in the synthesis method of Compound of Example 001 (Preparation Method 4, Step d-1) with the modifications that the reaction was carried out for 18 hours, and the purification was performed by flash column chromatography (hexane:ethyl acetate= 8:1), the above product was reacted with 4-(4,4,5,5-tetramethyl-1,3,2-dioxaborolan-2-yl)aniline (396 mg), 2 M aqueous sodium carbonate (1.0 ml) and (Ph$_3$P)$_4$Pd (110 mg) and treated to obtain the title compound (Intermediate 67, 313 mg).

Synthesis of ethyl 3-[3-(2-aminobenzothiazol-6-yl)-4-cyclopentyloxyphenyl]propionate (Compound No. 292) (Preparation Method 8, Step n)

According to the procedure described in the synthesis method of Compound of Example 286 (Preparation Method 8, Step n) with the modifications that the reaction was carried out for 12 hours, and the purification was performed by column chromatography (Quad, hexane:ethyl acetate= 9:5), Intermediate 67 (250 mg), potassium thiocyanate (286 mg) and bromine (39 µl) were reacted and treated to obtain the title compound (Compound No. 292, 209 mg).

Example 293

Synthesis of 3-[3-(2-aminobenzothiazol-6-yl)-4-cyclopentyloxyphenyl]propionic acid (Compound No. 293) (Preparation Method 1, Step a)

According to the procedure described in the synthesis method of Compound of Example 002 (Preparation Method 1, Step a) with the modification that the reaction was carried out for 1 hour, Compound of Example 292 (203 mg) and 2 N aqueous sodium hydroxide (1.00 ml) were reacted and treated to obtain the title compound (Compound No. 293, 161 mg). Rf=0.24 (chloroform:methanol=10:1).

Example 294

Synthesis of ethyl 3-(4'-amino-2-cyclohexyloxybiphenyl-5-yl)propionate (Intermediate 68) (Preparation Method 8, Step d-1)

According to the procedure described in the synthesis method of Intermediate 9 in Reference Example 2 (Step e-2), ethyl 3-(3-bromo-4-hydroxyphenyl)propionate and cyclohexanol were reacted and treated to obtain ethyl 3-(3-bromo-4-cyclohexyloxyphenyl)propionate (355 mg). According to the procedure described in the synthesis method of Compound of Example 001 (Preparation Method 4, Step d-1) with the modifications that the reaction was carried out for 17 hours, and the purification was performed by flash column chromatography (hexane:ethyl acetate 8:1), the above product was reacted with 4-(4,4,5,5-tetramethyl-1,3,2-dioxaborolan-2-yl)aniline (330 mg), 2 M aqueous sodium carbonate (0.9 ml) and (Ph$_3$P)$_4$Pd (105 mg) and treated to obtain the title compound (Intermediate 68, 260 mg).

Synthesis of ethyl 3-[3-(2-aminobenzothiazol-6-yl)-4-cyclohexyloxyphenyl]propionate (Compound No. 294) (Preparation Method 8, Step n)

According to the procedure described in the synthesis method of Compound of Example 286 (Preparation Method 8, Step n) with the modifications that the reaction was carried out for 12 hours, and the purification was performed by column chromatography (Quad, hexane:ethyl acetate= 9:5), Intermediate 68 (250 mg), potassium thiocyanate (265 mg) and bromine (35 u 1) were reacted and treated to obtain the title compound (Compound No. 294, 192 mg).

Example 295

Synthesis of 3-[3-(2-aminobenzothiazol-6-yl)-4-cyclohexyloxyphenyl]propionic acid (Compound No. 295) (Preparation Method 1, Step a)

According to the procedure described in the synthesis method of Compound of Example 002 (Preparation Method 1, Step a) with the modification that the reaction was carried out for 1 hour, Compound of Example 294 (186 mg) and 2 N aqueous sodium hydroxide (900 µl) were reacted and treated to obtain the title compound (Compound No. 295, 157 mg). Rf=0.25 (chloroform:methanol=10:1).

Example 296

Synthesis of ethyl 3-{2-cyclopentylmethyloxy-4'-[(N-methylamino)thiocarbonylamino]-1,1'-biphenyl-5-yl}propionate (Intermediate 69)

A solution of Intermediate 64 (156 mg) in THF (20 ml) was added dropwise with methyl isothiocyanate (642 mg, Ald) and stirred for 2 days. The solvent of the reaction mixture was concentrated under reduced pressure, and the residue was purified by column chromatography (Quad, hexane:ethyl acetate=4:1) to obtain the title compound (Intermediate 69, 176.1 mg).

Synthesis of ethyl 3-[4-cyclopentylmethyloxy-3-(2-methylaminobenzothiazol-6-yl)phenyl]propionate (Compound No. 296) (Preparation Method 8, Step n)

A solution of Intermediate 69 (176 mg) in chloroform (5 ml) was added dropwise with a solution of bromine (21 µl) in chloroform (1.0 ml) and stirred for 2.5 hours. The reaction mixture was added with water (30 ml) and ethyl acetate (90 ml) for extraction. The organic layer was washed with saturated brine and dried, and then the solvent was evaporated under reduced pressure. The residue was purified by column chromatography (Quad, hexane:ethyl acetate=2:1) to obtain the title compound (Compound No. 296, 127 mg).

Example 297
Synthesis of 3-[4-cyclopentylmethyloxy-3-(2-methylaminobenzothiazol-6-yl)phenyl]propionic acid (Compound No. 297) (Preparation Method 1, Step a)

According to the procedure described in the synthesis method of Compound of Example 002 (Preparation Method 1, Step a) with the modification that the reaction was carried out for 1 hour, Compound of Example 296 (126 mg) and 2 N aqueous sodium hydroxide (630 µl) were reacted and treated to obtain the title compound (Compound No. 297, 102 mg). Rf=0.39 (chloroform:methanol=10:1).

Example 298
Synthesis of ethyl 3 [3-(benzothiazol-6-yl)-4-cyclopentylmethyloxyphenyl]propionate (Compound No. 298) (Preparation Method 13, Step r-1)

A solution of Compound of Example 286 (243 mg) in acetonitrile (12 ml) was added with 30% aqueous hypophosphorous acid (3 ml, WAKO), cooled to 0° C., added dropwise with aqueous solution (1 ml) of sodium nitrite (199 mg), stirred for 30 minutes, then warmed to room temperature and further stirred for 22 hours. The reaction mixture was poured into water (50 ml), added with 2 N aqueous sodium hydroxide for neutralization and then added with ethyl acetate (90 ml×3) for extraction. The organic layer was washed with saturated brine and dried, and then the solvent was evaporated under reduced pressure. The residue was purified by column chromatography (Quad, hexane:ethyl acetate=10:1) to obtain the title compound (Compound No., 298, 85 mg).

Example 299
Synthesis of 3-[3-(benzothiazol-6-yl)-4-cyclopentylmethyloxyphenyl]propionic acid (Compound No. 299) (Preparation Method 1, Step a)

According to the procedure described in the synthesis method of Compound of Example 002 (Preparation Method 1, Step a) with the modification that the reaction was carried out for 4 hours, Compound of Example 298 (85 mg) and 2 N aqueous sodium hydroxide (510 µl) were reacted and treated to obtain the title compound (Compound No. 299, 66 mg). Rf=0.47 (chloroform:methanol=10:1).

Example 300
Synthesis of ethyl 3-{4-cyclopentylmethyloxy-3-[2-(N,N-dimethylamino)benzothiazol-6-yl]phenyl}propionate (Compound No. 300) (Preparation Method 13, Step r-2)

A solution of Compound of Example 286 (155 mg) in DMF (5 ml) was added with 60% sodium hydride (16 mg) under ice cooling, stirred for 5 minutes, then added with methyl iodide (68.5 µl), stirred for 10 minutes, then warmed to room temperature and further stirred for 4 hours. The reaction mixture was poured into water (50 ml) and extracted with ethyl acetate (80 ml). The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=7:1) to obtain the title compound (Compound No. 300, 48 mg).

Example 301
Synthesis of 3-{4-cyclopentylmethyloxy-3-[2-(N,N-dimethylamino)benzothiazol-6-yl]phenyl}propionic acid (Compound No. 301) (Preparation Method 1, Step a)

According to the procedure described in the synthesis method of Compound of Example 002 (Preparation Method 1, Step a) with the modification that the reaction was carried out for 3 hours, Compound of Example 300 (47 mg) and 2 N aqueous sodium hydroxide (200 µl) were reacted and treated to obtain the title compound (Compound No. 301, 35 mg). Rf=0.55 (chloroform:methanol=10:1).

Example 302
Synthesis of ethyl 3-[4-cyclopentylmethyloxy-3-(2-imino-3-methyl-2,3-dihydrobenzothiazol-6-yl)phenyl]propionate (Compound No. 302) (Preparation Method 13, Step r-3)

A solution of Compound of Example 286 (106 mg) in dimethoxyethane (1.0 ml) was added with methyl iodide (156 µl) and stirred in a shield tube at 60° C. for 24 hours. The reaction mixture was added with water (50 ml) and ethyl acetate (80 ml) for extraction. The organic layer was washed successively with saturated aqueous sodium hydrogencarbonate and saturated brine and dried, and then the solvent was evaporated under reduced pressure. The residue was purified by column chromatography (Quad, hexane:ethyl acetate=5:4) to obtain the title compound (Compound No. 302, 87 mg).

Example 303
Synthesis of 3-[4-cyclopentylmethyloxy-3-(2-imino-3-methyl-2,3-dihydrobenzothiazol-6-yl)phenyl]propionic acid (Compound No. 303) (Preparation Method 1, Step a)

According to the procedure described in the synthesis method of Compound of Example 002 (Preparation Method 1, Step a) with the modification that the reaction was carried out for 4 hours, Compound of Example 302 (85 mg) and 2 N aqueous sodium hydroxide (300 µl) were reacted and treated to obtain the title compound (Compound No. 303, 45 mg). Rf=0.41 (chloroform:methanol=10:1).

Example 304
Synthesis of ethyl 3-{4-cyclopentylmethyloxy-3-[3-methyl-2-(methylimino)-2,3-dihydrobenzothiazol-6-yl]phenyl}propionate (Compound No. 304) (Preparation Method 13, Step r-4)

A solution of Compound of Example 286 (100 mg) in acetone (3 ml) was added with potassium carbonate (70 mg) and methyl iodide (147 µl) and stirred at 45° C. for 4 days. The reaction mixture was poured into water (50 ml) and extracted with ethyl acetate (100 ml). The organic layer was washed successively with saturated aqueous sodium hydrogencarbonate and saturated brine and dried, and then the solvent was evaporated under reduced pressure. The residue was purified by column chromatography (Quad, hexane:ethyl acetate=5:2) to obtain the title compound (Compound No. 304, 49 mg).

Example 305
Synthesis of 3-{4-cyclopentylmethyloxy-3-[3-methyl-2-(methylimino)-2,3-dihydrobenzothiazol-6-yl]phenyl}propionic acid (Compound No. 305) (Preparation Method 1, Step a)

According to the procedure described in the synthesis method of Compound of Example 002 (Preparation Method 1, Step a) with the modification that the reaction was carried out for 3 hours, Compound of Example 304 (47 mg) and 2 N aqueous sodium hydroxide (200 µl) were reacted and treated to obtain the title compound (Compound No. 305, 40 mg). Rf=0.29 (chloroform:methanol=10:1).

Example 306
Synthesis of ethyl 3-[3-(2-bromobenzothiazol-6-yl)-4-cyclohexylmethyloxyphenyl]-propionate (Intermediate 70) (Preparation Method 13, Step r-5)

A solution obtained beforehand by adding t-butyl nitrite (178 µl, TCI) and copper(I) bromide (241 mg, WAKO) to acetonitrile (10 ml) and mixing them was added dropwise with a solution of Compound of Example 286 (381 mg) in acetonitrile (5 ml) and stirred at room temperature for 1.5 hours. The solvent of the reaction mixture was concentrated under reduced pressure, and the residue was purified by column chromatography (Quad, hexane:ethyl acetate=10:1) to obtain the title compound (Intermediate 70, 341 mg).

Synthesis of 3-[4-cyclopentylmethyloxy-3-(2-methoxybenzothiazol-6-yl)phenyl]propionic acid (Compound No. 306) (Preparation Method 13, Step r-7)

According to the procedure described in the synthesis method of Compound of Example 002 (Preparation Method 1, Step a) with the modification that the reaction was carried out for 18 hours, Intermediate 70 (169 mg) and 2 N aqueous sodium hydroxide (500 µl) were reacted and treated to obtain the title compound (Compound No. 306, 114 mg). Rf=0.64 (chloroform:methanol=10:1).

Example 307
Synthesis of ethyl 3-[4-cyclopentylmethyloxy-3-(2-methylbenzothiazol-6-yl)phenyl]propionate (Compound No. 307) (Preparation Method 13, Step r-6)

A solution of Intermediate 70 (151 mg) in DMF (5 ml) was added with potassium carbonate (260 mg), $(Ph_3P)_4Pd$ (45 mg) and trimethylboroxine (86 µl, Ald) and stirred at 115° C. for 18 hours. The reaction mixture was added with water (50 ml) and ethyl acetate (100 ml) for extraction. The organic layer was washed with saturated brine and dried, and then the solvent was evaporated under reduced pressure. The residue was purified by column chromatography (Quad, hexane:ethyl acetate=8:1) to obtain the title compound (Compound No. 307, 102 mg).

Example 308
Synthesis of 3-[4-cyclopentylmethyloxy-3-(2-methylbenzothiazol-6-yl)phenyl]propionic acid (Compound No. 308) (Preparation Method 1, Step a)

According to the procedure described in the synthesis method of Compound of Example 002 (Preparation Method 1, Step a) with the modification that the reaction was carried out for 3 hours, Compound of Example 307 (97 mg) and 2 N aqueous sodium hydroxide (460 µl) were reacted and treated to obtain the title compound (Compound No. 308, 71 mg). Rf=0.48 (chloroform:methanol=10:1).

Example 309
Synthesis of 3-[4-cyclopentylmethyloxy-3-(2-thioxo-2,3-dihydrobenzothiazol-6-yl)phenyl]propionic acid (Compound No. 309) (Preparation Method 13, Step r-8)

A solution obtained beforehand by adding thiourea (52 mg, WAKO) to 1 M sulfuric acid (5 ml) and mixing them was added with a solution of Intermediate 70 (101 mg) in acetonitrile (5 ml) and stirred at 90° C. for 20 hours. The reaction mixture was poured into water (20 ml), added with 1 N aqueous sodium hydroxide under ice cooling for neutralization and then extracted with ethyl acetate (80 ml×3). The organic layer was washed with saturated brine and dried, and then the solvent was evaporated under reduced pressure. The residue was purified by column chromatography (Quad, methylene chloride:ethanol=30:1) to obtain the title compound (46 mg). Rf=0.42 (chloroform:methanol=10:1).

Example 310
Synthesis of 3-[4-cyclopentylmethyloxy-3-(2-oxo-2,3-dihydrobenzothiazol-6-yl)-phenyl]propionic acid (Compound No. 310) (Preparation Method 13, Step r-9 and Preparation Method 1, Step a)

A solution of Intermediate 70 (202 mg) in ethanol (8 ml) was added with 5 N aqueous hydrochloric acid (1.5 ml) and stirred at 80° C. for 18.5 hours. The reaction mixture was concentrated under reduced pressure and added with water (20 ml) and ethyl acetate (80 ml) for extraction. The organic layer was washed with saturated brine and dried, and then the solvent was evaporated under reduced pressure. According to the procedure described in the synthesis method of Compound of Example 002 (Preparation Method 1, Step a) with the modification that the reaction was carried out for 2 hours, the residue obtained above was added with 2 N aqueous sodium hydroxide (1.0 ml), reacted and treated to obtain the title compound (Compound No., 310, 250 mg). Rf=0.40 (hexane:ethyl acetate=2:3).

Example 311
Synthesis of methyl 3-[4-cyclopentylmethyloxy-3-(2-oxo-2,3-dihydrobenzothiazol-6-yl)phenyl]propionate (Compound No. 311, Step c)

According to the procedure described in the synthesis method of Intermediate 1 in Reference Example 1 (Step c) with the modification that the purification was performed by column chromatography (Quad, hexane:ethyl acetate=3:1), Compound of Example 310 (150 mg) and thionyl chloride (67 µl) were reacted in methanol and treated to obtain the title compound (Compound No. 311, 139 mg).

Example 312
Synthesis of methyl 3-[4-cyclopentylmethyloxy-3-(2-oxo-3-methyl-2,3-dihydrobenzothiazol-6-yl)phenyl]propionate (Compound No. 312) (Preparation Method 13, Step r-10)

A solution of Compound of Example 311 (135 mg) in dimethoxyethane (5 ml) was added with potassium t-butoxide (40 mg, WAKO) under ice cooling, stirred for 5 minutes, then added with methyl iodide (102 µl), stirred for 10 minutes, then warmed to room temperature and further stirred for 15 hours. The reaction mixture was poured into water (50 ml) and extracted with ethyl acetate (80 ml). The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=9:2) to obtain the title compound (Compound No. 312, 108 mg).

Example 313
Synthesis of 3-[4-cyclopentylmethyloxy-3-(2-oxo-3-methyl-2,3-dihydrobenzothiazol-6-yl)phenyl]propionic acid (Compound No. 313) (Preparation Method 1, Step a)

According to the procedure described in the synthesis method of Compound of Example 002 (Preparation Method 1, Step a) with the modification that the reaction was carried out for 3 hours, Compound of Example 312 (103 mg) and 2 N aqueous sodium hydroxide (300 µl) were reacted and treated to obtain the title compound (Compound No. 313, 97 mg). Rf=0.44 (chloroform:methanol=20:1).

Example 314
Synthesis of methyl 3-[4-cyclopentylmethyloxy-3-(quinolin-3-yl)phenyl]propionate (Compound No. 314) (Preparation Method 4, Step d-1)

According to the procedure described in the synthesis method of Compound of Example 019 (Preparation Method 4, Step d-1) with the modification that the purification was performed by flash column chromatography (hexane:ethyl acetate=4:1), Intermediate 3 (346 mg), bispinacolate diboron (285 mg), PdCl₂(dppf) (48 mg) and potassium acetate (302 mg) were reacted at 80° C. for 3 hours, and then the reaction mixture was added with 3-bromoquinoline (163 μl, TCI), PdCl₂(dppf) (51 mg) and 2 M aqueous sodium carbonate (0.9 ml), reacted and treated at 80° C. for 14 hours to obtain the title compound (Compound No. 314, 55 mg).

Example 315

Synthesis of 3-[4-cyclopentylmethyloxy-3-(quinolin-3-yl) phenyl]propionic acid (Compound No. 315) (Preparation Method 1, Step a)

According to the procedure described in the synthesis method of Compound of Example 002 (Preparation Method 1, Step a) with the modification that the reaction was carried out for 1 hour, Compound of Example 314 (50 mg) and 2 N aqueous sodium hydroxide (200 μl) were reacted and treated to obtain the title compound (Compound No. 315, 43 mg). Rf=0.50 (chloroform:methanol=10:1).

Example 316

Synthesis of methyl 3-[4-cyclohexylmethyloxy-3-(quinolin-3-yl)phenyl]propionate (Compound No. 316) (Preparation Method 4, Step d-1)

According to the procedure described in the synthesis method of Compound of Example 019 (Preparation Method 4, Step d-1) with the modification that the purification was performed by flash column chromatography (hexane:ethyl acetate=10:1), 3-bromoquinoline (272 μl), bispinacolate diboron (561 mg), PdCl₂(dppf) (46 mg) and potassium acetate (383 mg) were reacted at 80° C. for 3.5 hours, and then the reaction mixture was added with Intermediate 3 (963 mg), PdCl₂(dppf) (58 mg) and 2 M aqueous sodium carbonate (0.9 ml), reacted at 80° C. for 42 hours and treated to obtain the title compound (Compound No. 316, 356 mg).

Example 317

Synthesis of 3-[4-cyclohexylmethyloxy-3-(quinolin-3-yl) phenyl]propionic acid (Compound No. 317) (Preparation Method 1, Step a)

According to the procedure described in the synthesis method of Compound of Example 002 (Preparation Method 1, Step a) with the modification that the reaction was carried out for 1 hour, Compound of Example 316 (319 mg) and 2 N aqueous sodium hydroxide (900 μl) were reacted and treated to obtain the title compound (Compound No. 317, 122 mg). Rf=0.53 (chloroform:methanol=10:1).

Example 318

Synthesis of methyl 3-[4-cyclohexylmethyloxy-3-(quinolin-6-yl)phenyl]propionate (Compound No. 318) (Preparation Method 4, Step d-1)

According to the procedure described in the synthesis method of Compound of Example 001 (Preparation Method 4, Step d-1) with the modifications that the reaction was carried out for 13.5 hours, and the purification was performed by column chromatography (Quad, hexane:ethyl acetate=6:1), crude 6-quinoline boronic acid prepared from 6-bromoquinoline (835 mg, TCI), 1.6 M solution of n-butyllithium in hexane (3.20 ml) and (ⁱPrO)₃B (1.40 ml) was reacted with Intermediate 7 (367 mg), 2 M aqueous sodium carbonate (0.9 ml) and (Ph₃P)₄Pd (131 mg) and treated to obtain the title compound (Compound No. 318, 202 mg).

Example 319

Synthesis of 3-[4-cyclohexylmethyloxy-3-(quinolin-6-yl) phenyl]propionic acid (Compound No. 319) (Preparation Method 1, Step a)

According to the procedure described in the synthesis method of Compound of Example 002 (Preparation Method 1, Step a) with the modification that the reaction was carried out for 3.5 hours, Compound of Example 318 (131 mg) and 2 N aqueous sodium hydroxide (330 μl) were reacted and treated to obtain the title compound (Compound No. 319, 119 mg). Rf=0.52 (chloroform:methanol=10:1).

Example 320

Synthesis of methyl 3-[4-cyclohexylmethyloxy-3-(2-oxo-1,2-dihydroquinolin-6-yl)phenyl]propionate (Compound No. 320) (Preparation Method 14, Step s)

According to a method described in a reference [M. R. Sabol et al., Synthetic Communications (Synth. Commun.), vol. 30, p.427, 2000], a solution of Compound of Example 318 (120 mg) in chloroform (3 ml) was added with 3-chloroperbenzoic acid (88 mg, TCI) and stirred for 20 hours. The reaction mixture was added with chloroform (50 ml) and washed successively with saturated aqueous sodium hydrogencarbonate, saturated aqueous ammonium chloride and saturated brine. The organic layer was dried, and then the solvent was evaporated under reduced pressure. A solution of the residue in acetic anhydride (1 ml) was stirred at 120° C. for 2 hours. The reaction mixture was added with chloroform (60 ml) and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (chloroform) to obtain the title compound (Compound No. 320, 48 mg).

Example 321

Synthesis of 3-[4-cyclohexylmethyloxy-3-(2-oxo-1,2-dihydroquinolin-6-yl)-phenyl]propionic acid (Compound No. 321) (Preparation Method 1, Step a)

According to the procedure described in the synthesis method of Compound of Example 002 (Preparation Method 1, Step a) with the modification that the reaction was carried out for 1.5 hours, Compound of Example 320 (46 mg) and 2 N aqueous sodium hydroxide (150 μl) were reacted and treated to obtain the title compound (Compound No. 321, 41 mg). Rf=0.18 (chloroform:methanol=10:1).

Example 322

Synthesis of methyl 3-[4-benzyloxy-3-(naphthalen-2-yl) phenyl]propionate (Compound No. 322) (Preparation Method 5, Step e-1)

According to the procedure described in the synthesis method of Compound of Example 030 (Preparation Method 5, Step e-1) with the modifications that the reaction was carried out for 16 hours, and the purification was performed by flash column chromatography (hexane:ethyl acetate=9:1), Intermediate 36 (100 mg), potassium carbonate (68 mg) and benzyl bromide (42 μl, TCI) were reacted and treated to obtain the title compound (Compound No. 322, 122 mg).

Example 323

Synthesis of 3-[4-benzyloxy-3-(naphthalen-2-yl)phenyl] propionic acid (Compound No. 323) (Preparation Method 1, Step a)

According to the procedure described in the synthesis method of Compound of Example 002 (Preparation Method 1, Step a) with the modification that the reaction was carried out for 3 hours, Compound of Example 322 (120 mg) and 2 N aqueous sodium hydroxide (500 μl) were reacted and treated to obtain the title compound (Compound No. 323, 110 mg). Rf=0.45 (chloroform:methanol=20:1).

Example 324

Synthesis of methyl 3-[4-benzyloxy-3-(1H-indol-5-yl)phenyl]propionate (Compound No. 324) (Preparation Method 5, Step e-1)

According to the procedure described in the synthesis method of the compound 030 in Example 30 (Preparation Method 5, Step e-1) with the modifications that the reaction was carried out for 16 hours, and the purification was performed by flash column chromatography (hexane:ethyl acetate=9:1), Intermediate 55 (140 mg), potassium carbonate (78 mg) and benzyl bromide (62 μl, TCI) were reacted and treated to obtain the title compound (Compound No. 324, 150 mg).

Example 325

Synthesis of 3-[4-benzyloxy-3-(1H-indol-5-yl)phenyl]propionic acid (Compound No. 325) (Preparation Method 1, Step a)

According to the procedure described in the synthesis method of Compound of Example 002 (Preparation Method 1, Step a) with the modification that the reaction was carried out for 2 hours, Compound of Example 324 (148 mg) and 2 N aqueous sodium hydroxide (400 g 1) were reacted and treated to obtain the title compound (Compound No. 325, 143 mg). Rf=0.50 (chloroform:methanol=10:1).

Example 326

Synthesis of methyl 3-[4-(4-t-butylphenylmethyloxy)-3-(1H-indol-5-yl)phenyl]-propionate (Compound No. 326) (Preparation Method 5, Step e-1)

According to the procedure described in the synthesis method of the compound 030 in Example 30 (Preparation Method 5, Step e-1) with the modifications that the reaction was carried out for 13 hours, and the purification was performed by column chromatography (Quad, hexane:ethyl acetate=6:1), Intermediate 55 (81 mg), potassium carbonate (116 mg) and 4-t-butylbenzyl bromide (75.9 μl, Ald) were reacted and treated to obtain the title compound (Compound No. 326, 95 mg).

Example 327

Synthesis of 3-[4-(4-t-butylphenylmethyloxy)-3-(1H-indol-5-yl)phenyl]propionic acid (Compound No. 327) (Preparation Method 1, Step a)

According to the procedure described in the synthesis method of Compound of Example 002 (Preparation Method 1, Step a) with the modification that the reaction was carried out for 1.5 hours, Compound of Example 326 (87 mg) and 2 N aqueous sodium hydroxide (400 μl) were reacted and treated to obtain the title compound (Compound No. 327, 73 mg). Rf=0.54 (chloroform:methanol=10:1)

Example 328

Synthesis of methyl 3-[3-(naphthalen-2-yl)-4-phenyloxyphenyl]propionate (Compound No. 328) (Preparation Method 5, Step e-4)

According to a procedure described in a reference [A. Aranyoset al., Journal of American Chemical Society (J. Am. Chem. Soc.), p.4369, 1999], a solution of Intermediate 36 (101 mg) in toluene (3 ml) was added with bromobenzene (69 μl, WAKO), tris(dibenzylideneacetone)dipalladium (21 mg, Ald), 2-(di-t-butylphosphino)biphenyl (22 mg, Strem) and potassium phosphate (141 mg, Ald) and stirred at 100° C. for 21 hours. The reaction mixture was added with ethyl acetate (90 ml), washed with saturated brine and dried, and then the solvent was evaporated under reduced pressure. The residue was purified by column chromatography (Quad, hexane:ethyl acetate=40:1) to obtain the title compound (Compound No. 328, 56 mg).

Example 329

Synthesis of 3-[4-(4-t-butylphenylmethyloxy)-3-(1H-indol-5-yl)phenyl]propionic acid (Compound No. 327) (Preparation Method 1, Step a)

According to the procedure described in the synthesis method of Compound of Example 002 (Preparation Method 1, Step a) with the modification that the reaction was carried out for 2 hours, Compound of Example 328 (56 mg) and 2 N aqueous sodium hydroxide (350 μl) were reacted and treated to obtain the title compound (Compound No. 329, 39 mg). Rf=0.50 (chloroform:methanol=10:1).

Example 330

Synthesis of 3-[3-(benzothiazol-6-yl)-4-cyclohexyloxyphenyl]propionic acid (Compound No. 330) (Preparation Method 13, Step r-1 and Preparation Method 1, Step a)

According to the procedure described in the synthesis method of Compound of Example 298 (Preparation Method 13, Step r-1) with the modifications that the reaction was carried out at 0° C. for 1 hour and at room temperature for 7 days, and the purification was performed by column chromatography (Quad, hexane:ethyl acetate=10:1), Compound of Example 294 (579 mg), 30% aqueous hypophosphorous acid (8 ml, WAKO) and sodium nitrite (490 mg) were reacted and treated to obtain oily substance. According to the procedure described in the synthesis method of Compound of Example 002 (Preparation Method 1, Step a) with the modification that the reaction was carried out for 1.5 hours, the oily substance was reacted with 2 N aqueous sodium hydroxide (420 u 1) and treated to obtain the title compound (Compound No. 330, 56 mg). Rf=0.47 (chloroform:methanol=10:1).

TABLE 1

EXP. Int. 1
$^1$H-NMR(CDCl$_3$): 2.59(2H, t, J=7.6), 2.88(2H, t, J=7.7), 3.67(3H, s), 5.05(1H, s), 6.75 (2H, d, J=8.5), 7.06(2H, d, J=8.7).
EXP. Int. 2
$^1$H-NMR(CDCl$_3$): 1.25–1.44(2H, m), 1.52–1.68(4H, m), 1.77–1.87(2H, m), 2.34(1H, qu, J=7.4), 2.59(2H, t, J=7.4), 2.88(2H, t, J=7.8), 3.66(3H, s), 3.79(2H, d, J=6.8), 6.82(2H, d, J=8.8), 7.09(2H, d, J=8.8).
EXP. Int. 3
$^1$H-NMR(CDCl$_3$): 1.37–1.45(2H, m), 1.57–1.69(4H, m), 1.79–1.89(2H, m), 2.40(1H, qu, J=7.4), 2.58(2H, t, J=7.6), 2.86(2H, t, J=7.7), 3.66(3H, s), 3.86(2H, d, J=6.9), 6.79(1H,

TABLE 1-continued d, J=8.2), 7.06(1H, dd, J=8.5, 2.2), 7.37(1H, d, J=2.2).
Mass: 341(M$^+$+1)
EXP. Int. 4
$^1$H-NMR(CDCl$_3$): 2.65(2H, t, J=7.7), 2.88(2H, t, J=7.5), 3.87(3H, s), 6.83(1H, d, J=8.5), 7.11(1H, dd, J=8.3, 2.0), 7.39(1H, d, J=1.9).
Mass: (LCMS) 257(M$^-$)
EXP. Int. 5
$^1$H-NMR(CDCl$_3$): 2.64(2H, t, J=7.4), 2.87(2H, t, J=7.5), 5.42(1H, s), 6.94(1H, d, J=8.3), 7.06(1H, dd, J=8.2, 2.2), 7.31(1H, d, J=1.9).
EXP. Int. 6
$^1$H-NMR(CDCl$_3$): 2.58(2H, t, J=7.6), 2.86(2H, t, J=7.7), 3.67(3H, s), 5.40(1H, s), 6.93 (1H, d, J=8.2), 7.05(1H, dd, J=8.5, 2.0), 7.30(1H, d, J=1.9).
EXP. Int. 7
$^1$H-NMR(CDCl$_3$): 1.06–1.34(5H, m), 1.68–1.92(6H, m), 2.58(2H, t, J=7.7), 2.85(2H, t, J=7.7), 3.66(3H, s), 3.77(2H, d, J=6.0), 6.78(1H, d, J=8.2), 7.06(1H, dd, J=8.2, 2.2), 7.36(1H, d, J=2.2).
Mass: 354(M$^+$)
EXP. Int. 8
$^1$H-NMR(CDCl$_3$): 1.61–1.64(2H, m), 1.81–1.90(6H, m), 2.58(2H, t, J=7.7), 2.85(2H, t, J=7.6), 3.67(3H, s), 4.77(1H, m), 6.81(1H, d, J=8.5), 7.05(1H, dd, J=8.5, 2.2), 7.36(1H, d, J=2.2).
Mass: 326(M$^+$)
EXP. Int. 9
$^1$H-NMR(CDCl$_3$): 1.23–1.69(6H, m), 1.80–1.96(4H, m), 2.58(2H, t, J=7.7), 2.85(2H, t, J=7.5), 3.67(3H, s), 4.25(1H, qu, J=3.6), 6.83(1H, d, J=8.5), 7.04(1H, dd, J=8.2, 2.2), 7.37(1H, d, J=1.9).
Mass: 340(M$^+$)
EXP. Int. 10
$^1$H-NMR(CDCl$_3$): 2.57(2H, t, J=7.7), 2.85(2H, t, J=7.7), 3.18(2H, t, J=6.7), 3.66(3H, s), 4.19(2H, t, J=6.9), 6.79(1H, d, J=8.5), 7.00–7.19(3H, m), 7.18–7.24(1H, m), 7.36 (1H, d, J=1.9), 7.39(1H, dd, J=7.4, 1.8).
Mass: 380(M$^+$)
EXP. Int. 11
$^1$H-NMR(CDCl$_3$): 1.92(2H, m), 2.36(2H, t, J=7.4), 2.60(2H, t, J=7.5), 3.87(3H, s), 6.82 (1H, d, J=8.2), 7.07(1H, dd, J=8.2, 2.2), 7.37(1H, d, J=1.9).
Mass: 272(M$^+$)
EXP. Int. 12
$^1$H-NMR(CDCl$_3$): 1.90(2H, m), 2.31(2H, t, J=7.4), 2.56(2H, t, J=7.6), 3.67(3H, s), 5.41 (1H, s), 6.93(1H, d, J=8.2), 7.02(1H, dd, J=8.3, 2.0), 7.27(1H, d, J=2.2).
Mass: 272(M$^+$)
EXP. Int. 13
$^1$H-NMR(CDCl$_3$): 1.35–1.47(2H, m), 1.55–1.70(4H, m), 1.80–1.95(4H, m), 2.31(2H, t, J=7.4), 2.40(1H, qu, J=7.4), 2.56(2H, t, J=7.5), 3.66(3H, s), 3.86(2H, d, J=6.8), 6.80 (1H, d, J=8.5), 7.03(1H, dd, J=8.5, 1.9), 7.34(1H, d, J=2.2).
Mass: 354(M$^+$)
EXP. Int. 14
$^1$H-NMR(CDCl$_3$): 1.39–1.45(2H, m), 1.57–1.65(4H, m), 1.77–1.86(2H, m), 2.44(1H, qu, J=7.4), 2.64(2H, t, J=7.4), 2.95(2H, t, J=7.5), 3.69(3H, s), 3.97(2H, d, J=6.8), 7.57(1H, dd, J=2.8, 0.5), 7.63(1H, d, J=2.2).
Mass: 385(M$^+$)
EXP. Int. 15
$^1$H-NMR(CDCl$_3$): 2.59(2H, t, J=7.6), 2.85(2H, t, J=7.3), 3.67(3H, s), 5.78(1H, s), 7.14 (1H, d, J=2.2), 7.25(1H, d, J=2.2).
Mass: 292(M$^+$+1)
EXP. Int. 16
$^1$H-NMR(CDCl$_3$): 1.46–1.55(2H, m), 1.57–1.68(4H, m), 1.80–1.91(2H, m), 2.45(1H, qu, J=7.1), 2.59(2H, t, J=7.6), 2.85(2H, t, J=7.5), 3.67(3H, s), 3.85(2H, d, J=6.8), 7.16(1H, d, J=2.2), 7.28(1H, d, J=2.2).
Mass: 375(M$^+$+1)
EXP. Int. 17
$^1$H-NMR(CDCl$_3$): 1.33(3H, t, J=7.1), 3.92(3H, s), 4.26(2H, q, J=7.1), 6.29(1H, d, J=15.9), 6.95(1H, t, J=8.4), 7.22(1H, br-s), 7.25–7.30(1H, m), 7.58(1H, d, J=16.2).
Mass: 224(M$^+$)
EXP. Int. 18
$^1$H-NMR(CDCl$_3$): 1.23(3H, t, J=7.1), 2.58(2H, t, J=7.7), 2.87(2H, t, J=7.7), 3.86(3H, s), 4.12(2H, q, J=7.1), 6.83–6.95(3H, m).
Mass: 226(M$^+$)
EXP. Int. 19
$^1$H-NMR(CDCl$_3$): 2.64(2H, t, J=7.4), 2.89(2H, t, J=7.6), 3.86(3H, s), 6.84–6.96(3H, m).
Mass: 198(M$^+$)
EXP. Int. 20
$^1$H-NMR(CDCl$_3$): 2.64(2H, t, J=7.4), 2.88(2H, t, J=7.5), 6.84–6.95(3H, m).
Mass: 184(M$^+$)
EXP. Int. 21
$^1$H-NMR(CDCl$_3$): 2.59(2H, t, J=7.6), 2.87(2H, t, J=7.6), 3.67(3H, s), 5.16(1H, br-s), 6.83–6.94(3H, m).
Mass: 198(M$^+$)

TABLE 1-continued

EXP. Int. 22
$^1$H-NMR(CDCl$_3$): 2.59(2H, t, J=7.6), 2.86(2H, t, J=7.3), 3.67(3H, s), 5.27(1H, br-s), 6.91(1H, dd, J=10.7, 2.0), 7.10–7.12(1H, m).
Mass: 276(M$^+$+1)
EXP. Int. 23
$^1$H-NMR(CDCl$_3$): 1.26–1.49(2H, m), 1.51–1.68(4H, m), 1.78–1.89(2H, m), 2.38(1H, qu, J=7.4), 2.59(2H, t, J=7.7), 2.86(2H, t, J=7.7), 3.67(3H, s), 3.92(2H, d, J=7.9), 6.88(1H, dd, J=11.4, 2.2), 7.14–7.15(1H, m).
EXP. Int. 24
$^1$H-NMR(CDCl$_3$): 6.21(1H, br-s), 7.16(1H, d, J=8.5), 7.78(1H, dd, J=8.5, 1.9), 8.04(1H, d, J=1.9), 9.83(1H, s).
Mass: 201(M$^+$+1)
EXP. Int. 25
$^1$H-NMR(CDCl$_3$): 1.06–1.40(5H, m), 1.70–1.92(6H, m), 3.90(2H, d, J=5.7), 6.96(1H, d, J=8.5), 7.78(1H, dd, J=8.3, 2.0), 8.07(1H, d, J=2.2), 9.83(1H, s).
Mass: 297(M$^+$+1)
EXP. 001
$^1$H-NMR(CDCl$_3$): 0.97–1.28(5H, m), 1.64–1.77(6H, m), 2.66(2H, t, J=7.8), 2.96(2H, t, J=7.8), 3.68(3H, s), 3.74(2H, d, J=5.8), 5.09(1H, s), 6.91(1H, d, J=8.5), 7.11–7.17(3H, m), 7.24–7.26(1H, m), 7.66(2H, d, J=1.3), 7.75(1H, d, J=8.7), 7.91(1H, s).
Mass: 418(M$^+$)
EXP. 002
$^1$H-NMR(DMSO-d$_6$): 0.94–1.20(5H, m), 1.62–1.73(6H, m), 2.54(2H, t, J=7.2), 2.82(2H, t, J=7.4), 3.77(2H, d, J=5.8), 7.00(1H, d, J=8.2), 7.07–7.17(3H, m), 7.25(1H, d, J=2.2), 7.57(1H, dd, J=8.8, 2.1), 7.68(1H, d, J=8.8), 7.75(1H, d, J=8.8), 7.88(1H, m), 9.73(1H, s), 12.09(1H, s).
Mass: 404(M$^+$)
EXP. 003
$^1$H-NMR(CDCl$_3$): 1.22–1.32(2H, m), 1.49–1.58(4H, m), 1.70–1.79(2H, m), 2.26(1H, qu, J=7.7), 2.66(2H, t, J=7.8), 2.96(2H, t, J=7.8), 3.68(3H, s), 3.83(2H, d, J=6.8), 5.22(1H, br-s), 6.91(1H, d, J=8.2), 7.08–7.17(3H, m), 7.25(1H, m), 7.67(2H, d, J=0.8), 7.75(1H, d, J=9.0), 7.91(1H, s).
Mass: (LCMS) 403(M$^-$)
EXP. 004
$^1$H-NMR(DMSO-d$_6$): 1.25–1.32(2H, m), 1.45–1.52(4H, m), 1.61–1.72(2H, m), 2.19(1H, qu, J=7.4), 2.54(2H, t, J=7.3), 2.82(2H, t, J=7.5), 3.84(2H, d, J=6.9), 7.01(1H, d, J=8.2), 7.06–7.17(3H, m), 7.25(1H, d, J=2.2), 7.57(1H, dd, J=8.5, 1.6), 7.68(1H, d, J=8.8), 7.75(1H, d, J=8.8), 7.88(1H, s), 9.72(1H, s), 12.09(1H, s).
Mass: (LCMS) 391(M$^+$+1)
EXP. 005
$^1$H-NMR(CDCl$_3$): 2.65(2H, t, J=7.8), 2.95(2H, t, J=7.6), 3.03(2H, t, J=6.4), 3.68(3H, s), 4.17(2H, t, J=6.5), 5.23(1H, br-s), 6.88–7.00(3H, m), 7.05–7.14(3H, m), 7.17(1H, s), 7.20(2H, dd, J=11.0, 2.2), 7.51(1H, dd, J=8.5, 1.6), 7.64(1H, d, J=8.8), 7.72(1H, d, J=8.8), 7.99(1H, s).
Mass: (LCMS) 443(M$^-$)
EXP. 006
$^1$H-NMR(DMSO-d$_6$): 2.54(2H, t, J=7.5), 2.81(2H, t, J=7.4), 2.99(2H, t, J=6.0), 4.20 (2H, t, J=6.3), 7.00–7.17(6H, m), 7.22–7.29(3H, m), 7.39(1H, dd, J=8.5, 1.6), 7.61(1H, d, J=8.8), 7.71(1H, d, J=8.5), 7.76(1H, s), 9.72(1H, s), 12.08(1H, s).
Mass: (LCMS) 431(M$^+$+1)
EXP. 007
$^1$H-NMR(CDCl$_3$): 1.29–1.38(2H, m), 1.43–1.62(4H, m), 1.68–1.78(2H, m), 2.25(1H, qu, J=7.4), 2.66(2H, t, J=7.7), 2.96(2H, t, J=7.8), 3.68(3H, s), 3.82(2H, d, J=6.8), 5.24(1H, s), 6.91(1H, d, J=8.5), 7.08(1H, dd, J=8.8, 2.4), 7.12–7.15(2H, m), 7.25(1H, d, J=1.6), 7.54(1H, dd, J=8.5, 1.9), 7.75(2H, dd, J=8.8, 2.5), 7.81(1H, s).
Mass: (LCMS) 405(M$^+$+1)
EXP. 008
$^1$H-NMR(DMSO-d$_6$): 1.23–1.35(2H, m), 1.45–1.53(4H, m), 1.62–1.73(2H, m), 2.19(1H, qu, J=7.4), 2.54(2H, t, J=7.5), 2.82(2H, t, J=7.4), 3.85(2H, d, J=6.5), 7.02(1H, d, J=8.2), 7.06(1H, dd, J=8.8, 2.4), 7.12(1H, d, J=2.6), 7.16(1H, dd, J=8.2, 2.1), 7.26(1H, d, J=2.2), 7.43(1H, dd, J=8.2, 2.1), 7.74(1H, s), 7.78(2H, d, J=4.1), 9.69(1H, s), 12.05 (1H, s).
Mass: (LCMS) 391(M$^+$+1)
EXP. 009
$^1$H-NMR(CDCl$_3$): 1.23–1.34(2H, m), 1.47–1.61(4H, m), 1.69–1.79(2H, m), 2.26(1H, qu, J=7.4), 2.66(2H, t, J=7.8), 2.96(2H, t, J=7.8), 3.68(3H, s), 3.83(2H, d, J=6.8), 5.51(1H, br-s), 6.82(1H, d, J=7.4), 6.92(1H, d, J=8.5), 7.15(1H, dd, J=8.2, 2.2), 7.28(1H, d, J=2.2), 7.31(1H, d, J=8.2), 7.45(1H, d, J=8.5), 7.72(1H, dd, J=8.8, 1.6), 7.95(1H, s), 8.16(1H, d, J=8.5)
Mass: (LCMS) 405(M$^+$+1)
EXP. 010
$^1$H-NMR(DMSO-d$_6$): 1.25–1.32(2H, m), 1.41–1.52(4H, m), 1.61–1.73(2H, m), 2.19(1H, qu, J=7.4), 2.55(2H, t, J=7.5), 2.83(2H, t, J=7.4), 3.85(2H, d, J=6.8), 6.85(1H, dd, J=6.5, 1.9), 7.03(1H, d, J=8.2), 7.18(1H, dd, J=8.2, 2.1), 7.27–7.34(3H, m), 7.61(1H, dd, J=8.8, 1.6), 7.92(1H, d, J=1.0), 8.10(1H, d, J=8.8), 10.08(1H, s), 12.09(1H, s).
Mass: (LCMS) 391(M$^+$+1)
EXP. 011
$^1$H-NMR(CDCl$_3$): 1.24–1.32(2H, m), 1.48–1.55(4H, m), 1.73–1.77(2H, m), 2.26(1H, qu, J=7.4), 2.65(2H, t, J=7.8), 2.95(2H, t, J=7.7), 3.68(3H, s), 3.82(2H, d, J=6.8), 3.87(2H, TABLE 1-continued br-s), 6.90(1H, d, J=8.2), 6.95(1H, dd, J=8.4, 2.2), 7.00(1H, s), 7.11(1H, dd, J=8.2, 2.2), 7.25(1H, d, J=1.9), 7.59–7.60(2H, m), 7.67(1H, d, J=8.5), 7.85(1H, s).
Mass: (LCMS) 404(M$^+$+1)
EXP. 012
$^1$H-NMR(DMSO-d$_6$): 1.24–1.35(2H, m), 1.45–1.53(4H, m), 1.63–1.74(2H, m), 2.20(1H, qu, J=7.4), 2.53(2H, t, J=7.2), 2.81(2H, t, J=7.4), 3.83(2H, d, J=6.8), 5.38(2H, br-s), 6.82(1H, s), 6.93(1H, dd, J=85, 2.2), 6.98(1H, d, J=8.5), 7.12(1H, dd, J=8.5, 1.8), 7.23 (1H, d, J=2.2), 7.49(2H, s), 7.58(1H, d, J=8.8), 7.76(1H, s), 12.08(1H, s).
Mass: (LCMS) 390(M$^+$+1)
EXP. Int. 26
$^1$H-NMR(CDCl$_3$): 3.90(2H, s), 6.86(1H, d, J=2.2), 6.93(1H, dd, J=8.8, 2.0), 7.26(1H, dd, J=10.0, 1.3), 7.54(1H, d, J=8.8), 7.61(1H, d, J=8.5), 7.73(1H, s).
EXP. 013
$^1$H-NMR(CDCl$_3$): 1.23–1.34(2H, m), 1.44–1.57(4H, m), 1.69–1.79(2H, m), 2.26(1H, qu, J=7.4), 2.65(2H, t, J=7.7), 2.95(2H, t, J=7.8), 3.67(3H, s), 3.82(2H, d, J=6.8), 3.84(2H, br-s), 6.90(1H, d, J=8.5), 6.93(1H, dd, J=8.5, 2.2), 7.00(1H, d, J=1.9), 7.12(1H, dd, J=8.3, 2.2), 7.25(1H, d, J=1.3), 7.45(1H, dd, J=8.5, 1.6), 7.65–7.73(3H, m).
Mass: (LCMS) 404(M$^+$+1)
EXP. 014
$^1$H-NMR(DMSO-d$_6$): 1.24–1.35(2H, m), 1.46–1.54(4H, m), 1.67–1.74(2H, m), 2.19(1H, qu, J=7.4), 2.54(2H, t, J=7.4), 2.81(2H, t, J=7.4), 3.83(2H, d, J=6.5), 5.36(2H, br-s), 6.82(1H, d, J=1.6), 6.92(1H, dd, J=8.5, 2.2), 6.99(1H, d, J=8.2), 7.14(1H, dd, J=8.2, 2.2), 7.23–7.27(2H, m), 7.57–7.63(3H, m), 12.08(1H, s).
Mass: (LCMS) 390(M$^+$+1)
EXP. Int. 27
$^1$H-NMR(CDCl$_3$): 2.92(3H, s), 3.92(1H, br-s), 6.73(1H, d, J=2.2), 6.87(1H, dd, J=8.8, 2.4), 7.40(1H, dd, J=8.8, 1.9), 7.48–7.53(2H, m), 7.80(1H, d, J=1.6).
EXP. 015
$^1$H-NMR(CDCl$_3$): 1.21–1.33(2H, m), 1.47–1.59(4H, m), 1.69–1.79(2H, m), 2.26(1H, qu, J=7.4), 2.65(2H, t, J=7.4), 2.94(2H, t, J=7.6), 2.95(3H, s), 3.68(3H, s), 3.82(2H, d, J=6.8), 6.82(1H, d, J=2.2), 6.86–6.91(2H, m), 7.10(1H, dd, J=8.3, 2.2), 7.26(1H, d, J=2.4), 7.59–7.65(3H, m), 7.84(1H, s).
Mass: (LCMS) 418(M$^+$+1)
EXP. 016
$^1$H-NMR(DMSO-d$_6$): 1.24–1.35(2H, m), 1.45–1.54(4H, m), 1.64–1.72(2H, m), 2.20(1H, qu, J=7.4), 2.54(2H, t, J=8.1), 2.77–2.84(5H, m), 3.83(2H, d, J=6.5), 5.99(1H, br-d, J=3.5), 6.67(1H, d, J=1.9), 6.94(1H, dd, J=8.8, 2.0), 6.99(1H, d, J=8.5), 7.12(1H, dd, J=8.2, 2.2), 7.24(1H, d, J=2.2), 7.50(1H, dd, J=8.5, 1.6), 7.59(2H, d, J=8.7), 7.77(1H, s), 12.08(1H, s).
Mass: (LCMS) 404(M$^+$+1)
EXP. 017
$^1$H-NMR(CDCl$_3$): 1.22–1.36(2H, m), 1.47–1.58(4H, m), 1.69–1.78(2H, m), 2.26(1H, qu, J=7.5), 2.65(2H, t, J=7.8), 2.95(2H, t, J=7.8), 3.06(6H, s), 3.68(3H, s), 3.82(2H, d, J=6.8), 6.90(1H, d, J=8.2), 6.95(1H, d, J=1.9), 7.10(1H, dd, J=8.3, 2.3), 7.17(1H, dd, J=9.0, 2.4), 7.27(1H, d, J=2.2), 7.59–7.79(3H, m), 7.85(1H, m).
Mass: (LCMS) 432(M$^+$+1)
EXP. 018
$^1$H-NMR(DMSO-d$_6$): 1.25–1.35(2H, m), 1.45–1.53(4H, m), 1.63–1.72(2H, m), 2.19(1H, qu, J=7.4), 2.54(2H, t, J=7.4), 2.81(2H, t, J=7.4), 3.01(6H, s), 3.84(2H, d, J=6.5), 6.95 (1H, d, J=2.2), 7.00(1H, d, J=8.5), 7.13(1H, dd, J=8.2, 2.2), 7.21–7.26(2H, m), 7.54(1H, dd, J=8.5, 1.6), 7.66(1H, d, J=8.7), 7.72(1H, d, J=9.0), 7.83(1H, s), 12.10(1H, s).
Mass: (LCMS) 418(M$^+$+1)
EXP. Int. 28
$^1$H-NMR(DMSO-d$_6$): 7.26(2H, s), 7.36(1H, dd, J=8.7, 2.2), 7.55(1H, dd, J=8.8, 1.9), 7.61(1H, d, J=1.9), 7.72(1H, d, J=8.7), 7.82(1H, d, J=8.7), 8.08(1H, d, J=1.9), 9.86(1H, s).
EXP. 019
$^1$H-NMR(CDCl$_3$): 1.23–1.31(2H, m), 1.49–1.58(4H, m), 1.65–1.78(2H, m), 2.25(1H, qu, J=7.5), 2.58(2H, t, J=7.7), 2.96(2H, t, J=7.8), 3.68(3H, s), 3.83(2H, d, J=6.8), 4.78(2H, br-s), 6.72(1H, br-s), 6.92(1H, d, J=8.2), 7.15(1H, dd, J=8.3, 2.2), 7.25(1H, d, J=2.2), 7.32(1H, dd, J=8.7.2.2), 7.70–7.85(4H, m), 7.95(1H, s).
Mass: (LCMS) 481(M$^-$)
EXP. 020
$^1$H-NMR(DMSO-d$_6$): 1.25–1.34(2H, m), 1.46–1.55(4H, m), 1.62–1.75(2H, m), 2.19(1H, qu, J=7.4), 2.54(2H, t, J=7.5), 2.82(2H, t, J=7.6), 3.85(2H, d, J=6.5), 7.02(1H, d, J=8.5), 7.17(1H, dd, J=8.2, 1.9), 7.22(2H, s), 7.28(1H, d, J=1.9), 7.34(1H, dd, J=8.8, 2.0), 7.62–7.66(2H, m), 7.75(1H, d, J=8.7), 7.82(1H, d, J=8.5), 7.98(1H, s), 9.74(1H, s), 12.05(1H, s).
Mass: (LCMS) 467(M$^-$)
EXP. 021
$^1$H-NMR(CDCl$_3$): 1.22–1.31(2H, m), 1.48–1.58(4H, m), 1.68–1.77(2H, m), 2.25(1H, qu, J=7.4), 2.66(2H, t, J=7.6), 2.97(2H, t, J=7.7), 3.14(3H, s), 3.68(3H, s), 3.86(2H, d, J=6.5), 6.94(1H, d, J=8.2), 7.19(1H, dd, J=8.5, 2.2), 7.28(1H, d, J=2.4), 7.89(2H, td, J=8.5, 1.6), 8.00(1H, t, J=7.6), 8.07(2H, s), 8.53(1H, s).
EXP. 022
$^1$H-NMR(DMSO-d$_6$): 1.24–1.32(2H, m), 1.44–1.52(4H, m), 1.61–1.72(2H, m), 2.19(1H, qu, J=7.5), 2.56(2H, t, J=7.5), 2.84(2H, t, J=7.5), 3.30(3H, s), 3.88(2H, d, J=6.8), 7.07 (1H, d, J=8.5), 7.24(1H, dd, J=8.5, 2.2), 7.34(1H, d, J=2.2), 7.85(1H, dd, J=8.5, 1.3), 7.95(1H, dd, J=8.7, 1.8), 8.16–8.22(3H, m), 8.59(1H, s), 12.08(1H, s).

TABLE 1-continued

Mass: (LCMS) 451(M⁻)
EXP. Int. 29
¹H-NMR(DMSO-d₆): 7.49(2H, s), 7.79(1H, dd, J=8.8, 1.9), 7.93(1H, dd, J=8.8, 1.6), 8.12(2H, t, J=7.7), 8.34(1H, d, J=1.6), 8.46(1H, s).
EXP. 023
¹H-NMR(CDCl₃): 1.24–1.31(2H, m), 1.51–1.61(4H, m), 1.67–1.78(2H, m), 2.25(1H, qu, J=7.4), 2.66(2H, t, J=7.5), 2.97(2H, t, J=7.7), 3.68(3H, s), 3.85(2H, d, J=6.8), 4.95–4.97(2H, m), 6.94(1H, d, J=8.2), 7.19(1H, d, J=8.2), 7.26(1H, d, J=1.3), 7.83–7.99 (4H, m), 8.05(1H, s), 8.50(1H, s).
Mass: (LCMS) 466(M⁻)
EXP. 024
¹H-NMR(DMSO-d₆): 1.25–1.29(2H, m), 1.42–1.54(4H, m), 1.61–1.72(2H, m), 2.20(1H, qu, J=7.4), 2.56(2H, t, J=7.6), 2.84(2H, t, J=7.5), 3.87(2H, d, J=6.5), 7.06(1H, d, J=8.5), 7.22(1H, dd, J=8.3, 2.2), 7.33(1H, d, J=2.2), 7.45(2H, s), 7.82(1H, dd, J=9.8, 1.6), 7.88(1H, dd, J=8.5, 1.8), 8.08–8.15(3H, m), 8.43(1H, s), 12.08(1H, s).
Mass: (LCMS) 452(M⁻)
EXP. Int. 30
¹H-NMR(CDCl₃): 2.70(3H, d, J=5.2), 4.48(1H, q, J=5.2), 7.69(1H, dd, J=8.7, 1.9), 7.82–7.91(3H, m), 8.09(1H, s), 8.40(1H, s).
EXP. 025
¹H-NMR(CDCl₃): 1.24–1.34(2H, m), 1.52–1.59(4H, m), 1.68–1.78(2H, m), 2.26(1H, qu, J=7.4), 2.66(2H, t, J=7.6), 2.70(3H, d, J=5.2), 2.97(2H, t, J=7.5), 3.68(3H, s), 3.85(2H, d, J=6.8), 4.46(1H, br-s), 6.93(1H, d, J=8.5), 7.19(1H, d, J=8.7), 7.27(1H, d, J=3.3), 7.84(2H, t, J=8.4), 7.97(2H, dd, J=8.3, 2.8), 8.05(1H, s), 8.44(1H, s).
Mass: (LCMS) 482(M⁺+1)
EXP. 026
¹H-NMR(DMSO-d₆): 1.25–1.32(2H, m), 1.40–1.54(4H, m), 1.62–1.73(2H, m), 2.20(1H, qu, J=7.2), 2.45(3H, d, J=4.9), 2.56(2H, t, J=7.5), 2.84(2H, t, J=7.4), 3.87(2H, d, J=6.8), 7.06(1H, d, J=8.5), 7.23(1H, dd, J=8.5, 2.2), 7.33(1H, d, J=1.9), 7.55(1H, q, J=4.9), 7.81(1H, dd, J=8.8, 1.9), 7.85(1H, m), 8.11–8.18(3H, m), 8.43(1H, s), 12.11(1H, br-s).
Mass: (LCMS) 468(M⁺+1)
EXP. Int. 31
¹H-NMR(DMSO-d₆): 2.67(6H, s), 7.83(2H, dd, J=8.4, 2.0), 8.18(2H, dd, J=11.9, 8.8), 8.40(1H, d, J=1.9), 8.49(1H, s).
EXP. 027
¹H-NMR(CDCl₃): 1.23–1.35(2H, m), 1.52–1.58(4H, m), 1.69–1.79(2H, m), 2.27(1H, qu, J=7.4), 2.66(2H, t, J=7.8), 2.78(6H, s), 2.97(2H, t, J=7.8), 3.68(3H, s), 3.86(2H, d, J=6.8), 6.94(1H, d, J=8.2), 7.19(1H, dd, J=8.2, 2.2), 7.28(1H, d, J=2.2), 7.77(1H, dd, J=8.5, 1.6), 7.86(1H, dd, J=8.5, 1.3), 7.98(2H, d, J=8.5), 8.06(1H, s), 8.35(1H, s).
Mass: (LCMS) 496(M⁺+1)
EXP. 028
¹H-NMR(DMSO-d₆): 1.23–1.34(2H, m), 1.45–1.52(4H, m), 1.64–1.73(2H, m), 2.20(1H, qu, J=7.4), 2.56(2H, t, J=7.3), 2.68(6H, s), 2.84(2H, t, J=7.4), 3.88(2H, d, J=6.5), 7.07 (1H, d, J=8.5), 7.23(1H, dd, J=8.2, 2.2), 7.33(1H, d, J=2.2), 7.78(1H, dd, J=8.7, 1.8), 7.87(1H, dd, J=8.5, 1.3), 8.14–8.23(3H, m), 8.45(1H, s), 12.09(1H, s).
Mass: (LCMS) 482(M⁺+1)
EXP. Int. 32
¹H-NMR(CDCl₃): 0.81–1.28(5H, m), 1.66–1.73(6H, m), 2.66(2H, t, J=8.0), 2.97(2H, t, J=7.8), 3.68(3H, s), 3.76(2H, d, J=5.8), 3.99(3H, s), 6.93(1H, d, J=8.2), 7.18(1H, dd, J=8.2, 2.1), 7.28(1H, d, J=2.2), 7.77(1H, dd, J=8.5, 2.1), 7.88(1H, d, J=9.1), 7.95(1H, d, J=8.8), 8.06(2H, dd, J=8.5, 1.6), 8.63(1H, s).
Mass: 461(M⁺+1)
EXP. 029
¹H-NMR(DMSO-d₆): 0.83–1.25(5H, m), 1.60–1.71(6H, m), 2.55(2H, t, J=7.4), 2.84(2H, t, J=7.5), 3.80(2H, d, J=5.8), 7.05(1H, d, J=8.5), 7.22(1H, dd, J=8.2, 2.2), 7.33(1H, d, J=2.2), 7.77(1H, dd, J=8.5, 1.6), 8.00(2H, s), 8.12(2H, d, J=9.1), 8.62(1H, s), 12.55(2H, br-s).
Mass: 432(M⁺)
EXP. Int. 33
¹H-NMR(CDCl₃): 2.60(2H, t, J=7.3), 2.87(2H, t, J=7.7), 3.67(3H, s), 3.87(3H, s), 6.82 (1H, d, J=8.2), 7.10(1H, dd, J=8.4, 2.2), 7.38(1H, d, J=2.2).
Mass: 272(M⁺)
EXP. Int. 34
¹H-NMR(CDCl₃): 2.67(2H, t, J=7.4), 2.97(2H, t, J=7.8), 3.68(3H, s), 3.80(3H, s), 6.94 (1H, d, J=8.2), 7.11(1H, td, J=8.8, 2.4), 7.25(1H, m), 7.44–7.50(2H, m), 7.67(1H, dd, J=8.6, 1.6), 7.84–7.87(3H, m), 7.94(1H, s).
Mass: 320(M⁺)
EXP. Int. 35
¹H-NMR(DMSO-d₆): 2.55(2H, t, J=7.4), 2.83(2H, t, J=7.8), 3.75(3H, s), 7.06(1H, d, J=8.5), 7.21–7.28(2H, m), 7.48–7.55(2H, m), 7.64(1H, dd, J=8.5, 1.9), 7.90–7.96(4H, m), 12.13(1H, br-s).
Mass: 307(M⁺+1)
EXP. Int. 36
¹H-NMR(CDCl₃): 2.64(2H, t, J=7.4), 2.94(2H, t, J=7.8), 3.67(3H, s), 5.27(1H, s), 6.94 (1H, d, J=8.2), 7.11(1H, dd, J=8.2, 2.2), 7.17(1H, d, J=2.2), 7.51–7.58(3H, m), 7.85–7.97 (4H, m).
Mass: 306(M⁺)

TABLE 1-continued

EXP. 030
¹H-NMR(CDCl₃): 2.67(2H, t, J=7.6), 2.98(2H, t, J=7.8), 3.68(3H, s), 5.13(2H, s), 6.99–7.05(3H, m), 7.15–7.25(2H, m), 7.30(1H, d, J=2.5), 7.35(1H, d, J=7.9), 7.46–7.50 (2H, m), 7.73(1H, dd, J=8.5, 1.6), 7.81–7.88(3H, m), 7.99(1H, s).
Mass: 414(M⁺)
EXP. 031
¹H-NMR(CDCl₃): 2.72(2H, t, J=7.6), 2.99(2H, t, J=7.7), 5.13(2H, s), 6.99–7.05(3H, m), 7.18(1H, dd, J=8.4, 2.3), 7.21–7.24(1H, m), 7.31–7.36(2H, m), 7.46–7.49(2H, m), 7.43 (1H, dd, J=8.4, 1.6), 7.83–7.86(3H, m), 7.99(1H, s).
Mass: 400(M⁺)
EXP. 032
¹H-NMR(CDCl₃): 2.66(2H, t, J=7.4), 2.98(2H, t, J=7.5), 3.68(3H, s), 5.05(2H, s), 6.89–6.97(2H, m), 7.01–7.08(2H, m), 7.15(1H, dd, J=8.2, 2.3), 7.20–7.28(1H, m), 7.31 (1H, d, J=2.5), 7.46–7.52(2H, m), 7.73(1H, dd, J=8.5, 1.9), 7.84–7.89(3H, m), 7.99(1H, s).
Mass: 414(M⁺)
EXP. 033
¹H-NMR(CDCl₃): 2.72(2H, t, J=7.5), 2.99(2H, t, J=7.7), 5.05(2H, s), 6.91–6.98(2H, m), 7.01–7.07(2H, m), 7.17(1H, dd, J=8.5, 2.2), 7.20–7.28(1H, m), 7.32(1H, d, J=2.2), 7.47–7.50(2H, m), 7.73(1H, dd, J=8.5, 2.2), 7.85–7.88(3H, m), 7.99(1H, s).
Mass: 400(M⁺)
EXP. 034
¹H-NMR(CDCl₃): 2.67(2H, t, J=7.6), 2.98(2H, t, J=7.8), 3.68(3H, s), 5.01(2H, s), 6.93–6.99(3H, m), 7.15(1H, dd, J=8.2, 2.3), 7.23–7.28(2H, m), 7.30(1H, d, J=2.2), 7.47–7.51(2H, m), 7.71(1H, dd, J=8.7, 1.5), 7.82–7.88(3H, m), 7.98(1H, s).
Mass: 414(M⁺)
EXP. 035
¹H-NMR(CDCl₃): 2.71(2H, t, J=7.7), 2.98(2H, t, J=7.8), 5.00(2H, s), 6.93–6.99(3H, m), 7.16(1H, dd, J=8.2, 2.2), 7.22–7.27(2H, m), 7.31(1H, d, J=2.2), 7.45–7.51(2H, m), 7.71 (1H, dd, J=8.5, 1.6), 7.83–7.87(3H, m), 7.97(1H, s).
Mass: 400(M⁺)
EXP. 036
¹H-NMR(CDCl₃): 0.89(3H, t, J=7.4), 1.41(2H, m), 1.68(2H, m), 2.66(2H, t, J=7.5), 2.96(2H, t, J=7.8), 3.68(3H, s), 3.95(2H, t, J=6.4), 6.93(1H, d, J=8.2), 7.15(1H, dd, J=8.5, 2.3), 7.27(1H, d, J=2.2), 7.45–7.50(2H, m), 7.70(1H, dd, J=8.5, 1.6), 7.82–7.87 (3H, m), 7.97(1H, s).
Mass: 362(M⁺)
EXP. 037
¹H-NMR(CDCl₃): 0.89(3H, t, J=7.4), 1.42(2H, m), 1.67(2H, m), 2.71(2H, t, J=7.6), 2.98(2H, t, J=7.7), 3.96(2H, t, J=6.3), 6.94(1H, d, J=8.5), 7.16(1H, dd, J=8.2, 2.3), 7.29(1H, d, J=2.2), 7.44–7.50(2H, m), 7.71(1H, dd, J=8.5, 1.6), 7.83–7.87(3H, m), 7.97 (1H, d, J=1.1).
Mass: 348(M⁺)
EXP. 038
¹H-NMR(CDCl₃): 1.24–1.35(2H, m), 1.46–1.58(4H, m), 1.69–1.79(2H, m), 2.26(1H, qu, J=7.4), 2.66(2H, t, J=7.8), 2.97(2H, t, J=7.8), 3.68(3H, s), 3.84(2H, d, J=6.9), 6.92(1H, d, J=8.5), 7.15(1H, dd, J=8.1, 2.5), 7.28(1H, d, J=2.5), 7.44–7.50(2H, m), 7.72(1H, dd, J=8.5, 1.6), 7.83–7.87(3H, m), 7.99(1H, s).
Mass: 388(M⁺)
EXP. 039
¹H-NMR(CDCl₃): 1.23–1.35(2H, m), 1.45–1.59(4H, m), 1.69–1.77(2H, m), 2.26(1H, qu, J=7.5), 2.71(2H, t, J=7.4), 2.97(2H, t, J=7.8), 3.83(2H, d, J=6.9), 6.93(1H, d, J=8.5), 7.16(1H, dd, J=8.4, 2.3), 7.29(1H, d, J=2.2), 7.44–7.50(2H, m), 7.72(1H, dd, J=8.4, 1.6), 7.83–7.87(3H, m), 7.99(1H, s).
Mass: 375(M⁺+1)
EXP. 040
¹H-NMR(CDCl₃): 1.21(6H, d, J=6.0), 2.67(2H, t, J=7.5), 2.96(2H, t, J=7.8), 3.68(3H, s), 4.39(1H, qu, J=6.0), 6.94(1H, d, J=8.2), 7.13(1H, dd, J=8.5, 2.3), 7.27(1H, d, J=2.2), 7.44–7.50(2H, m), 7.72(1H, dd, J=8.5, 1.6), 7.82–7.87(3H, m), 7.96(1H, d, J=1.1).
Mass: 348(M⁺)
EXP. 041
¹H-NMR(CDCl₃): 1.22(6H, d, J=6.0), 2.71(2H, t, J=7.5), 2.97(2H, t, J=7.8), 4.39(1H, qu, J=6.0), 6.95(1H, d, J=8.5), 7.14(1H, dd, J=8.2, 2.2), 7.28(1H, d, J=2.2), 7.43–7.50 (2H, m), 7.72(1H, dd, J=8.5, 1.6), 7.82–7.88(3H, m), 7.96(1H, s).
Mass: 334(M⁺)
EXP. 042
¹H-NMR(CDCl₃): 1.54–1.81(8H, m), 2.66(2H, t, J=7.8), 2.96(2H, t, J=7.8), 3.69(3H, s), 4.70–4.75(1H, m), 6.93(1H, d, J=8.2), 7.13(1H, dd, J=8.2, 2.3), 7.27(1H, d, J=2.2), 7.44–7.50(2H, m), 7.69(1H, dd, J=8.5, 1.6), 7.81–7.86(3H, m), 7.94(1H, s).
Mass: 374(M⁺)
EXP. 043
¹H-NMR(CDCl₃): 1.54–1.81(8H, m), 2.71(2H, t, J=7.6), 2.97(2H, t, J=7.6), 4.70–4.74 (1H, m), 6.93(1H, d, J=8.5), 7.14(1H, dd, J=8.5, 2.3), 7.28(1H, d, J=2.4), 7.43–7.49(2H, m), 7.69(1H, dd, J=8.5, 1.6), 7.81–7.86(3H, m), 7.94(1H, s).
Mass: 360(M⁺)
EXP. 044
¹H-NMR(CDCl₃): 1.21–1.31(3H, m), 1.41–1.69(5H, m), 1.80–1.88(2H, m), 2.66(2H, t, J=7.5), 2.96(2H, t, J=7.7), 3.69(3H, s), 4.18(1H, m), 6.95(1H, d, J=8.2), 7.13(1H, dd, J=8.5, 2.2), 7.28(1H, d, J=2.2), 7.45–7.49(2H, m), 7.74(1H, dd, J=8.8, 1.6), 7.82–7.87

TABLE 1-continued (3H, m), 7.98(1H, d, J=1.1).
Mass: 388(M$^+$)
EXP. 045
$^1$H-NMR(CDCl$_3$): 1.21–1.29(3H, m), 1.41–1.53(3H, m), 1.61–1.69(2H, m), 1.81–1.89(2H, m), 2.71(2H, t, J=7.7), 2.97(2H, t, J=7.7), 4.18(1H, m), 6.95(1H, d, J=8.2), 7.14(1H, dd, J=8.5, 2.3), 7.29(1H, d, J=2.2), 7.45–7.48(2H, m), 7.74(1H, dd, J=8.5, 1.7), 7.82–7.88(3H, m), 7.98(1H, d, J=1.1).
Mass: 374(M$^+$)
EXP. 046
$^1$H-NMR(CDCl$_3$): 1.03–1.12(2H, m), 1.42–1.59(4H, m), 1.67–1.76(4H, m), 1.88(1H, m), 2.66(2H, t, J=7.4), 2.96(2H, t, J=7.7), 3.68(3H, s), 3.96(2H, t, J=6.7), 6.94(1H, d, J=8.2), 7.15(1H, dd, J=8.2, 2.2), 7.26(1H, d, J=2.2), 7.44–7.50(2H, m), 7.69(1H, dd, J=8.5, 1.6), 7.82–7.86(3H, m), 7.96(1H, s).
Mass: 402(M$^+$)
EXP. 047
$^1$H-NMR(CDCl$_3$): 1.00–1.12(2H, m), 1.42–1.61(4H, m), 1.67–1.76(4H, m), 1.88(1H, m), 2.71(2H, t, J=7.8), 2.97(2H, t, J=7.7), 3.96(2H, t, J=6.7), 6.93(1H, d, J=8.2), 7.16(1H, dd, J=8.5, 2.3), 7.28(1H, d, J=2.2), 7.43–7.49(2H, m), 7.69(1H, dd, J=8.5, 1.6), 7.82–7.86(3H, m), 7.96(1H, s).
Mass: 388(M$^+$)
EXP. 048
$^1$H-NMR(CDCl$_3$): 0.81–1.19(5H, m), 1.43(2H, d, J=6.3), 1.37–1.67(6H, m), 2.66(2H, t, J=7.9), 2.96(2H, t, J=7.8), 3.68(3H, s), 3.98(2H, t, J=6.3), 6.93(1H, d, J=8.2), 7.15(1H, dd, J=8.2, 2.2), 7.27(1H, d, J=2.5), 7.44–7.50(2H, m), 7.68(1H, dd, J=8.5, 1.9), 7.83–7.87(3H, m), 7.96(1H, s).
Mass: 416(M$^+$)
EXP. 049
$^1$H-NMR(CDCl$_3$): 0.85–1.46(6H, m), 1.56(2H, t, J=6.6), 1.60–1.67(5H, m), 2.71(2H, t, J=7.6), 2.97(2H, t, J=7.6), 3.98(2H, t, J=6.6), 6.94(1H, d, J=8.5), 7.16(1H, dd, J=8.2, 2.2), 7.28(1H, d, J=2.2), 7.45–7.50(2H, m), 7.69(1H, dd, J=8.5, 1.6), 7.82–7.87(3H, m), 7.96(1H, s).
Mass: 402(M$^+$)
EXP. 050
$^1$H-NMR(CDCl$_3$): 2.64(2H, t, J=7.8), 2.97–3.00(4H, m), 3.67(3H, s), 4.18(2H, t, J=6.6), 6.91(1H, d, J=8.2), 7.12–7.15(3H, m), 7.19–7.26(4H, m), 7.46–7.50(2H, m), 7.57(1H, dd, J=8.5, 1.6), 7.79–7.88(4H, m).
Mass: 410(M$^+$+1)
EXP. 051
$^1$H-NMR(CDCl$_3$): 2.69(2H, t, J=7.8), 2.93–3.00(4H, m), 4.18(2H, t, J=6.7), 6.91(1H, d, J=8.2), 7.11–7.21(6H, m), 7.26(1H, d, J=1.9), 7.46–7.50(2H, m), 7.57(1H, dd, J=8.5, 1.6), 7.79–7.88(4H, m).
Mass: 396(M$^+$)
EXP. 052
$^1$H-NMR(CDCl$_3$): 2.64(2H, t, J=7.4), 2.95(2H, t, J=7.8), 3.03(2H, t, J=6.4), 3.67(3H, s), 4.18(2H, t, J=6.6), 6.87–7.00(3H, m), 7.06(1H, td, J=7.6, 1.8), 7.13–7.17(2H, m), 7.24(1H, d, J=2.2), 7.47–7.50(2H, m), 7.56(1H, dd, J=8.5, 1.9), 7.79–7.88(4H, m).
Mass: 428(M$^+$)
EXP. 053
$^1$H-NMR(CDCl$_3$): 2.69(2H, t, J=7.6), 2.96(2H, t, J=7.7), 3.02(2H, t, J=6.6), 4.18(2H, t, J=6.4), 6.87–6.99(3H, m), 7.07(1H, td, J=7.7, 1.9), 7.12–7.20(2H, m), 7.25(1H, d, J=1.9), 7.45–7.51(2H, m), 7.56(1H, dd, J=8.5, 1.6), 7.79–7.87(4H, m).
Mass: 414(M$^+$)
EXP. 054
$^1$H-NMR(CDCl$_3$): 2.64(2H, t, J=7.8), 2.92–2.98(4H, m), 3.67(3H, s), 4.16(2H, t, J=6.4), 6.84–6.91(4H, m), 7.09–7.16(2H, m), 7.24(1H, d, J=3.0), 7.47–7.50(2H, m), 7.54(1H, dd, J=8.5, 1.8), 7.80–7.88(4H, m).
Mass: 428(M$^+$)
EXP. 055
$^1$H-NMR(CDCl$_3$): 2.69(2H, t, J=7.6), 2.96(4H, t, J=6.7), 4.16(2H, t, J=6.4), 6.84–6.92(4H, m), 7.09–7.17(2H, m), 7.26(1H, d, J=1.4), 7.45–7.51(2H, m), 7.54(1H, dd, J=8.5, 1.6), 7.80–7.88(4H, m).
Mass: 414(M$^+$)
EXP. 056
$^1$H-NMR(CDCl$_3$): 2.65(2H, t, J=7.4), 2.90–2.98(4H, m), 3.67(3H, s), 4.13(2H, t, J=6.3), 6.82(2H, t, J=8.8), 6.90(1H, d, J=8.2), 7.01–7.05(2H, m), 7.14(1H, dd, J=8.5, 2.2), 7.24(1H, d, J=2.4), 7.48–7.51(2H, m), 7.54(1H, dd, J=8.4, 1.6), 7.79–7.89(4H, m).
Mass: 428(M$^+$)
EXP. 057
$^1$H-NMR(CDCl$_3$): 2.69(2H, t, J=7.4), 2.90–2.98(4H, m), 4.13(2H, t, J=6.3), 6.82(2H, t, J=8.5), 6.90(1H, d, J=8.2), 7.00–7.05(2H, m), 7.14(1H, dd, J=8.2, 1.9), 7.25(1H, d, J=2.7), 7.45–7.50(2H, m), 7.54(1H, dd, J=8.5, 1.6), 7.79–7.88(4H, m).
Mass: 414(M$^+$)
EXP. 058
$^1$H-NMR(CDCl$_3$): 2.71(2H, t, J=7.8), 2.98(2H, t, J=7.7), 4.86(2H, s), 6.26–6.31(2H, m), 7.05(1H, d, J=8.2), 7.17(1H, dd, J=8.5, 2.2), 7.30(1H, d, J=2.2), 7.38(1H, m), 7.45–7.50 (2H, m), 7.69(1H, dd, J=8.8, 1.3), 7.82–7.86(3H, m), 7.96(1H, s).
Mass: 372(M$^+$)
EXP. 059
$^1$H-NMR(CDCl$_3$): 2.68(2H, t, J=7.8), 2.99(2H, t, J=7.7), 3.69(3H, s), 5.07(2H, s), 7.01

TABLE 1-continued (1H, d, J=8.5), 7.17–7.22(2H, m), 7.32(1H, d, J=2.2), 7.48–7.51(2H, m), 7.59(1H, d, J=7.7), 7.71(1H, dd, J=8.5, 1.6), 7.84–7.88(3H, m), 7.96(1H, s), 8.50(1H, dd, J=5.0, 1.2), 8.57(1H, d, J=1.9).
Mass: 398(M$^+$+1)
EXP. 060
$^1$H-NMR(DMSO-d$_6$): 2.57(2H, t, J=7.5), 2.85(2H, t, J=7.5), 5.17(2H, s), 7.17–7.26(2H, m), 7.32–7.37(2H, m), 7.49–7.53(2H, m), 7.72(1H, dd, J=8.5, 1.6), 7.78(1H, d, J=7.7), 7.89–7.94(3H, m), 8.03(1H, s), 8.48(1H, dd, J=5.0, 1.4), 8.59(1H, s), 12.15(1H, s).
Mass: 384(M$^+$+1)
EXP. 061
$^1$H-NMR(CDCl$_3$): 1.21(3H, t, J=6.8), 2.53–2.67(4H, m), 2.95(2H, t, J=7.8), 3.10(2H, t, J=6.2), 3.69(3H, s), 4.34(2H, t, J=6.3), 6.89(1H, d, J=7.9), 6.96(1H, d, J=8.5), 7.16(2H, td, J=6.8, 2.2), 7.22(1H, d, J=2.5), 7.46–7.52(3H, m), 7.75–7.87(4H, m), 8.32(1H, d, J=2.5).
Mass: 440(M$^+$+1)
EXP. 062
$^1$H-NMR(DMSO-d$_6$): 1.16(3H, t, J=7.5), 2.57(4H, qu, J=7.6), 2.82(2H, t, J=7.3), 3.10(2H, t, J=6.0), 4.37(2H, t, J=6.3), 7.10(1H, d, J=8.2), 7.17–7.23(2H, m), 7.26(1H, d, J=2.2), 7.40(1H, dd, J=8.5, 2.2), 7.49–7.54(3H, m), 7.75–7.92(4H, m), 8.37(1H, s), 12.11(1H, s).
Mass: 426(M$^+$+1)
EXP. 063
$^1$H-NMR(CDCl$_3$): 1.93(3H, s), 2.64(2H, t, J=7.6), 2.86(2H, t, J=6.0), 2.95(2H, t, J=7.8), 3.67(3H, s), 4.27(2H, t, J=6.2), 6.97(1H, d, J=8.2), 7.14(1H, dd, J=8.5, 2.2), 7.22(1H, d, J=2.2), 7.40–7.48(5H, m), 7.54(1H, dd, J=8.5, 1.6), 7.75–7.85(4H, m), 7.93–7.96(2H, m).
Mass: 492(M$^+$+1)
EXP. 064
$^1$H-NMR(DMSO-d$_6$): 2.02(3H, s), 2.54(2H, t, J=7.5), 2.80–2.87(4H, m), 4.27(2H, t, J=6.0), 7.10(1H, d, J=8.5), 7.20(1H, dd, J=8.2, 2.2), 7.26(1H, d, J=1.9), 7.47–7.53(6H, m), 7.79–7.91(6H, m), 12.10(1H, s).
Mass: 478(M$^+$+1)
EXP. Int. 37
$^1$H-NMR(CDCl$_3$): 1.01–1.29(5H, m), 1.64–1.80(6H, m), 3.90(2H, d, J=5.8), 7.11(1H, d, J=8.8), 7.48–7.54(2H, m), 7.70(1H, dd, J=8.5, 1.6), 7.86–7.90(4H, m), 7.98(1H, d, J=2.2), 8.02(1H, s), 9.96(1H, s).
Mass: 345(M$^+$+1)
EXP. Int. 38
$^1$H-NMR(CDCl$_3$): 1.00–1.36(8H, m), 1.62–1.79(6H, m), 3.83(2H, d, J=6.0), 4.26(2H, q, J=7.1), 6.37(1H, d, J=16.0), 6.97–7.02(1H, m), 7.48–7.52(3H, m), 7.63–7.77(3H, m), 7.82–7.88(3H, m), 7.99(1H, s).
Mass: 415(M$^+$+1)
EXP. 065
$^1$H-NMR(CDCl$_3$): 0.95–1.27(8H, m), 1.66–1.78(6H, m), 2.66(2H, t, J=7.7), 2.96(2H, t, J=7.7), 3.75(2H, d, J=5.8), 4.14(2H, q, J=7.1), 6.92(1H, d, J=8.2), 7.15(1H, dd, J=8.8, 2.0), 7.26–7.28(1H, m), 7.46–7.49(2H, m), 7.69–7.72(1H, m), 7.83–7.86(3H, m), 7.98(1H, s).
Mass: 416(M$^+$)
EXP. 066
$^1$H-NMR(CDCl$_3$): 0.98–1.26(5H, m), 1.66–1.78(6H, m), 2.71(2H, t, J=7.9), 2.98(2H, t, J=7.8), 3.75(2H, d, J=6.0), 6.93(1H, d, J=8.5), 7.16(1H, dd, J=8.8, 2.0), 7.26–7.30(1H, m), 7.46–7.49(2H, m), 7.71(1H, dd, J=8.5, 1.6), 7.83–7.86(3H, m), 7.99(1H, s).
Mass: 388(M$^+$)
EXP. Int. 39
$^1$H-NMR(CDCl$_3$): 1.02–1.28(5H, m), 1.64–1.80(6H, m), 3.90(2H, d, J=5.8), 3.96(3H, s), 7.09(1H, d, J=8.5), 7.15–7.18(2H, m), 7.67(1H, dd, J=8.5, 1.6), 7.75–7.79(2H, m), 7.85(1H, dd, J=8.5, 2.0), 7.95–7.98(2H, m), 9.95(1H, s).
Mass: 374(M$^+$)
EXP. Int. 40
$^1$H-NMR(CDCl$_3$): 1.00–1.36(8H, m), 1.68–1.79(6H, m), 3.82(2H, d, J=5.8), 3.95(3H, s), 4.26(2H, q, J=7.1), 6.37(1H, d, J=15.9), 6.98(1H, d, J=8.5), 7.15–7.18(2H, m), 7.48(1H, dd, J=8.7, 2.2), 7.62–7.78(5H, m), 7.93(1H, s).
Mass: 444(M$^+$)
EXP. 067
$^1$H-NMR(CDCl$_3$): 0.98–1.27(8H, m), 1.66–1.78(6H, m), 2.64(2H, t, J=8.0), 2.95(2H, t, J=8.0), 3.74(2H, d, J=6.0), 3.95(3H, s), 4.14(2H, q, J=7.1), 6.91(1H, d, J=8.2), 7.12–7.17(3H, m), 7.27(1H, d, J=3.3), 7.68(1H, dd, J=8.5, 1.6), 7.74(2H, d, J=8.2), 7.92(1H, s).
Mass: 446(M$^+$)
EXP. 068
$^1$H-NMR(DMSO-d$_6$): 0.98–1.20(5H, m), 1.61–1.73(6H, m), 2.54(2H, t, J=7.4), 2.80(2H, t, J=7.4), 3.78(2H, d, J=5.5), 3.89(3H, s), 7.01(1H, d, J=8.5), 7.17(2H, dd, J=8.8, 2.4), 7.27(1H, d, J=2.2), 7.33–7.35(1H, m), 7.61–7.66(1H, m), 7.82(2H, d, J=8.8), 7.94(1H, s), 12.97(1H, br-s).
Mass: 418(M$^+$)
EXP. Int. 41
$^1$H-NMR(CDCl$_3$): 0.65–1.09(5H, m), 1.24–1.52(6H, m), 3.77(2H, d, J=5.8), 7.10(1H, d, J=8.5), 7.33–7.55(5H, m), 7.85–7.90(3H, m), 7.96(1H, dd, J=8.6, 2.1), 9.94(1H, s).
Mass: 345(M$^+$+1)

TABLE 1-continued

EXP. Int. 42
$^1$H-NMR(CDCl$_3$): 0.75–1.68(14H, m), 3.81(2H, d, J=6.0), 4.35(2H, q, J=7.1), 6.32(1H, d, J=15.9), 7.01(1H, d, J=8.2), 7.33–7.58(7H, m), 7.69(1H, d, J=15.9), 7.85–7.89(2H, m).
Mass: 415(M$^+$+1)

EXP. 069
$^1$H-NMR(CDCl$_3$): 0.55–1.09(5H, m), 1.20–1.56(8H, m), 2.63(2H, t, J=7.7), 2.96(2H, t, J=7.7), 3.61(2H, d, J=6.0), 4.12(2H, q, J=7.1), 6.93(1H, d, J=8.2), 7.13(2H, d, J=2.2), 7.21(1H, d, J=8.2, 2.5), 7.32–7.38(2H, m), 7.41–7.53(2H, m), 7.59(1H, d, J=8.2), 7.84 (2H, t, J=8.6).
Mass: 416(M$^+$)

EXP. 070
$^1$H-NMR(CDCl$_3$): 0.62–1.09(5H, m), 1.23–1.78(6H, m), 2.69(2H, t, J=7.6), 2.96(2H, t, J=7.7), 3.62(2H, d, J=6.0), 6.94(1H, d, J=8.2), 7.15(1H, d, J=2.2), 7.22(1H, dd, J=8.5, 2.5), 7.32–7.53(4H, m), 7.59(1H, dd, J=9.1, 0.8), 7.84(2H, t, J=8.2).
Mass: 388(M$^+$).

EXP. Int. 43
$^1$H-NMR(CDCl$_3$): 0.94–1.26(5H, m), 1.61–1.77(6H, m), 2.65(2H, t, J=7.5), 2.96(2H, t, J=7.6), 3.68(3H, s), 3.74(2H, d, J=5.8), 4.02–4.07(3H, m), 4.23(2H, m), 6.91(1H, d, J=8.2), 7.11–7.19(3H, m), 7.26(1H, d, J=2.2), 7.68(1H, dd, J=8.5, 1.6), 7.72–7.77(2H, m), 7.92(1H, m).
Mass: (LCMS) 463(M$^+$+1)

EXP. 071
$^1$H-NMR(DMSO-d$_6$): 0.98–1.23(5H, m), 1.61–1.72(6H, m), 2.55(2H, t, J=7.5), 2.82(2H, t, J=7.4), 3.77–3.78(4H, m), 4.12(2H, t, J=5.1), 4.93(1H, br-s), 7.01(1H, d, J=8.5), 7.15–7.20(2H, m), 7.27(1H, d, J=1.9), 7.34(1H, d, J=2.4), 7.63(1H, dd, J=8.5, 2.2), 7.78–7.83(2H, m), 7.93(1H, s), 12.10(1H, s).
Mass: (LCMS) 449(M$^+$+1)

EXP. Int. 44
$^1$H-NMR(CDCl$_3$): 0.98–1.26(5H, m), 1.66–1.77(6H, m), 2.65(2H, t, J=7.7), 2.96(2H, t, J=7.7), 3.68(3H, s), 3.74(2H, d, J=5.8), 3.85(3H, s), 4.78(2H, s), 6.91(1H, d, J=8.2), 7.10(1H, d, J=2.4), 7.13(1H, dd, J=8.5, 2.2), 7.22(1H, dd, J=8.2, 2.3), 7.25(1H, d, J=3.6), 7.66–7.71(2H, m), 7.78(1H, d, J=9.0), 7.92(1H, s).
Mass: (LCMS) 491(M$^+$+1)

EXP. 072
$^1$H-NMR(DMSO-d$_6$): 0.86–1.23(6H, m), 1.57–1.74(6H, m), 2.55(2H, t, J=7.4), 2.82(2H, t, J=7.4), 3.77(2H, d, J=5.8), 4.82(2H, s), 7.01(1H, d, J=8.5), 7.16–7.29(4H, m), 7.64 (1H, d, J=8.5), 7.80(1H, d, J=12.8), 7.83(1H, d, J=13.4), 7.95(1H, s), 12.65(1H, br-s).
Mass: (LCMS) 463(M$^+$+1)

EXP. 073
$^1$H-NMR(CDCl$_3$): 0.97–1.25(5H, m), 1.58–1.77(6H, m), 2.65(2H, t, J=8.0), 2.95(2H, t, J=7.7), 3.01(3H, s), 3.14(3H, s), 3.68(3H, s), 3.74(2H, d, J=5.7), 4.82(2H, s), 6.91(1H, d, J=8.2), 7.13(1H, dd, J=8.2, 2.2), 7.20–7.25(3H, m), 7.68(1H, dd, J=8.5, 1.6), 7.73–7.78(2H, m), 7.91(1H, s).
Mass: (LCMS) 504(M$^+$+1)

EXP. 074
$^1$H.NMR(DMSO-d$_6$): 0.98–1.22(5H, m), 1.56–1.72(6H, m), 2.54(2H, t, J=7.5), 2.82(2H, t, J=7.5), 2.88(3H, s), 3.05(3H, s), 3.77(2H, d, J=8.5), 4.93(2H, s), 7.00(1H, d, J=8.5), 7.16(1H, dd, J=8.5, 2.2), 7.21(1H, dd, J=9.0, 2.5), 7.28(1H, dd, J=6.0, 2.2), 7.63(1H, dd, J=8.5, 1.6), 7.77(1H, d, J=8.5), 7.83(1H, d, J=9.0), 7.95(1H, s), 12.10(1H, s).
Mass: (LCMS) 490(M$^+$+1)

EXP. Int. 45
$^1$H-NMR(CDCl$_3$): 1.21–1.34(2H, m), 1.49–1.59(4H, m), 1.68–1.77(2H, m), 2.26(1H, qu, J=7.4), 2.65(2H, t, J=7.6), 2.96(2H, t, J=7.8), 3.68(3H, s), 3.77(2H, t, J=5.6), 3.83(2H, d, J=6.8), 4.47(2H, t, J=5.5), 6.90(1H, br-s), 6.92(1H, d, J=8.2), 7.14(1H, dd, J=8.2, 2.2), 7.26(1H, d, J=3.2), 7.39(1H, dd, J=8.7, 2.2), 7.70(1H, dd, J=8.5, 1.6), 7.76–7.81 (2H, m), 7.92(1H, s), 7.98(1H, s).
Mass: (LCMS) 510(M$^+$+1)

EXP. 075
$^1$H-NMR(DMSO-d$_6$): 1.24–1.34(2H, m), 1.45–1.53(4H, m), 1.62–1.75(2H, m), 2.20(1H, qu, J=7.4), 2.54(2H, t, J=7.4), 2.81(2H, t, J=7.4), 3.17–3.24(2H, m), 3.64(2H, t, J=6.0), 3.83(2H, d, J=6.8), 4.74(1H, br-s), 5.87(1H, br-s), 6.73(1H, s), 6.97–7.02(2H, m), 7.12 (1H, dd, J=8.4, 2.0), 7.24(1H, d, J=1.9), 7.49(1H, dd, J=8.5, 1.6), 7.54–7.60(2H, m), 7.76(1H, s), 12.07(1H, s).
Mass: (LCMS) 434(M$^+$+1)

EXP. 076
$^1$H-NMR(CDCl$_3$): 1.21–1.32(2H, m), 1.49–1.57(4H, m), 1.66–1.89(2H, m), 2.23(1H, qu, J=7.1), 2.24(3H, s), 2.65(2H, t, J=7.9), 2.96(2H, t, J=7.8), 3.68(3H, s), 3.83(2H, d, J=6.5), 6.92(1H, d, J=8.2), 7.15(1H, dd, J=8.5, 2.2), 7.27(1H, d, J=2.5), 7.32(1H, br-s), 7.45(1H, d, J=9.0), 7.70(1H, d, J=8.5), 7.80(2H, d, J=8.5), 7.92(1H, s), 8.18(1H, s).
Mass: (LCMS) 446(M$^+$+1)

EXP. 077
$^1$H-NMR(DMSO-d$_6$): 1.24–1.34(2H, m), 1.44–1.52(4H, m), 1.63–1.74(2H, m), 2.11(3H, s), 2.20(1H, qu, J=7.4), 2.55(2H, t, J=7.7), 2.82(2H, t, J=7.4), 3.85(2H, d, J=6.5), 7.02 (1H, d, J=8.5), 7.17(1H, dd, J=8.2, 2.1), 7.28(1H, d, J=2.1), 7.57(1H, dd, J=8.9, 2.2), 7.64(1H, dd, J=8.5, 1.5), 7.78–7.85(2H, m), 7.93(1H, s), 8.28(1H, s), 10.14(1H, s), 12.05(1H, s).
Mass: (LCMS) 432(M$^+$+1)

TABLE 1-continued

EXP. Int. 46
$^1$H-NMR(CDCl$_3$): 1.21–1.31(2H, m), 1.44–1.57(13H, m), 1.67–1.77(2H, m), 2.25(1H, qu, J=7.4), 2.65(2H, t, J=7.6), 2.95(2H, t, J=7.8), 3.67(3H, s), 3.82(2H, d, J=6.8), 4.00(2H, d, J=5.5), 5.36(1H, br-s), 6.91(1H, d, J=8.2), 7.14(1H, dd, J=8.3, 2.3), 7.26(1H, d, J=1.6), 7.47(1H, dd, J=8.5, 2.0), 7.69(1H, dd, J=8.5, 1.6), 7.70–7.80(2H, m), 7.92(1H, s), 8.19(1H, s), 8.41(1H, br-s).
Mass: (LCMS) 561(M$^+$+1)

EXP. 078
$^1$H-NMR(DMSO-d$_6$): 1.20–1.38(2H, m), 1.42–1.56(4H, m), 1.63–1.75(2H, m), 2.20(1H, qu, J=7.4), 2.49–2.50(2H, m), 2.54(2H, t, J=7.6), 2.82(2H, t, J=7.1), 3.40(3H, br-s), 3.85(2H, d, J=6.5), 7.03(1H, d, J=8.5), 7.16(1H, dd, J=8.5, 2.0), 7.28(1H, d, J=2.2), 7.63–7.67(2H, m), 7.82(1H, d, J=13.9), 7.85(1H, d, J=14.5), 7.94(1H, s), 8.31(1H, s).
Mass: (LCMS) 447(M$^+$+1)

EXP. Int. 47
$^1$H-NMR(CDCl$_3$): 1.21–1.34(2H, m), 1.49–1.59(4H, m), 1.69–1.79(2H, m), 2.24(1H, qu, J=7.6), 2.27(3H, s), 2.65(2H, t, J=8.2), 2.96(2H, t, J=7.8), 3.68(3H, s), 3.84(2H, d, J=6.8), 4.76(2H, s), 6.92(1H, d, J=8.5), 7.14(1H, dd, J=8.2, 2.1), 7.27(1H, d, J=2.2), 7.51(1H, dd, J=8.7, 2.2), 7.72(1H, dd, J=8.8, 1.6), 7.79–7.84(2H, m), 7.94(2H, s), 8.21(1H, s).
Mass: (LCMS) 504(M$^+$+1)

EXP. 079
$^1$H-NMR(DMSO-d$_6$): 1.25–1.35(2H, m), 1.45–1.52(4H, m), 1.64–1.72(2H, m), 2.20(1H, qu, J=7.4), 2.55(2H, t, J=7.4), 2.83(2H, t, J=7.4), 3.86(2H, d, J=6.8), 4.06(2H, d, J=6.0), 5.71(1H, t, J=5.8), 7.03(1H, d, J=8.2), 7.17(1H, dd, J=8.5, 1.9), 7.29(1H, d, J=2.2), 7.67(1H, dd, J=8.5, 1.6), 7.75(1H, dd, J=9.0, 1.9), 7.81(1H, d, J=12.3), 7.85(1H, d, J=12.8), 7.95(1H, s), 8.37(1H, s), 9.86(1H, s), 12.06(1H, s).
Mass: (LCMS) 448(M$^+$+1)

EXP. 080
$^1$H-NMR(CDCl$_3$): 1.21–1.35(2H, m), 1.48–1.63(4H, m), 1.69–1.79(2H, m), 2.26(1H, qu, J=7.5), 2.66(2H, t, J=7.9), 2.96(2H, t, J=7.8), 3.68(3H, s), 3.84(2H, d, J=6.8), 6.59(1H, dd, J=3.5, 1.6), 6.92(1H, d, J=8.5), 7.14(1H, dd, J=8.2, 2.3), 7.24–7.29(2H, m), 7.54–7.55(1H, m), 7.61(1H, dd, J=8.7, 2.2), 7.72(1H, dd, J=8.5, 1.6), 7.81–7.85(2H, m), 7.95(1H, s), 8.24(1H, s), 8.34(1H, d, J=1.9).
Mass: (LCMS) 498(M$^+$+1)

EXP. 081
$^1$H-NMR(DMSO-d$_6$): 1.25–1.37(2H, m), 1.45–1.52(4H, m), 1.63–1.76(2H, m), 2.20(1H, qu, J=7.4), 2.56(2H, t, J=7.4), 2.83(2H, t, J=7.5), 3.86(2H, d, J=6.6), 6.74(1H, dd, J=3.5, 1.6), 7.03(1H, d, J=8.5), 7.18(1H, dd, J=8.2, 1.9), 7.30(1H, d, J=2.2), 7.40(1H, d, J=3.5), 7.67(1H, dd, J=8.5, 1.5), 7.81–7.91(3H, m), 7.97(2H, s), 8.40(1H, d, J=1.3), 10.39(1H, s), 12.09(1H, s).
Mass: (LCMS) 484(M$^+$+1)

EXP. 082
$^1$H-NMR(CDCl$_3$): 1.27–1.36(2H, m), 1.47–1.56(4H, m), 1.69–1.73(2H, m), 2.21(1H, qu, J=7.6), 2.63(2H, t, J=7.6), 2.90(2H, t, J=7.5), 3.63(3H, s), 3.81(2H, d, J=6.5), 4.85(2H, s), 4.88(1H, br-s), 6.94(1H, d, J=8.2), 7.11(1H, dd, J=8.3, 2.2), 7.22(1H, d, J=2.2), 7.41(1H, dd, J=8.7, 2.2), 7.59(1H, dd, J=8.5, 1.6), 7.70(1H, d, J=8.8), 7.75(1H, d, J=9.0), 7.86(1H, s), 7.94(1H, d, J=2.2).
Mass: (LCMS) 447(M$^+$+1)

EXP. 083
$^1$H-NMR(DMSO-d$_6$): 1.23–1.31(2H, m), 1.45–1.53(4H, m), 1.62–1.72(2H, m), 2.20(1H, qu, J=7.4), 2.55(2H, t, J=7.4), 2.82(2H, t, J=7.3), 3.85(2H, d, J=6.5), 5.98(2H, s), 7.02(1H, d, J=8.5), 7.16(1H, dd, J=8.2, 2.1), 7.27(1H, d, J=2.2), 7.45(1H, dd, J=8.7, 1.9), 7.60(1H, dd, J=8.7, 1.6), 7.75(2H, t, J=9.5), 7.89(1H, s), 8.03(1H, s), 8.74(1H, s), 12.09(1H, s).
Mass: (LCMS) 433(M$^+$+1)

EXP. 084
$^1$H-NMR(CDCl$_3$): 1.21–1.32(2H, m), 1.44–1.59(4H, m), 1.69–1.79(2H, m), 2.26(1H, qu, J=7.4), 2.62–2.69(2H, m), 2.96(2H, t, J=7.8), 3.07(3H, s), 3.68(3H, s), 3.84(2H, d, J=6.8), 6.93(1H, d, J=8.5), 7.15(1H, dd, J=8.3, 2.3), 7.26(1H, d, J=2.4), 7.32(1H, dd, J=8.7, 2.3), 7.71–7.86(4H, m), 7.96(1H, s).
Mass: (LCMS) 480(M$^-$)

EXP. 085
$^1$H-NMR(DMSO-d$_6$): 1.25–1.31(2H, m), 1.45–1.52(4H, m), 1.62–1.71(2H, m), 2.19(1H, qu, J=7.4), 2.55(2H, t, J=7.5), 2.82(2H, t, J=7.4), 3.06(3H, s), 3.85(2H, d, J=6.5), 7.03(1H, d, J=8.5), 7.18(1H, dd, J=8.5, 2.0), 7.28(1H, d, J=2.2), 7.39(1H, dd, J=8.7, 2.2), 7.66–7.69(2H, m), 7.85(1H, d, J=14.6), 7.88(1H, d, J=14.9), 7.97(1H, s), 9.97(1H, s), 12.08(1H, s).
Mass: (LCMS) 466(M$^-$)

EXP. 086
$^1$H-NMR(CDCl$_3$): 1.18–1.32(2H, m), 1.47–1.58(4H, m), 1.69–1.79(2H, m), 2.26(1H, qu, J=7.4), 2.65(2H, t, J=7.7), 2.89(6H, s), 2.96(2H, t, J=7.7), 3.68(3H, s), 3.84(2H, d, J=6.8), 6.67(1H, d, J=8.7), 6.92(1H, d, J=8.5), 7.15(1H, dd, J=8.4, 2.2), 7.26(1H, d, J=0.8), 7.32(1H, dd, J=8.7, 2.2), 7.63(1H, s), 7.71–7.82(3H, m), 7.94(1H, s).
Mass: (LCMS) 511(M$^+$+1)

EXP. 087
$^1$H-NMR(DMSO-d$_6$): 1.24–1.32(2H, m), 1.45–1.52(4H, m), 1.62–1.70(2H, m), 2.19(1H, qu, J=7.4), 2.55(2H, t, J=7.4), 2.74(6H, s), 2.82(2H, t, J=7.5), 3.85(2H, d, J=6.5), 7.03(1H, d, J=8.5), 7.17(1H, dd, J=8.2, 2.2), 7.28(1H, d, J=2.2), 7.42(1H, dd, J=8.6, 2.2), 7.64–7.67(2H, m), 7.79–7.87(2H, m), 7.94(1H, s), 10.12(1H, s), 12.09(1H, s).

TABLE 1-continued

Mass: (LCMS) 497(M$^+$+1)
EXP. Int. 48
$^1$H-NMR(CDCl$_3$): 1.22–1.35(2H, m), 1.49–1.58(4H, m), 1.68–1.78(2H, m), 2.26(1H, qu, J=7.5), 2.27(3H, s), 2.66(2H, t, J=7.8), 2.96(2H, t, J=7.5), 3.68(3H, s), 3.84(2H, d, J=6.8), 4.75(2H, s), 6.92(1H, d, J=8.5), 7.15(1H, dd, J=8.2, 2.2), 7.26(1H, d, J=1.0), 7.52(1H, dd, J=8.8, 1.9), 7.68(1H, dd, J=8.5, 1.4), 7.78–7.84(2H, m), 7.93(1H, s), 7.95 (1H, br-s), 8.18(1H, s).
Mass: (LCMS) 504(M$^+$+1)
EXP. 088
$^1$H-NMR(DMSO-d$_6$): 1.24–1.32(2H, m), 1.45–1.53(4H, m), 1.62–1.73(2H, m), 2.20(1H, qu, J=7.4), 2.56(2H, t, J=7.5), 2.83(2H, t, J=7.4), 3.86(2H, d, J=6.5), 4.05(2H, d, J=5.7), 5.69(1H, t, J=6.0), 7.03(1H, d, J=8.5), 7.18(1H, dd, J=8.4, 1.9), 7.30(1H, d, J=2.2), 7.58(1H, dd, J=8.5, 1.6), 7.74(1H, dd, J=8.8, 1.6), 7.85(2H, t, J=8.5), 7.91(1H, s), 8.37(1H, s), 9.85(1H, s), 12.08(1H, s).
Mass: (LCMS) 448(M$^+$+1)
EXP. 089
$^1$H-NMR(CDCl$_3$): 1.21–1.34(2H, m), 1.44–1.58(4H, m), 1.68–1.79(2H, m), 2.27(1H, qu, J=7.4), 2.66(2H, t, J=7.8), 2.96(2H, t, J=7.8), 3.68(3H, s), 3.83(2H, d, J=6.6), 6.58(1H, dd, J=3.5, 1.6), 6.92(1H, d, J=8.2), 7.15(1H, dd, J=8.2, 2.2), 7.28(1H, d, J=3.5), 7.53–7.54(1H, m), 7.62–7.67(2H, m), 7.81(1H, d, J=14.3), 7.84(1H, d, J=14.5), 7.95(1H, s), 8.24(1H, s), 8.29(1H, d, J=1.9).
Mass: (LCMS) 498(M$^+$+1)
EXP. 090
$^1$H-NMR(DMSO-d$_6$): 1.25–1.34(2H, m), 1.45–1.56(4H, m), 1.63–1.75(2H, m), 2.21(1H, qu, J=7.4), 2.56(2H, t, J=7.5), 2.83(2H, t, J=7.3), 3.87(2H, d, J=6.5), 6.73(1H, dd, J=3.5, 1.6), 7.04(1H, d, J=8.2), 7.19(1H, dd, J=8.2, 2.2), 7.31(1H, d, J=2.2), 7.40(1H, d, J=3.5), 7.61(1H, dd, J=8.5, 1.6), 7.80–7.97(5H, m), 8.40(1H, s), 10.38(1H, s), 12.10 (1H, s).
Mass: (LCMS) 484(M$^+$+1)
EXP. Int. 49
$^1$H-NMR(CDCl$_3$): 2.65(2H, t, J=7.6), 2.93(2H, t, J=7.7), 3.68(3H, s), 5.67(1H, s), 7.16 (1H, d, J=1.9), 7.21(1H, d, J=2.2), 7.49–7.53(2H, m), 7.65(1H, dd, J=8.5, 1.9), 7.84–7.92(3H, m), 7.97(1H, d, J=1.3).
Mass: 340(M$^+$)
EXP. 091
$^1$H-NMR(CDCl$_3$): 1.06–1.15(2H, m), 1.21–1.39(4H, m), 1.50–1.59(2H, m), 2.11(1H, qu, J=7.4), 2.66(2H, t, J=7.4), 2.95(2H, t, J=7.7), 3.41(2H, d, J=6.8), 3.69(3H, s), 7.18(1H, d, J=2.2), 7.24(1H, d, J=2.4), 7.49–7.52(2H, m), 7.70(1H, dd, J=8.5, 1.6), 7.84–7.89(3H, m), 8.01(1H, d, J=1.6).
Mass: 422(M$^+$)
EXP. 092
$^1$H-NMR(CDCl$_3$): 1.05–1.15(2H, m), 1.32–1.39(4H, m), 1.50–1.59(2H, m), 2.08(1H, qu, J=7.4), 2.70(2H, t, J=7.5), 2.96(2H, t, J=7.6), 3.41(2H, d, J=6.8), 7.19(1H, d, J=2.2), 7.25(1H, d, J=2.2), 7.49–7.52(2H, m), 7.71(1H, dd, J=8.5, 1.8), 7.85–7.89(3H, m), 8.01 (1H, d, J=1.6).
Mass: 408(M$^+$)
EXP. 093
$^1$H-NMR(CDCl$_3$): 0.96–1.05(2H, m), 1.23–1.38(4H, m), 1.45–1.55(2H, m), 2.03(1H, qu, J=7.4), 2.70(2H, t, J=7.5), 3.02(2H, t, J=7.5), 3.45(2H, d, J=6.8), 3.70(3H, s), 7.49(1H, d, J=2.2), 7.54(2H, dd, J=6.2, 3.0), 7.58(1H, d, J=2.5), 7.69(1H, dd, J=8.5, 1.6), 7.87–7.92(3H, m), 8.01(1H, s).
Mass: 433(M$^+$)
EXP. 094
$^1$H-NMR(CDCl$_3$): 1.01–1.11(2H, m), 1.34–1.40(4H, m), 1.57–1.62(2H, m), 2.00–2.10(1H, m), 2.65(2H, t, J=7.4), 2.89(2H, t, J=7.8), 3.30(2H, d, J=5.9), 3.68(3H, s), 3.93(2H, s), 6.63(1H, d, J=2.2), 6.67(1H, d, J=2.2), 7.47–7.51(2H, m), 7.74(1H, dd, J=8.5, 1.9), 7.84–7.88(3H, m), 8.02(1H, s).
Mass: 403(M$^+$)
EXP. 095
$^1$H-NMR(CDCl$_3$): 0.86–1.10(2H, m), 1.35–1.42(4H, m), 1.56–1.65(2H, m), 2.05(1H, qu, J=7.4), 2.69(2H, t, J=7.5), 2.89(2H, t, J=7.6), 3.30(2H, d, J=7.1), 5.01(2H, br-s), 6.63 (1H, d, J=2.2), 6.69(1H, d, J=2.2), 7.45–7.51(2H, m), 7.74(1H, dd, J=8.5, 1.6), 7.84–7.88(3H, m), 8.02(1H, s).
Mass: 389(M$^+$)
EXP. Int. 50
$^1$H-NMR(CDCl$_3$): 0.88–1.28(5H, m), 1.61–1.78(6H, m), 3.75–3.79(4H, m), 6.99(1H, d, J=8.5), 7.28(1H, dd, J=8.5, 2.5), 7.37(1H, d, J=2.5), 7.46–7.52(2H, m), 7.68(1H, dd, J=8.6, 1.5), 7.84–7.88(3H, m), 7.98(1H, d, J=1.1).
Mass: 355(M$^+$)
EXP. 096
$^1$H-NMR(CDCl$_3$): 0.88–1.25(5H, m), 1.61–1.77(6H, m), 3.66(2H, s), 3.76(2H, d, J=5.7), 6.95(1H, d, J=8.5), 7.23(1H, dd, J=8.4, 2.4), 7.35(1H, d, J=2.4), 7.44–7.49(2H, m), 7.70 (1H, dd, J=8.2, 1.8), 7.82–7.86(3H, m), 7.98(1H, s).
Mass: 374(M$^+$)
EXP. 097
$^1$H-NMR(CDCl$_3$): 1.25–1.35(2H, m), 1.47–1.59(4H, m), 1.69–1.79(2H, m), 1.98(2H, qu, J=7.5), 2.26(1H, qu, J=7.6), 2.37(2H, t, J=7.4), 2.66(2H, t, J=7.5), 3.66(3H, s), 3.84 (2H, d, J=6.8), 6.92(1H, d, J=8.5), 7.12(1H, dd, J=8.3, 2.2), 7.25(1H, m), 7.45–7.50(2H, m), 7.72(1H, dd, J=8.5, 1.6), 7.83–7.87(3H, m), 8.00(1H, br-s).

TABLE 1-continued

Mass: 402(M⁺)
EXP. 098
¹H-NMR(CDCl₃): 1.24–1.35(2H, m), 1.46–1.58(4H, m), 1.69–1.79(2H, m), 1.98(2H, qu, J=7.4), 2.26(1H, qu, J=7.4), 2.40(2H, t, J=7.4), 2.68(2H, t, J=7.4), 3.83(2H, d, J=6.5), 6.92(1H, d, J=8.2), 7.12(1H, dd, J=8.2, 2.2), 7.25–7.26(1H, m), 7.45–7.48(2H, m), 7.72 (1H, dd, J=8.3, 1.2), 7.82–7.86(3H, m), 7.99(1H, br-s).
Mass: 388(M⁺)
EXP. 099
¹H-NMR(CDCl₃): 1.23–1.34(2H, m), 1.43–1.61(4H, m), 1.68–1.78(2H, m), 2.27(1H, qu, J=7.0), 2.66(2H, t, J=7.9), 2.94(2H, t, J=7.7), 3.68(3H, s), 3.81(2H, d, J=6.9), 6.58–6.59(1H, m), 6.90(1H, d, J=8.2), 7.09(1H, dd, J=8.5, 2.0), 7.21–7.25(2H, m), 7.41–7.42(2H, m), 7.80(1H, s), 8.15(1H, s).
Mass: 377(M⁺)
EXP. 100
¹H-NMR(DMSO-d₆): 1.18–1.31(2H, m), 1.45–1.53(4H, m), 1.62–1.72(2H, m), 2.18(1H, qu, J=7.3), 2.53(2H, t, J=7.7), 2.80(2H, t, J=7.7), 3.80(2H, d, J=6.9), 6.42(1H, s), 6.96 (1H, d, J=8.2), 7.09(1H, dd, J=7.9, 2.5), 7.17(1H, d, J=1.9), 7.25(1H, dd, J=8.2, 1.6), 7.32–7.39(2H, m), 7.65(1H, s), 11.06(1H, s), 12.12(1H, s).
Mass: 363(M⁺)
EXP. 101
¹H-NMR(CDCl₃): 1.53–1.57(3H, m), 1.64–1.81(5H, m), 2.65(2H, t, J=7.5), 2.94(2H, t, J=8.0), 3.67(3H, s), 4.67–4.69(1H, m), 6.57(1H, t, J=2.5), 6.90(1H, d, J=8.5), 7.07(1H, dd, J=8.2, 2.2), 7.21–7.23(2H, m), 7.39(2H, d, J=1.4), 7.76(1H, s), 8.15(1H, s).
Mass: 363(M⁺)
EXP. 102
¹H-NMR(DMSO-d₆): 1.52–1.78(8H, m), 2.53(2H, t, J=7.9), 2.80(2H, t, J=7.4), 4.73(1H, m), 6.42(1H, m), 6.96(1H, d, J=8.5), 7.09(1H, dd, J=8.2, 2.2), 7.16(1H, d, J=1.6), 7.23 (1H, dd, J=8.1, 1.3), 7.32–7.38(2H, m), 7.60(1H, d, J=0.8), 11.06(1H, s), 12.05(1H, s).
Mass: 349(M⁺)
EXP. 103
¹H-NMR(CDCl₃): 1.30–1.42(3H, m), 1.52–1.64(3H, m), 1.72–1.82(2H, m), 1.92–1.98(2H, m), 2.76(2H, t, J=7.4), 3.05(2H, t, J=7.9), 3.79(3H, s), 4.22(1H, qu, J=3.9), 6.69(1H, t, J=2.2), 7.04(1H, d, J=8.5), 7.18(1H, dd, J=8.2, 2.4), 7.32–7.35(2H, m), 7.50(1H, d, J=8.5), 7.56(1H, dd, J=8.6, 1.6), 7.90(1H, s), 8.27(1H, s).
Mass: 377(M⁺)
EXP. 104
¹H-NMR(DMSO-d₆): 1.17–1.42(6H, m), 1.55–1.80(4H, m), 2.53(2H, t, J=7.5), 2.79(2H, t, J=7.7), 4.22(1H, m), 6.43(1H, m), 6.92–6.99(1H, m), 7.07(1H, dd, J=8.2, 2.2), 7.17 (1H, d, J=1.9), 7.26–7.39(3H, m), 7.64(1H, s), 11.05(1H, s), 12.06(1H, s).
Mass: 363(M⁺)
EXP. 105
¹H-NMR(CDCl₃): 1.26(2H, t, J=7.1), 2.65(2H, t, J=7.9), 2.93(2H, t, J=7.8), 3.03(2H, t, J=6.7), 3.67(3H, s), 6.57–6.59(1H, m), 6.89(1H, d, J=8.2), 6.97(1H, d, J=7.7), 7.02–7.17 (2H, m), 7.19–7.31(5H, m), 7.38(1H, d, J=8.5), 7.70(1H, s), 8.17(1H, s).
Mass: 417(M⁺)
EXP. 106
¹H-NMR(DMSO-d₆): 2.52(2H, t, J=7.4), 2.79(2H, t, J=7.3), 2.97(2H, t, J=6.6), 4.16 (2H, t, J=6.6), 6.41(1H, s), 6.98–7.18(6H, m), 7.27–7.34(4H, m), 7.53(1H, s), 11.06(1H, s), 12.06(1H, s).
Mass: 403(M⁺)
EXP. 107
¹H-NMR(CDCl₃): 1.49–1.81(8H, m), 2.65(2H, t, J=7.6), 2.94(2H, t, J=7.8), 3.68(3H, s), 3.82(3H, s), 4.68(1H, m), 6.49(1H, dd, J=2.2, 0.8), 6.90(1H, d, J=8.2), 7.04–7.08(2H, m), 7.22(1H, d, J=2.5), 7.31(1H, d, J=8.8), 7.42(1H, dd, J=8.5, 1.6), 7.74(1H, d, J=1.1).
Mass: 377(M⁺)
EXP. 108
¹H-NMR(DMSO-d₆): 1.47–1.79(8H, m), 2.49–2.56(2H, m), 2.79(2H, t, J=7.5), 3.80(3H, s), 4.74(1H, m), 6.42(1H, d, J=3.0), 6.96(1H, d, J=8.2), 7.09(1H, dd, J=8.5, 2.2), 7.17 (1H, d, J=2.2), 7.29(2H, m), 7.42(1H, d, J=8.2), 7.61(1H, s), 12.06(1H, s).
Mass: 363(M⁺)
EXP. 109
¹H-NMR(CDCl₃): 1.18–1.32(3H, m), 1.40–1.51(3H, m), 1.63–1.68(2H, m), 1.80–1.86(2H, m), 2.62–2.67(2H, m), 2.94(2H, t, J=7.4), 3.68(3H, s), 3.82(3H, s), 4.10(1H, m), 6.50 (1H, dd, J=3.0, 0.8), 6.92(1H, d, J=8.5), 7.04–7.08(2H, m), 7.22(1H, d, J=2.5), 7.32(1H, d, J=8.5), 7.47(1H, dd, J=8.5, 1.6), 7.77(1H, dd, J=1.6, 0.5).
Mass: 391(M⁺)
EXP. 110
¹H-NMR(DMSO-d₆): 1.15–1.43(6H, m), 1.52–1.61(2H, m), 1.73–1.80(2H, m), 2.53(2H, t, J=7.5), 2.80(2H, t, J=7.5), 3.80(3H, s), 4.23(1H, m), 6.43(1H, d, J=3.0), 6.98(1H, d, J=8.5), 7.08(1H, dd, J=8.2, 2.2), 7.17(1H, d, J=2.2), 7.31(1H, d, J=3.0), 7.34(1H, dd, J=8.6, 1.5), 7.43(1H, d, J=8.5), 7.65(1H, d, J=0.8), 12.07(1H, s).
Mass: 377(M⁺)
EXP. 111
¹H-NMR(CDCl₃): 1.24–1.36(2H, m), 1.48–1.59(4H, m), 1.70–1.80(2H, m), 2.26(1H, qu, J=7.5), 2.33(3H, s), 2.65(2H, t, J=7.6), 2.95(2H, t, J=7.8), 3.68(3H, s), 3.81(2H, d, J=6.9), 6.90(1H, d, J=8.2), 6.98(1H, s), 7.09(1H, d, J=10.2), 7.24–2.25(1H, m), 7.33–7.42(2H, m), 7.76(1H, s), 7.87(1H, s).
Mass: 391(M⁺)

TABLE 1-continued

EXP. 112
$^1$H-NMR(DMSO-d$_6$): 1.25–1.36(2H, m), 1.42–1.57(4H, m), 1.63–1.78(2H, m), 2.17(1H, qu, J=7.4), 2.23(3H, s), 2.53(2H, t, J=7.5), 2.81(2H, t, J=7.7), 3.81(2H, d, J=6.9), 6.96 (1H, d, J=8.2), 7.08(2H, dd, J=8.2, 1.9), 7.19–7.24(2H, m), 7.32(1H, d, J=8.5), 7.64(1H, s), 10.71(1H, s), 12.06(1H, s).
Mass: 377(M$^+$)
EXP. 113
$^1$H-NMR(CDCl$_3$): 1.13–1.28(2H, m), 1.40–1.46(4H, m), 1.54–1.64(2H, m), 2.15(1H, qu, J=7.4), 2.65(2H, t, J=7.4), 2.95(2H, t, J=7.8), 3.67(3H, s), 3.76(2H, d, J=6.6), 6.43–6.45(1H, m), 6.94(1H, d, J=8.5), 7.12–7.22(4H, m), 7.31(1H, d, J=2.2), 7.34–7.37 (1H, m), 8.16(1H, br-s).
Mass: 377(M$^+$)
EXP. 114
$^1$H-NMR(CDCl$_3$): 1.13–1.26(2H, m), 1.36–1.46(4H, m), 1.54–1.65(2H, m), 2.15(1H, qu, J=7.4), 2.69(2H, t, J=7.5), 2.95(2H, t, J=7.6), 3.76(2H, d, J=6.6), 6.44(1H, m), 6.95 (1H, d, J=8.2), 7.14–7.21(4H, m), 7.32–7.36(2H, m), 8.14(1H, s).
Mass: 363(M$^+$)
EXP. 115
$^1$H-NMR(CDCl$_3$): 0.84–1.28(5H, m), 1.56–1.63(6H, m), 2.65(2H, t, J=7.8), 2.95(2H, t, J=7.7), 3.66–3.68(5H, m), 6.44–6.45(1H, m), 6.94(1H, d, J=8.2), 7.14(1H, dd, J=8.5, 2.3), 7.18–7.23(3H, m), 7.30(1H, d, J=2.5), 7.36(1H, dd, J=8.0, 0.5), 8.17(1H, s).
Mass: 391(M$^+$)
EXP. 116
$^1$H-NMR(DMSO-d$_6$): 0.85–1.18(5H, m), 1.57–1.60(6H, m), 2.53(2H, t, J=7.1), 2.80(2H, t, J=7.4), 3.69(2H, d, J=6.0), 6.21–6.24(1H, m), 6.99–7.02(2H, m), 7.09(1H, t, J=7.5), 7.15(1H, dd, J=8.2, 2.1), 7.21(1H, d, J=2.2), 7.29–7.35(2H, m), 11.07(1H, s), 12.08(1H, s).
Mass: 377(M$^+$)
EXP. 117
$^1$H-NMR(CDCl$_3$): 1.41–1.57(4H, m), 1.69–1.75(4H, m), 2.65(2H, t, J=7.2), 2.95(2H, t, J=7.8), 3.67(3H, s), 4.63(1H, qu, J=4.1), 6.44(1H, m), 6.94(1H, d, J=8.5), 7.16–7.19 (3H, m), 7.23(1H, d, J=7.4), 7.30(1H, d, J=2.5), 7.35(1H, m), 8.16(1H, br-s)
Mass: 363(M$^+$)
EXP. 118
$^1$H-NMR(CDCl$_3$): 1.20–1.60(6H, m), 1.68–1.72(2H, m), 2.69(2H, t, J=7.6), 2.95(2H, t, J=7.7), 4.63(1H, qu, J=4.1), 6.42–6.44(1H, m), 6.94(1H, d, J=8.2), 7.12–7.17(3H, m), 7.23(1H, d, J=7.4), 7.31–7.35(2H, m), 8.14(1H, br-s).
Mass: 349(M$^+$)
EXP. 119
$^1$H-NMR(CDCl$_3$): 1.11–1.40(6H, m), 1.52–1.58(2H, m), 1.71–1.78(2H, m), 2.65(2H, t, J=7.4), 2.95(2H, t, J=7.9), 3.67(3H, s), 4.01(1H, m), 6.46(1H, m), 6.96(1H, d, J=8.2), 7.11(1H, dd, J=8.2, 2.2), 7.16–7.30(3H, m), 7.32(1H, d, J=8.5), 7.33–7.37(1H, m), 8.17 (1H, s).
Mass: 377(M$^+$)
EXP. 120
$^1$H-NMR(CDCl$_3$): 1.12–1.43(6H, m), 1.51–1.58(2H, m), 1.71–1.77(2H, m), 2.69(2H, t, J=7.4), 2.95(2H, t, J=7.8), 4.01(1H, m), 6.45–6.47(1H, m), 6.97(1H, d, J=8.5), 7.11–7.15(2H, m), 7.19–7.24(2H, m), 7.31–7.35(2H, m), 8.14(1H, s).
Mass: 363(M$^+$)
EXP. Int. 51
$^1$H-NMR(CDCl$_3$): 3.78(3H, s), 6.52(1H, dd, J=3.3, 0.8), 7.06(1H, d, J=8.0), 7.09(1H, d, J=3.0), 7.25–7.29(2H, m).
EXP. Int. 52
$^1$H-NMR(CDCl$_3$): 3.80(3H, s), 7.13(1H, d, J=3.0), 7.19(1H, dd, J=7.9, 6.9), 7.33(1H, d, J=2.7), 7.47(1H, d, J=7.9), 7.73(1H, d=6.8).
EXP. 121
$^1$H-NMR(CDCl$_3$): 1.14–1.28(2H, m), 1.39–1.46(4H, m), 1.57–1.66(2H, m), 2.16(1H, qu, J=7.4), 2.61–2.70(2H, m), 2.94(2H, t, J=7.9), 3.67(3H, s), 3.75(2H, d, J=6.6), 3.81(3H, s), 6.37(1H, dd, J=3.2, 0.7), 6.94(1H, d, J=8.5), 7.02(1H, d, J=3.3), 7.13(1H, dd, J=8.4, 2.4), 7.18–7.23(1H, m), 7.27–7.31(3H, m).
Mass: 391(M$^+$)
EXP. 122
$^1$H-NMR(CDCl$_3$): 1.14–1.25(2H, m), 1.39–1.46(4H, m), 1.55–1.67(2H, m), 2.16(1H, qu, J=7.4), 2.66–2.72(2H, m), 2.95(2H, t, J=7.8), 3.75(2H, d, J=6.8), 3.81(3H, s), 6.37(1H, d, J=3.0), 6.94(1H, d, J=8.2), 7.02(1H, d, J=3.0), 7.14(1H, dd, J=8.2, 2.4), 7.18–7.33 (4H, m).
Mass: 377(M$^+$)
EXP. 123
$^1$H-NMR(CDCl$_3$): 1.42–1.61(4H, m), 1.69–1.72(4H, m), 2.64(2H, t, J=7.8), 2.93(2H, t, J=7.8), 3.67(3H, s), 3.82(3H, s), 4.63(1H, qu, J=4.3), 6.36(1H, dd, J=3.3, 0.8), 6.93 (1H, d, J=8.2), 7.02(1H, d, J=3.0), 7.10–7.17(2H, m), 7.25–7.30(3H, m).
Mass: 377(M$^+$)
EXP. 124
$^1$H-NMR(CDCl$_3$): 1.42–1.61(4H, m), 1.68–1.75(4H, m), 2.66–2.72(2H, m), 2.95(2H, t, J=7.8), 3.80(3H, s), 4.63(1H, q, J=4.3), 6.37(1H, dd, J=3.3, 0.5), 6.94(1H, d, J=8.2), 7.01(1H, d, J=3.0), 7.11–7.17(2H, m), 7.24–7.31(3H, m).
Mass: 363(M$^+$)
EXP. 125
$^1$H.NMR(CDCl$_3$): 1.12–1.41(6H, m), 1.53–1.62(2H, m), 1.72–1.81(2H, m), 2.64(2H, t, TABLE 1-continued J=7.8), 2.93(2H, t, J=7.8), 3.67(3H, s), 3.81(3H, s), 4.01(1H, m), 6.39(1H, d, J=3.0), 6.96(1H, d, J=8.2), 7.02(1H, d, J=3.0), 7.11(1H, dd, J=8.2, 2.2), 7.19–7.30(4H, s).
Mass: 391($M^+$)
EXP. 126
$^1$H-NMR(CDCl$_3$): 1.12–1.41(6H, m), 1.51–1.61(2H, m), 1.72–1.78(2H, m), 2.66–2.71(2H, m), 2.95(2H, t, J=7.7), 3.80(3H, s), 4.02(1H, m), 6.39(1H, dd, J=3.1, 0.6), 6.96(1H, d, J=8.2), 7.02(1H, d, J=3.0), 7.12(1H, dd, J=8.5, 2.4), 7.19–7.32(4H, m).
Mass: 377($M^+$)
EXP. 127
$^1$H-NMR(CDCl$_3$): 0.97–1.28(5H, m), 1.66–1.78(6H, m), 2.66(2H, t, J=8.0), 2.94(2H, t, J=7.7), 3.68(3H, s), 3.72(2H, d, J=6.0), 6.56–6.59(1H, m), 6.90(1H, d, J=8.2), 7.09(1H, dd, J=8.7, 2.4), 7.22–7.26(2H, m), 7.32(1H, dd, J=7.1, 1.6), 7.57(1H, s), 7.64(1H, d, J=8.5), 8.16(1H, s).
Mass: 391($M^+$)
EXP. 128
$^1$H-NMR(DMSO-d$_6$): 0.97–1.15(5H, m), 1.62–1.73(6H, m), 2.53(2H, t, J=7.5), 2.80(2H, t, J=7.5), 3.74(2H, d, J=6.0), 6.40–6.47(1H, m), 6.96(1H, d, J=8.0), 7.08–7.19(3H, m), 7.35(1H, t, J=2.5), 7.50–7.53(2H, m), 11.10(1H, s), 12.03(1H, s).
Mass: 377($M^+$)
EXP. Int. 53
$^1$H-NMR(CDCl$_3$): 0.23(6H, s), 1.03(9H, s), 2.58(2H, t, J=7.5), 2.85(2H, t, J=7.7), 3.67 (3H, s), 6.78(1H, d, J=8.2), 6.98(1H, dd, J=8.2, 2.2), 7.35(1H, d, J=2.2).
[0801]
EXP. Int. 54
$^1$H-NMR(CDCl$_3$): −0.11(6H, s), 0.80(9H, s), 2.61–2.67(2H, m), 2.94(2H, t, J=7.8), 3.67 (3H, s), 6.54–6.56(1H, m), 6.84(1H, d, J=8.2), 7.00(1H, dd, J=8.3, 2.4), 7.20–7.22(2H, m), 7.32–7.40(2H, m), 7.74(1H, t, J=0.8), 8.14(1H, br-s).
EXP. Int. 55
$^1$H-NMR(CDCl$_3$): 2.64(2H, t, J=7.4), 2.93(2H, t, J=7.8), 3.67(3H, s), 5.36(1H, s), 6.59–6.61(1H, m), 6.93(1H, d, J=8.2), 7.08(1H, dd, J=8.2, 2.2), 7.12(1H, d, J=2.2), 7.23 (1H, d, J=1.6), 7.30(1H, t, J=2.7), 7.51(1H, d, J=8.5), 7.70(1H, d, J=0.8), 8.30(1H, s).
Mass: 295($M^+$)
EXP. 129
$^1$H-NMR(CDCl$_3$): 0.89(3H, t, J=7.2), 1.41(2H, m), 1.67(2H, qu, J=6.7), 2.65(2H, t, J=7.8), 2.95(2H, t, J=7.8), 3.68(3H, s), 3.93(2H, t, J=6.4), 6.57(1H, t, J=2.5), 6.90(1H, d, J=8.2), 7.09(1H, dd, J=8.4, 2.2), 7.20–7.23(2H, m), 7.40(2H, s), 7.78(1H, s), 8.16 (1H, s).
Mass: 351($M^+$)
EXP. 130
$^1$H-NMR(CDCl$_3$): 0.89(3H, t, J=7.3), 1.41(2H, m), 1.68(2H, qu, J=6.8), 2.70(2H, t, J=7.2), 2.95(2H, t, J=7.8), 3.93(2H, t, J=6.4), 6.57(1H, t, J=2.5), 6.91(1H, d, J=8.2), 7.10(1H, dd, J=8.5, 2.4), 7.20(1H, t, J=2.7), 7.24(1H, d, J=2.2), 7.40(2H, s), 7.78(1H, s), 8.13(1H, s).
Mass: 337($M^+$)
EXP. 131
$^1$H-NMR(CDCl$_3$): 1.47(3H, d, J=6.3), 2.60(2H, t, J=7.8), 2.89(2H, t, J=7.9), 3.66(3H, s), 5.19(2H, q, J=6.3), 6.58–6.62(1H, m), 6.74(1H, d, J=8.2), 6.94(1H, dd, J=8.3, 2.3), 7.21–7.28(6H, m), 7.43(1H, d, J=8.5), 7.49(1H, dd, J=8.5, 1.7), 7.83(1H, s), 8.18(1H, br-s).
Mass: (LCMS) 400($M^+$+1)
EXP. 132
$^1$H-NMR(DMSO-d$_6$): 1.41(3H, d, J=6.3), 2.50(2H, t, J=7.5), 2.75(2H, t, J=7.5), 5.38 (2H, q, J=6.3), 6.47(1H, s), 6.83(1H, d, J=8.5), 6.97(1H, dd, J=8.4, 1.9), 7.16(1H, d, J=2.2), 7.21–7.37(6H, m), 7.44(1H, d, J=8.5), 7.70(1H, s), 11.11(1H, br-s), 12.08(1H, br-s).
Mass: 385($M^+$)
EXP. 133
$^1$H-NMR(CDCl$_3$): 2.04(3H, s), 2.66(2H, t, J=7.4), 2.98(2H, t, J=7.8), 3.67(3H, s), 4.99 (2H, s), 6.54–6.56(1H, m), 6.97(1H, d, J=8.5), 7.08–7.26(6H, m), 7.32(1H, d, J=7.4), 7.37(1H, d, J=7.4), 7.43(1H, dd, J=8.2, 1.5), 7.80(1H, d, J=0.8), 8.15(1H, br-s).
Mass: (LCMS) 400($M^+$+1)
EXP. 134
$^1$H-NMR(DMSO-d$_6$): 2.23(3H, s), 2.54(2H, t, J=7.5), 2.82(2H, t, J=7.4), 5.04(2H, s), 6.40(1H, br-s), 7.06–7.19(6H, m), 7.24(1H, dd, J=8.5, 1.6), 7.30–7.38(3H, m), 7.64(1H, s), 11.06(1H, br-s), 12.08(1H, br-s).
Mass: (LCMS) 386($M^+$+1)
EXP. 135
$^1$H-NMR(CDCl$_3$): 2.35(3H, s), 2.65(2H, t, J=7.4), 2.97(2H, t, J=7.8), 3.67(3H, s), 4.98 (2H, s), 6.56–6.58(1H, m), 6.95(1H, d, J=8.2), 7.03–7.26(7H, m), 7.40(1H, d, J=8.5), 7.44(1H, dd, J=8.5, 1.6), 7.84(1H, t, J=0.8), 8.16(1H, br-s).
Mass: (LCMS) 400($M^+$+1)
EXP. 136
$^1$H-NMR(DMSO-d$_6$): 2.24(3H, s), 2.54(2H, t, J=7.4), 2.81(2H, t, J=7.4), 5.03(2H, s), 6.43(1H, br-s), 7.04–7.22(7H, m), 7.28(1H, dd, J=8.4, 1.5), 7.34(1H, t, J=2.7), 7.40(1H, d, J=8.2), 7.70(1H, s), 11.08(1H, br-s), 12.08(1H, br-s).
Mass: (LCMS) 386($M^+$+1)
EXP. 137
$^1$H-NMR(CDCl$_3$): 2.30(3H, s), 2.64(2H, t, J=7.9), 2.91(2H, t, J=7.8), 3.67(3H, s), 4.98 (2H, s), 6.56–6.58(1H, m), 6.94(1H, d, J=8.2), 7.05–7.10(3H, m), 7.19–7.25(4H, m), TABLE 1-continued 7.39(1H, d, J=8.5), 7.45(1H, dd, J=8.5, 1.6), 7.81(1H, d, J=0.8), 8.16(1H, br-s).
Mass: (LCMS) 400(M$^+$+1)
EXP. 138
$^1$H-NMR(DMSO-d$_6$): 2.26(3H, s), 2.53(2H, t, J=7.5), 2.80(2H, t, J=7.4), 5.01(2H, s), 6.42(1H, br-s), 7.02–7.13(4H, m), 7.18–7.29(4H, m), 7.33(1H, t, J=2.7), 7.38(1H, d, J=8.5), 7.66(1H, s), 11.07(1H, br-s), 12.07(1H, br-s).
Mass: (LCMS) 386(M$^+$+1)
EXP. 139
$^1$H-NMR(CDCl$_3$): 2.62(2H, t, J=7.8), 2.93(2H, t, J=7.8), 3.66(3H, s), 4.93(2H, s), 6.56–6.58(1H, m), 6.74(1H, d, J=8.2), 7.00(1H, dd, J=8.2, 2.2), 7.20–7.31(7H, m), 7.32–7.40(5H, m), 7.48–7.51(1H, m), 7.78(1H, s), 8.15(1H, br-s).
Mass: (LCMS) 462(M$^+$+1)
EXP. 140
$^1$H-NMR(DMSO-d$_6$): 2.52(2H, t, J=7.4), 2.78(2H, t, J=7.5), 4.91(2H, s), 6.42–6.43(1H, m), 6.83(1H, d, J=8.2), 7.04(1H, dd, J=8.3, 2.0), 7.16(1H, d, J=2.2), 7.19(1H, dd, J=8.3, 1.5), 7.25(1H, dd, J=8.0, 1.8), 7.31–7.43(9H, m), 7.52(1H, dd, J=8.7, 1.9), 7.60(1H, d, J=0.8), 11.07(1H, br-s), 12.07(1H, br-s).
Mass: (LCMS) 448(M$^+$+1)
EXP. 141
$^1$H-NMR(CDCl$_3$): 2.65(2H, t, J=7.9), 2.95(2H, t, J=7.8), 3.68(3H, s), 5.11(2H, s), 6.57–6.59(1H, m), 6.98(1H, d, J=8.5), 7.01–7.06(2H, m), 7.10(1H, dd, J=8.3, 2.3), 7.19–7.26(3H, m), 7.34–7.40(1H, m), 7.43–7.47(2H, m), 7.81(1H, d, J=0.8), 8.18(1H, br-s).
Mass: (LOMS) 404(M$^+$+1)
EXP. 142
$^1$H-NMR(DMSO-d$_6$): 2.54(2H, t, J=7.4), 2.82(2H, t, J=7.4), 5.11(2H, s), 6.40(1H, d, J=2.0), 7.08–7.18(3H, m), 7.20–7.27(3H, m), 7.32–7.38(3H, m), 7.44(1H, td, J=7.6, 1.6), 7.65(1H, d, J=0.5), 11.06(1H, s), 12.07(1H, br-s).
Mass: 389(M$^+$)
EXP. 143
$^1$H-NMR(CDCl$_3$): 2.65(2H, t, J=7.7), 2.95(2H, t, J=7.7), 3.68(3H, s), 5.02(2H, s), 6.58–6.62(1H, m), 6.88–6.96(2H, m), 7.02–7.16(5H, m), 7.21–7.28(2H, m), 7.44(1H, d, J=1.1), 7.81(1H, d, J=0.8), 8.19(1H, br-s).
Mass: (LCMS) 404(M$^+$+1)
EXP. 144
$^1$H-NMR(DMSO-d$_6$): 2.54(2H, t, J=7.5), 2.82(2H, t, J=7.5), 5.10(2H, s), 6.42–6.44(1H, m), 7.04–7.21(6H, m), 7.28(1H, dd, J=8.5, 1.5), 7.33–7.42(3H, m), 7.69(1H, s), 11.09(1H, s), 12.07(1H, br-s).
Mass: 389(M$^+$)
EXP. 145
$^1$H-NMR(CDCl$_3$): 2.65(2H, t, J=7.9), 2.95(2H, t, J=7.8), 3.68(3H, s), 4.98(2H, s), 6.57–6.59(1H, m), 7.08(1H, d, J=8.5), 7.11–7.23(4H, m), 7.31–7.49(5H, m), 7.72(1H, s), 8.16(1H, br-s).
Mass: (LCMS) 404(M$^+$+1)
EXP. 146
$^1$H-NMR(DMSO-d$_6$): 2.54(2H, t, J=7.5), 2.82(2H, t, J=7.4), 5.05(2H, s), 6.42–6.44(1H, m), 7.05(1H, d, J=8.5), 7.10–7.18(3H, m), 7.20(1H, d, J=2.2), 7.28(1H, dd, J=8.4, 1.5), 7.34(1H, t, J=2.7), 7.37–7.43(3H, m), 7.66(1H, s), 11.07(1H, br-s), 12.07(1H, br-s).
Mass: 389(M$^+$)
EXP. 147
$^1$H-NMR(CDCl$_3$): 2.66(2H, t, J=7.7), 2.96(2H, t, J=7.7), 3.68(3H, s), 5.13(2H, s), 6.49–6.64(1H, m), 6.95(1H, d, J=8.5), 7.10(1H, dd, J=8.3, 2.3), 7.15–7.19(2H, m), 7.23–7.27(2H, m), 7.32–7.35(1H, m), 7.41–7.48(3H, m), 7.83(1H, s), 8.19(1H, br-s).
Mass: (LCMS) 420(M$^+$+1)
EXP. 148
$^1$H-NMR(DMSO-d$_6$): 2.55(2H, t, J=7.7), 2.82(2H, t, J=7.4), 5.15(2H, s), 6.41(1H, s), 7.07(1H, d, J=8.2), 7.12–7.16(1H, m), 7.21(1H, s), 7.27–7.39(5H, m), 7.46–7.48(2H, m), 7.69(1H, s), 11.07(1H, s).
Mass: 405(M$^+$)
EXP. 149
$^1$H-NMR(CDCl$_3$): 2.65(2H, t, J=7.6), 2.96(2H, t, J=7.8), 3.68(3H, s), 4.99(2H, s), 6.60(1H, dd, J=3.2, 2.2), 6.92(1H, d, J=8.2), 7.08(1H, dd, J=8.4, 2.4), 7.16–7.23(3H, m), 7.24–7.32(3H, m), 7.44(2H, d, J=1.1), 7.81(1H, s), 8.18(1H, br-s).
Mass: (LCMS) 420(M$^+$+1)
EXP. 150
$^1$H-NMR(DMSO-d$_6$): 2.54(2H, t, J=7.5), 2.82(2H, t, J=7.4), 5.10(2H, s), 6.42–6.46(1H, m), 7.05(1H, d, J=8.2), 7.13(1H, dd, J=8.3, 2.0), 7.22(1H, d, J=1.9), 7.27–7.36(5H, m), 7.41(2H, d, J=9.0), 7.69(1H, s), 11.09(1H, s), 12.09(1H, br-s).
Mass: 405(M$^+$)
EXP. 151
$^1$H-NMR(CDCl$_3$): 2.65(2H, t, J=7.6), 2.95(2H, t, J=7.8), 3.76(3H, s), 4.98(2H, s), 6.56–6.58(1H, m), 6.91(1H, d, J=8.5), 7.08(1H, dd, J=8.3, 2.2), 7.20–7.26(6H, m), 7.41(2H, s), 7.79(1H, s), 8.18(1H, d, J=1.6).
Mass: (LCMS) 420(M$^+$+1)
EXP. 152
$^1$H-NMR(DMSO-d$_6$): 2.54(2H, t, J=7.7), 2.81(2H, t, J=7.4), 5.07(2H, s), 6.41–6.46(1H, m), 7.04(1H, d, J=8.5), 7.11(1H, dd, J=8.3, 2.0), 7.20(1H, d, J=1.9), 7.25(1H, dd, J=8.3, 1.4), 7.34(1H, t, J=2.7), 7.38–7.40(5H, m), 7.66(1H, s), 11.08(1H, s), 12.08(1H, s).
Mass: (LCMS) 406(M$^+$+1)

TABLE 1-continued

EXP. 153
$^1$H-NMR(CDCl$_3$): 2.65(2H, t, J=7.9), 2.96(2H, t, J=7.8), 3.68(3H, s), 5.09(2H, s), 6.58–6.61(1H, m), 6.95(1H, d, J=8.5), 7.08–7.13(2H, m), 7.19(1H, dd, J=8.5, 2.0), 7.23–7.28(2H, m), 7.41–7.46(3H, m), 7.52(1H, d, J=7.9), 7.84(1H, s), 8.18(1H, br-s).
Mass: (LCMS) 465(M$^+$+1)

EXP. 154
$^1$H-NMR(DMSO-d$_6$): 2.53(2H, t, J=7.6), 2.81(2H, t, J=7.5), 5.04(2H, s), 6.36–6.42(1H, m), 7.02–7.18(3H, m), 7.20–7.47(6H, m), 7.61(1H, d, J=7.4), 7.68(1H, s), 11.01(1H, br-s), 12.09(1H, br-s).
Mass: 451(M$^+$+1)

EXP. 155
$^1$H-NMR(CDCl$_3$): 2.65(2H, t, J=7.5), 2.96(2H, t, J=7.7), 3.68(3H, s), 5.02(2H, s), 6.56–6.58(1H, m), 6.71–6.80(2H, m), 6.97(1H, d, J=8.2), 7.10(1H, dd, J=8.3, 2.3), 7.22–7.32(3H, m), 7.40(2H, d, J =1.1), 7.78(1H, s), 8.18(1H, br-s).
Mass: (LCMS) 422(M$^+$+1)

EXP. 156
$^1$H-NMR(DMSO-d$_6$): 2.74(2H, t, J=7.5), 2.81(2H, t, J=7.5), 5.06(2H, s), 6.40(1H, t, J=2.0), 7.02(1H, dd, J=8.6, 2.4), 7.06–7.15(2H, m), 7.19–7.26(3H, m), 7.29–7.36(2H, m), 7.48(1H, dd, J=15.3, 8.5), 7.62(1H, s), 11.06(1H, br-s), 12.07(1H, s).
Mass: (LCMS) 408(M$^+$+1)

EXP. 157
$^1$H-NMR(CDCl$_3$): 2.65(2H, t, J=7.6), 2.96(2H, t, J=7.8), 3.68(3H, s), 4.95(2H, s), 6.58–6.59(1H, m), 6.91(1H, d, J=8.5), 6.99–7.15(4H, m), 7.23–7.27(2H, m), 7.41–7.45 (2H, m), 7.79(1H, s), 8.21(1H, br-s).
Mass: (LCMS) 422(M$^+$+1)

EXP. 158
$^1$H-NMR(DMSO-d$_6$): 2.54(2H, t, J=7.7), 2.82(2H, t, J=7.4), 5.06(2H, s), 6.43(1H, t, J=1.9), 7.05(1H, d, J=8.5), 7.13(1H, dd, J=8.2, 2.2), 7.17–7.26(2H, m), 7.27(1H, dd, J=8.3, 1.5), 7.34–7.43(4H, m), 7.67(1H, s), 11.09(1H, br-s), 12.09(1H, s).
Mass: (LCMS) 408(M$^+$+1)

EXP. 159
$^1$H-NMR(CDCl$_3$): 2.66(2H, t, J=7.8), 2.96(2H, t, J=7.8), 3.68(3H, s), 5.12(2H, s), 6.57–6.59(1H, m), 6.93(1H, d, J=8.2), 7.06–7.12(2H, m), 7.22–7.27(2H, m), 7.34(2H, d, J=7.4), 7.43(2H, s), 7.82(1H, s), 8.19(1H, br-s).
Mass: (LCMS) 455(M$^+$+1)

EXP. 160
$^1$H-NMR(DMSO-d$_6$): 2.55(2H, t, J=7.4), 2.82(2H, t, J=7.4), 5.15(2H, s), 6.41(1H, br-s), 7.07(1H, d, J=8.5), 7.14(1H, dd, J=8.4, 2.2), 7.22(1H, d, J=1.9), 7.26–7.45(5H, m), 7.58 (1H, dd, J=7.9, 1.3), 7.68(1H, s), 11.08(1H, br-s), 12.08(1H, br-s).
Mass: (LCMS) 441(M$^+$+1)

EXP. 161
$^1$H-NMR(CDCl$_3$): 2.65(2H, t, J=7.6), 2.93(2H, t, J=7.8), 3.68(3H, s), 5.06(2H, s), 6.57–6.58(1H, m), 6.93(1H, d, J=8.5), 7.11(2H, dd, J=8.3, 2.0), 7.22–7.27(2H, m), 7.31–7.34(2H, m), 7.41(2H, s), 7.80(1H, s), 8.20(1H, s).
Mass: (LCMS) 455(M$^+$+1)

EXP. 162
$^1$H-NMR(DMSO-d$_6$): 2.55(2H, t, J=7.5), 2.82(2H, t, J=7.5), 5.09(2H, s), 6.41–6.43(1H, m), 7.07(1H, d, J=8.2), 7.14(1H, dd, J=8.3, 2.3), 7.21(1H, d, J=2.2), 7.27(1H, dd, J=8.5, 1.6), 7.33–7.39(3H, m), 7.48(1H, d, J=8.2), 7.64(1H, d, J=1.9), 7.66(1H, s), 11.07(1H, s), 12.09(1H, s).
Mass: (LCMS) 441(M$^+$+1)

EXP. 163
$^1$H-NMR(CDCl$_3$): 2.66(2H, t, J=7.9), 2.96(2H, t, J=7.8), 3.68(3H, s), 5.15(2H, s), 6.50–6.51(1H, m), 7.07–7.15(4H, m), 7.21–7.24(3H, m), 7.30(1H, dd, J=8.4, 0.7), 7.41 (1H, dd, J=8.5, 1.6), 7.79(1H, d, J=0.8), 8.07(1H, br-s).
Mass: (LCMS) 455(M$^+$+1)

EXP. 164
$^1$H-NMR(DMSO-d$_6$): 2.65(2H, t, J=7.5), 2.83(2H, t, J=7.4), 5.18(2H, s), 6.33(1H, d, J=1.9), 7.15–7.30(6H, m), 7.36–7.42(1H, m), 7.49–7.52(2H, m), 7.64(1H, s), 11.01(1H, br-s), 12.10(1H, br-s).
Mass: (LCMS) 441(M$^+$+1)

EXP. 165
$^1$H-NMR(CDCl$_3$): 2.65(2H, t, J=7.8), 2.95(2H, t, J=7.7), 3.67(3H, s), 4.92(2H, s), 6.58–6.59(1H, m), 6.90(1H, d, J=8.2), 7.07–7.11(2H, m), 7.22–7.26(2H, m), 7.32(1H, d, J=8.2), 7.38–7.44(3H, m), 7.79(1H, s), 8.20(1H, s).
Mass: (LCMS) 455(M$^+$+1)

EXP. 166
$^1$H-NMR(DMSO-d$_6$): 2.55(2H, t, J=7.5), 2.82(2H, t, J=7.4), 5.09(2H, s), 6.44–6.45(1H, m), 7.05(1H, d, J=8.2), 7.13(2H, dd, J=8.1, 2.1), 7.22(1H, d, J=2.2), 7.26–7.36(2H, m), 7.41(1H, d, J=8.2), 7.57–7.60(2H, m), 7.68(1H, d, J=0.5), 11.10(1H, s), 12.09(1H, s).
Mass: (LCMS) 441(M$^+$+1)

EXP. 167
$^1$H-NMR(CDCl$_3$): 2.62–2.70(2H, m), 2.96(2H, t, J=7.8), 3.68(3H, s), 5.03(2H, s), 6.58 (1H, t, J=2.4), 6.95(1H, d, J=8.5), 7.10(1H, dd, J=8.3, 2.3), 7.14–7.25(5H, m), 7.40(2H, d, J=1.3), 7.78(1H, s), 8.19(1H, br-s).
Mass: (LCMS) 483(M$^+$+1)

EXP. 168
$^1$H-NMR(DMSO-d$_6$): 2.54(2H, t, J=7.5), 2.81(2H, t, J=7.3), 5.07(2H, s), 6.40–6.42(1H, m), 7.07–7.15(2H, m), 7.19–7.25(2H, m), 7.32–7.39(4H, m), 7.57(1H, dd, J=8.7, 1.6),

TABLE 1-continued 7.63(1H, s), 11.07(1H, br-s), 12.08(1H, s).
Mass: (LCMS) 469(M⁺+1)
EXP. 169
¹H-NMR(CDCl₃): 2.65(2H, t, J=7.8), 2.95(2H, t, J=7.8), 3.67(3H, s), 5.25(2H, s),
6.58–6.59(1H, m), 6.90(1H, d, J=8.5), 7.09(1H, dd, J=8.3, 2.2), 7.22–7.29(2H, m), 7.33
(1H, d, J=7.6), 7.34–7.47(3H, m), 7.62(2H, d, J=7.6), 7.83(1H, s), 8.19(1H, br-s).
Mass: (LCMS) 454(M⁺+1)
EXP. 170
¹H-NMR(DMSO-d₆): 2.55(2H, t, J=7.4), 2.82(2H, t, J=7.4), 5.20(2H, s), 6.41(1H, s),
7.02(1H, d, J=8.2), 7.14(1H, d, J=8.2), 7.22–7.28(2H, m), 7.34–7.39(2H, m), 7.50(1H, t,
J=7.1), 7.58–7.75(4H, m), 11.08(1H, br-s), 12.09(1H, br-s).
Mass: (LCMS) 440(M⁺+1)
EXP. 171
¹H-NMR(CDCl₃): 2.65(2H, t, J=7.9), 2.96(2H, t, J=7.8), 3.68(3H, s), 5.08(2H, s),
6.58–6.60(1H, m), 6.92(1H, d, J=8.2), 7.09(1H, dd, J=8.3, 2.3), 7.24–7.27(2H, m),
7.39–7.43(4H, d, J=1.1), 7.53(2H, d, J=8.5), 7.80(1H, s), 8.20(1H, br-s).
Mass: (LCMS) 454(M⁺+1)
EXP. 172
¹H-NMR(DMSO-d₆): 2.54(2H, t, J=7.7), 2.81(2H, t, J=7.7), 5.19(2H, s), 6.44(1H, t,
J=2.0), 7.05(1H, d, J=8.5), 7.12(1H, dd, J=8.5, 1.2), 7.21(1H, d, J=2.2), 7.29(1H, dd,
J=8.4, 1.5), 7.35(1H, t, J=2.7), 7.41(1H, d, J=8.5), 7.58(2H, d, J=7.9), 7.69(3H, d,
J=7.7), 11.09(1H, br-s), 12.07(1H, s).
Mass: (LCMS) 440(M⁺+1)
EXP. 173
¹H-NMR(CDCl₃): 1.20(6H, d, J=6.0), 2.69(2H, t, J=7.7), 2.95(2H, t, J=7.8), 4.32(1H,
qu, J=6.0), 6.56–6.58(1H, m), 6.92(1H, d, J=8.5), 7.08(1H, dd, J=8.2, 2.4), 7.20(1H, t,
J=2.7), 7.23(1H, d, J=2.2), 7.37–7.44(2H, m), 7.78(1H, d, J=0.8), 8.14(1H, s).
Mass: 323(M⁺)
EXP. 174
¹H-NMR(CDCl₃): 2.24(6H, s), 2.66(2H, t, J=7.6), 2.95(2H, t, J=7.8), 3.68(3H, s), 4.96
(2H, s), 6.57–6.59(1H, m), 6.87(1H, br-s), 6.92–6.99(3H, m), 7.08(1H, dd, J=8.2, 2.2),
7.22–7.27(2H, m), 7.40–7.47(2H, m), 7.85(1H, m), 8.18(1H, br-s).
Mass: (LCMS) 414(M⁺+1)
EXP. 175
¹H-NMR(DMSO-d₆): 2.20(6H, s), 2.54(2H, t, J=7.5), 2.81(2H, t, J=7.5), 4.98(2H, s),
6.43(1H, br-s), 6.87(1H, s), 6.94(2H, s), 7.05(1H, d, J=8.5), 7.12(1H, dd, J=8.4, 1.9),
7.21(1H, d, J=1.9), 7.27(1H, dd, J=8.5, 1.3), 7.35(1H, t, J=2.7), 7.41(1H, d, J=8.5),
7.71(1H, s), 11.09(1H, br-s), 12.07(1H, s).
Mass: (LCMS) 400(M⁺+1)
EXP. 176
¹H-NMR(CDCl₃): 0.67–2.28(11H, m), 2.65(2H, t, J=7.7), 2.94(2H, t, J=7.8), 3.58–3.95
(2H, m), 3.68(3H, s), 6.55–6.57(1H, m), 6.91(1H, t, J=9.1), 7.07–7.11(1H, m), 7.19–7.25
(2H, m), 7.36–7.44(2H, m), 7.79(1H, br-s), 8.16(1H, br-s).
Mass: (LCMS) 404(M⁺+1)
EXP. 177
¹H-NMR(DMSO-d₆): 0.68–2.20(11H, m), 2.52(2H, t, J=7.6), 2.80(2H, t, J=7.3),
3.60–3.96(2H, m), 6.41(1H, br-s), 7.00(1H, dd, J=8.5, 3.0), 7.07–7.11(1H, m), 7.17(1H,
s), 7.22–7.26(1H, m), 7.32–7.38(2H, m), 7.64(1H, s), 11.06(1H, br-s), 12.07(1H, br-s).
Mass: (LCMS) 390(M⁺+1)
EXP. 178
¹H-NMR(CDCl₃): 2.66(2H, t, J=7.6), 2.95(2H, t, J=7.8), 3.68(3H, s), 5.08(2H, s),
6.58–6.59(1H, m), 6.98(1H, d, J=8.2), 7.09(1H, dd, J=8.2, 2.4), 7.22–7.57(13H, m), 7.84
(1H, d, J=0.8), 8.17(1H, br-s).
Mass: (LCMS) 462(M⁺+1)
EXP. 179
¹H-NMR(DMSO-d₆): 2.55(2H, t, J=7.4), 2.82(2H, t, J=7.4), 5.13(2H, s), 6.45(1H, s),
7.08(1H, d, J=8.5), 7.13(1H, dd, J=8.5, 1.9), 7.21(1H, d, J=1.6), 7.29–7.47(8H, m),
7.60–7.65(4H, m), 7.70(1H, s), 11.08(1H, br-s), 12.08(1H, br-s).
Mass: (LCMS) 448(M⁺+1)
EXP. 180
¹H-NMR(CDCl₃): 0.80(3H, d, J=6.3), 0.86(6H, dd, J=6.3, 2.2), 1.67–1.78(2H, m), 2.65
(2H, t, J=7.8), 2.94(2H, t, J=7.8), 3.67(3H, s), 3.70–3.75(1H, m), 3.83–3.88(1H, m),
6.55–6.57(1H, m), 6.90(1H, d, J=8.5), 7.09(1H, dd, J=8.3, 2.3), 7.19–7.25(2H, m), 7.39
(2H, s), 7.78(1H, s), 8.15(1H, br-s).
Mass: (LCMS) 380(M⁺+1)
EXP. 181
¹H-NMR(DMSO-d₆): 0.78(3H, d, J=6.5), 0.83(6H, dd, J=6.9, 1.7), 1.59–1.90(2H, m),
2.53(2H, t, J=7.4), 2.80(2H, t, J=7.5), 3.71–3.76(1H, m), 3.81–3.86(1H, m), 6.41(1H,
br-s), 6.98(1H, d, J=8.5), 7.09(1H, dd, J=8.2, 2.2), 7.17(1H, d, J=2.1), 7.23(1H, dd,
J=8.4, 1.3), 7.33(1H, t, J=2.7), 7.37(1H, d, J=8.7), 7.63(1H, s), 11.05(1H, br-s), 12.06
(1H, s).
Mass: (LCMS) 366(M⁺+1)
EXP. 182
¹H-NMR(CDCl₃): 0.80–0.85(6H, m), 1.23–1.41(4H, m), 1.56(1H, qu, J=5.7), 2.62–2.66
(2H, m), 2.97(2H, t, J=7.9), 3.67(3H, s), 3.82(2H, d, J=5.4), 6.55–6.56(1H, m), 6.91
(1H, d, J=8.5), 7.09(1H, dd, J=8.3, 2.4), 7.19(1H, t, J=2.7), 7.23–7.25(1H, m), 7.38–7.42
(2H, m), 7.77(1H, s), 8.16(1H, br-s).
Mass: (LCMS) 380(M⁺+1)

TABLE 1-continued

EXP. 183
$^1$H-NMR(DMSO-d$_6$): 0.78–0.83(6H, m), 1.24–1.39(4H, m), 1.49(1H, qu, J=6.0), 2.53 (2H, t, J=7.7), 2.80(2H, t, J=7.4), 3.82(2H, d, J=5.5), 6.41(1H, br-s), 6.99(1H, d, J=8.2), 7.09(1H, dd, J=8.3, 2.0), 7.17(1H, d, J=2.2), 7.23(1H, dd, J=8.3, 1.2), 7.33(1H, t, J=2.7), 7.37(1H, d, J=8.5), 7.64(1H, s), 11.06(1H, br-s), 12.07(1H, br-s).
Mass: (LCMS) 366(M$^+$+1)

EXP. 184
$^1$H-NMR(DMSO-d$_6$): 1.24–1.68(10H, m), 1.78–1.86(2H, m), 2.53(2H, t, J=7.7), 2.79 (2H, t, J=7.5), 4.35–4.42(1H, m), 6.42–6.43(1H, m), 6.93(1H, d, J=8.5), 7.07(1H, dd, J=8.3, 2.4), 7.16(1H, d, J=2.2), 7.25(1H, dd, J=8.5, 1.6), 7.33(1H, d, J=8.2), 7.37(1H, d, J=8.2), 7.63(1H, d, J=0.8), 11.05(1H, br-s), 12.05(1H, br-s).
Mass: (LCMS) 378(M$^+$+1)

EXP. 185
$^1$H-NMR(CDCl$_3$): 0.95(3H, t, J=7.4), 1.41–1.53(2H, m), 1.69–1.78(2H, m), 2.64(2H, t, J=7.9), 2.94(2H, t, J=7.9), 3.67(3H, s), 3.92(2H, t, J=6.5), 4.95(2H, s), 6.56–6.58(1H, m), 6.80(2H, d, J=8.5), 6.95(1H, d, J=8.2), 7.07(1H, dd, J=8.3, 2.3), 7.20–7.26(4H, m), 7.40(1H, d, J=8.2), 7.44(1H, dd, J=8.5, 1.3), 7.80(1H, s), 8.16(1H, br-s).
Mass: (LCMS) 458(M$^+$+1)

EXP. 186
$^1$H-NMR(DMSO-d$_6$): 0.91(3H, t, J=7.4), 1.34–1.47(2H, m), 1.61–1.71(2H, m), 2.53(2H, t, J=7.4), 2.80(2H, t, J=7.4), 3.92(2H, t, J=6.4), 4.97(2H, s), 6.42(1H, br-s), 6.86(2H, d, J=8.7), 7.05(1H, d, J=8.2), 7.10(1H, dd, J=8.2, 1.9), 7.18(1H, d, J=1.9), 7.25–7.28(3H, m), 7.33(1H, t, J=2.7), 7.37(1H, d, J=8.2), 7.65(1H, s), 11.06(1H, s), 12.05(1H, br-s).
Mass: (LCMS) 444(M$^+$+1)

EXP. 187
$^1$H-NMR(CDCl$_3$): 2.66(2H, t, J=7.7), 2.96(2H, t, J=7.8), 3.68(3H, s), 4.93(2H, s), 6.59–6.61(1H, m), 6.90(1H, d, J=8.2), 7.10(1H, dd, J=8.3, 2.3), 7.16–7.28(5H, m), 7.40 (1H, dd, J=8.5, 1.6), 7.45(1H, d, J=8.2), 7.80(1H, s), 8.20(1H, br-s).
Mass: (LCMS) 455(M$^+$+1)

EXP. 188
$^1$H-NMR(DMSO-d$_6$): 2.55(2H, t, J=7.4), 2.82(2H, t, J=7.4), 5.10(2H, s), 6.44(1H, br-s), 7.05(1H, d, J=8.2), 7.15(1H, dd, J=8.3, 2.0), 7.23(1H, d, J=1.9), 7.28(1H, dd, J=9.3, 1.9), 7.36(1H, t, J=2.6), 7.38–7.43(3H, m), 7.49(1H, br-s), 7.69(1H, s), 11.11(1H, br-s), 12.08(1H, br-s).
Mass: (LCMS) 441(M$^+$+1)

EXP. 189
$^1$H-NMR(CDCl$_3$): 2.66(2H, t, J=7.6), 2.95(2H, t, J=7.8), 3.67(3H, s), 5.45(2H, s), 6.49 (1H, br-s), 7.06(1H, d, J=8.2), 7.10(1H, dd, J=8.2, 2.2), 7.16(1H, br-s), 7.23–7.50(7H, m), 7.75(1H, d, J=8.2), 7.80–7.85(2H, m), 7.95–7.98(1H, m), 8.12(1H, br-s).
Mass: (LCMS) 436(M$^+$+1)

EXP. 190
$^1$H-NMR(DMSO-d$_6$): 2.55(2H, t, J=7.4), 2.83(2H, t, J=7.3), 5.51(2H, s), 6.29(1H, br-s), 7.15–7.35(6H, m), 7.45(1H, t, J=7.5), 7.53–7.59(3H, m), 7.64(1H, s), 7.90(1H, d, J=8.2), 7.92–7.96(1H, m), 8.08–8.09(1H, m), 11.02(1H, br-s), 12.08(1H, s).
Mass: (LCMS) 422(M$^+$+1)

EXP. 191
$^1$H-NMR(CDCl$_3$): 2.65(2H, t, J=7.8), 2.95(2H, t, J=7.8), 3.67(3H, s), 5.20(2H, s), 6.58–6.60(1H, m), 6.99(1H, d, J=8.5), 7.08(1H, dd, J=8.3, 1.9), 7.21–7.23(1H, m), 7.28 (1H, d, J=1.6), 7.39–7.46(4H, m), 7.49(1H, dd, J=8.4, 1.5), 7.67–7.72(1H, m), 7.75–7.82 (3H, m), 7.87–7.88(1H, m), 8.18(1H, br-s).
Mass: (LCMS) 436(M$^+$+1)

EXP. 192
$^1$H-NMR(DMSO-d$_6$): 2.55(2H, t, J=7.5), 2.82(2H, t, J=7.4), 5.24(2H, s), 6.46(1H, br-s), 7.13(2H, d, J=0.8), 7.23(1H, s), 7.31–7.37(2H, m), 7.43(1H, d, J=8.2), 7.46–7.50(3H, m), 7.75–7.79(2H, m), 7.86–7.90(3H, m), 11.09(1H, s), 12.08(1H, br-s).
Mass: (LCMS) 422(M$^+$+1)

EXP. 193
$^1$H-NMR(CDCl$_3$): 2.65(2H, t, J=7.8), 2.95(2H, t, J=7.8), 3.67(3H, s), 4.91(2H, s), 6.24 (1H, d, J=3.2), 6.28–6.30(1H, m), 6.55–6.57(1H, m), 7.05(1H, d, J=8.5), 7.09(1H, dd, J=8.2, 2.2), 7.18–7.25(2H, m), 7.36–7.40(3H, m), 7.77(1H, s), 8.16(1H, br-s).
Mass: (LCMS) 376(M$^+$+1)

EXP. 194
$^1$H-NMR(DMSO-d$_6$): 2.54(2H, t, J=7.8), 2.80(2H, t, J=7.5), 5.01(2H, s), 6.41–6.42(2H, m), 6.47(1H, d, J=3.3), 7.09–7.17(3H, m), 7.21(1H, dd, J=8.5, 1.6), 7.32–7.37(2H, m), 7.61(1H, s), 7.64–7.65(1H, m), 11.06(1H, br-s), 12.08(1H, br-s).
Mass: (LCMS) 362(M$^+$+1)

EXP. 195
$^1$H-NMR(CDCl$_3$): 2.65(2H, t, J=7.7), 2.95(2H, t, J=7.8), 3.67(3H, s), 4.87(2H, s), 6.32 (1H, t, J=0.7), 6.56(1H, t, J=2.3), 6.97(1H, d, J=8.5), 7.09(1H, dd, J=8.3, 2.3), 7.18–7.21(1H, m), 7.25(1H, d, J=2.4), 7.32–7.33(2H, m), 7.33–7.40(2H, m), 7.78(1H, s), 8.18(1H, br-s).
Mass: (LCMS) 376(M$^+$+1)

EXP. 196
$^1$H-NMR(DMSO-d$_6$): 2.54(2H, t, J=7.5), 2.81(2H, t, J=7.5), 4.91(2H, s), 6.43(1H, br-s), 6.46(1H, s), 7.08(1H, d, J=8.5), 7.12(1H, dd, J=8.5, 1.9), 7.19(1H, d, J=1.9), 7.25(1H, dd, J=8.5, 1.6), 7.33(1H, t, J=2.6), 7.39(1H, d, J=8.5), 7.60–7.61(2H, m), 7.65(1H, s), 11.07(1H, br-s), 12.08(1H, s).
Mass: (LCMS) 362(M$^+$+1)

TABLE 1-continued

EXP. 197
¹H-NMR(CDCl₃): 2.62–2.68(2H, m), 2.95(2H, t, J=7.8), 3.67(3H, s), 5.13(2H, s), 6.57–6.59(1H, m), 6.90–6.96(2H, m), 6.99(1H, d, J=8.2), 7.09(1H, dd, J=8.2, 2.2), 7.17–7.25(3H, m), 7.42–7.43(2H, m), 7.80(1H, d, J=0.5), 8.15(1H, br-s).
Mass: (LCMS) 392(M⁺+1)

EXP. 198
¹H-NMR(DMSO-d₆): 2.54(2H, t, J=8.0), 2.81(2H, t, J=7.4), 5.23(2H, s), 6.39–6.46(1H, m), 6.98(1H, dd, J=5.2, 3.3), 7.10–7.12(3H, m), 7.19(1H, br-s), 7.25(1H, dd, J=8.5, 1.6), 7.33(1H, t, J=2.7), 7.37(1H, d, J=8.2), 7.49(1H, dd, J=5.0, 1.2), 7.66(1H, br-s), 11.06 (1H, br-s).
Mass: (LCMS) 378(M⁺+1)

EXP. 199
¹H-NMR(CDCl₃): 2.21(3H, s), 2.64(2H, t, J=7.7), 2.93(2H, t, J=7.3), 3.00(2H, t, J=7.1), 3.67(3H, s), 4.10(2H, t, J=7.4), 6.57–6.58(1H, m), 6.89(1H, d, J=8.2), 7.06–7.12 (5H, m), 7.21(1H, d, J=2.2), 7.23(1H, t, J=2.7), 7.34(1H, dd, J=8.2, 1.6), 7.40(1H, d, J=8.2), 7.72(1H, s), 8.16(1H, br-s).
Mass: (LCMS) 414(M⁺+1)

EXP. 200
¹H-NMR(DMSO-d₆): 2.22(3H, s), 2.58(2H, t, J=7.7), 2.85(2H, t, J=7.4), 2.97(2H, t, J=6.7), 4.16(2H, t, J=6.7), 6.46–6.48(1H, m), 7.04(1H, d, J=8.5), 7.09–7.16(4H, m), 7.19–7.23(3H, m), 7.38–7.43(2H, m), 7.62(1H, d, J=0.8), 11.11(1H, br-s), 12.14(1H, br-s).
Mass: 399(M⁺)

EXP. 201
¹H-NMR(CDCl₃): 2.38(3H, s), 2.68(2H, t, J=7.4), 2.87–2.97(4H, m), 3.68(3H, s), 4.13 (2H, t, J=7.2), 6.55–6.58(1H, m), 6.89(1H, d, J=8.5), 6.97–7.13(5H, m), 7.16–7.22(2H, m), 7.33(1H, dd, J=8.8, 1.6), 7.39(1H, d, J=8.5), 7.73(1H, s), 8.15(1H, br-s).
Mass: (LCMS) 414(M⁺+1)

EXP. 202
¹H-NMR(DMSO-d₆): 2.16(3H, s), 2.53(2H, t, J=7.5), 2.81(2H, t, J=7.4), 2.88(2H, t, J=6.3), 4.12(2H, t, J=6.3), 6.42(1H, m), 6.95–7.00(4H, m), 7.07–7.12(2H, m), 7.15(2H, dd, J=8.5, 1.3), 7.34–7.37(2H, m), 7.58(1H, s), 11.07(1H, br-s), 12.10(1H, br-s).
Mass: 399(M⁺)

EXP. 203
¹H-NMR(CDCl₃): 2.31(3H, s), 2.63(2H, t, J=7.9), 2.90–2.97(4H, m), 3.67(3H, s), 4.12 2H, t, J=6.7), 6.56–6.58(1H, m), 6.88(1H, d, J=8.5), 7.05–7.12(5H, m), 7.21(1H, d, J=2.2), 7.23(1H, t, J=3.0), 7.32(1H, dd, J=8.4, 1.5), 7.39(1H, d, J=8.5), 7.71(1H, d, J=0.8), 8.16(1H, br-s).
Mass: (LCMS) 414(M⁺+1)

EXP. 204
¹H-NMR(DMSO-d₆): 2.26(3H, s), 2.53(2H, t, J=7.4), 2.80(2H, t, J=7.5), 2.87(2H, t, J=6.4), 4.11(2H, t, J=6.4), 6.41–6.43(1H, m), 6.96(1H, d, J=8.5), 7.03–7.17(7H, m), 7.34–7.37(2H, m), 7.55(1H, s), 11.07(1H, br-s), 12.08(1H, br-s).
Mass: 399(M⁺)

EXP. 205
¹H-NMR(DMSO-d₆): 2.49–2.55(2H, m), 2.79(2H, t, J=7.5), 2.92(2H, t, J=6.4), 3.76(3H, s), 4.10(2H, t, J=6.5), 6.42(1H, br-s), 6.82(1H, t, J=6.7), 6.94–7.00(2H, m), 7.07–7.24 (5H, m), 7.33–7.37(2H, m), 7.57(1H, s), 11.06(1H, br-s).
Mass: (LCMS) 416(M⁺+1)

EXP. 206
¹H-NMR(CDCl₃): 2.63(2H, t, J=7.8), 2.89–2.96(4H, m), 3.67(3H, s), 3.77(3H, s), 4.10 (2H, t, J=6.7), 6.56–6.58(1H, m), 6.76(1H, d, J=8.5), 6.87(1H, d, J=0.8), 7.04–7.09(3H, m), 7.20(1H, d, J=2.4), 7.22(1H, t, J=2.8), 7.31(1H, dd, J=8.5, 1.6), 7.39(2H, d, J=18.2), 7.70(1H, s), 8.18(1H, br-s).
Mass: (LCMS) 430(M⁺+1)

EXP. 207
¹H-NMR(DMSO-d₆): 2.49–2.55(2H, m), 2.79(2H, t, J=7.5), 2.85(2H, t, J=6.5), 3.71(3H, s), 4.10(2H, t, J=6.6), 6.42(1H, br-s), 6.78(2H, d, J=8.5), 6.97(1H, d, J=8.5), 7.07–7.15 (5H, m), 7.33–7.37(2H, m), 7.65(1H, br-s), 11.06(1H, br-s), 12.00(1H, s).
Mass: (LCMS) 416(M⁺+1)

EXP. 208
¹H-NMR(CDCl₃): 2.70(2H, t, J=7.7), 2.94(2H, t, J=7.7), 3.12(2H, t, J=6.5), 3.67(3H, s), 4.17(2H, t, J=6.7), 6.56–6.59(1H, m), 6.91(1H, d, J=8.5), 7.06(1H, d, J=7.6), 7.15 (1H, dd, J=8.4, 2.1), 7.19–7.35(6H, m), 7.46(1H, d, J=8.2), 7.75(1H, d, J=0.8), 8.24(1H, br-s).
Mass: (LCMS) 434(M⁺+1)

EXP. 209
¹H-NMR(DMSO-d₆): 2.53(2H, t, J=7.4), 2.80(2H, t, J=7.4), 3.06(2H, t, J=6.5), 4.17 (2H, t, J=6.5), 6.41–6.43(1H, m), 7.01(1H, d, J=8.2), 7.08–7.12(1H, m), 7.14–7.19(3H, m), 7.24(1H, dd, J=7.6, 1.9), 7.31(1H, dd, J=7.4, 1.6), 7.34–7.37(2H, m), 7.41(1H, dd, J=7.9, 1.3), 7.56(1H, s), 11.07(1H, br-s), 12.08(1H, br-s).
Mass: 419(M⁺)

EXP. 210
¹H-NMR(CDCl₃): 2.63(2H, t, J=7.8), 2.83–2.96(4H, m), 3.67(3H, s), 4.13(2H, t, J=6.4), 6.57–6.58(1H, m), 6.87(1H, d, J=8.2), 7.01(1H, d, J=7.1), 7.08(1H, dd, J=8.4, 2.1), 7.12–7.28(6H, m), 7.39(1H, d, J=8.5), 7.68(1H, d, J=0.8), 8.17(1H, br-s).
Mass: (LCMS) 433(M⁺+1)

EXP. 211
¹H-NMR(DMSO-d₆): 2.54(2H, t, J=7.7), 2.78(2H, t, J=7.4), 2.94(2H, t, J=6.4), 4.17

TABLE 1-continued (2H, t, J=6.3), 6.39–6.43(1H, m), 6.98(1H, d, J=8.5), 7.10(2H, d, J=8.7), 7.15–7.19(2H, m), 7.25–7.27(2H, m), 7.33–7.36(3H, m), 7.52(1H, s), 11.06(1H, br-s).
Mass: 419(M$^+$)
EXP. 212
$^1$H-NMR(CDCl$_3$): 2.69(2H, t, J=7.3), 2.80(2H, t, J=7.5), 2.95(2H, t, J=6.4), 3.67(3H, s), 4.15(2H, t, J=6.3), 6.38–6.43(1H, m), 6.92(1H, d, J=8.5), 7.08–7.15(2H, m), 7.16 (1H, d, J=2.2), 7.21–7.28(4H, m), 7.30–7.38(2H, m), 7.50(1H, s), 8.17(1H, br-s).
Mass: (LCMS) 434(M$^+$+1)
EXP. 213
$^1$H-NMR(DMSO-d$_6$): 2.52(2H, t, J=7.4), 2.79(2H, t, J=7.5), 2.90(2H, t, J=6.3), 4.15 (2H, t, J=6.3), 6.40(1H, m), 6.97(1H, d, J=8.5), 7.06–7.11(2H, m), 7.14(1H, d, J=2.2), 7.19–7.26(4H, m), 7.32–7.36(2H, m), 7.49(1H, s), 11.06(1H, br-s), 12.06(1H, br-s).
Mass: 419(M$^+$)
EXP. 214
$^1$H-NMR(DMSO-d$_6$): 2.54(2H, t, J=7.5), 2.59–2.66(2H, m), 2.81(2H, t, J=7.7), 3.91(2H, t, J=6.0), 6.43–6.45(1H, m), 6.95(1H, d, J=8.2), 7.08–7.11(3H, m), 7.16–7.21(2H, m), 7.22–7.31(2H, m), 7.34(1H, t, J=2.7), 7.42(1H, d, J=8.2), 7.69(1H, s), 11.08(1H, br-s), 12.05(1H, s).
Mass: (LCMS) 454(M$^+$+1)
EXP. 215
$^1$H-NMR(DMSO-d$_6$): 2.52(2H, t, J=7.1), 2.77–2.83(4H, m), 3.33(6H, s), 4.06(2H, t, J=6.4), 6.43(1H, s), 6.60(2H, d, J=7.9), 6.95–7.17(6H, m), 7.37(2H, d, J=8.5), 7.56(1H, s), 11.06(1H, s), 12.06(1H, br-s).
Mass: 428(M$^+$)
EXP. 216
$^1$H-NMR(CDCl$_3$): 2.63(2H, t, J=7.9), 2.93(2H, t, J=7.5), 3.14(2H, t, J=6.4), 3.66(3H, s), 4.23(2H, t, J=6.7), 6.49–6.52(1H, m), 6.91(1H, d, J=8.2), 7.09(1H, dd, J=8.2, 2.2), 7.20–7.29(5H, m), 7.39–7.43(2H, m), 7.58(1H, s), 7.60–7.64(1H, m), 7.68–7.70(2H, m), 7.77–7.82(1H, m), 8.14(1H, br-s).
Mass: (LCMS) 450(M$^+$+1)
EXP. 217
$^1$H-NMR(DMSO-d$_6$): 2.49–2.54(2H, m), 2.79(2H, t, J=7.4), 3.10(2H, t, J=6.2), 4.26(2H, t, J=6.4), 6.30(1H, s), 7.01(1H, d, J=8.2), 7.10(2H, d, J=8.5), 7.14(1H, d, J=2.4), 7.28 (1H, d, J=8.5), 7.33(1H, t, J=2.7), 7.38–7.47(3H, m), 7.52(1H, s), 7.63–7.68(2H, m), 7.78(1H, d, J=8.5), 7.84–7.87(1H, m), 11.06(1H, br-s), 12.05(1H, br-s).
Mass: 435(M$^+$)
EXP. 218
$^1$H-NMR(CDCl$_3$): 2.63(2H, t, J=7.4), 2.93(2H, t, J=7.6), 3.15(2H, t, J=7.6), 3.67(3H, s), 4.20(2H, t, J=6.9), 6.54–6.59(1H, m), 6.88–7.15(5H, m), 7.21–7.26(1H, m), 7.33(1H, d, J=7.1), 7.39(3H, m), 7.45–7.51(1H, m), 7.75(1H, s), 7.88(1H, br-s), 8.20(1H, br-s).
Mass: (LCMS) 439(M$^+$+1)
EXP. 219
$^1$H-NMR(CDCl$_3$): 2.65(2H, t, J=7.5), 2.94(2H, t, J=7.9), 3.15(2H, t, J=6.8), 4.20(2H, t, J=6.9), 6.54–6.59(1H, m), 6.86–6.90(1H, m), 6.91(1H, d, J=7.9), 7.00–7.18(4H, m), 7.21–7.23(1H, m), 7.33(1H, d, J=7.9), 7.39(2H, s), 7.50(1H, d, J=8.2), 7.76(1H, s), 7.89(1H, br-s), 8.21(1H, br-s).
Mass: 424(M$^+$)
EXP. 220
$^1$H-NMR(DMSO-d$_6$): 2.60–2.66(2H, m), 2.93(2H, t, J=7.8), 3.07(2H, t, J=6.6), 3.15(2H, t, J=6.5), 4.13(2H, t, J=6.4), 6.57–6.59(1H, m), 6.87(1H, d, J=8.5), 7.08(1H, dd, J=8.3, 2.3), 7.16–7.20(2H, m), 7.23(1H, d, J=2.5), 7.30–7.43(3H, m), 7.48(1H, t, J=7.5), 7.57 (1H, d, J=7.4), 7.65(1H, d, J=7.9), 7.71(1H, t, J=0.8), 11.07(1H, br-s), 12.06(1H, br-s).
Mass: (LCMS) 400(M$^+$+1)
EXP. 221
$^1$H-NMR(CDCl$_3$): 2.65(2H, t, J=7.8), 2.96(2H, t, J=7.8), 3.68(3H, s), 4.18–4.22(2H, m), 4.25–4.29(2H, m), 6.49–6.51(1H, m), 6.87–6.99(4H, m), 7.11(1H, dd, J=8.3, 2.3), 7.20–7.30(3H, m), 7.32–7.36(1H, m), 7.44(2H, d, J=8.5, 1.6), 7.82(1H, t, J=0.8), 8.14 (1H, br-s).
Mass: (LCMS) 416(M$^+$+1)
EXP. 222
$^1$H-NMR(DMSO-d$_6$): 2.54(2H, t, J=7.8), 2.81(2H, t, J=7.4), 4.21–4.29(4H, m), 6.31–6.32(1H, m), 6.90–6.97(3H, m), 7.04(1H, d, J=8.2), 7.12(1H, dd, J=8.3, 2.0), 7.20 (1H, d, J=1.9), 7.24–7.30(5H, m), 7.70(1H, s), 11.02(1H, br-s), 12.05(1H, br-s).
Mass: (LCMS) 402(M$^+$+1)
EXP. 223
$^1$H-NMR(CDCl$_3$): 2.63–2.70(2H, m), 2.95(2H, t, J=7.8), 3.68(3H, s), 4.24–4.28(2H, m), 4.31–4.34(2H, m), 6.51–6.53(1H, m), 6.80–6.89(2H, m), 6.99–7.07(2H, m), 7.12(1H, dd, J=8.3, 1.3), 7.19(1H, t, J=2.7), 7.25(1H, d, J=3.2), 7.35(2H, dd, J=7.9, 1.4), 7.46(1H, dd, J=8.5, 1.6), 7.82(1H, t, J=0.8), 8.13(1H, br-s).
Mass: (LCMS) 450(M$^+$+1)
EXP. 224
$^1$H-NMR(DMSO-d$_6$): 2.54(2H, t, J=7.5), 2.82(2H, t, J=7.5), 4.30(4H, s), 6.30(1H, br-s), 6.95(1H, td, J=7.5, 1.2), 7.06(1H, d, J=8.2), 7.10–7.15(2H, m), 7.18–7.24(2H, m), 7.27–7.35(3H, m), 7.46(1H, dd, J=7.9, 1.3), 7.73(1H, s), 11.01(1H, br-s), 12.07(1H, br-s).
Mass: (LCMS) 436(M$^+$+1)
EXP. 225
$^1$H-NMR(CDCl$_3$): 2.63–2.70(2H, m), 2.96(2H, t, J=7.9), 3.68(3H, s), 4.14–4.17(2H, m), 4.24–4.26(2H, m), 6.49–6.52(1H, m), 6.77(1H, d, J=9.1), 6.96(1H, d, J=8.2), 7.10–7.14

TABLE 1-continued (3H, m), 7.21(1H, t, J=2.8), 7.25(1H, d, J=2.6), 7.33(1H, d, J=8.5), 7.40(2H, dd, J=8.5, 1.5), 7.78(1H, d, J=1.6), 8.15(1H, br-s).
Mass: (LCMS) 450(M$^+$+1)
EXP. 226
$^1$H-NMR(DMSO-d$_6$): 2.54(2H, t, J=7.7), 2.81(2H, t, J=7.3), 4.25(4H, m), 6.96(2H, d, J=9.1), 7.04(1H, d, J=8.2), 7.12(1H, dd, J=8.2, 2.2), 7.19(1H, d, J=2.2), 7.24–7.26(1H, m), 7.27–7.33(5H, m), 7.68(1H, s), 11.04(1H, br-s), 12.07(1H, br-s).
Mass: (LCMS) 436(M$^+$+1)
EXP. 227
$^1$H-NMR(CDCl$_3$): 2.64(2H, m), 2.94(2H, t, J=7.8), 3.17(2H, t, J=7.1), 3.67(3H, s), 4.07 (2H, t, J=7.1), 6.58(1H, t, J=2.6), 6.85(1H, d, J=8.5), 7.07(1H, dd, J=8.3, 2.3), 7.15–7.31(7H, m), 7.41(2H, d, J=1.1), 7.79(1H, d, J=0.8), 8.17(1H, br-s).
Mass: (LCMS) 432(M$^+$+1)
EXP. 228
$^1$H-NMR(DMSO-d$_6$): 2.53(2H, t, J=7.7), 2.80(2H, t, J=7.7), 3.25(2H, t, J=6.2), 4.08 (2H, t, J=6.3), 6.44(1H, br-s), 6.95(1H, d, J=8.5), 7.09(1H, dd, J=8.2, 1.6), 7.16–7.36 (8H, m), 7.39(1H, d, J=8.5), 7.70(1H, s), 11.08(1H, br-s), 12.01(1H, s).
Mass: (LCMS) 418(M$^+$+1)
EXP. 229
$^1$H-NMR(DMSO-d$_6$): 2.50–2.54(2H, m), 2.77(3H, s), 2.79(2H, t, J=7.4), 3.60(2H, t, J=5.2), 4.05(2H, t, J=5.0), 6.44(1H, br-s), 6.55(1H, t, J=7.1), 6.62(2H, d, J=7.9), 6.96 (1H, d, J=8.5), 7.02–7.10(3H, m), 7.16(1H, d, J=2.2), 7.24(1H, dd, J=8.5, 1.6), 7.35(1H, t, J=2.7), 7.39(1H, d, J=8.5), 7.64(1H, br-s), 11.08(1H, br-s).
Mass: (LCMS) 415(M$^+$+1)
EXP. Int. 56
$^1$H-NMR(CDCl$_3$): 1.01–1.28(5H, m), 1.63–1.81(6H, m), 3.88(2H, d, J=5.8), 6.58–6.60 (1H, m), 7.07(1H, d, J=8.5), 7.24–7.26(1H, m), 7.42(2H, m), 7.80–7.84(2H, m), 7.93 (1H, d, J=2.2), 8.21(1H, s), 9.94(1H, s).
Mass: 334(M$^+$+1)
EXP. Int. 57
$^1$H-NMR(CDCl$_3$): 1.00–1.35(8H, m), 1.63–1.80(6H, m), 3.80(2H, d, J=6.0), 4.25(2H, q, J=7.1), 6.35(1H, d, J=15.9), 6.58–6.60(1H, m), 6.96(1H, d, J=8.5), 7.24(1H, t, J=3.0), 7.41–7.46(3H, m), 7.60(1H, d, J=2.2), 7.70(1H, d, J=15.9), 7.79(1H, s), 8.19(1H, s).
Mass: 403(M$^+$)
EXP. 230
$^1$H-NMR(CDCl$_3$): 0.89–1.28(8H, m), 1.66–1.79(6H, m), 2.63(2H, t, J=7.7), 2.94(2H, t, J=7.8), 3.72(2H, d, J=6.0), 4.14(2H, q, J=7.1), 6.56–6.58(1H, m), 6.88(1H, d, J=8.2), 7.09(1H, dd, J=8.3, 2.2), 7.21–7.24(2H, m), 7.38–7.44(2H, m), 7.79(1H, s), 8.16(1H, s).
Mass: 405(M$^+$)
EXP. 231
$^1$H-NMR(DMSO-d$_6$): 0.97–1.20(5H, m), 1.60–1.73(6H, m), 2.53(2H, t, J=7.4), 2.80(2H, t, J=7.7), 3.73(2H, d, J=5.8), 6.41(1H, d, J=1.9), 6.95(1H, d, J=8.2), 7.09(1H, dd, J=8.3, 2.0), 7.24(1H, dd, J=8.5, 1.6), 7.32–7.39(3H, m), 7.64(1H, s), 11.06(1H, s), 12.07 (1H, s).
Mass: 377(M$^+$)
EXP. 232
$^1$H-NMR(CDCl$_3$): 0.97–1.28(5H, m), 1.66–1.79(6H, m), 2.65(2H, t, J=7.4), 2.94(2H, t, J=7.8), 3.68(3H, s), 3.72(2H, d, J=6.0), 3.82(3H, s), 6.50(1H, dd, J=3.0, 0.8), 6.89(1H, d, J=8.5), 7.05–7.10(2H, m), 7.24(1H, dd, J=7.9, 7.6), 7.33(1H, d, J=8.5), 7.44(1H, dd, J=8.6, 1.4), 7.77(1H, dd, J=1.7, 0.5)
Mass: 405(M$^+$)
EXP. 233
$^1$H-NMR(DMSO-d$_6$): 0.97–1.20(5H, m), 1.62–1.72(6H, m), 2.54(2H, t, J=8.0), 2.80(2H, t, J=7.5), 3.73(2H, d, J=6.0), 3.80(3H, s), 6.41(1H, d, J=3.0), 6.95(1H, d, J=8.2), 7.10 (1H, d, J=8.2), 7.17(1H, s), 7.29–7.32(2H, m), 7.42(1H, d, J=8.5), 7.65(1H, s), 12.09 (1H, s).
Mass: 391(M$^+$)
EXP. 234
$^1$H-NMR(CDCl$_3$): 0.83–1.34(4H, m), 1.52–1.74(4H, m), 2.27(1H, qu, J=7.3), 2.66(2H, t, J=7.9), 2.94(2H, t, J=7.7), 3.68(3H, s), 3.81(2H, d, J=7.1), 3.82(3H, s), 6.50(1H, d, J=3.0), 6.89(1H, d, J=8.5), 7.05–7.12(2H, m), 7.23(1H, d, J=1.9), 7.32(1H, d, J=8.5), 7.45(1H, dd, J=8.8, 0.9), 7.77(1H, d, J=0.8).
Mass: 391(M$^+$)
EXP. 235
$^1$H-NMR(DMSO-d$_6$): 1.18–1.69(8H, m), 2.18(1H, qu, J=7.1), 2.53(2H, t, J=7.5), 2.80 (2H, t, J=7.4), 3.80(3H, s), 3.81(2H, d, J=4.9), 6.41(1H, d, J=3.3), 6.97(1H, d, J=8.5), 7.10(1H, dd, J=8.0, 2.2), 7.18(1H, d, J=1.9), 7.31–7.35(2H, m), 7.43(1H, d, J=9.3), 7.65 (1H, s), 11.99(1H, s).
Mass: (LCMS) 378(M$^+$+1)
EXP. 236
$^1$H-NMR(DMSO-d$_6$): 1.19–1.32(2H, m), 1.37(3H, t, J=7.3), 1.42–1.54(4H, m), 1.62–1.73 (2H, m), 2.18(1H, qu, J=7.3), 2.53(2H, t, J=7.2), 2.80(2H, t, J=7.2), 3.81(2H, d, J=6.6), 4.22(2H, q, J=7.3), 6.42(1H, d, J=3.3), 6.97(1H, d, J=8.5), 7.10(1H, dd, J=8.2, 2.2), 7.18(1H, d, J=2.4), 7.31(1H, dd, J=8.6, 1.5), 7.38(1H, d, J=3.0), 7.46(1H, d, J=8.5), 7.66(1H, s), 12.21(1H, br-s).
Mass: 391(M$^+$)
EXP. 237
$^1$H-NMR(CDCl$_3$): 1.20–1.34(3H, m), 1.56(6H, d, J=6.9), 1.50–1.79(5H, m), 2.28(1H, qu, J=7.5), 2.67(2H, t, J=8.4), 2.93(2H, t, J=7.8), 3.68(3H, s), 3.81(2H, d, J=6.9), 4.70(1H, TABLE 1-continued qu, J=6.7), 6.53(1H, d, J=3.3), 6.89(1H, d, J=8.2), 7.08(1H, dd, J=8.4, 2.3), 7.22–7.26 (2H, m), 7.31(1H, d, J=8.8), 7.44(1H, dd, J=8.5, 1.6), 7.78(1H, s).
Mass: 419($M^+$)
EXP. 238
$^1$H-NMR(DMSO-$d_6$): 1.15–1.30(3H, m), 1.47(6H, d, J=6.6), 1.48–1.69(5H, m), 2.19(1H, qu, J=7.1), 2.53(2H, t, J=7.3), 2.80(2H, t, J=7.5), 3.81(2H, d, J=6.6), 4.77(1H, qu, J=6.4), 6.45(1H, d, J=2.8), 6.97(1H, d, J=8.5), 7.09(1H, dd, J=8.3, 2.2), 7.18(1H, d, J=1.9), 7.30(1H, dd, J=8.8, 0.9), 7.48–7.51(2H, m), 7.66(1H, s), 12.04(1H, s).
Mass: 405($M^+$)
EXP. 239
$^1$H-NMR(CDCl$_3$): 0.95(3H, t, J= 7.4), 1.24–1.55(8H, m), 1.74–1.87(4H, m), 2.28(1H, qu, J=7.3), 2.66(2H, t, J=7.4), 2.94(2H, t, J=8.0), 3.68(3H, s), 3.81(2H, d, J=6.9), 4.14(2H, t, J=7.1), 6.49(1H, d, J=3.0), 6.89(1H, d, J=8.2), 7.08(1H, dd, J=8.3, 2.4), 7.24(1H, d, J=2.5), 7.34(1H, d, J=8.5), 7.43(1H, dd, J=8.5, 1.6), 7.77(1H, d, J=0.8).
Mass: 433($M^+$)
EXP. 240
$^1$H-NMR(DMSO-$d_6$): 0.89(3H, t, J=7.3), 1.25–1.53(8H, m), 1.66–1.78(4H, m), 2.18(1H, qu, J=7.1), 2.53(2H, t, J=7.5), 2.80(2H, t, J=7.2), 3.81(2H, d, J=6.3), 4.18(2H, t, J=6.8), 6.42(1H, d, J=2.7), 6.96(1H, d, J=7.9), 7.10(1H, dd, J=8.0, 2.2), 7.18(1H, d, J=2.8), 7.30(1H, dd, J=9.3, 2.2), 7.36(1H, d, J=2.8), 7.45(1H, d, J=8.5), 7.65(1H, s), 11.94(1H, s)
Mass: 419($M^+$)
EXP. 241
$^1$H-NMR(CDCl$_3$): 1.23–1.31(5H, m), 1.74–2.05(9H, m), 2.17–2.30(3H, m), 2.63(2H, t, J=7.9), 2.94(2H, t, J=7.9), 3.68(3H, s), 3.81(2H, d, J=6.9), 4.81(1H, qu, J=7.1), 6.51 (1H, d, J=3.0), 6.89(1H, d, J=8.5), 7.07(1H, dd, J=8.2, 2.5), 7.22(2H, dd, J=8.9, 2.8), 7.38–7.45(2H, m), 7.78(1H, s).
Mass: 445($M^+$)
EXP. 242
$^1$H-NMR(DMSO-$d_6$): 1.24–1.89(14H, m), 2.15–2.21(3H, m), 2.52(2H, t, J=7.1), 2.79 (2H, t, J=7.1), 3.81(2H, d, J=6.6), 4.90(1H, qu, J=7.1), 6.44(1H, d, J=2.7), 6.97(1H, d, J=8.5), 7.10(1H, dd, J=8.5, 2.2), 7.17(1H, d, J=2.8), 7.31(1H, dd, J=8.5, 2.3), 7.45(1H, d, J=3.3), 7.50(1H, d, J=8.8), 7.66(1H, s), 12.04(1H, s).
Mass: 431($M^+$)
EXP. 243
$^1$H-NMR(DMSO-$d_6$): 1.23–1.32(2H, m), 1.45–1.57(4H, m), 1.63–1.72(2H, m), 2.19(1H, qu, J=7.4), 2.53(2H, t, J=7.6), 2.80(2H, t, J=7.4), 3.73(2H, t, J=5.2), 3.81(2H, d, J=6.8), 4.22(2H, t, J=5.6), 4.89(1H, br-s), 6.41(1H, d, J=3.3), 6.96(1H, d, J=8.2), 7.09 (1H, dd, J=8.2, 1.9), 7.18(1H, d, J=1.9), 7.24–7.39(2H, m), 7.46(1H, d, J=8.8), 7.66(1H, s), 12.07(1H, br-s).
Mass: 407($M^+$)
EXP. Int. 58
$^1$H-NMR(CDCl$_3$): −0.11(6H, s), 0.81(9H, s), 2.64(2H, t, J=7.9), 2.94(2H, t, J=7.9), 3.68 (3H, s), 3.82(3H, s), 6.48(1H, d, J=3.2), 6.84(1H, d, J=8.2), 7.01(1H, dd, J=8.0, 2.2), 7.05(1H, d, J=3.0), 7.20(1H, d, J=2.4), 7.31(1H, d, J=8.5), 7.38(1H, dd, J=8.5, 1.6), 7.73(1H, t, J=0.7).
Mass: (LCMS) 424($M^+$+1)
EXP. Int. 59
$^1$H-NMR(CDCl$_3$): 2.64(2H, t, J=7.8), 2.93(2H, t, J=7.9), 3.67(3H, s), 3.85(3H, s), 5.35 (1H, s), 6.53(1H, d, J=3.3), 6.93(1H, d, J=8.2), 7.08(1H, dd, J=8.5, 2.3), 7.11–7.14(2H, m), 7.26–7.28(1H, m), 7.45(1H, d, J=9.0), 7.68(1H, d, J=1.6).
Mass: (LCMS) 310($M^+$+1)
EXP. 244
$^1$H-NMR(CDCl$_3$): 2.66(2H, t, J=7.9), 2.96(2H, t, J=7.8), 3.68(3H, s), 3.83(3H, s), 5.13 (2H, s), 6.51(1H, dd, J=3.0, 0.8), 6.95(1H, d, J=8.5), 7.07–7.12(2H, m), 7.15–7.19(2H, m), 7.26(1H, d, J=3.0), 7.32–7.37(2H, m), 7.43(1H, m), 7.49(1H, dd, J=8.5, 1.6), 7.82 (1H, dd, J=1.6, 0.8).
Mass: (LCMS) 434($M^+$+1)
EXP. 245
$^1$H-NMR(DMSO-$d_6$): 2.54(2H, t, J=7.4), 2.82(2H, t, J=7.5), 3.79(3H, s), 5.11(2H, s), 6.40(1H, d, J=3.0), 7.08(1H, d, J=8.2), 7.15(1H, dd, J=8.5, 2.2), 7.22(1H, d, J=2.2), 7.26–7.37(4H, m), 7.42(1H, d, J=8.5), 7.47(2H, dd, J=8.6, 1.3), 7.69(1H, d, J=1.4), 12.11(1H, br-s).
Mass: 419($M^+$)
EXP. 246
$^1$H-NMR(DMSO-$d_6$): 1.37(3H, t, J=7.1), 1.53–1.68(6H, m), 1.75–1.77(2H, m), 2.55(2H, t, J=7.4), 2.79(2H, t, J=7.4), 4.21(2H, q, J=7.1), 4.75(1H, m), 6.42(1H, d, J=3.3), 6.96 (1H, d, J=8.2), 7.09(1H, dd, J=8.3, 2.3), 7.17(1H, d, J=2.4), 7.27(1H, dd, J=8.4, 1.5), 7.38(1H, d, J=3.0), 7.46(1H, d, J=8.5), 7.61(1H, m), 12.08(1H, br-s).
Mass: 377($M^+$)
EXP. Int. 60
$^1$H-NMR(CDCl$_3$): −0.11(6H, s), 0.80(9H, s), 1.48(3H, t, J=7.3), 2.64(2H, t, J=7.9), 2.94 (2H, t, J=7.9), 3.67(3H, s), 4.20(2H, q, J=7.4), 6.48(1H, d, J=3.2), 6.84(1H, d, J=8.2), 7.00(1H, dd, J=8.3, 2.2), 7.12(1H, d, J=3.3), 7.21(1H, d, J=2.2), 7.33(1H, d, J=8.2), 7.37(1H, dd, J=8.6, 1.5), 7.73(1H, s).
Mass: (LCMS) 438($M^+$+1)
EXP. Int. 61
$^1$H-NMR(DMSO-$d_6$): 1.50(3H, t, J=7.4), 2.64(2H, t, J=7.8), 2.93(2H, t, J=7.8), 3.67 (3H, s), 4.23(2H, q, J=7.4), 5.36(1H, s), 6.54(1H, d, J=3.2), 6.93(1H, d, J=8.2), 7.08

TABLE 1-continued (1H, dd, J=8.3, 2.2), 7.12(1H, d, J=2.2), 7.20(1H, d, J=3.0), 7.23–7.27(1H, m), 7.47(1H, d, J=8.5), 7.68(1H, d, J=0.8).
Mass: (LCMS) 324(M$^+$+1)
EXP. 247
$^1$H-NMR(CDCl$_3$): 1.19–1.28(4H, m), 1.41–1.55(2H, m), 1.49(3H, t, J=7.4), 1.63–1.67 (2H, m), 1.81–1.86(2H, m), 2.64(2H, t, J=7.7), 2.94(2H, t, J=7.9), 3.68(3H, s), 4.09–4.14(1H, m), 4.20(2H, q, J=7.2), 6.51(1H, d, J=3.0), 6.92(1H, d, J=8.2), 7.06(1H, dd, J=8.0, 2.3), 7.12(1H, d, J=3.3), 7.23(1H, d, J=2.2), 7.34(1H, d, J=8.5), 7.46(1H, dd, J=8.8, 1.5), 7.77(1H, d, J=1.6).
Mass: (LCMS) 406(M$^+$+1)
EXP. 248
$^1$H-NMR(DMSO-d$_6$): 1.14–1.40(6H, m), 1.38(3H, t, J=7.3), 1.57–1.63(2H, m), 1.73–1.82 (2H, m), 2.53(2H, t, J=7.4), 2.79(2H, t, J=7.6), 4.22(3H, m), 6.43(1H, d, J=2.7), 6.98 (1H, d, J=8.5), 7.08(1H, dd, J=8.3, 2.3), 7.17(1H, d, J=2.2), 7.32(1H, dd, J=8.5, 1.6), 7.38(1H, d, J=3.0), 7.46(1H, d, J=8.5), 7.65(1H, d, J=1.6), 12.06(1H, br-s).
Mass: 391(M$^+$)
EXP. 249
$^1$H-NMR(CDCl$_3$): 1.50(3H, t, J=7.3), 2.65(2H, t, J=7.8), 2.96(2H, t, J=7.8), 3.68(3H, s), 4.21(2H, q, J=7.1), 5.14(2H, s), 6.52(1H, d, J=2.4), 6.94(1H, d, J=8.2), 7.09(1H, dd, J=8.0, 2.4), 7.08–7.19(3H, m), 7.27(1H, m), 7.32–7.39(2H, m), 7.43–7.49(2H, m), 7.82 (1H, s).
Mass: (LCMS) 448(M$^+$+1)
EXP. 250
$^1$H-NMR(DMSO-d$_6$): 1.50(3H, t, J=7.1), 2.53(2H, t, J=7.7), 2.81(2H, t, J=7.9), 4.21 (2H, q, J=7.0), 5.12(2H, s), 6.41(1H, d, J=2.7), 7.07(1H, d, J=8.0), 7.11–7.16(1H, m), 7.21–7.22(1H, m), 7.28–7.38(4H, m), 7.44–7.51(3H, m), 7.69(1H, m), 12.04(1H, br-s).
Mass: 433(M$^+$)
EXP. 251
$^1$H-NMR(CDCl$_3$): 0.81–1.36(2H, m), 1.45–1.60(4H, m), 1.70–1.84(2H, m), 2.27(1H, qu, J=7.6), 2.33(3H, s), 2.60–2.70(2H, m), 2.94(2H, t, J=7.8), 3.68(3H, s), 3.75(3H, s), 3.81(2H, d, J=6.9), 6.82(1H, s), 6.89(1H, d, J=8.2), 7.08(1H, d, J=8.0), 7.24–7.29(2H, m,) 7.42(1H, d, J=8.5), 7.75(1H, s).
Mass: 405(M$^+$)
EXP. 252
$^1$H-NMR(DMSO-d$_6$): 1.26–1.76(8H, m), 2.17(1H, qu, J=7.1), 2.25(3H, s), 2.53(2H, t, J=7.6), 2.80(2H, t, J=7.4), 3.73(3H, s), 3.81(2H, d, J=6.3), 6.97(1H, d, J=8.5), 7.07–7.11(2H, m), 7.20(1H, d, J=8.8), 7.30(1H, dd, 8.1, 1.1), 7.37(1H, d, J=8.8), 7.64 (1H, d, J=0.8), 11.93(1H, s).
Mass: 391(M$^+$)
EXP. 253
$^1$H-NMR(CDCl$_3$): 1.26–1.77(8H, m), 2.26(1H, qu, J=7.3), 2.66(2H, t, J=7.1), 2.95(2H, t, J=7.8), 3.69(3H, s), 3.82(2H, d, J=6.9), 6.90(1H, d, J=8.2), 7.11(1H, dd, J=8.3, 2.6), 7.43(1H, d, J=8.5), 7.56(1H, dd, J=8.7, 1.5), 7.85(1H, d, J=3.0), 8.04(1H, d, J=4.1), 8.45(1H, s), 8.94(1H, s), 10.07(1H, s)
Mass: (LCMS) 406(M$^+$+1)
EXP. 254
$^1$H-NMR(DMSO-d$_6$): 1.15–1.71(8H, m), 2.17(1H, qu, J=7.7), 2.54(2H, t, J=7.7), 2.81 (2H, t, J=7.7), 3.82(2H, d, J=6.6), 6.99(1H, d, J=8.2), 7.13–7.18(2H, m), 7.40(1H, dd, J=8.5, 2.2), 7.51(1H, d, J=8.5), 8.24(1H, s), 8.28(1H, d, J=3.0), 9.95(1H, s), 12.07(1H, br-s), 12.12(1H, br-s).
Mass: 392(M$^+$+1)
EXP. 255
$^1$H-NMR(DMSO-d$_6$): 1.24–1.72(8H, m), 2.19(1H, qu, J=7.3), 2.54(2H, t, J=7.4), 2.82 (2H, t, J=7.6), 3.82(2H, d, J=6.6), 3.92(3H, s), 7.00(1H, d, J=8.5), 7.15–7.19(2H, m), 7.47(1H, d, J=8.8), 7.59(1H, d, J=4.4), 8.26(2H, d, J=4.4), 9.91(1H, s).
Mass: 406(M$^+$+1)
EXP. 256
$^1$H-NMR(CDCl$_3$): 0.82–0.96(1H, m), 1.22–1.32(2H, m), 1.46–1.78(5H, m), 2.26(1H, qu, J=7.7), 2.57(3H, s), 2.65(2H, t, J=7.7), 2.94(2H, t, J=7.8), 3.69(3H, s), 3.81(2H, d, J=6.9), 6.90(1H, d, J=8.2), 7.11(1H, dd, J=8.2, 2.2), 7.24–7.26(1H, m), 7.40(1H, d, J=8.5), 7.54(1H, d, J=8.0), 7.87(1H, d, J=2.7), 8.49(2H, s).
Mass: (LCMS) 420(M$^+$+1)
EXP. 257
$^1$H-NMR(DMSO-d$_6$): 1.15–1.70(8H, m), 2.18(1H, qu, J=7.7), 2.46(3H, s), 2.53(2H, t, J=7.7), 2.82(2H, t, J=7.7), 3.80(2H, d, J=6.1), 6.97(1H, d, J=8.0), 7.09–7.15(2H, m), 7.35(1H, d, J=8.2), 7.44(1H, d, J=8.2), 8.26–8.30(3H, m), 11.97(1H, s).
Mass: 406(M$^+$+1)
EXP. 258
$^1$H-NMR(CDCl$_3$): 1.22–1.36(3H, m), 1.52–1.76(5H, m), 2.27(1H, qu, J=7.4), 2.64(2H, t, J=7.8), 2.65(3H, s), 2.67(3H, s), 2.95(2H, t, J=7.6), 3.68(3H, s), 3.82(2H, d, J=6.6), 6.91(1H, d, J=8.5), 7.11(1H, d, J=10.16), 7.23(1H, s), 7.36(1H, d, J=8.5), 7.55(1H, dd, J=8.5, 1.6), 7.84(1H, s), 9.05(1H, s).
Mass: 434(M$^+$+1)
EXP. 259
$^1$H-NMR(DMSO-d$_6$): 1.25–1.71(8H, m), 2.19(1H, qu, J=7.2), 2.52(2H, t, J=7.4), 2.59 (3H, s), 2.81(2H, t, J=7.7), 3.30(3H, s), 3.83(2H, d, J=6.6), 6.97–7.00(1H, m), 7.10–7.16 (1H, m), 7.22(1H, d, J=2.2), 7.38–7.47(2H, m), 7.81(1H, s), 8.00–8.08(1H, m), 11.42 (1H, s).
Mass: 420(M$^+$+1)

TABLE 1-continued

EXP. 260
$^1$H-NMR(CDCl$_3$): 1.04–1.16(2H, m), 1.33–1.46(4H, m), 1.51–1.61(2H, m), 2.10(1H, qu, J=7.5), 2.65(2H, t, J=7.8), 2.93(2H, t, J=7.8), 3.58(2H, d, J=6.8), 3.68(3H, s), 6.58(1H, br-s), 6.87(1H, dd, J=11.5, 1.9), 7.00(1H, d, J=1.0), 7.22–7.25(1H, m), 7.42(2H, s), 7.78 (1H, d, J=0.8), 8.22(1H, br-s).
Mass: (LCMS) 396(M$^+$+1)

EXP. 261
$^1$H-NMR(DMSO-d$_6$): 1.05–1.19(2H, m), 1.32–1.41(4H, m), 1.45–1.55(2H, m), 2.02(1H, qu, J=7.3), 2.57(2H, t, J=7.6), 2.82(2H, t, J=7.4), 3.52(2H, d, J=6.8), 6.46(1H, br-s), 7.06–7.09(2H, m), 7.26(1H, dd, J=8.3, 1.5), 7.36(1H, t, J=2.7), 7.43(1H, d, J=8.5), 7.68 (1H, s), 11.13(1H, br-s), 12.13(1H, br-s).
Mass: (LCMS) 382(M$^+$+1)

EXP. 262
$^1$H-NMR(CDCl$_3$): 1.05–1.17(2H, m), 1.34–1.41(4H, m), 1.51–1.61(2H, m), 2.09(1H, qu, J=7.3), 2.64(2H, t, J=7.7), 2.92(2H, t, J=7.8), 3.39(2H, d, J=6.8), 3.68(3H, s), 6.57–6.59(1H, m), 7.13(2H, d, J=1.9), 7.17(1H, d, J=2.2), 7.23–7.25(1H, m), 7.41(1H, s), 7.79(1H, s), 8.25(1H, br-s).
Mass: (LCMS) 412(M$^+$+1)

EXP. 263
$^1$H-NMR(DMSO-d$_6$): 1.08–1.16(2H, m), 1.30–1.36(4H, m), 1.44–1.52(2H, m), 2.01(1H, qu, J=7.4), 2.57(2H, t, J=7.6), 2.82(2H, t, J=7.4), 3.31(2H, d, J=6.8), 6.46(1H, br-s), 7.20(1H, d, J=1.9), 7.26–7.29(2H, m), 7.37(1H, t, J=2.7), 7.43(1H, d, J=8.2), 7.69(1H, s), 11.14(1H, br-s), 12.14(1H, br-s).
Mass: (LCMS) 398(M$^+$+1)

EXP. 264
$^1$H-NMR(CDCl$_3$): 0.98–1.08(2H, m), 1.32–1.39(4H, m), 1.47–1.56(2H, m), 2.03(1H, qu, J=7.4), 2.68(2H, t, J=7.4), 2.99(2H, t, J=7.5), 3.43(2H, d, J=6.9), 3.69(3H, s), 6.60(1H, t, J=2.2), 7.26–7.28(1H, m), 7.38–7.46(3H, m), 7.50(1H, d, J=2.2), 7.80(1H, s), 8.28 (1H, s).
Mass: 422(M$^+$)

EXP. 265
$^1$H-NMR(CDCl$_3$ ): 1.03–1.12(2H, m), 1.37–1.42(4H, m), 1.56–1.63(2H, m), 2.06(1H, qu, J=7.1), 2.63(2H, t, J=7.8), 2.87(2H, t, J=7.9), 3.29(2H, d, J=5.8), 3.68(3H, s), 6.57–6.59(2H, m), 6.63(1H, d, J=2.2), 7.22(1H, t, J=2.7), 7.37–7.46(2H, m), 7.81(1H, d, J=0.8), 8.19(1H, s).
Mass: 392(M$^+$)

EXP. 266
$^1$H-NMR(DMSO-d$_6$): 0.96–1.11(2H, m), 1.26–1.33(4H, m), 1.46–1.55(2H, m), 2.03(1H, qu, J=7.4), 2.49(2H, t, J=7.2), 2.69(2H, t, J=7.4), 3.17(2H, d, J=6.9), 4.71(2H, br-s), 6.40–6, 42(2H, m), 6.51(1H, d, J=1.9), 7.26(1H, dd, J=8.2, 1.5), 7.32(1H, t, J=2.7), 7.38(1H, d, J=8.2), 7.61(1H, s), 11.02(1H, s), 12.03(1H, s).
Mass: 378(M$^+$)

EXP. 267
$^1$H-NMR(CDCl$_3$): 0.88–1.08(2H, m), 1.35–1.42(4H, m), 1.48–1.58(2H, m), 2.03(1H, qu, J=7.4), 2.68(2H, t, J=7.7), 2.99(2H, t, J=7.5), 3.43(2H, d, J=6.9), 3.69(3H, s), 3.84(3H, s), 6.53(1H, dd, J=3.0, 0.5), 7.10(1H, d, J=3.0), 7.37(1H, d, J=8.5), 7.42–7.45(2H, m), 7.49(1H, d, J=2.2), 7.78(1H, d, J=1.1).
Mass: 436(M$^+$)

EXP. 268
$^1$H-NMR(CDCl$_3$): 1.05–1.14(2H, m), 1.36–1.45(4H, m), 1.52–1.64(2H, m), 2.05(1H, qu, J=7.4), 2.60–2.66(2H, m), 2.86(2H, t, J=7.8), 3.29(2H, d, J=6.9), 3.68(3H, s), 3.82(3H, s), 3.89(2H, br-s), 6.50(1H, dd, J=3.0, 0.5), 6.57(1H, d, J=2.2), 6.63(1H, d, J=2.2), 7.06 (1H, d, J=3.3), 7.32(1H, d, J=8.5), 7.47(1H, dd, J=8.5, 1.6), 7.80(1H, d, J=1.4).
Mass: 406(M$^+$)

EXP. 269
$^1$H-NMR(DMSO-d$_6$): 0.99–1.11(2H, m), 1.30–1.34(4H, m), 1.47–1.54(2H, m), 2.03(1H, qu, J=7.4), 2.47–2.52(2H, m), 2.69(2H, t, J=7.5), 3.17(2H, d, J=6.9), 3.80(3H, s), 4.72 (2H, br-s), 6.41–6.42(2H, m), 6.52(1H, d, J=1.9), 7.30–7.34(2H, m), 7.42(1H, d, J=8.5), 7.66(1H, s), 12.04(1H, br-s).
Mass: 392(M$^+$)

EXP. 270
$^1$H-NMR(CDCl$_3$): 1.26–1.35(2H, m), 1.46–1.59(4H, m), 1.68–1.79(2H, m), 1.97(2H, qu, J=7.4), 2.26(1H, qu, J=7.6), 2.35(2H, t, J=7.4), 2.64(2H, t, J=7.5), 3.66(3H, s), 3.81 (2H, d, J=6.8), 6.75(1H, t, J=2.2), 6.90(1H, d, J=8.2), 7.06(1H, dd, J=8.2, 2.2), 7.20–7.22(2H, m), 7.37–7.45(2H, m), 7.80(1H, s), 8.15(1H, br-s).
Mass: 391(M$^+$)

EXP. 271
$^1$H-NMR(CDCl$_3$): 1.23–1.35(2H, m), 1.44–1.58(4H, m), 1.68–1.79(2H, m), 1.97(2H, qu, J=7.4), 2.26(1H, qu, J=7.6), 2.39(2H, t, J=7.4), 2.66(2H, t, J=7.4), 3.81(2H, d, J=6.8), 6.56–6.58(1H, m), 6.90(1H, d, J=8.2), 7.06(1H, dd, J=8.2, 2.2), 7.19–7.22(2H, m), 7.37–7.45(2H, m), 7.80(1H, t, J=0.8), 8.13(1H, br-s).
Mass: 377(M$^+$)

EXP. 272
$^1$H-NMR(CDCl$_3$): 0.99–1.26(5H, m), 1.62–1.82(6H, m), 2.22(3H, s), 2.37(3H, s), 2.64 (2H, t, J=7.7), 2.94(2H, t, J=7.9), 3.68(3H, s), 3.72(2H, d, J=6.3), 6.88(1H, d, J=8.2), 7.07(1H, dd, J=8.2, 2.5), 7.24–7.31(3H, m), 7.67(2H, br-s).
Mass: 419(M$^+$)

EXP. 273
$^1$H-NMR(CDCl$_3$): 0.98–1.28(5H, m), 1.67–1.82(6H, m), 2.22(3H, s), 2.36(3H, s), 2.69

TABLE 1-continued (2H, t, J=7.8), 2.95(2H, t, J=7.7), 3.72(2H, d, J=7.1), 6.88(1H, d, J=8.2), 7.08(1H, dd, J=8.2, 2.2), 7.23–7.31(3H, m), 7.66(1H, s), 7.67(1H, s).
Mass: 405($M^+$)
EXP. 274
$^1$H-NMR(CDCl$_3$): 0.81–1.33(5H, m), 1.48–1.76(3H, m), 2.27(1H, qu, J=8.0), 2.33(3H, s), 2.64(2H, t, J=8.2), 2.70(3H, s), 3.02(2H, t, J=7.8), 3.67(3H, s), 3.75(3H, s), 3.81(2H, d, J=6.3), 6.83(1H, m), 6.88(1H, d, J=8.2), 7.04(1H, d, J=8.8), 7.21(1H, t, J=2.5), 7.42(1H, dd, J=8.1, 2.2), 7.75(1H, d, J=0.8).
Mass: (LCMS) 420($M^+$+1)
EXP. 275
$^1$H-NMR(DMSO-d$_6$): 1.05–1.70(8H, m), 2.17(1H, qu, J=7.6), 2.25(3H, s), 2.50(3H, s), 2.62(2H, t, J=7.8), 2.86(2H, t, J=7.7), 3.73(3H, s), 3.82(2H, d, J=6.3), 6.96(1H, d, J=8.8), 7.06(1H, dd, J=8.8, 2.2), 7.16(1H, d, J=1.9), 7.28(1H, dd, J=8.5, 2.3), 7.37(1H, d, J=8.5), 7.65(1H, d, J=0.8), 12.00(1H, s).
Mass: (LCMS) 406($M^+$+1)
EXP. 276
$^1$H-NMR(CDCl$_3$): 0.95–1.25(5H, m), 1.66–1.75(6H, m), 2.64(2H, t, J=7.9), 2.94(2H, t, J=7.8), 3.67(3H, s), 3.72(2H, d, J=5.8), 6.78(1H, d, J=2.2), 6.89(1H, d, J=8.2), 7.11(1H, dd, J=8.8, 2.2), 7.19(1H, d, J=2.4), 7.48–7.49(2H, m), 7.63(1H, d, J=2.2), 7.72(1H, s).
Mass: (LCMS) 393($M^+$+1)
EXP. 277
$^1$H-NMR(DMSO-d$_6$): 0.86–1.23(5H, m), 1.61–1.71(6H, m), 2.53(2H, t, J=6.3), 2.80(2H, t, J=7.1), 3.75(2H, d, J=6.3), 6.96–7.00(2H, m), 7.25(1H, dd, J=7.6, 2.2), 7.20(1H, d, J=2.2), 7.43(1H, d, J=8.8, 2.2), 7.60(1H, d, J=8.8), 7.72(1H, d, J=1.9), 8.00(1H, d, J=2.2), 12.06(1H, br-s).
Mass: 378($M^+$)
EXP. 278
$^1$H-NMR(CDCl$_3$): 0.98–1.28(5H, m), 1.63–1.79(6H, m), 2.15(3H, s), 2.39(3H, s), 2.64(2H, t, J=7.5), 2.94(2H, t, J=7.8), 3.67(3H, s), 3.72(2H, d, J=6.0), 6.88(1H, d, J=8.5), 7.10(1H, dd, J=8.4, 2.2), 7.21(1H, d, J=2.5), 7.35–7.36(2H, m), 7.59(1H, t, J=1.1).
Mass: 420($M^+$)
EXP. 279
$^1$H-NMR(DMSO-d$_6$): 0.95–1.23(5H, m), 1.59–1.73(6H, m), 2.14(3H, s), 2.39(3H, s), 2.53(2H, t, J=7.5), 2.80(2H, t, J=7.3), 3.75(2H, d, J=7.1), 6.97(1H, d, J=8.2), 7.13(1H, dd, J=8.2, 2.0), 7.20(1H, d, J=2.2), 7.31(1H, dd, J=8.5, 1.6), 7.43(1H, d, J=8.5), 7.61(1H, d, J=1.1), 12.09(1H, s).
Mass: 406($M^+$)
EXP. 280
$^1$H-NMR(CDCl$_3$): 1.25–1.34(2H, m), 1.42–1.61(4H, m), 1.68–1.79(2H, m), 2.26(1H, qu, J=7.7), 2.65(2H, t, J=7.9), 2.95(2H, t, J=7.7), 3.68(3H, s), 3.86(2H, d, J=3.86), 6.91(1H, d, J=8.5), 7.13(1H, dd, J=8.3, 2.4), 7.23(1H, d, J=2.2), 7.35(1H, d, J=5.2), 7.44(1H, d, J=5.5), 7.55(1H, dd, J=8.2, 1.7), 7.88(1H, d, J=8.5), 7.98(1H, d, J=1.3).
Mass: (LCMS) 395($M^+$+1)
EXP. 281
$^1$H-NMR(DMSO-d$_6$): 1.25–1.31(2H, m), 1.45–1.52(4H, m), 1.63–1.71(2H, m), 2.19(1H, qu, J=7.7), 2.54(2H, t, J=7.8), 2.81(2H, t, J=7.7), 3.84(2H, d, J=6.8), 7.02(1H, d, J=8.2), 7.17(1H, dd, J=8.6, 2.3), 7.24(1H, d, J=2.2), 7.46(1H, d, J=5.2), 7.52(1H, dd, J=8.2, 1.6), 7.77(1H, d, J=5.5), 7.98(1H, s), 7.99(1H, d, J=8.5), 12.08(1H, br-s).
Mass: 380($M^+$)
EXP. 282
$^1$H-NMR(CDCl$_3$): 1.23–1.32(2H, m), 1.44–1.63(4H, m), 1.68–1.78(2H, m), 2.27(1H, qu, J=7.5), 2.64(2H, t, J=7.8), 2.85(3H, s), 2.94(2H, t, J=7.7), 3.68(3H, s), 3.83(2H, d, J=6.8), 6.92(1H, d, J=8.2), 7.14(1H, dd, J=8.4, 2.2), 7.22(1H, d, J=2.4), 7.56(1H, dd, J=8.2, 1.6), 7.81(1H, d, J=8.2), 8.09(1H, d, J=1.6).
Mass: (LCMS) 410($M^+$+1)
EXP. 283
$^1$H-NMR(DMSO-d$_6$): 1.24–1.31(2H, m), 1.42–1.53(4H, m), 1.64–1.72(2H, m), 2.19(1H, qu, J=7.4), 2.54(2H, t, J=7.4), 2.81(3H, s), 2.82(2H, t, J=7.4), 3.85(2H, d, J=6.8), 7.03(1H, d, J=8.5), 7.18(1H, dd, J=8.3, 1.9), 7.25(1H, d, J=2.2), 7.54(1H, dd, J=8.5, 1.3), 8.03(2H, dd, J=4.5, 3.3), 12.07(1H, s).
Mass: (LCMS) 396($M^+$+1)
EXP. Int. 62
$^1$H-NMR(DMSO-d$_6$): 7.23–7.30(2H, m), 7.32–7.37(1H, m), 7.58(2H, br-s), 7.82(1H, s), 9.79(1H, s).
EXP. Int. 63
$^1$H-NMR(CDCl$_3$): 5.44(2H, br-s), 7.24(1H, dd, J=8.4, 1.9), 7.44(1H, d, J=8.2), 7.67(1H, d, J=1.9).
EXP. 284
$^1$H-NMR(CDCl$_3$): 1.24–1.31(2H, m), 1.47–1.59(4H, m), 1.67–1.77(2H, m), 2.27(1H, qu, J=7.4), 2.63(2H, t, J=7.8), 2.93(2H, t, J=7.8), 3.68(3H, s), 3.82(2H, d, J=6.8), 5.27(2H, br-s), 6.90(1H, d, J=8.2), 7.12(1H, dd, J=8.2, 2.2), 7.20(1H, d, J=2.4), 7.34(1H, dd, J=8.2, 1.6), 7.59(1H, d, J=8.2), 7.71(1H, d, J=1.6).
Mass: (LCMS) 411($M^+$+1)
EXP. 285
$^1$H-NMR(DMSO-d$_6$): 1.23–1.30(2H, m), 1.46–1.54(4H, m), 1.68–1.75(2H, m), 2.19(1H, qu, J=7.4), 2.53(2H, t, J=7.4), 2.80(2H, t, J=7.3), 3.82(2H, d, J=6.5), 6.98(1H, d, J=8.5), 7.12–7.17(3H, m), 7.48(3H, m), 7.65(1H, d, J=7.9), 12.08(1H, s).
Mass: (LCMS) 397($M^+$+1)

TABLE 1-continued

EXP. Int. 64
$^1$H-NMR(CDCl$_3$): 1.23(3H, t, J=7.1), 1.25–1.34(2H, m), 1.50–1.62(4H, m), 1.71–1.79 (2H, m), 2.28(1H, qu, J=7.4), 2.60(2H, t, J=7.7), 2.91(2H, t, J=7.8), 3.68(2H, br-s), 3.79(2H, d, J=6.9), 4.13(2H, q, J=7.1), 6.72(2H, d, J=8.6), 6.85(1H, d, J=8.5), 7.05(1H, dd, J=8.2, 2.2), 7.14(1H, d, J=2.2), 7.37(2H, d, J=8.6).
Mass: 367(M$^+$)
EXP. 286
$^1$H-NMR(CDCl$_3$): 1.21–1.33(2H, m), 1.48–1.59(4H, m), 1.68–1.78(3H, m), 2.26(1H, qu, J=7.7), 2.64(2H, t, J=7.7), 2.93(2H, t, J=7.7), 3.68(3H, s), 3.81(2H, d, J=6.8), 5.29(2H, br-s), 6.89(1H, d, J=8.2), 7.10(1H, dd, J=8.3, 2.2), 7.19(1H, d, J=2.2), 7.49(1H, dd, J=8.5, 1.6), 7.56(1H, d, J=8.5), 7.79(1H, d, J=1.3).
Mass: (LCMS) 425(M$^+$+1)
EXP. 287
$^1$H-NMR(DMSO-d$_6$): 1.22–1.34(2H, m), 1.47–1.54(4H, m), 1.62–1.74(2H, m), 2.20(1H, qu, J=7.4), 2.53(2H, t, J=7.8), 2.79(2H, t, J=7.5), 3.82(2H, d, J=6.5), 6.97(1H, d, J=8.5), 7.11(1H, dd, J=8.4, 2.0), 7.18(1H, d, J=2.2), 7.31–7.38(2H, m), 7.49(2H, s), 7.77(1H, d, J=1.1), 12.04(1H, s).
Mass: (LCMS) 397(M$^+$+1)
EXP. Int. 65
$^1$H-NMR(CDCl$_3$): 0.95–1.35(5H, m), 1.54–1.83(6H, m), 2.62(2H, t, J=7.4), 2.91(2H, t, J=7.4), 3.67(3H, s), 3.71(2H, d, J=6.0), 6.71(2H, m), 6.84(1H, d, J=8.2), 7.04(1H, dd, J=8.2, 2.2), 7.12(1H, d, J=2.2), 7.36(2H, m).
Mass: 367(M$^+$)
EXP. 288
$^1$H-NMR(CDCl$_3$): 0.94–1.28(5H, m), 1.63–1.76(6H, m), 2.64(2H, t, J=7.6), 2.93(2H, t, J=7.7), 3.68(3H, s), 3.72(2H, d, J=5.8), 5.36(2H, br-s), 6.88(1H, d, J=8.5), 7.10(1H, dd, J=8.4, 2.3), 7.19(1H, d, J=2.2), 7.48(1H, dd, J=8.3, 1.7), 7.56(1H, d, J=8.2), 7.78(1H, d, J=1.3).
Mass: (LCMS) 425(M$^+$+1)
EXP. 289
$^1$H-NMR(DMSO-d$_6$): 0.99–1.24(5H, m), 1.57–1.72(6H, m), 2.52(2H, t, J=7.6), 2.79(2H, t, J=7.6), 3.75(2H, d, J=5.7), 6.95(1H, d, J=8.5), 7.11(1H, dd, J=8.5, 2.2), 7.18(1H, d, J=2.5), 7.33(2H, s), 7.49(2H, s), 7.77(1H, s), 12.02(1H, s).
Mass: (LCMS) 411(M$^+$+1)
EXP. Int. 66
$^1$H-NMR(CDCl$_3$): 0.95(3H, t, J=7.3), 1.23(3H, t, J=7.1), 1.41(2H, m), 1.69(2H, m), 2.26(2H, t, J=7.6), 2.91(2H, t, J=7.8), 3.68(2H, br-s), 3.91(2H, t, J=6.4), 4.12(2H, q, J=7.1), 6.72(2H, d, J=8.5), 6.86(1H, dd, J=8.5), 7.05(1H, d, J=8.5, 2.4), 7.13(1H, d, J=2.2), 7.36(2H, d, J=8.6).
Mass: 341(M$^+$)
EXP. 290
$^1$H-NMR(CDCl$_3$): 0.90(3H, t, J=7.3), 1.23(3H, t, J=7.1), 1.40(2H, m), 1.63–1.72(2H, m), 2.62(2H, t, J=7.4), 2.93(2H, t, J=7.8), 3.93(2H, t, J=6.4), 4.13(2H, q, J=7.1), 5.32 (2H, br-s), 6.90(1H, d, J=8.2), 7.11(1H, dd, J=8.3, 2.2), 7.19(1H, d, J=2.5), 7.48(1H, dd, J=8.5, 1.8), 7.56(1H, d, J=8.5), 7.70(1H, d, J=1.6).
Mass: 399(M$^+$+1)
EXP. 291
$^1$H-NMR(DMSO-d$_6$): 0.87(3H, t, J=7.3), 1.37(2H, m), 1.61(2H, qu, J=6.6), 2.52(2H, t, J=7.7), 2.79(2H, t, J=7.4), 3.93(2H, t, J=6.3), 6.98(1H, d, J=8.2), 7.11(1H, dd, J=8.5, 2.2), 7.17(1H, d, J=2.2), 7.30–7.37(2H, m), 7.48(2H, s), 7.75(1H, t, J=0.7), 12.05(1H, s).
3Mass: 71(M$^+$+1)
EXP. Int. 67
$^1$H-NMR(CDCl$_3$): 1.17–1.31(1H, m), 1.23(3H, t, J=6.3), 1.53–1.80(9H, m), 2.61(2H, t, J=7.5), 2.91(2H, t, J=7.8), 4.13(2H, q, J=7.1), 4.67(1H, qu, J=3.8), 6.71(2H, d, J=8.5), 6.85(1H, d, J=8.2), 7.03(1H, dd, J=8.2, 2.3), 7.13(1H, d, J=2.2), 7.34(2H, d, J=8.5).
Mass: 353(M$^+$)
EXP. 292
$^1$H-NMR(CDCl$_3$): 1.23(3H, t, J=7.2), 1.48–1.70(5H, m), 1.76–1.81(3H, m), 2.62(2H, t, J=7.9), 2.93(2H, t, J=7.8), 4.13(2H, q, J=7.1), 4.70(1H, qu, J=4.2), 5.21(2H, br-s), 6.90 (1H, d, J=8.2), 7.09(1H, dd, J=8.2, 2.2), 7.18(1H, d, J=2.2), 7.47(1H, dd, J=8.2, 1.8), 7.55(1H, d, J=8.2), 7.75(1H, d, J=1.6).
Mass: 411(M$^+$+1)
EXP. 293
$^1$H-NMR(DMSO-d$_6$): 1.53–1.80(8H, m), 2.53(2H, t, J=7.7), 2.79(2H, t, J=7.3), 4.76(1H, qu, J=2.5), 6.97(1H, d, J=8.5), 7.10(1H, dd, J=8.2, 2.0), 7.17(1H, d, J=2.2), 7.30–7.36 (2H, m), 7.48(2H, s), 7.72(1H, s), 12.07(1H, s).
Mass: 383(M$^+$+1)
EXP. Int. 68
$^1$H-NMR(CDCl$_3$): 1.23(3H, s), 1.26–1.53(6H, m), 1.64–1.83(4H, m), 2.61(2H, t, J=7.5), 2.91(2H, t, J=7.4), 3.68(2H, br-s), 4.08–4.16(3H, m), 6.71(2H, d, J=8.5), 6.87(1H, d, J=8.2), 7.02(1H, dd, J=8.5, 2.3), 7.13(1H, d, J=2.5), 7.37(2H, d, J=8.5).
Mass: 367(M$^+$)
EXP. 294
$^1$H-NMR(CDCl$_3$): 1.23(3H, t, J=7.1), 1.26–1.53(6H, m), 1.62–1.85(4H, m), 2.62(2H, t, J=7.7), 2.93(2H, t, J=7.8), 4.13(3H, q, J=7.2), 5.24(2H, s), 6.91(1H, d, J=8.2), 7.08(1H, dd, J=8.3, 2.2), 7.19(1H, d, J=2.2), 7.49–7.57(2H, m), 7.79(1H, d, J=1.1).
Mass: 425(M$^+$+1)

TABLE 1-continued

EXP. 295
$^1$H-NMR(DMSO-d$_6$): 1.15–1.42(6H, m), 1.54–1.81(4H, m), 2.53(2H, t, J=7.4), 2.80(2H, t, J=7.7), 4.26(1H, m), 6.99(1H, d, J=8.5), 7.09(1H, dd, J=8.5, 2.2), 7.18(1H, d, J=2.2), 7.33(1H, d, J=8.2), 7.39(1H, dd, J=8.5, 1.5), 7.48(2H, br-s), 7.77(1H, d, J=1.6), 12.05 (1H, s).
Mass: 397(M$^+$+1)

EXP. Int. 69
$^1$H-NMR(CDCl$_3$): 1.23(3H, t, J=7.1), 1.20–1.33(2H, m), 1.48–1.59(4H, m), 1.70–1.79 (2H, m), 2.28(1H, qu, J=7.4), 2.62(2H, t, J=7.7), 2.93(2H, t, J=7.7), 3.16(3H, d, J=4.6), 3.83(2H, d, J=6.8), 4.13(2H, q, J=7.1), 6.12(1H, br-s), 6.90(1H, d, J=8.9), 7.12–7.16 (2H, m), 7.22(2H, d, J=8.5), 7.60(2H, d, J=8.6), 7.77(1H, br-s).
Mass: (LCMS) 441(M$^+$+1)

EXP. 296
$^1$H-NMR(CDCl$_3$): 1.23(3H, t, J=7.1), 1.21–1.34(2H, m), 1.48–1.59(4H, m), 1.68–1.78 (2H, m), 2.26(1H, qu, J=7.6), 2.62(2H, t, J=7.4), 2.93(2H, t, J=7.8), 3.12(3H, s), 3.81 (2H, d, J=6.8), 4.13(2H, q, J=7.1), 5.52(1H, br-s), 6.88(1H, d, J=8.2), 7.10(1H, dd, J=8.3, 2.2), 7.20(1H, d, J=2.2), 7.48(1H, dd, J=8.5, 1.6), 7.55(1H, d, J=8.2), 7.79(1H, d, J=1.6).
Mass: (LCMS) 439(M$^+$+1)

EXP. 297
$^1$H-NMR(DMSO-d$_6$): 1.24–1.32(2H, m), 1.45–1.54(4H, m), 1.62–1.73(2H, m), 2.20(1H, qu, J=7.4), 2.52(2H, t, J=7.4), 2.79(2H, t, J=7.5), 2.95(3H, m), 3.82(2H, d, J=6.6), 6.97 (1H, d, J=8.2), 7.11(2H, dd, J=8.3, 2.0), 7.38–7.41(2H, m), 7.78(1H, d, J=1.3), 7.94(1H, d, J=4.6), 12.06(1H, s).
Mass: (LCMS) 411(M$^+$+1)

EXP. 298
$^1$H-NMR(CDCl$_3$): 1.23(3H, t, J=7.1), 1.22–1.34(2H, m), 1.45–1.57(4H, m), 1.67–1.78 (2H, m), 2.26(1H, qu, J=7.2), 2.63(2H, t, J=7.9), 2.95(2H, t, J=7.7), 3.84(2H, d, J=6.6), 4.13(2H, q, J=7.1), 6.92(1H, d, J=8.5), 7.16(1H, dd, J=8.3, 2.3), 7.24(1H, d, J=2.5), 7.71(1H, dd, J=8.5, 1.6), 8.12–8.15(2H, m), 8.99(1H, s).
Mass: (LCMS) 410(M$^+$+1)

EXP. 299
$^1$H-NMR(DMSO-d$_6$): 1.22–1.33(2H, m), 1.42–1.56(4H, m), 1.60–1.71(2H, m), 2.19(1H, qu, J=7.4), 2.54(2H, t, J=7.4), 2.84(2H, t, J=7.2), 3.85(2H, d, J=6.5), 7.04(1H, d, J=8.4), 7.24(1H, dd, J=7.9, 2.1), 7.27(1H, d, J=1.9), 7.69(1H, dd, J=8.2, 1.3), 8.09(1H, d, J=8.7), 8.26(1H, s), 9.39(1H, s), 12.06(1H, s).
Mass: (LCMS) 382(M$^+$+1)

EXP. 300
$^1$H-NMR(CDCl$_3$): 1.23(3H, t, J=7.1), 1.23–1.33(2H, m), 1.48–1.59(4H, m), 1.68–1.78 (2H, m), 2.26(1H, qu, J=7.6), 2.62(2H, t, J=7.4), 2.93(2H, t, J=7.8), 3.32(6H, s), 3.80 (2H, d, J=6.8), 4.13(2H, q, J=7.1), 6.68(1H, d, J=8.2), 7.09(1H, dd, J=8.2, 2.2), 7.20 (1H, d, J=2.2), 7.47(1H, dd, J=8.2, 1.7), 7.57(1H, d, J=8.5), 7.80(1H, d, J=1.6).
Mass: (LCMS) 453(M$^+$+1)

EXP. 301
$^1$H-NMR(DMSO-d$_6$): 1.19–1.30(2H, m), 1.46–1.55(4H, m), 1.62–1.72(2H, m), 2.20(1H, qu, J=7.3), 2.48–2.55(2H, m), 2.79(2H, t, J=7.2), 3.16(6H, s), 3.82(2H, d, J=6.6), 6.98 (1H, d, J=8.5), 7.11(1H, dd, J=8.5, 2.2), 7.20(1H, d, J=2.2), 7.38–7.46(2H, m), 7.87(1H, s), 12.04(1H, br-s).
Mass: 424(M$^+$)

EXP. 302
$^1$H-NMR(CDCl$_3$): 1.23(3H, t, J=7.1), 1.23–1.34(2H, m), 1.51–1.62(4H, m), 1.71–1.81 (2H, m), 2.27(1H, qu, J=7.4), 2.61(2H, t, J=7.8), 2.92(2H, t, J=7.8), 3.46(3H, s), 3.81 (2H, d, J=6.6), 4.13(2H, q, J=7.1), 6.87(2H, d, J=8.2), 7.10(1H, dd, J=8.2, 2.2), 7.14 (1H, d, J=2.2), 7.41(1H, dd, J=8.4, 1.7), 7.47(1H, d, J=1.6).
Mass: 439(M$^+$+1)

EXP. 303
$^1$H-NMR(DMSO-d$_6$): 1.23–1.33(2H, m), 1.45–1.58(4H, m), 1.63–1.73(2H, m), 2.20(1H, qu, J=7.5), 2.49–2.55(2H, m), 2.78(2H, t, J=7.4), 3.29(1H, br-s), 3.34(3H, s), 3.82(2H, d, J=6.8), 6.97(1H, d, J=8.2), 7.04(1H, d, J=8.5), 7.11(1H, dd, J=8.2, 1.9), 7.16(1H, d, J=2.2), 7.38(1H, dd, J=8.2, 1.6), 7.54(1H, d, J=1.6), 12.05(1H, br-s).
Mass: 411(M$^+$+1)

EXP. 304
$^1$H-NMR(CDCl$_3$): 1.23(3H, t, J=7.1), 1.21–1.32(2H, m), 1.50–1.57(4H, m), 1.69–1.79 (2H, m), 2.27(1H, qu, J=7.5), 2.50(3H, s), 2.61(2H, t, J=7.7), 2.93(2H, t, J=7.7), 3.32 (3H, s), 3.81(2H, d, J=6.8), 4.13(2H, q, J=7.1), 6.90(1H, d, J=8.2), 7.12–7.17(2H, m), 7.33(2H, d, J=1.0), 7.42(1H, s).
Mass: (LCMS) 453(M$^+$+1)

EXP. 305
$^1$H-NMR(DMSO-d$_6$): 1.25–1.31(2H, m), 1.48–1.55(4H, m), 1.62–1.75(2H, m), 2.21(1H, qu, J=7.4), 2.50–2.55(2H, m), 2.80(2H, t, J=7.3), 3.01(3H, s), 3.41(3H, s), 3.82(2H, d, J=6.5), 6.98(1H, d, J=8.5), 7.11–7.19(3H, m), 7.45(1H, d, J=8.5), 7.71(1H, s), 12.08 (1H, s).
Mass: 425(M$^+$+1)

EXP. Int. 70
$^1$H-NMR(CDCl$_3$): 1.23(3H, t, J=7.2), 1.23–1.31(2H, m), 1.48–1.56(4H, m), 1.66–1.77 (2H, m), 2.25(1H, qu, J=7.6), 2.62(2H, t, J=7.7), 2.94(2H, t, J=7.7), 3.83(2H, d, J=6.8), 4.13(2H, q, J=7.1), 6.91(1H, d, J=8.2), 7.15(1H, dd, J=8.2, 2.2), 7.20(1H, d, J=2.4), 7.64(1H, dd, J=8.5, 1.4), 7.96–7.99(2H, m).
Mass: 488(M$^+$+1)

TABLE 1-continued

EXP. 306
$^1$H-NMR(CDCl$_3$): 1.25–1.33(2H, m), 1.48–1.59(4H, m), 1.67–1.78(2H, m), 2.25(1H, qu, J=7.4), 2.69(2H, t, J=7.7), 2.95(2H, t, J=7.7), 3.81(2H, d, J=6.6), 4.21(3H, s), 6.89(1H, d, J=8.3), 7.13(1H, dd, J=8.3, 2.3), 7.20(1H, d, J=2.2), 7.54(1H, dd, J=8.3, 1.8), 7.70 (1H, d, J=8.5), 7.82(1H, d, J=1.6).
Mass: 412(M$^+$+1)

EXP. 307
$^1$H-NMR(CDCl$_3$): 1.23(3H, t, J=7.1), 1.23–1.33(2H, m), 1.44–1.58(4H, m), 1.67–1.77 (2H, m), 2.24(1H, qu, J=7.4), 2.64(2H, t, J=7.7), 2.85(3H, s), 2.94(2H, t, J=7.8), 3.82 (2H, d, J=6.5), 4.13(2H, q, J=7.1), 6.91(1H, d, J=8.2), 7.14(1H, dd, J=8.3, 2.3), 7.22 (1H, d, J=2.2), 7.63(1H, dd, J=8.3, 1.8), 7.93(1H, d, J=8.5), 7.99(1H, dd, J=1.6, 0.5).
Mass: (LCMS) 424(M$^+$+1)

EXP. 308
$^1$H-NMR(DMSO-d$_6$): 1.22–1.32(2H, m), 1.42–1.54(4H, m), 1.61–1.71(2H, m), 2.19(1H, qu, J=7.4), 2.54(2H, t, J=7.4), 2.80(2H, t, J=7.4), 2.81(3H, s), 3.84(2H, d, J=6.6), 7.02 (1H, d, J=8.2), 7.17(1H, dd, J=8.5, 1.9), 7.25(1H, d, J=1.9), 7.61(1H, dd, J=8.5, 1.6), 7.90(1H, d, J=8.5), 8.12(1H, d, J=1.3), 12.07(1H, s).
Mass: (LCMS) 396(M$^+$+1)

EXP. 309
$^1$H-NMR(DMSO-d$_6$): 1.20–1.33(2H, m), 1.42–1.58(4H, m), 1.62–1.73(2H, m), 2.19(1H, qu, J=6.6), 2.55(2H, t, J=7.6), 2.79(2H, t, J=7.2), 3.83(2H, d, J=6.4), 7.00(1H, d, J=8.4), 7.15–7.19(2H, m), 7.32(1H, d, J=8.4), 7.54(1H, d, J=8.0), 7.79(1H, s), 12.06 (1H, s), 13.79(1H, s)
Mass: (LCMS) 414(M$^+$+1)

EXP. 310
$^1$H-NMR(CDCl$_3$, add. DMSO-d$_6$): 1.20–1.33(2H, m), 1.48–1.59(4H, m), 1.69–1.79(2H, m), 2.26(1H, qu, J=7.3), 2.60(2H, t, J=7.6), 2.93(2H, t, J=7.7), 3.81(2H, d, J=6.8), 6.88 (1H, d, J=8.2), 7.13(2H, d, J=8.2), 7.16(1H, d, J=2.2), 7.41(1H, dd, J=8.2, 1.6), 7.56 (1H, d, J=1.6), 10.90(1H, s).
Mass: 398(M$^+$+1)

EXP. 311
$^1$H-NMR(CDCl$_3$): 1.23–1.33(2H, m), 1.52–1.60(4H, m), 1.69–1.78(2H, m), 2.27(1H, qu, J=7.6), 2.64(2H, t, J=7.7), 2.94(2H, t, J=7.7), 3.67(3H, s), 3.82(2H, d, J=6.6), 6.89(1H, d, J=7.9), 7.10–7.17(3H, m), 7.45(1H, dd, J=8.3, 1.8), 7.60(1H, d, J=1.3), 9.59(1H, s).
Mass: 412(M$^+$+1)

EXP. 312
$^1$H-NMR(CDCl$_3$): 1.25–1.33(2H, m), 1.52–1.59(4H, m), 1.69–1.79(2H, m), 2.27(1H, qu, J=7.5), 2.63(2H, t, J=7.6), 2.93(2H, t, J=7.7), 3.49(3H, s), 3.67(3H, s), 3.82(2H, d, J=6.6), 6.89(1H, d, J=8.2), 7.06(1H, d, J=8.2), 7.10–7.16(2H, m), 7.50(1H, dd, J=8.2, 1.6), 7.63(1H, d, J=1.9).
Mass: 426(M$^+$+1)

EXP. 313
$^1$H-NMR(CDCl$_3$): 1.25–1.33(2H, m), 1.48–1.61(4H, m), 1.69–1.79(2H, m), 2.27(1H, qu, J=7.5), 2.68(2H, t, J=7.7), 2.94(2H, t, J=7.7), 3.48(3H, s), 3.82(2H, d, J=6.6), 6.89(1H, d, J=8.2), 7.06(1H, d, J=8.2), 7.11–7.17(2H, m), 7.51(1H, dd, J=8.3, 1.8), 7.63(1H, d, J=1.6).
Mass: 412(M$^+$+1)

EXP. 314
$^1$H-NMR(CDCl$_3$): 1.21–1.47(4H, m), 1.52–1.72(5H, m), 2.64(2H, t, J=7.3), 2.88(2H, t, J=7.4), 3.69(3H, s), 3.87(2H, d, J=6.6), 6.95(1H, d, J=8.5), 7.21(1H, dd, J=8.5, 2.2), 7.39(1H, d, J=2.2), 7.57(1H, td, J=7.1, 0.9), 7.72(1H, td, J=7.4, 1.6), 7.85(1H, d, J=9.0), 8.15(1H, d, J=9.0), 8.30(1H, d, J=1.9), 9.15(1H, d, J=2.2).
Mass: (LCMS) 390(M$^+$+1)

EXP. 315
$^1$H-NMR(DMSO-d$_6$): 1.19–1.32(4H, m), 1.47–1.71(5H, m), 2.57(2H, t, J=7.4), 2.86(2H, t, J=7.5), 3.90(2H, d, J=6.9), 7.09(1H, d, J=8.5), 7.27(1H, dd, J=8.2, 2.2), 7.39(1H, d, J=2.2), 7.64(1H, t, J=7.7), 7.77(1H, t, J=8.3), 7.99–8.06(2H, m), 8.45(1H, d, J=2.2), 9.05(1H, d, J=2.2), 12.01(1H, br-s).
Mass: 376(M$^+$+1)

EXP. 316
$^1$H-NMR(CDCl$_3$): 0.97–1.28(5H, m), 1.69–1.77(6H, m), 2.67(2H, t, J=7.8), 2.98(2H, t, J=7.7), 3.69(3H, s), 3.78(2H, d, J=5.8), 6.95(1H, d, J=8.5), 7.20(1H, dd, J=8.2, 2.5), 7.27(1H, d, J=3.0), 7.56(1H, td, J=6.9, 1.1), 7.72(1H, td, J=6.8, 1.6), 7.84(1H, dd, J=8.0, 1.1), 8.14(1H, d, J=8.8), 8.28(1H, d, J=2.2), 9.12(1H, d, J=2.2).
Mass: 404(M$^+$+1)

EXP. 317
$^1$H-NMR(DMSO-d$_6$): 0.97–1.20(5H, m), 1.57–1.71(6H, m), 2.58(2H, t, J=7.5), 2.86(2H, t, J=7.7), 3.84(2H, d, J=5.5), 7.11(1H, d, J=8.5), 7.30(1H, dd, J=8.5, 2.2), 7.44(1H, d, J=2.2), 7.76(1H, t, J=7.5), 7.90(1H, t, J=7.6), 8.12(2H, t, J=8.5), 8.74(1H, s), 9.22(1H, s).
Mass: 390(M$^+$+1)

EXP. 318
$^1$H-NMR(CDCl$_3$): 0.93–1.28(5H, m), 1.66–1.76(6H, m), 2.66(2H, t, J=7.7), 2.97(2H, t, J=7.7), 3.68(3H, s), 3.78(2H, d, J=6.0), 6.93(1H, d, J=8.2), 7.18(1H, dd, J=8.2, 2.2), 7.23(1H, d, J=8.0), 7.42(1H, dd, J=8.2, 3.8), 7.94–7.97(2H, m), 8.11(1H, d, J=9.4), 8.17 (1H, d, J=8.2), 8.91(1H, dd, J=4.1, 1.6).
Mass: (LCMS) 404(M$^+$+1)

TABLE 1-continued

EXP. 319
$^1$H-NMR(DMSO-d$_6$): 0.98–1.23(5H, m), 1.61–1.71(6H, m), 2.56(2H, t, J=7.4), 2.84(2H, t, J=7.4), 3.80(2H, d, J=5.8), 7.05(1H, d, J=8.5), 7.22(1H, d, J=8.8), 7.54–7.65(2H, m), 7.94(1H, d, J=8.5), 8.02(1H, d, J=9.1), 8.07(1H, s), 8.37(1H, d, J=7.7), 8.90(1H, d, J=3.3), 12.09(1H, s).
Mass: 390(M$^+$+1)
EXP. 320
$^1$H-NMR(CDCl$_3$): 0.96–1.27(5H, m), 1.66–1.78(6H, m), 2.67(2H, t, J=7.9), 2.97(2H, t, J=7.8), 3.68(3H, s), 3.74(2H, d, J=5.5), 6.70(1H, d, J=9.3), 6.90(1H, d, J=7.9), 7.13–7.18(2H, m), 7.26–7.29(1H, m), 7.72–7.74(2H, m), 7.82(1H, d, J=9.6).
Mass: (LCMS) 420(M$^+$+1)
EXP. 321
$^1$H-NMR(DMSO-d$_6$): 0.97–1.23(5H, m), 1.63–1.71(6H, m), 2.53(2H, t, J=7.6), 2.80(2H, t, J=7.3), 3.76(2H, d, J=5.8), 6.52(1H, d, J=9.3), 6.98(1H, d, J=8.2), 7.15(1H, dd, J=8.6, 2.3), 7.21(1H, d, J=2.2), 7.31(1H, d, J=8.8), 7.66(1H, dd, J=8.7, 1.8), 7.78(1H, d, J=1.9), 7.90(1H, d, J=9.6), 11.76(1H, br-s), 12.06(1H, br-s).
Mass: (LCMS) 406(M$^+$+1)
EXP. 322
$^1$H-NMR(CDCl$_3$): 2.66(2H, t, J=7.7), 2.97(2H, t, J=7.8), 3.68(3H, s), 5.07(2H, s), 6.98 (1H, d, J=8.2), 7.15(1H, dd, J=8.3, 2.3), 7.24–7.33(6H, m), 7.46–7.49(2H, m), 7.75(1H, dd, J=8.8, 1.6), 7.84–7.86(3H, m), 8.00(1H, s).
Mass: (LCMS) 397(M$^+$+1)
EXP. 323
$^1$H-NMR(CDCl$_3$): 2.71(2H, t, J=7.7), 2.98(2H, t, J=7.7), 5.07(2H, s), 6.99(1H, d, J=8.5), 7.16(1H, dd, J=8.2, 2.2), 7.22–7.32(6H, m), 7.44–7.49(2H, m), 7.74(1H, dd, J=8.5, 1.6), 7.83–7.86(3H, m), 8.00(1H, s).
Mass: 382(M$^+$)
EXP. 324
$^1$H-NMR(CDCl$_3$): 2.65(2H, t, J=7.8), 2.95(2H, t, J=7.7), 3.69(3H, s), 5.05(2H, s), 6.59 (1H, s), 6.94(1H, d, J=8.2), 7.08(1H, dd, J=8.3, 2.3), 7.22–7.34(7H, m), 7.40–7.49(2H, m), 7.83(1H, s), 8.16(1H, s).
Mass: (LCMS) 386(M$^+$+1)
EXP. 325
$^1$H-NMR(DMSO-d$_6$): 2.54(2H, t, J=7.4), 2.81(2H, t, J=7.7), 5.08(2H, s), 6.43(1H, s), 7.04–7.13(2H, m), 7.19–7.40(9H, m), 7.68(1H, s), 11.07(1H, s), 12.00(1H, s).
Mass: 371(M$^+$)
EXP. 326
$^1$H-NMR(CDCl$_3$): 1.28(9H, s), 2.66(2H, t, J=7.4), 2.97(2H, t, J=7.8), 3.67(3H, s), 5.01 (2H, s), 6.57(1H, m), 6.96(1H, d, J=8.5), 7.09(1H, dd, J=8.2, 2.2), 7.21–7.33(6H, m), 7.41(1H, d, J=7.7), 7.44(1H, dd, J=8.5, 1.6), 7.82(1H, t, J=0.7), 8.16(1H, br-s).
Mass: (LCMS) 442(M$^+$+1)
EXP. 327
$^1$H-NMR(DMSO-d$_6$): 1.24(9H, s), 2.53(2H, t, J=7.7), 2.81(2H, t, J=7.5), 5.03(2H, s), 6.45(1H, br-s), 7.06(1H, d, J=6.8), 7.11(1H, dd, J=8.3, 2.0), 7.18(1H, d, J=1.9), 7.27–7.35(6H, m), 7.39(1H, d, J=8.2), 7.66(1H, s), 11.07(1H, br-s), 12.07(1H, br-s).
Mass: (LCMS) 427(M$^+$+1)
EXP. 328
$^1$H-NMR(CDCl$_3$): 2.67(2H, t, J=7.8), 2.99(2H, t, J=7.8), 3.69(3H, s), 6.91–6.98(3H, m), 7.12–7.26(4H, m), 7.36–7.46(3H, m), 7.68(1H, dd, J=8.5, 1.6), 7.78–7.83(3H, m), 7.96 (1H, br-s).
Mass: (LCMS) 383(M$^+$+1)
EXP. 329
$^1$H-NMR(DMSO-d$_6$): 2.62(2H, t, J=7.5), 2.91(2H, t, J=7.4), 6.88(2H, d, J=7.6), 6.97–7.00(2H, m), 7.24–7.32(3H, m), 7.48–7.52(3H, m), 7.69(1H, dd, J=8.7, 2.2), 7.87–7.93(3H, m), 8.04(1H, s), 12.10(1H, s).
Mass: (LCMS) 369(M$^+$+1)
EXP. 330
$^1$H-NMR(DMSO-d$_6$): 1.24–1.59(8H, m), 1.73–1.87(2H, m), 2.55(2H, t, J=7.5), 2.84(2H, t, J=7.3), 4.29–4.36(1H, m), 7.06(1H, d, J=8.5), 7.18(1H, d, J=8.5), 7.27(1H, d, J=1.9), 7.71(1H, dd, J=8.6, 1.3), 8.09(1H, d, J=8.5), 8.26(1H, s), 9.39(1H, s), 12.09(1H, s).
Mass: (LCMS) 382(M$^+$+1)

Examples 331 to 381

The data of the compounds of the Compound No.s 331 to 381 are shown in Tables 5 to 9. Meanings of the indications used in the tables are as follows: Exp., No. of Compound of Example; SM, compound as starting material; Int., No. of intermediate compound; Syn., synthetic method; and Reagent, name of reagent. "RO", "Y" and "Z" represent the substituents in the compound represented by the following formula (LXVIII):

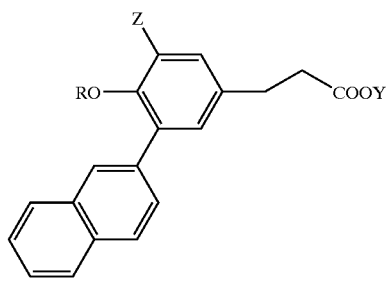

(LXVIII)

In the columns of "LCMS", the data of the aforementioned liquid chromatography-mass spectrometry are shown, and in the columns of "method", the elution conditions of liquid chromatography are described. In the columns of "RTime", retention times in the liquid chromatography are shown. In the columns of "Mass", the data of mass spectrometry are shown (the indication "N.D" means that no molecular ion peak was detected). Further, as for the compounds indicated with "C" in the columns of "method", data of mass spectrometry measured by fast atomic bombardment mass spectrometry (FAB-MS) using JEOL-JMS-SX102 are shown in the columns of "Mass".

The starting compound, Intermediate 74 (Int. 74), was produced by the method described below.

Syntesis of methyl 3-(3-bromo-4-methoxy-5-nitrophenyl) propionate (Intermediate 71)

A solution of Intermediate 4 (3.20 g) in acetic anhydride (25 ml) was added with potassium nitrate (1.30 g) under ice cooling, stirred for 10 minutes and added dropwise with concentrated sulfuric acid (730 μl) over 10 minutes. After the mixture was stirred at the same temperature for 10 minutes, the mixture was warmed to room temperature and further stirred for 30 minutes. The reaction mixture was poured into 1 N aqueous sodium hydroxide (250 ml) containing ice and extracted with isopropyl ether (200 ml×2). The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=10:1) to obtain the title compound (Intermediate 71, 2.73 g). Mass (LCMS): N.D, retention time: 4.27 minutes (elution condition: A).

Synthesis of methyl 3-[4-methoxy-3-(naphthalen-2-yl)-5-nitrophenyl]propionate (Intermediate 72) (Preparation Method 4, Step d-1)

According to the procedure described in the synthesis method of Compound of Example 001 (Preparation Method 4, Step d-1) with the modifications that the reaction was carried out at 80° C. for 15 hours, and the purification was performed by column chromatography (Quad, hexane:ethyl acetate=10:1), Intermediate 71 (2.65 g), 2-naphthaleneboronic acid (2.87 g), 2 M aqueous sodium carbonate (7.5 ml) and (Ph$_3$P)$_4$Pd (960 mg) were reacted and treated to obtain the title compound (Intermediate 72, 2.47 g). Mass (LCMS): N.D, retention time: 5.28 minutes (elution condition: A).

Synthesis of 3-[4-methoxy-3-(naphthalen-2-yl)-5-nitrophenyl]propionic acid (Intermediate 73) (Preparation Method 1, Step a)

According to the procedure described in the synthesis method of Compound of Example 002 (Preparation Method 1, Step a) with the modification that the reaction was carried out for 40 minutes, Intermediate 72 (2.45 g) and 2 N aqueous sodium hydroxide (6.7 ml) were reacted and treated to obtain the title compound (Intermediate 73, 1.96 g). Mass (LCMS): 352 (M$^+$+1), retention time: 4.57 minutes (elution condition: A).

Syntesis of methyl 3-[4-hydroxy-3-(naphthalen-2-yl)-5-nitrophenyl]propionate (Intermediate 74) (Step f and Step c)

According to the procedure described in the synthesis method of Intermediate 20 (Step f) with the modification that the reaction was carried out for 3 hours, pyridine, concentrated hydrochloric acid (10 ml each) and Intermediate 73 (1.00 g) were reacted and treated to obtain a crude powdery product. According to the procedure described in the synthesis method of Intermediate 1 in Reference Example 1 (Step c), the above product was reacted with thionyl chloride (282 μl) in methanol to obtain the title compound (Intermediate 74, 306 mg). Mass (LCMS): 350 (M$^-$–1), retention time: 5.25 minutes (elution condition: A).

In the columns of "Syn." in the tables, the indications of "5e2", "2b", "1a" and "5e1" mean that the target compounds were produced according to the production methods of the compounds described below, respectively.

Preparation Method "5e2":

Example 331

Syntesis of methyl 3-[4-cyclopentyloxy-3-(naphthalen-2-yl)-5-nitrophenyl]propionate (Compound No. 331) (Preparation Method 5, Step e-2)

According to the procedure described in the synthesis method of Compound of Example 038 (Preparation Method 5, Step e-2) with the modifications that the reaction was carried out for 15 hours, and the purification was performed by column chromatography (Quad, hexane:ethyl acetate= 19:1), Intermediate 74 (84 mg, corresponding to the compound mentioned in the column of "SM" in the table), PH$_3$P (125 mg), cyclopentanol (50 μl, TCI, corresponding to the compound mentioned in the column of "Reagent" in the table) and 40% DIAD (224 μl) were reacted and treated to obtain the title compound (Compound No.: 331, 90 mg). Mass (LCMS): N.D, retention time: 5.91 minutes (elution condition: A).

Preparation Method "2b":

Example 332

Syntesis of methyl 3-[3-amino-4-cyclopentyloxy-5-(naphthalen-2-yl)phenyl]propionate (Compound No. 332) (Preparation Method 2, Step b)

A solution of Compound of Example 331 (59.1 mg, corresponding to the compound mentioned in the column of "SM" in the table) in methanol (5 ml) was added with platinum oxide (5 mg, Ald) and stirred at room temperature for 30 minutes under hydrogen atmosphere. The reaction mixture was filtered, and the solvent of the filtrate was evaporated under reduced pressure. The residue was purified by column chromatography (Quad, hexane:ethyl acetate= 4:1) to obtain the title compound (Compound No. 332, 49 mg). Mass (LCMS): 390 (M$^+$+1), retention time: 4.87 minutes (elution condition: A).

Preparation Method "1a":

Example 333

Synthesis of 3-[3-amino-4-cyclopentyloxy-5-(naphthalen-2-yl)phenyl]propionic acid (Compound No. 333) (Preparation Method 1, Step a)

According to the procedure described in the synthesis method of Compound of Example 002 (Preparation Method 1, Step a) with the modification that the reaction was carried out for 2 hours, Compound of Example 332 (40 mg, corresponding to the compound mentioned in the column of "SM" in the table) and 2 N aqueous sodium hydroxide (150 μl) were reacted and treated to obtain the title compound. Mass (LCMS): 376 (M$^+$+1), retention time: 4.78 minutes (elution condition: A).

Preparation Method "5e1":

Example 337

Syntesis of methyl 3-[3-(naphthalen-2-yl)-5-nitro-4-(1-phenylethyloxy)phenyl]propionate (Compound No. 337) (Preparation Method 5, Step e-1)

According to the procedure described in the synthesis method of Compound of Example 030 (Preparation Method 5, Step e-1) with the modifications that the reaction was carried out for 10 hours at room temperature, and 7 hours after, the temperature was increased to 50° C., and the purification was performed by column chromatography (Quad, hexane:ethyl acetate=15:1), Intermediate 74 (232 mg, corresponding to the compound mentioned in the column of "SM" in the table), potassium carbonate (251 mg) and (1-bromoethyl)benzene (178 μl, TCI, corresponding to the compound mentioned in the column of "Reagent" in the table) were reacted and treated to obtain the title compound (Compound No.: 337, 312 mg). Mass (LCMS): N.D, retention time: 5.80 minutes (elution condition: A).

The names of the reagents represented by the indications used in the columns of "Reagent" are shown in Tables 2 and 3. The indications mentioned in the columns of "Manufacturer" represent the manufacturers of the reagents, i.e., "TCI", Tokyo Kasei Kogyo (Tokyo Chemical Industries, Inc.); "Ald", Aldrich; "WAKO", Wako Pure Chemical Industries; "LANC", Lancaster; "KOEI", KOEI Chemical; and "ACRO", Acros Organics. Among the regents indicated as "synthesized product" in the columns of "Manufacturer", those mentioned in Table 4 were obtained by reduction of the compounds mentioned in the column of "starting material" in THF with sodium borohydride, extraction and evaporation of the solvent. Further, A149 was obtained by reduction of 4-(trifluoromethyl)phenylacetic acid (TCI) with aluminum lithium hydride, extraction and evaporation of the solvent.

TABLE 2

| Reagent | Name of reagent | Manufacturer |
|---|---|---|
| Al1 | Cyclopentanemethanol | Ald |
| Al2 | 1-Cyclopentaneethanol | Ald |
| Al3 | Cyclopentanol | TCI |
| Al4 | Trans-2-methylcyclopentanol | Ald |
| Al5 | Cyclohexanol | WAKO |
| Al6 | Cis-2-methylcyclohexanol | Ald |
| Al7 | Trans-2-methylcyclohexanol | Ald |
| Al8 | Trans-4-methylcyclohexanol | TCI |
| Al9 | 3-Methylcyclohexanol | TCI |
| Al10 | 2,3-Dimethylcyclohexanol | TCI |
| Al11 | 3,4-Dimethylcyclohexanol | TCI |
| Al12 | 3,5-Dimethylcyclohexanol | TCI |
| Al13 | 3,3,5,5-tetramethylcyclohexanol | Synthesized product |
| Al14 | Cycloheptanol | TCI |
| Al15 | DL-menthol | TCI |
| Al16 | 1-Propanol | WAKO |
| Al17 | 2-Butanol | WAKO |
| Al18 | 2-Mehtyl-1-propanol | TCI |
| Al19 | 3,3-Dimethyl-1-butanol | Ald |
| Al20 | 3-Methyl-1-butanol | TCI |
| Al21 | 3-Methyl-2-buten-1-ol | TCI |
| Al22 | 1,2-Dimethyl-1-propanol | TCI |
| Al23 | DL-2-methyl-1-butanol | TCI |
| Al24 | 2,4-Dimethyl-3-pentanol | TCI |
| Al25 | 2-Ethyl-1-butanol | TCI |
| Al26 | 4-Hydroxymethylbenzoic acid methyl ester | TCI |
| Al27 | 3-(Trifluoromethyl)benzyl alcohol | LANC |
| Al28 | 4-(Methoxy)benzyl alcohol | TCI |
| Al29 | Pyridine-4-methanol | TCI |
| Al30 | 1-Phenylethyl alcohol | TCI |
| Al31 | (R)-(+)-1-Phenylethyl alcohol | TCI |
| Al32 | (S)-(−)-2-Phenylethyl alcohol | TCI |
| Al33 | p-Tolylmethylcarbinol | TCI |
| Al34 | 1-(4-Fluorophenyl)ethyl alcohol | Synthesized product |
| Al35 | 1-(4-Chlorophenyl)ethyl alcohol | Synthesized product |
| Al36 | 1-[4-(Trifluoromethyl)phenyl]ethyl alcohol | Synthesized product |
| Al37 | [3-(N,N-Dimethylamino)phenyl]methylcarbinol | TCI |
| Al38 | 1-(3-Fluoro-4-methoxyphenyl)ethyl alcohol | Synthesized product |

TABLE 2-continued

| Reagent | Name of reagent | Manufacturer |
|---|---|---|
| Al39 | (S)-(−)-1-Phenylpropanol | WAKO |
| Al40 | (R)-(+)-1-Phenylpropanol | WAKO |
| Al41 | 1-Phenylisobutyl alcohol | Synthesized product |
| Al42 | 1-Phenylbutyl alcohol | Synthesized product |
| Al43 | 2-Hydroxyacetophenone | TCI |
| Al44 | Phenethyl alcohol | TCI |
| Al45 | 4-Methylphenethyl alcohol | Ald |
| Al46 | 2-(2-Fluorophenyl)ethyl alcohol | TCI |
| Al47 | 2-(3-Fluorophenyl)ethyl alcohol | TCI |
| Al48 | 4-(N,N-dimethylamino)phenethyl alcohol | Ald |
| Al49 | 2-[4-(Trifluoromethyl)phenyl]ethyl alcohol | Synthesized product |
| Al50 | 2-Pyridineethanol | TCI |
| Al51 | 5-Ethyl-2-pyridineethanol | KOEI |
| Al52 | 1-Methyl-2-[4-(trifluoromethyl)phenyl]ethyl alcohol | Synthesized product |
| Al53 | 2-(2-Fluorophenyl)-1-methylethyl alcohol | Synthesized product |
| Al54 | 2-Hydroxyindane | TCI |
| Al55 | 1-Indanol | TCI |
| Al56 | 1,2,3,4-Tetrahydro-1-naphthol | TCI |
| Al57 | 1,2,3,4-Tetrahydro-2-naphthol | ACRO |
| Al58 | 3-Phenylpropanol | TCI |
| Al59 | Cinnamyl alcohol | TCI |
| Al60 | 3-Pyridinepropanol | TCI |
| Al61 | 4-Pyridinepropanol | Ald |
| Al62 | 2-(N-methylanilino)ethanol | TCI |
| Al63 | 2-(N-ethylanilino)ethanol | TCI |
| Al64 | N-Ethyl-N-(2-hydroxyethyl)-m-toluidine | TCI |
| Al65 | 2-Phenxypropanol | TCI |
| Al66 | N-Benzyl-N-methylethanolamine | Ald |
| Al67 | 3-Phenyl-1-butanol | Ald |
| Al68 | 2-Hydroxymethyl-1,4-benzodioxane | TCI |
| Al69 | Piperonyl alcohol | TCI |
| Al70 | 4S,5S-(−)-4-Hydroxymethyl-2-methyl-5-phenyl-2-oxazoline | TCI |
| Al71 | 2,3-Dimethyl-1-butanol | Ald |

TABLE 3

| Reagent | Name of Reagent | Manufacturer |
|---|---|---|
| Hal1 | Cyclopentane bromide | TCI |
| Hal2 | (1-Bromoethyl)benzene | TCI |
| Hal3 | 4-Methylbenzyl chloride | TCI |
| Hal4 | 4-(Trifluoromethyl)benzyl bromide | TCI |
| Hal5 | 4-Fluorobenzyl bromide | TCI |

TABLE 4

| Reagent | Starting compound | Manufacturer |
|---|---|---|
| Al13 | 3,3,5,5-Tetramethylcyclohexanone | Ald |
| Al34 | 4-Fluoroacetophenone | TCI |
| Al35 | 4-Chloroacetophenone | TCI |
| Al36 | 4-(Trifluoromethyl)acetophenone | TCI |
| Al38 | 3-Fluoro-4-methoxyacetophenone | TCI |
| Al41 | Isobutyrophenone | TCI |
| Al42 | Butyrophenone | TCI |
| Al52 | 4-(Trifluoromethyl)phenylacetone | TCI |
| Al53 | 2-Fluorophenylacetone | TCI |

TABLE 5

| Exp. | Syn. | SM | Reagent | RO | Y | Z | LCMS method | RTime | Mass |
|---|---|---|---|---|---|---|---|---|---|
| 331 | 5e2 | Int. 74 | Al3 | cyclopentyl-O | Me | NO2 | A | 5.91 | N.D |
| 332 | 2b | Exp. 331 | | cyclopentyl-O | Me | NH2 | A | 4.87 | 390 (M+ + 1) |
| 333 | 1a | Exp. 332 | | cyclopentyl-O | H | NH2 | A | 4.78 | 376 (M+ + 1) |
| 334 | 5e2 | Int. 74 | Al5 | cyclohexyl-O | Me | NO2 | A | 6.10 | N.D |
| 335 | 2b | Exp. 334 | | cyclohexyl-O | Me | NH2 | A | 4.66 | 404 (M+ + 1) |
| 336 | 1a | Exp. 335 | | cyclohexyl-O | H | NH2 | A | 4.95 | 390 (M+ + 1) |
| 337 | 5e1 | Int. 74 | Hal2 | PhCH(-)O | Me | NO2 | A | 5.80 | N.D |
| 338 | 2b | Exp. 337 | | PhCH(-)O | Me | NH2 | A | 5.57 | 426 (M+ + 1) |
| 339 | 1a | Exp. 338 | | PhCH(-)O | H | NH2 | A | 4.87 | 412 (M+ + 1) |
| 340 | 5e2 | Int. 74 | Hal3 | 4-Me-C6H4-CH2-O | Me | NO2 | A | 6.03 | N.D |

TABLE 6

| Exp. | Syn. | SM | Reagent | RO | Y | Z | LCMS method | RTime | Mass |
|---|---|---|---|---|---|---|---|---|---|
| 341 | 2b | Exp. 340 | | 4-Me-C6H4-CH2-O | Me | NH2 | A | 5.64 | 426 (M+ + 1) |

TABLE 6-continued

| Exp. | Syn. | SM | Reagent | RO | Y | Z | LCMS method | RTime | Mass |
|---|---|---|---|---|---|---|---|---|---|
| 342 | 1a | Exp. 341 | 4-methylbenzyloxy | H | NH2 | A | 5.00 | 412 (M⁺ + 1) |
| 343 | 5e2 | Int. 74 | Al45 | 4-methylphenethyloxy | Me | NO2 | B | 5.52 | N.D |
| 344 | 2b | Exp. 343 | 4-methylphenethyloxy | Me | NH2 | A | 5.87 | 440 (M⁺ + 1) |
| 345 | 1a | Exp. 344 | 4-methylphenethyloxy | H | NH2 | A | 5.15 | 426 (M⁺ + 1) |
| 346 | 5e2 | Int. 74 | Al58 | 3-phenylpropyloxy | Me | NO2 | N | 5.41 | N.D |
| 347 | 2b | Exp. 346 | 3-phenylpropyloxy | Me | NH2 | A | 5.79 | 440 (M⁺ + 1) |
| 348 | 1a | Exp. 347 | 3-phenylpropyloxy | H | NH2 | A | 5.02 | 426 (M⁺ + 1) |
| 349 | 5e2 | Int. 74 | Al36 | 1-(4-trifluoromethylphenyl)ethoxy | Me | NO2 | B | 5.71 | N.D |
| 350 | 2b | Exp. 349 | 1-(4-trifluoromethylphenyl)ethoxy | Me | NH2 | A | 6.12 | 494 (M⁺ + 1) |

TABLE 7

| Exp. | Syn. | SM | Reagent | RO | Y | Z | LCMS method | RTime | Mass |
|---|---|---|---|---|---|---|---|---|---|
| 351 | 1a | Exp. 350 | 1-(4-trifluoromethylphenyl)ethoxy | H | NH2 | A | 5.54 | 480 (M⁺ + 1) |

TABLE 7-continued
| Exp. | Syn. | SM | Reagent | RO | Y | Z | LCMS method | RTime | Mass |
|---|---|---|---|---|---|---|---|---|---|
| 352 | 5e2 | Int. 7 | Al54 | 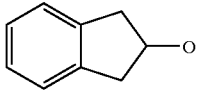 | Me | NO2 | B | 5.15 | N.D |
| 353 | 2b | Exp. 352 | | 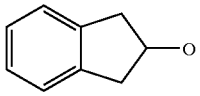 | Me | NH2 | A | 5.81 | 438 (M$^+$ + 1) |
| 354 | 1a | Exp. 353 | | 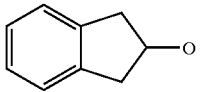 | H | NH2 | A | 5.10 | 424 (M$^+$ + 1) |
| 355 | 5e2 | Int. 7 | Al46 | 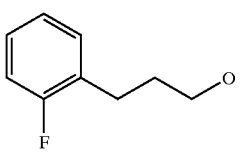 | Me | NO2 | B | 5.11 | N.D |
| 356 | 2b | Exp. 355 | | 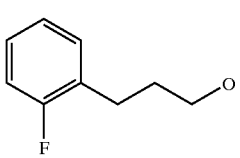 | Me | NH2 | A | 5.63 | 444 (M$^+$ + 1) |
| 357 | 1a | Exp. 356 | | 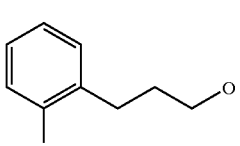 | H | NH2 | A | 4.86 | 430 (M$^+$ + 1) |
| 358 | 5e1 | Int. 7 | Al20 | 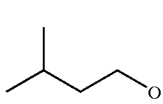 | Me | NO2 | B | 5.54 | N.D |
| 359 | 2b | Exp. 358 | | 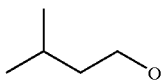 | Me | NH2 | A | 5.75 | 392 (M$^+$ + 1) |
| 360 | 1a | Exp. 359 | | 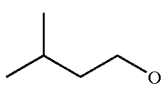 | H | NH2 | A | 5.01 | 378 (M$^+$ + 1) |
TABLE 8
| Exp. | Syn. | SM | Reagent | RO | Y | Z | LCMS method | RTime | Mass |
|---|---|---|---|---|---|---|---|---|---|
| 361 | 5e2 | Int. 7 | Al71 | 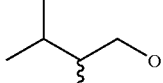 | Me | NO2 | B | 5.97 | N.D |
| 362 | 2b | Exp. 361 | | 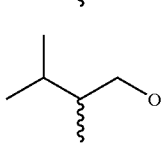 | Me | NH2 | A | 6.02 | 406 (M$^+$ + 1) |

TABLE 8-continued

| Exp. | Syn. | SM | Reagent | RO | Y | Z | LCMS method | RTime | Mass |
|---|---|---|---|---|---|---|---|---|---|
| 363 | 1a | Exp. 362 | | isobutyl-CH(–)CH2O– | H | NH2 | A | 5.31 | 392 (M+ + 1) |
| 364 | 5e2 | Int. 74 | Al48 | 4-(Me2N)C6H4CH2CH2O– | Me | NO2 | B | 5.01 | N.D |
| 365 | 2b | Exp. 364 | | 4-(Me2N)C6H4CH2CH2O– | Me | NH2 | A | 5.19 | 469 (M+ + 1) |
| 366 | 1a | Exp. 365 | | 4-(Me2N)C6H4CH2CH2O– | H | NH2 | A | 4.28 | 455 (M+ + 1) |
| 367 | 5e2 | Int. 74 | Al62 | PhN(Me)CH2CH2O– | Me | NO2 | B | 5.35 | N.D |
| 368 | 2b | Exp. 367 | | PhN(Me)CH2CH2O– | Me | NH2 | A | 5.66 | 455 (M+ + 1) |
| 369 | 1a | Exp. 368 | | PhN(Me)CH2CH2O– | H | NH2 | A | 4.97 | 441 (M++ 1) |
| 370 | 5e1 | Int. 74 | Hal4 | 4-(F3C)C6H4CH2O– | Me | NO2 | B | 5.43 | N.D |

TABLE 9

| Exp. | Syn. | SM | Reagent | RO | Y | Z | LCMS method | RTime | Mass |
|---|---|---|---|---|---|---|---|---|---|
| 371 | 2b | Exp. 370 | | 4-(F₃C)C₆H₄CH₂O– | Me | NH2 | A | 5.84 | 480 (M⁺ + 1) |
| 372 | 1a | Exp. 371 | | 4-(F₃C)C₆H₄CH₂O– | H | NH2 | A | 5.26 | 466 (M⁺ + 1) |
| 373 | 5e2 | Int. 74 | Al4 | trans-2-methylcyclopentyloxy | Me | NO2 | B | 5.54 | N.D |
| 374 | 2b | Exp. 373 | | trans-2-methylcyclopentyloxy | Me | NH2 | A | 5.98 | 404 (M⁺ + 1) |
| 375 | 1a | Exp. 374 | | trans-2-methylcyclopentyloxy | H | NH2 | A | 5.26 | 390 (M⁺ + 1) |
| 376 | 5e1 | Int. 74 | Al18 | iso-Bu-CH2-O– | Me | NO2 | B | 5.28 | N.D |
| 377 | 2b | Exp. 378 | | iso-Bu-CH2-O– | e | NH2 | A | 5.56 | 378 (M⁺ + 1) |
| 378 | 1a | Exp. 377 | | iso-Bu-CH2-O– | H | NH2 | A | 4.82 | 364 (M⁺ + 1) |
| 379 | 5e2 | Int. 74 | Al8 | trans-4-methylcyclohexyloxy | Me | NO2 | B | 5.81 | N.D |
| 380 | 2b | Exp. 379 | | trans-4-methylcyclohexyloxy | Me | NH2 | A | 6.00 | 418 (M⁺ + 1) |
| 381 | 1a | Exp. 380 | | trans-4-methylcyclohexyloxy | H | NH2 | A | 5.28 | 404 (M⁺+ 1) |

Examples 382 to 417

The data of the compounds of the Compound No.s 382 to 417 are shown in Tables 10 to 13. The abbreviations used in the tables have the same meanings as those defined for Tables 5 to 9. The substituents mentioned in the columns of "RO", "Y", "Z" and "Br or Ar" indicate the substituents in the compound represented by the following formula (LXIX):

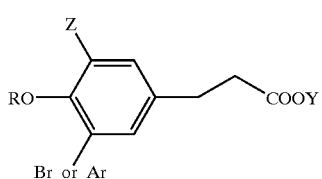

(LXIX)

The indications used in the columns of "Br or Ar" have the following meanings: "Br", bromo group; "Ind", 1H-indol- 5-yl group; "MeInd", 1-methyl-1H-indol-5-yl group; and "EtInd", 1-ethyl-1H-indol-5-yl group.

The starting compound, Intermediate 77 (Int. 77), was produced by the method described below.

Synthesis of 3-(3-bromo-4-methoxy-5-nitrophenyl) propionic acid (Intermediate 75) (Preparation Method 1, Step a)

According to the procedure described in the synthesis method of Compound of Example 002 (Preparation Method 1, Step a) with the modification that the reaction was carried out for 1 hour, Intermediate 71 (12.73 g) and 2 N aqueous sodium hydroxide (40 ml) were reacted and treated to obtain the title compound (Intermediate 75, 11.53 g). Mass (LCMS): 304 (M), retention time: 3.62 minutes (elution condition: A).

Synthesis of 3-(3-bromo-4-hydroxy-5-nitrophenyl) propionic acid (Intermediate 76) (Step f)

According to the procedure described in the synthesis method of Intermediate 5 in Reference Example 2 (Step f) with the modification that the reaction was carried out for 2 hours, Intermediate 75 (11.53 g) and 1 M solution of boron tribromide in methylene chloride (100 ml) were reacted and treated to obtain the title compound (Intermediate 76, 10.68 g). Mass (LCMS): 290 (M$^-$), retention time: 3.39 minutes (elution condition: A).

Syntesis of methyl 3-(3-bromo-4-hydroxy-5-nitrophenyl) propionate (Intermediate 77) (Step c)

According to the procedure described in the synthesis method of Intermediate 1 in Reference Example 1 (Step c) with the modification that the reaction was carried out for 17.5 hours, Intermediate 76 (10.68 g) were reacted with thionyl chloride (8.06 ml) in methanol and treated to obtain the title compound (Intermediate 77, 8.27 g). Mass (LCMS): 304 (M$^-$), retention time: 4.05 minutes (elution condition: A).

The indications "4e2", "4d1a", "11e1" and "4e1" used in the columns of indicating the production method mean that target compounds or intermediates were prepared by the methods for preparing compounds described below or similar methods.

Preparation Method "4e2":

Synthesis of methyl 3-[3-bromo-4-indan-2-yloxy-5-nitrophenyl]propionate (Intermediate 81) (Preparation Method 4, Step e-2)

According to the procedure described in the synthesis method of Intermediate 9 in Reference Example 2 (Step e-2) with the modifications that the reaction was carried out for 15 hours, and the purification was performed by column chromatography (Quad, hexane:ethyl acetate=19:1), Intermediate 77 (151 mg, corresponding to the compound mentioned in the column of "SM" in the table), PH$_3$P (260 mg), 2-hydroxyindane (133 mg, TCI, corresponding to the compound mentioned in the column of "Reagent" in the table) and 40% DIAD (470 µl) were reacted and treated to obtain the title compound (Intermediate 78, 192 mg). Mass (LCMS): N.D, retention time: 4.44 minutes (elution condition: B).

Preparation Method "4d1a":

Example 406

Syntesis of methyl 3-[4-(indan-2-yloxy)-3-(1H-indol-5-yl)-5-nitrophenyl]propionate (Compound No. 406) (Preparation Method 4, Step d-1)

According to the procedure described in the synthesis method of Compound of Example 001 (Preparation Method 4, Step d-1) with the modifications that the reaction was carried out at 80° C. for 16 hours, and the purification was performed by column chromatography (Quad, hexane:ethyl acetate=4:1), Intermediate 81 (187 mg, corresponding to the compound mentioned in the column of "SM" in the table), 5-indoleboronic acid (143 mg), 2 M aqueous sodium carbonate (400 µl) and (PH$_3$P)$_4$Pd (51 mg) were reacted and treated to obtain the title compound (Compound No. 406, 208 mg). Mass (LCMS): 457 (M$^+$+1), retention time: 4.32 minutes (elution condition: B).

Preparation Method "11e1":

Example 409

Syntesis of methyl 3-[4-(indan-2-yloxy)-3-(1-methyl-1H-indol-5-yl)-5-nitrophenyl]propionate (Compound No. 409) (Preparation Method 11, Step e)

According to the procedure described in the synthesis method of Compound of Example 232 (Preparation Method 11, Step e) with the modifications that the reaction was carried out for 3 hour, and the purification was performed by flash column chromatography (hexane:ethyl acetate=9:1), Compound of Example 406 (108 mg, corresponding to the compound mentioned in the column of "SM" in the table), 60% sodium hydride (10 mg) and methyl iodide (18 µl, corresponding to the compound mentioned in the column of "Reagent" in the table) were reacted and treated to obtain the title compound (Compound No. 409, 82 mg). Mass (LCMS): 471 (M$^+$+1), retention time: 4.80 minutes (elution condition: B).

Preparation Method "4e1":

Syntesis of methyl 3-[3-bromo-5-nitro-4-[4-(trifluoromethyl)benzyloxy]-phenyl]propionate (Intermediate 82) (Preparation Method 4, Step e-1)

According to the procedure described in the synthesis method of Intermediate 7 in Reference Example 2 (Step e-1) with the modifications that the reaction was carried out at room temperature for 64 hours, and the purification was performed by column chromatography (Quad, hexane:ethyl acetate=10:1), Intermediate 77 (80.3 mg, corresponding to the compound mentioned in the column of "SM" in the table), potassium carbonate (54.7 mg) and 4-(trifluoromethyl)benzyl bromide (122 µl, TCI, corresponding to the compound mentioned in the column of "Reagent" in the table) were reacted and treated to obtain the title compound (Intermediate 82, 109 mg). Mass (LCMS): N.D, retention time: 4.69 minutes (elution condition: B).

As for the indications used in the columns of "Reagent" in the tables, "MeI" means methyl iodide, "EtI" means ethyl iodide, and the others have the same meanings as defined above.

TABLE 10

| Exp. | Syn. | SM | Reagent | R | Y | Z | Br or Ar | LCMS method | RTime | Mass |
|---|---|---|---|---|---|---|---|---|---|---|
| Int.78 | 4e2 | Int. 77 | Al3 | cyclopentyl-O | Me | NO2 | Br | C | | 372 (M$^+$ + 1) |
| 382 | 4d1a | A | | cyclopentyl-O | Me | NO2 | Ind | A | 5.04 | N.D |
| 383 | 2b | Exp. 382 | | cyclopentyl-O | Me | NH2 | Ind | A | 4.37 | 379 (M$^+$ + 1) |
| 384 | 1a | Exp. 383 | | cyclopentyl-O | H | NH2 | Ind | A | 3.75 | 365 (M$^+$ + 1) |
| 385 | 11e1 | Exp. 382 | MeI | cyclopentyl-O | Me | NO2 | MeInd | A | 5.48 | N.D |
| 386 | 2b | Exp. 385 | | cyclopentyl-O | Me | NH2 | MeInd | A | 4.91 | 393 (M$^+$ + 1) |
| 387 | 1a | Exp. 386 | | cyclopentyl-O | H | NH2 | MeInd | A | 4.19 | 379 (M$^+$ + 1) |
| 388 | 11e1 | Exp. 382 | EtI | cyclopentyl-O | Me | NO2 | EtInd | A | 5.69 | N.D |
| 389 | 2b | Exp. 388 | | cyclopentyl-O | Me | NH2 | EtInd | A | 5.14 | 407 (M$^+$ + 1) |
| 390 | 1a | Exp. 389 | | cyclopentyl-O | H | NH2 | EtInd | A | 4.47 | 393 (M$^+$ + 1) |

TABLE 11

| Exp. | Syn. | SM | Reagent | R | Y | Z | Br or Ar | LCMS method | RTime | Mass |
|---|---|---|---|---|---|---|---|---|---|---|
| Int.79 | 4e2 | Int. 77 | Al5 | cyclohexyl-O | Me | NO2 | Br | C | | 386 (M$^+$ + 1) |
| 391 | 4d1a | 0 | | cyclohexyl-O | Me | NO2 | Ind | A | 5.20 | N.D |
| 392 | 2b | Exp. 391 | | cyclohexyl-O | Me | NH2 | Ind | A | 4.53 | 393 (M$^+$ + 1) |

TABLE 11-continued
| Exp. | Syn. | SM | Reagent | R | | Y | Z | Br or Ar | LCMS method | RTime | Mass |
|---|---|---|---|---|---|---|---|---|---|---|---|
| 393 | 1a | Exp. 392 | | O | | H | NH2 | Ind | A | 3.97 | 379 (M⁺ + 1) |
| 394 | 11e1 | Exp. 391 | MeI | O | | Me | NO2 | MeInd | A | 5.65 | N.D |
| 395 | 2b | Exp. 394 | | O | | Me | NH2 | MeInd | A | 5.09 | 407 (M⁺ + 1) |
| 396 | 1a | Exp. 395 | | O | | H | NH2 | MeInd | A | 4.33 | 393 (M⁺ + 1) |
| 397 | 11e1 | Exp. 391 | EtI | O | | Me | NO2 | EtInd | A | 5.85 | N.D |
| 398 | 2b | Exp. 397 | | O | | Me | NH2 | EtInd | A | 5.31 | 421 (M⁺ + 1) |
| 399 | 1a | Exp. 398 | | O | | H | NH2 | EtInd | A | 4.58 | 407 (M⁺ + 1) |
TABLE 12
| Exp. | Syn. | SM | Reagent | R | Y | Z | Br or Ar | LCMS method | RTime | Mass |
|---|---|---|---|---|---|---|---|---|---|---|
| Int. 80 | 4e1 | Int. 77 | Hal2 |  | Me | NO2 | Br | B | 4.20 | N.D |
| 400 | 4d1a | 0 | |  | Me | NO2 | Ind | A | 4.95 | 445 (M⁺ + 1) |
| 401 | 2b | Exp. 400 | |  | Me | NH2 | Ind | A | 4.45 | 415 (M⁺ + 1) |

TABLE 12-continued
| Exp. | Syn. | SM | Reagent | R | | Y | Z | Br or Ar | LCMS method | RTime | Mass |
|---|---|---|---|---|---|---|---|---|---|---|---|
| 402 | 1a | Exp. 401 | | 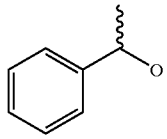 | | H | NH2 | Ind | A | 3.95 | 401 (M⁺ + 1) |
| 403 | 11e1 | Exp. 400 | MeI | 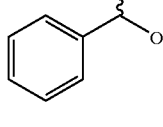 | | Me | NO2 | MeInd | A | 5.40 | 459 (M⁺ + 1) |
| 404 | 2b | Exp. 403 | | 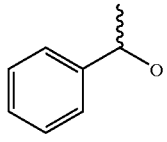 | | Me | NH2 | MeInd | A | 4.97 | 439 (M⁺ + 1) |
| 405 | 1a | Exp. 404 | | 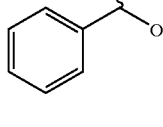 | | H | NH2 | MeInd | A | 4.31 | 415 (M⁺ + 1) |
| Int. 81 | 4e2 | Int. 77 | Al54 | 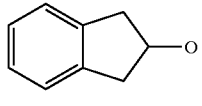 | | Me | NO2 | Br | B | 4.44 | N.D |
| 406 | 4d1a | 0 | | 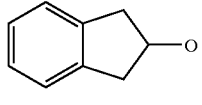 | | Me | NO2 | Ind | B | 4.32 | 457 (M⁺ + 1) |
| 407 | 2b | Exp. 406 | | 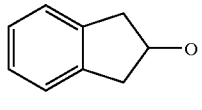 | | Me | NH2 | Ind | A | 4.31 | 427 (M⁺ + 1) |
| 408 | 1a | Exp. 407 | | 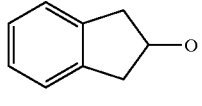 | | H | NH2 | Ind | A | 4.18 | 413 (M⁺+ 1) |
TABLE 13
| Exp. | Syn. | SM | Reagent | R | | Y | Z | Br or Ar | LCMS method | RTime | Mass |
|---|---|---|---|---|---|---|---|---|---|---|---|
| 409 | 11e1 | Exp. 406 | MeI | 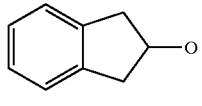 | | Me | NO2 | MeInd | B | 4.80 | 471 (M⁺ + 1) |
| 410 | 2b | Exp. 409 | | 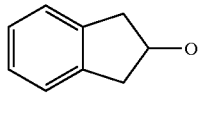 | | Me | NH2 | MeInd | A | 5.32 | 441 (M⁺ + 1) |

TABLE 13-continued

| Exp. | Syn. | SM | Reagent | R | Y | Z | Br or Ar | LCMS method | RTime | Mass |
|---|---|---|---|---|---|---|---|---|---|---|
| 411 | 1a | Exp. 410 | | (2,3-dihydro-1H-inden-2-yl)oxy | H | NH2 | MeInd | A | 4.63 | 427 (M⁺ + 1) |
| Int. 82 | 4e1 | Int. 77 | Hal4 | (4-(trifluoromethyl)benzyl)oxy | Me | NO2 | Br | B | 4.69 | N.D |
| 412 | 4d1a | 0 | | (4-(trifluoromethyl)benzyl)oxy | Me | NO2 | Ind | A | 5.40 | 499 |
| 413 | 2b | Exp. 412 | | (4-(trifluoromethyl)benzyl)oxy | Me | NH2 | Ind | A | 4.84 | 469 (M⁺ + 1) |
| 414 | 1a | Exp. 413 | | (4-(trifluoromethyl)benzyl)oxy | H | NH2 | Ind | A | 4.20 | 455 (M⁺ + 1) |
| Int. 83 | 4e1 | Int. 77 | Al25 | (2-ethylbutoxy) | Me | NO2 | Br | B | 5.18 | N.D |
| 415 | 4d1a | Int. 83 | | (2-ethylbutoxy) | Me | NO2 | Ind | A | 5.56 | 425 (M⁺ + 1) |
| 416 | 2b | Exp. 415 | | (2-ethylbutoxy) | Me | NH2 | Ind | A | 4.93 | 395 (M⁺ + 1) |
| 417 | 1a | Exp. 416 | | (2-ethylbutoxy) | H | NH2 | Ind | A | 4.26 | 381 (M⁺+ 1) |

Examples 418 to 429

Data of optically active compounds (Compound No.s 418 to 429) among the compounds of the present invention and their intermediates are shown in Tables 14 and 15. In the column of "Chiral HPLC" in the tables, data of optical purity measured by liquid chromatography are shown. As for the measurement conditions, CHIRALPAK AD-H (0.46 cm×25 cm, Daicel Chemical Industries) was used as the column, the column temperature was 40° C., monitoring was performed based on UV absorption at 254 nm, normal hexane [containing 0.1% (v/v) TFA]:ethanol [containing 0.1% (v/v) TFA]=85:15 was used as the elution solvent, and the flow rate was 0.5 ml/minute. The retention times are shown in the columns of "RTime", and the optical purities are shown in the columns of "ee %".

The indications used in the columns of "Br or Ar" have the following meanings: "Br", bromo group; "Nap", naphthalen-2-yl group; "Ind", 1H-indol-5-yl group; and "MeInd", 1-methyl-1H-indol-5-yl group, and the other abbreviations used in the tables have the same meanings as defined above.

TABLE 14

| Exp. | Syn. | SM | Reagent | R | Y | Z | Br or Ar | Chiral HPLC RTime | ee % |
|---|---|---|---|---|---|---|---|---|---|
| 418 | 5e2 | Int. 74 | Al30 | (S)-1-phenylethoxy | Me | NO2 | Nap | | |
| 419 | 2b | Exp. 418 | | (S)-1-phenylethoxy | Me | NH2 | Nap | | |
| 420 | 1a | Exp. 419 | | (S)-1-phenylethoxy | H | NH2 | Nap | 13.68 | 97 |
| 421 | 5e2 | Int. 74 | Al31 | (R)-1-phenylethoxy | Me | NO2 | Nap | | |
| 422 | 2b | Exp. 421 | | (R)-1-phenylethoxy | Me | NH2 | Nap | | |
| 423 | 1a | Exp. 422 | | (R)-1-phenylethoxy | H | NH2 | Nap | 19.94 | 98 |
| Int. 84 | 4e2 | Int. 77 | Al30 | (S)-1-phenylethoxy | Me | NO2 | Br | | |
| 424 | 4d1 | Int. 84 | | (S)-1-phenylethoxy | Me | NO2 | Ind | | |
| 425 | 2b | Exp. 424 | | (S)-1-phenylethoxy | Me | NH2 | Ind | | |
| 426 | 1a | Exp. 425 | | (S)-1-phenylethoxy | H | NH2 | Ind | 26.94 | 98 |

TABLE 15

| Exp. | Syn. | SM | Reagent | R | Y | Z | Br or Ar | Chiral HPLC RTime | ee % |
|---|---|---|---|---|---|---|---|---|---|
| 427 | 11e1 | Exp.424 | MeI | PhCH(–)O | Me | NO2 | MeInd | | |
| 428 | 2b | Exp.427 | | PhCH(–)O | Me | NH2 | MeInd | | |
| 429 | 1a | Exp.428 | | PhCH(–)O | H | NH2 | MeInd | 23.38 | 98 |

The $^1$H-NMR data of the compounds of Examples 331 to 417 are shown in Table 16.

TABLE 16

EXP. Int. 71
$^1$H-NMR(CDCl$_3$): 2.65(2H, t, J=7.5), 2.96(2H, t, J=7.5), 3.69(3H, s), 3.99(3H, s), 7.60(1H, d, J=2.2), 7.66(1H, d, J=2.2).
EXP. Int. 72
$^1$H-NMR(CDCl$_3$): 2.70(2H, t, J=7.5), 3.03(2H, t, J=7.5), 3.49(3H, s), 3.70(3H, s), 7.51–7.57(3H, m), 7.60(1H, d, J=2.2), 7.68(1H, dd, J=8.4, 1.9), 7.82–7.94(3H, m), 8.00–8.01(1H, m).
EXP. Int. 73
$^1$H-NMR(DMSO-d$_6$): 2.36(2H, t, J=7.0), 2.81(2H, t, J=7.3), 3.34(3H, s), 7.51–7.67(4H, m), 7.91–7.97(3H, m), 8.09(1H, s).
EXP. Int. 74
$^1$H-NMR(CDCl$_3$): 2.70(2H, t, J=7.5), 3.01(2H, t, J=7.4), 3.69(3H, s), 7.49–7.55(3H, m), 7.61(1H, d, J=1.9), 7.68(1H, dd, J=8.5, 1.6), 7.87–7.93(3H, m), 7.98–8.00(1H, m), 11.06(1H, s).
EXP. 331
$^1$H-NMR(CDCl$_3$): 1.23–1.34(4H, m), 1.42–1.48(2H, m), 1.58–1.63(2H, m), 2.70(2H, t, J=7.4), 3.03(2H, t, J=7.5), 3.69(3H, s), 4.10–4.13(1H, m), 7.49(1H, d, J=2.2), 7.52–7.57(3H, m), 7.70(1H, dd, J=8.5, 1.6), 7.87–7.92(3H, m), 8.01(1H, m).
EXP. 332
$^1$H-NMR(CDCl$_3$): 1.23–1.38(4H, m), 1.52–1.68(4H, m), 2.64(2H, t, J=8.0), 2.89(2H, t, J=7.9), 3.68(3H, s), 3.87(2H, br-s), 4.06–4.10(1H, m), 6.62(1H, d, J=1.9), 6.67(1H, d, J=2.1), 7.46–7.50(2H, m), 7.73(1H, dd, J=8.5, 1.9), 7.84–7.89(3H, m), 8.00(1H, m).
EXP. 333
$^1$H-NMR(DMSO-d$_6$): 1.17–1.27(4H, m), 1.32–1.37(2H, m), 1.51–1.58(2H, m), 2.52(2H, t, J=7.6), 2.72(2H, t, J=7.5), 4.03–4.08(1H, m), 4.79(2H, br-s), 6.53(1H, d, J=1.9), 6.61(1H, d, J=1.9), 7.49–7.52(2H, m), 7.67(1H, dd, J=8.5, 1.6), 7.90–7.95(3H, m), 8.01(1H, s), 12.09(1H, br-s)
EXP. 334
$^1$H-NMR(CDCl$_3$): 0.83–0.99(3H, m), 1.11–1.28(3H, m), 1.45–1.49(2H, m), 1.52–1.62(2H, m), 2.70(2H, t, J=7.7), 3.02(2H, t, J=7.5), 3.44–3.50(1H, m), 3.70(3H, s), 7.47–7.48(1H, m), 7.52–7.58(3H, m), 7.71(1H, dd, J=8.5, 1.6), 7.87–7.92(3H, m), 8.02(1H, m).
EXP. 335
$^1$H-NMR(CDCl$_3$): 0.84–1.00(3H, m), 1.12–1.36(3H, m), 1.48–1.52(2H, m), 1.66–1.72(2H, m), 2.64(2H, t, J=7.8), 2.88(2H, t, J=7.8), 3.35–3.41(1H, m), 3.68(3H, s), 3.89(2H, br-s), 6.61(1H, d, J=2.1), 6.65(1H, d, J=2.1), 7.46–7.50(2H, m), 7.73(1H, dd, J=8.3, 1.7), 7.83–7.88(3H, m), 7.99(1H, m).

TABLE 16-continued

EXP. 336
$^1$H-NMR(DMSO-d$_6$): 0.75–0.93(3H, m), 1.07–1.29(3H, m), 1.40–1.46(2H, m), 1.56–1.61(2H, m), 2.52(2H, t, J=7.5), 2.72(2H, t, J=7.3), 3.33–3.36(1H, m), 5.11(2H, br-s), 6.54(1H, d, J=1.9), 6.61(1H, d, J=1.9), 7.49–7.54(2H, m), 7.69 (1H, dd, J=8.5, 1.6), 7.90–7.95(3H, m), 8.01(1H, m), 12.08(1H, br-s).
EXP. 337
$^1$H-NMR(CDCl$_3$): 1.31(3H, d, J=6.3), 2.66(2H, t, J=7.4), 2.98(2H, t, J=7.4), 3.67(3H, s), 4.58(1H, q, J=6.0), 6.84–6.88(2H, m), 7.04–7.15(4H, m), 7.44(1H, d, J=1.6), 7.49(1H, d, J=1.8), 7.65–7.70(1H, m), 7.83(2H, m), 7.95(1H, m).
EXP. 338
$^1$H-NMR(CDCl$_3$): 1.21(3H, d, J=6.5), 1.53(2H, br-s), 2.63(2H, t, J=7.9), 2.87(2H, t, J=7.8), 3.67(3H, s), 4.57(1H, q, J=6.5), 6.55(1H, d, J=1.9), 6.66(1H, d, J=2.1), 7.05–7.08(2H, m), 7.11–7.20 (3H, m), 7.45–7.51(2H, m), 7.70(1H, dd, J=8.5, 1.9), 7.80–7.87(3H, m), 7.96(1H, m).
EXP. 339
$^1$H-NMR(DMSO-d$_6$): 1.12(3H, d, J=6.3), 2.53(2H, t, J=7.9), 2.72(2H, t, J=7.4), 4.52(1H, q, J=6.3), 4.52(2H, br-s), 6.49(1H, d, J=1.9), 6.56(1H, d, J=1.9), 7.04–7.15(5H, m), 7.48–7.53(2H, m), 7.64(1H, dd, J=8.5, 1.6), 7.87–7.94(3H, m), 7.97(1H, m), 12.06(1H, br-s).
EXP. 343
$^1$H-NMR(CDCl$_3$): 2.24(3H, s), 2.66–2.74(4H, m), 3.02(2H, t, J=7.5), 3.69(3H, s), 3.76(2H, t, J=7.3), 6.71(2H, d, J=7.9), 6.89(2H, d, J=7.9), 7.47–7.61(5H, m), 7.80–7.89(3H, m), 7.93(1H, d, J=1.3).
EXP. 344
$^1$H-NMR(CDCl$_3$): 1.53(2H, br-s), 2.62(2H, t, J=7.7), 2.70(2H, t, J=6.7), 2.87(2H, t, J=7.8), 3.61(2H, t, J=6.7), 3.67(3H, s), 6.57(1H, d, J=1.9), 6.65(1H, d, J=1.9), 6.93(2H, d, J=7.9), 6.99(2H, d, J=7.9), 7.47–7.50(2H, m), 7.73(1H, dd, J=8.5, 1.6), 7.81–7.88(3H, m), 7.99(1H, br-s).
EXP. 345
$^1$H-NMR(DMSO-d$_6$): 2.20(2H, br-s), 2.48–2.53(2H, m), 2.64–2.74(4H, m), 3.49(2H, t, J=7.0), 4.73(2H, br-s), 6.50(1H, d, J=1.9), 6.56(1H, d, J=1.9), 6.84(2H, d, J=7.9), 6.93(2H, d, J=7.9), 7.50–7.53(2H, m), 7.66(1H, dd, J=8.5, 1.6), 7.84–7.93(3H, m), 7.99(1H, br-s), 12.04(1H, br-s).
EXP. 352
$^1$H-NMR(CDCl$_3$): 2.69–2.77(4H, m), 2.85–2.95(2H, m), 3.05(2H, t, J=7.7), 3.70(3H, s), 4.49–4.56(1H, m), 6.85–6.93(4H, m), 7.48–7.56(3H, m), 7.60(1H, d, J=2.4), 7.63(1H, dd, J=8.5, 1.6), 7.79–7.87(3H, m), 7.95–7.96(1H, m).
EXP. 353
$^1$H-NMR(CDCl$_3$): 1.54(2H, br-s), 2.63–2.76(4H, m), 2.87–2.95(3H, m), 3.00(2H, d, J=1.9), 3.69(3H, s), 4.34–4.38(1H, m),

TABLE 16-continued 6.61(1H, d, J=2.4), 6.70(1H, d, J=2.2), 7.04–7.11(4H, m),
7.48–7.51(2H, m), 7.76(1H, dd, J=8.5, 1.5),
7.85–7.89(3H, m), 8.02–8.03(1H, m).
EXP. 354
$^1$H-NMR(DMSO-$d_6$): 2.49–2.56(4H, m), 2.65–2.89(4H, m),
4.26–4.31(1H, m), 4.62(2H, br-s), 6.59(2H, dd, J=11.1, 2.2),
6.99(4H, s), 7.49–7.52(2H, m), 7.69(1H, dd, J=8.5, 1.6),
7.87–7.93(3H, m), 8.04(1H, br-s), 12.07(1H, br-s).
EXP. 376
$^1$H-NMR(CDCl$_3$): 0.70(6H, d, J=6.8), 1.71–1.79(1H, m), 2.70(2H, t,
J=7.5), 3.03(2H, t, J=7.5), 3.35(2H, d, J=6.3), 3.69(3H, s),
7.49(1H, d, J=2.2), 7.52–7.55(2H, m), 7.57(1H, d, J=2.2),
7.68(1H, dd, J=8.5, 1.6), 7.86–7.92(3H, m),
8.01(1H, m).
EXP. 377
$^1$H-NMR(CDCl$_3$): 0.78(6H, d, J=6.8), 1.68(2H, br-s),
1.70–1.83(1H, m), 2.64(2H, t, J=7.8), 2.89(2H, t, J=7.8), 3.20(2H,
d, J=6.3), 3.68(3H, s), 6.65(1H, d, J=2.2), 6.69(1H, d, J=2.2),
7.47–7.50(2H, m), 7.74(1H, dd, J=8.5, 1.6),
7.84–7.87(3H, m), 8.02(1H, m).
EXP. 378
$^1$H-NMR(DMSO-$d_6$): 0.67(6H, d, J=6.8), 1.69–1.78(1H, m), 2.52(2H, t,
J=7.6), 2.72(2H, t, J=7.5), 3.11(2H, d, J=6.3), 4.82(2H, br-s), 6.51(1H, d,
J=1.9), 6.61(1H, d, J=1.9), 7.49–7.52(2H, m), 7.68(1H, dd,
J=8.2, 1.6), 7.90–7.94(3H, m), 8.03(1H, m), 12.04(1H, br-s).
EXP. Int. 75
$^1$H-NMR(DMSO-$d_6$): 2.59(2H, t, J=7.3), 2.86(2H, t, J=7.4),
3.88(3H, s), 7.84(1H, d, J=2.2), 7.92(1H, d, J=1.9), 12.19(1H, s).
EXP. Int. 76
$^1$H-NMR(DMSO-$d_6$): 2.56(2H, t, J=7.4), 2.80(2H, t, J=7.4),
7.84(1H, d, J=2.2), 7.87(1H, d, J=1.9), 10.84(1H, br-s), 12.16(1H, br-s).
EXP. Int. 77
$^1$H-NMR(CDCl$_3$): 2.64(2H, t, J=7.4), 2.93(2H, t, J=7.4),
3.68(3H, s), 7.75(1H, d, J=2.2), 7.94(1H, d, J=2.2), 11.01(1H, s).
EXP. Int. 78
$^1$H-NMR(CDCl$_3$): 1.54–1.66(2H, m), 1.69–1.78(2H, m),
1.81–1.93(4H, m), 2.64(2H, t, J=7.5), 2.94(2H, t, J=7.4),
3.69(3H, s), 4.69–4.72(1H, m), 7.53(1H, d,
J=2.2), 7.63(1H, d, J=2.2).
EXP. 382
$^1$H-NMR(CDCl$_3$): 1.23–1.30(4H, m), 1.48–1.51(2H, m),
1.55–1.59(2H, m), 2.68(2H, t, J=7.6), 3.00(2H, t, J=7.5),
3.69(3H, s), 4.08–4.15(1H, m), 6.60–6.61(1H, m), 7.24–7.28(1H, m),
7.42–7.44(3H, m), 7.78(1H, d, J=2.4), 7.80(1H, s), 8.25(1H, br-s).
EXP. 383
$^1$H-NMR(CDCl$_3$): 1.28–1.38(4H, m), 1.48–1.68(4H, m), 2.63(2H, t,
J=8.0), 2.87(2H, t, J=8.5), 3.67(3H, s), 3.83(2H, br-s), 4.08(1H, br-s),
6.56–6.59(2H, m), 6.63(1H, d, J=2.1), 7.23(1H, t, J=2.9), 7.41(2H, m),
7.79(1H, m), 8.16(1H, br-s).
EXP. 384
$^1$H-NMR(DMSO-$d_6$): 1.36–1.53(4H, m), 1.58–1.68(2H, m),
1.73–1.76(2H, m), 2.72(2H, t, J=7.6), 2.91(2H, t, J=7.6), 4.22(1H, s),
5.02(2H, br-s), 6.65(2H, d, J=1.6), 6.73(1H, d, J=1.9), 7.46(1H, dd,
J=8.4, 1.6), 7.53(1H, t, J=2.5),
7.60(1H, d, J=8.5), 7.84(1H, s), 11.27(1H, s), 12.21(1H, br-s).
EXP. 385
$^1$H-NMR(CDCl$_3$): 1.24–1.32(4H, m), 1.42–1.53(2H, m),
1.55–1.61(2H, m), 2.68(2H, t, J=7.6), 2.99(2H, t, J=7.5),
3.69(3H, s), 3.84(3H, s), 4.09–4.13(1H, m), 6.53(1H, d, J=3.0),
7.11(1H, d, J=2.7), 7.37(1H, d, J=8.2), 7.42–7.48(3H, m),
7.78–7.79(1H, m).
EXP. 386
$^1$H-NMR(CDCl$_3$): 1.28–1.49(4H, m), 1.54–1.68(4H, m), 2.63(2H, t,
J=7.7), 2.87(2H, t, J=7.9), 3.69(3H, s), 3.84(2H, br-s), 4.05–4.10(1H, m),
6.50(1H, d, J=3.0), 6.56(1H, d, J=2.2), 6.62(1H, d, J=3.0),
7.06(1H, d, J=3.0), 7.32(1H, d, J=8.5), 7.46(1H, dd, J=8.5,
1.9), 7.77–7.78(1H, m).
EXP. 387
$^1$H-NMR(DMSO-$d_6$): 1.23–1.26(4H, m), 1.39–1.55(4H, m), 2.50(2H, t,
J=7.4), 2.70(2H, t, J=7.5), 3.81(3H, s), 4.01(1H, br-s), 4.82(2H, br-s),
6.42–6.43(1H, m), 6.53(1H, d, J=1.9), 7.30–7.33(2H, m), 7.43(1H, d,
J=8.5), 7.64(1H, s), 12.06(1H, br-s).
EXP. 388
$^1$H-NMR(CDCl$_3$): 1.23–1.32(4H, m), 1.48–1.64(4H, m), 1.50(3H, d,
J=7.1), 2.67(2H, t, J=7.2), 2.99(2H, t, J=7.6), 3.69(3H, s),
4.08–4.13(1H, m), 4.22(1H, q, J=7.2), 6.54(1H, d, J=3.3),
7.18(1H, d, J=3.0), 7.38(1H, d, J=8.5), 7.41–7.47(3H, m),
7.78–7.79(1H, m).

TABLE 16-continued

EXP. 389
$^1$H-NMR(CDCl$_3$): 1.31–1.36(4H, m), 1.49(3H, t, J=7.3),
1.52–1.66(4H, m), 2.63(2H, t, J=7.9), 2.87(2H, t, J=7.8),
3.67(3H, s), 4.06–4.10(1H, m), 4.20(2H, q, J=7.2), 6.51(1H,
dd, J=3.8, 0.5), 6.56(1H, d, J=2.2), 6.63(1H, d, J=2.4),
7.13(1H, d, J=3.0), 7.35(1H, d,
J=8.7), 7.44(1H, dd, J=8.4, 1.3), 7.77–7.78(1H, m).
EXP. 390
$^1$H-NMR(DMSO-$d_6$): 1.24–1.29(4H, m), 1.37(3H, t, J=7.1),
1.36–1.45(2H, m), 1.52–1.55(2H, m), 2.50(2H, t, J=7.4), 2.70(2H, t,
J=7.5), 4.02–4.03(1H, m), 4.21(2H, q, J=7.1), 4.70(2H, br-s),
6.42–6.44(2H, m), 6.52(1H, d, J=2.1), 7.30(1H, dd, J=8.5, 1.5), 7.37
(1H, d, J=3.0), 7.47(1H, d, J=8.5), 7.64(1H, d, J=0.8), 12.05(1H, br-s).
EXP. 391
$^1$H-NMR(CDCl$_3$): 0.84–1.01(3H, m), 1.15–1.31(3H, m), 1.44–1.56
4H, m), 2.67(2H, t, J=7.7), 2.99(2H, t, J=7.7), 3.42–3.48(1H, m),
3.68(3H, s), 6.59–6.61(1H, m), 7.24–7.28(1H, m), 7.41–7.43(3H, m),
7.48(1H, d, J=2.2), 7.80(1H, m), 8.26(1H, br-s).
EXP. 392
$^1$H-NMR(CDCl$_3$): 0.85–1.02(3H, m), 1.12–1.31(3H, m),
1.48–1.55(2H, m), 1.66–1.72(2H, m), 2.62(2H, t, J=7.8),
2.86(2H, t, J=7.8), 3.37–3.39(1H, m), 3.67(3H, s), 3.87(2H, br-s),
6.55–6.59(2H, m), 6.61(1H, d, J=1.9), 7.23(1H, t,
J=2.8), 7.37–7.44(2H, m), 7.78(1H, s), 8.16(1H, br-s).
EXP. 393
$^1$H-NMR(DMSO-$d_6$): 0.73–1.00(3H, m), 1.06–1.30(3H, m),
1.43–1.47(2H, m), 1.54–1.58(2H, m), 2.50(2H, t, J=7.9), 2.70(2H,
t, J=7.4), 3.27–3.36(1H, m), 4.98(2H, br-s), 6.42–6.43(2H, m), 6.52(1H,
d, J=2.2), 7.26(1H, dd, J=8.4, 1.3), 7.32(1H, t, J=2.7), 7.38
(1H, d, J=8.5), 7.63(1H, s), 11.05(1H, s).
EXP. 394
$^1$H-NMR(CDCl$_3$): 0.85–1.03(3H, m), 1.15–1.28(3H, m),
1.42–1.52(2H, m), 1.54–1.61(2H, m), 2.67(2H, t, J=7.2),
2.99(2H, t, J=7.7), 3.42–3.49(1H, m), 3.69(3H, s), 3.84(3H, s),
6.52(1H, d, J=2.4), 7.10(1H, d, J=3.0), 7.35(1H, dd,
J=8.5, 1.9), 7.42(2H, dd, J=4.9, 2.1), 7.45–7.48(1H, m), 7.78(1H, m).
EXP. 395
$^1$H-NMR(CDCl$_3$): 0.84–1.03(3H, m), 1.13–1.38(3H, m),
1.48–1.54(2H, m), 1.67–1.74(2H, m), 2.62(2H, t, J=7.9),
2.86(2H, t, J=7.9), 3.35–3.46(1H, m),
3.67(3H, s), 3.82(2H, br-s), 3.88(2H, br-s), 6.50(1H, d, J=3.3),
6.55(1H, d, J=1.9), 6.60(1H, d, J=1.9), 7.06
(1H, d, J=3.0), 7.31(1H, d, J=8.2), 7.45(1H, dd, J=8.2, 1.6), 7.76(1H, m).
EXP. 396
$^1$H-NMR(DMSO-$d_6$): 0.78–0.99(3H, m), 1.05–1.30(3H, m),
1.43–1.48(2H, m), 1.54–1.58(2H, m), 2.50(2H, t, J=7.5), 2.69(2H,
t, J=7.5), 3.41(3H, s), 4.79(2H, br-s), 6.40(1H, d, J=1.6), 6.43(1H, d,
J=3.0), 6.51(1H, d, J=1.9), 7.30–7.34(2H, m), 7.43(1H, d, J=8.5),
7.64(1H, s), 12.04(1H, br-s).
EXP. 397
$^1$H-NMR(CDCl$_3$): 0.83–1.02(3H, m), 1.12–1.29(3H, m),
1.41–1.58(4H, m), 1.50(3H, t, J=7.4), 2.67(2H, t, J=7.9),
2.99(2H, t, J=7.8), 3.43–3.50(1H, m), 3.69(3H, s), 4.22(1H, q, J=7.4),
6.53(1H, d, J=3.0), 7.18(1H, d, J=3.0), 7.38(1H, d, J=8.7),
7.40–7.42(2H, m), 7.45–7.47(1H, m), 7.78–7.79(1H, m).
EXP. 398
$^1$H-NMR(CDCl$_3$): 0.84–1.03(3H, m), 1.14–1.32(3H, m),
1.47–1.73(4H, m), 1.49(3H, t, J=7.1), 2.62(2H, t, J=7.9), 2.86(2H, t,
J=7.8), 3.36–3.43(1H, m), 3.67(3H, s), 4.20(2H, q, J=7.1), 6.51(1H,
J=3.0), 6.58(1H, d, J=1.6), 6.63(1H, d, J=1.6), 7.13(1H, d, J=3.0),
7.34(1H, d, J=8.5), 7.43(1H, dd, J=8.7, 1.3), 7.76(1H, m).
EXP. 399
$^1$H-NMR(DMSO-$d_6$): 0.80–0.91(3H, m), 1.04–1.28(3H, m),
1.37(3H, t, J=7.1), 1.42–1.49(2H, m), 1.52–1.59(2H, m),
2.49–2.51(2H, m), 2.69(2H, t, J=7.8), 3.31–3.34(1H, m),
4.22(2H, q, J=7.2), 4.71(2H, br-s), 6.39–6.44(2H, m), 6.50–6.52
(1H, m), 7.30(1H, dd, J=8.5, 1.6), 7.37(1H, d, J=3.0), 7.46(1H, d,
J=8.2), 7.63(1H, m), 12.07(1H, br-s).
EXP. 400
$^1$H-NMR(CDCl$_3$): 1.29(3H, d, J=6.5), 2.64(2H, t, J=7.8), 2.95(2H,
t, J=7.6), 3.66(3H, s), 4.58(1H, q, J=6.8), 6.60(1H, m), 6.92(1H, dd,
J=6.3, 1.6), 7.11–7.19(3H, m), 7.29(1H, t, J=2.7), 7.39(2H, dd,
J=7.1, 2.3), 7.44(2H, dd, J=8.5, 1.3), 7.80(1H, s), 8.26(1H, br-s).
EXP. 401
$^1$H-NMR(CDCl$_3$): 1.20(3H, d, J=6.5), 1.56(2H, br-s), 2.61(2H,
t, J=7.9), 2.85(2H, t, J=8.0), 3.67(3H, s), 4.56(1H, q, J=6.4),
6.48(1H, d, J=2.2), 6.56–6.58(1H, m), 6.62(1H, d, J=2.2),
7.10–7.13(1H, m), 7.18–7.21(3H, m), 7.24(1H, t, J=2.9), 7.39(1H, d,
J=8.5), 7.43(1H, dd, J=8.5, 1.4), 7.80(1H, m), 8.26(1H, br-s).

TABLE 16-continued

EXP. 402
$^1$H-NMR(DMSO-d$_6$): 1.09(3H, d, J=6.3), 2.48(2H, t, J=7.6),
2.68(2H, t, J=7.5), 4.48(1H, q, J=6.4), 4.61(2H, br-s), 6.39(1H, d,
J=1.9), 6.42–6.44(2H, m), 7.08–7.12(2H, m), 7.17–7.19(3H, m),
7.24(1H, dd, J=8.2, 1.6), 7.33–7.39(2H, m), 7.63(1H, s), 11.07(1H,
s), 12.04(1H, br-s).
EXP. 403
$^1$H-NMR(CDCl$_3$): 1.29(3H, d, J=6.3), 2.63(2H, t, J=7.8),
2.95(2H, t, J=7.8), 3.66(3H, s), 3.86(3H, s), 4.57(1H, q, J=6.2),
6.53(1H, d, J=3.2), 6.91–6.95(2H, m), 7.11–7.19(4H,
m), 7.36–7.40(3H, m), 7.46(1H, dd, J=8.6, 1.6), 7.80(1H, s),
8.26(1H, br-s).
EXP. 404
$^1$H-NMR(CDCl$_3$): 1.20(3H, d, J=6.5), 1.55(2H, br-s),
2.61(2H, t, J=7.8), 2.85(2H, t, J=7.9), 3.66(3H, s), 3.85(3H, s),
4.56(1H, q, J=6.3), 6.47(1H, d, J=1.9), 6.50(1H, d,
J=2.7), 6.62(1H, d, J=2.2), 7.07(1H, d, J=3.2),
7.11–7.14(2H, m), 7.19–7.21(3H, m),
7.31(1H, d, J=8.2), 7.46(1H, dd, J=8.5, 1.6), 7.79(1H, m).
EXP. 405
$^1$H-NMR(DMSO-d$_6$): 1.09(3H, d, J=6.5), 2.49(2H, t, J=7.9),
2.68(2H, t, J=7.5), 3.81(3H, s), 4.48(1H, q, J=6.5), 4.60(2H, br-s),
6.39–6.45(3H, m), 7.09–7.12(2H, m),
7.17–7.19(3H, m), 7.29–7.34(3H, m), 7.63(1H, s), 12.07(1H, br-s).
EXP. Int. 81
$^1$H-NMR(CDCl$_3$): 2.63(2H, t, J=7.4), 2.96(2H, t, J=7.4),
3.21–3.25(4H, m), 3.69(3H, s), 5.04–5.11(1H, m), 7.16–7.24(4H, m),
7.58(1H, d, J=2.2), 7.65(1H, d, J=2.2).
EXP. 406
$^1$H-NMR(CDCl$_3$): 2.69(2H, t, J=7.1), 2.72–2.77(2H, m),
2.85–2.92(2H, m), 3.01(2H, t, J=7.6), 3.70(3H, s), 4.46–4.53(1H, m),
6.57–6.61(1H, m), 6.94–7.04(4H, m), 7.24–7.27
(1H, m), 7.38(2H, s), 7.49(2H, dd, J=8.5, 2.2), 7.78(1H, br-s),
8.23(1H, br-s).
EXP. 407
$^1$H-NMR(CDCl$_3$): 1.55(2H, br-s), 2.64(2H, t, J=7.1),
2.73(2H, dd, J=13.5, 5.5), 2.88(2H, t, J=7.8), 2.97(2H, dd,
J=16.4, 2.4), 3.68(3H, s), 4.34–4.39(1H, m), 6.54(1H, d,
J=2.2), 6.58–6.60(1H, m), 6.65(1H, d, J=1.9), 7.07–7.13(4H, m),
7.23–7.26(1H, m), 7.39–7.48(2H, m), 7.83(1H, br-s), 8.19(1H, br-s).
EXP. 408
$^1$H-NMR(DMSO-d$_6$): 2.48–2.53(2H, m), 2.63–2.73(4H, m),
2.85(2H, dd, J=16.3, 3.1), 4.21–4.24(1H, m), 4.46(2H, br-s), 6.45(2H, d,
J=1.9), 6.50(1H, d, J=2.2), 7.04–7.10(4H, m), 7.28–7.40(3H, m),
7.68(1H, s), 11.09(1H, s), 12.04(1H, br-s).
EXP. 409
$^1$H-NMR(CDCl$_3$): 2.69(2H, t, J=7.6), 2.70–2.77(2H, m),
2.88(2H, dd, J=15.9, 4.5), 3.01(2H, t, J=7.6), 3.69(3H, s),
3.83(3H, s), 4.45–4.53(1H, m), 6.51(1H, d, J=3.0), 6.93–7.02
(4H, m), 7.10(1H, d, J=3.3), 7.30(1H, d, J=8.5), 7.40(2H, dd,
J=8.5, 1.6), 7.47(2H, dd, J=10.4, 2.2), 7.76(1H, m).
EXP. 410
$^1$H-NMR(CDCl$_3$): 1.55(2H, br-s), 2.61–2.76(4H, m),
2.88(2H, t, J=7.9), 2.97(2H, dd, J=14.9, 2.4), 3.68(3H, s),
3.83(3H, s), 4.34–4.38(1H, m), 6.52(1H, dd, J=3.0, 0.8), 6.56
(1H, d, J=2.2), 6.66(1H, d, J=2.2), 7.08–7.15(5H, m), 7.34
(1H, d, J=8.5), 7.49(1H, dd, J=7.7, 1.7), 7.89(1H, m).
EXP. 411
$^1$H-NMR(DMSO-d$_6$): 2.50–2.53(2H, m), 2.63–2.73(4H, m),
2.84(2H, dd, J=16.1, 3.0), 3.80(3H, s), 4.21–4.28(1H, m),
4.49(2H, br-s), 6.43–6.45(2H, m), 6.50(1H, d, J=1.9),
7.06(4H, s), 7.32–7.43(3H, m), 7.68(1H, s), 12.04(1H, br-s).
EXP. 412
$^1$H-NMR(CDCl$_3$): 2.70(2H, t, J=7.5), 3.03(2H, t, J=7.7),
3.70(3H, s), 4.62(2H, s), 6.58–6.61(1H, m), 7.13–7.16(2H, m),
7.23–7.31(2H, m), 7.37–7.58(5H, m), 7.81(1H, s), 8.28(1H, br-s).
EXP. 413
$^1$H-NMR(CDCl$_3$): 1.55(2H, br-s), 2.65(2H, t, J=7.8),
2.89(2H, t, J=7.6), 3.68(3H, s), 4.48(2H, s), 6.57–6.59(1H, m),
6.62(1H, d, J=1.9), 6.69(1H, d, J=1.9), 7.21–7.24(3H,
m), 7.39–7.47(4H, m), 7.83(1H, s), 8.19(1H, br-s).
EXP. 414
$^1$H-NMR(DMSO-d$_6$): 2.51(2H, t, J=7.9), 2.71(2H, t, J=7.5),
4.45(2H, s), 4.86(2H, br-s), 6.42–6.45(2H, m), 6.56(1H, d, J=1.9),
7.28–7.39(5H, m), 7.56(2H, d, J=7.9), 7.68(1H,
s), 11.07(1H, s), 12.03(1H, br-s).

Examples 430 to 479

The data of the compounds of the compounds Nos. 430 to 479 are shown in Tables 17 to 22. As for the abbreviations used in the tables, "SM1" represents a starting compound 1, "SM2" represents a starting compound 2, and the other abbreviations have the same meanings as those defined above. The indications used in the columns of "Br or Ar" have the following meanings: "Br", bromo group; "1HIZ4", 1H-indazol-4-yl group; "1MIZ4", 1-methyl-1H-indazol-4-yl group; "2MIZ4", 2-methyl-2H-indazol-4-yl group; "1HIZ6", 1H-indazol-6-yl group; "1MIZ6", 1-methyl-1H-indazol-6-yl group; "2MIZ6", 2-methyl-2H-indazol-6-yl group; "1HIZ5", 1H-indazol-5-yl group; "1MIZ5", 1-methyl-1H-indazol-5-yl group; "2MIZ5", 2-methyl-2H-indazol-5-yl group; "1EIZ5", 1-ethyl-1H-indazol-5-yl group; and "2EIZ5", 2-ethyl-2H-indazol-5-yl group. Intermediates 85 to 95 mentioned in the tables were prepared as follows.

Synthesis of 4-bromo-1H-indazole (Intermediate 85)

According to a method similar to a method known from a literature [P. Schumann et al, Bioorganic & Medicinal Chemistry Letters (Bioorg. Med. Chem. Lett.), 2001, vol. 11, p.1153], the title compound (Intermediate 85, 1.68 g) was obtained from commercially available 3-bromotoluidine (4.51 g, Ald). Mass (LCMS): 197 (M$^+$), retention time: 2.00 minutes (elution condition: B).

Syntheses of 4-bromo-1-methyl-1H-indazole (Intermediate 86) and 4-bromo-2-methyl-2H-indazole (Intermediate 87)

According to the procedure described in the synthesis method of Compound of Example 232 (Preparation Method 11, Step e) with the modifications that the reaction was carried out for 8 hours, and the purification was performed by column chromatography (Quad, hexane:ethyl acetate= 5:1), Intermediate 85 (600 mg), 60% sodium hydride (191 mg) and methyl iodide (379 μl) were reacted and treated to obtain the title compounds (Intermediate 86, 432 mg; Intermediate 87, 164 mg). Mass (LCMS): Intermediate 86, 211 (M$^+$), retention time: 2.73 minutes (elution condition: B); Intermediate 87: 211 (M$^+$), retention time: 2.15 minutes (elution condition: B).

Synthesis of 6-bromo-1H-indazole (Intermediate 88)

According to a method similar to a method known from a literature [Bioorg. Med. Chem. Lett., 2001, vol. 11, p.1153], the title compound (Intermediate 88, 0.42 g) was obtained from commercially available 5-bromotoluidine (3.33 g, Ald). Mass (LCMS): 197 (M$^+$), retention time: 3.32 minutes (elution condition: B).

Synthesis of 6-bromo-1-methyl-1H-indazole (Intermediate 89) and 6-bromo-2-methyl-2H-indazole (Intermediate 90)

According to the procedure described in the synthesis method of Compound of Example 232 (Preparation Method 11, Step e) with the modifications that the reaction was carried out for 2.5 hours, and the purification was performed by column chromatography (Quad, hexane:ethyl acetate= 5:1), Intermediate 88 (277 mg), 60% sodium hydride (86 mg) and methyl iodide (175 μl) were reacted and treated to obtain the title compound (Intermediate 89, 196 mg; Intermediate 90, 89 mg).

Synthesis of 5-bromo-1H-indazole (Intermediate 91)

According to a method known from a literature [Bioorg. Med. Chem. Lett., 2001, vol. 11, p.1153], the title compound (Intermediate 91, 0.91 g) was obtained from commercially available 4-bromotoluidine (3.33 g, Ald). Mass (LCMS): 197 (M$^+$), retention time: 3.35 minutes (elution condition: B).

Syntheses of 5-bromo-1-methyl-1H-indazole (Intermediate 92) and 5-bromo-2-methyl-2H-indazole (Intermediate 93)

According to the procedure described in the synthesis method of Compound of Example 232 (Preparation Method 11, Step e) with the modifications that the reaction was carried out for 4.5 hours, and the purification was performed by column chromatography (Quad, hexane:ethyl acetate= 5:1), Intermediate 91 (300 mg), 60% sodium hydride (80 mg) and methyl iodide (161 µl) were reacted and treated to obtain the title compounds (Intermediate 92, 201 mg; Intermediate 93, 87 mg). Mass (LCMS): Intermediate 92, 211 ($M^+$), retention time: 2.70 minutes (elution condition: B); Intermediate 93, 211 ($M^+$), retention time: 2.15 minutes (elution condition: B).

Syntheses of 5-bromo-1-ethyl-1H-indazole (Intermediate 94) and 5-bromo-2-ethyl-2H-indazole (Intermediate 95)

According to the procedure described in the synthesis method of Compound of Example 232 (Preparation Method 11, Step e) with the modifications that the reaction was carried out for 2 hours, and the purification was performed by column chromatography (Quad, hexane:ethyl acetate= 5:1), Intermediate 91 (420 mg), 60% sodium hydride (111 mg) and ethyl iodide (375 µl) were reacted and treated to obtain the title compounds (Intermediate 94, 250 mg; Intermediate 95, 127 mg). Mass (LCMS): Intermediate 94, 225 ($M^+$), retention time: 4.56 minutes (elution condition: B); Intermediate 95: 225 ($M^+$), retention time: 2.15 minutes (elution condition: B).

The indication "4d1b" used in the columns of "Syn." representing the preparation method means that the target compounds were prepared according to the method for preparing the compounds described below.

Preparation Method "4d1b":

Example 430

Syntesis of methyl 3-[4-cyclopentyloxy-3-(111H-indazol-4-yl)phenyl]propionate (Compound No. 430) (Preparation Method 4, Step d-1)

According to the procedure described in the synthesis method of Compound of Example 019 (Preparation Method 4, Step d-1) with the modification that the purification was performed by flash column chromatography (hexane:ethyl acetate=2:1), Intermediate 8 (328 mg, corresponding to the compound mentioned in the column of "SM1" in the table), bispinacolate diboron (281 mg), $PdCl_2(dppf)$ (61 mg) and potassium acetate (303 mg) were reacted at 80° C. for 4 hours, and then the reaction mixture was added with Intermediate 85 (161 mg) (corresponding to the compound mentioned in the column of "SM2" in the table), $PdCl_2$(dppf) (64 mg) and 2 M aqueous sodium carbonate (1.5 ml), reacted at 80° C. for 9 hours and treated to obtain the title compound (Compound No. 430, 111 mg). Mass (LCMS): 365 ($M^+$+1), retention time: 3.63 minutes (elution condition: B).

TABLE 17

| Exp. | Syn. | SM1 | SM2 | RO | Y | Z | Br or A | LCMS method | RTime | Mass |
|---|---|---|---|---|---|---|---|---|---|---|
| 430 | 4d1b | Int.8 | Int.85 |  | Me | H | 1HIZ4 | B | 3.63 | 365 ($M^+$ + 1) |
| 431 | 1a | Exp.430 | |  | H | H | 1HIZ4 | B | 2.89 | 350 ($M^+$ + 1) |
| 432 | 4d1b | Int.8 | Int.86 |  | Me | H | 1MI74 | B | 4.15 | 379 ($M^+$ + 1) |
| 433 | 1a | Exp.432 | |  | H | H | 1MIZ4 | B | 3.34 | 365 ($M^+$ + 1) |
| 434 | 4d1b | Int.8 | Int.87 |  | Me | H | 2MIZ4 | B | 3.75 | 379 ($M^+$ + 1) |
| 435 | 1a | Exp.434 | |  | H | H | 2MIZ4 | B | 2.96 | 365 ($M^+$ + 1) |
| 436 | 4d1b | Int.8 | Int.88 |  | Me | H | 1HIZ6 | B | 3.79 | 365 ($M^+$ + 1) |
| 437 | 1a | Exp.436 | |  | H | H | 1HIZ6 | A | 3.97 | 351 ($M^+$ + 1) |

TABLE 17-continued

| | | | | | | | | | LCMS | |
| | | | | | | | | | | |
| Exp. | Syn. | SM1 | SM2 | RO | | Y | Z | Br or A | method | RTime | Mass |
|---|---|---|---|---|---|---|---|---|---|---|---|
| 438 | 4d1b | Int.8 | Int.89 | cyclopentyl-O | | Me | H | 1MIZ6 | B | 4.30 | 379 (M⁺ + 1) |
| 439 | 1a | Exp.438 | | cyclopentyl-O | | H | H | 1MIZ6 | B | 4.33 | 365 (M⁺ + 1) |

TABLE 18

| | | | | | | | | | LCMS | |
| | | | | | | | | | | |
| Exp. | Syn. | SM1 | SM2 | RO | | Y | Z | Br or A | method | RTime | Mass |
|---|---|---|---|---|---|---|---|---|---|---|---|
| 440 | 4d1b | Int.8 | Int.90 | cyclopentyl-O | | Me | H | 2MIZ6 | B | 3.82 | 379 (M⁺ + 1) |
| 441 | 1a | Exp.440 | | cyclopentyl-O | | H | H | 2MIZ6 | A | 4.00 | 365 (M⁺ + 1) |
| 442 | 4d1b | Int.8 | Int.91 | cyclopentyl-O | | Me | H | 1HIZ5 | B | 3.66 | 365 (M⁺ + 1) |
| 443 | 1a | Exp.442 | | cyclopentyl-O | | H | H | 1HI75 | B | 2.82 | 351 (M⁺ + 1) |
| 444 | 4d1b | Int.8 | Int.92 | cyclopentyl-O | | Me | H | 1MIZ5 | B | 4.20 | 379 (M⁺ + 1) |
| 445 | 1a | Exp.444 | | cyclopentyl-O | | H | H | 1MI75 | A | 4.32 | 365 (M⁺ + 1) |
| 446 | 4d1b | Int.8 | Int.93 | cyclopentyl-O | | Me | H | 2MIZ5 | B | 3.70 | 379 (M⁺ + 1) |
| 447 | 1a | Exp.446 | | cyclopentyl-O | | H | H | 2MIZ5 | A | 3.96 | 365 (M⁺ + 1) |
| 448 | 4d1b | Int.8 | Int.94 | cyclopentyl-O | | Me | H | 1EIZ5 | A | 5.36 | 393 (M⁺ + 1) |
| 449 | 1a | Exp.448 | | cyclopentyl-O | | H | H | 1EIZ5 | A | 4.53 | 379 (M⁺ + 1) |

TABLE 19

| Exp. | Syn. | SM1 | SM2 | RO | Y | Z | Br or Ar | LCMS method | RTime | Mass |
|---|---|---|---|---|---|---|---|---|---|---|
| 450 | 4d1b | Int.8 | Int.95 | cyclopentyl-O | Me | H | 2EIZ5 | B | 3.94 | 393 (M⁺ + 1) |
| 451 | 1a | Exp.450 | | cyclopentyl-O | H | H | 2EIZ5 | A | 4.13 | 379 (M⁺ + 1) |
| 452 | 4d1b | Int.3 | Int.91 | cyclopentyl-CH₂-O | Me | H | 1HIZ5 | B | 4.08 | 379 (M⁺ + 1) |
| 453 | 1a | Exp.452 | | cyclopentyl-CH₂-O | H | H | 1HIZ5 | A | 4.19 | 365 (M⁺ + 1) |
| 454 | 4d1b | Int.9 | Int.91 | cyclohexyl-O | Me | H | 1HIZ5 | B | 4.02 | 379 (M⁺ + 1) |
| 455 | 1a | Exp.454 | | cyclohexyl-O | H | H | 1HI75 | A | 4.10 | 365 (M⁺ + 1) |
| 456 | 4d1b | Int.9 | Int.92 | cyclohexyl-O | Me | H | 1MIZ5 | A | 4.57 | 393 (M⁺ + 1) |
| 457 | 1a | Exp.456 | | cyclohexyl-O | H | H | 1MIZ5 | B | 3.64 | 377 (M⁺ + 1) |
| 458 | 4d1b | Int.9 | Int.93 | cyclohexyl-O | Me | H | 2MIZ5 | B | 4.07 | 393 (M⁺ + 1) |
| 459 | 1a | Exp.458 | | cyclohexyl-O | H | H | 2M1Z5 | A | 4.17 | 379 (M⁺ + 1) |

TABLE 20

| Exp. | Syn. | SM1 | SM2 | RO | Y | Z | Br or Ar | LCMS method | RTime | Mass |
|---|---|---|---|---|---|---|---|---|---|---|
| Int.96 | 4e2 | Int.6 | Al14 | cycloheptyl-O | Me | H | Br | B | 5.11 | N.D |
| 460 | 4d1b | Int.96 | Int.91 | cycloheptyl-O | Me | H | 1HI75 | B | 4.21 | 393 (M⁺ + 1) |

TABLE 20-continued

| Exp. | Syn. | SM1 | SM2 | RO | Y | Z | Br or Ar | LCMS method | RTime | Mass |
|---|---|---|---|---|---|---|---|---|---|---|
| 461 | 1a | Exp.460 | | cycloheptyl-O | H | H | 1HI75 | B | 3.33 | 379 (M+ + 1) |
| Int.97 | 4e2 | Int.6 | Al25 | sec-pentyl-O | Me | H | Br | B | 5.15 | ND |
| 462 | 4d1b | Int.97 | Int.91 | sec-pentyl-O | Me | H | 1HIZ5 | B | 4.25 | 393 (M+ + 1) |
| 463 | 1a | Exp.462 | | sec-pentyl-O | H | H | 1HIZ5 | B | 3.36 | 367 (M+ + 1) |
| Int.98 | 4e2 | Int.6 | Al54 | indan-2-yl-O | Me | H | Br | B | 4.48 | N.D |
| 464 | 4d1b | Int.98 | Int.91 | indan-2-yl-O | Me | H | 1HIZ5 | B | 4.70 | 413 (M+ + 1) |
| 465 | 1a | Exp.464 | | indan-2-yl-O | H | H | 1HIZ5 | B | 4.02 | 399 (M+ + 1) |
| 466 | 4d1b | Int.98 | Int.92 | indan-2-yl-O | Me | H | 1MIZ5 | A | 5.11 | 427 |

TABLE 21

| Exp. | Syn. | SM1 | SM2 | RO | Y | Z | Br or Ar | LCMS method | RTime | Mass |
|---|---|---|---|---|---|---|---|---|---|---|
| 467 | 1a | Exp.466 | | indan-2-yl-O | H | H | 1MIZ5 | A | 4.36 | 413 (M+ + 1) |
| 468 | 4d1b | Int.98 | Int.94 | indan-2-yl-O | Me | H | 1EIZ5 | B | 5.38 | 441 (M+ + 1) |
| 469 | 1a | Exp.468 | | indan-2-yl-O | H | H | 1EIZ5 | B | 4.59 | 427 (M+ + 1) |
| Int.99 | 4e1 | Int.6 | Hal5 | 4-fluorobenzyl-O | Me | H | Br | | | |

TABLE 21-continued

| Exp. | Syn. | SM1 | SM2 | RO | Y | Z | Br or Ar | LCMS method | RTime | Mass |
|---|---|---|---|---|---|---|---|---|---|---|
| 470 | 4d1b | Int.99 | Int.91 | 4-F-C6H4-CH2-O- | Me | H | 1HIZ5 | A | 4.50 | 405 (M+ + 1) |
| 471 | 1a | Exp.470 | | 4-F-C6H4-CH2-O- | H | H | 1HIZ5 | A | 3.92 | 391 (M+ + 1) |
| 472 | 4d1b | Int.99 | Int.92 | 4-F-C6H4-CH2-O- | Me | H | 1MI75 | A | 4.87 | 419 (M+ + 1) |
| 473 | 1a | Exp.472 | | 4-F-C6H4-CH2-O- | H | H | 1MIZ5 | A | 4.15 | 405 (M+ + 1) |
| Int.100 | 4e1 | Int.6 | Hal4 | 4-F3C-C6H4-CH2-O- | Me | H | Br | B | 4.64 | N.D |
| 474 | 4d1b | Int.100 | Int.91 | 4-F3C-C6H4-CH2-O- | Me | H | 1HIZ5 | B | 3.91 | 455 (M+ + 1) |

TABLE 22

| Exp. | Syn. | SM1 | SM2 | RO | Y | Z | Br or Ar | LCMS method | RTime | Mass |
|---|---|---|---|---|---|---|---|---|---|---|
| 475 | 1a | Exp.474 | | 4-F3C-C6H4-CH2-O- | H | H | 1HIZ5 | A | 4.20 | 441 (M+ + 1) |
| 476 | 4d1b | Int.10 | Int.91 | 2-F-C6H4-CH2CH2-O- | Me | H | 1HIZ5 | A | 4.60 | 419 (M+ + 1) |
| 477 | 1a | Exp.476 | | 2-F-C6H4-CH2CH2-O- | H | H | 1HIZ5 | A | 3.92 | 405 (M+ + 1) |
| 478 | 4d1b | Int.10 | Int.92 | 2-F-C6H4-CH2CH2-O- | Me | H | 1MIZ5 | A | 5.08 | 433 (M+ + 1) |

TABLE 22-continued

| | | | | | | | | LCMS | | |
|---|---|---|---|---|---|---|---|---|---|---|
| Exp. | Syn. | SM1 | SM2 | RO | Y | Z | Br or Ar | method | RTime | Mass |
| 479 | 1a | Exp.478 | | 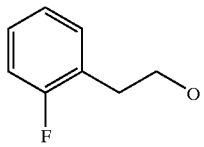 | H | H | 1MIZ5 | A | 4.32 | 419 (M⁺ + 1) |

Example 480
Syntesis of methyl 3-(3-bromo-5-fluoro-4-cyclopentyloxyphenyl)propionate (Intermediate 101) (Preparation Method 4, Step e-2)

According to the procedure described in the synthesis method of Intermediate 9 in Reference Example 2 (Step e-2) with the modifications that the reaction was carried out for 24 hours, and the purification was performed by column chromatography (Quad, hexane:ethyl acetate=10:1), Intermediate 22 (443 mg), PH$_3$P (1.25 g), cyclopentanol (435 µl) and 40% DIAD (2.26 ml) were reacted and treated to obtain the title compound (Intermediate 101, 522 mg). Mass (FAB): 345 (M⁺+1).

Synthesis of 4-(4,4,5,5-tetramethyl-1,3,2-dioxaborolan-2-yl)-2-methylnitrobenzene (Intermediate 102) (Preparation Method 4, Step d-2)

According to the procedure described in the synthesis method of Compound of Example 019 (Preparation Method 4, Step d-1), 5-bromo-2-nitrotoluene (4.30 g) prepared by nitrating 3-bromotoluene (WAKO) in a known manner, bispinacolate dibron (5.59 g), PdCl$_2$(dppf) (440 mg) and potassium acetate (6.09 g) were stirred at 80° C. for 3 hours with heating under an argon gas atmosphere. The reaction mixture was added with ethyl acetate (300 ml) and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=8:1) to obtain the title compound (Intermediate 102, 4.21 g).

Synthesis of 4-(4,4,5,5-tetramethyl-1,3,2-dioxaborolan-2-yl)-2-methylaniline (Intermediate 103) (Step b)

A solution of Intermediate 102 (4.20 g) in methanol (100 ml) was added with platinum oxide (50 mg, Ald) and stirred at room temperature for 30 minutes under a hydrogen atmosphere. The reaction mixture was filtered, and the solvent of the filtrate was evaporated under reduced pressure to obtain the title compound (Intermediate 103, 2.81 g). Mass (LCMS): 234 (M⁺+1), retention time: 3.04 minutes (elution condition: B).

Syntesis of methyl 3-(4'-amino-6-cyclopentyloxy-5-fluoro-3'-methylbiphenyl-3-yl)propionate (Intermediate 104) (Preparation Method 15, Step d-1)

According to the procedure described in the synthesis method of Compound of Example 001 (Preparation Method 4, Step d-1) with the modifications that the reaction was carried for 15.5 hours, and the purification was performed by column chromatography (Quad, hexane:ethyl acetate=6:1), Intermediate 101 (698 mg), Intermediate 103 (603 mg), 2 M aqueous sodium carbonate (1.8 ml) and (PH$_3$P)$_4$Pd (180 mg) were reacted and treated to obtain the title compound (Intermediate 104, 765 mg). Mass (LCMS): 372 (M⁺+1), retention time: 5.08 minutes (elution condition: A).

Syntesis of methyl 3-[4-cyclopentyloxy-3-fluoro-5-(1H-indazol-5-yl)phenyl]propionate (Compound No. 480) (Preparation Method 15, Step t)

A solution of Intermediate 104 (764 mg) in acetic acid (4 ml) was added with an aqueous solution (0.7 ml) of sodium nitrite (156 mg, TCI) under ice cooling and stirred for 30 minutes. The reaction mixture was added with urea (350.2 mg), warmed to room temperature, stirred for 30 minutes, then added with toluene (8 ml) and water (4 ml) and further stirred for 60 hours. The reaction mixture was extracted with toluene (50 ml×2), the organic layer was washed successively with saturated aqueous sodium hydrogencarbonate and saturated brine and dried, and then the solvent was evaporated under reduced pressure. The residue was purified by column chromatography (Quad, hexane:ethyl acetate= 6:1) to obtain the title compound (Compound No. 480, 414 mg). Mass (LCMS): 383 (M⁺+1), retention time: 4.73 minutes (elution condition: A).

Example 481
Synthesis of 3-[4-cyclopentyloxy-3-fluoro-5-(1H-indazol-5-yl)phenyl]propionic acid (Compound No. 481) (Preparation Method 1, Step a)

According to the procedure described in the synthesis method of Compound of Example 002 (Preparation Method 1, Step a) with the modification that the reaction was carried out for 2.5 hours, Compound of Example 480 (86 mg) and 2 N aqueous sodium hydroxide (250 µl) were reacted and treated to obtain the title compound (Compound No. 481, 82 mg). Mass (LCMS): 369 (M⁺+1), retention time: 4.03 minutes (elution condition: A).

Example 482
Syntesis of methyl 3-[4-cyclopentyloxy-3-fluoro-5-(1-methyl-1H-indazol-5-yl)phenyl]propionate (Compound No. 482) (Preparation Method 16, Step e-1)

According to the procedure described in the synthesis method of Compound of Example 232 (Preparation Method 11, Step e) with the modifications that the reaction was carried out for 3 hours, and the purification was performed by column chromatography (Quad, hexane:ethyl acetate= 6:1), Compound of Example 480 (143 mg), 60% sodium hydride (21 mg) and methyl iodide (50 µl) were reacted and treated to obtain the title compound (Compound No. 482, 63 mg). Mass (LCMS): 397 (M⁺+1), retention time: 5.26 minutes (elution condition: A).

Example 483
Synthesis of 3-[4-cyclopentyloxy-3-fluoro-5-(1-methyl-1H-indazol-5-yl)phenyl]propionic acid (Compound No. 483) (Preparation Method 1, Step a)

According to the procedure described in the synthesis method of Compound of Example 002 (Preparation Method 1, Step a) with the modification that the reaction was carried out for 2.5 hours, Compound of Example 482 (61 mg) and 2 N aqueous sodium hydroxide (250 μl) were reacted and treated to obtain the title compound (Compound No. 483, 58 mg). Mass (LCMS): 383 (M$^+$+1), retention time: 4.40 minutes (elution condition: A).

Example 484

Syntesis of methyl 3-[4'-amino-6-(indan-2-yloxy)-3'-methyl-5-nitrobiphenyl-3-yl]propionate (Intermediate 105) (Preparation Method 15, Step d-1)

According to the procedure described in the synthesis method of Compound of Example 001 (Preparation Method 4, Step d-1) with the modifications that the reaction was carried out for 24 hours, and the purification was performed by column chromatography (Quad, hexane:ethyl acetate= 2:1), Intermediate 81 (384 mg), Intermediate 103 (262 mg), 2 M aqueous sodium carbonate (830 μl) and (PH$_3$P)$_4$Pd (131 mg) were reacted and treated to obtain the title compound (Intermediate 105, 421 mg). Mass (LCMS): 447 (M$^+$+1), retention time: 4.97 minutes (elution condition: A).

Syntesis of methyl 3-[4-(indan-2-yloxy)-3-(1H-indazol-5-yl)-5-nitrophenyl]propionate (Compound No. 484) (Preparation Method 15, Step t)

According to the procedure described in the synthesis method of Compound of Example 480 (Preparation Method 15, Step t) with the modifications that the reaction was carried out for 48 hours, and the purification was performed by column chromatography (Quad, hexane:ethyl acetate= 5:1), Intermediate 105 (420 mg) and sodium nitrite (71 mg) were reacted and treated to obtain the title compound (Compound No. 484, 282 mg). Mass (LCMS): 458 (M$^+$+1), retention time: 4.54 minutes (elution condition: A).

Example 485

Syntesis of methyl 3-[3-amino-4-(indan-2-yloxy)-5-(1H-indazol-5-yl)phenyl]-propionate (Compound No. 485) (Preparation Method 2, Step b)

According to the procedure described in the synthesis method of Compound of Example 331 (Preparation Method 2, Step b) with the modifications that the reaction was carried out for 1.5 hours, and the purification was performed by column chromatography (Quad, hexane:ethyl acetate= 5:1), Compound of Example 484 (65 mg) was reacted and treated to obtain the title compound (Compound No. 485, 38 mg). Mass (LCMS): 428 (M$^+$+1), retention time: 4.17 minutes (elution condition: A).

Example 486

Synthesis of 3-[3-amino-4-(indan-2-yloxy)-5-(1H-indazol-5-yl)phenyl]propionic acid (Compound No. 486) (Preparation Method 1, Step a)

According to the procedure described in the synthesis method of Compound of Example 002 (Preparation Method 1, Step a) with the modification that the reaction was carried out for 1.5 hours, Compound of Example 485 (35 mg) and 2 N aqueous sodium hydroxide (100 μl) were reacted and treated to obtain the title compound (Compound No. 486, 30 mg). Mass (LCMS): 414 (M$^+$+1), retention time: 3.68 minutes (elution condition: A).

Example 487

Syntesis of methyl 3-[3-(1-ethyl-1H-indazol-5-yl)-4-(indan-2-yloxy)-5-nitrophenyl]propionate (Compound No. 487) (Preparation Method 16, Step e-1)

According to the procedure described in the synthesis method of Compound of Example 232 (Preparation Method 11, Step e) with the modifications that the reaction was carried out for 1 hour, and the purification was performed by column chromatography (Quad, hexane:ethyl acetate=4:1), Compound of Example 484 (66 mg), 60% sodium hydride (18 mg) and ethyl iodide (35 μl) were reacted and treated to obtain the title compound (Compound No. 487, 37 mg). Mass (LCMS): 486 (M$^+$+1), retention time: 5.24 minutes (elution condition: A).

Example 488

Syntesis of methyl 3-[3-amino-5-(1-ethyl-1H-indazol-5-yl)-4-(indan-2-yloxy)phenyl]propionate (Compound No. 488) (Preparation Method 2, Step b)

According to the procedure described in the synthesis method of Compound of Example 331 (Preparation Method 2, Step b) with the modifications that the reaction was carried out for 2 hours, and the purification was performed by column chromatography (Quad, hexane:ethyl acetate= 3:1), Compound of Example 487 (35 mg) was reacted and treated to obtain the title compound (Compound No. 488, 18 mg). Mass (LCMS): 456 (M$^+$+1), retention time: 4.82 minutes (elution condition: A).

Example 489

Synthesis of 3-[3-amino-5-(1-ethyl-1H-indazol-5-yl)-4-(indan-2-yloxy)phenyl]propionic acid (Compound No. 489) (Preparation Method 1, Step a)

According to the procedure described in the synthesis method of Compound of Example 002 (Preparation Method 1, Step a) with the modification that the reaction was carried out for 1.5 hours, Compound of Example 488 (16 mg) and 2 N aqueous sodium hydroxide (40 μl) were reacted and treated to obtain the title compound (Compound No. 489, 10 mg). Mass (LCMS): 442 (M$^+$+1), retention time: 4.14 minutes (elution condition: A).

Examples 490 to 509

The data of the compounds of the Compound Nos. 490 to 509 are shown in Tables 23 and 24. The substituents mentioned in the columns of "RO", "Y" and "Ar" indicate the substituents in the compound represented by the following formula (LXX):

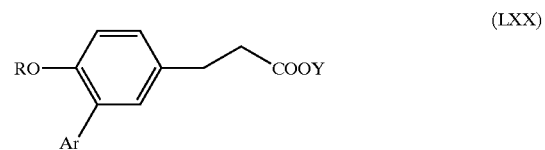

The indications used in the columns of "Ar" have the following meanings: "BdIT5", benzo[d]isothiazol-5-yl group; "BcIT5", benzo[c]isothiazol-5-yl group; "IMaP6", imidazo[1,2-a]pyridin-6-yl group; "HPbP5", 1H-pyrrolo[2,3-b]pyridin-5-yl group; "MPbP5", 1-methyl-1H-pyrrolo[2,3-b]pyridin-5-yl group; "IQ6", isoquinolin-6-yl group; and "OIQ6", 1-oxo-1,2-dihydroisoquinolin-6-yl group. Intermediates 107 to 113 mentioned in the tables were prepared as follows.

Synthesis of 5-bromo-2-t-butylthiobenzaldehyde (Intermediate 106)

A solution of 5-bromo-2-fluorobenzaldehyde (4.06 g, Avocado) in 2-propanol (20 ml) was added with 2-methyl-2-propanethiol (2.26 ml, Ald) and potassium carbonate (3.04 g) and stirred for 18 hours with heating. The reaction mixture was cooled to room temperature, then poured into water (50 ml) and extracted with chloroform (75 ml×3). The organic layer was washed twice with saturated brine and dried, and then the solvent was evaporated under reduced pressure. The residue was purified by flash column chromatography (hexane:ethyl acetate=20:1) to obtain the title compound (Intermediate 106, 754 mg). Mass (LCMS): 198 (M⁺+1), retention time: 4.62 minutes (elution condition: B).

Synthesis of 5-bromobenzo[d]isothiazole (Intermediate 107)

A solution prepared beforehand by mixing an aqueous solution (5 ml) of hydroxylamine hydrochloride (308 mg, WAKO) with 2 N aqueous sodium hydroxide (2.19 ml) was added dropwise to a solution of Intermediate 106 (401 mg) in ethanol (5 ml) at room temperature over 15 minutes. Further, the reaction mixture was refluxed by heating for 2 hours, then cooled to room temperature, poured into water (30 ml) and extracted with ethyl acetate (100 ml×3). The organic layer was successively washed with saturated aqueous ammonium chloride, saturated aqueous sodium hydrogencarbonate and saturated brine and dried, and then the solvent was evaporated under reduced pressure. The residue was added with polyphosphoric acid (21.4 g) and stirred with heating at 100° C. for 2 hours. The reaction mixture was poured into ice water (100 ml), neutralized with 5 N aqueous sodium hydroxide under ice cooling and extracted with ethyl acetate (100 ml×3). The organic layer was washed twice with saturated brine and dried, and then the solvent was evaporated under reduced pressure. The residue was purified by flash column chromatography (hexane:ethyl acetate=20:1) to obtain the title compound (Intermediate 107, 143 mg). Mass (LCMS): 214 (M⁺), retention time: 2.91 minutes (elution condition: B).

Synthesis of 5-bromobenzo[c]isothiazole (Intermediate 108)

A solution of methanesulfonamide (5.34 g, TCI) in dehydrated benzene (9 ml) was added with thionyl chloride (6.0 ml) under ice cooling and refluxed by heating for 24 hours. The reaction mixture was concentrated under reduced pressure, and a solution of the residue in dehydrated benzene (4 ml) was added dropwise to a solution of 4-bromotoluidine (1.49 g) in dehydrated benzene (40 ml) under ice cooling. This mixture was added dropwise with a solution of pyridine (0.97 ml) in dehydrated benzene (4 ml) under ice cooling and refluxed by heating for 80 hours under an argon gas atmosphere. The reaction mixture was cooled to room temperature, poured into water (100 ml) and extracted with chloroform (100 ml×3). The organic layer was dried, and then the solvent was evaporated under reduced pressure. The residue was purified by flash column chromatography (hexane:ethyl acetate=10:1) to obtain the title compound (Intermediate 108, 618 mg). Mass (LCMS): 214 (M⁺), retention time: 2.88 minutes (elution condition: B).

Synthesis of 6-bromoimidazo[1,2-a]pyridine (Intermediate 109)

According to a method known from a literature [M. Yamanaka et al., Chemical & Pharmaceutical Bulletin (Chem. Pharm. Bull.), 1991, vol. 39, p.1556], the title compound (Intermediate 109, 3.36 g) was obtained from commercially available bromoacetaldehyde-diethyl acetal (4.7 ml, WAKO) and 2-amino-5-bromopyridine (4.32 g, Ald). Mass (LCMS): 197 (M⁺), retention time: 0.73 minutes (elution condition: B).

Synthesis of 5-bromo-1H-pyrrolo[2,3-b]pyridine (Intermediate 110)

According to a method known from a literature [D. Mazeas et al., Heterocycles, 1999, vol. 50, p.1065], the title compound (Intermediate 110, 182 mg) was obtained from commercially available 1H-pyrrolo[2,3-b]pyridine (1.3 g, TCI). Mass (LCMS): 197 (M⁺), retention time: 3.44 minutes (elution condition: B).

Synthesis of 5-bromo-1-methyl-1H-pyrrolo[2,3-b]pyridine (Intermediate 111)

According to the procedure described in the synthesis method of Compound of Example 232 (Preparation Method 11, Step e) with the modifications that the reaction was carried out for 2 hours, and the purification was performed by column chromatography (Quad, hexane:ethyl acetate= 15:1), Compound of Example 110 (98 mg), 60% sodium hydride (33 mg) and methyl iodide (53 μl) were reacted and treated to obtain the title compound (Intermediate 111, 88 mg).

Synthesis of 6-bromoisoquinoline (Intermediate 112)

According to a method known from a literature [H. Nerenz et al., Journal of Chemical Society Perkin Trans 2 (J. Chem. Soc. Perkin Trans 2), 1998, p.437], the title compound (Intermediate 112, 1.46 g) was obtained from commercially available 4-bromobenzaldehyde (15.0 g, WAKO). Mass (LCMS): 208 (M⁺), retention time: 1.34 minutes (elution condition: B).

Synthesis of 6-bromo-2H-isoquinolin-1-one (Intermediate 113)

A solution of Intermediate 112 (1.04 g) in methylene chloride (3 ml) was added with a solution of 3-chloroperbenzoic acid (2.16 g) in methylene chloride (10 ml) and stirred for 20 hours. The reaction mixture was added with methylene chloride (200 ml) and washed successively with saturated aqueous sodium hydrogencarbonate, saturated aqueous ammonium chloride and saturated brine. The organic layer was dried, and then the solvent was evaporated under reduced pressure. A solution of the residue in acetic anhydride (10 ml) was refluxed by heating for 5 hours. The reaction mixture was concentrated under reduced pressure, and the residue was added with 2.5 N aqueous sodium hydroxide (20 ml) and stirred at 100° C. for 1 hour. The reaction mixture was cooled to room temperature and neutralized with 5 N aqueous hydrochloric acid under ice cooling to obtain the deposited title compound (Intermediate 113, 623 mg). Mass (LCMS): 224 (M⁺), retention time: 3.16 minutes (elution condition: B).

The other abbreviations used in the tables have the same meanings as defined above.

TABLE 23

| | | | | | | | | LCMS | |
| --- | --- | --- | --- | --- | --- | --- | --- | --- | --- |
| Exp. | Syn. | SM1 | SM2 | RO | Y | Br or Ar | method | RTime | Mass |
| 490 | 4d1 | Int.8 | Int.107 | ⌬O | Me | BdIT5 | B | 4.79 | 382 (M⁺ + 1) |
| 491 | 1a | Exp.490 | | ⌬O | H | BdIT5 | B | 3.87 | 368 (M⁺ + 1) |

TABLE 23-continued

| Exp. | Syn. | SM1 | SM2 | RO | Y | Br or Ar | LCMS method | RTime | Mass |
|---|---|---|---|---|---|---|---|---|---|
| 492 | 4d1 | Int.8 | Int.108 | cyclopentyl-O | Me | BcIT5 | B | 4.52 | 382 ($M^+ + 1$) |
| 493 | 1a | Exp.492 | | cyclopentyl-O | H | BcIT5 | B | 3.58 | 368 ($M^+ + 1$) |
| 494 | 4d1 | Int.8 | Int.109 | cyclopentyl-O | Me | IMaP6 | B | 0.45 | 365 ($M^+ + 1$) |
| 495 | 1a | Exp.494 | | cyclopentyl-O | H | IMaP6 | A | 2.57 | 351 ($M^+ + 1$) |
| 496 | 4d1 | Int.8 | Int.110 | cyclopentyl-O | Me | HPbP5 | B | 3.61 | 365 ($M^+ + 1$) |
| 497 | 1a | Exp.496 | | cyclopentyl-O | H | HPbP5 | A | 3.84 | 351 ($M^+ + 1$) |
| 498 | 4d1 | Int.8 | Int.111 | cyclopentyl-O | Me | MPbP5 | B | 4.20 | 379 ($M^+ + 1$) |
| 499 | 1a | Exp.498 | | cyclopentyl-O | H | MPbP5 | A | 4.28 | 365 ($M^+ + 1$) |

TABLE 24

| Exp. | Syn. | SM1 | SM2 | RO | Y | Br or Ar | LCMS method | RTime | Mass |
|---|---|---|---|---|---|---|---|---|---|
| 500 | 4d1 | Int.112 | Int.9 | cyclohexyl-O | Me | IQ6 | B | 3.24 | 390 ($M^+ + 1$) |
| 501 | 1a | Exp.500 | | cyclohexyl-O | H | IQ6 | B | 2.15 | 376 ($M^+ + 1$) |
| 502 | 4d1 | Int.112 | Int.8 | cyclopentyl-O | Me | IQ6 | B | 2.92 | 376 ($M^+ + 1$) |
| 503 | 1a | Exp.502 | | cyclopentyl-O | H | IQ6 | B | 1.71 | 362 ($M^+ + 1$) |
| 504 | 4d1 | Int.112 | Int.100 | 4-($F_3C$)-C$_6$H$_4$-CH$_2$-O | Me | IQ6 | B | 3.40 | 466 ($M^+ + 1$) |

TABLE 24-continued

| Exp. | Syn. | SM1 | SM2 | RO | Y | Br or Ar | LCMS method | RTime | Mass |
|---|---|---|---|---|---|---|---|---|---|
| 505 | 1a | Exp.504 | | 4-CF₃-benzyl-O | H | IQ6 | A | 3.91 | 452 (M⁺ + 1) |
| 506 | 4d1 | Int.112 | Int.98 | indan-2-yl-O | Me | IQ6 | B | 3.06 | 424 (M⁺ + 1) |
| 507 | 1a | Exp.506 | | indan-2-yl-O | H | IQ6 | A | 3.99 | 410 (M⁺ + 1) |
| 508 | 4d1 | Int.113 | Int.8 | cyclopentyl-O | Me | OIQ6 | A | 4.48 | 392 (M⁺ + 1) |
| 509 | 1a | Exp.508 | | cyclopentyl-O | H | OIQ6 | A | 3.74 | 378 (M⁺ + 1) |

The ¹H-NMR data of the compounds of Examples 430 to 509 are shown in Table 25.

TABLE 25

EXP. 430
¹H-NMR(CDCl₃): 1.40–1.53(4H, m), 1.64–1.79(4H, m), 2.66(2H, t, J=7.7), 2.96(2H, t, J=7.8), 3.68(3H, s), 4.65–4.71 (1H, m), 7.17(1H, t, J=2.3), 7.19(1H, d, J=2.2), 7.27(1H, d, J=2.4), 7.41–7.45(2H, m), 7.96(1H, m).
EXP. 431
¹H-NMR(DMSO-d₆): 1.39–1.44(4H, m), 1.49–1.58(2H, m), 1.71–1.80(2H, m), 2.56(2H, t, J=7.4), 2.82(2H, t, J=7.5), 4.72–4.76(1H, m), 7.04(1H, d, J=8.5), 7.08(1H, d, J=7.1), 7.20–7.25(2H, m), 7.36(1H, t, J=7.6), 7.48(1H, d, J=8.5), 7.80(1H, s), 12.19(1H, br-s), 12.97(1H, br-s).
EXP. 432
¹H-NMR(CDCl₃): 1.43–1.57(4H, m), 1.64–1.79(4H, m), 2.65(2H, t, J=7.7), 2.95(2H, t, J=7.7), 3.67(3H, s), 4.10(3H, s), 4.66–4.70(1H, m), 6.95(1H, d, J=8.2), 7.17(2H, d, J=6.8), 7.26(1H, d, J=1.3), 7.41(1H, d, J=6.8), 7.43(1H, d, J=6.8), 7.85(1H, s).
EXP. 433
¹H-NMR(DMSO-d₆): 1.40–1.45(4H, m), 1.50–1.58(2H, m), 1.71–1.80(2H, m), 2.55(2H, t, J=7.5), 2.82(2H, t, J=7.3), 4.05(3H, s), 4.72–4.76(1H, m), 7.04(1H, d, J=9.3), 7.11 (1H, d, J=7.1), 7.20–7.23(2H, m), 7.42(1H, t, J=7.6), 7.57(1H, d, J=8.2), 7.76(1H, s), 12.07(1H, br-s).
EXP. 434
¹H-NMR(CDCl₃): 1.45–1.52(2H, m), 1.66–1.73(4H, m), 2.01–2.04(2H, m), 2.64(2H, t, J=7.8), 2.94(2H, t, J=7.7), 3.67(3H, s), 4.19(3H, s), 4.61–4.66(1H, m), 6.94(1H, d, J=8.2), 7.10(1H, d, J=6.8), 7.14(1H, dd, J=8.1, 2.1), 7.31(1H, d, J=7.0), 7.34(1H, d, J=6.8), 7.65(1H, d, J=8.5), 7.79(1H, s).
EXP. 435
¹H-NMR(DMSO-d₆): 1.42–1.47(4H, m), 1.51–1.60(2H, m), 1.70–1.78(2H, m), 2.54(2H, t, J=7.5), 2.81(2H, t, J=7.4), 4.14(3H, s), 4.70–4.74(1H, m), 6.99–7.04(2H, m), 7.19(1H, dd, J=8.2, 2.2), 7.23–7.28(2H, m), 7.52(1H, d, J=8.5), 8.07(1H, s), 12.08(1H, br-s).
EXP. 436
¹H-NMR(CDCl₃): 1.50–1.69(4H, m), 1.76–1.81(4H, m), 2.65(2H, t, J=7.8), 2.94(2H, t, J=7.8), 3.67(3H, s), 4.68–4.74 (1H, m), 6.92(1H, d, J=8.2), 7.13(1H, dd, J=8.3, 2.3), 7.21(1H, d, J=2.1), 7.35(1H, dd, J=8.0, 1.2), 7.61(1H, m), 7.73(1H, d, J=7.6), 8.08(1H, s), 10.29(1H, br-s).
EXP. 437
¹H-NMR(DMSO-d₆): 1.48–1.57(4H, m), 1.61–1.68(2H, m), 1.75–1.84(2H, m), 2.54(2H, t, J=7.5), 2.81(2H, t, J=7.5), 4.76–4.81(1H, m), 7.02(1H, d, J=8.5), 7.16(1H, dd, J=8.2, 1.9), 7.20–7.23(2H, m), 7.59(1H, s), 7.73(1H, d, J=8.5), 8.05(1H, s), 12.10(1H, br-s), 13.02(1H, br-s).
EXP. Int. 89
¹H-NMR(CDCl₃): 4.04(3H, s), 7.22–7.26(1H, m), 7.56–7.59(2H, m), 7.94(1H, s).
EXP. 438
¹H-NMR(CDCl₃): 1.53–1.72(4H, m), 1.77–1.81(4H, m), 2.65(2H, t, J=7.7), 2.95(2H, t, J=7.8), 3.68(3H, s), 4.08(3H, s), 4.70–4.75(1H, m), 6.92(1H, d, J=8.2), 7.13(1H, dd, J=8.3, 2.0), 7.24(1H, d, J=2.4), 7.32(1H, d, J=8.5), 7.53(1H, s), 7.70(1H, d, J=8.5), 7.97(1H, s).
EXP. 439
¹H-NMR(DMSO-d₆): 1.49–1.59(4H, m), 1.62–1.69(2H, m), 1.76–1.83(2H, m), 2.55(2H, t, J=7.7), 2.82(2H, t, J=7.4), 4.05(3H, s), 4.78–4.81(1H, m), 7.02(1H, d, J=8.5), 7.18 (1H, dd, J=8.3, 2.0), 7.25–7.28(2H, m), 7.66(1H, s), 7.72(1H, d, J=8.2), 8.02(1H, s), 12.11(1H, br-s).
EXP. Int. 90
¹H-NMR(CDCl₃): 4.20(3H, s), 7.15(1H, dd, J=8.7, 1.3), 7.51(1H, d, J=8.8), 7.86–7.87(2H, m).
EXP. 440
¹H-NMR(CDCl₃): 1.48–1.57(2H, m), 1.63–1.71(3H, m), 1.78–1.82(3H, m), 2.64(2H, t, J=7.9), 2.94(2H, t, J=7.7), 3.67(3H, s), 4.22(3H, s), 4.68–4.73(1H, m), 6.91(1H, d, J=8.5), 7.11(1H, dd, J=8.3, 2.0), 7.22(1H, d, J=2.2), 7.25–7.29(1H, m), 7.60(1H, s), 7.77(1H, d, J=7.6), 7.86(1H, s).
EXP. 441
¹H-NMR(DMSO-d₆): 1.48–1.57(4H, m), 1.61–1.68(2H, m), 1.73–1.82(2H, m), 2.54(2H, t, J=7.5), 2.81(2H, t, J=7.5), 4.17(3H, s), 4.76–4.80(1H, m), 6.99(1H, d, J=8.5), 7.13–7.17(2H, m), 7.21(1H, d, J=1.0), 7.62(1H, s), 7.65(1H, d, J=8.7), 8.29(1H, s), 12.10(1H, br-s).
EXP. 442
¹H-NMR(CDCl₃): 1.52–1.69(2H, m), 1.77–1.79(4H, m), 1.93–2.10(2H, m), 2.65(2H, t, J=7.6), 2.94(2H, t, J=7.7), 3.68(3H, s), 4.68–4.73(1H, m), 6.91(1H, d, J=8.2), 7.11(1H, d, J=8.5), 7.20(1H, s), 7.48(1H, d, J=7.6), 7.58(1H, dd,

TABLE 25-continued

J=7.1, 1.6), 7.84(1H, s), 8.09(1H, s), 10.08(1H, br-s).
EXP. 443
¹H-NMR(DMSO-d₆): 1.52–1.58(4H, m), 1.59–1.69(2H, m),
1.72–1.82(2H, m), 2.54(2H, t, J=7.6), 2.80(2H, t, J=7.5),
4.74–4.76(1H, m), 6.99(1H, d, J=8.2), 7.13(1H, dd, J=8.5,
1.6), 7.19(1H, d, J=2.2), 7.46–7.53(2H, m), 7.79(1H, s),
8.07(1H, s), 12.11(1H, br-s), 13.00(1H, br-s).
EXP. 445
¹H-NMR(DMSO-d₆): 1.48–1.58(4H, m), 1.60–1.68(2H, m),
1.73–1.82(2H, m), 2.54(2H, t, J=7.5), 2.80(2H, t, J=7.4),
4.06(3H, s), 4.75–4.79(1H, m), 6.99(1H, d, J=8.2), 7.14
(1H, dd, J=8.3, 2.2), 7.20(1H, d, J=2.1), 7.53(1H, dd,
J=8.7, 1.6), 7.62(1H, d, J=8.7),
8.78(1H, s), 8.04(1H, s), 12.13(1H, br-s).
EXP. 447
¹H-NMR(DMSO-d₆): 1.47–1.58(4H, m), 1.61–1.68(2H, m),
1.71–1.83(2H, m), 2.53(2H, t, J=7.6), 2.80(2H, t, J=7.5),
4.74–4.77(1H, m), 6.98(1H, d, J=8.5), 7.12(1H, dd, J=8.6,
2.2), 7.19(1H, d, J=2.2), 7.36(1H, d, J=8.9, 1.5), 7.55(1H, d,
J=9.0), 7.71(1H, s), 8.33(1H, s), 12.13(1H, br-s).
EXP. 448
¹H-NMR(CDCl₃): 1.54(3H, t, J=7.3), 1.58–1.70(4H, m),
1.75–1.82(4H, m), 2.65(2H, t, J=7.9), 2.94(2H, t, J=7.8),
3.68(3H, s), 4.46(2H, q, J=7.1), 4.68–4.74(1H, m), 6.91(1H,
d, J=8.2), 7.10(1H, dd, J=8.3, 2.2), 7.20(1H, d, J=2.1),
7.40(1H, d, J=8.7), 7.58(1H, dd,
J=8.7, 1.6), 7.82(1H, s), 8.00(1H, s).
EXP. 449
¹H-NMR(DMSO-d₆): 1.41(3H, t, J=7.1), 1.48–1.57(4H, m),
1.61–1.67(2H, m), 1.75–1.82(2H, m), 2.54(2H, t, J=7.6),
2.81(2H, t, J=7.3), 4.45(2H, q, J=7.1), 4.75–4.79(1H, m),
6.99(1H, d, J=8.2), 7.14(1H, dd, J=8.2, 1.9), 7.20(1H, d, J=1.9),
7.52(1H, dd, J=8.6, 1.0), 7.66(1H, d, J=8.7),
7.79(1H, s), 8.05(1H, s), 12.10(1H, br-s).
EXP. 450
¹H-NMR(CDCl₃): 1.65(3H, t, J=7.3), 1.51–1.69(4H, m),
1.76–1.82(4H, m), 2.64(2H, t, J=7.8), 2.93(2H, t, J=7.8),
3.67(3H, s), 4.48(2H, q, J=7.4), 4.67–4.73(1H, m), 6.90(1H,
d, J=8.5), 7.09(1H, dd, J=8.1, 2.4), 7.20(1H, d, J=2.1),
7.48(1H, dd, J=9.0, 1.6), 7.65–7.71(2H, m), 7.93(1H, s).
EXP. 451
¹H-NMR(DMSO-d₆): 1.51(3H, t, J=7.3), 1.49–1.57(4H, m),
1.60–1.69(2H, m), 1.75–1.79(2H, m), 2.53(2H, t, J=7.5),
2.80(2H, t, J=7.4), 4.45(2H, q, J=7.3), 4.74–4.79(1H, m),
6.98(1H, d, J=8.5), 7.12(1H, dd, J=8.3, 2.2), 7.18(1H, d,
J=2.2), 7.36(1H, dd, J=8.0, 1.6), 7.56(1H, d, J=9.0),
7.71(1H, s), 8.37(1H, s), 12.10(1H, br-s).
EXP. 452
¹H-NMR(CDCl₃): 1.21–1.32(2H, m), 1.42–1.57(4H, m),
1.66–1.77(2H, m), 2.17–2.32(1H, m), 2.65(2H, t, J=7.7),
2.95(2H, t, J=7.7), 3.68(3H, s), 3.82(2H, d, J=6.5), 6.91(1H, d,
J=8.2), 7.12(1H, dd, J=8.3, 2.3), 7.22(1H, d, J=2.2),
7.49(1H, d, J=8.7), 7.62(1H, dd,
J=8.5, 1.5), 7.88(1H, s), 8.12(1H, s).
EXP. 453
¹H-NMR(DMSO-d₆): 1.23–1.30(2H, m), 1.43–1.52(4H, m),
1.62–1.68(2H, m), 2.14–2.20(1H, m), 2.50(2H, t, J=7.5),
2.80(2H, t, J=7.4), 6.99(1H, d, J=8.2), 7.11–7.14(1H, m),
7.20(1H, s), 7.51(2H, m), 7.82(1H, s), 8.07(1H, br-s), 13.04(1H, br-s).
EXP. 454
¹H-NMR(CDCl₃): 1.16–1.31(4H, m), 1.39–1.50(2H, m),
1.58–1.68(2H, m), 1.80–1.88(2H, m), 2.65(2H, t, J=7.8),
2.95(2H, t, J=7.8), 3.68(3H, s), 4.10–4.18(1H, m), 6.93(1H, d,
J=8.5), 7.10(1H, dd, J=8.3, 2.2), 7.21(1H, d, J=2.2),
7.48(1H, d, J=8.5), 7.65(1H, dd,
J=8.5, 1.4), 7.88(1H, s), 8.11(1H, s).
EXP. 455
¹H-NMR(DMSO-d₆): 1.16–1.42(6H, m), 1.52–1.58(2H, m),
1.74–1.80(2H, m), 2.53(2H, t, J=7.7), 2.79(2H, t, J=7.9),
4.22–4.28(1H, m), 7.01(1H, d, J=8.5), 7.12(1H, dd, J=8.5,
2.0), 7.19(1H, s), 7.53(2H, s), 7.82(1H, s), 8.08(1H, s), 13.04(1H, br-s).
EXP. 456
¹H-NMR(CDCl₃): 1.22–1.32(3H, m), 1.40–1.51(3H, m),
1.59–1.68(2H, m), 1.80–1.88(2H, m), 2.65(2H, t, J=7.8),
2.94(2H, t, J=7.9), 3.68(3H, s), 4.08–4.18(1H, m), 4.10(3H, s),
6.93(1H, d, J=8.2), 7.10(1H, dd, J=8.4, 2.2), 7.20(1H, d, J=2.4),
7.39(1H, d, J=8.7), 7.64(1H, dd, J=8.4, 1.5), 7.84(1H, s), 7.99(1H, s).
EXP. 457
¹H-NMR(CDCl₃): 1.22–1.31(3H, m), 1.40–1.52(3H, m),
1.59–1.65(2H, m), 1.80–1.86(2H, m), 2.70(2H, t, J=77), 2.96(2H,
t, J=7.7), 4.09(3H, s), 4.12–4.17(1H, m), 6.94(1H, d,
J=8.2), 7.11(1H, dd, J=8.3, 2.2), 7.22(1H, d, J=2.2), 7.39(1H,
d, J=8.8), 7.65(1H, dd, J=8.3, 1.5), 7.84(1H, d, J=0.5), 8.00(1H, s).
EXP. 458
¹H-NMR(CDCl₃): 1.21–1.30(3H, m), 1.40–1.52(3H, m),
1.60–1.67(2H, m), 1.78–1.87(2H, m), 2.64(2H, t, J=7.8), 2.94(2H,
t, J=7.8), 3.67(3H, s), 4.09–4.17(1H, m), 4.23(3H, s),
6.92(1H, d, J=8.2), 7.08(1H, dd, J=8.3, 2.2), 7.20(1H, d,
J=2.2), 7.53(1H, dd, J=9.0,
1.6), 7.67(1H, d, J=8.7), 7.73(1H, s), 7.90(1H, s).
EXP. 459
¹H-NMR(DMSO-d₆): 1.15–1.30(3H, m), 1.34–1.40(3H, m),
1.53–1.59(2H, m), 1.73–1.79(2H, m), 2.54(2H, t, J=7.6),
2.80(2H, t, J=7.4), 4.17(3H, s), 4.21–4.25(1H, m), 7.00(1H,
d, J=8.2), 7.12(1H, dd, J=8.4, 2.1), 7.20(1H, d, J=2.2), 7.42(1H, d,
J=8.9, 1.5), 7.57(1H, d, J=9.0), 7.75(1H, s), 8.33(1H, s), 12.10(1H, br-s).
EXP. 460
¹H-NMR(CDCl₃): 1.17–1.30(2H, m), 1.45–2.00(10H, m),
2.65(2H, t, J=7.8), 2.94(2H, t, J=7.7), 3.68(3H, s), 4.28–4.37
(1H, m), 6.88(1H, d, J=8.7), 7.11(1H, d, J=7.9, 1.8),
7.20(1H, d, J=2.1), 7.50(1H, d, J=8.2), 7.64(1H, dd, J=7.6, 1.9),
7.87(1H, s), 8.10(1H, s).
EXP. 461
¹H-NMR(DMSO-d₆): 1.24–1.69(10H, m), 1.80–1.90(2H, m),
2.53(2H, t, J=7.6), 2.80(2H, t, J=7.2), 4.35–4.46(1H, m),
6.96(1H, d, J=7.9), 7.13(1H, dd, J=8.2, 1.9), 7.19(1H,
d, J=1.9), 7.51(2H, m), 7.81(1H, s), 8.07(1H, s), 13.03(1H, br-s).
EXP. 462
¹H-NMR(CDCl₃): 0.82(6H, t, J=7.4), 1.10–1.39(5H, m),
2.65(2H, t, J=7.7), 2.95(2H, t, J=7.6), 3.68(3H, s), 3.83(2H, d,
J=5.2), 6.93(1H, d, J=8.5), 7.14(1H, dd, J=8.2, 2.0),
7.21(1H, d, J=2.1), 7.49(1H, d, J=8.7), 7.62(1H, dd,
J=8.7, 2.0), 7.86(1H, s), 8.09(1H, s).
EXP. 463
¹H-NMR(DMSO-d₆): 0.88(6H, t, J=7.4), 1.32–1.43(4H, m),
1.54–1.62(1H, m), 2.63(2H, t, J=7.8), 2.90(2H, t, J=7.1),
3.93(2H, d, J=5.4), 7.11(1H, d, J=7.1), 7.23(1H, dd, J=8.5,
2.0), 7.29(1H, s), 7.56–7.63(2H, m), 7.90(1H, d, J=1.0), 8.16(1H, s),
13.12(1H, br-s).
EXP. 464
¹H-NMR(CDCl₃): 2.66(2H, t, J=7.6), 2.96(2H, t, J=7.6),
3.11(2H, dd, J=16.2, 3.1), 3.26(2H, dd, J=16.7, 5.9), 3.69(3H, s),
5.10–5.15(1H, m), 7.00(1H, d, J=8.5), 7.14–7.17(5H,
m), 7.21(1H, d, J=2.2), 7.32(1H, d, J=8.5), 7.40(1H, dd, J=8.7,
1.6), 7.65(1H, s), 7.94(1H, s).
EXP. 465
¹H-NMR(DMSO-d₆): 2.55(2H, t, J=7.5), 2.82(2H, t,
J=7.3), 2.97(2H, dd, J=16.8, 2.3), 3.00–3.32(2H, m),
5.21–5.23(1H, m), 7.12(1H, d, J=7.5), 7.16–7.24(6H, m),
7.27(1H, dd, J=8.8, 1.3), 7.32(1H, d, J=8.2), 7.57(1H, s),
7.87(1H, s), 12.09(1H, br-s), 12.96(1H, br-s).
EXP. 466
¹H-NMR(CDCl₃): 2.66(2H, t, J=7.9), 2.97(2H, t, J=7.9),
3.11(2H, dd, J=16.6, 3.4), 3.26(2H, dd, J=16.6, 6.0), 3.69(3H, s),
4.06(3H, s), 5.11–5.13(1H, m), 6.99(1H, d, J=8.5),
7.10–7.30(5H, m), 7.40–7.48(2H, m), 7.61–7.63(1H, m),
7.85(1H, s), 7.91(1H, s).
EXP. 467
¹H-NMR(DMSO-d₆): 2.69(2H, t, J=7.7), 2.82(2H, t,
J=7.7), 2.93–3.00(2H, m), 3.26–3.35(2H, m), 4.00(3H, s),
5.21–5.22(1H, m), 6.64–6.66(1H, m), 6.93–7.01(1H, m),
7.11–7.20(4H, m), 7.35–7.37(1H, m), 7.42–7.46(1H, m),
7.56(1H, s), 7.83–7.84(1H, m), 9.14(1H, s), 11.98(1H, br-s).
EXP. 468
¹H-NMR(CDCl₃): 1.50(3H, t, J=7.3), 2.65(2H, t,
J=7.8), 2.95(2H, t, J=7.8), 3.11(1H, dd, J=16.3, 3.3),
3.26(2H, dd, J=16.4, 6.0), 3.68(3H, s), 4.40(2H, q, J=7.1),
5.08–5.15(1H, m), 6.99(1H, d, J=8.5), 7.12(1H, d, J=1.9),
7.16(3H, s), 7.20–7.22(2H, m), 7.24–7.25(1H, m), 7.40(1H,
dd, J=8.7, 1.3), 7.62(1H, s), 7.85(1H, s).
EXP. 469
¹H-NMR(DMSO-d₆): 1.37(3H, t, J=7.1), 2.56(2H, t, J=7.6),
2.82(2H, t, J=7.5), 2.97(2H, dd, J=16.9, 2.3), 3.26–3.38(2H, m),
4.39(2H, q, J=7.1), 5.21–5.25(1H, m), 7.10–7.23(7H, m),
7.35(1H, dd, J=8.9, 1.5), 7.48(1H, d, J=8.7), 7.56(1H, s), 7.84(1H,
s), 12.12(1H, br-s).
EXP. 470
¹H-NMR(CDCl₃): 2.65(2H, t, J=7.7), 2.96(2H, t, J=8.0),

TABLE 25-continued 3.68(3H, s), 5.00(2H, s), 6.94–6.99(3H, m), 7.13(1H, dd, J=8.2, 1.9), 7.21–7.26(3H, m), 7.50(1H, d, J=8.7), 7.63 (1H, dd, J=8.8, 1.3), 7.88(1H, s), 8.09(1H, s).
EXP. 471
$^1$H-NMR(DMSO-d$_6$): 2.54(2H, t, J=7.5), 2.81(2H, t, J=7.8), 5.02(2H, s), 7.09(1H, d, J=8.2), 7.12–7.18(3H, m), 7.22(1H, d, J=2.2), 7.37–7.42(2H, m), 7.53(2H, s), 7.84(1H, s), 8.07(1H, s), 12.10(1H, br-s), 13.06(1H, br-s).
EXP. 472
$^1$H-NMR(CDCl$_3$): 2.65(2H, t, J=7.7), 2.95(2H, t, J=7.8), 3.68(3H, s), 4.10(3H, s), 4.99(2H, s), 6.94–7.00(3H, m), 7.12(1H, dd, J=8.3, 2.2), 7.21–7.28(3H, m), 7.40(1H, d, J=8.5), 7.62(1H, dd, J=8.5, 1.5), 7.84(1H, d, J=0.8), 7.99(1H, d, J=0.8).
EXP. 473
$^1$H-NMR(DMSO-d$_6$): 2.54(2H, t, J=7.3), 2.81(2H, t, J=7.6), 4.05(3H, s), 5.07(2H, s), 7.10(1H, d, J=8.5), 7.12–7.18(3H, m), 7.23(1H, d, J=2.2), 7.37–7.42(2H, m), 7.56–7.63 (2H, m), 7.84(1H, s), 8.04(1H, s), 12.11(1H, br-s).
EXP. 475
$^1$H-NMR(DMSO-d$_6$): 2.55(2H, t, J=7.3), 2.82(2H, t, J=7.9), 5.21(2H, s), 7.08(1H, d, J=8.5), 7.14–7.19(1H, m), 7.25(1H, d, J=2.2), 7.55–7.58(4H, m), 7.77(2H, d, J=8.5), 7.87(1H, d, J=1.0), 8.09(1H, s), 12.11(1H, br-s).
EXP. 476
$^1$H-NMR(CDCl$_3$): 2.63(2H, t, J=7.9), 2.93(2H, t, J=7.5), 3.02(2H, t, J=6.7), 3.67(3H, s), 4.18(2H, t, J=6.7), 6.89–7.01(3H, m), 7.03–7.14(2H, m), 7.16–7.19(2H, m), 7.46(2H, m), 7.76(1H, s), 8.08(1H, s).
EXP. 477
$^1$H-NMR(DMSO-d$_6$): 2.53(2H, t, J=7.8), 2.80(2H, t, J=7.3), 2.98(2H, t, J=6.2), 4.19(2H, t, J=6.3), 7.04(2H, t, J=7.9), 7.10–7.19(3H, m), 7.26(2H, t, J=7.0), 7.34(1H, dd, J=8.6, 1.1), 7.47(1H, d, J=8.5), 7.70(1H, s), 8.04(1H, s), 12.18(1H, br-s), 12.92(1H, br-s).
EXP. 478
$^1$H-NMR(CDCl$_3$): 2.63(2H, t, J=7.6), 2.93(2H, t, J=7.8), 3.02(2H, t, J=6.8), 3.67(3H, s), 4.11(3H, s), 4.17(2H, t, J=6.6), 6.89–7.01(3H, m), 7.05–7.13(2H, m), 7.17–7.20(2H, m), 7.26–7.28(1H, m), 7.35(1H, d, J=8.5), 7.48(1H, dd, J=8.8, 1.6), 7.72(1H, m), 7.98(1H, d, J=0.8).
EXP. 479
$^1$H-NMR(DMSO-d$_6$): 2.53(2H, t, J=7.4), 2.80(2H, t, J=7.5), 2.98(2H, t, J=6.3), 4.07(3H, s), 4.19(2H, t, J=6.4), 7.04(2H, t, J=7.8), 7.09–7.19(3H, m), 7.26(2H, t, J=6.8), 7.39(1H, dd, J=8.7, 1.6), 7.56(1H, d, J=8.7), 7.68(1H, d, J=0.5), 8.01(1H, s), 12.09(1H, br-s).
EXP. Int. 102
$^1$H-NMR(CDCl$_3$): 1.36(12H, s), 2.58(3H, s), 7.73–7.77(2H, m), 7.91(1H, d, J=7.9).
EXP. Int. 103
$^1$H-NMR(CDCl$_3$): 1.32(12H, s), 2.16(3H, s), 3.82(2H, br-s), 6.66(1H, d, J=7.9), 7.49–7.51(2H, m).
EXP. Int. 104
$^1$H-NMR(CDCl$_3$): 1.41–1.72(10H, m), 2.21(3H, s), 2.63(2H, t, J=7.8), 2.91(2H, t, J=7.8), 3.68(3H, s), 4.36–4.39(1H, m), 6.71(1H, d, J=8.2), 6.84(1H, dd, J=11.4, 2.2), 6.91–6.92(1H, s), 7.22(1H, dd, J=8.0, 2.0), 7.26–7.29(1H, m).
EXP. 480
$^1$H-NMR(CDCl$_3$): 1.28–1.65(8H, m), 2.66(2H, t, J=7.7), 2.95(2H, t, J=7.7), 3.69(3H, s), 4.40–4.44(1H, m), 6.93(1H, d, J=8.2), 7.00(1H, s), 7.51(1H, d, J=8.5), 7.61(1H, dd, J=8.5, 1.5), 7.61(1H, dd, J=8.5, 1.5), 7.88(1H, s), 8.12(1H, s).
EXP. 481
$^1$H-NMR(DMSO-d$_6$): 1.23–1.39(6H, m), 1.51–1.56(2H, m), 2.59(2H, t, J=7.5), 2.84(2H, t, J=7.5), 4.34(1H, br-s), 7.11–7.15(2H, m), 7.51(1H, dd, J=8.6, 1.2), 7.58(1H, d, J=8.5), 7.87(1H, s), 8.12(1H, s), 12.21(1H, br-s), 13.06(1H, br-s).
EXP. 482
$^1$H-NMR(CDCl$_3$): 1.29–1.43(6H, m), 1.62–1.70(2H, m), 2.65(2H, t, J=7.6), 2.94(2H, t, J=7.7), 3.68(3H, s), 4.11(3H, s), 4.37–4.41(1H, m), 6.93(1H, d, J=11.8, 2.1), 6.99–7.01 (1H, m), 7.41(1H, d, J=8.5), 7.60(1H, dd, J=8.8, 1.3), 7.84(1H, s), 8.01(1H, d, J=0.8).
EXP. 483
$^1$H-NMR(DMSO-d$_6$): 1.24–1.39(6H, m), 1.51–1.56(2H, m), 2.59(2H, t, J=7.5), 2.84(2H, t, J=7.4), 4.07(3H, s), 4.31–4.34(1H, m), 7.11–7.15(2H, m), 7.56(1H, dd, J=8.8, 1.3), 7.69(1H, d, J=8.5), 7.87(1H, s), 8.09(1H, s), 12.17(1H, br-s).

EXP. Int. 105
$^1$H-NMR(CDCl$_3$): 2.13(3H, s), 2.67(2H, t, J=7.5), 2.77–2.90(4H, m), 2.98(2H, t, J=7.5), 3.69(3H, s), 4.53–4.57(1H, m), 6.67(1H, d, J=7.7), 7.01–7.11(2H, m), 7.22–7.27(1H, m), 7.32–7.37(2H, m), 7.46–7.53(3H, m).
EXP. 484
$^1$H-NMR(CDCl$_3$): 2.70(2H, t, J=7.6), 2.80–2.83(2H, m), 3.03(2H, t, J=7.5), 3.60(1H, s), 3.68(1H, s), 3.70(3H, s), 4.51–4.55(1H, m), 6.84–6.88(1H, m), 6.93–6.96(1H, m), 7.42–7.45(2H, m), 7.48(1H, d, J=2.4), 7.54(1H, dd, J=8.8, 2.2), 7.57–7.59(2H, m), 7.82–7.84(1H, m), 8.05(1H, s).
EXP. 490
$^1$H-NMR(CDCl$_3$): 1.46–1.64(4H, m), 1.66–1.73(2H, m), 1.77–1.80(2H, m), 2.65(2H, t, J=7.7), 2.95(2H, t, J=7.7), 3.68(3H, s), 4.71–4.77(1H, m), 6.93(1H, d, J=8.2), 7.15(1H, dd, J=8.3, 2.0), 7.22(1H, d, J=2.2), 7.73(1H, dd, J=8.4, 1.3), 7.94(1H, d, J=8.5), 8.16(1H, s), 8.92(1H, s).
EXP. 491
$^1$H-NMR(DMSO-d$_6$): 1.51–1.58(4H, m), 1.62–1.70(2H, m), 1.78–1.84(2H, m), 2.55(2H, t, J=7.5), 2.82(2H, t, J=7.5), 4.79–4.83(1H, m), 7.04(1H, d, J=8.2), 7.21(1H, d, J=8.7), 7.27(1H, s), 7.74(1H, t, J=8.5), 8.21(1H, d, J=8.5), 8.26(1H, s), 9.13(1H, s), 12.13(1H, br-s).
EXP. 492
2.65(2H, t, J=7.7), 2.95(2H, t, J=7.8), 3.68(3H, s), 4.71–4.77 (1H, m), 6.92(1H, d, J=8.5), 7.14(1H, dd, J=8.2, 2.2), 7.22(1H, d, J=2.4), 7.66(1H, dd, J=9.2, 1.6), 7.79–7.82(2H, m), 9.16(1H, s).
EXP. 493
$^1$H-NMR(DMSO-d$_6$): 1.48–1.60(4H, m), 1.62–1.69(2H, m), 1.75–1.83(2H, m), 2.55(2H, t, J=7.6), 2.82(2H, t, J=7.6), 4.79–4.83(1H, m), 7.03(1H, d, J=8.2), 7.19(1H, dd, J=8.3, 2.3), 7.26(1H, d, J=2.2), 7.63(1H, dd, J=9.2, 1.6), 7.77(1H, d, J=9.3), 7.92(1H, s), 9.74(1H, s), 12.12(1H, br-s).
EXP. 494
$^1$H-NMR(CDCl$_3$): 1.57–1.69(4H, m), 1.73–1.85(4H, m), 2.64(2H, t, J=7.8), 2.94(2H, t, J=7.6), 3.67(3H, s), 4.73–4.78(1H, m), 6.91(1H, d, J=8.1), 7.13–7.18(2H, m), 7.37(1H, dd, J=8.8, 1.5), 7.58–7.63(3H, m), 8.27(1H, s).
EXP. 495
$^1$H-NMR(DMSO-d$_6$): 1.51–1.61(4H, m), 1.63–1.72(2H, m), 1.78–1.86(2H, m), 2.55(2H, t, J=7.6), 2.81(2H, t, J=7.5), 4.80–4.84(1H, m), 7.03(1H, d, J=8.5), 7.20(1H, dd, J=8.5, 1.9), 7.27(1H, d, J=2.2), 7.38(1H, dd, J=9.2, 1.6), 7.53–7.57 (2H, m), 7.95(1H, s), 8.62(1H, s), 12.12(1H, br-s).
EXP. 496
$^1$H-NMR(CDCl$_3$): 1.51–1.71(4H, m), 1.78–1.81(4H, m), 2.66(2H, t, J=7.6), 2.96(2H, t, J=7.8), 3.68(3H, s), 4.71–4.76(1H, m), 6.52(1H, d, J=3.3), 6.93(1H, d, J=8.2), 7.13(1H, dd, J=8.2, 2.2), 7.21(1H, s), 7.35(1H, s), 8.07(1H, m), 8.49(1H, s), 10.23(1H, br-s).
EXP. 497
$^1$H-NMR(DMSO-d$_6$): 1.50–1.57(4H, m), 1.61–1.67(2H, m), 1.77–1.82(2H, m), 2.55(2H, t, J=7.5), 2.81(2H, t, J=7.5), 4.76–4.79(1H, m), 6.45(1H, s), 7.01(1H, d, J=8.2), 7.15 (1H, dd, J=8.5, 1.9), 7.27(1H, s), 7.45–7.48(1H, m), 7.99(1H, s), 8.38(1H, s), 11.60(1H, s), 12.12(1H, br-s).
EXP. Int. 111
$^1$H-NMR(CDCl$_3$): 3.87(3H, s), 6.39(1H, d, J=3.3), 7.19(1H, d, J=3.5), 8.01(1H, d, J=2.2), 8.34(1H, d, J=1.9).
EXP. 498
$^1$H-NMR(CDCl$_3$): 1.47–1.59(2H, m), 1.62–1.72(2H, m), 1.77–1.83(4H, m), 2.65(2H, t, J=7.8), 2.95(2H, t, J=7.7), 3.68(3H, s), 3.92(3H, s), 4.69–4.75(1H, m), 6.46(1H, d, J=3.3), 6.92(1H, d, J=8.2), 7.12(1H, dd, J=8.2, 2.2), 7.17–7.19(2H, m), 8.01(1H, d, J=1.9), 8.50(1H, d, J=1.9).
EXP. 499
$^1$H-NMR(DMSO-d$_6$): 1.50–1.58(4H, m), 1.61–1.69(2H, m), 1.77–1.85(2H, m), 2.55(2H, t, J=7.6), 2.81(2H, t, J=7.5), 3.84(3H, s), 4.77–4.81(1H, m), 6.47(1H, d, J=3.5), 7.01 (1H, d, J=8.2), 7.16(1H, d, J=8.2, 2.2), 7.21(1H, d, J=2.2), 7.51(1H, d, J=3.5), 7.99(1H, d, J=2.2), 8.36(1H, d, J=1.9), 12.10(1H, br-s).
EXP. 500
$^1$H-NMR(CDCl$_3$): 1.17–1.34(2H, m), 1.42–1.53(2H, m), 1.58–1.68(2H, m), 1.81–1.87(2H, m), 2.03–2.08(2H, m),

TABLE 25-continued 2.66(2H, t, J=7.8), 2.96(2H, t, J=7.7), 3.68(3H, s), 4.19–4.26(1H, m), 6.96(1H, d, J=8.5), 7.17(1H, dd, J=8.2, 2.2), 7.26(1H, d, J=1.9), 7.66(1H, d, J=6.0), 7.86(1H, dd, J=8.1, 1.5), 7.95–7.98(2H, m), 8.51(1H, d, J=5.7), 9.25(1H, s).
EXP. 501
$^1$H-NMR(DMSO-d$_6$): 1.18–1.60(8H, m), 1.74–1.84(2H, m), 2.56(2H, t, J=7.5), 2.83(2H, t, J=7.1), 4.31–4.41(1H, m), 7.09(1H, d, J=7.9), 7.23(1H, d, J=7.9), 7.32(1H, s), 7.82–7.89(2H, m), 8.05–8.13(2H, m), 8.50(1H, d, J=5.7), 9.31(1H, s), 12.15(1H, br-s).
EXP. 502
$^1$H-NMR(CDCl$_3$): 1.55–1.69(2H, m), 1.78–1.83(4H, m), 2.04–2.09(2H, m), 2.66(2H, t, J=7.8), 2.96(2H, t, J=7.8), 3.68(3H, s), 4.73–4.78(1H, m), 6.95(1H, d, J=8.5), 7.18(1H, dd, J=8.4, 2.1), 7.25(1H, d, J=2.1), 7.65(1H, d, J=5.7), 7.81(1H, dd, J=8.5, 1.6), 7.91–7.97(2H, m), 8.51(1H, d, J=5.7), 9.24(1H, s).
EXP. 503
$^1$H-NMR(DMSO-d$_6$): 1.52–1.57(4H, m), 1.62–1.70(2H, m), 1.75–1.84(2H, m), 2.56(2H, t, J=7.5), 2.83(2H, t, J=7.4), 4.81–4.84(1H, m), 7.06(1H, d, J=8.2), 7.24(1H, dd, J=8.3, 2.0), 7.32(1H, d, J=2.2), 7.82(2H, d, J=6.5), 8.02(1H, s), 8.11(1H, d, J=8.5), 8.50(1H, d, J=5.7), 9.30(1H, s), 12.17(1H, br-s).
EXP. 504
$^1$H-NMR(CDCl$_3$): 2.67(2H, t, J=7.7), 2.99(2H, t, J=7.7), 3.68(3H, s), 5.14(2H, s), 6.98(1H, d, J=8.3), 7.21(1H, dd, J=8.3, 2.4), 7.30(1H, d, J=2.4), 7.38(2H, d, J=8.1), 7.54 (2H, d, J=8.1), 7.66(1H, d, J=5.6), 7.83–7.86(1H, m), 7.95(1H, s), 7.99(1H, d, J=5.6), 8.54(1H, d, J=5.6), 9.29(1H, s).
EXP. 505
$^1$H-NMR(DMSO-d$_6$): 2.59(2H, t, J=7.3), 2.87(2H, t, J=7.3), 5.28(2H, s), 7.20(1H, d, J=8.9), 7.32(1H, d, J=8.9), 7.40(1H, s), 7.59(2H, d, J=8.0), 7.79(2H, d, J=8.0), 8.08 (1H, d, J=8.8), 8.15(1H, d, J=5.8), 8.28(1H, s), 8.33(1H, d, J=8.8), 8.60(1H, d, J=5.8), 9.59(1H, s), 12.05(1H, br-s).
EXP. 506
$^1$H-NMR(CDCl$_3$): 2.68(2H, t, J=7.8), 2.98(2H, t, J=7.8), 3.12(2H, dd, J=16.6, 3.0), 3.29(2H, dd, J=16.6, 5.8), 3.69(3H, s), 5.16–5.20(1H, m), 7.04(1H, d, J=8.2), 7.17–7.24(6H, m), 7.41(1H, d, J=5.8), 7.59(2H, d, J=8.6), 7.71(1H, s), 7.79(1H, d, J=8.6), 8.45(1H, d, J=5.8), 9.18(1H, s).
EXP. 507
$^1$H-NMR(DMSO-d$_6$): 2.66(2H, t, J=7.6), 2.94(2H, t, J=7.6), 3.09(2H, d, J=17.0), 3.25–3.38(2H, m), 5.35–5.43(1H, m), 7.24–7.41(7H, m), 7.63(1H, d, J=5.8), 7.71(1H, d, J=8.8), 7.90(1H, s), 8.01(1H, d, J=8.8), 8.52(1H, d, J=5.8), 9.34(1H, s), 12.21(1H, br-s).
EXP. 508
$^1$H-NMR(CDCl$_3$): 1.54–1.71(4H, m), 1.77–1.82(4H, m), 2.65(2H, t, J=7.7), 2.95(2H, t, J=7.7), 3.68(3H, s), 4.71–4.77(1H, m), 6.58(1H, d, J=7.1), 6.93(1H, d, J=8.2), 7.14–7.18(2H, m), 7.23(1H, d, J=2.2), 7.68–7.71(2H, m), 8.42(1H, d, J=8.6), 11.03(1H, br-s).
EXP. 509
$^1$H-NMR(DMSO-d$_6$): 1.53–1.59(4H, m), 1.62–1.68(2H, m), 1.75–1.84(4H, m), 2.55(2H, t, J=7.5), 2.82(2H, t, J=7.5),

TABLE 25-continued 4.79–4.82(1H, m), 6.54(1H, d, J=6.8), 7.04(1H, d, J=8.5), 7.15–7.27(3H, m), 7.59(1H, d, J=8.2), 7.72(1H, s), 8.16(1H, d, J=8.5), 11.20(1H, br-s), 12.11(1H, br-s).

Examples 510 to 567

The data of the compounds of the Compound Nos. 551 to 567 are shown in Tables 27 to 33. The indications used in the tables have the same meanings as those used in Tables 17 to 22 mentioned above. The reagents represented by the indications of "Al (number)" and "Hal (number)" mentioned in the column of "SM2 (Starting Material 2)" in the tables have the same meanings as those mentioned in Tables 2 and 3. In addition, the following indications represent the following reagents: Al72, 2-phenoxyethanol (TCI); Al73, 2-(4-chlorophenoxy)ethanol (LANC); Hal6,4-chlorobenzyl chloride (TCI); Hal7,2-(4-fluorophenoxy)ethyl bromide (ACRO); Hal8, isobutyl bromide (TCI); Hal9, n-butyl iodide (TCI); and Hal10, 2-fluorobenzyl bromide (TCI).

The starting compound, Intermediate 114 (Int. 114), was produced by the method described below.

Synthesis of 1-methyl-1H-indazole-5-boronic acid (Intermediate 114)

According to the procedure described in the synthesis method of Intermediate 52, Intermediate 92 (1.69 g), 1.6 M solution of n-butyllithium in hexane (7.50 ml) and ($^i$PrO)$_3$B (3.23 ml) were reacted to obtain the title compound (Intermediate 114, 1.39 g).

The indication of "2bn" in the columns of "Syn." in the tables means that the target compounds were produced according to the production method of the compounds described below.

Preparation Method "2bn";

Example 545

Syntesis of methyl 3-[3-amino-4-cyclopentyloxy-5-(1-methyl-1H-indazol-5-yl)phenyl]propionate (Compound No. 545) (Preparation Method 2, Step b)

A solution of Compound of Example 544 (578 mg) in a mixture of ethyl acetate (2 ml) and methanol (5 ml) was added with Raney 2800 nickel (230 mg, Ald) and stirred at room temperature for 6 hours under hydrogen atmosphere. The reaction mixture was filtered, and the solvent of the filtrate was evaporated under reduced pressure. The residue was purified by column chromatography (Quad, hexane-:ethyl acetate=5:2) to obtain the title compound (Compound No. 545, 484 mg). Mass (LCMS): 394 (M$^+$+1), retention time: 4.40 minutes (elution condition: A).

TABLE 26
| Exp. | Syn. | SM1 | SM2 | RO | Y | Z | Br or Ar | LCMS method | RTime | Mass |
|---|---|---|---|---|---|---|---|---|---|---|
| Int.115 | 4e1 | Int.6 | Hal2 | 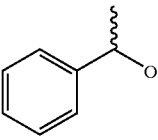 | Me | H | Br | A | 5.26 | N.D |
| 510 | 4d1b | Int.115 | Int.91 | 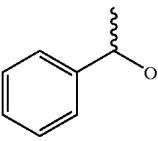 | Me | H | 1HIZ5 | A | 4.53 | 401 (M$^+$ + 1) |
| 511 | 1a | Exp.510 | | 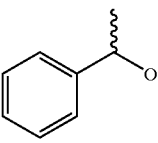 | H | H | 1HIZ5 | A | 3.98 | 387 (M$^+$ + 1) |
| 512 | 4d1a | Int.115 | Int.114 | 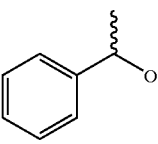 | Me | H | 1MIZ5 | A | 4.98 | 415 (M$^+$ + 1) |
| 513 | 1a | Exp.512 | | 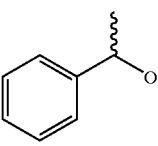 | H | H | 1MIZ5 | A | 4.33 | 401 (M$^+$ + 1) |
| Int.116 | 4e2 | Int.6 | Al35 | 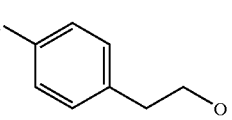 | Me | H | Br | A | 4.82 | N.D |
| 514 | 4d1a | Int.116 | Int.114 | 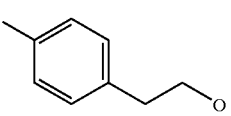 | Me | H | 1MIZ5 | A | 5.32 | 449 (M$^+$ + 1) |
| 515 | 1a | Exp.514 | | 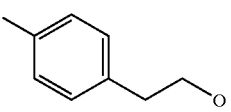 | H | H | 1MIZ5 | A | 4.47 | 435 (M$^+$ + 1) |
| Int.117 | 4e1 | Int.6 | Hal6 | 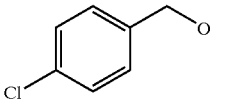 | Me | H | Br | A | 4.85 | N.D |
| 516 | 4d1a | Int.117 | Int.114 | 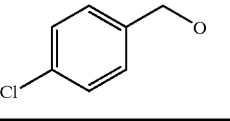 | Me | H | 1MIZ5 | A | 5.32 | 435 (M$^+$ + 1) |

TABLE 27

| Exp. | Syn. | SM1 | SM2 | RO | Y | Z | Br or Ar | LCMS method | RTime | Mass |
|---|---|---|---|---|---|---|---|---|---|---|
| 517 | 1a | Exp.516 | | 4-Cl-C6H4-CH2-O | H | H | 1MIZ5 | A | 4.36 | 421 (M+ + 1) |
| Int.118 | 4e1 | Int.6 | Hal3 | 4-Me-C6H4-CH2-O | Me | H | Br | A | 4.88 | N.D |
| 518 | 4d1a | Int.118 | Int.114 | 4-Me-C6H4-CH2-O | Me | H | 1MIZ5 | A | 5.35 | 415 (M+ + 1) |
| 519 | 1a | Exp.518 | | 4-Me-C6H4-CH2-O | H | H | 1MIZ5 | A | 4.36 | 401 (M+ + 1) |
| Int.119 | 4e1 | Int.6 | Hal7 | 4-F-C6H4-O-CH2CH2-O | Me | H | Br | A | 4.10 | N.D |
| 520 | 4d1a | Int.119 | Int.114 | 4-F-C6H4-O-CH2CH2-O | Me | H | 1MIZ5 | A | 4.81 | 449 (M+ + 1) |
| 521 | 1a | Exp.520 | | 4-F-C6H4-O-CH2CH2-O | H | H | 1MIZ5 | A | 4.19 | 435 (M+ + 1) |
| Int120 | 4e2 | Int.6 | Al34 | 4-F-C6H4-CH2CH2-O | Me | H | Br | A | 4.78 | N.D |
| 522 | 4d1a | Int.120 | Int.114 | 4-F-C6H4-CH2CH2-O | Me | H | 1MIZ5 | A | 5.25 | 433 (M+ + 1) |
| 523 | 1a | Exp.522 | | 4-F-C6H4-CH2CH2-O | H | H | 1MIZ5 | A | 4.36 | 419 (M+ + 1) |

TABLE 28

| Exp. | Syn. | SM1 | SM2 | RO | Y | Z | Br or Ar | LCMS method | RTime | Mass |
|---|---|---|---|---|---|---|---|---|---|---|
| Int.121 | 4e1 | Int.6 | Hal8 | iBu-CH2-O | Me | H | Br | A | 5.34 | N.D |

TABLE 28-continued

| Exp. | Syn. | SM1 | SM2 | RO | Y | Z | Br or Ar | LCMS method | RTime | Mass |
|---|---|---|---|---|---|---|---|---|---|---|
| 524 | 4d1b | Int.121 | Int.91 | isobutoxy | Me | H | 1HIZ5 | A | 4.62 | 353 (M$^+$ + 1) |
| 525 | 1a | Exp.524 | | isobutoxy | H | H | 1HIZ5 | A | 4.00 | 339 (M$^+$ + 1) |
| 526 | 4d1a | Int.121 | Int.114 | isobutoxy | Me | H | 1MIZ5 | A | 5.06 | 367 (M$^+$ + 1) |
| 527 | 1a | Exp.526 | | isobutoxy | H | H | 1MIZ5 | A | 4.26 | 353 (M$^+$ + 1) |
| Int.122 | 4e2 | Int.6 | Al48 | 4-(dimethylamino)phenethoxy | Me | H | Br | A | 4.84 | 406 (M$^+$ + 1) |
| 528 | 4d1a | Int.122 | Int.114 | 4-(dimethylamino)phenethoxy | Me | H | 1MIZ5 | A | 4.56 | 458 (M$^+$ + 1) |
| 529 | 1a | Exp.528 | | 4-(dimethylamino)phenethoxy | H | H | 1MIZ5 | A | 3.60 | 444 (M$^+$ + 1) |
| Int.123 | 4e1 | Int.6 | Hal9 | n-butoxy | Me | H | Br | A | 5.34 | N.D |
| 530 | 4d1a | Int.123 | Int.114 | n-butoxy | Me | H | 1MIZ5 | A | 5.04 | 367 (M$^+$ + 1) |

TABLE 29

| Exp. | Syn. | SM1 | SM2 | RO | Y | Z | Br or Ar | LCMS method | RTime | Mass |
|---|---|---|---|---|---|---|---|---|---|---|
| 531 | 1a | Exp.530 | | n-butoxy | H | H | 1MIZ5 | A | 4.25 | 353 (M$^+$ + 1) |
| Int.124 | 4e1 | Int.6 | Hal10 | 2-fluorobenzyloxy | Me | H | Br | A | 5.12 | N.D |
| 532 | 4d1a | Int.124 | Int.114 | 2-fluorobenzyloxy | Me | H | 1MIZ5 | A | 4.92 | 419 (M$^+$ + 1) |

TABLE 29-continued

| Exp. | Syn. | SM1 | SM2 | RO | Y | Z | Br or Ar | LCMS method | RTime | Mass |
|---|---|---|---|---|---|---|---|---|---|---|
| 533 | 1a | Exp.532 | | 2-F-benzyloxy | H | H | 1MIZ5 | A | 4.15 | 405 (M+ + 1) |
| 534 | 4d1a | Int.100 | Int.114 | 4-CF3-benzyloxy | Me | H | 1MIZ5 | A | 5.24 | 469 (M+ + 1) |
| 535 | 1a | Exp.534 | | 4-CF3-benzyloxy | H | H | 1MIZ5 | A | 4.54 | 455 (M+ + 1) |
| Int.125 | 4e2 | Int.6 | Al72 | PhOCH2CH2O | Me | H | Br | A | 5.04 | N.D |
| 536 | 4d1a | Int.125 | Int.114 | PhOCH2CH2O | Me | H | 1MIZ5 | A | 4.88 | 431 (M+ + 1) |
| 537 | 1a | Exp.536 | | PhOCH2CH2O | H | H | 1MIZ5 | A | 4.14 | 417 (M+ + 1) |
| Int.126 | 4e2 | Int.6 | Al73 | 4-Cl-PhOCH2CH2O | Me | H | Br | A | 5.37 | N.D |

TABLE 30

| Exp. | Syn. | SM1 | SM2 | RO | Y | Z | Br or Ar | LCMS method | RTime | Mass |
|---|---|---|---|---|---|---|---|---|---|---|
| 538 | 4d1a | Int.126 | Int.114 | 4-Cl-PhOCH2CH2O | Me | H | 1MIZ5 | A | 5.15 | 465 (M+ + 1) |
| 539 | 1a | Exp.538 | | 4-Cl-PhOCH2CH2O | H | H | 1MIZ5 | A | 4.44 | 451 (M+ + 1) |
| Int.127 | 4e1 | Int.6 | Al31 | (R)-1-phenylethoxy | Me | H | Br | A | 5.26 | N.D |

TABLE 30-continued

| Exp. | Syn. | SM1 | SM2 | RO | Y | Z | Br or Ar | LCMS method | RTime | Mass |
|---|---|---|---|---|---|---|---|---|---|---|
| 540 | 4d1b | Int.127 | Int.91 | benzyl-O | Me | H | 1HIZ5 | A | 4.50 | 401 (M$^+$ + 1) |
| 541 | 1a | Exp.540 | | benzyl-O | H | H | 1HIZ5 | A | 3.92 | 387 (M$^+$ + 1) |
| 542 | 4d1a | Int.127 | Int.114 | benzyl-O | Me | H | 1MIZ5 | A | 4.99 | 415 (M$^+$ + 1) |
| 543 | 1a | Exp.542 | | benzyl-O | H | H | 1MIZ5 | A | 4.30 | 401 (M$^+$ + 1) |
| 544 | 4d1a | Int.74 | Int.114 | cyclopentyl-O | Me | NO2 | 1MIZ5 | A | 4.87 | 424 (M$^+$ + 1) |
| 545 | 2bn | Exp.544 | | cyclopentyl-O | Me | NH2 | 1MIZ5 | A | 4.40 | 394 (M$^+$ + 1) |
| 546 | 1a | Exp.545 | | cyclopentyl-O | H | NH2 | 1MIZ5 | A | 3.80 | 380 (M$^+$ + 1) |

TABLE 31

| Exp. | Syn. | SM1 | SM2 | RO | Y | Z | Br or Ar | LCMS method | RTime | Mass |
|---|---|---|---|---|---|---|---|---|---|---|
| 547 | 4d1b | Int.84 | Int.91 | benzyl-O | Me | NO2 | 1HIZ5 | A | 5.04 | ND |
| 548 | 2bn | Exp.547 | | benzyl-O | Me | NH2 | 1HI25 | A | 3.93 | 416 (M$^+$ + 1) |
| 549 | 1a | Exp.548 | | benzyl-O | H | NH2 | 1HIZ5 | A | 3.46 | 402 (M$^+$ + 1) |

TABLE 31-continued

| Exp. | Syn. | SM1 | SM2 | RO | Y | Z | Br or Ar | LCMS method | RTime | Mass |
|---|---|---|---|---|---|---|---|---|---|---|
| 550 | 4d1a | Int.84 | Int.114 | (S)-1-phenylethoxy | Me | NO2 | 1MIZ5 | A | 483 | 460 (M⁺ + 1) |
| 551 | 2bn | Exp.550 | | (S)-1-phenylethoxy | Me | NH2 | 1MIZ5 | A | 4.47 | 430 (M⁺ + 1) |
| 552 | 1a | Exp.551 | | (S)-1-phenylethoxy | H | NH2 | 1MIZ5 | A | 3.76 | 416 (M⁺ + 1) |
| Int.128 | 4e1 | Int.77 | Hal5 | 4-F-benzyloxy | Me | NO2 | Br | A | 5.10 | N.D |
| 553 | 4d1a | Int.128 | Int.114 | 4-F-benzyloxy | Me | NO2 | 1MIZ5 | A | 4.87 | 464 (M⁺ + 1) |
| 554 | 2bn | Exp.552 | | 4-F-benzyloxy | Me | NH2 | 1MIZ5 | A | 4.38 | 434 (M⁺ + 1) |
| 555 | 1a | Exp.553 | | 4-F-benzyloxy | H | NH2 | 1MIZ5 | A | 3.72 | 420 (M⁺ + 1) |

TABLE 32

| Exp. | Syn. | SM1 | SM2 | RO | Y | Z | Br or Ar | LCMS method | RTime | Mass |
|---|---|---|---|---|---|---|---|---|---|---|
| Int.129 | 4e2 | Int.77 | Al34 | 2-(4-F-phenyl)ethoxy | Me | NO2 | Br | A | 5.29 | N.D |
| 556 | 4d1a | Int.129 | Int.114 | 2-(4-F-phenyl)ethoxy | Me | NO2 | 1MIZ5 | A | 5.02 | 478 (M⁺ + 1) |
| 557 | 2bn | Exp.555 | | 2-(4-F-phenyl)ethoxy | Me | NH2 | 1MIZ5 | A | 4.48 | 448 (M⁺ + 1) |

TABLE 32-continued

| | | | | | | | | LCMS | | |
|---|---|---|---|---|---|---|---|---|---|---|
| Exp. | Syn. | SM1 | SM2 | RO | Y | Z | Br or Ar | method | RTime | Mass |
| 558 | 1a | Exp.556 | | 4-F-C6H4-CH2CH2-O- | H | NH2 | 1M1Z5 | A | 3.86 | 434 (M+ + 1) |
| Int.130 | 4e2 | Int.77 | Al48 | 4-(Me2N)-C6H4-CH2CH2-O- | Me | NO2 | Br | A | 4.82 | 451 (M+ + 1) |
| 559 | 4d1a | Int.130 | Int.114 | 4-(Me2N)-C6H4-CH2CH2-O- | Me | NO2 | 1MIZ5 | A | 4.54 | 503 (M+ + 1) |
| 560 | 2bn | Exp.558 | | 4-(Me2N)-C6H4-CH2CH2-O- | Me | NH2 | 1MIZ5 | A | 3.73 | 473 (M+ + 1) |
| 561 | 1a | Exp.559 | | 4-(Me2N)-C6H4-CH2CH2-O- | H | NH2 | 1MIZ5 | A | 3.12 | 459 (M+ + 1) |
| Int.131 | 4e1 | Int.77 | Hal8 | iBuO- | Me | NO2 | Br | A | 5.34 | N.D |
| 562 | 4d1a | Int.131 | Int.114 | iBuO- | Me | NO2 | 1MIZ5 | A | 5.02 | 412 (M+ + 1) |

TABLE 33

| | | | | | | | | LCMS | | |
|---|---|---|---|---|---|---|---|---|---|---|
| Exp. | Syn. | SM1 | SM2 | RO | Y | Z | Br or Ar | method | RTime | Mass |
| 563 | 2bn | Exp.561 | | iBuO- | Me | NH2 | 1MIZ5 | A | 4.30 | 382 (M+ + 1) |
| 564 | 1a | Exp.562 | | iBuO- | H | NH2 | 1MIZ5 | A | 3.66 | 368 (M+ + 1) |
| 565 | 4d1a | Int.81 | Int.114 | 2-indanyl-O- | Me | NO2 | 1MIZ5 | A | 5.08 | 472 (M+ + 1) |
| 566 | 2bn | Exp.564 | | 2-indanyl-O- | Me | NH2 | 1MIZ5 | A | 4.77 | 442 (M+ + 1) |

TABLE 33-continued

| | | | | | | | | | LCMS | |
|---|---|---|---|---|---|---|---|---|---|---|
| Exp. | Syn. | SM1 | SM2 | RO | Y | Z | Br or Ar | method | RTime | Mass |
| 567 | 1a | Exp.565 | | 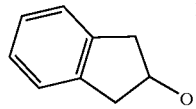 | H | NH2 | 1MI75 | A | 4.14 | 428 (M$^+$ + 1) |

Example 568
Synthesis of 3-[4-cyclopentylmethyloxy-3-hydroxy-5-(naphthalen-2-yl)phenyl]propionic acid (Compound No. 568)

A solution of Compound of Example 94 (403 mg) in acetic acid (1.5 ml) was added with 20% sulfuric acid (1.0 ml). The mixture was added dropwise with an aqueous solution (0.5 ml) of sodium nitrite (76 mg) over 10 minutes and further stirred for 5 minutes, while the temperature of the mixture was maintained below 10° C. This reaction solution was added dropwise to a solution of sodium acetate (328 mg) in acetic acid (3.5 ml), which was heated to 100° C. and stirred beforehand, over 5 minutes and further stirred for 10 minutes with heating. The reaction solution was poured into ice water (50 ml) and extracted with isopropyl ether (100 ml×2). The organic layer was washed successively with saturated aqueous sodium hydrogencarbonate, saturated ammonium chloride and saturated brine and dried, and the solvent was evaporated under reduced pressure. The residue was purified by column chromatography (Quad, hexane:ethyl acetate=10:1). The substance obtained above was reacted with 2 N aqueous sodium hydroxide (500 μl) and treated according to the procedure described in the synthesis method of Compound of Example 002 (Preparation Method 1, Step a) to obtain the title compound (Compound No. 510, 78 mg). Mass (LCMS): 391 (M$^+$+1), retention time: 5.03 minutes (elution condition: A).

Example 569
Synthesis of 3-[4-(indan-2-yloxy)-3-hydroxy-5-(1-methyl-1H-indazol-5-yl)phenyl]propionic acid (Compound No. 569)

According to the procedure described in the synthesis method of Compound of Example 568, Compound of Example 566 (441 mg) was reacted and treated to obtain the title compound (Compound No. 569, 151 mg). Mass (LCMS): 429 (M$^+$+1), retention time: 3.91 minutes (elution condition: A).

Example 570
Synthesis of 4-cyclopentyloxy-3-methylbenzaldehyde (Intermediate 132) (Step e-1)

According to the procedure described in the synthesis method of the Intermediate 7 in Reference Example 2 (Step e-1) with the modifications that the reaction was carried out for 16 hours, and the purification was performed by column chromatography (Quad, hexane:ethyl acetate=9:1), 4-hydroxy-3-methylbenzaldehyde (283 mg, TCI), potassium carbonate (578 mg) and bromocyclopentane (430 μl) were reacted and treated to obtain the title compound (Intermediate 132, 350 mg). Mass (LCMS): 205 (M$^+$+1), retention time: 5.01 minutes (elution condition: A).

Synthesis of ethyl 3-(4-cyclopentyl-3-methylphenyl) Acrylate (Intermediate 133) (Step k)

According to the procedure described in the synthesis method of Intermediate 38 in Example 65 (Preparation Method 6, Step k) with the modifications that the reaction was carried out for 2 hours, and the purification was performed by column chromatography (Quad, hexane:ethyl acetate=9:1), Intermediate 132 (342 mg), ethyl diethylphosphonoacetate (408 μl) and 60% sodium hydride (82 mg) were reacted and treated to obtain the title compound (Intermediate 133, 450 mg). Mass (LCMS): 275 (M$^+$+1), retention time: 6.01 minutes (elution condition: A).

Synthesis of ethyl 3-(4-cyclopentyl-3-methylphenyl) propionate (Intermediate 134) (Step j)

According to the procedure described in the synthesis method of Compound of Example 065 (Preparation Method 6, Step j), Intermediate 133 (446 mg) and 10% palladium carbon (20 mg) were reacted under hydrogen gas atmosphere and treated to obtain the title compound (Intermediate 134, 439 mg). Mass (LCMS): N.D, retention time: 5.80 minutes (elution condition: A).

Synthesis of ethyl 3-(3-bromo-4-cyclopentyl-5-methylphenyl)propionate (Intermediate 135) (Step g)

According to the procedure described in the synthesis method of Intermediate 3 in Reference Example 1 (Step g), Intermediate 134 (437 mg) and NBS (320 mg) were reacted and treated to obtain the title compound (Intermediate 135, 545 mg). Mass (LCMS): N.D, retention time: 5.82 minutes (elution condition: A).

Synthesis of 3-[4-cyclopentyloxy-3-methyl-5-(naphthalen-2-yl)phenyl]propionic acid (Compound No. 570) (Preparation Method 4, Step d-1 and Preparation Method 1, Step a)

According to the procedure described in the synthesis method of Compound of Example 001 (Preparation Method 4, Step d-1) with the modifications that the reaction was carried out at 80° C. for 6 hours, and the purification was performed by column chromatography (Quad, hexane:ethyl acetate=20:1), Intermediate 135 (63 mg), 2-naphthaleneboronic acid (67 mg), 2 M aqueous sodium carbonate (130 μl) and (Ph$_3$P)$_4$Pd (18 mg) were reacted and treated. The substance obtained above was reacted with 2 N aqueous sodium hydroxide (200 μl) and treated according to the procedure described in the synthesis method of Compound of Example 002 (Preparation Method 1, Step a) to obtain the title compound (Compound No. 570, 25 mg). Mass (LCMS): 375 (M$^+$+1), retention time: 5.65 minutes (elution condition: A).

Example 571
Synthesis of 3-[4-cyclopentyloxy-3-(1H-indol-5-yl)-5-methylphenyl]propionic acid (Compound No. 571) (Preparation Method 4, Step d-1 and Preparation Method 1, Step a)

According to the procedure described in the synthesis method of Compound of Example 570 (Preparation Method 4, Step d-1 and Preparation Method 1, Step a), Intermediate 135 (109 mg) and 5-indoleboronic acid (101 mg) were reacted and treated to obtain the title compound (Compound No. 571, 36 mg). Mass (LCMS): 364 (M⁺+1), retention time: 4.64 minutes (elution condition: A).

Example 572

Synthesis of 3-[4-cyclopentyloxy-3-methyl-5-(1-methyl-1H-indazol-5-yl)phenyl]propionic acid (Compound No. 572) (Preparation Method 4, Step d-1 and Preparation Method 1, Step a)

According to the procedure described in the synthesis method of Compound of Example 570 (Preparation Method 4, Step d-1 and Preparation Method 1, Step a), Intermediate 135 (292 mg) and Intermediate 114 (252 mg) were reacted and treated to obtain the title compound (Compound No. 572, 54 mg). Mass (LCMS): 379 (M⁺+1), retention time: 4.55 minutes (elution condition: A).

Example 573

Synthesis of 5-bromo-3-methyl-1H-indazole (Intermediate 136)

According to the aforementioned known method described in a reference [Bioorg. Med. Chem. Lett., 2001, vol. 11, p.1153], the title compound (Intermediate 136, 3.30 g) was obtained from commercially available 4-bromo-2-ethylaniline (5.01 g, LANC). Mass (LCMS): 211 (M+), retention time: 3.76 minutes (elution condition:A).

Syntesis of methyl 3-[4-cyclopentyloxy-3-(3-methyl-1H-indazol-5-yl)phenyl]propionate (Compound No. 573) (Preparation Method 4, Step d-1)

According to the procedure described in the synthesis method of Compound of Example 019 (Preparation Method 4, Step d-1) with the modification that the purification was performed by column chromatography (Quad, hexane:ethyl acetate=5:2), Intermediate 8 (434 mg), bis(pinacolate)diboron (367 mg), PdCl₂(dppf) (101 mg) and potassium acetate (339 mg) were reacted at 80° C. for 4 hours, then the reaction mixture was added with Intermediate 136 (273 mg), PdCl₂(dppf) (104 mg) and 2 M aqueous sodium carbonate (1.1 ml), reacted and treated at 80° C. for 18 hours to obtain the title compound (Compound No. 573, 98 mg). Mass (LCMS): 379 (M⁺+1), retention time: 4.88 minutes (elution condition: A).

Example 574

Synthesis of 3-[4-cyclopentyloxy-3-(3-methyl-1H-indazol-5-yl)phenyl]propionic acid (Compound No. 574) (Preparation Method 1, Step a)

According to the procedure described in the synthesis method of Compound of Example 002 (Preparation Method 1, Step a) with the modification that the reaction was carried out for 2 hours, Compound of Example 573 (97 mg) and 2 N aqueous sodium hydroxide (400 µl) to obtain the title compound (Compound No. 574, 54 mg). Mass (LCMS): 365 (M⁺+1), retention time: 3.99 minutes (elution condition: A).

Example 575

Syntesis of methyl 3-[4-cyclopentyloxy-3-(1,3-dimethyl-1H-indazol-5-yl)phenyl]propionate (Compound No. 575) (Preparation Method 16, Step e-1)

According to the procedure described in the synthesis method of Compound of Example 232 (Preparation Method 11, Step e) with the modifications that the reaction was carried out for 16 hours, and the purification was performed by column chromatography (Quad, hexane:ethyl acetate=3:1), Compound of Example 573 (112 mg), 60% sodium hydride (24 mg) and methyl iodide (95 µl) were reacted and treated to obtain the title compound (Compound No. 575, 45 mg). Mass (LCMS): 393 (M⁺+1), retention time: 5.30 minutes (elution condition: A).

Example 576

Synthesis of 3-[4-cyclopentyloxy-3-(1,3-dimethyl-1H-indazol-5-yl)phenyl]propionic acid (Compound No. 576) (Preparation Method 1, Step a)

According to the procedure described in the synthesis method of Compound of Example 002 (Preparation Method 1, Step a) with the modification that the reaction was carried out for 3 hours, Compound of Example 575 (45 mg) and 2 N aqueous sodium hydroxide (120 µl) were reacted and treated to obtain the title compound (Compound No. 576, 42 mg). Mass (LCMS): 379 (M⁺+1), retention time: 4.46 minutes (elution condition: A).

Example 577

Synthesis of 3-bromo-4-(t-butyldimethylsilyloxy)-5-methoxybenzaldehyde (Intermediate 137) (Step i)

According to the procedure described in the synthesis method of Compound of Example 129, Intermediate 53 (Preparation Method 5, Step i), with the modifications that the reaction was carried out for 3 hours, and the purification was performed by flash column chromatography (hexane:ethyl acetate=9:1), 3-bromovanilline (1.16 g, TCI), imidazole (408 mg), 4-(N,N-dimethylamino)pyridine (25 mg) and butyldimethylsilyl chloride (904 mg) were reacted and treated to obtain the title compound (Intermediate 137, 1.75 g). Mass (LCMS): N.D, retention time: 5.64 minutes (elution condition: A).

Synthesis of 4-(t-butyldimethylsilyloxy)-3-(1H-indol-5-yl)-5-methoxybenzaldehyde (Intermediate 138) (Step d)

According to the procedure described in the synthesis method of Compound of Example 001 (Preparation Method 4, Step d-1) with the modifications that the reaction was carried out for 12.5 hours, and the purification was performed by flash column chromatography (hexane:ethyl acetate=7:1), 5-indoleboronic acid (1.29 g), Intermediate 137 (1.75 g), 2 M aqueous sodium carbonate (4.8 ml) and (Ph₃P)₄Pd (400 mg) were reacted and treated to obtain the title compound (Intermediate 138, 910 mg). Mass (LCMS): 382 (M⁺+1), retention time: 4.90 minutes (elution condition: A).

Synthesis of ethyl 3-[4-(t-butyldimethylsilyloxy)-3-(1H-indol-5-yl)-5-methoxyphenyl]acrylate (Intermediate 139) (Step k)

According to the procedure described in the synthesis method of Intermediate 38 in Example 65 (Preparation Method 6, Step k) with the modifications that the reaction was carried out for 1.5 hours, and the purification was performed by flash column chromatography (hexane:ethyl acetate=3:1), Intermediate 138 (910 mg), ethyl diethylphosphonoacetate (500 µl) and 60% sodium hydride (100 mg) were reacted and treated to obtain the title compound (Intermediate 139, 945 mg). Mass (LCMS): 452 (M⁺+1), retention time: 5.69 minutes (elution condition: A).

Synthesis of ethyl 3-[4-(t-butyldimethylsilyloxy)-3-(1H-indol-5-yl)-5-methoxyphenyl]propionate (Intermediate 140) (Step j)

According to the procedure described in the synthesis method of Compound of Example 065 (Preparation Method 6, Step j), Intermediate 139 (945 mg) and 10% palladium carbon (95 mg) were reacted under hydrogen gas atmosphere and treated to obtain the title compound (Intermediate 140, 940 mg). Mass (LCMS): 454 (M⁺+1), retention time: 5.40 minutes (elution condition: B).

Synthesis of ethyl 3-[4-hydroxy-3-(1H-indol-5-yl)-5-methoxyphenyl]propionate (Intermediate 141) (Preparation Method 5, Step h)

According to the procedure described in the synthesis method of Compound of Example 129, Intermediate 55

(Preparation Method 5, Step h), with the modifications that the reaction was carried out for 1.5 hours, and the purification was performed by flash column chromatography (hexane:ethyl acetate=2:1), Intermediate 140 (750 mg) and 1 M solution of tetrabutylammonium fluoride in THF (5.0 ml) were reacted and treated to obtain the title compound (Intermediate 141, 555 mg). Mass (LCMS): 340 ($M^+$+1), retention time: 4.10 minutes (elution condition: A).

Synthesis of ethyl 3-[4-cyclopentyloxy-3-(1H-indol-5-yl)-5-methoxyphenyl]propionate (Compound No. 577) (Preparation Method 5, Step e-2)

According to the procedure described in the synthesis method of Compound of Example 038 (Preparation Method 5, Step e-2) with the modifications that the reaction was carried out for 16 hours, and the purification was performed by column chromatography (Quad, hexane:ethyl acetate= 7:1), Intermediate 141 (340 mg), $Ph_3P$ (1.31 g), cyclopentanol (450 µl) and TMAD (860 mg) were reacted and treated to obtain the title compound (Compound No. 577, 376 mg). Mass (LCMS): 408 ($M^+$+1), retention time: 5.24 minutes (elution condition: A).

Example 578

Synthesis of 3-[4-cyclopentyloxy-3-(1H-indol-5-yl)-5-methoxyphenyl]propionic acid (Compound No. 578) (Preparation Method 1, Step a)

According to the procedure described in the synthesis method of Compound of Example 002 (Preparation Method 1, Step a) with the modification that the reaction was carried out for 2 hours, Compound of Example 577 (99 mg) and 2 N aqueous sodium hydroxide (500 µl) were reacted and treated to obtain the title compound (Compound No. 578, 76 mg). Mass (LCMS): 380 ($M^+$+1), retention time: 4.26 minutes (elution condition: A).

Example 579

Synthesis of ethyl 3-[4-cyclopentyloxy-3-methoxy-5-(1-methyl-1H-indol-5-yl)phenyl]propionate (Compound No. 579) (Preparation Method 11, Step e)

According to the procedure described in the synthesis method of Compound of Example 232 (Preparation Method 11, Step e) with the modifications that the reaction was carried out for 2 hours, and the purification was performed by column chromatography (Quad, hexane:ethyl acetate= 6:1), Compound of Example 577 (115 mg), 60% sodium hydride (25 mg) and methyl iodide (60 µl) were reacted and treated to obtain the title compound (Compound No. 579, 110 mg). Mass (LCMS): 422 ($M^+$+1), retention time: 5.67 minutes (elution condition: A).

Example 580

Synthesis of 3-[4-cyclopentyloxy-3-methoxy-5-(1-methyl-1H-indol-5-yl)phenyl]propionic acid (Compound No. 580) (Preparation Method 1, Step a)

According to the procedure described in the synthesis method of Compound of Example 002 (Preparation Method 1, Step a) with the modification that the reaction was carried out for 2 hours, Compound of Example 579 (105 mg) and 2 N aqueous sodium hydroxide (300 µl) were reacted and treated to obtain the title compound (Compound No. 580, 86 mg). Mass (LCMS): 394 ($M^+$+1), retention time: 4.72 minutes (elution condition: A).

Example 581

Synthesis of ethyl 3-[4-cyclopentyloxy-3-(1-ethyl-1H-indol-5-yl)-5-methoxyphenyl]propionate (Compound No. 581) (Preparation Method 11, Step e)

According to the procedure described in the synthesis method of Compound of Example 232 (Preparation Method 11, Step e) with the modifications that the reaction was carried out for 3 hours, and the purification was performed by column chromatography (Quad, hexane:ethyl acetate= 7:1), Compound of Example 577 (118 mg), 60% sodium hydride (28 mg) and ethyl iodide (60 µl) were reacted and treated to obtain the title compound (Compound No. 581, 116 mg). Mass (LCMS): 436 ($M^+$+1), retention time: 5.94 minutes (elution condition: A).

Example 582

Synthesis of 3-[4-cyclopentyloxy-3-(1-ethyl-1H-indol-5-yl)-5-methoxyphenyl]propionic acid (Compound No. 582) (Preparation Method 1, Step a)

According to the procedure described in the synthesis method of Compound of Example 002 (Preparation Method 1, Step a) with the modification that the reaction was carried out for 3 hours, Compound of Example 581 (116 mg) and 2 N aqueous sodium hydroxide (300 µl) were reacted and treated to obtain the title compound (Compound No. 582, 112 mg). Mass (LCMS): 408 ($M^+$+1), retention time: 4.98 minutes (elution condition: A).

Example 583

Syntesis of methyl 3-[4-cyclopentylmethyloxy-3-(2-methyl-1H-indol-5-yl)phenyl]propionate (Compound No. 583) (Preparation Method 4, Step d-1)

According to the procedure described in the synthesis method of Compound of Example 011 (Preparation Method 4, Step d-1) with the modifications that the reaction was carried out for 18 hours, and the purification was performed by column chromatography (Quad, hexane:ethyl acetate= 10:1), 5-bromo-2-methylindole (660 mg, Ald), 30% potassium hydride (240 mg), 1.7 M solution of t-butyllithium in pentane (1.75 ml) and ($^i$PrO)$_3$B (690 µl) were reacted and treated to obtain crude 2-methyl-5indoleboronic acid, and this product, Intermediate 3 (336 mg), 2 M aqueous sodium carbonate (0.9 ml) and ($Ph_3P$)$_4$Pd (118 mg) were reacted and treated to obtain the title compound (Compound No. 583, 320 mg). Mass (LCMS): 392 ($M^+$+1), retention time: 5.69 minutes (elution condition: A).

Example 584

Synthesis of 3-[4-cyclopentylmethyloxy-3-(2-methyl-1H-indol-5-yl)phenyl]propionic acid (Compound No. 584) (Preparation Method 1, Step a)

According to the procedure described in the synthesis method of Compound of Example 002 (Preparation Method 1, Step a) with the modification that the reaction was carried out for 1 hour, Compound of Example 583 (112 mg) and 2 N aqueous sodium hydroxide (300 µl) were reacted and treated to obtain the title compound (Compound No. 584, 104 mg). Mass (LCMS): 378 ($M^+$+1), retention time: 4.93 minutes (elution condition: A).

Example 585

Syntesis of methyl 3-[3-(1-ethoxycarbonylmethyl-1H-indol-5-yl)-4-cyclopentylmethyloxyphenyl]propionate (Intermediate 142) (Preparation Method 11, Step e)

According to the procedure described in the synthesis method of Compound of Example 232 (Preparation Method 11, Step e) with the modifications that the reaction was carried out for 2.5 hours, and the purification was performed by column chromatography (Quad, hexane:ethyl acetate= 10:1), Compound of Example 099 (127 mg), 60% sodium hydride (22 mg) and ethyl bromoacetate (60 µl) were reacted and treated to obtain the title compound (Intermediate 142, 85 mg). Mass (LCMS): 464 ($M^+$+1), retention time: 5.87 minutes (elution condition: A).

Synthesis of 3-[3-(1-carboxymethyl-1H-indol-5-yl)-4-cyclopentylmethyloxyphenyl]Propionic acid (Compound No. 586) (Preparation Method 1, Step a)

According to the procedure described in the synthesis method of Compound of Example 002 (Preparation Method 1, Step a) with the modification that the reaction was carried out for 4.5 hours, Intermediate 142 (83 mg) and 2 N aqueous sodium hydroxide (580 μl) were reacted and treated to obtain the title compound (Compound No. 585, 77 mg). Mass (LCMS): 422 (M⁺+1), retention time: 4.56 minutes (elution condition: A).

Example 586
Synthesis of 3-[4-(indan-2-yloxy)-3-(N,N-dimethylamino)-5-(1-methyl-1H-indazol-5-yl)phenyl]propionic acid (Compound No. 586)

A solution of Compound of Example 566 (40 mg) in DMF (2 ml) was added with 60% sodium hydride (18 mg) and stirred for 10 minutes under ice cooling. The reaction mixture was added with methyl iodide (50 μl), stirred for 10 minutes, and then, after the reaction mixture was warmed to 60° C., further stirred for 2 hours. The reaction mixture was poured into water and added with ethyl acetate (50 ml) for extraction. The organic layer was washed successively with saturated aqueous sodium hydrogencarbonate, saturated ammonium chloride and saturated brine and dried, and then the solvent was evaporated under reduced pressure. The residue was purified by column chromatography (Quad, hexane:ethyl acetate=8:1). The substance obtained above was reacted with 2 N aqueous sodium hydroxide (100 μl) and treated according to the procedure described in the synthesis method of Compound of Example 002 (Preparation Method 1, Step a) to obtain the title compound (Compound No. 586, 37 mg). Mass (LCMS): 456 (M⁺+1), retention time: 4.18 minutes (elution condition: A).

Example 587
Synthesis of 3-[4-(indan-2-yloxy)-3-(N-methylamino)-5-(1-methyl-1H-indazol-5-yl)phenyl]propionic acid (Compound No. 587)

A solution of Compound of Example 566 (110 mg) in DMF (3 ml) was added with 60% sodium hydride (20 mg) and stirred for 10 minutes under ice cooling. The reaction mixture was added dropwise with methyl iodide (32 μl), stirred for 10 minutes, then warmed to room temperature and further stirred for 16 hours. The reaction mixture was poured into water and added with ethyl acetate (50 ml) for extraction. The organic layer was washed successively with saturated aqueous sodium hydrogencarbonate, saturated ammonium chloride and saturated brine and dried, and then the solvent was evaporated under reduced pressure. The residue was purified by column chromatography (Quad, hexane-:ethyl acetate=6:1). The substance obtained above was reacted with 2 N aqueous sodium hydroxide (100 μl) and treated according to the procedure described in the synthesis method of Compound of Example 002 (Preparation Method 1, Step a) to obtain the title compound (Compound No. 587, 17 mg). Mass (LCMS): 442 (M⁺+1), retention time: 4.47 minutes (elution condition: A).

Examples 588 to 605

The data of the compounds of the Compound Nos. 588 to 605 are shown in Tables 34 and 35. The indications used in the tables have the same meanings as those used in Tables 17 to 22 mentioned above. The substituents mentioned in the columns of "RO" indicate the substituent in the compound represented by the following formula (LXXI):

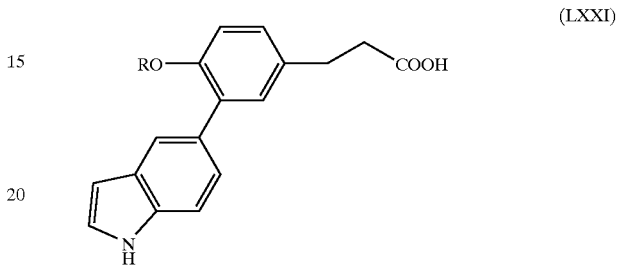

(LXXI)

In the tables, the indication of "D" in the columns of "method" among the columns of "LCMS" means that an apparatus produced by Waters Ltd. was used as a liquid chromatography apparatus, Develosil C30-UG-5 (50×4.6 mm, Nomura Chemical) was used as a separation column, and measurement was performed with elution using a linear gradient of 5 to 98% (v/v) of Solvent B from 0 minute to 4 minutes, and then 98% of Solvent B until 6 minutes.

The indication of "5e2-1a" mentioned in the columns of "Syn. (Preparation Method)" in the tables means that the target compounds were produced according to the production method of the compound described below.
Preparation Method "5e2-1a";

Example 588
Synthesis of 3-[4-n-propyloxy-3-(1H-indol-5-yl)phenyl] propionic acid (Compound No. 588) (Preparation Method 5, Step e-2 and Preparation Method 1, Step a)

According to the procedure described in the synthesis method of Compound of Example 038 (Preparation Method 5, Step e-2), Intermediate 55 (74 mg, corresponding to the compounds mentioned in the columns of "SM1" in the tables), n-propyl alcohol (56 μl, corresponding to the compounds mentioned in the columns of "SM2" in the tables), Ph₃P (197 mg) and TMAD (129 mg) were reacted and treated. The substance obtained above was reacted with 1 N aqueous sodium hydroxide (807 μl) and treated according to the procedure described in the synthesis method of Compound of Example 002 (Preparation Method 1, Step a) to obtain the title compound (Compound No. 588, 55 mg).

TABLE 34

| | | | | | LCMS | | |
| Exp. | Syn. | SM1 | SM2 | RO | method | RTime | Mass |
| 588 | 5e2-1a | Int.55 | Al16 | ~~~O | D | 4.90 | 324(M⁺ + 1) |
| 589 | 5e2-1a | Int.55 | Al18 | ⋎O | D | 5.13 | 338(M⁺ + 1) |

TABLE 34-continued

| | | | | | LCMS | | |
|---|---|---|---|---|---|---|---|
| Exp. | Syn. | SM1 | SM2 | RO | method | RTime | Mass |
| 590 | 5e2-1a | Int.55 | Al20 | (isopentyloxy) | A | 4.62 | 352(M$^+$ + 1) |
| 591 | 5e2-1a | Int.55 | Al19 | (3,3-dimethylbutoxy) | D | 5.40 | 366(M$^+$ + 1) |
| 592 | 5e2-1a | Int.55 | Al6 | trans-2-methylcyclohexyloxy | D | 5.45 | 378(M$^+$ + 1) |
| 593 | 5e2-1a | Int.55 | Al7 | cis-2-methylcyclohexyloxy | D | 5.46 | 378(M$^+$ + 1) |
| 594 | 5e2-1a | Int.55 | Al8 | cis-4-methylcyclohexyloxy | D | 5.47 | 378(M$^+$ + 1) |
| 595 | 5e2-1a | Int.55 | Al2 | cyclopentylmethoxy | D | 5.45 | 378(M$^+$ + 1) |
| 596 | 5e2-1a | Int.55 | Al40 | 1-phenylpropoxy | D | 5.24 | 400(M$^+$ + 1) |
| 597 | 5e2-1a | Int.55 | Al39 | 1-phenylpropoxy | D | 5.25 | 400(M$^+$ + 1) |

TABLE 35

| | | | | | LCMS | | |
|---|---|---|---|---|---|---|---|
| Exp. | Syn. | SM1 | SM2 | RO | method | RTime | Mass |
| 598 | 5e2-1a | Int.55 | Al41 | 1-phenyl-2-methylpropoxy | D | 5.40 | 414(M$^+$ + 1) |

TABLE 35-continued

| Exp. | Syn. | SM1 | SM2 | RO | LCMS method | RTime | Mass |
|---|---|---|---|---|---|---|---|
| 599 | 5e2-1a | Int.55 | Al53 | | D | 5.41 | 418(M⁺ + 1) |
| 600 | 5e2-1a | Int.55 | Al54 | | A | 4.44 | 398(M⁺ + 1) |
| 601 | 5e2-1a | Int.55 | Al55 | | D | 5.19 | 398(M⁺ + 1) |
| 602 | 5e2-1a | Int.55 | Al57 | | D | 5.46 | 412(M⁺ + 1) |
| 603 | 5e2-1a | Int.55 | Al65 | | D | 5.17 | 416(M⁺ + 1) |
| 604 | 5e2-1a | Int.55 | Al68 | | D | 5.11 | 430(M⁺ + 1) |
| 605 | 5e2-1a | Int.55 | Al64 | | D | 5.37 | 443(M⁺ + 1) |

The $^1$H-NMR data of the representative compounds among the compounds of Examples 510 to 605 are shown in Table 36.

TABLE 36

EXP. 525
$^1$H-NMR(CDCl$_3$): 0.87(6H, d, J=6.6), 1.85–1.94(1H, m), 2.54(2H, t, J=7.8), 2.81(2H, t, J=7.8), 3.72(2H, d, J=6.3), 6.99(1H, d, J=8.5), 7.14(1H, dd, J=8.2, 2.4), 7.20(1H, d, J=2.2), 7.51(2H, d, J=1.3), 7.82(1H, m), 8.07(1H, m), 12.10(1H, br-s), 13.04(1H, br-s).
EXP. 527
$^1$H-NMR(CDCl$_3$): 0.88(6H, d, J=6.9), 1.85–1.94(1H, m), 2.54(2H, t, J=7.8), 2.81(2H, t, J=7.5), 3.72(2H, d, J=6.3), 4.06(3H, s), 6.99(1H, d, J=8.0), 7.15(1H, dd, J=8.2, 2.4), 7.20(1H, d, J=1.9), 7.56(1H, dd, J=8.8, 1.6), 7.64(1H, d, J=9.0), 7.81(1H, s), 8.04(1H, s), 12.08(1H, br-s).
EXP. 541
$^1$H-NMR(CDCl$_3$): 1.42(3H, d, J=6.3), 2.50(2H, t, J=7.1), 2.76(2H, t, J=7.4), 5.41(1H, q, J=6.3), 6.86(1H, d, J=8.8), 7.02(1H, dd, J=8.4, 2.4), 7.18–7.31(6H, m), 7.58(2H, s), 7.87(1H, s), 8.11(1H, s), 12.07(1H, br-s), 13.08(1H, br-s).

TABLE 36-continued

EXP. 543
$^1$H-NMR(CDCl$_3$): 1.42(3H, d, J=6.3), 2.51(2H, t, J=7.4), 2.76(2H, t, J=7.3), 4.08(3H, s), 5.42(1H, q, J=6.2), 6.86(1H, d, J=8.8), 7.03(1H, m), 7.18–7.31(6H, m), 7.58(2H, s), 7.87(1H, s), 8.11(1H, s), 12.07(1H, br-s).
EXP. 546
$^1$H-NMR(CDCl$_3$): 1.20–1.41(6H, m), 1.50–1.58(2H, m), 2.50(2H, t, J=7.3), 2.70(2H, t, J=7.5), 4.01–4.06(1H, m), 4.06(3H, s), 4.73(2H, s), 6.43(1H, m), 6.56(1H, m), 7.54(1H, dd, J=8.7, 2.4), 7.64(1H, d, J=9.3), 7.81(1H, s), 8.05(1H, s), 12.15(1H, br-s).
EXP. 549
$^1$H-NMR(CDCl$_3$): 1.11(3H, d, J=6.3), 2.49(2H, t, J=7.6), 2.69(2H, t, J=7.8), 4.47(1H, q, J=6.5), 4.69(2H, br-s), 6.40(1H, d, J=1.9), 6.50(1H, d, J=2.0), 7.04–7.17(5H, m), 7.45–7.62(2H, m), 7.78(1H, s), 8.04(1H, s), 12.10(1H, br-s), 13.04(1H, br-s).
EXP. 552
$^1$H-NMR(CDCl$_3$): 1.11(3H, d, J=6.3), 2.50(2H, t, J=7.1), 2.68(2H, t, J=7.7), 4.06(3H, s), 4.48(1H, q, J=7.1), 4.67(2H, br-s), 6.45(1H, m), 6.49(1H, m), 7.04–7.18(5H, m), 7.51(1H, m), 7.60(1H, m), 7.77(1H, s), 8.02(1H, s), 12.07(1H, br-s).

TABLE 36-continued

EXP. 558
$^1$H-NMR(CDCl$_3$): 2.46–2.51(2H, m), 2.66–2.72(4H, m), 3.48(2H, t, J=6.4), 4.05(3H, s), 4.68(2H, br-s), 6.40(1H, d, J=1.9), 6.52(1H, d, J=2.1), 6.93–7.06(4H, m), 7.47(1H, dd, J=8.8, 1.3), 7.53(1H, d, J=8.8), 7.76(1H, s), 8.00(1H, s), 12.08(1H, br-s).
EXP. 561
$^1$H-NMR(CDCl$_3$): 2.49(2H, t, J=7.6), 2.57(2H, t, J=6.8), 2.69(2H, t, J=7.6), 2.81(6H, s), 3.42(2H, t, J=7.0), 4.06(3H, s), 4.68(2H, br-s), 6.41(1H, d, J=2.2), 6.51–6.55(3H, m), 6.80(2H, d, J=8.8), 7.54(1H, dd, J=8.8, 1.4), 7.59(1H, d, J=8.5), 7.81(1H, s), 8.02(1H, s), 12.07(1H, br-s).
EXP. 567
$^1$H-NMR(CDCl$_3$): 2.49–2.54(2H, m), 2.64–2.74(4H, m), 2.83(2H, dd, J=15.4, 2.8), 4.05(3H, s), 4.26–4.31(1H, m), 4.58(2H, br-s), 6.47(1H, d, J=1.9), 6.55(1H, d, J=1.9), 7.00(4H, s), 7.52–7.58(2H, m), 7.83(1H, s), 8.02(1H, s), 12.08(1H, br-s).

1. Suppressing Action on PGE$_2$ Production from IL-1β-Stimulated MG-63 Cells (1) Method for Measurement An action of suppressing PGE$_2$ production caused by interleukin (IL) 1β as an inflammatory stimulant was studied by the following method. Cells of MG-63, which is a human osteosarcoma cell line (purchased from Dainippon Pharmaceutical), were suspended in EMEM medium (GIBCO) containing 10% fetal bovine serum (BioFluid), and then inoculated to each well of 96-well culture plate at a density of 2×10$^4$ cells/well and cultured overnight. The medium was changed to EMEM medium containing 0.5% fetal bovine serum, and then a test compound was added with each well. Human interleukin-1β (ENDOGEN) was further added as an inflammatory stimulant at a final concentration of 1 ng/ml. The cells were further cultured for 18 hours. The culture supernatant was collected, and the PGE$_2$ concentration in the culture supernatant was measured by using EIA kit (CAYMAN). By using a well which was not added with the stimulant as a negative control and a well which was added only with the stimulant as a positive control, suppression ratios on PGE$_2$ production were calculated from produced amounts of PGE$_2$ in the well added with the test compound using the following equation.

$$PGE_2 \text{ production suppression ratio} = [1-(C-B)/(A-B)] \times 100$$

A: PGE$_2$ production amount of positive control
B: PGE$_2$ production amount of negative control
C: PGE$_2$ production amount in well added with test compound Further, cytotoxicity of the compounds was studied by using the cells after the collection of the supernatant according to the methylene blue uptake method. Specifically, the cells remained after the collection of the supernatant were fixed with glutaraldehyde and stained with a 0.05% methylene blue solution, then methylene blue taken up by the cells was extracted with 0.3 N hydrochloric acid, and absorbance of the extract was measured at 670 nm. The absorbance of the well of the aforementioned positive control was taken as 100%, and a test compound that gave absorbance in well of less than 80% was judged to be positive in cytotoxicity.

(2) Measurement Results

The test compounds (Compound Nos. 002, 004, 006, 008, 010, 012, 014, 016, 018, 020, 022, 024, 026, 028, 029, 031, 033, 035, 037, 039, 041, 043, 045, 047, 049, 051, 053, 055, 057, 058, 060, 062, 064, 066, 068, 070, 071, 072, 074, 075, 077, 078, 079, 081, 083, 085, 087, 088, 090, 092, 094, 095, 096, 099, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 173, 175, 177, 179, 181, 183, 184, 186, 188, 190, 192, 194, 196, 198, 200, 202, 204, 205, 207, 209, 211, 213, 214, 215, 217, 219, 220, 222, 224, 226, 228, 229, 231, 233, 235, 236, 238, 240, 242, 243, 245, 246, 248, 250, 252, 254, 255, 259, 261, 263, 266, 269, 273, 277, 279, 281, 283, 285, 287, 289, 291, 293, 295, 297, 299, 303, 305, 306, 308, 309, 310, 313, 315, 317, 319, 321, 323, 325, 327, 329, and 330) suppressed the PGE$_2$ production caused by IL-1β by 50% or more at 0.4 μM. Other test compounds (Compound Nos. 331, 333, 336, 339, 342, 345, 348, 351, 354, 357, 360, 363, 366, 369, 372, 375, 378, 381, 384, 387, 390, 393, 396, 399, 402, 405, 408, 411, 414, 417, 420, 423, 426, 429, 433, 437, 439, 441, 443, 445, 447, 449, 453, 455, 457, 459, 461, 463, 465, 467, 469, 471, 473, 475, 477, 479, 481, 483, 486, 489, 491, 493, 495, 497, 499, 501, 503, 505, 507, and 509) also suppressed the PGE$_2$ production caused by IL-1β by 50% or more at 0.4 μM. Further other test compounds (Compound Nos. 511, 513, 515, 517, 519, 521, 523, 525, 527, 529, 531, 533, 535, 537, 539, 541, 543, 546, 549, 552, 555, 558, 561, 564, 567, 568, 569, 570, 571, 572, 574, 576, 578, 580, 582, 584, 586, 587, 588, 589, 590, 591, 592, 593, 594, 595, 596, 597, 598, 599, 600, 601, 602, 603, 604, and 605) also suppressed the PGE$_2$ production caused by IL-1 β by 50% or more at 0.4 μM. Moreover, all the test compounds did not exhibit cytotoxicity at that concentration.

Therefore, the novel substituted phenylalkanoic acid derivatives or salts thereof according to the present invention are useful as agents for suppressing inflammatory prostaglandin production.

2. Suppressing Action on PGD$_2$ and LTB$_4$ Production from IgE-Stimulated RBL-2H3 Cells (1) Method for Measurement Suppressing action on PGD$_2$ and LTB$_4$ production caused by IgE as an allergic stimulant was investigated by the following method. Cells of RBL-2H3, which is a rat mastocytoma cell line (purchased from ATCC), were suspended in DEMEM medium (GIBCO) containing 10% fetal bovine serum (BioFluid), inoculated to each well of 48-well culture plate at a density of 2×10$^4$ cells/well and cultured overnight. Then, IgE antiserum directed to dinitrophenylated BSA (henceforth DNP-BSA) was further added to each well, and the cells were cultured for 30 minutes. Then, the medium was changed to DEMEM medium containing 0.5% fetal bovine serum, a test compound was added with each well, and DNP-BSA was further added at a final concentration of 100 ng/ml as a stimulant. Ten minutes after the stimulant was added, the culture supernatant was collected, and the PGD$_2$ concentration and LTB$_4$ concentration in the culture supernatant were measured by using EIA kit (CAYMAN). By using a well which was not added with the stimulant as a negative control and a well which was added only with the stimulant as a positive control, suppressing ratios on mediator production were calculated from the production amounts of the mediators in the well added with the test compound using the following equation.

$$PGD_2 \text{ or } LTB_4 \text{ production suppression ratio} = [1-(C-B)/(A-B)] \times 100$$

A: PGD$_2$ or LTB$_4$ production amount of positive control
B: PGD$_2$ or LTB$_4$ production amount of negative control
C: PGD$_2$ or LTB$_4$ production amount in well added with test compound Cytotoxicity of the compounds was studied in the same manner as those described above, by using the cells after the collection of the supernatant according to the methylene blue uptake method.

Further, as control compounds for comparison, reference compound (1), 3-(2-cyclohexylmethyloxy-1,1'-biphenyl-5-yl)propionic acid described in WO99/19291, reference compounds (2) and (3), [2-(5,6,7,8-tetrahydro-5,5,8,8-tetramethyl-2-naphthalenyl)methyloxy-1,1'-biphenyl-5-yl] carboxylic acid [reference compound (2)] and 3-[3'-carboxy-2-(5,6,7,8-tetrahydro-5,5,8,8-tetramethyl-2naphthalenyl)methyloxy-1,1'-biphenyl-6-yl]propionic acid [reference compound (3)] described in U.S. Pat. No. 5,391,817 and Japanese Patent Unexamined Publication (Kokai) No. 7-22399, respectively, were used, and activities thereof were similarly measured.

(2) Measurement Results

The test compounds (Compound Nos. 002, 004, 010, 012, 014, 016, 035, 039, 043, 045, 047, 053, 066, 075, 079, 081, 095, 099, 100, 102, 104, 108, 110, 132, 142, 146, 148, 150, 152, 154, 160, 162, 166, 173, 177, 179, 181, 185, 186, 190, 204, 211, 214, 217, 220, 229, 231, 233, 235, 236, 243, 245, 246, 248, 250, 261, 281, 287, 289, 293, 295, 299 and 317) suppressed the $PGD_2$ and $LTB_4$ production caused by IgE stimulation by 50% or more at 0.4 μM. Other test compounds (Compound Nos. 339, 354, 357, 369, 375, 390, 399, 405, 408, 411, 420, 426, 429, 437, 443, 445, 449, 453, 455, 457, 461, 463, 465, 467, 469, 471, 473, 475, 477, 479, 481, 483, 486, 489, 491, 493, 501 and 503) also suppressed the $PGD_2$ and $LTB_4$ production caused by IgE stimulation by 50% or more at 0.4 μM. Further other test compounds (Compound Nos. 511, 513, 523, 525, 527, 529, 531, 533, 535, 541, 543, 549, 552, 558, 561, 564, 567, 569, 572, 586, 589, 590, 592, 593, 594, 596, 598, 600, and 602) also suppressed the $PGD_2$ and $LTB_4$ production caused by IgE stimulation by 50% or more at 0.4 μM. Moreover, all the test compounds did not exhibit cytotoxicity at that concentration. Whilst, the suppressing ratios of the $PGD_2$ production of the reference compounds (1), (2) and (3), which were examined as comparative compounds, were −12.9%, −17.6% and 2.1%, respectively, and suppressing ratios of the $LTB_4$ production of the reference compounds (1), (2) and (3) were −5.9%, −15.3% and −6.3%, respectively.

Therefore, the compounds used as references have no suppressing action on prostaglandin and leukotriene production. Whilst the novel substituted phenylalkanoic acid derivatives or salts thereof according to the present invention exhibit suppressing action on the allergic prostaglandin and leukotriene production, and are useful as suppressing agents for the production thereof.

3. Suppressing Effect on Mouse Zymosan-stimulated Footpad Edema Reaction (1) Method for Measurement A suppressing effect on footpad edema caused by zymosan as an inflammatory stimulant was studied by the following method. Groups of ICR female mice (6- to 7-week old) each consisting of eight mice were used for the test. A test compound was suspended or dissolved in purified water containing 0.5% methylcellulose and orally administered to the test animals at 0.1 to 500 mg/0.2 ml/kg. To the control group, purified water containing 0.5% methylcellulose was administered in a similar manner, which was not added with a test compound. One hour after the administration of the test compound, 0.02 ml of a suspension of zymosan suspended in physiological saline (Otsuka Pharmaceutical) at 1 mg/ml was subcutaneously administered to right hind leg footpad of each mouse. One and two hours after the administration of the zymosan suspension, volume of the right hind leg footpad was measured by using an apparatus for measuring a volume of mouse hind leg footpad edema (Unicom). A difference of the volume of footpad measured above and the footpad volume before the administration of the test compound measured beforehand was regarded as a volume of the edema.

For the volume of the edema at 1 hour or 2 hours after the zymosan administration, a graph was prepared by indicating time in abscissa and the edema volume in ordinate, and an edema volume AUC (area under the curve) was obtained up to 2 hours by calculation using the following equation.

Edema volume $AUC$ (1·hour)=$1/2 \times 1 \times A + 1 \times (A+B)/2$

A: Edema volume 1 hour after zymosan administration
B: Edema volume 2 hour after zymosan administration A suppression ratio on edema of test compound was obtained by calculation using the following equation.

Edema suppression ratio (%)=$[1-B/A] \times 100$

A: Edema volume AUC of positive control
B: Edema volume AUC of test compound administered group (2) Measurement Results The test compounds (Compound Nos. 002, 004, 006, 010, 012, 031, 033, 039, 043, 047, 053, 055, 057, 066, 078, 079, 095, 099, 100, 102, 104, 106, 108, 110, 114, 116, 126, 132, 140, 142, 146, 148, 150, 152, 154, 164, 168, 173, 177, 179, 181, 183, 185, 186, 200, 202, 204, 205, 207, 209, 215, 220, 222, 224, 226, 228, 229, 229, 231, 233, 235, 236, 243, 245, 246, 248, 261, 281, 289, 291, 293, 295, 299, 317, and 329) suppressed footpad edema caused by subcutaneous administration of zymosan compared with the positive control group by oral administration at 0.1 to 500 mg/kg.

Therefore, the novel substituted phenylalkanoic acid derivatives or salts thereof according to the present invention exhibit a suppressing action on footpad edema caused by zymosan as an inflammatory stimulant, and thus they are useful as agents for prophylactic and/or therapeutic drugs for inflammatory diseases.

4. Suppressing Effect on Mouse IgE-stimulated Footpad Edema Reaction (1) Method for Measurement Suppression on footpad edema caused by IgE antibody as an allergic stimulant was studied by the following method. Groups of C57BL/6 male mice (9- to 11-week old) each consisting of five mice were used for the test. Anti-DNP-BSA IgE serum was subcutaneously administered in a volume of 20 μl to right hind leg footpad of each mouse one day before the test. A test compound was suspended or dissolved in purified water containing 0.5% methylcellulose and orally administered to the test animals at 0.1 to 500 mg/0.2 ml/kg. To the control group, purified water containing 0.5% methylcellulose was administered in a similar manner, which was not added with the test compound. Two hours after the administration of the test compound, 0.2 ml of a solution of DNP-BSA dissolved in physiological saline (Otsuka Pharmaceutical) at 2.5 μg/ml was intravenously administered. The thickness of right hind leg footpad was measured by using a digital thickness gauge (MITSUTOYO) 10, 15, 20, and 30 minutes after the administration of DNP-BSA. A difference of the thickness of footpad measured above and the thickness before the administration of the test compound measured beforehand was regarded as a thickness of edema.

For the thickness of the edema at 10, 15, 20 and 30 minutes after the DNP-BSA administration, a graph was prepared indicating time in abscissa and the edema thickness in ordinate, and edema thickness AUC up to 2 hours was obtained by calculation according to the following equation.

$$\text{Edema thickness } AUC \text{ (mm·minute)} = 1/2 \times 10 \times A + 5 \times (A+B)/2 + 5 \times (B+C)/2 + 10 \times (C+D)/2$$

A: Edema thickness 10 minutes after DNP-BSA administration
B: Edema thickness 15 minutes after DNP-BSA administration
C: Edema thickness 20 minutes after DNP-BSA administration
D: Edema thickness 30 minutes after DNP-BSA administration A suppressing ratio on edema of a test compound was obtained by calculation in accordance with the following equation.

$$\text{Edema suppression ratio (\%)} = [1 - B/A] \times 100$$

A: Edema thickness AUC of positive control
B: Edema thickness AUC of test compound administered group (2) Measurement Results The test compounds (Compound Nos. 002, 012, 014, 033, 035, 039, 043, 047, 051, 053, 055, 057, 100, 108, 116, 126, 132, 140, 146, 156, 158, 160, 166, 168, 177, 181, 183, 186, 190, 192, 200, 202, 205, 209, 213, 214, 217, 220, 226, 228, 229, 231, 233, 236, 243, 245, 248, 261, 266, 281, 289, 293, 299, 317, and 325) suppressed the footpad edema caused by IgE stimulation, i.e., footpad edema observed when DNP-BSA was administered to the mice sensitized with the anti-DNP-BSA IgE serum, compared with the positive control group by oral administration of 0.1 to 500 mg/kg.

Therefore, the novel substituted phenylalkanoic acid derivatives or salts thereof according to the present invention exhibit suppressing action on footpad edema caused by IgE antibody, which is an allergic stimulant, and thus they are useful as prophylactic and/or therapeutic drugs for allergic diseases.

5. Suppressing Effect on Mouse Acetic Acid Writhing Reaction (1) Method for Measurement A suppressing effect on acetic acid writhing reaction, which is an acute pain model, was studied by the following method. Groups of ICR female mice (6-week old) each consisting of eight mice were used for the test. A test compound was suspended or dissolved in purified water containing 0.5% methylcellulose and orally administered to the test animals at 0.1 to 500 mg/0.2 ml/kg. To the control group, purified water containing 0.5% methylcellulose was administered in a similar manner, which was not added with a test compound. One hour after the administration of the test compound, 0.9% aqueous acetic acid was intraperitoneally administered to the mice in a volume of 5 ml/kg, and number of writhing reactions during 15 minutes immediately after the administration of acetic acid was counted. Suppression ratio relative to the control group was obtained by calculation according to the following equation.

$$\text{Writhing suppression ratio (\%)} = [1 - B/A] \times 100$$

A: Writhing number of positive control
B: Writhing number of test compound administered group (2) Measurement Results The representative compounds of the compound (I) of the present invention suppressed writhing caused by administration of aqueous acetic acid compared with the positive control group at oral administration of 0.1 to 500 mg/kg.

It has been elucidated that a writhing reaction caused by intraperitoneal administration of acetic acid is caused due to production of prostaglandin [Matsumoto et al., European Journal of Pharmacology (Eur. J. Pharmacol), 1998, vol. 352, p.47; Ueno et al., Biochemical Pharmacology (Biochem. Pharmacol), 2001, vol. 15, p.157].

Therefore, the novel substituted phenylalkanoic acid derivatives or salts thereof according to the present invention are useful as prophylactic and/or therapeutic agents for acute pain caused by prostaglandins.

6. Prophylactic and Therapeutic Effects for Rat Adjuvant Arthritis (1) Method for Measurement A suppressing effect on footpad edema observed in rat adjuvant arthritis, which is a disease model of rheumatoid arthritis as being one of autoimmune diseases and also a chronic inflammatory disease, was studied by the following method. Groups of Lewis female rats (8-week old) each consisting of six mice were used for the test. The test animals were immunized by subcutaneously administering, to right hind leg footpads, 50 µl of liquid paraffin containing 10 mg/ml of M. tuberclulosis H37 RA (DIFCO) as an adjuvant. A test compound was suspended or dissolved in purified water containing 0.5% methylcellulose and orally administered to the test animals at 0.1 to 500 mg/0.2 ml/kg. The test compound was administered twice a day for 14 days, from the 12th day after the immunization. To the control group, purified water containing 0.5% methylcellulose was administered in a similar manner, which was not added with a test compound. Every 2 or 3 days after the administration of adjuvant, volume of left hind leg footpad, which was not administered with the adjuvant, was measured by using an apparatus for measuring a volume of edema of a rat hind leg footpad (Unicom). A suppression ratio on edema was obtained by calculation using the following equation.

$$\text{Edema suppression ratio (\%)} = \{1 - [(D-C)/C]/[(B-A)/A]\} \times 100$$

A: Left hind leg footpad volume of positive control immediately before administration of adjuvant
B: Left hind leg footpad volume of positive control on each measurement day
C: Left hind leg footpad volume of test compound administered group immediately before administration of adjuvant
D: Left hind leg footpad volume of test compound administered group on each measurement day (2) Measurement Results The representative compounds of the compound (I) of the present invention suppressed footpad edema in adjuvant arthritis compared with the positive control group.

Therefore, the novel substituted phenylalkanoic acid derivatives or salts thereof according to the present invention are useful as agents for prophylactic and/or therapeutic drugs for rheumatoid arthritis and autoimmune diseases.

Industrial Applicability

The compounds of the present invention have superior suppressing action on prostaglandin production and leukotriene production, and they are useful as active ingredients of medicament for prophylactic and/or therapeutic treatment of various inflammatory diseases, autoimmune diseases, allergic diseases, pain and the like caused by these lipid mediators.

What is claimed is:

1. A compound represented by the formula (I) or a salt thereof:

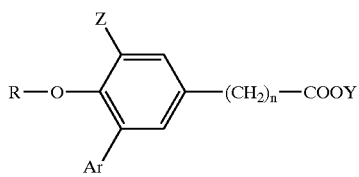
(I)

wherein n represents an integer of 1 to 3, R represents a linear or branched alkyl group having 3 to 8 carbon atoms, a group Ra represented by the following formula:

(Ra)

or a group Rb represented by the following formula:

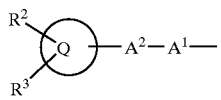
(Rb)

wherein k in the substituent Ra represents 0 or an integer of 1 to 3; $R^1$ represents a saturated cyclic alkyl group having 3 to 7 carbon atoms or a saturated condensed cyclic alkyl group having 6 to 8 carbon atoms, and the group $R^1$ may be substituted with a lower alkyl group having 1 to 4 carbon atoms; Q in the group Rb represents a monocyclic or bicyclic aryl group, and Q may contain 1 or 2 heteroatoms; $A^1$ represents a single bond or an alkylene (a) having 1 to 3 carbon atoms, and the alkylene (a) may be substituted with a lower alkyl group having 1 to 4 carbon atoms or phenyl group; $A^2$ represents a single bond, oxygen atom, sulfur atom, —S(O)—, —S(O)$_2$—, or —N($R^4$)— (wherein, when $A^2$ represents oxygen atom, sulfur atom, —S(O)—, —S(O)$_2$—, or —N($R^4$)—, $A^1$ represents ethylene or trimethylene); $R^2$ and $R^3$ both or each independently represent hydrogen atom, a linear or branched saturated alkyl group having 1 to 4 carbon atoms, phenyl group, fluorine atom, chlorine atom, bromine atom, trifluoromethyl group, an —O$R^5$ group, an —N($R^6$)$_2$ group, an —NHCO$R^7$ group, or an NHSO$_2R^8$ group, wherein $R^4$, $R^6$, and $R^7$ each independently represent hydrogen atom or a lower alkyl group having 1 to 4 carbon atoms, and $R^5$ and $R^8$ represent a lower alkyl group having 1 to 4 carbon atoms; Z represents hydrogen atom, fluorine atom, chlorine atom, nitro group, amino group, methyl group, or an O$R^9$ group wherein $R^9$ represents hydrogen atom or a lower alkyl group having 1 to 4 carbon atoms; the substituent Ar represents a substituent selected from the group consisting of condensed bicyclic substituents of ArI, ArII, ArIII, ArIV, ArV, ArVI, ArVII, ArVIII, ArIX, ArX, ArXI, and ArXII represented by the following formulas:

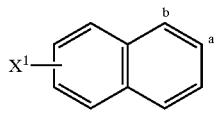
(ArI)

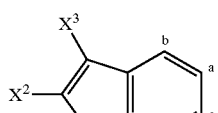
(ArII)

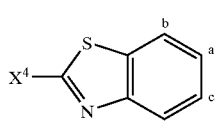
(ArIII)

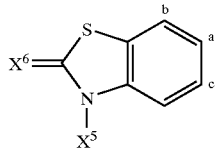
(ArIV)

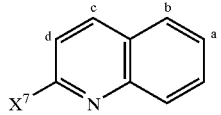
(ArV)

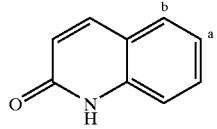
(ArVI)

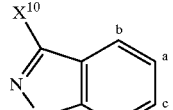
(ArVII)

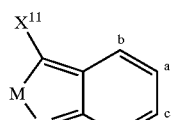
(ArVIII)

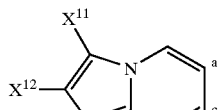
(ArIX)

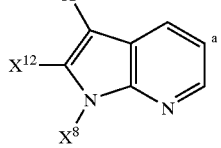
(ArX)

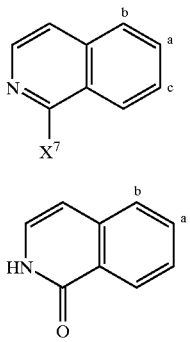

(ArXI)

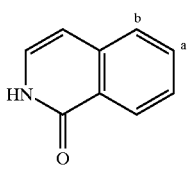

(ArXII)

which bind at any of the positions of a, b, c, and d on the rings, and wherein the substituent $X^1$ in the group ArI represents hydrogen atom, a —$OR^{10}$ group, a —$N(R^{11})(R^{12})$ group, a —$SO_2R^{13}$ group, or carboxyl group, wherein $R^{10}$ represents hydrogen atom, a lower alkyl group having 1 to 4 carbon atoms, or a $(CH_2)_iR^{14}$ group wherein i represents an integer of 1 to 3, and $R^{14}$ represents hydroxyl group, carboxyl group, or N,N-dimethylcarbamoyl group, $R^{11}$ represents hydrogen atom or a lower alkyl group having 1 to 4 carbon atoms, $R^{12}$ represents hydrogen atom, a lower alkyl group having 1 to 4 carbon atoms, 2-hydroxyethyl group, a —$COR^{15}$ group, or a $SO_2R^{16}$ group, wherein $R^{15}$ represents amino group, a lower alkyl group having 1 to 4 carbon atoms, hydroxymethyl group, aminomethyl group, dimethylaminomethyl group, phenyl group, or furyl group, and $R^{13}$ and $R^{16}$ each independently represent a lower alkyl group having 1 to 4 carbon atoms, amino group, methylamino group, or dimethylamino group; in the group ArII, W represents oxygen atom, sulfur atom, or $NX^8$, the substituent $X^2$ represents hydrogen atom, a linear or branched saturated alkyl group having 1 to 4 carbon atoms, or carboxyl group, the substituent $X^3$ represents hydrogen atom, a linear or branched saturated alkyl group having 1 to 4 carbon atoms, acetyl group, formyl group, carboxymethyl group, or hydroxymethyl group, the substituent $X^8$ represents hydrogen atom, a linear or branched saturated alkyl group having 1 to 4 carbon atoms, a saturated cyclic alkyl group having 3 to 7 carbon atoms, or a $(CH_2)_jR^{17}$ group wherein j represents an integer of 1 to 3, and $R^{17}$ represents hydroxyl group or carboxyl group; the substituent $X^4$ in the group ArIII represents hydrogen atom, methyl group, methoxy group, amino group, methylamino group, or dimethylamino group; in the group ArIV, $X^6$ represents oxygen atom, sulfur atom, or $NX^9$, and the substituents $X^5$ and $X^9$ both represent hydrogen atom or methyl group; the substituent $X^7$ in the groups ArV and ArXI represents hydrogen atom or methyl group; M in the groups ArVII and ArVIII represents sulfur atom or $NX^8$; the substituent $X^{10}$ in the group ArVII represents hydrogen atom, a linear or branched saturated alkyl group having 1 to 4 carbon atoms, carboxyl group, acetyl group, formyl group, or an $OR^{22}$ group (wherein, when M in the group ArvII represents sulfur atom, the substituent $X^{10}$ represents hydrogen atom or a linear or branched saturated alkyl group having 1 to 4 carbon atoms), wherein $R^{22}$ represents hydrogen atom or a lower alkyl group having 1 to 4 carbon atoms; the substituent $X^{11}$ in the groups ArVIII, ArIX, and ArX represents hydrogen atom or a linear or branched saturated alkyl group having 1 to 4 carbon atoms; and the substituent $X^{12}$ in the groups ArIX and ArX represents hydrogen atom, a linear or branched saturated alkyl group having 1 to 4 carbon atoms, or carboxyl group; and the group Y represents hydrogen atom, a lower alkyl group having 1 to 4 carbon atoms, a —$(CH_2)_m N(R^{18})(R^{19})$ group, or a —$C(R^{20})_2OC(O)A^3R^{21}$ group, wherein m represents an integer of 2 or 3, $R^{18}$ is the same as $R^{19}$, or represents a saturated alkyl group binding to $R^{19}$ to form a 3- to 6-membered ring together with the nitrogen atom or forms morpholino group together with the nitrogen atom, $R^{19}$ represents methyl group, ethyl group, or propyl group, $R^{20}$ represents hydrogen atom, methyl group, ethyl group, or propyl group, $R^{21}$ represents a lower alkyl group having 1 to 4 carbon atoms, a saturated cyclic alkyl group having 3 to 6 carbon atoms, or phenyl group, and $A^3$ represents a single bond or oxygen atom.

2. The compound or salt thereof according to claim 1, wherein, in the formula (I), the substituent Ar represents a substituent selected from the group consisting of ArI, ArII, ArIII, ArIV, ArV, ArV, and ArVI, which is bound at any of positions of a, b, c, and d on the ring.

3. The compound or salt thereof according to claim 1, wherein, in the formula (I), the substituent Ar represents a substituent selected from the group consisting of ArI, ArII, ArIII, ArIV, ArV, ArV, and ArVI, which is bound at a position of a or d on the ring.

4. The compound or salt thereof according to claim 1, wherein, in the formula (I), the substituent Ar represents a substituent selected from the group consisting of ArVII, ArVIII, ArIX, ArX, ArXI, and ArXII, which is bound at any of positions of a, b, and c on the ring.

5. The compound or salt thereof according to claim 1, wherein, in the formula (I), the substituent Ar represents a substituent selected from the group consisting of ArVII, ArVIII, ArIX, ArX, ArXI, and ArXII, which is bound at a position of a on the ring.

6. The compound or salt thereof according to claim 1, wherein, in the formula (I), the substituent Ar represents ArI, which is bound at any of positions of a and b on the ring.

7. The compound or salt thereof according to claim 1, wherein, in the formula (I), the substituent Ar represents ArII, which is bound at any of positions of a, b, and c on the ring.

8. The compound or salt thereof according to claim 1, wherein, in the formula (I), the substituent Ar represents ArIII or ArIV, which is bound at any of positions of a, b, and c on the ring.

9. The compound or salt thereof according to claim 1, wherein, in the formula (I), the substituent Ar represents ArV or ArVI, which is bound at any of positions of a, b, c, and d on the ring.

10. The compound or salt thereof according to claim 1, wherein, in the formula (I), the substituent Ar represents ArVII, which is bound at any of positions of a, b, and c on the ring.

11. The compound or salt thereof according to claim 1, wherein, in the formula (I), the substituent Ar represents a substituent selected from the group consisting of ArVIII, ArIX, and ArX, which is bound at any of positions of a, b, and c on the ring.

12. The compound or salt thereof according to claim 2, wherein, in the formula (I), the substituent Ar represents ArXI or ArXII, which is bound at any of positions of a, b, and c on the ring.

13. The compound or salt thereof according to claim 2, wherein, in the formula (I), R represents a linear or branched alkyl group having 3 to 8 carbon atoms or the group Ra, k represents 0 or an integer of 1 to 3, $R^1$ represents a saturated cyclic alkyl group having 3 to 7 carbon atoms, which is unsubstituted or substituted with a lower alkyl group having 1 to 4 carbon atoms, or a saturated condensed cyclic alkyl group having 6 to 8 carbon atoms, which is unsubstituted or substituted with a lower alkyl group having 1 to 4 carbon atoms.

14. The compound or salt thereof according to claim 2, wherein, in the formula (I), R represents the substituent Rb (wherein, when Q represents phenyl group, $A^1$ represents a single bond or an unsubstituted methylene, and $A^2$ represents a single bond, at least one of $R^2$ and $R^3$ represents a substituent other than hydrogen atom).

15. The compound or salt thereof according to claim 4, wherein, in the formula (I), R represents a linear or branched alkyl group having 3 to 8 carbon atoms or the group Ra, k represents 0 or an integer of 1 to 3, $R^1$ represents a saturated cyclic alkyl group having 3 to 7 carbon atoms, which is unsubstituted or substituted with a lower alkyl group having 1 to 4 carbon atoms, or a saturated condensed cyclic alkyl group having 6 to 8 carbon atoms, which is unsubstituted or substituted with a lower alkyl group having 1 to 4 carbon atoms.

16. The compound or salt thereof according to claim 4, wherein, in the formula (I), R represents the substituent Rb (wherein, when Q represents phenyl group, $A^1$ represents a single bond or an unsubstituted methylene, and $A^2$ represents a single bond, at least one of $R^2$ and $R^3$ represents a substituent other than hydrogen atom).

17. The compound or salt thereof according to claim 2, wherein, in the formula (I), n represents an integer of 2; R represents butyl group, isobutyl group, 2-ethylbutyl group, cyclopentyl group, cyclohexyl group, cyclopentylmethyl group, cyclohexylmethyl group, or the substituent Rb, wherein Q in the group Rb represents phenyl group; $A^1$ represents a methylene group, which is unsubstituted or substituted with methyl group or ethyl group, or represents an ethylene group, which is unsubstituted or substituted with methyl group or ethyl group; $A^2$ represents a single bond, oxygen atom, sulfur atom, or —N($R^4$)—, wherein, when $A^2$ represents oxygen atom, sulfur atom, or —N($R^4$)—, $A^1$ represents ethylene; $R^2$ and $R^3$ both represent hydrogen atom, or both or each independently represent methyl group, fluorine atom, chlorine atom, trifluoromethyl group, methoxy group, or dimethylamino group, wherein, when $A^1$ represents a single bond or unsubstituted methylene, and $A^2$ represents a single bond, one of $R^2$ and $R^3$ represents a substituent other than hydrogen atom; $R^4$ represents methyl group or ethyl group; Z represents hydrogen atom, fluorine atom, chlorine atom, amino group, or methoxy group; the substituent Ar represents a substituent selected from the group consisting of ArI, ArII, ArIII, ArIV, ArV, ArV, and ArVI, which binds at the position of a or d on the ring, wherein the substituent $X^1$ in the group ArI represents hydrogen atom, hydroxyl group, methoxy group, 2-hydroxyethyloxy group, amino group, methylamino group, dimethylamino group, 2-hydroxyethylamino group, acetylamino group, aminoacetylamino group, hydroxyacetylamino group, furan-2-carbonylamino group, carbamoylamino group, methanesulfonylamino group, N,N-dimethylsulfamoylamino group, methanesulfonyl group, sulfamoyl group, N-methylsulfamoyl group, N,N-dimethylsulfamoyl group, or carboxyl group; W in the group ArII represents oxygen atom, sulfur atom, or $NX^8$; the substituent $X^2$ represents hydrogen atom or methyl group; the substituent $X^3$ represents hydrogen atom, methyl group, acetyl group, or hydroxymethyl group; the substituent $X^8$ represents hydrogen atom, methyl group, ethyl group, propyl group, 2-hydroxyethyl group, or carboxymethyl group; the substituent $X^4$ in the group ArIII represents hydrogen atom, methyl group, methoxy group, or amino group; the substituent $X^5$ in the group ArIV represents hydrogen atom or methyl group; $X^6$ represents oxygen atom or sulfur atom; the substituent $X^7$ in the group ArV represents hydrogen atom; and Y represents hydrogen atom, methyl group, or ethyl group.

18. The compound or salt thereof according to claim 4, wherein, in the formula (I), n represents an integer of 2; R represents butyl group, isobutyl group, 2-ethylbutyl group, cyclopentyl group, cyclohexyl group, cycloheptyl group, cyclopentylmethyl group, cyclohexylmethyl group, indan-2-yl group, or the substituent Rb, wherein Q in the group Rb represents phenyl group; $A^1$ represents a methylene group, which is unsubstituted or substituted with methyl group or ethyl group, or represents an ethylene group, which is unsubstituted or substituted with methyl group or ethyl group; $A^2$ represents a single bond, oxygen atom, sulfur atom, or —N($R^4$)— (wherein, when $A^2$ represents oxygen atom, sulfur atom, or —N($R^4$)—, $A^1$ represents ethylene); $R^2$ and $R^3$ both represent hydrogen atom, or both or each independently represent methyl group, fluorine atom, chlorine atom, trifluoromethyl group, methoxy group, or dimethylamino group (wherein, when $A^1$ represents a single bond or unsubstituted methylene, and $A^2$ represents a single bond, one of $R^2$ and $R^3$ represents a substituent other than hydrogen atom); $R^4$ represents methyl group or ethyl group; Z represents hydrogen atom, fluorine atom, chlorine atom, amino group, or methoxy group; the substituent Ar represents a substituent selected from the group consisting of ArVII, ArVIII, ArIX, ArX, ArXI, and ArXII, which binds at the position of a on the ring, wherein M in the groups ArVII and ArVIII represents sulfur atom or $NX^8$; the substituent $X^8$ represents hydrogen atom, methyl group, ethyl group, propyl group, 2-hydroxyethyl group, or carboxymethyl group; each or all of the substituents $X^{10}$, $X^{11}$, and $X^{12}$ independently represent hydrogen atom or methyl group; the substituent $X^7$ in the group ArXI represents hydrogen atom; and Y represents hydrogen atom, methyl group, or ethyl group.

19. The compound or salt thereof according to claim 1, wherein the compound represented by the formula (I) is selected from the group consisting of:

methyl 3-[4-cyclohexylmethyloxy-3-(6-hydroxynaphthalen-2-yl)phenyl]propionate;

3-[4-cyclohexylmethyloxy-3-(6-hydroxynaphthalen-2-yl)phenyl]propionic acid;

methyl 3-[4-cyclopentylmethyloxy-3-(6-hydroxynaphthalen-2-yl)phenyl]propionate;

3-[4-cyclopentylmethyloxy-3-(6-hydroxynaphthalen-2-yl)phenyl]propionic acid;

methyl 3-{4-[2-(2-fluorophenyl)ethyloxy]-3-(6-hydroxynaphthalen-2-yl)phenyl}propionate;

3-{4-[2-(2-fluorophenyl)ethyloxy]-3-(6-hydroxynaphthalen-2-yl)phenyl}propionic acid;

methyl 3-[4-cyclopentylmethyloxy-3-(7-hydroxynaphthalen-2-yl)phenyl]propionate;

3-[4-cyclopentylmethyloxy-3-(7-hydroxynaphthalen-2-yl)phenyl]propionic acid;

methyl 3-[4-cyclopentylmethyloxy-3-(5-hydroxynaphthalen-2-yl)phenyl]propionate;

3-[4-cyclopentylmethyloxy-3-(5-hydroxynaphthalen-2-yl)phenyl]propionic acid;

methyl 3-[3-(6-aminonaphthalen-2-yl)-4-cyclopentylmethyloxyphenyl]propionate;

3-[3-(6-aminonaphthalen-2-yl)-4-cyclopentylmethyloxyphenyl]propionic acid;

methyl 3-[3-(7-aminonaphthalen-2-yl)-4-cyclopentylmethyloxyphenyl]propionate;

3-[3-(7-aminonaphthalen-2-yl)-4-cyclopentylmethyl-oxyphenyl]propionic acid;
methyl 3-{4-cyclopentylmethyloxy-3-[6-(N-methylamino) naphthalen-2-yl]phenyl}-propionate;
3-{4-cyclopentylmethyloxy-3-[6-(N-methylamino) naphthalen-2-yl]phenyl}propionic acid;
methyl 3-{4-cyclopentylmethyloxy-3-[6-(N,N-dimethylamino)naphthalen-2-yl]phenyl}-propionate;
3-{4-cyclopentylmethyloxy-3-[6-(N,N-dimethylamino) naphthalen-2-yl]phenyl}-propionic acid;
methyl 3-[4-cyclopentylmethyloxy-3-(6-sulfamoylaminonaphthalen-2-yl)phenyl]propionate;
3-[4-cyclopentylmethyloxy-3-(6-sulfamoylamino-naphthalen-2-yl)phenyl]propionic acid;
methyl 3-[4-cyclopentylmethyloxy-3-(6-methanesulfonylnaphthalen-2-yl)phenyl]-propionate;
3-[4-cyclopentylmethyloxy-3-(6-methanesulfonyl-naphthalen-2-yl)phenyl]propionic acid;
methyl 3-[4-cyclopentylmethyloxy-3-(6-sulfamoylnaphthalen-2-yl)phenyl]propionate;
3-[4-cyclopentylmethyloxy-3-(6-sulfamoylnaphthalen-2-yl)phenyl]propionic acid;
methyl 3-{4-cyclopentylmethyloxy-3-[6-(N-methylsulfamoyl)naphthalen-2-yl]phenyl}-propionate;
3-{4-cyclopentylmethyloxy-3-[6-(N-methylsulfamoyl) naphthalen-2-yl]phenyl}propionic acid;
methyl 3-{4-cyclopentylmethyloxy-3-[6-(N,N-dimethylsulfamoyl)naphthalen-2-yl]-phenyl}propionate;
3-{4-cyclopentylmethyloxy-3-[6-(N,N-dimethylsulfamoyl)naphthalen-2-yl]phenyl}-propionic acid;
3-[3-(6-carboxynaphthalen-2-yl)-4-cyclohexylmethyl-oxyphenyl]propionic acid;
methyl 3-[4-(2-fluorophenylmethyloxy)-3-(naphthalen-2-yl)phenyl]propionate;
3-[4-(2-fluorophenylmethyloxy)-3-(naphthalen-2-yl) phenyl]propionic acid;
methyl 3-[4-(3-fluorophenylmethyloxy)-3-(naphthalen-2-yl)phenyl]propionate;
3-[4-(3-fluorophenylmethyloxy)-3-(naphthalen-2-yl) phenyl]propionic acid;
methyl 3-[4-(4-fluorophenylmethyloxy)-3-(naphthalen-2-yl)phenyl]propionate;
3-[4-(4-fluorophenylmethyloxy)-3-(naphthalen-2-yl) phenyl]propionic acid;
methyl 3-[4-butyloxy-3-(naphthalen-2-yl)phenyl] propionate;
3-[4-butyloxy-3-(naphthalen-2-yl)phenyl]propionic acid;
methyl 3-[4-cyclopentylmethyloxy-3-(naphthalen-2-yl) phenyl]propionate;
3-[4-cyclopentylmethyloxy-3-(naphthalen-2-yl)phenyl] propionic acid;
methyl 3-[4-isopropyloxy-3-(naphthalen-2-yl)phenyl] propionate;
3-[4-isopropyloxy-3-(naphthalen-2-yl)phenyl]propionic acid;
methyl 3-[4-cyclopentyloxy-3-(naphthalen-2-yl)phenyl] propionate;
3-[4-cyclopentyloxy-3-(naphthalen-2-yl)phenyl] propionic acid;
methyl 3-[4-cyclohexyloxy-3-(naphthalen-2-yl)phenyl] propionate;
3-[4-cyclohexyloxy-3-(naphthalen-2-yl)phenyl]propionic acid;
methyl 3-[4-(2-cyclopentylethyloxy)-3-(naphthalen-2-yl) phenyl]propionate;
3-[4-(2-cyclopentylethyloxy)-3-(naphthalen-2-yl)phenyl] propionic acid;
methyl 3-[4-(2-cyclohexylethyloxy)-3-(naphthalen-2-yl) phenyl]propionate;
3-[4-(2-cyclohexylethyloxy)-3-(naphthalen-2-yl)phenyl] propionic acid;
methyl 3-[3-(naphthalen-2-yl)-4-(2-phenylethyloxy) phenyl]propionate;
3-[3-(naphthalen-2-yl)-4-(2-phenylethyloxy)phenyl] propionic acid;
methyl 3-{4-[2-(2-fluorophenyl)ethyloxy]-3-(naphthalen-2-yl)phenyl}propionate;
3-{4-[2-(2-fluorophenyl)ethyloxy]-3-(naphthalen-2-yl) phenyl}propionic acid;
methyl 3-{4-[2-(3-fluorophenyl)ethyloxy]-3-(naphthalen-2-yl)phenyl}propionate;
3-{4-[2-(3-fluorophenyl)ethyloxy]-3-(naphthalen-2-yl) phenyl}propionic acid;
methyl 3-{4-[2-(4-fluorophenyl)ethyloxy]-3-(naphthalen-2-yl)phenyl}propionate;
3-{4-[2-(4-fluorophenyl)ethyloxy]-3-(naphthalen-2-yl) phenyl}propionic acid;
3-{4-[(furan-2-yl)methyloxy]-3-(naphthalen-2-yl) phenyl}propionic acid;
methyl 3-{3-(naphthalen-2-yl)-4-[(pyridin-3-yl) methyloxy]phenyl}propionate;
3-{3-(naphthalen-2-yl)-4-[(pyridin-3-yl)methyloxy] phenyl}propionic acid;
methyl 3-{4-[2-(5-ethylpyridin-2-yl)ethyloxy]-3-(naphthalen-2-yl)phenyl}propionate;
3-{4-[2-(5-ethylpyridin-2-yl)ethyloxy]-3-(naphthalen-2-yl)phenyl}propionic acid;
methyl 3-{4-[2-(5-methyl-2-phenyloxazol-4-yl) ethyloxy]-3-(naphthalen-2-yl)phenyl}-propionate;
3-{4-[2-(5-methyl-2-phenyloxazol-4-yl)ethyloxy]-3-(naphthalen-2-yl)phenyl}propionic acid;
ethyl 3-[4-cyclohexylmethyloxy-3-(naphthalen-2-yl) phenyl]propionate;
3-[4-cyclohexylmethyloxy-3-(naphthalen-2-yl)phenyl] propionic acid;
ethyl 3-[4-cyclohexylmethyloxy-3-(6-methoxy-naphthalen-2-yl)phenyl]propionate;
3-[4-cyclohexylmethyloxy-3-(6-methoxynaphthalen-2-yl)phenyl]propionic acid;
ethyl 3-[4-cyclohexylmethyloxy-3-(naphthalen-1-yl) phenyl]propionate;
3-[4-cyclohexylmethyloxy-3-(naphthalen-1-yl)phenyl] propionic acid;
3-{4-cyclohexylmethyloxy-3-[6-(2-hydroxyethyloxy) naphthalen-2-yl]phenyl}propionic acid;
3-[3-(6-carboxymethyloxynaphthalen-2-yl)-4-cyclohexylmethyloxyphenyl]propionic acid;
methyl 3-{4-cyclohexylmethyloxy-3-[6-(N,N-dimethylcarbamoylmethyloxy)naphthalen-2-yl]-phenyl}propionate;
3-{4-cyclohexylmethyloxy-3-[6-(N,N-dimethylcarbamoylmethyloxy)naphthalen-2-yl]-phenyl}propionic acid;

3-{4-cyclopentylmethyloxy-3-[6-(2-hydroxyethylamino) naphthalen-2-yl]phenyl}-propionic acid;

methyl 3-[3-(6-acetylaminonaphthalen-2-yl)-4-cyclopentylmethyloxyphenyl]-propionate;

3-[3-(6-acetylaminonaphthalen-2-yl)-4-cyclopentylmethyloxyphenyl]propionic acid;

3-{3-[6-(aminoacetylamino)naphthalen-2-yl]-4-cyclopentylmethyloxyphenyl}propionic acid;

3-{4-cyclopentylmethyloxy-3-[6-(hydroxyacetylamino) naphthalen-2-yl]phenyl}-propionic acid;

methyl 3-(4-cyclopentylmethyloxy-3-{6-[(furan-2-carbonyl)amino]naphthalen-2-yl}-phenyl)propionate;

3-(4-cyclopentylmethyloxy-3-{6-[(furan-2-carbonyl) amino]naphthalen-2-yl}phenyl)-propionic acid;

methyl 3-[3-(6-carbamoylaminonaphthalen-2-yl)-4-cyclopentylmethyloxyphenyl]propionate;

3-[3-(6-carbamoylaminonaphthalen-2-yl)-4-cyclopentylmethyloxyphenyl]propionic acid;

methyl 3-[4-cyclopentylmethyloxy-3-(6-methanesulfonylaminonaphthalen-2-yl)-phenyl]propionate;

3-[4-cyclopentylmethyloxy-3-(6-methanesulfonylaminonaphthalen-2-yl)phenyl]-propionic acid;

methyl 3-{4-cyclopentylmethyloxy-3-[6-(N,N-dimethylsulfamoylamino)naphthalen2-yl]phenyl}propionate;

3-{4-cyclopentylmethyloxy-3-[6-(N,N-dimethylsulfamoylamino)naphthalen-2-yl]-phenyl}propionic acid;

3-{4-cyclopentylmethyloxy-3-[7-(hydroxyacetylamino) naphthalen-2-yl]-phenyl}propionic acid;

methyl 3-(4-cyclopentylmethyloxy-3-{7-[(furan-2-carbonyl)amino]naphthalen-2-yl}-phenyl)propionate;

3-(4-cyclopentylmethyloxy-3-{7-[(furan-2-carbonyl) amino]naphthalen-2-yl}phenyl)-propionic acid;

methyl 3-[3-chloro-4-cyclopentylmethyloxy-5-(naphthalen-2-yl)phenyl]propionate;

3-[3-chloro-4-cyclopentylmethyloxy-5-(naphthalen-2-yl) phenyl]propionic acid;

methyl 3-[4-cyclopentylmethyloxy-3-(naphthalen-2-yl)-5-nitrophenyl]propionate;

methyl 3-[3-amino-4-cyclopentylmethyloxy-5-(naphthalen-2-yl)phenyl]propionate;

3-[3-amino-4-cyclopentylmethyloxy-5-(naphthalen-2-yl) phenyl]propionic acid;

4-cyclohexylmethyloxy-3-(naphthalen-2-yl)phenylacetic acid;

methyl 4-[4-cyclopentylmethyloxy-3-(naphthalen-2-yl) phenyl]butyrate;

4-[4-cyclopentylmethyloxy-3-(naphthalen-2-yl)phenyl] butyric acid;

methyl 3-[4-cyclopentylmethyloxy-3-(1H-indol-5-yl) phenyl]propionate;

3-[4-cyclopentylmethyloxy-3-(1H-indol-5-yl)phenyl] propionic acid;

methyl 3-[4-cyclopentyloxy-3-(1H-indol-5-yl)phenyl] propionate;

3-[4-cyclopentyloxy-3-(1H-indol-5-yl)phenyl]propionic acid;

methyl 3-[4-cyclohexyloxy-3-(1H-indol-5-yl)phenyl] propionate;

3-[4-cyclohexyloxy-3-(1H-indol-5-yl)phenyl]propionic acid;

methyl 3-{4-[2-(2-fluorophenyl)ethyloxy]-3-(1H-indol-5-yl)phenyl}propionate;

3-4-[2-{2-fluorophenyl)ethyloxy]-3-(1H-indol-5-yl) phenyl}propionic acid;

methyl 3-[4-cyclopentyloxy-3-(1-methyl-1H-indol-5-yl) phenyl]propionate;

3-[4-cyclopentyloxy-3-(1-methyl-1H-indol-5-yl)phenyl] propionic acid;

methyl 3-[4-cyclohexyloxy-3-(1-methyl-1H-indol-5-yl) phenyl]propionate;

3-[4-cyclohexyloxy-3-(1-methyl-1H-indol-5-yl)phenyl] propionic acid;

methyl 3-[4-cyclopentylmethyloxy-3-(3-methyl-1H-indol-5-yl)phenyl]propionate;

3-[4-cyclopentylmethyloxy-3-(3-methyl-1H-indol-5-yl) phenyl]propionic acid;

methyl 3-[4-cyclopentylmethyloxy-3-(1H-indol-4-yl) phenyl]propionate;

3-[4-cyclopentylmethyloxy-3-(1H-indol-4-yl)phenyl] propionic acid;

methyl 3-[4-cyclohexylmethyloxy-3-(1H-indol-4-yl) phenyl]propionate;

3-[4-cyclohexylmethyloxy-3-(1H-indol-4-yl)phenyl] propionic acid;

methyl 3-[4-cyclopentyloxy-3-(1H-indol-4-yl)phenyl] propionate;

3-[4-cyclopentyloxy-3-(1H-indol-4-yl)phenyl]propionic acid;

methyl 3-[4-cyclohexyloxy-3-(1H-indol-4-yl)phenyl] propionate;

3-[4-cyclohexyloxy-3-(1H-indol-4-yl)phenyl]propionic acid;

methyl 3-[4-cyclopentylmethyloxy-3-(1-methyl-1H-indol-4-yl)phenyl]propionate;

3-[4-cyclopentylmethyloxy-3-(1-methyl-1H-indol-4-yl) phenyl]propionic acid;

methyl 3-[4-cyclopentyloxy-3-(1-methyl-1H-indol-4-yl) phenyl]propionate;

3-[4-cyclopentyloxy-3-(1-methyl-1H-indol-4-yl)phenyl] propionic acid;

methyl 3-[4-cyclohexyloxy-3-(1-methyl-1H-indol-4-yl) phenyl]propionate;

3-[4-cyclohexyloxy-3-(1-methyl-1H-indol-4-yl)phenyl] propionic acid;

methyl 3-[4-cyclohexylmethyloxy-3-(1H-indol-6-yl) phenyl]propionate;

3-[4-cyclohexylmethyloxy-3-(1H-indol-6-yl)phenyl] propionic acid;

methyl 3-[4-butyloxy-3-(1H-indol-5-yl)phenyl] propionate;

3-[4-butyloxy-3-(1H-indol-5-yl)phenyl]propionic acid;

methyl 3-[3-(1H-indol-5-yl)-4-(1-phenylethyloxy) phenyl]propionate;

3-[3-(1H-indol-5-yl)-4-(1-phenylethyloxy)phenyl] propionic acid;

methyl 3-[3-(1H-indol-5-yl)-4-(2-methylphenylmethyloxy)phenyl]propionate;

3-[3-(1H-indol-5-yl)-4-(2-methylphenylmethyloxy) phenyl]propionic acid;

methyl 3-[3-(1H-indol-5-yl)-4-(3-methylphenylmethyloxy)phenyl]propionate;
3-[3-(1H-indol-5-yl)-4-(3-methylphenylmethyloxy)phenyl]propionic acid;
methyl 3-[3-(1H-indol-5-yl)-4-(4-methylphenylmethyloxy)phenyl]propionate;
3-[3-(1H-indol-5-yl)-4-(4-methylphenylmethyloxy)phenyl]propionic acid;
methyl 3-{4-[(biphenyl-2-yl)methyloxy]-3-(1H-indol-5-yl)phenyl}propionate;
3-{4-[(biphenyl-2-yl)methyloxy]-3-(1H-indol-5-yl)phenyl}propionic acid;
methyl 3-[4-(2-fluorophenylmethyloxy)-3-(1H-indol-5-yl)phenyl]propionate;
3-[4-(2-fluorophenylmethyloxy)-3-(1H-indol-5-yl)phenyl]propionic acid;
methyl 3-[4-(3-fluorophenylmethyloxy)-3-(1H-indol-5-yl)phenyl]propionate;
3-[4-(3-fluorophenylmethyloxy)-3-(1H-indol-5-yl)phenyl]propionic acid;
methyl 3-[4-(4-fluorophenylmethyloxy)-3-(1H-indol-5-yl)phenyl]propionate;
3-[4-(4-fluorophenylmethyloxy)-3-(1H-indol-5-yl)phenyl]propionic acid;
methyl 3-[4-(2-chlorophenylmethyloxy)-3-(1H-indol-5-yl)phenyl]propionate;
3-[4-(2-chlorophenylmethyloxy)-3-(1H-indol-5-yl)phenyl]propionic acid;
methyl 3-[4-(3-chlorophenylmethyloxy)-3-(1H-indol-5-yl)phenyl]propionate;
3-[4-(3-chlorophenylmethyloxy)-3-(1H-indol-5-yl)phenyl]propionic acid;
methyl 3-[4-(4-chlorophenylmethyloxy)-3-(1H-indol-5-yl)phenyl]propionate;
3-[4-(4-chlorophenylmethyloxy)-3-(1H-indol-5-yl)phenyl]propionic acid;
methyl 3-[4-(2-bromophenylmethyloxy)-3-(1H-indol-5-yl)phenyl]propionate;
3-[4-(2-bromophenylmethyloxy)-3-(1H-indol-5-yl)phenyl]propionic acid;
methyl 3-[4-(2,4-difluorophenylmethyloxy)-3-(1H-indol-5-yl)phenyl]propionate;
3-[4-(2,4-difluorophenylmethyloxy)-3-(1H-indol-5-yl)phenyl]propionic acid;
methyl 3-[4-(3,4-difluorophenylmethyloxy)-3-(1H-indol-5-yl)phenyl]propionate;
3-[4-(3,4-difluorophenylmethyloxy)-3-(1H-indol-5-yl)phenyl]propionic acid;
methyl 3-[4-(2,3-dichlorophenylmethyloxy)-3-(1H-indol-5-yl)phenyl]propionate;
3-[4-(2,3-dichlorophenylmethyloxy)-3-(1H-indol-5-yl)phenyl]propionic acid;
methyl 3-[4-(2,4-dichlorophenylmethyloxy)-3-(1H-indol-5-yl)phenyl]propionate;
3-[4-(2,4-dichlorophenylmethyloxy)-3-(1H-indol-5-yl)phenyl]propionic acid;
methyl 3-[4-(2,6-dichlorophenylmethyloxy)-3-(1H-indol-5-yl)phenyl]propionate;
3-[4-(2,6-dichlorophenylmethyloxy)-3-(1H-indol-5-yl)phenyl]propionic acid;
methyl 3-[4-(3,4-dichlorophenylmethyloxy)-3-(1H-indol-5-yl)phenyl]propionate;
3-[4-(3,4-dichlorophenylmethyloxy)-3-(1H-indol-5-yl)phenyl]propionic acid;
methyl 3-[4-(4-bromo-2-fluorophenylmethyloxy)-3-(1H-indol-5-yl)phenyl]propionate;
3-[4-(4-bromo-2-fluorophenylmethyloxy)-3-(1H-indol-5-yl)phenyl]propionic acid;
methyl 3-{3-(1H-indol-5-yl)-4-[2-(trifluoromethyl)phenylmethyloxy]phenyl}propionate;
3-{3-(1H-indol-5-yl)-4-[2-(trifluoromethyl)phenylmethyloxy]phenyl}propionic acid;
methyl 3-{3-(1H-indol-5-yl)-4-[4-(trifluoromethyl)phenylmethyloxy]phenyl}propionate;
3-{3-(1H-indol-5-yl)-4-[4-(trifluoromethyl)phenylmethyloxy]phenyl}propionic acid;
3-[4-isopropyloxy-3-(1H-indol-5-yl)phenyl]propionic acid;
methyl 3-[4-(3,5-dimethylphenylmethyloxy)-3-(1H-indol-5-yl)phenyl]propionate;
3-[4-(3,5-dimethylphenylmethyloxy)-3-(1H-indol-5-yl)phenyl]propionic acid;
methyl 3-[4-(bicyclo[2,2,1]hept-2-ylmethyloxy)-3-(1H-indol-5-yl)phenyl]propionate;
3-[4-(bicyclo[2,2,1]hept-2-ylmethyloxy)-3-(1H-indol-5-yl)phenyl]propionic acid;
methyl 3-{4-[(biphenyl-4-yl)methyloxy]-3-(1H-indol-5-yl)phenyl}propionate;
3-{4-[(biphenyl-4-yl)methyloxy]-3-(1H-indol-5-yl)phenyl}propionic acid;
methyl 3-[4-(2,3-dimethylbutyloxy)-3-(1H-indol-5-yl)phenyl]propionate;
3-[4-(2,3-dimethylbutyloxy)-3-(1H-indol-5-yl)phenyl]propionic acid;
methyl 3-[4-(2-ethylbutyloxy)-3-(1H-indol-5-yl)phenyl]propionate;
3-[4-(2-ethylbutyloxy)-3-(1H-indol-5-yl)phenyl]propionic acid;
3-[4-cycloheptyloxy-3-(1H-indol-5-yl)phenyl]propionic acid;
methyl 3-{4-[4-(butyloxy)phenylmethyloxy]-3-(1H-indol-5-yl)phenyl}propionate;
3-{4-[4-(butyloxy)phenylmethyloxy]-3-(1H-indol-5-yl)phenyl}propionic acid;
methyl 3-[4-(3,5-dichlorophenylmethyloxy)-3-(1H-indol-5-yl)phenyl]propionate;
3-[4-(3,5-dichlorophenylmethyloxy)-3-(1H-indol-5-yl)phenyl]propionic acid;
methyl 3-{3-(1H-indol-5-yl)-4-[(naphthalen-1-yl)methyloxy]phenyl}propionate;
3-{3-(1H-indol-5-yl)-4-[(naphthalen-1-yl)methyloxy]phenyl}propionic acid;
methyl 3-{3-(1H-indol-5-yl)-4-[(naphthalen-2-yl)methyloxy]phenyl}propionate;
3-{3-(1H-indol-5-yl)-4-[(naphthalen-2-yl)methyloxy]phenyl}propionic acid;
methyl 3-{4-[(furan-2-yl)methyloxy]-3-(1H-indol-5-yl)phenyl}propionate;
3-{4-[(furan-2-yl)methyloxy]-3-(1H-indol-5-yl)phenyl}propionic acid;
methyl 3-{4-[(furan-3-yl)methyloxy]-3-(1H-indol-5-yl)phenyl}propionate;
3-{4-[(furan-3-yl)methyloxy]-3-(1H-indol-5-yl)phenyl}propionic acid;

methyl 3-{3-(1H-indol-5-yl)-4-[(thiophen-2-yl)methyloxy]phenyl}propionate;
3-{3-(1H-indol-5-yl)-4-[(thiophen-2-yl)methyloxy]phenyl}propionic acid;
methyl 3-{3-(1H-indol-5-yl)-4-[2-(2-methylphenyl)ethyloxy]phenyl}propionate;
3-{3—(1H-indol-5-yl)-4-[2-(2-methylphenyl)ethyloxy]phenyl}propionic acid;
methyl 3-{3-(1H-indol-5-yl)-4-[2-(3-methylphenyl)ethyloxy]phenyl}propionate;
3-{3-(1H-indol-5-yl)-4-[2-(3-methylphenyl)ethyloxy]phenyl}propionic acid;
methyl 3-{3-(1H-indol-5-yl)-4-[2-(4-methylphenyl)ethyloxy]phenyl}propionate;
3-{3-(1H-indol-5-yl)-4-[2-(4-methylphenyl)ethyloxy]phenyl}propionic acid;
3-{3-(1H-indol-5-yl)-4-[2-(2-methoxyphenyl)ethyloxy]phenyl}propionic acid;
methyl 3-{3-(1H-indol-5-yl)-4-[2-(4-methoxyphenyl)ethyloxy]phenyl}propionate;
3-{3-(1H-indol-5-yl)-4-[2-(4-methoxyphenyl)ethyloxy]phenyl}propionic acid;
methyl 3-{4-[2-(2-chlorophenyl)ethyloxy]-3-(1H-indol-5-yl)phenyl}propionate;
3-{4-[2-(2-chlorophenyl)ethyloxy]-3-(1H-indol-5-yl)phenyl}propionic acid;
methyl 3-{4-[2-(3-chlorophenyl)ethyloxy]-3-(1H-indol-5-yl)phenyl}propionate;
3-{4-[2-(3-chlorophenyl)ethyloxy]-3-(1H-indol-5-yl)phenyl}propionic acid;
methyl 3-{4-[2-(4-chlorophenyl)ethyloxy]-3-(1H-indol-5-yl)phenyl}propionate;
3-{4-[2-(4-chlorophenyl)ethyloxy]-3-(1H-indol-5-yl)phenyl}propionic acid;
3-[3-(1H-indol-5-yl)-4-{2-[2-(trifluoromethyl)phenyl]ethyloxy}phenyl]propionic acid
3-(4-{2-[4-(N,N-dimethylamino)phenyl]ethyloxy}-3-[1H-indol-5-yl]phenyl)propionic acid;
methyl 3-{4-[2-(naphthalen-2-yl)ethyloxy]-3-(1H-indol-5-yl)phenyl}propionate;
3-{4-[2-(naphthalen-2-yl)ethyloxy]-3-(1H-indol-5-yl)phenyl}propionic acid;
methyl 3-{3-(1H-indol-5-yl)-4-[2-(1H-indol-3-yl)ethyloxy]phenyl}propionate;
3-{3-(1H-indol-5-yl)-4-[2-(1H-indol-3-yl)ethyloxy]phenyl}propionic acid;
3-[3-(1H-indol-5-yl)-4-(3-phenylpropyloxy)phenyl]propionic acid;
methyl 3-{3-(1H-indol-5-yl)-4-[2-(phenyloxy)ethyloxy]phenyl}propionate;
3-{3-(1H-indol-5-yl)-4-[2-(phenyloxy)ethyloxy]phenyl}propionic acid;
methyl 3-{4-[2-(2-chlorophenyloxy)ethyloxy]-3-(1H-indol-5-yl)phenyl}propionate;
3-{4-[2-(2-chlorophenyloxy)ethyloxy]-3-(1H-indol-5-yl)phenyl}propionic acid;
methyl 3-{4-[2-(4-chlorophenyloxy)ethyloxy]-3-(1H-indol-5-yl)phenyl}propionate;
3-{4-[2-(4-chlorophenyloxy)ethyloxy]-3-(1H-indol-5-yl)phenyl}propionic acid;
methyl 3-{3-(1H-indol-5-yl)-4-[2-(phenylthio)ethyloxy]phenyl}propionate;
3-{3-(1H-indol-5-yl)-4-[2-(phenylthio)ethyloxy]phenyl}propionic acid;
3-{3-(1H-indol-5-yl)-4-[2-(N-phenyl-N-methylamino)ethyloxy]phenyl}propionic acid;
ethyl 3-[4-cyclohexylmethyloxy-3-(1H-indol-5-yl)phenyl]propionate;
3-[4-cyclohexylmethyloxy-3-(1H-indol-5-yl)phenyl]propionic acid;
methyl 3-[4-cyclohexylmethyloxy-3-(1-methyl-1H-indol-5-yl)phenyl]propionate;
3-[4-cyclohexylmethyloxy-3-(1-methyl-1H-indol-5-yl)phenyl]propionic acid;
methyl 3-[4-cyclopentylmethyloxy-3-(1-methyl-1H-indol-5-yl)phenyl]propionate;
3-[4-cyclopentylmethyloxy-3-(1-methyl-1H-indol-5-yl)phenyl]propionic acid;
3-[4-cyclopentylmethyloxy-3-(1-ethyl-1H-indol-5-yl)phenyl]propionic acid;
methyl 3-[4-cyclopentylmethyloxy-3-(1-isopropyl-1H-indol-5-yl)phenyl]propionate;
3-[4-cyclopentylmethyloxy-3-(1-isopropyl-1H-indol-5-yl)phenyl]propionic acid;
methyl 3-[3-(1-butyl-1H-indol-5-yl)-4-cyclopentylmethyloxyphenyl]propionate;
3-[3-(1-butyl-1H-indol-5-yl)-4-cyclopentylmethyloxyphenyl]propionic acid;
methyl 3-[3-(1-cyclopentyl-1H-indol-5-yl)-4-cyclopentylmethyloxyphenyl]propionate;
3-[3-(1-cyclopentyl-1H-indol-5-yl)-4-cyclopentylmethyloxyphenyl]propionic acid;
3-{4-cyclopentylmethyloxy-3-[1-(2-hydroxyethyl)-1H-indol-5-yl]phenyl}propionic acid;
methyl 3-[4-(2-chlorophenylmethyloxy)-3-(1-methyl-1H-indol-5-yl)phenyl]propionate;
3-[4-(2-chlorophenylmethyloxy)-3-(1-methyl-1H-indol-5-yl)phenyl]propionic acid;
3-[4-cyclopentyloxy-3-(1-ethyl-1H-indol-5-yl)phenyl]propionic acid;
methyl 3-[4-cyclohexyloxy-3-(1-ethyl-1H-indol-5-yl)phenyl]propionate;
3-[4-cyclohexyloxy-3-(1-ethyl-1H-indol-5-yl)phenyl]propionic acid;
methyl 3-[4-(2-chlorophenylmethyloxy)-3-(1-ethyl-1H-indol-5-yl)phenyl]propionate;
3-[4-(2-chlorophenylmethyloxy)-3-(1-ethyl-1H-indol-5-yl)phenyl]propionic acid;
methyl 3-[4-cyclopentylmethyloxy-3-(1,3-dimethyl-1H-indol-5-yl)phenyl]propionate;
3-[4-cyclopentylmethyloxy-3-(1,3-dimethyl-1H-indol-5-yl)phenyl]propionic acid;
methyl 3-[4-cyclopentylmethyloxy-3-(3-formyl-1H-indol-5-yl)phenyl]propionate;
3-[4-cyclopentylmethyloxy-3-(3-formyl-1H-indol-5-yl)phenyl]propionic acid;
3-[4-cyclopentylmethyloxy-3-(3-formyl-1-methyl-1H-indol-5-yl)phenyl]propionic acid;
methyl 3-[3-(3-acetyl-1H-indol-5-yl)-4-cyclopentylmethyloxyphenyl]propionate;
3-[3-(3-acetyl-1H-indol-5-yl)-4-cyclopentylmethyloxyphenyl]propionic acid;
methyl 3-[3-(3-acetyl-1-methyl-1H-indol-5-yl)-4-cyclopentylmethyloxyphenyl]-propionate;

3-[3-(3-acetyl-1-methyl-1H-indol-5-yl)-4-cyclopentylmethyloxyphenyl]propionic acid;

methyl 3-[4-cyclopentylmethyloxy-3-fluoro-5-(1H-indol-5-yl)phenyl]propionate;

3-[4-cyclopentylmethyloxy-3-fluoro-5-(1H-indol-5-yl)phenyl]propionic acid;

methyl 3-[3-chloro-4-cyclopentylmethyloxy-5-(1H-indol-5-yl)phenyl]propionate;

3-[3-chloro-4-cyclopentylmethyloxy-5-(1H-indol-5-yl)phenyl]propionic acid;

methyl 3-[4-cyclopentylmethyloxy-3-(1H-indol-5-yl)-5-nitrophenyl]propionate;

methyl 3-[3-amino-4-cyclopentylmethyloxy-5-(1H-indol-5-yl)phenyl]propionate;

3-[3-amino-4-cyclopentylmethyloxy-5-(1H-indol-5-yl)phenyl]propionic acid;

methyl 3-[4-cyclopentylmethyloxy-3-(1-methyl-1H-indol-5-yl)-5-nitrophenyl]-propionate;

methyl 3-[3-amino-4-cyclopentylmethyloxy-5-(1-methyl-1H-indol-5-yl)phenyl]-propionate;

3-[3-amino-4-cyclopentylmethyloxy-5-(1-methyl-1H-indol-5-yl)phenyl]propionic acid;

methyl 4-[4-cyclopentylmethyloxy-3-(1H-indol-5-yl)phenyl]butyrate;

4-[4-cyclopentylmethyloxy-3-(1H-indol-5-yl)phenyl]butyric acid;

methyl 3-[4-cyclohexylmethyloxy-3-(2,3-dimethyl-1H-indol-5-yl)phenyl]propionate;

3-[4-cyclohexylmethyloxy-3-(2,3-dimethyl-1H-indol-5-yl)phenyl]propionic acid;

methyl 3-[4-cyclopentylmethyloxy-3-(1,2,3-trimethyl-1H-indol-5-yl)phenyl]propionate;

3-[4-cyclopentylmethyloxy-3-(1,2,3-trimethyl-1H-indol-5-yl)phenyl]propionic acid;

methyl 3-[3-(benzo[b]furan-5-yl)-4-cyclopentylmethyloxyphenyl]propionate;

3-[3-(benzo[b]furan-5-yl)-4-cyclopentylmethyloxyphenyl]propionic acid;

methyl 3-[4-cyclohexylmethyloxy-3-(2,3-dimethylbenzo[b]furan-5-yl)phenyl]-propionate;

3-[4-cyclohexylmethyloxy-3-(2,3-dimethylbenzo[b]furan-5-yl)phenyl]propionic acid;

methyl 3-[3-(benzo[b]thiophen-5-yl)-4-cyclopentylmethyloxyphenyl]propionate;

3-[3-(benzo[b]thiophen-5-yl)-4-cyclopentylmethyloxyphenyl]propionic acid;

methyl 3-[4-cyclopentylmethyloxy-3-(2-methylbenzothiazol-5-yl)phenyl]propionate;

3-[4-cyclopentylmethyloxy-3-(2-methylbenzothiazol-5-yl)phenyl]propionic acid;

methyl 3-[3-(2-aminobenzothiazol-5-yl)-4-cyclopentylmethyloxyphenyl]propionate;

3-[3-(2-aminobenzothiazol-5-yl)-4-cyclopentylmethyloxyphenyl]propionic acid;

ethyl 3-[3-(2-aminobenzothiazol-6-yl)-4-cyclopentylmethyloxyphenyl]propionate;

3-[3-(2-aminobenzothiazol-6-yl)-4-cyclopentylmethyloxyphenyl]propionic acid;

methyl 3-[3-(2-aminobenzothiazol-6-yl)-4-cyclohexylmethyloxyphenyl]propionate;

3-[3-(2-aminobenzothiazol-6-yl)-4-cyclohexylmethyloxyphenyl]propionic acid;

ethyl 3-[3-(2-aminobenzothiazol-6-yl)-4-butyloxyphenyl]propionate;

3-[3-(2-aminobenzothiazol-6-yl)-4-butyloxyphenyl]propionic acid;

ethyl 3-[3-(2-aminobenzothiazol-6-yl)-4-cyclopentyloxyphenyl]propionate;

3-[3-(2-aminobenzothiazol-6-yl)-4-cyclopentyloxyphenyl]propionic acid;

ethyl 3-[3-(2-aminobenzothiazol-6-yl)-4-cyclohexyloxyphenyl]propionate;

3-[3-(2-aminobenzothiazol-6-yl)-4-cyclohexyloxyphenyl]propionic acid;

ethyl 3-[4-cyclopentylmethyloxy-3-(2-methylaminobenzothiazol-6-yl)phenyl]-propionate;

3-[4-cyclopentylmethyloxy-3-(2-methylaminobenzothiazol-6-yl)phenyl]propionic acid;

ethyl 3-[3-(benzothiazol-6-yl)-4-cyclopentylmethyloxyphenyl]propionate;

3-[3-(benzothiazol-6-yl)-4-cyclopentylmethyloxyphenyl]propionic acid;

ethyl 3-{4-cyclopentylmethyloxy-3-[2-(N,N-dimethylamino)benzothiazol-6-yl]phenyl}-propionate;

3-{4-cyclopentylmethyloxy-3-[2-(N,N-dimethylamino)benzothiazol-6-yl]phenyl}-propionic acid;

ethyl 3-[4-cyclopentylmethyloxy-3-(2-imino-3-methyl-2,3-dihydrobenzothiazol-6-yl)-phenyl]propionate;

3-[4-cyclopentylmethyloxy-3-(2-imino-3-methyl-2,3-dihydrobenzothiazol-6-yl)-phenyl]propionic acid;

ethyl 3-{4-cyclopentylmethyloxy-3-[3-methyl-2-(methylimino)-2,3-dihydrobenzothiazol-6-yl]phenyl}propionate;

3-{4-cyclopentylmethyloxy-3-[3-methyl-2-(methylimino)-2,3-dihydrobenzothiazol-6-yl]-phenyl}propionic acid;

3-[4-cyclopentylmethyloxy-3-(2-methoxybenzothiazol-6-yl)phenyl]propionic acid;

ethyl 3-[4-cyclopentylmethyloxy-3-(2-methylbenzothiazol-6-yl)phenyl]propionate;

3-[4-cyclopentylmethyloxy-3-(2-methylbenzothiazol-6-yl)phenyl]propionic acid;

3-[4-cyclopentylmethyloxy-3-(2-thioxo-2,3-dihydrobenzothiazol-6-yl)phenyl]propionic acid;

3-[4-cyclopentylmethyloxy-3-(2-oxo-2,3-dihydrobenzothiazol-6-yl)phenyl]propionic acid;

methyl 3-[4-cyclopentylmethyloxy-3-(2-oxo-2,3-dihydrobenzothiazol-6-yl)phenyl]-propionate;

methyl 3-[4-cyclopentylmethyloxy-3-(2-oxo-3-methyl-2,3-dihydrobenzothiazol-6-yl)-phenyl]propionate;

3-[4-cyclopentylmethyloxy-3-(2-oxo-3-methyl-2,3-dihydrobenzothiazol-6-yl)phenyl]-propionic acid;

methyl 3-[4-cyclopentylmethyloxy-3-(quinolin-3-yl)phenyl]propionate;

3-[4-cyclopentylmethyloxy-3-(quinolin-3-yl)phenyl]-propionic acid;

methyl 3-[4-cyclohexylmethyloxy-3-(quinolin-3-yl)phenyl]propionate;

3-[4-cyclohexylmethyloxy-3-(quinolin-3-yl)phenyl]propionic acid;

methyl 3-[4-cyclohexylmethyloxy-3-(quinolin-6-yl)phenyl]propionate;

3-[4-cyclohexylmethyloxy-3-(quinolin-6-yl)phenyl]propionic acid;

methyl 3-[4-cyclohexylmethyloxy-3-(2-oxo-1,2-dihydroquinolin-6-yl)phenyl]propionate;
3-[4-cyclohexylmethyloxy-3-(2-oxo-1,2-dihydroquinolin-6-yl)phenyl]propionic acid;
methyl 3-[4-benzyloxy-3-(naphthalen-2-yl)phenyl]propionate;
3-[4-benzyloxy-3-(naphthalen-2-yl)phenyl]propionic acid;
methyl 3-[4-benzyloxy-3-(1H-indol-5-yl)phenyl]propionate;
3-[4-benzyloxy-3-(1H-indol-5-yl)phenyl]propionic acid;
methyl 3-[4-(4-t-butylphenylmethyloxy)-3-(1H-indol-5-yl)phenyl]propionate;
3-[4-(4-t-butylphenylmethyloxy)-3-(1H-indol-5-yl)phenyl]propionic acid;
methyl 3-[3-(naphthalen-2-yl)-4-phenyloxyphenyl]propionate;
3-[3-(naphthalen-2-yl)-4-phenyloxyphenyl]propionic acid;
3-[3-(benzothiazol-6-yl)-4-cyclohexyloxyphenyl]propionic acid;
3-[3-(1H-indol-5-yl)-4-(3-methylcyclopentyloxy)phenyl]propionic acid;
3-[4-(2-fluorophenyloxy)-3-(1H-indol-5-yl)phenyl]propionic acid;
3-{4-[2-(acetylamino)phenylmethyloxy]-3-(1H-indol-5-yl)phenyl}propionic acid;
3-[3-(1H-indol-5-yl)-4-(2-methanesulfonylaminophenylmethyloxy)phenyl]propionic acid;
3-{4-[(2-chlorothiophen-5-yl)methyloxy]-3-(1H-indol-5-yl)phenyl}propionic acid;
3-{4-[2-(benzenesulfonyl)ethyloxy]-3-(1H-indol-5-yl)phenyl}propionic acid;
3-[4-cyclopentylmethyloxy-3-(2-methyl-1H-indol-5-yl)phenyl]propionic acid;
3-[4-cyclopentylmethyloxy-3-(3-hydroxymethyl-1H-indol-5-yl)phenyl]propionic acid;
3-[3-(2-carboxy-1H-indol-5-yl)-4-cyclopentylmethyloxyphenyl]propionic acid;
3-[3-(3-carboxymethyl-1H-indol-5-yl)-4-cyclopentylmethyloxyphenyl]propionic acid;
3-[4-(4-fluorophenylmethyloxy)-3-(1-methyl-1H-indol-5-yl)phenyl]propionic acid;
3-{3-(1-methyl-1H-indol-5-yl)-4-[4-(trifluoromethyl)phenylmethyloxy]phenyl}propionic acid;
3-(4-{2-[4-(N,N-dimethylamino)phenyl]ethyloxy}-3-[1-methyl-1H-indol-5-yl]phenyl)-propionic acid;
3-[3-(1-ethyl-1H-indol-5-yl)-4-(4-fluorophenylmethyloxy)phenyl]propionic acid;
3-{3-(1-ethyl-1H-indol-5-yl)-4-[4-(trifluoromethyl)phenylmethyloxy]phenyl}propionic acid;
3-(3-[1-ethyl-1H-indol-5-yl]-4-{2-[4-(N,N-dimethylamino)phenyl]ethyloxy}phenyl)-propionic acid;
3-[5-(1-carboxymethyl-1H-indol-5-yl)-4-cyclopentylmethyloxyphenyl]propionic acid;
3-[4-cyclopentylmethyloxy-3-(1H-indol-5-yl)-5-methoxyphenyl]propionic acid;
3-[4-cyclopentyloxy-3-fluoro-5-(1H-indol-5-yl)phenyl]propionic acid;
3-[4-cyclohexyloxy-3-fluoro-5-(1H-indol-5-yl)phenyl]propionic acid;
3-[4-cyclopentyloxy-3-fluoro-5-(1-methyl-1H-indol-5-yl)phenyl]propionic acid;
3-[4-cyclohexyloxy-3-fluoro-5-(1-methyl-1H-indol-5-yl)phenyl]propionic acid;
3-[4-cyclopentyloxy-3-(1-ethyl-1H-indol-5-yl)-5-fluorophenyl]propionic acid;
3-[4-cyclohexyloxy-3-(1-ethyl-1H-indol-5-yl)-5-fluorophenyl]propionic acid;
3-[3-amino-4-cyclopentyloxy-5-(1H-indol-5-yl)phenyl]propionic acid;
3-[3-amino-4-cyclohexyloxy-5-(1H-indol-5-yl)phenyl]propionic acid;
3-[3-amino-4-cyclopentyloxy-5-(1-methyl-1H-indol-5-yl)phenyl]propionic acid;
3-[3-amino-4-cyclohexyloxy-5-(1-methyl-1H-indol-5-yl)phenyl]propionic acid;
3-[4-cyclopentylmethyloxy-3-(1-propyl-1H-indol-5-yl)phenyl]propionic acid;
3-[4-cyclopentyloxy-3-(1-propyl-1H-indol-5-yl)phenyl]propionic acid;
3-[4-cyclohexyloxy-3-(1-propyl-1H-indol-5-yl)phenyl]propionic acid;
3-[3-(benzo[b]thiophen-5-yl)-4-cyclopentyloxyphenyl]propionic acid;
3-[3-(benzo[b]thiophen-5-yl)-4-cyclohexyloxyphenyl]propionic acid;
3-[3-(benzothiazol-6-yl)-4-cyclopentyloxyphenyl]propionic acid;
3-[3-(benzothiazol-6-yl)-4-(2-chlorophenylmethyloxyphenyl)propionic acid;
3-[3-(benzothiazol-6-yl)-4-(4-fluorophenylmethyloxy)phenyl]propionic acid;
3-{3-(benzothiazol-6-yl)-4-[4-(trifluoromethyl)phenylmethyloxy]phenyl}propionic acid;
3-(3-[benzothiazol-6-yl]-4-{2-[4-(N,N-dimethylamino)phenyl]ethyl}phenyl)propionic acid;
3-[3-(2-aminobenzothiazol-6-yl)-4-(4-fluorophenylmethyloxy)phenyl]propionic acid;
3-[3-(2-aminobenzothiazol-6-yl)-4-(2-chlorophenylmethyloxy)phenyl]propionic acid;
3-{3-(2-aminobenzothiazol-6-yl)-4-[4-(trifluoromethyl)phenylmethyloxy]phenyl}-propionic acid;
3-(3-[2-aminobenzothiazol-6-yl]-4-{2-[4-(N,N-dimethylamino)phenyl]ethyl}phenyl)-propionic acid;
3-[3-(2-aminobenzothiazol-6-yl)-4-(cyclopentyloxy)-5-fluorophenyl]propionic acid;
3-[3-(2-aminobenzothiazol-6-yl)-4-(cyclohexyloxy)-5-fluorophenyl]propionic acid;
3-[4-cyclopentyloxy-3-(quinolin-3-yl)phenyl]propionic acid;
3-[4-cyclohexyloxy-3-(quinolin-3-yl)phenyl]propionic acid;
3-[4-(2-chlorophenylmethyloxy)-3-(quinolin-3-yl)phenyl]propionic acid;
3-[4-cyclopentyloxy-3-(quinolin-6-yl)phenyl]propionic acid;
3-[4-cyclohexyloxy-3-(quinolin-6-yl)phenyl]propionic acid;
3-[4-(2-chlorophenylmethyloxy)-3-(quinolin-6-yl)phenyl]propionic acid;
3-[4-cyclohexylmethyloxy-3-(2-methylquinolin-6-yl)phenyl]propionic acid;

methyl 3-[4-cyclopentyloxy-3-(naphthalen-2-yl)-5-nitrophenyl]propionate;
methyl 3-[3-amino-4-cyclopentyloxy-5-(naphthalen-2-yl)phenyl]propionate;
3-[3-amino-4-cyclopentyloxy-5-(naphthalen-2-yl)phenyl]propionic acid;
methyl 3-[4-cyclohexyloxy-3-(naphthalen-2-yl)-5-nitrophenyl]propionate;
methyl 3-[3-amino-4-cyclohexyloxy-5-(naphthalen-2-yl)phenyl]propionate;
3-[3-amino-4-cyclohexyloxy-5-(naphthalen-2-yl)phenyl]propionic acid;
methyl 3-[3-(naphthalen-2-yl)-5-nitro-4-(1-phenylethyloxy)phenyl]propionate;
methyl 3-[3-amino-5-(naphthalen-2-yl)-4-(1-phenylethyloxy)phenyl]propionate;
3-[3-amino-5-(naphthalen-2-yl)-4-(1-phenylethyloxy)phenyl]propionic acid;
methyl 3-[4-(4-methylbenzyloxy)-3-(naphthalen-2-yl)-5-nitrophenyl]propionate;
methyl 3-[3-amino-4-(4-methylbenzyloxy)-5-(naphthalen-2-yl)phenyl]propionate;
3-[3-amino-4-(4-methylbenzyloxy)-5-(naphthalen-2-yl)phenyl]propionic acid;
methyl 3-{4-[2-(4-methylphenyl)ethyloxy]-3-(naphthalen-2-yl)-5-nitrophenyl}-propionate;
methyl 3-{3-amino-4-[2-(4-methylphenyl)ethyloxy]-5-(naphthalen-2-yl)phenyl}-propionate;
3-{3-amino-4-[2-(4-methylphenyl)ethyloxy]-5-(naphthalen-2-yl)phenyl}propionic acid;
methyl 3-[3-(naphthalen-2-yl)-5-nitro-4-(3-phenylpropyloxy)phenyl]propionate;
methyl 3-[3-amino-5-(naphthalen-2-yl)-4-(3-phenylpropyloxy)phenyl]propionate;
3-[3-amino-5-(naphthalen-2-yl)-4-(3-phenylpropyloxy)phenyl]propionic acid;
methyl 3-(3-[naphthalen-2-yl]-5-nitro-4-{1'-[4-(trifluoromethyl)phenyl]ethyloxy}-phenyl)propionate;
methyl 3-(3-amino-5-[naphthalen-2-yl]-4-{1'-[4-(trifluoromethyl)phenyl]ethyloxy}-phenyl)propionate;
3-(3-amino-5-[naphthalen-2-yl]-4-{1-[4-(trifluoromethyl)phenyl]ethyloxy}phenyl)-propionic acid;
methyl 3-[4-(indan-2-yloxy)-3-(naphthalen-2-yl)-5-nitrophenyl]propionate;
methyl 3-[3-amino-4-(indan-2-yloxy)-5-(naphthalen-2-yl)phenyl]propionate;
3-[3-amino-4-(indan-2-yloxy)-5-(naphthalen-2-yl)phenyl]propionic acid;
methyl 3-{4-[2-(2-fluorophenyl)ethyloxy]-3-(naphthalen-2-yl)-5-nitrophenyl}-propionate;
methyl 3-{3-amino-4-[2-(2-fluorophenyl)ethyloxy]-5-(naphthalen-2-yl)phenyl}-propionate;
3-{3-amino-4-[2-(2-fluorophenyl)ethyloxy]-5-(naphthalen-2-yl)phenyl}propionic acid;
methyl 3-[4-(3-methylbutyloxy)-3-(naphthalen-2-yl)-5-nitrophenyl]propionate;
methyl 3-[3-amino-4-(3-methylbutyloxy)-5-(naphthalen-2-yl)phenyl]propionate;
3-[3-amino-4-(3-methylbutyloxy)-5-(naphthalen-2-yl)phenyl]propionic acid;
methyl 3-[4-(2,3-dimethylbutyloxy)-3-(naphthalen-2-yl)-5-nitrophenyl]propionate;
methyl 3-[3-amino-4-(2,3-dimethylbutyloxy)-5-(naphthalen-2-yl)phenyl]propionate;
3-[3-amino-4-(2,3-dimethylbutyloxy)-5-(naphthalen-2-yl)phenyl]propionic acid;
methyl 3-{4-(2-[4-(N,N-dimethylamino)phenyl]ethyloxy}-3-[naphthalen-2-yl]-5-nitrophenyl)propionate;
methyl 3-{3-amino-4-(2-[4-(N,N-dimethylamino)phenyl]ethyloxy}-5-[naphthalen-2-yl]-phenyl)propionate;
3-(3-amino-4-{2-[4-(N,N-dimethylamino)phenyl]ethyloxy}-5-[naphthalen-2-yl]phenyl)-propionic acid;
methyl 3-{3-(naphthalen-2-yl)-5-nitro-4-[2-(N-phenyl-N-methylamino)ethyloxy]-phenyl}propionate;
methyl 3-{3-amino-5-(naphthalen-2-yl)-4-[2-(N-phenyl-N-methylamino)ethyloxy]-phenyl}propionate;
3-{3-amino-5-(naphthalen-2-yl)-4-[2-(N-phenyl-N-methylamino)ethyloxy]phenyl}-propionic acid;
methyl 3-{3-(naphthalen-2-yl)-5-nitro-4-[4-(trifluoromethyl)phenylmethyloxy]-phenyl}propionate;
methyl 3-{3-amino-5-(naphthalen-2-yl)-4-[4-(trifluoromethyl)phenylmethyloxy]phenyl}-propionate;
3-{3-amino-5-(naphthalen-2-yl)-4-[4-(trifluoromethyl)phenylmethyloxy]phenyl}-propionic acid;
methyl 3-[4-(cis-2-methylcyclopentyloxy)-3-(naphthalen-2-yl)-5-nitrophenyl]-propionate;
methyl 3-[3-amino-4-(cis-2-methylcyclopentyloxy)-5-(naphthalen-2-yl)phenyl]-propionate;
3-[3-amino-4-(cis-2-methylcyclopentyloxy)-5-(naphthalen-2-yl)phenyl]propionic acid;
methyl 3-[4-(2-methylpropyloxy)-3-(naphthalen-2-yl)-5-nitrophenyl]propionate;
methyl 3-[3-amino-4-(2-methylpropyloxy)-3-(naphthalen-2-yl)phenyl]propionate;
3-[3-amino-4-(2-methylpropyloxy)-3-(naphthalen-2-yl)phenyl]propionic acid;
methyl 3-[4-(trans-4-methylcyclohexyloxy)-3-(naphthalen-2-yl)-5-nitrophenyl]-propionate;
methyl 3-[3-amino-4-(trans-4-methylcyclohexyloxy)-5-(naphthalen-2-yl)phenyl]-propionate;
3-[3-amino-4-(trans-4-methylcyclohexyloxy)-5-(naphthalen-2-yl)phenyl]propionic acid;
methyl 3-[4-cyclopentyloxy-3-(1H-indol-5-yl)-5-nitrophenyl]propionate;
methyl 3-[3-amino-4-cyclopentyloxy-5-(1H-indol-5-yl)phenyl]propionate;
methyl 3-[4-cyclopentyloxy-3-(1-methyl-1H-indol-5-yl)-5-nitrophenyl]propionate;
methyl 3-[3-amino-4-cyclopentyloxy-5-(1-methyl-1H-indol-5-yl)phenyl]propionate;
methyl 3-[4-cyclopentyloxy-3-(1-ethyl-1H-indol-5-yl)-5-nitrophenyl]propionate;
methyl 3-[3-amino-4-cyclopentyloxy-5-(1-ethyl-1H-indol-5-yl)phenyl]propionate;
3-[3-amino-4-cyclopentyloxy-5-(1-ethyl-1H-indol-5-yl)phenyl]propionic acid;
methyl 3-[4-cyclohexyloxy-3-(1H-indol-5-yl)-5-nitrophenyl]propionate;
methyl 3-[3-amino-4-cyclohexyloxy-5-(1H-indol-5-yl)phenyl]propionate;
methyl 3-[4-cyclohexyloxy-3-(1-methyl-1H-indol-5-yl)-5-nitrophenyl]propionate;

methyl 3-[3-amino-4-cyclohexyloxy-5-(1-methyl-1H-indol-5-yl)phenyl]propionate;
methyl 3-[4-cyclohexyloxy-3-(1-ethyl-1H-indol-5-yl)-5-nitrophenyl]propionate;
methyl 3-[3-amino-4-cyclohexyloxy-5-(1-ethyl-1H-indol-5-yl)phenyl]propionate;
3-[3-amino-4-cyclohexyloxy-5-(1-ethyl-1H-indol-5-yl)phenyl]propionic acid;
methyl 3-[3-(1H-indol-5-yl)-5-nitro-4-(1-phenylethyloxy)phenyl]propionate;
methyl 3-[3-amino-5-(1H-indol-5-yl)-4-(1-phenylethyloxy)phenyl]propionate;
3-[3-amino-5-(1H-indol-5-yl)-4-(1-phenylethyloxy)phenyl]propionic acid;
methyl 3-[3-(1-methyl-1H-indol-5-yl)-5-nitro-4-(1-phenylethyloxy)phenyl]propionate;
methyl 3-[3-amino-5-(1-methyl-1H-indol-5-yl)-4-(1-phenylethyloxy)phenyl]propionate;
3-[3-amino-5-(1-methyl-1H-indol-5-yl)-4-(1-phenylethyloxy)phenyl]propionic acid;
methyl 3-[4-(indan-2-yloxy)-3-(1H-indol-5-yl)-5-nitrophenyl]propionate;
methyl 3-[3-amino-4-(indan-2-yloxy)-5-(1H-indol-5-yl)phenyl]propionate;
3-[3-amino-4-(indan-2-yloxy)-5-(1H-indol-5-yl)phenyl]propionic acid;
methyl 3-[4-(indan-2-yloxy)-3-(1-methyl-1H-indol-5-yl)-5-nitrophenyl]propionate;
methyl 3-[3-amino-4-(indan-2-yloxy)-5-(1-methyl-1H-indol-5-yl)phenyl]propionate;
3-[3-amino-4-(indan-2-yloxy)-5-(1-methyl-1H-indol-5-yl)phenyl]propionic acid;
methyl 3-{3-(1H-indol-5-yl)-5-nitro-4-[4-(trifluoromethyl)benzyloxy]phenyl}propionate;
methyl 3-{3-amino-5-(1H-indol-5-yl)-4-[4-(trifluoromethyl)benzyloxy]phenyl}propionate;
3-{3-amino-5-(1H-indol-5-yl)-4-[4-(trifluoromethyl)benzyloxy]phenyl}propionic acid;
3-[4-(2-ethylbutyloxy)-3-(1H-indol-5-yl)-5-nitrophenyl]propionate;
methyl 3-[3-amino-4-(2-ethylbutyloxy)-5-(1H-indol-5-yl)phenyl]propionate;
3-[3-amino-4-(2-ethylbutyloxy)-5-(1H-indol-5-yl)phenyl]propionic acid;
methyl 3-[4-cyclopentyloxy-3-(1H-indazol-4-yl)phenyl]propionate;
3-[4-cyclopentyloxy-3-(1H-indazol-4-yl)phenyl]propionic acid;
methyl 3-[4-cyclopentyloxy-3-(1-methyl-1H-indazol-4-yl)phenyl]propionate;
3-[4-cyclopentyloxy-3-(1-methyl-1H-indazol-4-yl)phenyl]propionic acid;
methyl 3-[4-cyclopentyloxy-3-(2-methyl-2H-indazol-4-yl)phenyl]propionate;
3-[4-cyclopentyloxy-3-(2-methyl-2H-indazol-4-yl)phenyl]propionic acid;
methyl 3-[4-cyclopentyloxy-3-(1H-indazol-6-yl)phenyl]propionate;
3-[4-cyclopentyloxy-3-(1H-indazol-6-yl)phenyl]propionic acid;
methyl 3-[4-cyclopentyloxy-3-(1-methyl-1H-indazol-6-yl)phenyl]propionate;
3-[4-cyclopentyloxy-3-(1-methyl-1H-indazol-6-yl)phenyl]propionic acid;
methyl 3-[4-cyclopentyloxy-3-(2-methyl-2H-indazol-6-yl)phenyl]propionate;
3-[4-cyclopentyloxy-3-(2-methyl-2H-indazol-6-yl)phenyl]propionic acid;
methyl 3-[4-cyclopentyloxy-3-(1H-indazol-5-yl)phenyl]propionate;
3-[4-cyclopentyloxy-3-(1H-indazol-5-yl)phenyl]propionic acid;
methyl 3-[4-cyclopentyloxy-3-(1-methyl-1H-indazol-5-yl)phenyl]propionate;
3-[4-cyclopentyloxy-3-(1-methyl-1H-indazol-5-yl)phenyl]propionic acid;
methyl 3-[4-cyclopentyloxy-3-(2-methyl-2H-indazol-5-yl)phenyl]propionate;
3-[4-cyclopentyloxy-3-(2-methyl-2H-indazol-5-yl)phenyl]propionic acid;
methyl 3-[4-cyclopentyloxy-3-(1-ethyl-1H-indazol-5-yl)phenyl]propionate;
3-[4-cyclopentyloxy-3-(1-ethyl-1H-indazol-5-yl)phenyl]propionic acid;
methyl 3-[4-cyclopentyloxy-3-(2-ethyl-2H-indazol-5-yl)phenyl]propionate;
3-[4-cyclopentyloxy-3-(2-ethyl-2H-indazol-5-yl)phenyl]propionic acid;
methyl 3-[4-cyclopentylmethyloxy-3-(1H-indazol-5-yl)phenyl]propionate;
3-[4-cyclopentylmethyloxy-3-(1H-indazol-5-yl)phenyl]propionic acid;
methyl 3-[4-cyclohexyloxy-3-(1H-indazol-5-yl)phenyl]propionate;
3-[4-cyclohexyloxy-3-(1H-indazol-5-yl)phenyl]propionic acid;
methyl 3-[4-cyclohexyloxy-3-(1-methyl-1H-indazol-5-yl)phenyl]propionate;
3-[4-cyclohexyloxy-3-(1-methyl-1H-indazol-5-yl)phenyl]propionic acid;
methyl 3-[4-cyclohexyloxy-3-(2-methyl-2H-indazol-5-yl)phenyl]propionate;
3-[4-cyclohexyloxy-3-(2-methyl-2H-indazol-5-yl)phenyl]propionic acid;
methyl 3-[4-cycloheptyloxy-3-(1H-indazol-5-yl)phenyl]propionate;
3-[4-cycloheptyloxy-3-(1H-indazol-5-yl)phenyl]propionic acid;
methyl 3-[4-(2-ethylbutyloxy)-3-(1H-indazol-5-yl)phenyl]propionate;
3-[4-(2-ethylbutyloxy)-3-(1H-indazol-5-yl)phenyl]propionic acid;
methyl 3-[4-(indan-2-yloxy)-3-(1H-indazol-5-yl)phenyl]propionate;
3-[4-(indan-2-yloxy)-3-(1H-indazol-5-yl)phenyl]propionic acid;
methyl 3-[4-(indan-2-yloxy)-3-(1-methyl-1H-indazol-5-yl)phenyl]propionate;
3-[4-(indan-2-yloxy)-3-(1-methyl-1H-indazol-5-yl)phenyl]propionic acid;
methyl 3-[3-(1-ethyl-1H-indazol-5-yl)-4-(indan-2-yloxy)phenyl]propionate;
3-[3-(1-ethyl-1H-indazol-5-yl)-4-(indan-2-yloxy)phenyl]propionic acid;

methyl 3-[4-(4-fluorobenzyloxy)-3-(1H-indazol-5-yl)phenyl]propionate;
3-[4-(4-fluorobenzyloxy)-3-(1H-indazol-5-yl)phenyl]propionic acid;
methyl 3-[4-(4-fluorobenzyloxy)-3-(1-methyl-1H-indazol-5-yl)phenyl]propionate;
3-[4-(4-fluorobenzyloxy)-3-(1-methyl-1H-indazol-5-yl)phenyl]propionic acid;
methyl 3-{3-(1H-indazol-5-yl)-4-[4-(trifluoromethyl)benzyloxy]phenyl}propionate;
3-{3-(1H-indazol-5-yl)-4-[4-(trifluoromethyl)benzyloxy]phenyl}propionic acid;
methyl 3-{4-[2-(2-fluorophenyl)ethyloxy]-3-(1H-indazol-5-yl)phenyl}-propionate;
3-{4-[2-(2-fluorophenyl)ethyloxy]-3-(1H-indazol-5-yl)phenyl}propionic acid;
methyl 3-{4-[2-(2-fluorophenyl)ethyloxy]-3-(1-methyl-1H-indazol-5-yl)phenyl}-propionate
3-{4-[2-(2-fluorophenyl)ethyloxy]-3-(1-methyl-1H-indazol-5-yl)phenyl}propionic acid;
methyl 3-[4-cyclopentyloxy-3-fluoro-5-(1H-indazol-5-yl)phenyl]propionate;
3-[4-cyclopentyloxy-3-fluoro-5-(1H-indazol-5-yl)phenyl]propionic acid;
methyl 3-[4-cyclopentyloxy-3-fluoro-5-(1-methyl-1H-indazol-5-yl)phenyl]propionate;
3-[4-cyclopentyloxy-3-fluoro-5-(1-methyl-1H-indazol-5-yl)phenyl]propionic acid;
methyl 3-[4-(indan-2-yloxy)-3-(1H-indazol-5-yl)-5-nitrophenyl]propionate;
methyl 3-[3-amino-4-(indan-2-yloxy)-5-(1H-indazol-5-yl)phenyl]propionate;
3-[3-amino-4-(indan-2-yloxy)-5-(1H-indazol-5-yl)phenyl]propionic acid;
methyl 3-[3-(1-ethyl-1H-indazol-5-yl)-4-(indan-2-yloxy)-5-nitrophenyl]propionate;
methyl 3-[3-amino-5-(1-ethyl-1H-indazol-5-yl)-4-(indan-2-yloxy)phenyl]propionate;
3-[3-amino-5-(1-ethyl-1H-indazol-5-yl)-4-(indan-2-yloxy)phenyl]propionic acid;
methyl 3-[3-(benzo[d]isothiazol-5-yl)-4-cyclopentyloxyphenyl]propionate;
3-[3-(benzo[d]isothiazol-5-yl)-4-cyclopentyloxyphenyl]propionic acid;
methyl 3-[3-(benzo[c]isothiazol-5-yl)-4-cyclopentyloxyphenyl]propionate;
3-[3-(benzo[c]isothiazol-5-yl)-4-cyclopentyloxyphenyl]propionic acid;
methyl 3-[4-cyclopentyloxy-3-(imidazo[1,2-a]pyridin-6-yl)phenyl]propionate;
3-[4-cyclopentyloxy-3-(imidazo[1,2-a]pyridin-6-yl)phenyl]propionic acid;
methyl 3-[4-cyclopentyloxy-3-(1H-pyrrolo[2,3-b]pyridin-6-yl)phenyl]propionate;
3-[4-cyclopentyloxy-3-(1H-pyrrolo[2,3-b]pyridin-6-yl)phenyl]propionic acid;
methyl 3-[4-cyclopentyloxy-3-(1-methyl-1H-pyrrolo[2,3-b]pyridin-6-yl)phenyl]-propionate;
3-[4-cyclopentyloxy-3-(1-methyl-1H-pyrrolo[2,3-b]pyridin-6-yl)phenyl]propionic acid;
methyl 3-[4-cyclohexyloxy-3-(isoquinolin-6-yl)phenyl]propionate;
3-[4-cyclohexyloxy-3-(isoquinolin-6-yl)phenyl]propionic acid;
methyl 3-[4-cyclopentyloxy-3-(isoquinolin-6-yl)phenyl]propionate;
3-[4-cyclopentyloxy-3-(isoquinolin-6-yl)phenyl]propionic acid;
methyl 3-{4-[4-(trifluoromethyl)phenylmethyloxy]-3-(isoquinolin-6-yl)phenyl}-propionate;
3-{4-[4-(trifluoromethyl)phenylmethyloxy]-3-(isoquinolin-6-yl)phenyl}propionic acid;
methyl 3-[4-(indan-2-yloxy)-3-(isoquinolin-6-yl)phenyl]propionate;
3-[4-(indan-2-yloxy)-3-(isoquinolin-6-yl)phenyl]propionic acid;
methyl 3-[4-cyclopentyloxy-3-(1-oxo-1,2-dihydroisoquinolin-6-yl)phenyl]propionate;
3-[4-cyclopentyloxy-3-(1-oxo-1,2-dihydroisoquinolin-6-yl)phenyl]propionic acid;
3-[4-n-butyloxy-3-(1H-indazol-5-yl)phenyl]propionic acid;
3-[3-(1H-indazol-5-yl)-4-(2-methylpropyloxy)phenyl]propionic acid;
3-[4-cyclohexylmethyloxy-3-(1H-indazol-5-yl)phenyl]propionic acid;
3-[3-(1H-indazol-5-yl)-4-(1-phenylethyloxy)phenyl]propionic acid;
3-[3-(1H-indazol-5-yl)-4-(4-methylphenylmethyloxy)phenyl]propionic acid;
3-[4-(2-fluorophenylmethyloxy)-3-(1H-indazol-5-yl)phenyl]propionic acid;
3-[4-(3-fluorophenylmethyloxy)-3-(1H-indazol-5-yl)phenyl]propionic acid;
3-[4-(4-chlorophenylmethyloxy)-3-(1H-indazol-5-yl)phenyl]propionic acid;
3-{3-(1H-indazol-5-yl)-4-[2-(2-methylphenyl)ethyloxy]phenyl}propionic acid;
3-{3-(1H-indazol-5-yl)-4-[2-(4-methylphenyl)ethyloxy]phenyl}propionic acid;
3-{4-[2-(3-fluorophenyl)ethyloxy]-3-(1H-indazol-5-yl)phenyl}propionic acid;
3-{4-[2-(4-fluorophenyl)ethyloxy]-3-(1H-indazol-5-yl)phenyl}propionic acid;
3-{4-[2-(2-chlorophenyl)ethyloxy]-3-(1H-indazol-5-yl)phenyl}propionic acid;
3-(3-[1H-indazol-5-yl]-4-{2-[2-(trifluoromethyl)phenyl]ethyloxy}phenyl)propionic acid;
3-(4-{2-[4-(N,N-dimethylamino)phenyl]ethyl}-3-[1H-indazol-5-yl]phenyl)propionic acid;
3-{3-(1H-indazol-5-yl)-4-[2-(N-phenyl-N-methylamino)ethyloxy]phenyl}propionic acid;
3-[4-n-butyloxy-3-(1-methyl-1H-indazol-5-yl)phenyl]propionic acid;
3-[3-(1-methyl-1H-indazol-5-yl)-4-(2-methylpropyloxy)phenyl]propionic acid;
3-[4-(2-ethylbutyloxy)-3-(1-methyl-1H-indazol-5-yl)phenyl]propionic acid;
3-[4-cycloheptyloxy-3-(1-methyl-1H-indazol-5-yl)phenyl]propionic acid;
3-[4-cyclopentylmethyloxy-3-(1-methyl-1H-indazol-5-yl)phenyl]propionic acid;
3-[4-cyclohexylmethyloxy-3-(1-methyl-1H-indazol-5-yl)phenyl]propionic acid;

3-[3-(1-methyl-1H-indazol-5-yl)-4-(1-phenylethyloxy)phenyl]propionic acid;

3-[3-(1-methyl-1H-indazol-5-yl)-4-(4-methylphenylmethyloxy)phenyl]propionic acid;

3-[4-(2-fluorophenylmethyloxy)-3-(1-methyl-1H-indazol-5-yl)phenyl]propionic acid;

3-[4-(3-fluorophenylmethyloxy)-3-(1-methyl-1H-indazol-5-yl)phenyl]propionic acid;

3-[4-(4-chlorophenylmethyloxy)-3-(1-methyl-1H-indazol-5-yl)phenyl]propionic acid;

3-{3-(1-methyl-1H-indazol-5-yl)-4-[4-(trifluoromethyl)phenylmethyloxy]phenyl}-propionic acid;

3-{3-(1-methyl-1H-indazol-5-yl)-4-[2-(2-methylphenyl)ethyloxy]phenyl}propionic acid;

3-{3-(1-methyl-1H-indazol-5-yl)-4-[2-(4-methylphenyl)ethyloxy]phenyl}propionic acid;

3-{4-[2-(3-fluorophenyl)ethyloxy]-3-(1-methyl-1H-indazol-5-yl)phenyl}propionic acid;

3-{4-[2-(4-fluorophenyl)ethyloxy]-3-(1-methyl-1H-indazol-5-yl)phenyl}propionic acid;

3-{4-[2-(2-chlorophenyl)ethyloxy]-3-(1-methyl-1H-indazol-5-yl)phenyl}propionic acid;

3-(3-[1-methyl-1H-indazol-5-yl]-4-{2-[2-(trifluoromethyl)phenyl]ethyloxy}phenyl)-propionic acid;

3-(4-{2-[4-(N,N-dimethylamino)phenyl]ethyl}-3-[1-methyl-1H-indazol-5-yl]phenyl)-propionic acid;

3-{3-(1-methyl-1H-indazol-5-yl)-4-[2-(N-phenyl-N-methylamino)ethyloxy]phenyl}-propionic acid;

3-[4-n-butyloxy-3-(1-ethyl-1H-indazol-5-yl)phenyl]propionic acid;

3-[3-(1-ethyl-1H-indazol-5-yl)-4-(2-methylpropyloxy)phenyl]propionic acid;

3-[4-(2-ethylbutyloxy)-3-(1-ethyl-1H-indazol-5-yl)phenyl]propionic acid;

3-[4-cyclohexyloxy-3-(1-ethyl-1H-indazol-5-yl)phenyl]propionic acid;

3-[4-cycloheptyloxy-3-(1-ethyl-1H-indazol-5-yl)phenyl]propionic acid;

3-[4-cyclopentylmethyloxy-3-(1-ethyl-1H-indazol-5-yl)phenyl]propionic acid;

3-[4-cyclohexylmethyloxy-3-(1-ethyl-1H-indazol-5-yl)phenyl]propionic acid;

3-[3-(1-ethyl-1H-indazol-5-yl)-4-(1-phenylethyloxy)phenyl]propionic acid;

3-[3-(1-ethyl-1H-indazol-5-yl)-4-(4-methylphenylmethyloxy)phenyl]propionic acid;

3-[3-(1-ethyl-1H-indazol-5-yl)-4-(2-fluorophenylmethyloxy)phenyl]propionic acid;

3-[3-(1-ethyl-1H-indazol-5-yl)-4-(3-fluorophenylmethyloxy)phenyl]propionic acid;

3-[3-(1-ethyl-1H-indazol-5-yl)-4-(4-fluorophenylmethyloxy)phenyl]propionic acid;

3-[4-(4-chlorophenylmethyloxy)-3-(1-ethyl-1H-indazol-5-yl)phenyl]propionic acid;

3-{3-(1-ethyl-1H-indazol-5-yl)-4-[4-(trifluoromethyl)phenylmethyloxy]phenyl}propionic acid;

3-{3-(1-ethyl-1H-indazol-5-yl)-4-[2-(2-methylphenyl)ethyloxy]phenyl}propionic acid;

3-{3-(1-ethyl-1H-indazol-5-yl)-4-[2-(4-methylphenyl)ethyloxy]phenyl}propionic acid;

3-{3-(1-ethyl-1H-indazol-5-yl)-4-[2-(2-fluorophenyl)ethyloxy]phenyl}propionic acid;

3-{3-(1-ethyl-1H-indazol-5-yl)-4-[2-(3-fluorophenyl)ethyloxy]phenyl}propionic acid;

3-{3-(1-ethyl-1H-indazol-5-yl)-4-[2-(4-fluorophenyl)ethyloxy]phenyl}propionic acid;

3-4-[2-(2-chlorophenyl)ethyloxy-3-(1-ethyl-1H-indazol-5-yl)phenyl]propionic acid;

3-(3-[1-ethyl-1H-indazol-5-yl]-4-{2-[2-(trifluoromethyl)phenyl]ethyloxy}phenyl)-propionic acid;

3-(4-{2-[4-(N,N-dimethylamino)phenyl]ethyl}-3-[1-ethyl-1H-indazol-5-yl]phenyl)-propionic acid;

3-{3-(1-ethyl-1H-indazol-5-yl)-4-[2-(N-phenyl-N-methylamino)ethyloxy]phenyl}-propionic acid;

3-[4-cyclohexyloxy-3-fluoro-5-(1H-indazol-5-yl)phenyl]propionic acid;

3-[3-fluoro-4-(indan-2-yloxy)-5-(1H-indazol-5-yl)phenyl]propionic acid;

3-[3-fluoro-4-(4-fluorophenylmethyloxy)-5-(1H-indazol-5-yl)phenyl]propionic acid;

3-{3-fluoro-4-[2-(2-fluorophenyl)ethyloxy]-5-(1H-indazol-5-yl)phenyl}propionic ac 3-[4-cyclohexyloxy-3-fluoro-5-(1-methyl-1H-indazol-5-yl)phenyl]propionic acid;

3-[3-fluoro-4-(indan-2-yloxy)-5-(1-methyl-1H-indazol-5-yl)phenyl]propionic acid;

3-[4-cyclopentyloxy-3-(1-ethyl-1H-indazol-5-yl)-5-fluorophenyl]propionic acid;

3-[4-cyclohexyloxy-3-(1-ethyl-1H-indazol-5-yl)-5-fluorophenyl]propionic acid;

3-[3-(1-ethyl-1H-indazol-5-yl)-5-fluoro-4-(indan-2-yloxy)phenyl]propionic acid;

3-[3-(1-ethyl-1H-indazol-5-yl)-5-fluoro-4-(1-phenylethyloxy)phenyl]propionic acid;

3-[3-amino-4-cyclopentyloxy-5-(1H-indazol-5-yl)phenyl]propionic acid;

3-[3-amino-4-cyclohexyloxy-5-(1H-indazol-5-yl)phenyl]propionic acid;

3-[3-amino-4-(4-fluorophenylmethyloxy)-5-(1H-indazol-5-yl)phenyl]propionic acid;

3-{3-amino-4-[2-(2-fluorophenyl)ethyloxy]-5-(1H-indazol-5-yl)phenyl}propionic acid;

3-[3-amino-5-(1H-indazol-5-yl)-4-(1-phenylethyloxy)phenyl]propionic acid;

3-[3-amino-4-cyclopentyloxy-5-(1-methyl-1H-indazol-5-yl)phenyl]propionic acid;

3-[3-amino-4-cyclohexyloxy-5-(1-methyl-1H-indazol-5-yl)phenyl]propionic acid;

3-[3-amino-4-(indan-2-yloxy)-5-(1-methyl-1H-indazol-5-yl)phenyl]propionic acid;

3-[3-amino-5-(1-methyl-1H-indazol-5-yl)-4-(1-phenylethyloxy)phenyl]propionic acid;

3-[3-amino-4-cyclopentyloxy-5-(1-ethyl-1H-indazol-5-yl)phenyl]propionic acid;

3-[3-amino-4-cyclohexyloxy-5-(1-ethyl-1H-indazol-5-yl)phenyl]propionic acid;

3-[3-amino-5-(1-ethyl-1H-indazol-5-yl)-4-(1-phenylethyloxy)phenyl]propionic acid;

3-[4-cyclopentyloxy-3-(3-methyl-1H-indazol-5-yl)phenyl]propionic acid;

3-[4-cyclopentyloxy-3-(1,3-dimethyl-1H-indazol-5-yl)phenyl]propionic acid;

3-[4-cyclopentyloxy-3-(1-ethyl-3-methyl-1H-indazol-5-yl)phenyl]propionic acid;

3-[3-(3-carboxyl-1H-indazol-5-yl)-4-cyclopentyl-oxyphenyl]propionic acid;

3-[3-(3-carboxyl-1-methyl-1H-indazol-5-yl)-4-cyclopentyloxyphenyl]propionic acid;

3-[3-(3-acetyl-1H-indazol-5-yl)-4-cyclopentyloxyphenyl]propionic acid;

3-[3-(3-acetyl-1-methyl-1H-indazol-5-yl)-4-cyclopentyloxyphenyl]propionic acid;

3-[4-cyclopentyloxy-3-(3-formyl-1H-indazol-5-yl)phenyl]propionic acid;

3-[4-cyclopentyloxy-3-(3-hydroxy-1H-indazol-5-yl)phenyl]propionic acid;

3-[4-cyclopentyloxy-3-(3-hydroxy 1-methyl-1H-indazol-5-yl)phenyl]propionic acid;

3-[4-cyclopentyloxy-3-(3-methoxy-1H-indazol-5-yl)phenyl]propionic acid; and

3-[4-cyclopentyloxy-3-(3-methoxy-1-methyl-1H-indazol-5-yl)phenyl]propionic acid.

20. A medicament comprising the compound or the pharmaceutically acceptable salt thereof according to any one of claims 1 to 19 as an active ingredient.

21. An agent for inhibiting production of prostaglandin and/or leukotriene, which comprises the compound or the pharmaceutically acceptable salt thereof according to any one of claims 1 to 19 as an active ingredient.

22. The medicament according to claim 20, which is for prophylactic and/or therapeutic treatment of a disease for which inhibition of prostaglandin and/or leukotriene production is effective.

23. The medicament according to claim 20, which is for prophylactic and/or therapeutic treatment of an inflammatory disease of a mammal.

24. The medicament according to claim 20, which is for prophylactic and/or therapeutic treatment of an autoimmune disease of a mammal.

25. The medicament according to claim 20, which is for prophylactic and/or therapeutic treatment of an allergic disease of a mammal.

26. The medicament according to claim 20, which is for antipyretic and/or analgetic treatment of a mammal.

27. A pharmaceutical composition for prophylactic and/or therapeutic treatment of a condition in a living body of a mammal where an acute or chronic inflammatory reaction is observed, which comprises the compound or the pharmaceutically acceptable salt thereof according to any one of claims 1 to 19 in an amount effective for the prophylactic and/or therapeutic treatment together with a pharmaceutically acceptable carrier.

28. A method for prophylactic and/or therapeutic treatment of a condition in a living body of a mammal where an acute or chronic inflammatory reaction is observed, which comprises the, Step of administering the compound or the pharmaceutically acceptable salt thereof according to any one of claims 1 to 19 to the mammal in an amount effective for the prophylactic and/or therapeutic treatment.

* * * * *

UNITED STATES PATENT AND TRADEMARK OFFICE
CERTIFICATE OF CORRECTION

PATENT NO.        : 6,867,320 B2
APPLICATION NO.   : 10/368435
DATED             : March 15, 2005
INVENTOR(S)       : Motoshi Shoda et al.

It is certified that error appears in the above-identified patent and that said Letters Patent is hereby corrected as shown below:

Please correct the following errors in the specification.

At column 37, lines 25-26 should read,
--3-(3-[benzothiazol-6-yl]-4-{2-[4-(N,N-dimethylamino)phenyl]ethyloxy}phenyl)propionic acid--

At column 37, lines 34-35 should read,
--3(3-[2-aminobenzothiazol-6-yl]-4-{2-[4-(N,N-dimethylamino)phenyl]ethyloxy}phenyl)-propionic acid--

At column 40, lines 34-35 should read,
--methyl 3-[4-(2-ethylbutyloxy)-3-(1H-indol-5-yl)-5-nitrophenyl]propionate--

At column 43, lines 42-43 should read,
--3-(4-{2-[4-(N,N-dimethylamino)phenyl]ethyloxy}-3-[1H-indazol-5-yl]phenyl)propionic acid--

At column 44, lines 19-20 should read,
--3-(4-{2-[4-(N,N-dimethylamino)phenyl]ethyloxy}-3-[1-methyl-1H-indazol-5-yl]phenyl)-propionic acid--

At column 45, lines 1-2 should read,
--3-(4-{2-[4-(N,N-dimethylamino)phenyl]ethyloxy}-3-[1-ethyl-1H-indazol-5-yl]phenyl)-propionic acid--

At column 50, lines 60-61 should read,
--3-(3-[benzothiazol-6-yl]-4-{2-[4-(N,N-dimethylamino)phenyl]ethyloxy}phenyl)propionic acid--

At column 51, lines 1-2 should read,
--3-(3-[2-aminobenzothiazol-6-yl]-4-{2-[4-(N,N-dimethylamino)phenyl]ethyloxy}phenyl)-propionic acid--

Signed and Sealed this
Eighth Day of May, 2012

David J. Kappos
*Director of the United States Patent and Trademark Office*

CERTIFICATE OF CORRECTION (continued)
U.S. Pat. No. 6,867,320 B2

At column 53, lines 27-28 should read,
--3-(4-{2-[4-(N,N-dimethylamino)phenyl]ethyl<u>oxy</u>}-3-[1H-indazol-5-yl]phenyl)propionic acid--

At column 54, lines 4-5 should read,
--3-(4-{2-[4-(N,N-dimethylamino)phenyl]ethyl<u>oxy</u>}-3-[1-methyl-1H-indazol-5-yl]phenyl)-propionic acid--

At column 54, lines 53-54 should read,
--3-(4-{2-[4-(N,N-dimethylamino)phenyl]ethyl<u>oxy</u>}-3-[1-ethyl-1H-indazol-5-yl]phenyl)-propionic acid--

Please amend Table 2, in columns 311 and 312 as follows.

| Exp. | Syn. | SM1 | SM2 | RO | Y | Z | Br or Ar | LCMS method | RTime | Mass |
|---|---|---|---|---|---|---|---|---|---|---|
| 550 | 4d1a | Int.84 | Int.114 | [structure] | Me | NO2 | 1MIZ5 | A | 4.83 | 460 (M⁺ + 1) |
| 551 | 2ba | Exp.550 | | [structure] | Me | NH2 | 1MIZ5 | A | 4.47 | 430 (M⁺ + 1) |
| 552 | 1a | Exp.551 | | [structure] | H | NH2 | 1MIZ5 | A | 3.76 | 436 (M⁺ + 1) |
| Int.128 | 4e1 | Int.77 | Hal5 | [structure] | Me | NO2 | Br | A | 5.10 | N.D |
| 553 | 4d1a | Int.128 | Int.114 | [structure] | Me | NO2 | 1MIZ5 | A | 4.97 | 464 (M⁺ + 1) |
| 554 | 2ba | ~~Exp.553~~ <u>Exp. 553</u> | | [structure] | Me | NH2 | 1MIZ5 | A | 4.38 | 434 (M⁺ + 1) |
| 555 | 1a | ~~Exp.553~~ <u>Exp. 554</u> | | [structure] | H | NH2 | 1MIZ5 | A | 3.72 | 420 (M⁺ + 1) |

Please amend Table 2, in columns 311 -314 as follows.

CERTIFICATE OF CORRECTION (continued)
U.S. Pat. No. 6,867,320 B2

Page 3 of 4

TABLE 32

| Exp. | Sys. | SM1 | SM2 | RO | | Y | Z | Br or Ar | LCMS method | RTime | Mass |
|---|---|---|---|---|---|---|---|---|---|---|---|
| Int.129 | 4c2 | Int.77 | A134 | (4-F-phenyl-CH₂CH₂-O-) | | Me | NO2 | Br | A | 5.29 | N.D |
| 556 | 4d1a | Int.129 | Int.114 | (4-F-phenyl-CH₂CH₂-O-) | | Me | NO2 | 1MIZ5 | A | 5.02 | 478 (M⁺ + 1) |
| 557 | 2bb | Exp. 556 | | (4-F-phenyl-CH₂CH₂-O-) | | Me | NH2 | 1MIZ5 | A | 4.48 | 448 (M⁺ + 1) |
| 558 | 3a | Exp. 557 | | (4-F-phenyl-CH₂CH₂-O-) | | H | NH2 | 1MIZ5 | A | 3.86 | 434 (M⁺ + 1) |
| Int.130 | 4e2 | Int.77 | A148 | (4-NMe₂-phenyl-CH₂CH₂-O-) | | Me | NO2 | Br | A | 4.82 | 451 (M⁺ + 1) |
| 559 | 4e1a | Int.130 | Int.114 | (4-NMe₂-phenyl-CH₂CH₂-O-) | | Me | NO2 | 1MIZ5 | A | 4.54 | 503 (M⁺ + 1) |
| 560 | 2bn | Exp. 559 | | (4-NMe₂-phenyl-CH₂CH₂-O-) | | Me | NH2 | 1MIZ5 | A | 3.73 | 473 (M⁺ + 1) |
| 561 | 1a | Exp. 560 | | (4-NMe₂-phenyl-CH₂CH₂-O-) | | H | NH2 | 1MIZ5 | A | 3.12 | 459 (M⁺ + 1) |
| Int.131 | 4e1 | Int.77 | Ha38 | (isobutyl-O-) | | Me | NO2 | Br | A | 5.34 | N.D |
| 562 | 4d1a | Int.131 | Int.114 | (isobutyl-O-) | | Me | NO2 | 1MIZ5 | A | 5.02 | 412 (M⁺ + 1) |

Please amend Table 2, in columns 313-316 as follows.

CERTIFICATE OF CORRECTION (continued)
U.S. Pat. No. 6,867,320 B2

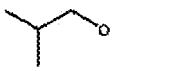

Please correct the following errors in Claim 19, as indicated at the corresponding column and line number.

At column 350, lines 38-39 should read,
   --3-(3-[benzothiazol-6-yl]-4-{2-[4-(N,N-dimethylamino)phenyl]ethyl<u>oxy</u>}phenyl)propionic acid--

At column 350, lines 46-47 should read,
   --3-(3-[2-aminobenzothiazol-6-yl]-4-{2-[4-(N,N-dimethylamino)phenyl]ethyl<u>oxy</u>}phenyl)-propionic acid--

At column 353, lines 42-43 should read,
   --methyl 3-[4-(2-ethylbutyloxy)-3-(1H-indol-5-yl)-5-nitrophenyl]propionate--

At column 356, lines 51-52 should read,
   --3-(4-{2-[4-(N,N-dimethylamino)phenyl]ethyl<u>oxy</u>}-3-[1H-indazol-5-yl]phenyl)propionic acid--

At column 357, lines 27-28 should read,
   --3-(4-{2-[4-(N,N-dimethylamino)phenyl]ethyl<u>oxy</u>}-3-[1-methyl-1H-indaozl-5-yl]phenyl)-propionic acid--

At column 358, lines 10-11 should read,
   --3-(4-{2-[4-{N,N-dimethylamino)phenyl]ethyl<u>oxy</u>)-3-[1-ethyl-1H-indazol-5-yl]phenyl)-propionic acid--

UNITED STATES PATENT AND TRADEMARK OFFICE
CERTIFICATE OF CORRECTION

PATENT NO. : 6,867,320 B2
APPLICATION NO. : 10/368435
DATED : March 15, 2005
INVENTOR(S) : Motoshi Shoda et al.

It is certified that error appears in the above-identified patent and that said Letters Patent is hereby corrected as shown below:

Please correct the following errors in the specification.

At column 37, lines 25-26 should read,
 --3-(3-[benzothiazol-6-yl]-4-{2-[4-(N,N-dimethylamino)phenyl]ethyloxy}phenyl)propionic acid--

At column 37, lines 34-35 should read,
 --3(3-[2-aminobenzothiazol-6-yl]-4-{2-[4-(N,N-dimethylamino)phenyl]ethyloxy}phenyl)-propionic acid--

At column 40, lines 34-35 should read,
 --methyl 3-[4-(2-ethylbutyloxy)-3-(1H-indol-5-yl)-5-nitrophenyl]propionate--

At column 43, lines 42-43 should read,
 --3-(4-{2-[4-(N,N-dimethylamino)phenyl]ethyoxy}-3-[1H-indazol-5-yl]phenyl)propionic acid--

At column 44, lines 19-20 should read,
 --3-(4-{2-[4-(N,N-dimethylamino)phenyl]ethyoxy}-3-[1-methyl-1H-indazol-5-yl]phenyl)-propionic acid--

At column 45, lines 1-2 should read,
 --3-(4-{2-[4-(N,N-dimethylamino)phenyl]ethyoxy}-3-[1-ethyl-1H-indazol-5-yl]phenyl)-propionic acid--

At column 50, lines 60-61 should read,
 --3-(3-[benzothiazol-6-yl]-4-{2-[4-(N,N-dimethylamino)phenyl]ethyloxy}phenyl)propionic acid--

This certificate supersedes the Certificate of Correction issued May 8, 2012.

Signed and Sealed this
Nineteenth Day of June, 2012

David J. Kappos
*Director of the United States Patent and Trademark Office*

CERTIFICATE OF CORRECTION (continued)
U.S. Pat. No. 6,867,320 B2

At column 51, lines 1-2 should read,
 --3-(3-[2--aminobenzothiazol-6-yl]-4-{2-[4-(N,N-dimethylamino)phenyl]ethyl<u>oxy</u>}phenyl)-propionic acid--

At column 53, lines 27-28 should read,
 --3-(4-{2-[4-(N,N-dimethylamino)phenyl]ethyl<u>oxy</u>}-3-[1H-indazol-5-yl]phenyl)propionic acid--

At column 54, lines 4-5 should read,
 --3-(4-{2-[4-(N,N-dimethylamino)phenyl]ethyl<u>oxy</u>}-3-[1-methyl-1H-indazol-5-yl]phenyl)-propionic acid--

At column 54, lines 53-54 should read,
 --3-(4-{2-[4-(N,N-dimethylamino)phenyl]ethyl<u>oxy</u>}-3-[1-ethyl-1H-indazol-5-yl]phenyl)-propionic acid--

Please amend Table 31, in columns 311 and 312 as follows.

Please amend Table 32, in columns 311-314 as follows.

TABLE 32

| Exp. | Syn. | SM1 | SM2 | RO | Y | Z | Br or Ar | LCMS method | LCMS Rtime | LCMS Mass |
|---|---|---|---|---|---|---|---|---|---|---|
| Int.329 | 4c2 | Int.77 | A134 | | Me | NO2 | Br | A | 5.29 | N.D |
| 556 | 4d1x | Int.129 | Int.114 | | Me | NO2 | 3MIZ5 | A | 5.02 | 473 (M⁺ + 1) |
| 557 | 2bn | Exp. 556 | | Me | NH2 | 3MIZ5 | A | 4.58 | 443 (M⁺ + 1) |
| 558 | 1a | Exp. 557 | | H | NH2 | 3MIZ5 | A | 3.86 | 434 (M⁺ + 1) |
| Int.330 | 4c2 | Int.77 | A143 | | Me | NO2 | Br | A | 4.82 | 451 (M⁺ + 1) |
| 559 | 4d1x | Int.130 | Int.114 | | Me | NO2 | 3MIZ5 | A | 4.54 | 503 (M⁺ + 1) |
| 560 | 2bn | Exp. 559 | | Me | NH2 | 3MIZ5 | A | 3.73 | 473 (M⁺ + 1) |
| 561 | 1a | Exp. 560 | | H | NH2 | 3MIZ5 | A | 5.12 | 459 (M⁺ + 1) |
| Int.331 | 4c1 | Int.77 | In48 | | Me | NO2 | Br | A | 5.34 | N.D |
| 562 | 4d1x | Int.131 | Int.114 | | Me | NO2 | 3MIZ5 | A | 5.02 | 412 (M⁺ − 1) |

CERTIFICATE OF CORRECTION (continued)

Please amend Table 33, in columns 313-316 as follows.

TABLE 33

| Exp. | Syn. | SM1 | SM2 | RO | Y | Z | Br or Ar | LCMS method | RTime | Mass |
|---|---|---|---|---|---|---|---|---|---|---|
| 563 | 2ba | ~~Exp.561~~ Exp. 562 | | (isobutoxy) | Me | NH2 | 1MIZ5 | A | 4.30 | 382 (M⁺ + 1) |
| 564 | 1a | ~~Exp.562~~ Exp. 563 | | (isobutoxy) | H | NH2 | 1MIZ5 | A | 3.66 | 368 (M⁺ + 1) |
| 565 | 4d1a | Int.81 | Int.214 | (indanyloxy) | Me | NO2 | 1MIZ5 | A | 5.08 | 472 (M⁺ + 1) |
| 566 | 2ba | ~~Exp.564~~ Exp. 565 | | (indanyloxy) | Me | NH2 | 1MIZ5 | A | 4.77 | 442 (M⁺ + 1) |
| 567 | 1a | ~~Exp.565~~ Exp. 566 | | (indanyloxy) | H | NH2 | 1MIZ5 | A | 4.14 | 428 (M⁺ + 1) |

Please correct the following errors in Claim 19, as indicated at the corresponding column and line number.

At column 350, lines 38-39 should read,
--3-(3-[benzothiazol-6-yl]-4-{2-[4-(N,N-dimethylamino)phenyl]ethyloxy}phenyl)propionic acid--

At column 350, lines 46-47 should read,
--3-(3-[2-animobenzothiazol-6-yl]-4-{2-[4-(N,N-dimethylamino)phenyl]ethyloxy}phenyl)-propionic acid--

At column 353, lines 42-43 should read,
--methyl 3-[4-(2-ethylbutyloxy)-3-(1H-indol-5-yl)-5-nitrophenyl]propionate--

At column 356, lines 51-52 should read,
--3-(4-{2-[4-(N,N-dimethylamino)phenyl]ethyloxy}-3-[1H-indazol-5-yl]phenyl)propionic acid--

At column 357, lines 27-28 should read,
--3-(4-{2-[4-(N,N-dimethylamino)phenyl]ethyloxy}-3-[1-methyl-1H-indaozl-5-yl]phenyl)-propionic acid--

At column 358, lines 10-11 should read,
--3-(4-{2-[4-{N,N-dimethylamino)phenyl]ethyloxy)-3-[1-ethyl-1H-indazol-5-yl]phenyl)-propionic acid--

UNITED STATES PATENT AND TRADEMARK OFFICE
CERTIFICATE OF CORRECTION

PATENT NO. : 6,867,320 B2
APPLICATION NO. : 10/368435
DATED : March 15, 2005
INVENTOR(S) : Motoshi Shoda et al.

It is certified that error appears in the above-identified patent and that said Letters Patent is hereby corrected as shown below:

Please correct the following errors in the specification.

At column 37, lines 25-26 should read,
--3-(3-[benzothiazol-6-yl]-4-{2-[4-(N,N-dimethylamino)phenyl]ethyloxy}phenyl)propionic acid--

At column 37, lines 34-35 should read,
--3(3-[2-aminobenzothiazol-6-yl]-4-{2-[4-(N,N-dimethylamino)phenyl]ethyloxy}phenyl)-propionic acid--

At column 40, lines 34-35 should read,
--methyl 3-[4-(2-ethylbutyloxy)-3-(1H-indol-5-yl)-5-nitrophenyl]propionate--

At column 43, lines 42-43 should read,
--3-(4-{2-[4-(N,N-dimethylamino)phenyl]ethyloxy}-3-[1H-indazol-5-yl]phenyl)propionic acid--

At column 44, lines 19-20 should read,
--3-(4-{2-[4-(N,N-dimethylamino)phenyl]ethyloxy}-3-[1-methyl-1H-indazol-5-yl]phenyl)-propionic acid--

At column 45, lines 1-2 should read,
--3-(4-{2-[4-(N,N-dimethylamino)phenyl]ethyloxy}-3-[1-ethyl-1H-indazol-5-yl]phenyl)-propionic acid--

At column 50, lines 60-61 should read,
--3-(3-[benzothiazol-6-yl]-4-{2-[4-(N,N-dimethylamino)phenyl]ethyloxy}phenyl)propionic acid--

This certificate supersedes the Certificates of Correction issued May 8, 2012 and June 19, 2012.

Signed and Sealed this
Thirty-first Day of July, 2012

David J. Kappos
*Director of the United States Patent and Trademark Office*

CERTIFICATE OF CORRECTION (continued)
U.S. Pat. No. 6,867,320 B2

At column 51, lines 1-2 should read,
--3-(3-[2--aminobenzothiazol-6-yl]-4-{2-[4-(N,N-dimethylamino)phenyl]ethyloxy}phenyl)-propionic acid--

At column 53, lines 27-28 should read,
--3-(4-{2-[4-(N,N-dimethylamino)phenyl]ethyloxy}-3-[1H-indazol-5-yl]phenyl)propionic acid--

At column 54, lines 4-5 should read,
--3-(4-{2-[4-(N,N-dimethylamino)phenyl]ethyloxy}-3-[1-methyl-1H-indazol-5-yl]phenyl)-propionic acid--

At column 54, lines 53-54 should read,
--3-(4-{2-[4-(N,N-dimethylamino)phenyl]ethyloxy}-3-[1-ethyl-1H-indazol-5-yl]phenyl)-propionic acid--

Please amend Table 31, in columns 311 and 312 as follows.

Please amend Table 32, in columns 311-314 as follows.

TABLE 32

| Exp. | Syn. | SM1 | SM2 | RO | Y | Z | Br or Ar | LCMS method | LCMS Rtime | LCMS Mass |
|---|---|---|---|---|---|---|---|---|---|---|
| Int.329 | 4c2 | Int.77 | A134 | (structure) | Me | NO2 | Br | A | 5.29 | N.D |
| 556 | 4d1x | Int.129 | Int.114 | (structure) | Me | NO2 | 2MIZ5 | A | 5.02 | 479 (M⁺ + 1) |
| 557 | 2ba | Exp. 556 | (structure) | Me | NH2 | 2MIZ5 | A | 4.68 | 449 (M⁺ + 1) |
| 558 | 1a | Exp. 557 | (structure) | H | NH2 | 2MIZ5 | A | 3.86 | 434 (M⁺ + 1) |
| Int.330 | 4c2 | Int.77 | A143 | (structure) | Me | NO2 | Br | A | 4.82 | 451 (M⁺ + 1) |
| 559 | 4d1x | Int.130 | Int.114 | (structure) | Me | NO2 | 13MIZ5 | A | 4.54 | 503 (M⁺ + 1) |
| 560 | 2ba | Exp. 559 | (structure) | Me | NH2 | 2MIZ5 | A | 3.73 | 473 (M⁺ + 1) |
| 561 | 1a | Exp. 560 | (structure) | H | NH2 | 13MIZ5 | A | 5.12 | 459 (M⁺ + 1) |
| Int.331 | 4c1 | Int.77 | Int.8 | (structure) | Me | NO2 | Br | A | 5.34 | N.D |
| 562 | 4d1a | Int.131 | Int.114 | (structure) | Me | NO2 | 3MIZ5 | A | 5.02 | 412 (M⁺ - 1) |

Please amend Table 33, in columns 313-316 as follows.

TABLE 33

| Exp. | Syn. | SM1 | SM2 | RO | Y | Z | Br or Ar | LCMS method | RTime | Mass |
|---|---|---|---|---|---|---|---|---|---|---|
| 563 | 2ba | ~~Exp562~~ Exp. 562 | | (isobutoxy) | Me | NH2 | 1MEZ5 | A | 4.30 | 382 (M⁺+1) |
| 564 | 1a | ~~Exp563~~ Exp. 563 | | (isobutoxy) | H | NH2 | 1MEZ5 | A | 3.66 | 368 (M⁺+1) |
| 565 | 4d1a | Int.81 | Int.214 | (indanyloxy) | Me | NO2 | 1MEZ5 | A | 5.08 | 472 (M⁺+1) |
| 566 | 2ba | ~~Exp564~~ Exp. 565 | | (indanyloxy) | Me | NH2 | 1MEZ5 | A | 4.77 | 442 (M⁺+1) |
| 567 | 1a | ~~Exp565~~ Exp. 566 | | (indanyloxy) | H | NH2 | 1M75 | A | 4.14 | 428 (M⁺+1) |

Please correct the following errors in Claim 19, as indicated at the corresponding column and line number.

At column 350, lines 38-39 should read,
--3-(3-[benzothiazol-6-yl]-4-{2-[4-(N,N-dimethylamino)phenyl]ethyloxy}phenyl)propionic acid--

At column 350, lines 46-47 should read,
--3-(3-[2-aminobenzothiazol-6-yl]-4-{2-[4-(N,N-dimethylamino)phenyl]ethyloxy}phenyl)-propionic acid--

At column 353, lines 42-43 should read,
--methyl 3-[4-(2-ethylbutyloxy)-3-(1H-indol-5-yl)-5-nitrophenyl]propionate--

At column 356, lines 51-52 should read,
--3-(4-{2-[4-(N,N-dimethylamino)phenyl]ethyloxy}-3-[1H-indazol-5-yl]phenyl)propionic acid--

At column 357, lines 27-28 should read,
--3-(4-{2-[4-(N,N-dimethylamino)phenyl]ethyloxy}-3-[1-methyl-1H-indazol-5-yl]phenyl)-propionic acid--

At column 358, lines 10-11 should read,
--3-(4-{2-[4-{N,N-dimethylamino)phenyl]ethyloxy)-3-[1-ethyl-1H-indazol-5-yl]phenyl)-propionic acid--